(12) United States Patent
Owen et al.

(10) Patent No.: US 11,452,711 B2
(45) Date of Patent: Sep. 27, 2022

(54) NITRILE-CONTAINING ANTIVIRAL COMPOUNDS

(71) Applicant: Pfizer Inc., New York, NY (US)

(72) Inventors: Dafydd Rhys Owen, Concord, MA (US); Matthew Richard Reese, Mystic, CT (US); Matthew Forrest Sammons, Quincy, MA (US); Jamison Bryce Tuttle, Marblehead, MA (US); Patrick Robert Verhoest, Newton, MA (US); Qingyi Yang, Lexington, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 17/660,270

(22) Filed: Apr. 22, 2022

(65) Prior Publication Data
US 2022/0257563 A1 Aug. 18, 2022

Related U.S. Application Data

(60) Continuation of application No. 17/554,091, filed on Dec. 17, 2021, which is a division of application No. 17/395,139, filed on Aug. 5, 2021, now Pat. No. 11,351,149.

(60) Provisional application No. 63/194,241, filed on May 28, 2021, provisional application No. 63/170,158, filed on Apr. 2, 2021, provisional application No. 63/143,435, filed on Jan. 29, 2021, provisional application No. 63/073,982, filed on Sep. 3, 2020.

(51) Int. Cl.
| | |
|---|---|
| *C07D 403/12* | (2006.01) |
| *A61K 31/403* | (2006.01) |
| *A61P 31/14* | (2006.01) |
| *A61K 31/427* | (2006.01) |
| *A61K 31/401* | (2006.01) |

(52) U.S. Cl.
CPC .......... *A61K 31/403* (2013.01); *A61K 31/401* (2013.01); *A61K 31/427* (2013.01); *A61P 31/14* (2018.01); *C07D 403/12* (2013.01); *C07B 2200/13* (2013.01)

(58) Field of Classification Search
CPC .................................................. C07D 403/12
See application file for complete search history.

(56) References Cited

U.S. PATENT DOCUMENTS

| | | | |
|---|---|---|---|
| 5,583,238 A | 12/1996 | Ng et al. | |
| 6,037,157 A | 3/2000 | Norbeck et al. | |
| 6,514,997 B2 | 2/2003 | Dragovich et al. | |
| 6,894,072 B2 | 5/2005 | Arasappan et al. | |
| 7,012,066 B2 | 3/2006 | Saksena et al. | |
| 7,173,057 B2 | 2/2007 | Chen et al. | |
| 7,186,747 B2 | 3/2007 | Arasappan et al. | |
| 7,205,330 B2 | 4/2007 | Bogen et al. | |
| 7,244,721 B2 | 7/2007 | Saksena et al. | |
| 7,423,058 B2 | 9/2008 | Bogen et al. | |
| 7,425,576 B2 | 9/2008 | Arasappan et al. | |
| 7,449,447 B2 | 11/2008 | Chen et al. | |
| 7,485,625 B2 | 2/2009 | Velazquez et al. | |
| 7,504,392 B2 | 3/2009 | Fobes et al. | |
| 7,592,316 B2 | 9/2009 | Njoroge et al. | |
| 7,619,094 B2 | 11/2009 | Chen et al. | |
| 7,816,326 B2 | 10/2010 | Velazquez et al. | |
| 8,067,379 B2 | 11/2011 | Bennett et al. | |
| RE43,298 E | 4/2012 | Saksena et al. | |
| 8,686,145 B2 | 4/2014 | Ruijter et al. | |
| 9,309,284 B2 | 4/2016 | Chang et al. | |
| 9,474,759 B2 | 10/2016 | Chang et al. | |
| 9,975,885 B2 | 5/2018 | St. John et al. | |
| 11,072,634 B2 | 7/2021 | Nils et al. | |
| 11,124,497 B1 | 9/2021 | Arnold et al. | |
| 11,174,231 B1 | 11/2021 | Arnold et al. | |

(Continued)

FOREIGN PATENT DOCUMENTS

| | | |
|---|---|---|
| CN | 102838523 | 12/2012 |
| CN | 103130710 | 6/2013 |

(Continued)

OTHER PUBLICATIONS

Abranyi-Balogh, Peter et al., "A road map for prioritizing warheads for cysteine targeting covalent inhibitors", European Journal of Medicinal Chemistry, 2018, pp. 94-107, vol. 160.

(Continued)

*Primary Examiner* — Brian E McDowell
(74) *Attorney, Agent, or Firm* — John A. Wichtowski

(57) ABSTRACT

The invention relates to compounds of Formula I''

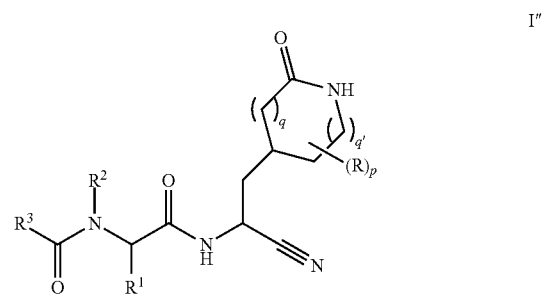

wherein R, $R^1$, $R^2$, $R^3$, p, q and q' are as defined herein, pharmaceutical compositions comprising the compounds, methods of treating coronavirus infection such as COVID-19 in a patient by administering therapeutically effective amounts of the compounds, and methods of inhibiting or preventing replication of coronaviruses such as SARS-CoV-2 with the compounds.

8 Claims, 15 Drawing Sheets

Specification includes a Sequence Listing.

(56) References Cited

U.S. PATENT DOCUMENTS

| | | | |
|---|---|---|---|
| 11,358,953 | B2 | 6/2022 | Panarese et al. |
| 2003/0207861 | A1 | 11/2003 | Arasappan et al. |
| 2003/0216325 | A1 | 11/2003 | Saksena et al. |
| 2004/0186114 | A1 | 9/2004 | Girillo et al. |
| 2004/0235952 | A1 | 11/2004 | Fuhrman et al. |
| 2004/0254117 | A9 | 12/2004 | Saksena et al. |
| 2005/0085425 | A1 | 4/2005 | Chen et al. |
| 2005/0143320 | A1 | 6/2005 | Yang et al. |
| 2005/1043319 | | 6/2005 | Yang et al. |
| 2005/0153900 | A1 | 7/2005 | Velazquez et al. |
| 2005/0222047 | A1 | 10/2005 | Chen et al. |
| 2005/0245458 | A1 | 11/2005 | Arasappan et al. |
| 2005/0267043 | A1 | 12/2005 | Bogen et al. |
| 2005/0267148 | A1 | 12/2005 | Tsuchiya et al. |
| 2005/0288338 | A1 | 12/2005 | Yao et al. |
| 2006/0014821 | A1 | 1/2006 | He et al. |
| 2006/0205672 | A1 | 9/2006 | Saksena et al. |
| 2006/0276406 | A1 | 12/2006 | Gupta et al. |
| 2006/0281689 | A1 | 12/2006 | Malcolm |
| 2007/0032433 | A1 | 2/2007 | Saksena et al. |
| 2007/0042968 | A1 | 2/2007 | Bennett et al. |
| 2007/0093430 | A1 | 4/2007 | Chen et al. |
| 2007/0142300 | A1 | 6/2007 | Arasappan et al. |
| 2007/0142301 | A1 | 6/2007 | Bogen et al. |
| 2007/0197448 | A1 | 8/2007 | Velazquez et al. |
| 2007/0232549 | A1 | 10/2007 | Njoroge et al. |
| 2010/0160320 | A1 | 6/2010 | Fan et al. |
| 2010/0311753 | A1 | 12/2010 | Fan et al. |
| 2011/0117057 | A1 | 5/2011 | Saksena et al. |
| 2012/0329704 | A1 | 12/2012 | Ruijter et al. |
| 2012/0330015 | A1 | 12/2012 | Ruijter et al. |
| 2013/0018045 | A1 | 1/2013 | Woods |
| 2013/0310555 | A1 | 11/2013 | Chong |
| 2014/0005168 | A1 | 1/2014 | Do et al. |
| 2014/0243341 | A1 | 4/2014 | Chang et al. |
| 2014/0213788 | A1 | 7/2014 | Ruijter et al. |
| 2015/0133368 | A1 | 5/2015 | Chang et al. |
| 2015/0148342 | A1 | 5/2015 | Yue et al. |
| 2015/0210655 | A1 | 7/2015 | Lonn et al. |
| 2017/0008863 | A1 | 1/2017 | Chong |
| 2017/0355708 | A1 | 12/2017 | Jefson et al. |
| 2018/0289676 | A1 | 10/2018 | Arnatt et al. |
| 2019/0016726 | A1 | 1/2019 | Lin et al. |
| 2019/0151400 | A1 | 5/2019 | Chang et al. |
| 2019/0282703 | A1 | 9/2019 | Gallatin et al. |
| 2019/0322700 | A1 | 10/2019 | Nils et al. |
| 2020/0157078 | A1 | 5/2020 | Fan et al. |
| 2021/0008150 | A1 | 1/2021 | Schinazi et al. |
| 2022/0033383 | A1 | 2/2022 | Panarese et al. |

FOREIGN PATENT DOCUMENTS

| | | |
|---|---|---|
| CN | 103145608 | 6/2013 |
| CN | 105037367 | 11/2015 |
| CN | 110054596 | 7/2019 |
| CN | 110105348 | 8/2019 |
| CN | 108690043 | 10/2019 |
| CN | 110818691 | 2/2020 |
| CN | 105566321 | 4/2020 |
| CN | 107459511 | 5/2020 |
| CN | 108069984 | 2/2021 |
| DE | 19748470 | 5/1999 |
| EA | 032794 | 7/2019 |
| EP | 3342779 | 4/2018 |
| FR | 3037955 | 12/2016 |
| GB | 2422829 | 8/2006 |
| GB | 2422831 | 8/2006 |
| GB | 2548542 | 9/2017 |
| JP | 2008260716 | 10/2008 |
| JP | 2013032343 | 2/2013 |
| JP | 2014133739 | 7/2014 |
| JP | 2015151458 | 8/2015 |
| JP | 2017137291 | 8/2017 |
| WO | 1994014436 | 7/1994 |
| WO | 1996012817 | 5/1996 |
| WO | 1997030073 | 8/1997 |
| WO | 1997031937 | 9/1997 |
| WO | 1997037997 | 10/1997 |
| WO | 2000003997 | 1/2000 |
| WO | 2001010894 | 2/2001 |
| WO | 2001040189 | 6/2001 |
| WO | 2002008244 | 1/2002 |
| WO | 2003053988 | 7/2003 |
| WO | 2003062228 | 7/2003 |
| WO | 2003062265 | 7/2003 |
| WO | 2003074532 | 9/2003 |
| WO | 2003080633 | 10/2003 |
| WO | 2003104202 | 12/2003 |
| WO | 2003105666 | 12/2003 |
| WO | 2004020441 | 3/2004 |
| WO | 2004058717 | 7/2004 |
| WO | 2004093860 | 11/2004 |
| WO | 2004098600 | 11/2004 |
| WO | 2005009479 | 2/2005 |
| WO | 2005021584 | 3/2005 |
| WO | 2005023294 | 3/2005 |
| WO | 2005058821 | 6/2005 |
| WO | 2005074598 | 8/2005 |
| WO | 2005085242 | 9/2005 |
| WO | 2005085275 | 9/2005 |
| WO | 2005087725 | 9/2005 |
| WO | 2005087731 | 9/2005 |
| WO | 2005113580 | 12/2005 |
| WO | 2006024820 | 3/2006 |
| WO | 2006035067 | 4/2006 |
| WO | 2006035068 | 4/2006 |
| WO | 2006045828 | 5/2006 |
| WO | 2006061714 | 6/2006 |
| WO | 2006108488 | 10/2006 |
| WO | 2006108489 | 10/2006 |
| WO | 2006130552 | 12/2006 |
| WO | 2006130626 | 12/2006 |
| WO | 2007039802 | 4/2007 |
| WO | 2007057092 | 5/2007 |
| WO | 2007058832 | 5/2007 |
| WO | 2007068465 | 6/2007 |
| WO | 2007104560 | 9/2007 |
| WO | 2007115409 | 10/2007 |
| WO | 2007120160 | 10/2007 |
| WO | 2007126362 | 11/2007 |
| WO | 2008011074 | 1/2008 |
| WO | 2008037266 | 4/2008 |
| WO | 2008040820 | 4/2008 |
| WO | 2008055959 | 5/2008 |
| WO | 2008077551 | 7/2008 |
| WO | 2008077554 | 7/2008 |
| WO | 2008104994 | 9/2008 |
| WO | 2008124148 | 10/2008 |
| WO | 2008126889 | 10/2008 |
| WO | 2008147812 | 12/2008 |
| WO | 2009061761 | 5/2009 |
| WO | 2009138789 | 11/2009 |
| WO | 2009138790 | 11/2009 |
| WO | 2009138791 | 11/2009 |
| WO | 2009138792 | 11/2009 |
| WO | 2009138795 | 11/2009 |
| WO | 2009138796 | 11/2009 |
| WO | 2009146406 | 12/2009 |
| WO | 2010014179 | 2/2010 |
| WO | 2010039982 | 4/2010 |
| WO | 2010042646 | 4/2010 |
| WO | 2010042649 | 4/2010 |
| WO | 2010111060 | 9/2010 |
| WO | 2010138652 | 12/2010 |
| WO | 2010138659 | 12/2010 |
| WO | 2010138685 | 12/2010 |
| WO | 2010138695 | 12/2010 |
| WO | 2010138706 | 12/2010 |
| WO | 2010144686 | 12/2010 |
| WO | 2011003932 | 1/2011 |
| WO | 2011011303 | 1/2011 |
| WO | 2011014817 | 2/2011 |
| WO | 2011018170 | 2/2011 |
| WO | 2011087837 | 7/2011 |

(56) References Cited

FOREIGN PATENT DOCUMENTS

| | | |
|---|---|---|
| WO | 2011088303 | 7/2011 |
| WO | 2011088345 | 7/2011 |
| WO | 2011103932 | 9/2011 |
| WO | 2011103933 | 9/2011 |
| WO | 2011132048 | 10/2011 |
| WO | 2011133659 | 10/2011 |
| WO | 2011146748 | 11/2011 |
| WO | 2012022045 | 2/2012 |
| WO | 2012028578 | 3/2012 |
| WO | 2012058173 | 5/2012 |
| WO | 2012058531 | 5/2012 |
| WO | 2012087372 | 6/2012 |
| WO | 2012125668 | 9/2012 |
| WO | 2012151271 | 11/2012 |
| WO | 2012151283 | 11/2012 |
| WO | 2012169649 | 12/2012 |
| WO | 2012171337 | 12/2012 |
| WO | 2013026726 | 2/2013 |
| WO | 2013049382 | 4/2013 |
| WO | 2013087581 | 6/2013 |
| WO | 2013100632 | 7/2013 |
| WO | 2013128465 | 9/2013 |
| WO | 2013155422 | 10/2013 |
| WO | 2013157229 | 10/2013 |
| WO | 2013166319 | 11/2013 |
| WO | 2013181135 | 12/2013 |
| WO | 2013185124 | 12/2013 |
| WO | 2014076170 | 5/2014 |
| WO | 2014078214 | 5/2014 |
| WO | 2014113620 | 7/2014 |
| WO | 2014172871 | 10/2014 |
| WO | 2015028427 | 3/2015 |
| WO | 2015036058 | 3/2015 |
| WO | 2015036059 | 3/2015 |
| WO | 2015049351 | 4/2015 |
| WO | 2015104254 | 7/2015 |
| WO | 2015110481 | 7/2015 |
| WO | 2015110826 | 7/2015 |
| WO | 2015143653 | 10/2015 |
| WO | 2015155332 | 10/2015 |
| WO | 2015192981 | 12/2015 |
| WO | 2015193454 | 12/2015 |
| WO | 2016033243 | 3/2016 |
| WO | 2016050921 | 4/2016 |
| WO | 2015079760 | 5/2016 |
| WO | 2016079760 | 5/2016 |
| WO | 2016123576 | 8/2016 |
| WO | 2016124796 | 8/2016 |
| WO | 2016124938 | 8/2016 |
| WO | 2016133832 | 8/2016 |
| WO | 2016134314 | 8/2016 |
| WO | 2017018924 | 2/2017 |
| WO | 2017060431 | 4/2017 |
| WO | 2017114509 | 7/2017 |
| WO | 2016204816 | 9/2017 |
| WO | 2017155816 | 9/2017 |
| WO | 2017165311 | 9/2017 |
| WO | 2017193034 | 11/2017 |
| WO | 2017193041 | 11/2017 |
| WO | 2017193063 | 11/2017 |
| WO | 2017197377 | 11/2017 |
| WO | 2017222935 | 12/2017 |
| WO | 2018009938 | 1/2018 |
| WO | 2018015818 | 1/2018 |
| WO | 2018042343 | 3/2018 |
| WO | 2018108627 | 6/2018 |
| WO | 2018122419 | 7/2018 |
| WO | 2018222598 | 12/2018 |
| WO | 2018234139 | 12/2018 |
| WO | 2019009412 | 1/2019 |
| WO | 2019068726 | 4/2019 |
| WO | 2019075386 | 4/2019 |
| WO | 2019086474 | 5/2019 |
| WO | 2019101551 | 5/2019 |
| WO | 2019104070 | 5/2019 |
| WO | 2019129121 | 7/2019 |
| WO | 2019129213 | 7/2019 |
| WO | 2019145726 | 8/2019 |
| WO | 2019166628 | 9/2019 |
| WO | 2019191504 | 10/2019 |
| WO | 2019201432 | 10/2019 |
| WO | 2019202052 | 10/2019 |
| WO | 2019204816 | 10/2019 |
| WO | 2019232245 | 12/2019 |
| WO | 2020014599 | 1/2020 |
| WO | 2020027704 | 2/2020 |
| WO | 2020030143 | 2/2020 |
| WO | 2020037166 | 2/2020 |
| WO | 2020046991 | 3/2020 |
| WO | 2020109297 | 6/2020 |
| WO | 2020142748 | 7/2020 |
| WO | 2020169682 | 8/2020 |
| WO | 2020172093 | 8/2020 |
| WO | 2020192750 | 10/2020 |
| WO | 2020247665 | 12/2020 |
| WO | 2021252491 | 12/2021 |
| WO | 2021252644 | 12/2021 |
| WO | 2022020242 | 1/2022 |

OTHER PUBLICATIONS

Adedej, Adeyemi O., et al., "Antiviral drugs specific for coronaviruses in preclinical development", Current Opinion Virology, Oct. 2014, pp. 45-53, vol. 8.

Albuquerque, Nadine De., et al., "Murine Hepatitis Virus Strain 1 Produces a Clinically Relevant Model of Severe Acute Respiratory Syndrome in A/J Mice", Journal of Virology, Nov. 2006, pp. 10382-10394, 80(21).

Amblard, Franck, et al., "Synthesis and antiviral evaluation of novel peptidomimetics as norovirus protease inhibitors", Bioorganic & Medicinal Chemistry Letters, 2018, pp. 2165-2170, vol. 28, Issue 12.

Bandyopadhyay, Anupam, et al., "Targeting biomolecules with reversible covalent chemistry", Current Opinion in Chemical Biology, 2016, pp. 110-116, vol. 34.

Bernassola, Francesca, et al., "HECT-Type E3 Ubiquitin Ligases in Cancer", Trends in Biochemical Sciences, Dec. 2019, pp. 1057-1075, 44(12).

Berteotti, Anna, et al., "Predicting the Reactivity of Nitrile-Carrying Compounds with Cysteine: A Combined Computational and Experimental Study", ACS Medicinal Chemistry Letters, Feb. 24, 2014, pp. 501-505, 5(5).

Boras, Brittton, et al., "Discovery of a Novel Inhibitor of Coronavirus 3CL Protease for the Potential Treatment of COVID-19", bioRxiv 2020, 09.12.293498; doi: https://doi.org/10.1101/2020.09.12.293498, pp. 1-67.

Cai, Jiaqiang, et al., "4-(3-Trifluoromethylpheny)-pyrimidine-2-carbonitrile as cathepsin S inhibitors: N3, not N1 is critically important", Bioorganic & Medicinal Chemistry Letters, Aug. 1, 2010, pp. 4507-4510, 20(15).

Casimiro-Garcia, Augstin, et al., "Identification of Cyanamide-Based Janus Kinase 3 (JAK3) Covalent Inhibitors", Journal of Medicinal Chemistry, 2018, pp. 10665-10699, 61(23).

Chatterjee, Payal, et al., "Can Relative Binding Free Energy Predict Selectivity of Reversible Covalent Inhibitors?", Journal of American Chemical Society, 2017, pp. 17945-17952, 139(49).

Clinical Trials: "Study of PF-07321332 in Health Participants", ClinicalTrials.gov Identifier: NCT04756531, last updated post: Jul. 2, 2021, 12 pages.

Chuck, C.P., et al., "Design, synthesis and cystallographic analysis of nitrile-based broad-sprectrum peptidomimetic inhibitors for coronavirus 3C-like protease", European Journal Medicinal Chemistry, 2013, pp. 1-6, vol. 59.

Coteron, Jose M., et al., "Falcipain Inhibitors: Optimization Studies of the 2-Pyrimidinecarbonitrile Lead Series", Journal of Medicinal Chemistry, 2010, pp. 6129-6152, 53(16).

Dai, Wenhao, et al., "Structure-based design of antiviral drug candidates targeting the SARS-CoV-2 main protease", Science, Jun. 19, 2020, pp. 1331-1335, 368(6497).

(56) References Cited

OTHER PUBLICATIONS

Damalanka, Vishnu C., et al., "Structure-guided design, synthesis and evaluation of oxazolidinone-base inhibitors of norovirus 3CL protease", European Journal of Medicinal Chemistry, 2018, pp. 881-890, vol. 143.
De Cesco, Stephane, et al., "Covalent inhibitors and discovery", European Journal Medicinal Chemistry, Sep. 29, 2017, pp. 96-114, vol. 138.
Dong, Liying, et al., "Discovering drugs to treat coronavirus disease 2019 (COVID-19)," Drug Discoveries & Therapeutics, 2020, pp. 58-60, 14(1).
Dragovich, P.S., et al., "Structure-Based Design of Ketone-Containing, Tripeptidyl Human Rhinovirus 3C Protease Inhibitors", Bioorganic & Medicinal Chemistry Letters, 2000, pp. 45-48, 10(1).
Dragovich, P.S., et al., "Structure-Based Design, Synthesis, and Biological Evaluation of Irreversible Human Rhinovirus 3C Protease Inhibitors. 4. Incorporation of P1 Lactam Moieties as L-Glutamine Replacements", Journal of Medicinal Chemistry, 1999, pp. 1213-1224, 42(7).
Eaton, John K., et al., "Selective covalent targeting of GPX4 using masked nitrile-oxide electrophiles", Nature Chemical Biology, 2020, pp. 497-506, vol. 16.
Ehmke, Veronika, et al., "Tuning and predicting biological affinity: aryl nitriles as cysteine protease inhibitors", Organic Biomolecular Chemistry, 2012, pp. 5764-5768., vol. 10.
Fischer, Mark E., et al., "Inhibitors for Novel Coronavirus Protease Identified by Virtual Screening of 687 Million Compounds", Mar. 2020; pp.-1-21; Preprint, https://doi.org/10.26434/chemrxiv.11923239.v1.
Flanagan, et al., "Chemical and Computational Methods for the Characterization of Covalent Reactive Groups for the Prospective Design of Irreversible Inhibitors", Journal of Medicinal Chemistry, 2014, pp. 10072-10079, 57(23).
Fleming, Fraser F., et al., "Nitrile-Containing Pharmaceuticals: Efficacious Roles of the Nitrile Pharmacophore", Journal of Medicinal Chemistry, 2010, pp. 7902-7917, 53(22).
Gehringer, Matthias, et al., "Emerging and Re-Emerging Warheads for Targeted Covalent Inhibitors: Applications in Medicinal Chemistry and Chemical Biology", Journal of Medicinal Chemistry, Jun. 27, 2019, pp. 5673-5724, 62(12).
Halford, Bethany, To conquer COVID-19 create the perfect pill, Chemical & Engineering News, May 20, 2021, pp. 28-31, 99(19).
Hou, Yixuan J., et al., "SARS-CoV-2 Reverse Genetics Reveals a Variable Infection Gradient in the Respiratory Tract",Cell, Jul. 23, 2020, pp. 429-446.e14, 182(2).
International Patent Application No. PCT/IB2021/051768, filed Mar. 3, 2021, Specification and Drawings.
International Patent Application No. PCT/IB2021/052689, filed Mar. 31, 2021. Specification, Drawings, and Sequence Listing.
International Patent Application No. PCT/IB2021/052738, filed Apr. 1, 2021. Specification, Drawings, and Sequence Listing.
International Patent Application No. PCT/IB2021/056093, filed Jul. 7, 2021. Specification and Sequence Listing.
International Patent Application No. PCT/IB2021/0157281, filed Aug. 6, 2021, International Search Report and Written Opinion, dated Oct. 15, 2021, 16 pages.
Jeon, Sangeun, et al., "Identification of Antiviral Drug Candidates against SARS-CoV-2 from FDA-Approved Drugs", Antimicrobial Agents and Chemotherapy, Jul. 2020, pp. e00819-e00820, 64(7).
Johnson, Theodore O., et al., "Structure-Based Design of a Parallel Synthetic Array Directed Toward the Discovery of Irreversible Inhibitors of Human Rhinovirus 3C Protease", Journal of Medicinal Chemistry, May 9, 2002, pp. 2016-2023, 45(10).
Keyser, Samantha G., et al., "Computation-Guided Rational Design of a Peptide Motif That Reacts with Cyanobenzothiazoles via Internal Cysteine-Lysine Relay", Journal of Organic Chemistry, 2018, pp. 7467-7479, 83(14).
Kim, et al., "Reversal of the Progression of Fatal Coronavirus Infection in Cats by a Broad-Spectrum Coronavirus Protease Inhibitor", PLoS Pathogens, Mar. 30, 2016, pp. 1-18, e1005531, 12(3).

Kim, YunJeong, et al., "Broad-Spectrum Antivirals against 3C or 3C-Like Proteases of Picornaviruses, Noroviruses, and Coronaviruses", Journal of Virology, Nov. 2012, pp. 11754-11762, 86(21).
Kim, Yunjeong, et al., "Broad-Spectrum Inhibitors against 3C-Like Proteases of Feline Coronaviruses and Feline Caliciviruses", Journal of Virology, May 2015, pp. 4942-4950, 89(9).
Kitamura, Naoya, et al., "Expedited Approach toward the Rational Design or Noncovalent SARS-CoV-2 Main Protease Inhibitors", Journal of Medicinal Chemistry, 2021, Publication Date, Apr. 23, 2021; https://doi.org/10.1021/acs.jmedchem.1c00509.
Konno, Sho, et al., "Design and synthesis of new tripeptide-type SARS-CoV 3CL protease inhibitors containing an electrophilic arylketone, moiety", Bioorganic & Medicinal Chemistry, Jan. 15, 2013, pp. 412-424, 21(2).
Kruse, R.L., et al., "Therapeutic strategies in a outbreak scenario to treat the novel coronavirus originated in Wuhan, China", F1000Res. Jan. 31, 2020; pp. 1-14, 9:72.
Kuhn, Bernd, et al., "Prospective Evaluation of Free Energy Calculations for the Prioritization of Cathepsin L Inhibitors", Journal of Medicinal Chemistry, 2017, pp. 2485-2497, 60(6).
Lagoutte, Roman, et al., "Covalent inhibitors: an opportunity for rational target selectivity", Current Opinion Chemical Biology, Aug. 2017, pp. 54 63, vol. 39.
Laine, Dramane, et al., Discovery of Novel Cyanamide-Based Inhibitors of Cathepsin C , ACS Medicinal Chemistry Letters, 2011, pp. 142-147, 2(2).
Liu, Cynthia, et al., "Research and Development on Therapeutic Agents and Vaccines for COVID-19 and Related Human Coronavirus Diseases", ACS Central Science, 2020, pp. 315-331, 6(3).
Lonsdale, Richard, et al., "Structure-based design of targeted covalent inhibitors", Chemical Society Review, 2018, pp. 3816-3830, 47(11).
Ma, Chunlong, et al., "Boceprevir, GC-376, and calpain inhibitors II, XII inhibit SARS-CoV-2 viral replication by targeting the viral main protease", Cell Research, Aug. 2020, pp. 678-692, 30(8).
Macfaul, Philip A., et al., "A simple in vitro assay for assessing the reactivity of nitrile containing compounds", Bioorganic & Medicinal Chemistry Letters, 2009, pp. 1136-1138, 19(4).
Martin, James S., et al.,"Characterising covalent warhead reactivity", Bioorganic & Medicinal Chemistry, May 15, 2019, pp. 2066-2074, 27(10).
Montagutelli, Xavier, et al., "The B1.351 and P.1 variants extend SARS-CoV-2 host range to mice", bioRxiv 2021.03.18.436013., doi: http://doi.org/10.1101/2021.03.18.436013, pp. 1-16.
Mott, Bryan T., et al., Identification and Optimization of Inhibitors of Trypanosomal Cysteine Proteases: Cruzain Rhodesain, and TbCatB, Journal of Medicinal Chemistry, Jan. 14, 2020, pp. 52-60, 53(1).
Mamoto, Kenji, et al., "Structure-based design and synthesis of macrocyclic human rhinovirus 3C protease inhibitors", Bioorganic & Medicinal Chemistry Letters, Mar. 1, 2018, pp. 906-909, 28(5).
Oballa, Renata M., et al., "A generally applicable method for assessing the electrophilicity and reactivity of diverse nitrile-containing compounds", Bioorganic & Medicinal Chemistry Letters, 2007, pp. 998-1002, 17(4).
Paasche, Alexander, et al., Mechanistic Insights into SARS Coronavirus Main Protease by Computational Chemistry Methods:, 2021, n. pag. Print. Doctoral Thesis,pp. 1-183, University of Würzburg. Germany. https://d-nb.info/1037687825/34.
Patick, A.K., et al., "Protease Inhibitors as Antiviral Agents", Clinical Microbiol Reviews, Oct. 1998, pp. 614-627, 11(4).
Pillaiyar, Thanigaimalai, et al., "An Overview of Severe Acute Respiratory Syndrome-Coronavirus (SAR-CoV) 3CL Protease Inhibitors: Peptidomimetics and Small Molecule Chemotherapy", Journal of Medicinal Chemistry, 2016, pp. 6595-6628, 59(14).
Press Release: "Pfizer Initiates Phase 1 Study of Novel Oral Antiviral Therapeutic Agent Against SARS-Cov-2"; Mar. 23, 2021, https://ww.businesswire.com/new/home/2021023005644/en/.
Prior, Allan M., et al., "Design, synthesis, and bioevaluation of viral 3C and 3C-like protease inhibitors", Bioorganic & Medicinal Chemistry Letters, 2013, pp. 6317-6320, 23(23).
Rathnayake, Athri D., et al., "3C-like protease inhibitors block coronavirus replication in vitro and improve survival in MERS-

(56) References Cited

OTHER PUBLICATIONS

CoV-infected mice", Science Translational Medicine, Aug. 19, 2020, pp. 1-11, eabc5332, 12(557).

Ray, Sneha, et al., "New Electrophilies and Strategies for Mechanism-Based and Targeted Covalent Inhibitor Design", Biochemistry, 2019, pp. 5234-5244, 58(52).

Santos, Alberto Monteiro Dos, et al., "Experimental study and computational modelling of cruzain cysteine protease inhibition by dipeptidyl nitriles", Physical Chemistry Chemical Physics, 2018, pp. 24317-24328, vol. 20.

Santos, Maria M., et al., "Michael Acceptors as Cysteine Protease Inhibitors", Mini Reviews Medicinal Chemistry, Oct. 2007, pp. 1040-1050, 7(10).

Schade, Markus, et al., "Highly Selective Sub-Nanomolar Cathepsin S Inhibitors by Merging Fragment Binders with Nitrile Inhibitors", Journal of Medicinal Chemistry, 2020, pp. 11801-11808, 63(20).

Schnute, Mark E., et al., "Aminopyrazole Carboxamide Bruton's Tyrosine Kinase Inhibitors. Irreversible to Reversible Covalent Reactive Group Tuning", ACS Medicinal Chemistry Letters, 2019, pp. 80-85, 10(1).

Serafimova, Iana M., et al., Reversible targeting of noncatalytic cysteines with chemically tuned electrophiles. 2013, pp. 1-174 UCSF ProQuest ID: Serafimova_ucsf_0034D_10695.REDACTED. Merritt ID: ark:/13030/m5x36bhx. Retrieved from https://escholarship.org/uc/item/0cj6m628.

Silva, Daniel G., et al., A comparative study of warheads for design of cysteine protease inhibitors, Bioorganic & Medicinal Chemistry Letters, Nov. 15, 2017, pp. 5031-5035, 27(22).

Sinha, Sarmistha, et al., "Electrophilicity of Pyridazine-3-carbonitrile,Pyrimidine-2-carbonitrile, and Pyridine-carbonitrile Derivatives: A Chemical Model to Describe the Formation of Thiazoline Derivatives in Human Liver Microsomes", Chemical Research in Toxicology, Dec. 15, 2014, pp. 2052-2061, 27(12).

Steuten, Kas, et al., "Challenges for Targeting SARS-CoV-2 Proteases as a Therapeutic Strategy for COVID-19", ACS Infectious Diseases, 2021, Publication date Feb. 11, 2021, pp. 1457-1468, 7(6). https://doi.org/10.1021/acsinfecdis.0c00815.

STN Registry Database Entry for 1831065-26-9 entered STN Dec. 16, 2015.

STN Registry Database Entry for 2248095-92-1 entered STN Nov. 13, 2018.

Tomar, et al., "Understanding the determinants for substrate recognition, regulation of enzymatic activity and the development of broad-spectrum inhibitors of coronavirus 3-chymotrypsin-like proteases", 2015, Open Access Dissertations. 1332. https;//docs.lib.purdue.edu/open_access_dessertations/1322.

Totura, Allison L., et al., "Broad-spectrum coronavirus antiviral drug discovery", Expert Opinion on Drug Discovery, Apr. 2019, pp. 397-412, 14(4).

U.S. Appl. No. 17/221,676, filed Apr. 2, 2021.

U.S. Appl. No. 17/365,213, filed Jul. 1, 2021.

Venkatraman, S., "Discovery of boceprevir, a direct-acting NS3/4A protease inhibitor for treatment of chronic hepatitis C infections", Trends in Pharmacological Sciences, 2012, pp. 289-294, 33(5).

Venkatraman, S., et al., "Discovery of (1R,5S)-N-[3-Amino-1-(cyclobutylmethyl)-2,3-dioxopropyl]-3-[2(S)-[[[(1,1-dimethylethyl)amino]carbonyl]amino]-3,3-dimethyl-1-oxobutyl]-6,6-dimethyl-3-azabicyclo[3.1.0]hexan-2(S)-carboxamide (SCH 503034), a Selective, Potent, Orally Bioavailable Hepatitis C Virus NS3 Protease Inhibitor: A Potential Therapeutic Agent for the Treatment of Hepatitis C Infection", Journal of Medicinal Chemistry, 2006, pp. 6074-6086, 49(20).

Venkatraman, S., et al., "Potent inhibitors of HCV-NS3 protease derived from boronic acids", Bioorganic & Medicinal Chemistry Letters, 2009, pp. 180-183, 19(1).

Vuong, Wayne, et al., "Feline coronavirus drug inhibits the main protease of SARS-CoV-2 and blocks virus replications", Nature Communications, Aug. 27, 2020, pp. 1-11, 4282, 11(1).

Wang, Luhong, et al., "Covalent binding design strategy: A prospective method for discovery of potent targeted anticancer agents", European Journal of Medicinal Chemistry, 2017, pp. 493-505, vol. 142.

Wang, Yaxin, et al., "Inhibition of enterovirus 71 replication by an α-hydroxy-nitrile derivative NK-1.9K", Antiviral Research, Jan. 5, 2017, pp. 91-100, vol. 141.

White, Kris M., et al., "Plitidepsin has potent preclinical efficacy against SARS-CoV-2 by targeting the host protein eEF1A", Science, Feb. 26, 2021, pp. 926-931, 371(6532).

WIPO Patent Landscape Reports Project on Ritonavir, Oct. 2011, pp. 1-105.

Ye, Gang, et al., "Structural Basis for Inhibiting Porcine Epidemic Diarrhea Virus Replication with the 3C-Like Protease Inhibitor GC376", Viruses, Feb. 21, 2020, pp. 240, 12(2).

Zaidman, et al., "An automatic pipeline for the design of irreversible derivatives identifies a potent SARS-CoV-2 Mpro Inhibitors", bioRxiv 2020.09 21.299776.

Zhai, et al., "Cyanohydrin as an Anchoring Group for Potent and Selective Inhibitors of Enterovirus 71 3C Protease", Journal of Medicinal Chemistry, 2015, pp. 9414-9420, 58(23).

Zhao, Zheng, et al., "Progress with covalent small-molecule kinase inhibitors", Drug Discovery Today, 2018, pp. 727-735, 23(3), ISSN 1359-6446.

STN Registry Database Entry for 2628280-0-8 entered STN Apr. 7, 2021.

U.S. Appl. No. 63/054,048, filed Jul. 20, 2020, Enanta Pharmaceuticals, Inc., 87 pages.

U.S. Appl. No. 63/012,039, filed Apr. 17, 2020, Pardes Biosciences, Inc.

U.S. Appl. No. 63/031,357, filed May 28, 2020, Pardes Biosciences, Inc.

U.S. Appl. No. 63/036,866, filed, Jun. 9, 2020, Pardes Biosciences, Inc.

U.S. Appl. No. 63/039,297, filed Jun. 15, 2020, Pardes Biosciences, Inc.

U.S. Appl. No. 63/067,669, filed Aug. 19, 2020, Pardes Biosciences, Inc.

U.S. Appl. No. 63/091,630, filed Oct. 14, 2020, Pardes Biosciences, Inc.

U.S. Appl. No. 63/129,018, filed Dec. 22, 2020, Pardes Biosciences, Inc.

U.S. Appl. No. 63/171,675, filed Apr. 7, 2021, Pardes Biosciences Inc.

U.S. Appl. No. 63/172,478, filed Apr. 8, 2021, Pardes Biosciences, Inc.

U.S. Appl. No. 63/173,146, filed Apr. 9, 2021, Pardes Biosciences Inc.

U.S. Appl. No. 17/384,369, filed, Jul. 23, 2021, Pardes Biosciences, Inc.

Anand, Kanchan, et al., Coronavirus Main Proteinase (3CLpro) Structure: Basis for Design of Anti-SARS Drugs, Science, Jun. 13, 2003, pp. 1763-1767, vol. 300.

Cannalire, Rolando, et al., "A Journey around the Medicinal Chemistry of Hepatitis C Virus Inhibitors Targeting NS4B: From Target to Preclinical Drug Candidates", Journal of Medicinal Chemistry, 2016, pp. 16-41, vol. 59.

Chuck, C.P., et al., "Supplementary Material: Design, synthesis and crystallographic analysis of nitrile-base broad-spectrum peptidomimetic inhibitors for coronavirus 3C-like proteases", European Journal Medicinal Chemistry, Jan. 2013, pp. 1-4, vol. 59.

Clinical Trials: "EPCI-HR: Study of Oral PF-07321332/Ritovavir Compared with Placebo in Nonhospitalized High Risk Adults With COVID-19" ClinicalTrials.gov Identifier: NCT04960202, 8 pages, First Posted: Jul. 13, 2021; Last Posted: Dec. 2, 2021.

Corman, Victor M., et al., Hosts and Sources of Endemic Human Coronaviruses, Advanced Virus Research, 2018, pp. 163-188, vol. 100.

Cvetkovic, Risto S., et al., "Lopinavir/Ritonavir: A Review of its Use in the Management of HIV Infection", Drugs, 2003, pp. 769-802, vol. 63.

(56) References Cited

OTHER PUBLICATIONS

Ghosh, Arun K., et al., "Recent Progress in the Development of HIV-1 Protease Inhibitors for the Treatment of HIV/AIDS", Journal of Medicinal Chemistry, 2016, pp. 5172-5208, vol. 59.

Halford, Dr. Bethany, Apr. 6, 2021, "This is the new oral clinical candidate", snap shot, of Twitter account Dr. Bethany Halford@beth_halford, 2 pages.

Halford, Bethany, "Pfizer unveils its oral SARS-CoV-2 inhibitor. The antiviral candidate is the first orally administered compound to enter clinical trials that targets the virus's main protease", ACS Meeting News COVID-19, Apr. 7, 2021, vol. 99, issue 13, 2 pages.

Hoffman, Robert L., et al., Discovery of Ketone-Based Covalent Inhibitors of Coronavirus 3CL Proteases for the Potential Therapeutic Treatment of COVID-19, Journal of Medicinal Chemistry, 2020, pp. 12725-12747, vol. 63(21).

McKeage, Kate, et al., "Darunavir: A Review of its Use in the Management of HIV Infection in Adults", Drugs, 2009, pp. 477-503, vol. 69.

Moon, Joseph B., et al., "Reversible Covalent Inhibition of Papain by a Peptide Nitrile. Carbon-13 NMR Evidence for a Thioimidate Ester Adduct", Journal of American Chemical Society,(1986)2002, pp. 1350-1351, vol. 108.

Owen, Dafydd, "Oral Inhibitors of the SARS-CoV-2 Main Protease for the Treatment of COVID-19", Presentation from American Chemical Society Spring Meeting, Apr. 6, 2021, 18 pages.

Pfizer Inc., Press Release, Mar. 23, 2021; "Pfizer Initiates Phase 1 Study of Novel Oral Antiviral Therapeutic Agent Against SARS-COV-2", 4 pages.

Pfizer Inc., Press Release,Sep. 1, 2021, "First Participant Dosed in Phase 2/3 Study of Oral Antiviral Candidate in Non-Hopitalized Adults with COVID-19 Who Are at Low Risk of Severe Illness", 2 pages.

Reddy, M.B., et al., "Pharmacokinetic/Pharmacodynamic Predictors of Clinical Potency for Hepatitis C Virus Nonucleoside Polymerase and Protease Inhibitors", Antimicrobial. Agents Chemotherapy, Jun. 2012, pp. 3144-3156, 56(6).

Thanigaimalai, P., et al., "Development of Potent Dipeptide-type SARS-CoV 3CL Protease Inhibitors with Novel P3 Scaffolds: Design, Synthesis, biological Evaluation, and Docking Studies", European Journal Medicinall Chemistry , 2013, pp. 372-384, vol. 68.

Wu, Fan, et al., "A new coronavirus associated with human respiratory disease in China", Nature, Mar. 2020, pp. 265-269, vol. 579.

Zhang, Linlin, et al., "Crystal Structure of SARS-CoV-2 Main Protease Provides a Basis for Design of Improved α-Ketoamide Inhibitors", Science, 2020, pp. 409-412, vol. 368.

Zhang, Linlin, et al., "α-Ketoamides as Broad-Spectrum Inhibitors of Coronavirus and Enterovirus Replication: Structure-Baed Design, Synthesis, and Activity Assessment", Journal of Medicinal Chemistry, 2020, pp. 4562-4578, vol. 63.

Zhou, Peng, et al., "A pneumonia outbreak associated with a new coronavirus of probable bat origin", Nature, Feb. 2020, pp. 270-273, vol. 579.

Russian Patent application No. 202113257, filed Aug. 6, 2021, Search Report dated Jul. 15, 2022, 2 pages.

Singapore Patent application No. 11202112508R, filed Aug. 6, 2021, Examination and Search Report, dated Jun. 28, 2022, 8 pages.

Spain application No. EA032794, filed Jan. 23, 2015, published Jul. 31, 2019, equivalent to WO2015/110826 and U.S. Appl. No. 2015/210655.

SEQUENCE LISTING

```
<160> NUMBER OF SEQ ID NOS: 2

<210> SEQ ID NO 1
<211> LENGTH: 306
<212> TYPE: PRT
<213> ORGANISM: Homo sapiens

<400> SEQUENCE: 1

Ser Gly Phe Arg Lys Met Ala Phe Pro Ser Gly Lys Val Glu Gly Cys
```

```
              1               5               10              15
            Met Val Gln Val Thr Cys Gly Thr Thr Thr Leu Asn Gly Leu Trp Leu
                           20                  25                  30

Asp Asp Val Val Tyr Cys Pro Arg His Val Ile Cys Thr Ser Glu Asp
                           35                  40                  45

Met Leu Asn Pro Asn Tyr Glu Asp Leu Leu Ile Arg Lys Ser Asn His
                50                  55                  60

Asn Phe Leu Val Gln Ala Gly Asn Val Gln Leu Arg Val Ile Gly His
            65                  70                  75                  80

Ser Met Gln Asn Cys Val Leu Lys Leu Lys Val Asp Thr Ala Asn Pro
                           85                  90                  95

Lys Thr Pro Lys Tyr Lys Phe Val Arg Ile Gln Pro Gly Gln Thr Phe
                           100                 105                 110

Ser Val Leu Ala Cys Tyr Asn Gly Ser Pro Ser Gly Val Tyr Gln Cys
                           115                 120                 125

Ala Met Arg Pro Asn Phe Thr Ile Lys Gly Ser Phe Leu Asn Gly Ser
                           130                 135                 140

Cys Gly Ser Val Gly Phe Asn Ile Asp Tyr Asp Cys Val Ser Phe Cys
            145                 150                 155                 160

Tyr Met His His Met Glu Leu Pro Thr Gly Val His Ala Gly Thr Asp
                           165                 170                 175

Leu Glu Gly Asn Phe Tyr Gly Pro Phe Val Asp Arg Gln Thr Ala Gln
                           180                 185                 190

Ala Ala Gly Thr Asp Thr Thr Ile Thr Val Asn Val Leu Ala Trp Leu
                           195                 200                 205

Tyr Ala Ala Val Ile Asn Gly Asp Arg Trp Phe Leu Asn Arg Phe Thr
                           210                 215                 220

Thr Thr Leu Asn Asp Phe Asn Leu Val Ala Met Lys Tyr Asn Tyr Glu
            225                 230                 235                 240

Pro Leu Thr Gln Asp His Val Asp Ile Leu Gly Pro Leu Ser Ala Gln
                           245                 250                 255

Thr Gly Ile Ala Val Leu Asp Met Cys Ala Ser Leu Lys Glu Leu Leu
                           260                 265                 270

Gln Asn Gly Met Asn Gly Arg Thr Ile Leu Gly Ser Ala Leu Leu Glu
                           275                 280                 285

Asp Glu Phe Thr Pro Phe Asp Val Val Arg Gln Cys Ser Gly Val Thr
                           290                 295                 300

Phe Gln
            305

<210> SEQ ID NO 2
<211> LENGTH: 306
<212> TYPE: PRT
<213> ORGANISM: Homo sapiens

<400> SEQUENCE: 2
```

```
Ser Gly Phe Arg Lys Met Ala Phe Pro Ser Gly Lys Val Glu Gly Cys
1               5                   10                  15

Met Val Gln Val Thr Cys Gly Thr Thr Thr Leu Asn Gly Leu Trp Leu
            20                  25                  30

Asp Asp Val Val Tyr Cys Pro Arg His Val Ile Cys Thr Ser Glu Asp
            35                  40                  45

Met Leu Asn Pro Asn Tyr Glu Asp Leu Leu Ile Arg Lys Ser Asn His
        50                  55                  60

Asn Phe Leu Val Gln Ala Gly Asn Val Gln Leu Arg Val Ile Gly His
65                  70                  75                  80

Ser Met Gln Asn Cys Val Leu Lys Leu Lys Val Asp Thr Ala Asn Pro
                85                  90                  95

Lys Thr Pro Lys Tyr Lys Phe Val Arg Ile Gln Pro Gly Gln Thr Phe
                100                 105                 110

Ser Val Leu Ala Cys Tyr Asn Gly Ser Pro Ser Gly Val Tyr Gln Cys
                115                 120                 125

Ala Met Arg Pro Asn Phe Thr Ile Lys Gly Ser Phe Leu Asn Gly Ser
            130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175

Leu Glu Gly Asn Phe Tyr Gly Pro Phe Val Asp Arg Gln Thr Ala Gln
                180                 185                 190

Ala Ala Gly Thr Asp Thr Thr Ile Thr Val Asn Val Leu Ala Trp Leu
            195                 200                 205

Tyr Ala Ala Val Ile Asn Gly Asp Arg Trp Phe Leu Asn Arg Phe Thr
210                 215                 220

Thr Thr Leu Asn Asp Phe Asn Leu Val Ala Met Lys Tyr Asn Tyr Glu
225                 230                 235                 240

Pro Leu Thr Gln Asp His Val Asp Ile Leu Gly Pro Leu Ser Ala Gln
            245                 250                 255

Thr Gly Ile Ala Val Leu Asp Met Cys Ala Ser Leu Lys Glu Leu Leu
            260                 265                 270

Gln Asn Gly Met Asn Gly Arg Thr Ile Leu Gly Ser Ala Leu Leu Glu
            275                 280                 285

Asp Glu Phe Thr Pro Phe Asp Val Val Arg Gln Cys Ser Gly Val Thr
            290                 295                 300

Phe Gln
305
```

NITRILE-CONTAINING ANTIVIRAL COMPOUNDS

This application is a Continuation of application Ser. No. 17/554,091, filed Dec. 17, 2021, which is a Divisional of application Ser. No. 17/395,139, filed Aug. 5, 2021 which claims the benefit of U.S. Provisional Patent Application No. 63/194,241, filed on May 28, 2021 and U.S. Provisional Patent Application No. 63/170,158, filed on Apr. 2, 2021 and U.S. Provisional Patent Application No. 63/143,435, filed on Jan. 29, 2021 and U.S. Provisional Patent Application No. 63/073,982, filed on Sep. 3, 2020 under 35 USC 119(e), the disclosures of which are hereby incorporated in their entirety.

BACKGROUND OF THE INVENTION

The invention relates to compounds and methods of inhibiting viral replication activity comprising contacting a SARS-CoV-2-related 3C-like ("3CL") proteinase with a therapeutically effective amount of a SARS-CoV-2-related 3C-like protease inhibitor. The invention also relates to methods of treating Coronavirus Disease 2019 ("COVID-19") in a patient by administering a therapeutically effective amount of a SARS-CoV-2-related 3C-like protease inhibitor to a patient in need thereof. The invention further relates to methods of treating COVID-19 in a patient, the method comprising administering a pharmaceutical composition comprising a therapeutically effective amount of the SARS-CoV-2-related 3C-like protease inhibitor to a patient in need thereof.

A worldwide outbreak of Coronavirus Disease 2019 ("COVID-19") has been associated with exposures originating in late 2019 in Wuhan, Hubei Province, China. By mid-2020 the outbreak of COVID-19 has evolved into a global pandemic with millions of people having been confirmed as infected and resulting in hundreds of thousands of deaths. The causative agent for COVID-19 has been identified as a novel coronavirus which has been named Severe Acute Respiratory Syndrome Corona Virus 2 ("SARS-CoV-2"). The genome sequence of SARS-CoV-2 has been sequenced from isolates obtained from nine patients in Wuhan, China and has been found to be of the subgenus Sarbecovirus of the genus Betacoronavirus. Lu, R. et al. The Lancet, 395, 10224, 565-574; online Jan. 29, 2020. The sequence of SARS-CoV-2 was found to have 88% homology with two bat-derived SARS-like coronaviruses, bat-SL-CoVZC45 and bat-SL-CoVZXC21, which were collected in 2018 in Zhoushan, eastern China. SARS-CoV-2 was also found to share about 79% homology with Severe Acute Respiratory Syndrome Corona Virus ("SARS-CoV"), the causative agent of the SARS outbreak in 2002-2003, and about 50% homology with Middle East Respiratory Syndrome Coronavirus ("MERS-CoV"), the causative agent of a respiratory viral outbreak originating in the Middle East in 2012. Based on a recent analysis of 103 sequenced genomes of SARS-CoV-2 it has been proposed that SARS-CoV-2 can be divided into two major types (L and S types) with the S type being ancestral and the L type having evolved from the S-type. Lu, J.; Cui, J. et al. On the origin and continuing evolution of SARS-CoV-2; National Science Review, 7(6), June 2020, 1012-1023, http://doi.org/10.1093/nsr/nwaa036. The S and L types can be clearly defined by just two tightly linked SNPs at positions 8,782 (orf1ab:T8517C, synonymous) and 28,144 (ORF8: C251T, S84L). In the 103 genomes analyzed approximately 70% were of the L-type and approximately 30% were of the S-type. It is unclear if the evolution of the L-type from the S-type occurred in humans or through a zoonotic intermediate but it appears that the L-type is more aggressive than the S-type and human interference in attempting to contain the outbreak may have shifted the relative abundance of the L and S types soon after the SARS-CoV-2 outbreak began. The discovery of the proposed S- and L-subtypes of SARS-CoV-2 raises the possibility that an individual could potentially be infected sequentially with the individual subtypes or be infected with both subtypes at the same time. In view of this evolving threat there is an acute need in the art for an effective treatment for COVID-19 and for methods of inhibiting replication of the SARS-CoV-2 coronavirus.

Recent evidence clearly shows that the newly emerged coronavirus SARS-CoV-2, the causative agent of COVID-19 (Centers for Disease Control, CDC) has acquired the ability of human-to-human transmission leading to community spread of the virus. The sequence of the SARS-CoV-2 spike protein receptor-binding domain ("RBD"), including its receptor-binding motif (RBM) that directly contacts the angiotensin-converting enzyme 2 receptor, ACE2, is similar to the RBD and RBM of SARS-CoV, strongly suggesting that SARS-CoV-2 uses ACE2 as its receptor. Wan, Y.; Shang, J.; Graham, R.; Baric, R. S.; Li, F.; Receptor recognition by the novel coronavirus from Wuhan: An analysis based on decade-long structural studies of SARS coronavirus; J. Virol. 2020; doi:10.1128/JVI.00127-20. Several critical residues in SARS-CoV-2 RBM (particularly Gln$^{493}$) provide favorable interactions with human ACE2, consistent with SARS-CoV-2's capacity for human cell infection. Several other critical residues in SARS-CoV-2's RBM (particularly Asn$^{501}$) are compatible with, but not ideal for, binding human ACE2, suggesting that SARS-CoV-2 uses ACE2 binding in some capacity for human-to-human transmission.

Coronavirus replication and transcription function is encoded by the so-called "replicase" gene (Ziebuhr, J., Snijder, E. J., and Gorbalenya, A. E.; Virus-encoded proteinases and proteolytic processing in the Nidovirales. J. Gen. Virol. 2000, 81, 853-879; and Fehr, A. R.; Perlman, S.; Coronaviruses: An Overview of Their Replication and Pathogenesis, Methods Mol. Biol. 2015; 1282: 1-23. doi: 10.1007/978-1-4939-2438-7_1), which consists of two overlapping polyproteins that are extensively processed by viral proteases. The C-proximal region is processed at eleven conserved interdomain junctions by the coronavirus main or "3C-like" protease (Ziebuhr, Snijder, Gorbalenya, 2000 and Fehr, Perlman et al., 2015). The name "3C-like" protease derives from certain similarities between the coronavirus enzyme and the well-known picornavirus 3C proteases. These include substrate preferences, use of cysteine as an active site nucleophile in catalysis, and similarities in their putative overall polypeptide folds. The SARS-CoV-2 3CL protease sequence (Accession No. YP_009725301.1) has been found to share 96.08% homology when compared with the SARS-CoV 3CL protease (Accession No. YP_009725301.1) Xu, J.; Zhao, S.; Teng, T.; Abdalla, A. E.; Zhu, W.; Xie, L.; Wang, Y.; Guo, X.; Systematic Comparison of Two Animal-to-Human Transmitted Human Coronaviruses: SARS-CoV-2 and SARS-CoV; Viruses 2020, 12, 244; doi:10.3390/v12020244. Very recently, Hilgenfeld and colleagues published a high-resolution X-ray structure of the SARS-CoV-2 coronavirus main protease (3CL) Zhang, L.; Lin, D.; Sun, X.; Rox, K.; Hilgenfeld, R.; X-ray Structure of Main Protease of the Novel Coronavirus SARS-CoV-2 Enables Design of α-Ketoamide Inhibitors; bioRxiv preprint doi: htt. The structure indicates that there are differences when comparing the 3CL proteases of SARS-CoV-2 and SARS-CoV. In the SARS-CoV but not in the SARS-CoV-2 3CL protease dimer, there is a polar interaction between the two domains III involving a 2.60-Å hydrogen bond between the side-chain hydroxyl groups of residue Thr[285] of each protomer, and supported by a hydrophobic contact between the side-chain of Ile[286] and Thr[285] Cγ2. In the SARS-CoV-2 3CL, the threonine is replaced by alanine, and the isoleucine by leucine when compared with the same residues in the SARS-CoV 3CL. The Thr285Ala replacement observed in the SARS-CoV-2 3CL protease allows the two domains III to approach each other somewhat closer (the distance between the Cα atoms of residues 285 in molecules A and B is 6.77 Å in SARS-CoV 3CL protease and 5.21 Å in SARS-CoV-2 3CL protease and the distance between the centers of mass of the two domains III shrinks from 33.4 Å to 32.1 Å). In the active site of SARS-CoV-2 3CL, Cys[145] and His [41] form a catalytic dyad, which when taken together with a with a buried water molecule that is hydrogen-bonded to His[41] can be considered to constitute a catalytic triad of the SARS-CoV-2 3CL protease. In view of the ongoing SARS-CoV-2 spread that has caused the current worldwide COVID-19 outbreak, it is desirable to have new methods of inhibiting SARS-CoV-2 viral replication and of treating COVID-19 in patients.

SUMMARY OF THE INVENTION

The present invention provides novel compounds which act in inhibiting or preventing SARS-CoV-2 viral replication and thus are useful in the treatment of COVID-19. The present invention also provides pharmaceutical compositions comprising the compounds and methods of treating COVID-19 and inhibiting SARS-CoV-2 viral replication by administering the compounds of the invention or pharmaceutical compositions comprising the compounds of the invention. It is to be understood that each of the method of treatment embodiments hereinbelow can also be formulated as corresponding use type embodiments. For example, any of the compounds, or pharmaceutically acceptable salts, or solvates or hydrates thereof, or pharmaceutically acceptable salts of the compounds, solvates or hydrates as set forth in any of embodiments E1 to E30, E45 to E46, E50, E50a, E59 to E68 and E80 to E83 can be employed for use as a medicament or alternatively for use in a method of treatment as described in any of embodiments E36 to E41, E47 to E49, E52 to E58a, E69 to E74, E77 to R79, E85 to E93 and E95 to E98.

E1 is a compound of E45 or E59, hereinbelow, of Formula I

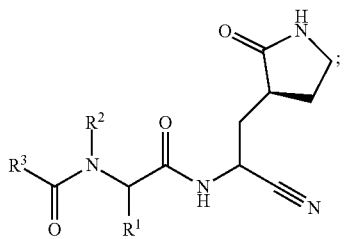

or a pharmaceutically acceptable salt thereof; wherein $R^1$ is selected from the group consisting of $C_1$-$C_6$ alkyl which is optionally substituted with a cyano or with one to five fluoro; $C_2$-$C_6$ alkynyl; and ($C_3$-$C_6$ cycloalkyl)-$C_1$-$C_3$ alkyl which is optionally substituted with one to two substituents selected from trifluoromethyl and $C_1$-$C_3$ alkyl or with one to five fluoro; $R^2$ is hydrogen or $R^2$ and $R^1$ taken together with the nitrogen and carbon atoms to which they are attached are a pyrrolidine or piperidine ring which is optionally substituted with one to four $R^{2a}$; $R^{2a}$ at each occurrence is independently selected from the group consisting of fluoro, $C_1$-$C_6$ alkyl optionally substituted with one to three fluoro and $C_1$-$C_6$ alkoxy optionally substituted with one to three fluoro; or two $R^{2a}$ groups when attached to adjacent carbons and taken together with the carbons to which they are attached are a fused $C_3$-$C_6$ cycloalkyl which is optionally substituted with one to four $R^{2b}$; or two $R^{2a}$ groups when attached to the same carbon and taken together with the carbon to which they are attached are a spiro $C_3$-$C_6$ cycloalkyl which is optionally substituted with one to four $R^{2b}$; $R^{2b}$ at each occurrence is independently selected from fluoro, $C_1$-$C_3$ alkyl optionally substituted with one to three fluoro, and $C_1$-$C_3$ alkoxy optionally substituted with one to three fluoro; $R^3$ is selected from the group consisting of $C_1$-$C_8$ alkyl, $C_1$-$C_8$ alkoxy, ($C_1$-$C_6$ alkoxy)-$C_1$-$C_6$ alkyl, $C_2$-$C_6$ alkynyl, $C_2$-$C_6$ alkynyloxy, $C_3$-$C_{12}$ cycloalkyl optionally fused with a 5- to 6-membered heteroaryl or phenyl, ($C_3$-$C_{12}$ cycloalkyl)-$C_1$-$C_6$ alkyl, $C_3$-$C_{12}$ cycloalkoxy, ($C_3$-$C_{12}$ cycloalkoxy)-$C_1$-$C_6$ alkyl, 4- to 12-membered heterocycloalkyl which is optionally fused with a 5- to 6-membered heteroaryl or phenyl and wherein said heterocycloalkyl comprises one to four heteroatoms independently selected from N, O and $S(O)_n$, (4- to 12-membered heterocycloalkyl)-$C_1$-$C_6$ alkyl wherein said heterocycloalkyl moiety comprises one to four heteroatoms independently selected from N, O and $S(O)_n$, $C_6$-$C_{10}$ aryl optionally fused with a $C_4$-$C_6$ cycloalkyl or a 4- to 7-membered heterocycloalkyl, ($C_6$-$C_{10}$ aryl)-$C_1$-$C_6$ alkyl, 5- to 10-membered heteroaryl comprising one to five heteroatoms independently selected from N, O and S, which is optionally fused with a $C_5$-$C_6$ cycloalkyl; (5- to 10-membered heteroaryl)-$C_1$-$C_6$ alkyl wherein the heteroaryl moiety comprises one to five heteroatoms independently selected from N, O and S; ($C_6$-$C_{10}$ aryl)-(5- to 10-membered heteroaryl)- wherein the heteroaryl moiety comprises one to five heteroatoms independently selected from N, O and S, (5- to 10-membered heteroaryloxy)-$C_1$-$C_6$ alkyl wherein the heteroaryl moiety comprises one to five heteroatoms independently selected from N, O and S; (5- to 6-membered heteroaryl)-(5- to 6-membered heteroaryl)- wherein each heteroaryl moiety comprises one to four heteroatoms independently selected from N, O and S; (4- to 7-membered heterocycloalkyl)-(5- to 6-membered heteroaryl)- wherein the heterocycloalkyl moiety comprises one to three heteroatoms independently selected from N, O and $S(O)_n$ and the heteroaryl moiety comprises one to four heteroatoms independently selected from N, O and S; (5- to 6-membered heteroaryl)-(4- to 7-membered heterocycloalkyl)- wherein the heterocycloalkyl moiety comprises one to three heteroatoms independently selected from N, O and $S(O)_n$ and the heteroaryl moiety comprises one to four heteroatoms independently selected from N, O and S; wherein each $R^3$ group is optionally substituted with one to five $R^4$; $R^4$ at each occurrence is independently selected from the group consisting of oxo, halo, hydroxy, cyano, phenyl, benzyl, amino, ($C_1$-$C_6$ alkyl)amino optionally substituted with one to five fluoro, di($C_1$-$C_6$ alkyl)amino optionally substituted with one to ten fluoro, $C_1$-$C_6$ alkyl optionally substituted with one to five fluoro, $C_1$-$C_6$ alkoxy optionally substituted with one to five fluoro, $C_1$-$C_3$ alkoxy-$C_1$-$C_3$ alkyl optionally substituted with one to five fluoro, $C_3$-$C_6$ cycloalkyl optionally substituted with one to three fluoro or $C_1$-$C_3$ alkyl, $C_1$-$C_6$ alkyl- C(O)NH— optionally substituted with one to five fluoro, $C_1$-$C_6$ alkyl-S(O)$_2$NH— optionally substituted with one to five fluoro, $C_1$-$C_6$ alkyl-C(O)— optionally substituted with one to five fluoro, $C_1$-$C_6$ alkyl-S(O)$_n$— optionally substituted with one to five fluoro; and n at each occurrence is independently selected from 0, 1 and 2.

E2 is the compound of any one of E1, E45 and E59 wherein $R^1$ is selected from the group consisting of $(CH_3)_2CHCH_2$—, $(CH_3)_3CCH_2$—, cyanomethyl, 2-cyanoethyl, 2,2-difluoroethyl, 2,2,2-trifluoroethyl, 3,3-difluoropropyl, 3,3,3-trifluoropropyl, 3,3,3-trifluoro-2-methylpropyl, cyclopropylmethyl, (2,2-difluorocyclopropyl)methyl, [1-(trifluoromethyl) cyclopropyl]methyl, (2-methylcyclopropyl)methyl, (3,3-difluorocyclobutyl)methyl, cyclopentylmethyl and propynyl; and $R^2$ is hydrogen; or a pharmaceutically acceptable salt thereof.

E3 is the compound of any one of E1, E45 and E59 wherein $R^2$ and $R^1$ taken together with the nitrogen and carbon atoms to which they are attached are a pyrrolidine or piperidine ring which is optionally substituted with one to four $R^{2a}$; or a pharmaceutically acceptable salt thereof.

E4 is the compound of any one of E1, E45, E59 and E3 wherein $R^{2a}$ at each occurrence is independently selected from the group consisting of fluoro, methyl, isopropyl, trifluoromethyl and tert-butoxy; or two $R^{2a}$ groups when attached to adjacent carbons and taken together with the carbons to which they are attached are a fused cyclopentane or cyclopropane which is optionally substituted with one to four $R^{2b}$; or two $R^{2a}$ groups when attached to the same carbon and taken together with the carbon to which they are attached are a spirocyclopropane ring which is optionally substituted with one to four $R^{2b}$; or a pharmaceutically acceptable salt thereof.

E5 is the compound of E1, E3, E4, E45 and E59 wherein $R^{2b}$ at each occurrence is independently selected from the group consisting of fluoro, methyl and methoxy; or a pharmaceutically acceptable salt thereof.

E6 is the compound of any one of E1, E2, E45 and E59 selected from the group consisting of formulae Ia through Ig

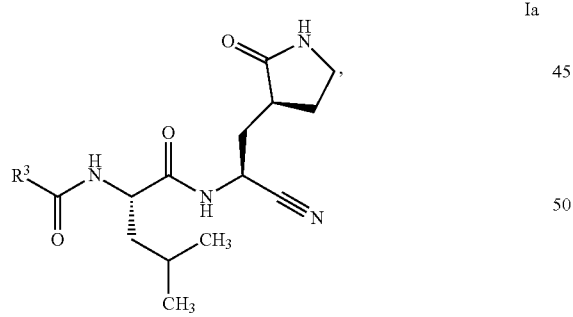

Ia

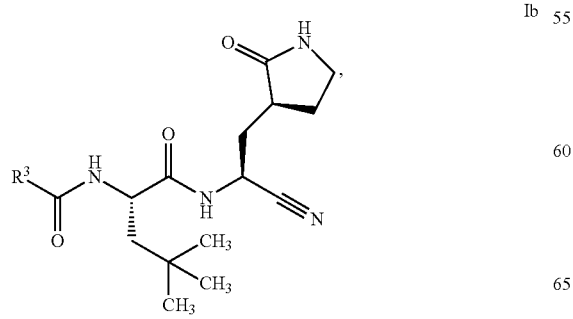

Ib

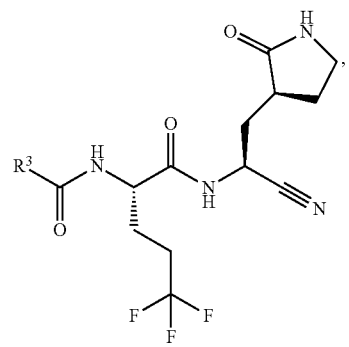

Ic

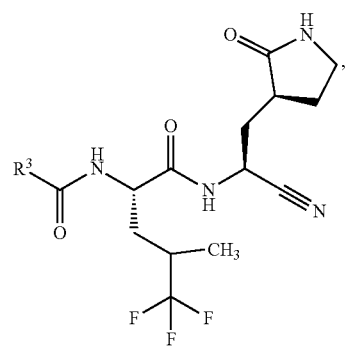

Id

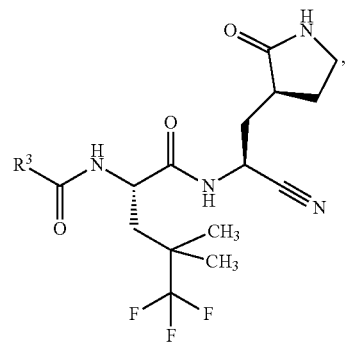

Ie

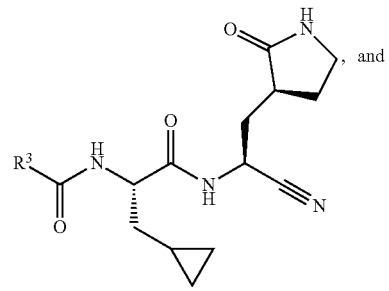

If, and

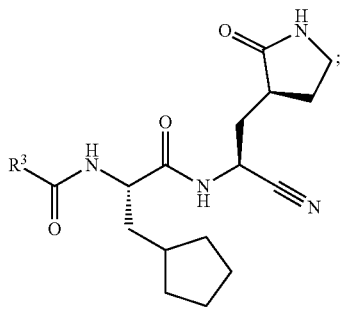
Ig
or a pharmaceutically acceptable salt thereof.
E7 is the compound of any one of E1, E3, E4, E45 and E59 selected from the group consisting of formulae Ih through Ik
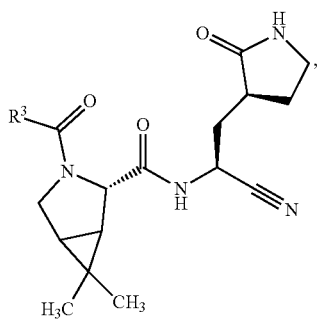
Ih
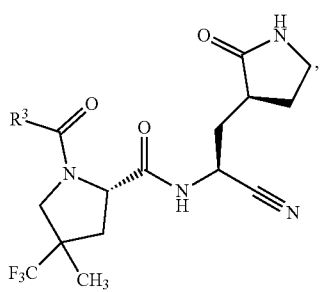
Ii
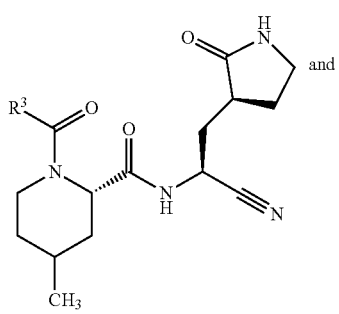
Ij
and
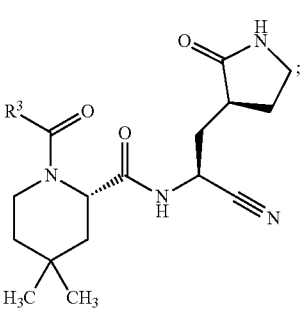
Ik
or a pharmaceutically acceptable salt thereof.
E8 is the compound of any one of E1, E3, E4, E7, E45 and E59 selected from the group consisting of
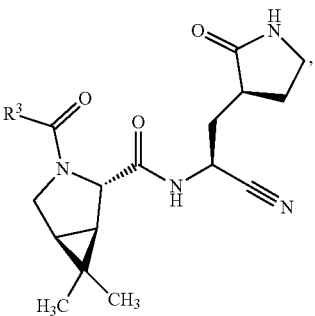
Ih-1
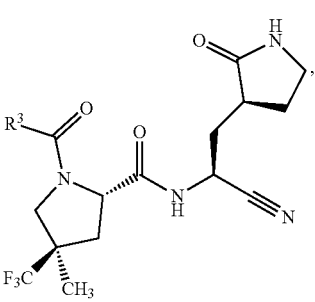
Ii-1
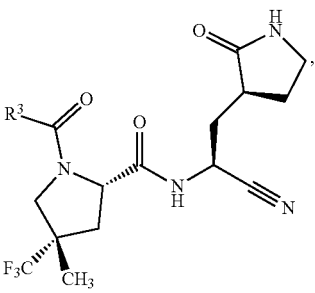
Ii-2

Ij-1
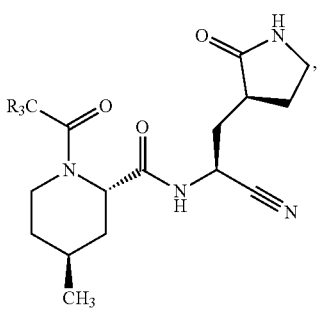

Ij-2
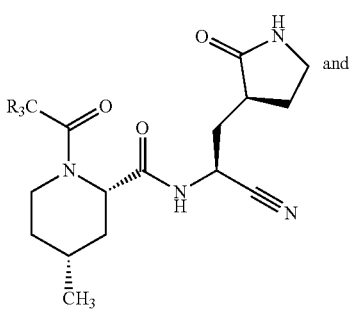
and

Ik
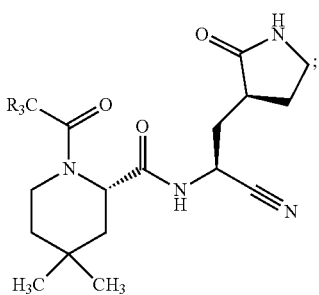

or a pharmaceutically acceptable salt thereof.

E9 is the compound of any one of E1, E3, E4, E7, E8, E45 and E59 wherein $R^3$ is selected from the group consisting of $C_1$-$C_6$ alkyl and ($C_3$-$C_6$ cycloalkyl)-$C_1$-$C_3$ alkyl; each of which is substituted with one to four $R^4$; or a pharmaceutically acceptable salt thereof.

E10 is the compound of any one of E1, E3, E4, E7 to E9, E45 and E59 wherein $R^3$ is selected from the group consisting of $(CH_3)_2CHCH(R^4)$—, $(CH_3)_3CCH(R^4)$— and (cyclohexyl)$CH(R^4)$—; or a pharmaceutically acceptable salt thereof.

E11 is the compound of any one of E1, E3, E4, E7 to E10, E45 and E59 selected from the group consisting of Ih-1a
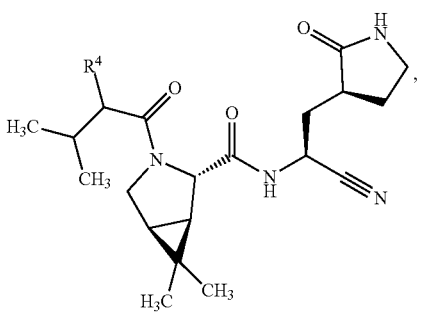

Ih-1b
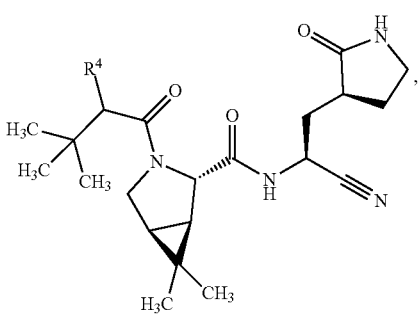

Ih-1c
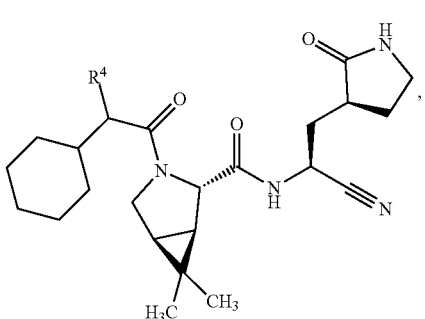

Ii-1a
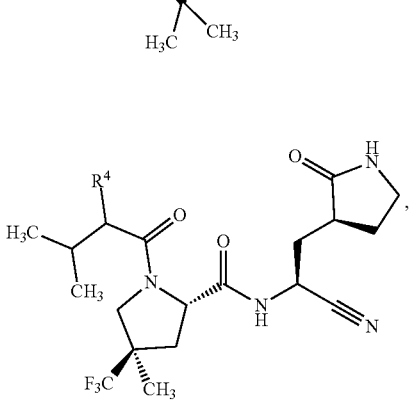

Ii-1b
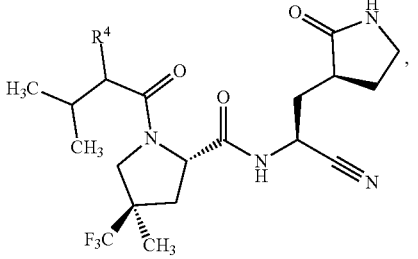

Ii-1c
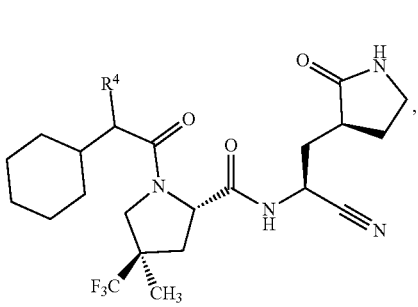

Ij-1a 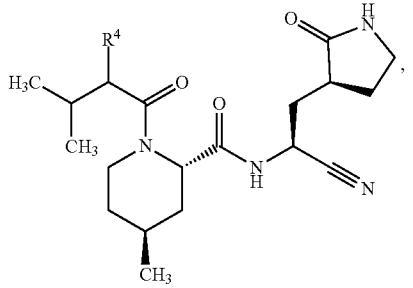,

Ij-1b 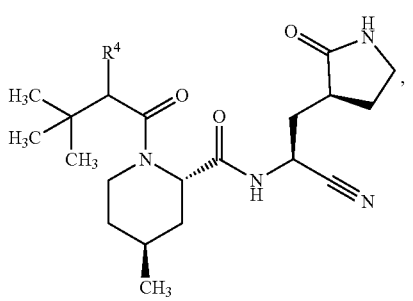,

Ij-1c 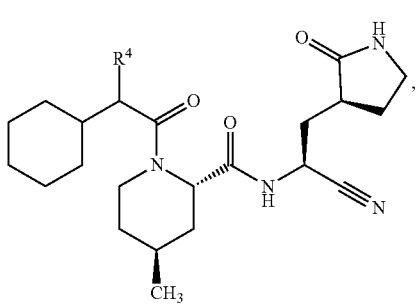,

Ik-a 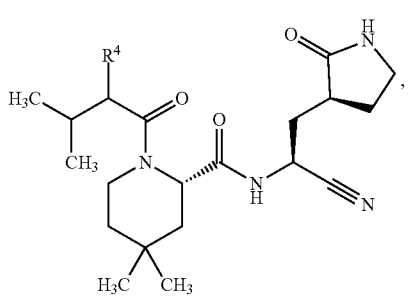,

Ik-b 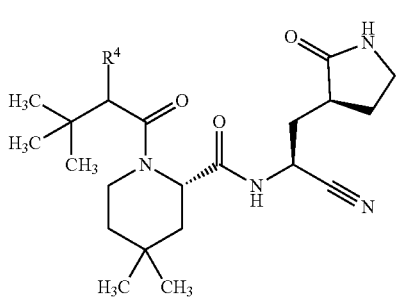 and

Ik-c 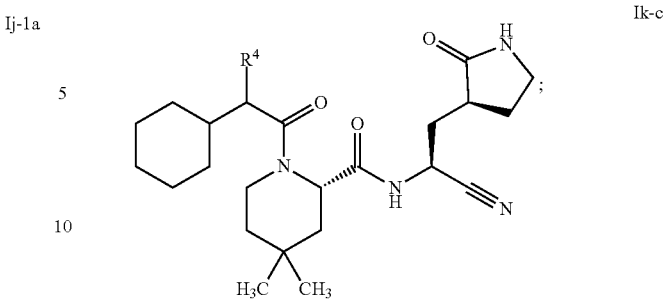;

or a pharmaceutically acceptable salt thereof.

E12 is the compound of any one of E1, E3, E4, E7 to E11, E45 and E59 wherein $R^4$ is selected from the group consisting of ($C_1$-$C_6$ alkyl)amino optionally substituted with one to five fluoro, $C_1$-$C_6$ alkyl-C(O)NH— optionally substituted with one to five fluoro, and $C_1$-$C_6$ alkyl-S(O)$_2$NH— optionally substituted with one to five fluoro; or a pharmaceutically acceptable salt thereof.

E13 is the compound of any one of E1, E3, E4, E7 to E12, E45 and E59 wherein $R^4$ is selected from the group consisting of CF$_3$C(O)NH—, CF$_3$S(O)$_2$NH—, CH$_3$C(O)NH—, CH$_3$CH$_2$C(O)NH— and CF$_3$CH$_2$NH—; or a pharmaceutically acceptable salt thereof.

E14 is the compound of any one of E1, E3, E4, E7 to E13, E45 and E59 wherein $R^4$ is CF$_3$C(O)NH— or CF$_3$S(O)$_2$NH—; or a pharmaceutically acceptable salt thereof.

E15 is the compound of any one of E1 to E8, E45 and E59 wherein $R^3$ is a 4- to 12-membered heterocycloalkyl which is optionally fused with a 5- to 6-membered heteroaryl or phenyl and wherein said heterocycloalkyl comprises one to four heteroatoms independently selected from N, O and S(O)$_n$, or is a (4- to 12-membered heterocycloalkyl)-$C_1$-$C_6$ alkyl wherein said heterocycloalkyl moiety comprises one to four heteroatoms independently selected from N, O and S(O)$_n$; each of which is optionally substituted with one to five $R^4$; or a pharmaceutically acceptable salt thereof.

E16 is the compound of any one of E1 to E8, E15, E45 and E59 wherein the 4- to 12-membered heterocycloalkyl moiety in $R^3$ is selected from the group consisting of azetidinyl, pyrrolidinyl, piperidinyl, piperazinyl, morpholinyl, oxetanyl, tetrahydrofuranyl, pyranyl, 2-oxo-1,3-oxazolidinyl, oxabicyclo[2.2.1]heptyl, 1-oxa-8-azaspiro[4.5]decyl, 1,1-dioxido-1,2-thiazolidinyl and 1,1-dioxido-1,2-thiazinanyl; each of which is optionally substituted with one to three $R^4$; or a pharmaceutically acceptable salt thereof.

E17 is the compound of any one of E1 to E8, E45 and E59 wherein $R^3$ is selected from the group consisting of phenyl, benzyl, phenethyl, a 5- to 10-membered heteroaryl comprising one to five heteroatoms independently selected from N, O and S; (5- to 10-membered heteroaryl)-$C_1$-$C_8$ alkyl wherein the heteroaryl moiety comprises one to five heteroatoms independently selected from N, O and S; and a (5- to 10-membered heteroaryloxy)-$C_1$-$C_6$ alkyl wherein the heteroaryl moiety comprises one to five heteroatoms independently selected from N, O and S; each of which is optionally substituted with one to five $R^4$; or a pharmaceutically acceptable salt thereof.

E18 is the compound of any one of E1 to E8, E17, E45 and E59 wherein the 5- to 10-membered heteroaryl moiety in $R^3$ is selected from the group consisting of imidazolyl, pyrazolyl, oxazolyl, isoxazolyl, thiazolyl, isothiazolyl, oxadiazolyl, triazolyl, pyridinyl, pyrimidinyl, pyrazinyl, pyridazinyl, indolyl, benzimidazolyl, pyridinopyrrolyl, quinolinyl, quinoxalinyl, benzotriazolyl, imidazo[1,2-a]pyridinyl, imidazo[2,1-b][1,3]thiazolyl, 4H-furo[3,2-b]pyrrolyl, 4H-thieno[3,2-b]pyrrolyl, [1,2,4]triazolo[1,5-a]pyrimidinyl, [1,2,3]triazolo[1,5-a]pyridinyl and naphthyridinyl; each of which is optionally substituted with one to four R⁴; or a pharmaceutically acceptable salt thereof.

E19 is the compound of any one of E1 to E8, E17 to E18, E45 and E59 wherein R³ is indolyl; which is optionally substituted with one to four R⁴; or a pharmaceutically acceptable salt thereof.

E20 is the compound of any one of E1 to E8, E17 to E19, E45 and E59 wherein R³ is indol-2-yl; which is optionally substituted with one to four R⁴; and R⁴ at each occurrence is independently selected from the group consisting of fluoro, chloro, bromo, hydroxy, methyl, ethyl, propyl, isopropyl, 1-methylpropyl, butyl, tert-butyl, acetyl, methoxy, ethoxy, propoxy, butoxy, trifluoromethyl, trifluoromethoxy, cyclohexyl and diethylamino; or a pharmaceutically acceptable salt thereof.

E21 is the compound of any one of E1, E2, E6, E9 to E10, E12 to E20, E45 and E59 of the formula

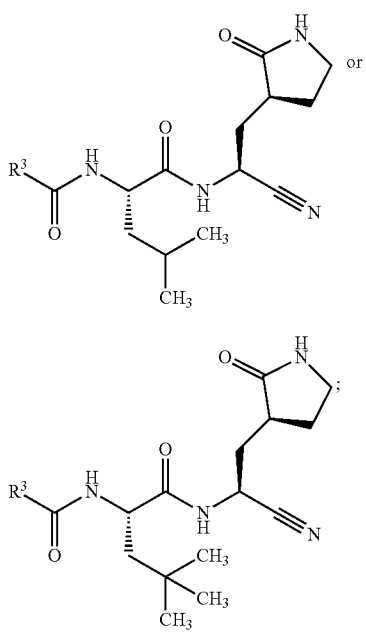

or a pharmaceutically acceptable salt thereof.

E22 is the compound of any one of E1, E2, E6, E9 to E10, E12 to E21, E45 and E59 wherein R³ is selected from the group consisting of 1H-indol-2-yl, 7-fluoro-4-methoxy-1H-indol-2yl, 4-methoxy-7-(trifluoromethyl)-1H-indol-2-yl, 4-methoxy-1H-indol-2-yl, 4-(trifluoromethoxy)-1H-indol-2-yl, 6-(trifluoromethyl)-1H-indol-2-yl, 4-methoxy-3,6,7-tris(trifluoromethyl)-1H-indol-2-yl, 3-fluoro-4-methoxy-1H-indol-2-yl and 3,5-difluoro-4-methoxy-1H-indol-2-yl; or a pharmaceutically acceptable salt thereof.

E23 is the compound of any one of E1 to E8, E21, E45 and E59 wherein R³ is $C_1$-$C_6$ alkoxy; or a pharmaceutically acceptable salt thereof.

E24 is the compound of any one of E1 to E8, E21, E23, E45 and E59 wherein R³ is selected from the group consisting of methoxy, ethoxy and prop-2-oxy; or a pharmaceutically acceptable salt thereof.

E25 is the compound of any one of E1 to E8, E21, E45 and E59 wherein R³ is selected from the group consisting of $C_3$-$C_{12}$ cycloalkyl optionally fused with a 5- to 6-membered heteroaryl or phenyl, ($C_3$-$C_{12}$ cycloalkyl)-$C_1$-$C_6$ alkyl, $C_3$-$C_{12}$ cycloalkoxy and ($C_3$-$C_{12}$ cycloalkoxy)-$C_1$-$C_6$ alkyl; each of which is optionally substituted with one to three R⁴; or a pharmaceutically acceptable salt thereof.

E26 is the compound of any one of E1 to E8, E21, E25, E45 and E59 wherein R³ is selected from the group consisting of cyclopropyl, cyclobutyl, cyclopentyl, cyclohexyl, 1-(cyclohexyloxy)ethyl, cyclohexoxymethyl, cyclopropylmethyl, cyclopropylethyl, cyclobutylmethyl, cyclobutylethyl, cyclopentylmethyl, cyclopentylethyl, cyclohexylmethyl and cyclohexylethyl; each of which is optionally substituted with one to three R⁴; or a pharmaceutically acceptable salt thereof.

E27 is the compound of any one of E1 to E8, E17, E45 and E59 wherein R³ is selected from the group consisting of phenyl, benzyl and phenethyl, each of which is optionally substituted with one to three R⁴; or a pharmaceutically acceptable salt thereof.

E28 is the compound of any one of E1 to E8, E17, E27, E45 and E59 wherein R⁴ is selected from the group consisting of fluoro, chloro, dimethylamino, trifluoromethyl, $CF_3C(O)NH$— and $CF_3S(O)_2NH$—; or a pharmaceutically acceptable salt thereof.

E29 is a compound of any one of E1, E45 and E59 selected from the group consisting of
N-{(1S)-1-cyano-2-[(3S)-2-oxopyrrolidin-3-yl]ethyl}-N²-{(2R)-2-(dimethylamino)-2-[4-(trifluoromethyl)phenyl]acetyl}-4-methyl-L-leucinamide;
N-{(1S)-1-cyano-2-[(3S)-2-oxopyrrolidin-3-yl]ethyl}-N²-{(2R)-2-(dimethylamino)-2-[3-(trifluoromethyl)phenyl]acetyl}-4-methyl-L-leucinamide;
N-[(2S)-1-({(1S)-1-cyano-2-[(3S)-2-oxopyrrolidin-3-yl]ethyl}amino)-4,4-dimethyl-1-oxopentan-2-yl]-6-(trifluoromethyl)-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-6-(trifluoromethyl)-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-4-methoxy-3,6,7-tris(trifluoromethyl)-1H-indole-2-carboxamide;
N-[(2S)-1-({(1S)-1-cyano-2-[(3S)-2-oxopyrrolidin-3-yl]ethyl}amino)-4,4-dimethyl-1-oxopentan-2-yl]-4-(trifluoromethoxy)-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-4-(trifluoromethoxy)-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-3-fluoro-4-methoxy-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-3,5-difluoro-4-methoxy-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-5,7-difluoro-4-methoxy-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-5-fluoro-4-methoxy-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-4-methoxy-3,5,7-tris(trifluoromethyl)-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-4-methoxy-3,7-bis(trifluoromethyl)-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-(trifluoromethyl)-1H-indole-2-carboxamide;
7-chloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;
N-[(2S)-1-({(1S)-1-cyano-2-[(3S)-2-oxopyrrolidin-3-yl]ethyl}amino)-4,4-dimethyl-1-oxopentan-2-yl]-4-methoxy-7-methyl-1H-indole-2-carboxamide;
6-chloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;
4-chloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;
5-chloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;
N-[(2S)-1-({(1S)-1-cyano-2-[(3S)-2-oxopyrrolidin-3-yl]ethyl}amino)-4,4-dimethyl-1-oxopentan-2-yl]-7-(trifluoromethyl)-1H-indole-2-carboxamide;
4,6-dichloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;
N-[(2S)-1-({(1S)-1-cyano-2-[(3S)-2-oxopyrrolidin-3-yl]ethyl}amino)-4,4-dimethyl-1-oxopentan-2-yl]-4-(trifluoromethyl)-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-5-(trifluoromethyl)-1H-indole-2-carboxamide;
7-chloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-4-methoxy-7-methyl-1H-indole-2-carboxamide;
6-chloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;
4-chloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;
5,7-dichloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;
5-chloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-7-(trifluoromethyl)-1H-indole-2-carboxamide;
4,6-dichloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-4-(trifluoromethyl)-1H-indole-2-carboxamide;
N-[(2S)-1-({(1S)-1-cyano-2-[(3S)-2-oxopyrrolidin-3-yl]ethyl}amino)-4,4-dimethyl-1-oxopentan-2-yl]-3-methyl-5-(trifluoromethyl)imidazo[2,1-b][1,3]thiazole-2-carboxamide;
N-{(1S)-1-cyano-2-[(3S)-2-oxopyrrolidin-3-yl]ethyl}-4-methyl-$N^2$-{[4-methyl-2-(trifluoromethyl)-1,3-thiazol-5-yl]carbonyl}-L-leucinamide;
N-{(1S)-1-cyano-2-[(3S)-2-oxopyrrolidin-3-yl]ethyl}-4-methyl-$N^2$-{[5-methyl-2-(trifluoromethyl)-1,3-thiazol-4-yl]carbonyl}-L-leucinamide;
$N^2$-[(4-bromo-1-ethyl-3-methyl-1H-pyrazol-5-yl)carbonyl]-N-{(1S)-1-cyano-2-[(3S)-2-oxopyrrolidin-3-yl]ethyl}-L-leucinamide;
$N^2$-[(4-chloro-1,3-dimethyl-1H-pyrazol-5-yl)carbonyl]-N-{(1S)-1-cyano-2-[(3S)-2-oxopyrrolidin-3-yl]ethyl}-L-leucinamide;
3-acetyl-N-[(2S)-1-({(1S)-1-cyano-2-[(3S)-2-oxopyrrolidin-3-yl]ethyl}amino)-4-methyl-1-oxopentan-2-yl]-4-methoxy-1H-indole-2-carboxamide;
N-[(2S)-1-({(1S)-1-cyano-2-[(3R)-2,5-dioxopyrrolidin-3-yl]ethyl}amino)-4-methyl-1-oxopentan-2-yl]-4-methoxy-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-4-hydroxy-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-5-hydroxy-4-methoxy-1H-indole-2-carboxamide;
N-{(1S)-1-cyano-2-[(3S)-2-oxopyrrolidin-3-yl]ethyl}-$N^2$-[(3,3-difluorocyclobutyl)acetyl]-4-methyl-L-leucinamide;
$N^2$-[(trans-4-cyanocyclohexyl)carbonyl]-N-{(1S)-1-cyano-2-[(3S)-2-oxopyrrolidin-3-yl]ethyl}-4-methyl-L-leucinamide;
$N^2$-[(trans-4-cyanocyclohexyl)carbonyl]-N-{(1R)-1-cyano-2-[(3S)-2-oxopyrrolidin-3-yl]ethyl}-4-methyl-L-leucinamide;
N-{(1S)-1-cyano-2-[(3S)-2-oxopyrrolidin-3-yl]ethyl}-$N^2$-[2-(cyclohexyloxy)propanoyl]-4-methyl-L-leucinamide;
N-{(1S)-1-cyano-2-[(3S)-2-oxopyrrolidin-3-yl]ethyl}-$N^2$-[cyclohexyl(methoxy)acetyl]-4-methyl-L-leucinamide;
N-{(1S)-1-cyano-2-[(3S)-2-oxopyrrolidin-3-yl]ethyl}-$N^2$-[cyclohexyl(methoxy)acetyl]-4-methyl-L-leucinamide;
N-{(1S)-1-cyano-2-[(3S)-2-oxopyrrolidin-3-yl]ethyl}-$N^2$-[(2S)-2-(dimethylamino)-2-phenylacetyl]-4-methyl-L-leucinamide;
N-{(1S)-1-cyano-2-[(3S)-2-oxopyrrolidin-3-yl]ethyl}-4-methyl-$N^2$-(pyrrolidin-1-ylacetyl)-L-leucinamide;
N-{(1S)-1-cyano-2-[(3S)-2-oxopyrrolidin-3-yl]ethyl}-$N^2$-[(2R)-2-(dimethylamino)-2-phenylacetyl]-4-methyl-L-leucinamide;
$N^2$-[(4-chloro-1,3-dimethyl-1H-pyrazol-5-yl)carbonyl]-N-{(1S)-1-cyano-2-[(3S)-2-oxopyrrolidin-3-yl]ethyl}-4-methyl-L-leucinamide;
N-[(2S)-1-({(1S)-1-cyano-2-[(3S)-2-oxopyrrolidin-3-yl]ethyl}amino)-4,4-dimethyl-1-oxopentan-2-yl]-4-methoxy-3-(trifluoromethyl)-1H-indole-2-carboxamide;
N-[(2S)-1-({(1S)-1-cyano-2-[(3S)-2-oxopyrrolidin-3-yl]ethyl}amino)-4,4-dimethyl-1-oxopentan-2-yl]-4-methoxy-7-(trifluoromethyl)-1H-indole-2-carboxamide;
N-[(2S)-1-({(1S)-1-cyano-2-[(3S)-2-oxopyrrolidin-3-yl]ethyl}amino)-4,4-dimethyl-1-oxopentan-2-yl]-4-methoxy-3,7-bis(trifluoromethyl)-1H-indole-2-carboxamide;
N-[(2S)-1-({(1S)-1-cyano-2-[(3S)-2-oxopyrrolidin-3-yl]ethyl}amino)-4,4-dimethyl-1-oxopentan-2-yl]-4-methoxy-3,5-bis(trifluoromethyl)-1H-indole-2-carboxamide;
N-[(2S)-1-({(1S)-1-cyano-2-[(3S)-2-oxopyrrolidin-3-yl]ethyl}amino)-4,4-dimethyl-1-oxopentan-2-yl]-4-methoxy-3,6-bis(trifluoromethyl)-1H-indole-2-carboxamide;
N-[(2S)-1-({(1S)-1-cyano-2-[(3S)-2-oxopyrrolidin-3-yl]ethyl}amino)-4-methyl-1-oxopentan-2-yl]-4-methoxy-3-(trifluoromethyl)-1H-indole-2-carboxamide;
N-{(1S)-1-cyano-2-[(3S)-2-oxopyrrolidin-3-yl]ethyl}-$N^2$-(cyclohexylcarbonyl)-4-methyl-L-leucinamide;

N-{(1S)-1-cyano-2-[(3S)-2-oxopyrrolidin-3-yl]ethyl}-N²-(cyclohexylcarbonyl)-4-methyl-L-leucinamide;

N-{(1S)-1-cyano-2-[(3S)-2-oxopyrrolidin-3-yl]ethyl}-4-methyl-N²-{[2-(trifluoromethyl)-1,3-thiazol-4-yl]carbonyl}-L-leucinamide;

N-{(1S)-1-cyano-2-[(3S)-2-oxopyrrolidin-3-yl]ethyl}-4-methyl-N²-[(propan-2-yloxy)acetyl]-L-leucinamide;

N-{(1S)-1-cyano-2-[(3S)-2-oxopyrrolidin-3-yl]ethyl}-N²-[(cyclohexyloxy)acetyl]-4-methyl-L-leucinamide;

N-{(1S)-1-cyano-2-[(3S)-2-oxopyrrolidin-3-yl]ethyl}-4-methyl-N²-(4,4,4-trifluoro-3-methylbutanoyl)-L-leucinamide;

N-[(2S)-1-({(1S)-1-cyano-2-[(3S)-2-oxopyrrolidin-3-yl]ethyl}amino)-4,4-dimethyl-1-oxopentan-2-yl]-3-methylimidazo[2,1-b][1,3]thiazole-2-carboxamide;

(1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide;

N-[(2S)-1-({(1S)-1-cyano-2-[(3S)-2-oxopyrrolidin-3-yl]ethyl}amino)-5,5,5-trifluoro-1-oxopentan-2-yl]-4-methoxy-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-7-fluoro-4-methoxy-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-4-methoxy-1H-indole-2-carboxamide;

(1R,2S,5S)—N-{(1S)-1-cyano-2-[(3S)-2-oxopyrrolidin-3-yl]ethyl}-6,6-dimethyl-3-[N-(trifluoroacetyl)-L-valyl]-3-azabicyclo[3.1.0]hexane-2-carboxamide;

N²-[(4-bromo-1-ethyl-3-methyl-1H-pyrazol-5-yl)carbonyl]-N-{(1S)-1-cyano-2-[(3S)-2-oxopyrrolidin-3-yl]ethyl}-4-methyl-L-leucinamide;

N-[(2S)-1-({(1S)-1-cyano-2-[(3S)-2-oxopyrrolidin-3-yl]ethyl}amino)-4-methyl-1-oxopentan-2-yl]-4-methoxy-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-4-methoxy-7-(trifluoromethyl)-1H-indole-2-carboxamide;

N-{(1S)-1-cyano-2-[(3S)-2-oxopyrrolidin-3-yl]ethyl}-N²-(2,6-dichlorobenzoyl)-4-methyl-L-leucinamide;

(2S)—N-{(1S)-1-cyano-2-[(3S)-2-oxopyrrolidin-3-yl]ethyl}-4,4-dimethyl-1-[3-methyl-N-(trifluoroacetyl)-L-valyl]piperidine-2-carboxamide;

3-methyl-N-(trifluoroacetyl)-L-valyl-(4R)—N-{(1S)-1-cyano-2-[(3S)-2-oxopyrrolidin-3-yl]ethyl}-4-methyl-4-(trifluoromethyl)-L-prolinamide;

(2S,4S)—N-{(1S)-1-cyano-2-[(3S)-2-oxopyrrolidin-3-yl]ethyl}-4-methyl-1-{3-methyl-N-[(trifluoromethyl)sulfonyl]-L-valyl}piperidine-2-carboxamide;

N-{(1S)-1-cyano-2-[(3S)-2-oxopyrrolidin-3-yl]ethyl}-N²-{[2-(trifluoromethyl)-1,3-thiazol-5-yl]carbonyl}-L-leucinamide;

N-{(1S)-1-cyano-2-[(3S)-2-oxopyrrolidin-3-yl]ethyl}-N²-[(2S)-2-(dimethylamino)-2-phenylacetyl]-4-methyl-L-leucinamide;

N²-[(trans-4-cyanocyclohexyl)carbonyl]-N-{(1S)-1-cyano-2-[(3S)-2-oxopyrrolidin-3-yl]ethyl}-4-methyl-L-leucinamide;

N²-[(trans-4-cyanocyclohexyl)carbonyl]-N-{(1R)-1-cyano-2-[(3S)-2-oxopyrrolidin-3-yl]ethyl}-4-methyl-L-leucinamide;

N-{(1R)-1-cyano-2-[(3S)-2-oxopyrrolidin-3-yl]ethyl}-N²-[2-(cyclohexyloxy)propanoyl]-4-methyl-L-leucinamide;

(2S,4R)—N-{(1S)-1-cyano-2-[(3S)-2-oxopyrrolidin-3-yl]ethyl}-4-methyl-1-[N-(trifluoroacetyl)-L-valyl]piperidine-2-carboxamide;

5-(butan-2-yl)-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

N-{(1S)-1-cyano-2-[(3S)-2-oxopyrrolidin-3-yl]ethyl}-N²-[(4,5-dichloro-1H-imidazol-2-yl)carbonyl]-4-methyl-L-leucinamide;

N-{(1S)-1-cyano-2-[(3S)-2-oxopyrrolidin-3-yl]ethyl}-N²-[(4,5-dichloro-1H-pyrazol-3-yl)carbonyl]-4-methyl-L-leucinamide;

N-[(2S)-1-({(1S)-1-cyano-2-[(3S)-2-oxopyrrolidin-3-yl]ethyl}amino)-4,4-dimethyl-1-oxopentan-2-yl]-2,3-dimethyl-4H-furo[3,2-b]pyrrole-5-carboxamide;

5-chloro-N-[(2S)-1-({(1S)-1-cyano-2-[(3S)-2-oxopyrrolidin-3-yl]ethyl}amino)-4,4-dimethyl-1-oxopentan-2-yl]-1H-pyrrolo[2,3-b]pyridine-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-(trifluoromethyl)-1H-benzimidazole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-methoxy-1H-pyrrolo[3,2-b]pyridine-2-carboxamide;

5-chloro-N-[(2S)-1-({(1S)-1-cyano-2-[(3S)-2-oxopyrrolidin-3-yl]ethyl}amino)-4,4-dimethyl-1-oxopentan-2-yl]-1H-pyrrolo[3,2-b]pyridine-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-4-fluoro-1H-benzimidazole-2-carboxamide;

N-{(1S)-1-cyano-2-[(3S)-2-oxopyrrolidin-3-yl]ethyl}-4-methyl-N²-{[3-(propan-2-yl)-1H-pyrazol-5-yl]carbonyl}-L-leucinamide;

N-[(2S)-1-({(1S)-1-cyano-2-[(3S)-2-oxopyrrolidin-3-yl]ethyl}amino)-4,4-dimethyl-1-oxopentan-2-yl]-5-fluoro-1H-benzimidazole-2-carboxamide;

5-chloro-N-[(2S)-1-({(1S)-1-cyano-2-[(3S)-2-oxopyrrolidin-3-yl]ethyl}amino)-4,4-dimethyl-1-oxopentan-2-yl]-1H-benzimidazole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5,6-difluoro-1H-benzimidazole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-4H-thieno[3,2-b]pyrrole-5-carboxamide;

N-{(1S)-1-cyano-2-[(3S)-2-oxopyrrolidin-3-yl]ethyl}-4-methyl-N²-{[3-(2-methylpropyl)-1H-pyrazol-5-yl]carbonyl}-L-leucinamide;

N²-{[4-(3-chlorophenyl)-1H-imidazol-2-yl]carbonyl}-N-{(1S)-1-cyano-2-[(3S)-2-oxopyrrolidin-3-yl]ethyl}-4-methyl-L-leucinamide;

N²-[(3-tert-butyl-1H-pyrazol-5-yl)carbonyl]-N-{(1S)-1-cyano-2-[(3S)-2-oxopyrrolidin-3-yl]ethyl}-4-methyl-L-leucinamide;

6-bromo-N-[(2S)-1-({(1S)-1-cyano-2-[(3S)-2-oxopyrrolidin-3-yl]ethyl}amino)-4,4-dimethyl-1-oxopentan-2-yl]-1H-benzimidazole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-methyl-1H-benzimidazole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-4,5,6,7-tetrahydro-1H-indazole-3-carboxamide;

4,6-dichloro-N-[(2S)-1-({(1S)-1-cyano-2-[(3S)-2-oxopyrrolidin-3-yl]ethyl}amino)-4,4-dimethyl-1-oxopentan-2-yl]-1H-benzimidazole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-6-(1-methylcyclopropyl)-4-(trifluoromethyl)-1H-pyrrolo[2,3-b]pyridine-2-carboxamide;

N²-{[5-(2-chlorophenyl)-4-fluoro-1H-pyrazol-3-yl]carbonyl}-N-{(1S)-1-cyano-2-[(3S)-2-oxopyrrolidin-3-yl]ethyl}-4-methyl-L-leucinamide;

N-[(2S)-1-({(1S)-1-cyano-2-[(3S)-2-oxopyrrolidin-3-yl]ethyl}amino)-4,4-dimethyl-1-oxopentan-2-yl]-2-methyl-4H-thieno[3,2-b]pyrrole-5-carboxamide;

N-{(1S)-1-cyano-2-[(3S)-2-oxopyrrolidin-3-yl]ethyl}-N²-{[3-(4-methoxyphenyl)-1H-pyrazol-5-yl]carbonyl}-4-methyl-L-leucinamide;

N-{(1S)-1-cyano-2-[(3S)-2-oxopyrrolidin-3-yl]ethyl}-N²-{[3-(2-methoxyphenyl)-1H-pyrazol-5-yl]carbonyl}-4-methyl-L-leucinamide;

N-{(1S)-1-cyano-2-[(3S)-2-oxopyrrolidin-3-yl]ethyl}-N²-{[4-(4-methoxyphenyl)-1H-imidazol-2-yl]carbonyl}-4-methyl-L-leucinamide;

N-{(1S)-1-cyano-2-[(3S)-2-oxopyrrolidin-3-yl]ethyl}-4-methyl-N²-{[3-(4-methylphenyl)-1H-pyrazol-5-yl]carbonyl}-L-leucinamide;

7-bromo-N-[(2S)-1-({(1S)-1-cyano-2-[(3S)-2-oxopyrrolidin-3-yl]ethyl}amino)-4,4-dimethyl-1-oxopentan-2-yl]-5-methyl-1H-indole-2-carboxamide;

7-bromo-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

(2S,4R)—N-{(1S)-1-cyano-2-[(3S)-2-oxopyrrolidin-3-yl]ethyl}-4-methyl-1-[3-methyl-N-(methylsulfonyl)-L-valyl]piperidine-2-carboxamide;

(2S,4S)—N-{(1S)-1-cyano-2-[(3S)-2-oxopyrrolidin-3-yl]ethyl}-4-methyl-1-[N-(trifluoroacetyl)-L-valyl]piperidine-2-carboxamide;

(2S,4S)—N-{(1S)-1-cyano-2-[(3S)-2-oxopyrrolidin-3-yl]ethyl}-4-methyl-1-[3-methyl-N-(trifluoroacetyl)-L-valyl]piperidine-2-carboxamide;

(2S,4R)—N-{(1S)-1-cyano-2-[(3S)-2-oxopyrrolidin-3-yl]ethyl}-4-methyl-1-[3-methyl-N-(trifluoroacetyl)-L-valyl]piperidine-2-carboxamide;

5-[(2S)-butan-2-yl]-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

(1R,2S,5S)—N-{(1S)-1-cyano-2-[(3S)-2-oxopyrrolidin-3-yl]ethyl}-6,6-dimethyl-3-[3',3',3'-trifluoro-N-(trifluoroacetyl)-L-isoleucyl]-3-azabicyclo[3.1.0]hexane-2-carboxamide;

(1R,2S,5S)—N-{(1S)-1-cyano-2-[(3S)-2-oxopyrrolidin-3-yl]ethyl}-3-{(2S)-2-cyclohexyl-2-[(trifluoroacetyl)amino]acetyl}-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-3-{(2S)-2-cyclopentyl-2-[(trifluoroacetyl)amino]acetyl}-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-[4-methyl-N-(trifluoroacetyl)-L-leucyl]-3-azabicyclo[3.1.0]hexane-2-carboxamide;

(1R,2S,5S)—N-{(1S)-1-cyano-2-[(3S)-2-oxopyrrolidin-3-yl]ethyl}-3-{(2S)-2-(4,4-difluorocyclohexyl)-2-[(trifluoroacetyl)amino]acetyl}-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-3-[3-cyclopentyl-N-(trifluoroacetyl)-L-alanyl]-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-3-[3-cyclohexyl-N-(trifluoroacetyl)-L-alanyl]-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-[N-(trifluoroacetyl)-L-leucyl]-3-azabicyclo[3.1.0]hexane-2-carboxamide;

(1R,2S,5S)—N-{(1S)-1-cyano-2-[(3S)-2-oxopyrrolidin-3-yl]ethyl}-3-[6,6-difluoro-N-(trifluoroacetyl)-L-norleucyl]-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-{(2S)-4,4,4-trifluoro-2-[(trifluoroacetyl)amino]butanoyl}-3-azabicyclo[3.1.0]hexane-2-carboxamide;

(1R,2S,5S)—N-{(1S)-1-cyano-2-[(3S)-2-oxopyrrolidin-3-yl]ethyl}-3-[3-fluoro-N-(trifluoroacetyl)-L-valyl]-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-3-{(2S)-2-cyclopropyl-2-[(trifluoroacetyl)amino]acetyl}-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-3-[3-(3,3-difluorocyclobutyl)-N-(trifluoroacetyl)-L-alanyl]-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-[N-(trifluoroacetyl)-O-(trifluoromethyl)-L-seryl]-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-{(2S)-2-phenyl-2-[(trifluoroacetyl)amino]acetyl}-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-[N-(trifluoroacetyl)-L-phenylalanyl]-3-azabicyclo[3.1.0]hexane-2-carboxamide;

(1R,2S,5S)—N-{(1S)-1-cyano-2-[(3S)-2-oxopyrrolidin-3-yl]ethyl}-3-[3,5-difluoro-N-(trifluoroacetyl)-L-phenylalanyl]-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-[N-(trifluoroacetyl)-3-(trifluoromethyl)-L-phenylalanyl]-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-[N-(2,2,2-trifluoroethyl)-L-valyl]-3-azabicyclo[3.1.0]hexane-2-carboxamide;

(2S,4R)—N-{(1S)-1-cyano-2-[(3S)-2-oxopyrrolidin-3-yl]ethyl}-4-methyl-1-{(2S)-3-methyl-2-[(trifluoroacetyl)amino]butyl}piperidine-2-carboxamide;

(2S,4R)—N-{(1S)-1-cyano-2-[(3S)-2-oxopyrrolidin-3-yl]ethyl}-4-methyl-1-{(2S)-3-methyl-2-[(2,2,2-trifluoroethyl)amino]butyl}piperidine-2-carboxamide;

(1R,2S,5S)—N-{(1S)-1-cyano-2-[(3S)-2-oxopyrrolidin-3-yl]ethyl}-6,6-dimethyl-3-[N-(3,3,3-trifluoropropanoyl)-L-valyl]-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-(N-propanoyl-L-valyl)-3-azabicyclo[3.1.0]hexane-2-carboxamide;

(2S,4R)—N-{(1S)-1-cyano-2-[(3S)-2-oxopyrrolidin-3-yl]ethyl}-4-methyl-1-[N-(2,2,2-trifluoroethyl)-L-valyl]piperidine-2-carboxamide;

N²-[(4-chloro-1-ethyl-3-methyl-1H-pyrazol-5-yl)carbonyl]-N-{(1S)-1-cyano-2-[(3S)-2-oxopyrrolidin-3-yl]ethyl}-L-leucinamide;

5-chloro-N-[(2S)-1-({(1S)-1-cyano-2-[(3S)-2-oxopyrrolidin-3-yl]ethyl}amino)-4-methyl-1-oxopentan-2-yl]-3-ethyl-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-5-cyclohexyl-1H-indole-2-carboxamide;

5-chloro-N-[(2S)-1-({(1S)-1-cyano-2-[(3S)-2-oxopyrrolidin-3-yl]ethyl}amino)-4-methyl-1-oxopentan-2-yl]-3-methyl-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-3,5-dimethyl-1H-indole-2-carboxamide;

5-tert-butyl-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-5-(propan-2-yl)-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-3-ethyl-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-6-ethyl-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-5-ethyl-1H-indole-2-carboxamide;

4-butoxy-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-5-(trifluoromethoxy)-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-6-(diethylamino)-1H-indole-2-carboxamide;

4-bromo-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;

5-bromo-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;

6-bromo-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-3-methyl-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-6-propoxy-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-7-fluoro-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-7-methoxy-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-6-fluoro-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-5-fluoro-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-5-methoxy-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-4,5-dimethoxy-1H-indole-2-carboxamide;

N-{(1S)-1-cyano-2-[(3S)-2-oxopyrrolidin-3-yl]ethyl}-4-methyl-$N^2$-[(4-methyl-1,3-thiazol-5-yl)carbonyl]-L-leucinamide;

N-{(1S)-1-cyano-2-[(3S)-2-oxopyrrolidin-3-yl]ethyl}-$N^2$-(ethoxycarbonyl)-L-leucinamide;

N-{(1S)-1-cyano-2-[(3S)-2-oxopyrrolidin-3-yl]ethyl}-$N^2$-(ethoxycarbonyl)-4-methyl-L-leucinamide;

N-[(2S)-1-({(1S)-1-cyano-2-[(3S)-2-oxopyrrolidin-3-yl]ethyl}amino)-5,5,5-trifluoro-1-oxopentan-2-yl]-4-methoxy-1H-indole-2-carboxamide;

N-{(1S)-1-cyano-2-[(3S)-2-oxopyrrolidin-3-yl]ethyl}-4-methyl-$N^2$-{[2-(trifluoromethyl)-1,3-oxazol-4-yl]carbonyl}-L-leucinamide;

N-{(1S)-1-cyano-2-[(3S)-2-oxopyrrolidin-3-yl]ethyl}-4-methyl-$N^2$-{[3-(trifluoromethyl)-1,2-thiazol-4-yl]carbonyl}-L-leucinamide;

N-{(1S)-1-cyano-2-[(3S)-2-oxopyrrolidin-3-yl]ethyl}-4-methyl-$N^2$-{[3-(trifluoromethyl)-1,2-oxazol-4-yl]carbonyl}-L-leucinamide;

N-{(1S)-1-cyano-2-[(3S)-2-oxopyrrolidin-3-yl]ethyl}-$N^2$-{[2-(trifluoromethyl)-1,3-thiazol-4-yl]carbonyl}-L-leucinamide;

N-{(1S)-1-cyano-2-[(3S)-2-oxopyrrolidin-3-yl]ethyl}-5,5,5-trifluoro-$N^2$-{[2-(trifluoromethyl)-1,3-thiazol-4-yl]carbonyl}-L-norvalinamide;

(4S)—N-{(1S)-1-cyano-2-[(3S)-2-oxopyrrolidin-3-yl]ethyl}-5,5,5-trifluoro-$N^2$-{[2-(trifluoromethyl)-1,3-thiazol-4-yl]carbonyl}-L-leucinamide;

(4R)—N-{(1S)-1-cyano-2-[(3S)-2-oxopyrrolidin-3-yl]ethyl}-5,5,5-trifluoro-$N^2$-{[2-(trifluoromethyl)-1,3-thiazol-4-yl]carbonyl}-L-leucinamide;

N-[(2S)-1-({(1S)-1-cyano-2-[(3S)-2-oxopyrrolidin-3-yl]ethyl}amino)-3-cyclopentyl-1-oxopropan-2-yl]-2-(trifluoromethyl)-1,3-thiazole-4-carboxamide;

N-{(1S)-1-cyano-2-[(3S)-2-oxopyrrolidin-3-yl]ethyl}-4-methyl-$N^2$-{[5-(trifluoromethyl)-1,2-thiazol-4-yl]carbonyl}-L-leucinamide;

N-{(1S)-1-cyano-2-[(3S)-2-oxopyrrolidin-3-yl]ethyl}-4-methyl-$N^2$-{[5-(trifluoromethyl)-1,2-oxazol-4-yl]carbonyl}-L-leucinamide;

N-{(1S)-1-cyano-2-[(3S)-2-oxopyrrolidin-3-yl]ethyl}-4-methyl-$N^2$-{[2-(trifluoromethyl)-1,3-oxazol-5-yl]carbonyl}-L-leucinamide;

N-{(1S)-1-cyano-2-[(3S)-2-oxopyrrolidin-3-yl]ethyl}-4-methyl-$N^2$-{[2-(trifluoromethyl)-1,3-thiazol-5-yl]carbonyl}-L-leucinamide;

N-{(1S)-1-cyano-2-[(3S)-2-oxopyrrolidin-3-yl]ethyl}-5,5,5-trifluoro-4-methyl-$N^2$-{[2-(trifluoromethyl)-1,3-thiazol-4-yl]carbonyl}-L-leucinamide;

N-{(1S)-1-cyano-2-[(3S)-2-oxopyrrolidin-3-yl]ethyl}-4-methyl-$N^2$-{[(2S)-2-methyltetrahydrofuran-2-yl]carbonyl}-L-leucinamide;

N-[(2S,4R)-1-({(1S)-1-cyano-2-[(3S)-2-oxopyrrolidin-3-yl]ethyl}amino)-5,5,5-trifluoro-4-methyl-1-oxopentan-2-yl]-4-methoxy-1H-indole-2-carboxamide;

N-[(2S,4S)-1-({(1S)-1-cyano-2-[(3S)-2-oxopyrrolidin-3-yl]ethyl}amino)-5,5,5-trifluoro-4-methyl-1-oxopentan-2-yl]-4-methoxy-1H-indole-2-carboxamide;

N-[(2S)-1-({(1S)-1-cyano-2-[(3S)-2-oxopyrrolidin-3-yl]ethyl}amino)-5,5,5-trifluoro-4,4-dimethyl-1-oxopentan-2-yl]-4-methoxy-1H-indole-2-carboxamide;

N-[(2S)-1-({(1S)-1-cyano-2-[(3S)-2-oxopyrrolidin-3-yl]ethyl}amino)-3-cyclopentyl-1-oxopropan-2-yl]-4-methoxy-1H-indole-2-carboxamide;

5,7-dichloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

5-chloro-N-[(2S)-1-({(1S)-1-cyano-2-[(3S)-2-oxopyrrolidin-3-yl]ethyl}amino)-4,4-dimethyl-1-oxopentan-2-yl]-3-ethyl-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-cyclohexyl-1H-indole-2-carboxamide;

5-chloro-N-[(2S)-1-({(1S)-1-cyano-2-[(3S)-2-oxopyrrolidin-3-yl]ethyl}amino)-4,4-dimethyl-1-oxopentan-2-yl]-3-methyl-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-3,5-dimethyl-1H-indole-2-carboxamide;

5-tert-butyl-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-(propan-2-yl)-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-7-(propan-2-yl)-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-3-ethyl-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-6-ethyl-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-ethyl-1H-indole-2-carboxamide;

4-butoxy-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-(trifluoromethoxy)-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-6-(diethylamino)-1H-indole-2-carboxamide;

4-bromo-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

5-bromo-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

6-bromo-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-3-methyl-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-6-propoxy-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-4-methyl-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-methyl-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-6-methyl-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-7-fluoro-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-7-methoxy-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-6-fluoro-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-fluoro-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-6-methoxy-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-5-methoxy-1H-indole-2-carboxamide;

N-[(2S)-1-({(1S)-1-cyano-2-[(3S)-2-oxopyrrolidin-3-yl]ethyl}amino)-4,4-dimethyl-1-oxopentan-2-yl]-4,5-dimethoxy-1H-indole-2-carboxamide;

5-(butan-2-yl)-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-7-(propan-2-yl)-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-4-methyl-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-5-methyl-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-6-methyl-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-6-methoxy-1H-indole-2-carboxamide;

5-(butan-2-yl)-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide;

N-{(1S)-1-cyano-2-[(3S)-2-oxopyrrolidin-3-yl]ethyl}-$N^2$-[(2R)-2-cyclohexyl-2-methoxyacetyl]-L-leucinamide;

N-{(1S)-1-cyano-2-[(3S)-2-oxopyrrolidin-3-yl]ethyl}-$N^2$-[(2R)-2-(cyclohexyloxy)propanoyl]-L-leucinamide;

N-{(1S)-1-cyano-2-[(3S)-2-oxopyrrolidin-3-yl]ethyl}-4-methyl-$N^2$-(4,4,4-trifluoro-3-methylbutanoyl)-L-leucinamide;

$N^2$-[(trans-4-cyanocyclohexyl)carbonyl]-N-{(1S)-1-cyano-2-[(3S)-2-oxopyrrolidin-3-yl]ethyl}-L-leucinamide;

N-{(1S)-1-cyano-2-[(3S)-2-oxopyrrolidin-3-yl]ethyl}-$N^2$-[(1-ethyl-4-methyl-1H-pyrazol-5-yl)carbonyl]-L-leucinamide;

N-{(1S)-1-cyano-2-[(3S)-2-oxopyrrolidin-3-yl]ethyl}-$N^2$-(cyclohexylcarbonyl)-L-leucinamide;

N-{(1S)-1-cyano-2-[(3S)-2-oxopyrrolidin-3-yl]ethyl}-$N^2$-[(cyclohexyloxy)acetyl]-L-leucinamide;

N-{(1S)-1-cyano-2-[(3S)-2-oxopyrrolidin-3-yl]ethyl}-$N^2$-[(3,3-difluorocyclobutyl)acetyl]-L-leucinamide;

N-{(1S)-1-cyano-2-[(3S)-2-oxopyrrolidin-3-yl]ethyl}-$N^2$-[(propan-2-yloxy)acetyl]-L-leucinamide;

N-[(2S)-1-({(1S)-1-cyano-2-[(3S)-2-oxopyrrolidin-3-yl]ethyl}amino)-4-methyl-1-oxopentan-2-yl]-3-methylimidazo[2,1-b][1,3]thiazole-2-carboxamide;

N-{(1S)-1-cyano-2-[(3S)-2-oxopyrrolidin-3-yl]ethyl}-N²-[(2R)-2-cyclohexyl-2-methoxyacetyl]-4-methyl-L-leucinamide;

N-{(1S)-1-cyano-2-[(3S)-2-oxopyrrolidin-3-yl]ethyl}-N²-[(1-ethyl-4-methyl-1H-pyrazol-5-yl)carbonyl]-4-methyl-L-leucinamide;

N²-[2-chloro-4-(methylsulfonyl)benzoyl]-N-{(1S)-1-cyano-2-[(3S)-2-oxopyrrolidin-3-yl]ethyl}-L-leucinamide;

N-{(1S)-1-cyano-2-[(3S)-2-oxopyrrolidin-3-yl]ethyl}-N²-(2,6-dichlorobenzoyl)-L-leucinamide;

(1R,2S,5S)-3-[N-(tert-butylsulfonyl)-3-methyl-L-valyl]-N-{(1S)-1-cyano-2-[(3S)-2-oxopyrrolidin-3-yl]ethyl}-6,6-dimethyl-3-azabicyclo[3.1.0]hexane-2-carboxamide;

(1R,2S,5S)-3-{[(3R)-1-benzyl-5-oxopyrrolidin-3-yl]carbonyl}-N-{(1S)-1-cyano-2-[(3S)-2-oxopyrrolidin-3-yl]ethyl}-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-{[(3R)-5-oxo-1-phenylpyrrolidin-3-yl]carbonyl}-3-azabicyclo[3.1.0]hexane-2-carboxamide;

(1R,2S,5S)-3-{[(3R)-1-tert-butyl-5-oxopyrrolidin-3-yl]carbonyl}-N-{(1S)-1-cyano-2-[(3S)-2-oxopyrrolidin-3-yl]ethyl}-6,6-dimethyl-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-[(3-methylimidazo[2,1-b][1,3]thiazol-2-yl)carbonyl]-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-{[2-(trifluoromethyl)-1,3-thiazol-4-yl]carbonyl}-3-azabicyclo[3.1.0]hexane-2-carboxamide;

N-[(2S)-1-({(1S)-1-cyano-2-[(3S)-2-oxopyrrolidin-3-yl]ethyl}amino)-3-cyclopropyl-1-oxopropan-2-yl]-4-methoxy-1H-indole-2-carboxamide; and N-[(2S)-1-({(1S)-1-cyano-2-[(3S)-2-oxopyrrolidin-3-yl]ethyl}amino)-3-cyclopropyl-1-oxopropan-2-yl]-1H-indole-2-carboxamide;

or a pharmaceutically acceptable salt thereof.

E30 is a compound of any one of E1, E45 and E59 selected from the group consisting of N-[(2S)-1-({(1S)-1-cyano-2-[(3S)-2-oxopyrrolidin-3-yl]ethyl}amino)-4,4-dimethyl-1-oxopentan-2-yl]-7-fluoro-4-methoxy-1H-indole-2-carboxamide;

N-[(2S)-1-({(1S)-1-cyano-2-[(3S)-2-oxopyrrolidin-3-yl]ethyl}amino)-4-methyl-1-oxopentan-2-yl]-4-methoxy-7-(trifluoromethyl)-1H-indole-2-carboxamide;

(1R,2S,5S)—N-{(1S)-1-cyano-2-[(3S)-2-oxopyrrolidin-3-yl]ethyl}-6,6-dimethyl-3-[N-(trifluoroacetyl)-L-valyl]-3-azabicyclo[3.1.0]hexane-2-carboxamide;

(1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide;

N-[(2S)-1-({(1S)-1-cyano-2-[(3S)-2-oxopyrrolidin-3-yl]ethyl}amino)-4-methyl-1-oxopentan-2-yl]-7-fluoro-4-methoxy-1H-indole-2-carboxamide;

(2S,4S)—N-{(1S)-1-cyano-2-[(3S)-2-oxopyrrolidin-3-yl]ethyl}-4-methyl-1-[N-(trifluoroacetyl)-L-valyl]piperidine-2-carboxamide;

(2S,4S)—N-{(1S)-1-cyano-2-[(3S)-2-oxopyrrolidin-3-yl]ethyl}-4-methyl-1-[3-methyl-N-(trifluoroacetyl)-L-valyl]piperidine-2-carboxamide;

(1R,2S,5S)—N-{(1S)-1-cyano-2-[(3S)-2-oxopyrrolidin-3-yl]ethyl}-3-{(2S)-2-cyclohexyl-2-[(trifluoroacetyl)amino]acetyl}-6,6-dimethyl-3-azabicyclo[3.1.0]hexane-2-carboxamide;

(2S,4S)—N-{(1S)-1-cyano-2-[(3S)-2-oxopyrrolidin-3-yl]ethyl}-4-methyl-1-{3-methyl-N-[(trifluoromethyl)sulfonyl]-L-valyl}piperidine-2-carboxamide;

3-methyl-N-(trifluoroacetyl)-L-valyl-(4R)—N-{(1S)-1-cyano-2-[(3S)-2-oxopyrrolidin-3-yl]ethyl}-4-methyl-4-(trifluoromethyl)-L-prolinamide; and (2S)—N-{(1S)-1-cyano-2-[(3S)-2-oxopyrrolidin-3-yl]ethyl}-4,4-dimethyl-1-[3-methyl-N-(trifluoroacetyl)-L-valyl]piperidine-2-carboxamide;

or a pharmaceutically acceptable salt thereof.

E31 is a pharmaceutical composition comprising a therapeutically effective amount of a compound of any one of E1 to E30 or a pharmaceutically acceptable salt thereof, together with a pharmaceutically acceptable carrier.

E32 is the pharmaceutical composition of E31 wherein the composition is in the form of an intravenous, subcutaneous, inhaled or oral dosage form.

E33 is the pharmaceutical composition of E31 or E32 wherein the composition is in an oral dosage form.

E34 is the pharmaceutical composition of any one of E31 to E33 further comprising an additional therapeutic agent.

E35 is the pharmaceutical composition of any one of E31 to E34 wherein the pharmaceutical composition further comprises one or more of dexamethasone, azithromycin, and remdesivir.

E36 is a method of treating a coronavirus infection in a patient, the method comprising administering a therapeutically effective amount of a compound of any one of E1 to E30 or a pharmaceutically acceptable salt thereof to a patient in need thereof.

E37 is the method of E36 wherein the coronavirus infection is COVID-19.

E38 is a method of treating a coronavirus infection in a patient, the method comprising administering a pharmaceutical composition of any one of E31 to E35 to a patient in need thereof.

E39 is the method of E38 wherein the coronavirus infection is COVID-19.

E40 is a method of inhibiting or preventing SARS-CoV-2 viral replication comprising contacting the SARS-CoV-2 coronavirus 3CL protease with a therapeutically effective amount of a compound or a pharmaceutically acceptable salt thereof of any one of E1 to E30.

E41 is a method of inhibiting or preventing SARS-CoV-2 viral replication in a patient comprising administering to the patient in need of inhibition of or prevention of SARS-CoV-2 viral replication a therapeutically effective amount of a compound or a pharmaceutically acceptable salt thereof of any one of E1 to E30.

E42 is the use of a compound or a pharmaceutically acceptable salt thereof of any one of E1 to E30 for the treatment of a coronavirus infection.

E43 is the use of E42 wherein the coronavirus infection is COVID-19.

E44 is the use of a compound or a pharmaceutically acceptable salt thereof of any one of E1 to E30 for the preparation of a medicament that is useful for the treatment of a coronavirus infection.

E44a is the use of E44 wherein the coronavirus infection is COVID-19.

E45 is a compound of Formula I'

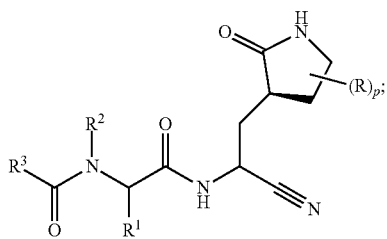

or a pharmaceutically acceptable salt thereof; wherein R at each occurrence is independently hydroxy or oxo; p is 0, 1 or 2; $R^1$ is selected from the group consisting of $C_1$-$C_6$ alkyl which is optionally substituted with a cyano or with one to five fluoro; $C_2$-$C_6$ alkynyl; and ($C_3$-$C_6$ cycloalkyl)-$C_1$-$C_3$ alkyl which is optionally substituted with one to two substituents selected from trifluoromethyl and $C_1$-$C_3$ alkyl or with one to five fluoro; $R^2$ is hydrogen or $R^2$ and $R^1$ taken together with the nitrogen and carbon atoms to which they are attached are a pyrrolidine or piperidine ring which is optionally substituted with one to four $R^{2a}$; $R^{2a}$ at each occurrence is independently selected from the group consisting of fluoro, hydroxy, $C_1$-$C_6$ alkyl optionally substituted with one to three fluoro and $C_1$-$C_6$ alkoxy optionally substituted with one to three fluoro; or two $R^{2a}$ groups when attached to adjacent carbons and taken together with the carbons to which they are attached are a fused $C_3$-$C_6$ cycloalkyl which is optionally substituted with one to four $R^{2b}$; or two $R^{2a}$ groups when attached to the same carbon and taken together with the carbon to which they are attached are a spiro $C_3$-$C_6$ cycloalkyl which is optionally substituted with one to four $R^{2b}$; $R^{2b}$ at each occurrence is independently selected from fluoro, hydroxy, $C_1$-$C_3$ alkyl optionally independently substituted with one to three fluoro or hydroxy and $C_1$-$C_3$ alkoxy optionally independently substituted with one to three fluoro or hydroxy; $R^3$ is selected from the group consisting of $C_1$-$C_8$ alkyl, $C_1$-$C_8$ alkoxy, ($C_1$-$C_6$ alkoxy)-$C_1$-$C_6$ alkyl, $C_2$-$C_6$ alkynyl, $C_2$-$C_6$ alkynyloxy, $C_3$-$C_{12}$ cycloalkyl optionally fused with a 5- to 6-membered heteroaryl or phenyl, ($C_3$-$C_{12}$ cycloalkyl)-$C_1$-$C_6$ alkyl, $C_3$-$C_{12}$ cycloalkoxy, ($C_3$-$C_{12}$ cycloalkoxy)-$C_1$-$C_6$ alkyl, 4- to 12-membered heterocycloalkyl which is optionally fused with a 5- to 6-membered heteroaryl or phenyl and wherein said heterocycloalkyl comprises one to four heteroatoms independently selected from N, O and S(O)$_n$, (4- to 12-membered heterocycloalkyl)-$C_1$-$C_6$ alkyl wherein said heterocycloalkyl moiety comprises one to four heteroatoms independently selected from N, O and S(O)$_n$, $C_6$-$C_{10}$ aryl optionally fused with a $C_4$-$C_6$ cycloalkyl or a 4- to 7-membered heterocycloalkyl, ($C_6$-$C_{10}$ aryl)-$C_1$-$C_6$ alkyl, 5- to 10-membered heteroaryl comprising one to five heteroatoms independently selected from N, O and S, which is optionally fused with a $C_5$-$C_6$ cycloalkyl; (5- to 10-membered heteroaryl)-$C_1$-$C_6$ alkyl wherein the heteroaryl moiety comprises one to five heteroatoms independently selected from N, O and S; ($C_6$-$C_{10}$ aryl)-(5- to 10-membered heteroaryl)- wherein the heteroaryl moiety comprises one to five heteroatoms independently selected from N, O and S, (5- to 10-membered heteroaryloxy)-$C_1$-$C_6$ alkyl wherein the heteroaryl moiety comprises one to five heteroatoms independently selected from N, O and S; (5- to 6-membered heteroaryl)-(5- to 6-membered heteroaryl)- wherein each heteroaryl moiety comprises one to four heteroatoms independently selected from N, O and S; (4- to 7-membered heterocycloalkyl)-(5- to 6-membered heteroaryl)- wherein the heterocycloalkyl moiety comprises one to three heteroatoms independently selected from N, O and S(O)$_n$ and the heteroaryl moiety comprises one to four heteroatoms independently selected from N, O and S; (5- to 6-membered heteroaryl)-(4- to 7-membered heterocycloalkyl)- wherein the heterocycloalkyl moiety comprises one to three heteroatoms independently selected from N, O and S(O)$_n$ and the heteroaryl moiety comprises one to four heteroatoms independently selected from N, O and S; wherein each $R^3$ group is optionally substituted with one to five $R^4$; $R^4$ at each occurrence is independently selected from the group consisting of oxo, halo, hydroxy, cyano, phenyl, benzyl, amino, ($C_1$-$C_6$ alkyl)amino optionally substituted with one to five fluoro, di($C_1$-$C_6$ alkyl)amino optionally substituted with one to ten fluoro, $C_1$-$C_6$ alkyl optionally substituted with one to five fluoro, $C_1$-$C_6$ alkoxy optionally substituted with one to five fluoro, $C_1$-$C_3$ alkoxy-$C_1$-$C_3$ alkyl optionally substituted with one to five fluoro, $C_3$-$C_6$ cycloalkyl optionally substituted with one to three fluoro or $C_1$-$C_3$ alkyl, $C_1$-$C_6$ alkyl-C(O)NH— optionally substituted with one to five fluoro, $C_1$-$C_6$ alkyl-OC(O)NH— optionally substituted with one to five fluoro or with one $R^5$, $C_1$-$C_6$ alkyl-NHC(O)NH— optionally substituted with one to five fluoro or with one $R^5$, $C_1$-$C_6$ alkyl-S(O)$_2$NH— optionally substituted with one to five fluoro or with one $R^5$, $C_1$-$C_6$ alkyl-C(O)— optionally substituted with one to five fluoro or with one $R^5$, $C_1$-$C_6$ alkyl-S(O)$_n$— optionally substituted with one to five fluoro or with one $R^5$; $R^5$ is selected from phenyl, phenoxy, $C_3$-$C_6$ cycloalkyl, $C_3$-$C_6$ cycloalkoxy, 4- to 7-membered heterocycloalkyl- wherein the heterocycloalkyl moiety comprises one to three heteroatoms independently selected from N, O and S(O)$_n$ and 5- to 6-membered heteroaryl- wherein the heteroaryl moiety comprises one to four heteroatoms independently selected from N, O and S; wherein each $R^5$ is optionally independently substituted with one to three halo, $C_1$-$C_3$ alkyl and $C_1$-$C_3$ alkoxy; and n at each occurrence is independently selected from 0, 1 and 2.

E46 is a compound of selected from the group consisting of (2S,4R)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide; (2R,4S)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide; 3-methyl-N-(trifluoroacetyl)-L-valyl-(4R)—N-{(1S)-1-cyano-2-[(3S)-2-oxopyrrolidin-3-yl]ethyl}-4-(trifluoromethyl)-L-prolinamide; (1R,2S,5S)—N-{(1S)-1-cyano-2-[(3S)-2-oxopyrrolidin-3-yl]ethyl}-6,6-dimethyl-3-[3-methyl-N-(methylcarbamoyl)-L-valyl]-3-azabicyclo[3.1.0]hexane-2-carboxamide; methyl {(2S)-1-[(1R,2S,5S)-2-({(1S)-1-cyano-2-[(3S)-2-oxopyrrolidin-3-yl]ethyl}carbamoyl)-6,6-dimethyl-3-azabicyclo[3.1.0]hexan-3-yl]-3,3-dimethyl-1-oxobutan-2-yl}carbamate; and N-(trifluoroacetyl)-L-valyl-(4R)—N-{(1S)-1-cyano-2-[(3S)-2-oxopyrrolidin-3-yl]ethyl}-4-(trifluoromethyl)-L-prolinamide; or a pharmaceutically acceptable salt thereof.

E47 is a method of treating a coronavirus infection in a patient, the method comprising administering a therapeutically effective amount of a compound of any one of E45 and E46 or a pharmaceutically acceptable salt thereof to a patient in need thereof.

E48 is the method of E47 wherein the coronavirus infection is COVID-19.

E49 is a method of treating a coronavirus infection in a patient, the method comprising administering a therapeutically effective amount of a compound of any one of E1 to E30 and E45 to E46 or a pharmaceutically acceptable salt thereof wherein an additional therapeutic agent is administered and the additional therapeutic agent is selected from the group consisting of remdesivir, galidesivir, favilavir/avifavir, molnupiravir, AT-527, AT-301, BLD-2660, favipiravir, camostat, SLV213, emtrictabine/tenofivir, clevudine, dalcetrapib, boceprevir, ABX464, dexamethasone, hydrocortisone, convalescent plasma, gelsolin (Rhu-p65N), regdanvimab (Regkirova), ravulizumab (Ultomiris), VIR-7831/VIR-7832, BRII-196/BRII-198, COVI-AMG/COVI DROPS (STI-2020), bamlanivimab (LY-CoV555), mavrilimab, leronlimab (PRO140), AZD7442, lenzilumab, infliximab, adalimumab, JS 016, STI-1499 (COVIGUARD), lanadelumab (Takhzyro), canakinumab (Ilaris), gimsilumab, otilimab, casirivimab/imdevimab (REGN-Cov2), MK-7110 (CD24Fc/SACCOVID), heparin, apixaban, tocilizumab (Actemra), sarilumab (Kevzara), apilimod dimesylate, DNL758, DC402234, PB1046, dapaglifozin, abivertinib, ATR-002, bemcentinib, acalabrutinib, baricitinib, tofacitinib, losmapimod, famotidine, ritonavir, niclosamide and diminazene.

E50 is the compound (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a pharmaceutically acceptable salt thereof.

E50a is the compound (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide.

E51 is a pharmaceutical composition comprising a therapeutically effective amount of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a pharmaceutically acceptable salt thereof together with a pharmaceutically acceptable carrier.

E51a is a pharmaceutical composition comprising a therapeutically effective amount of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide together with a pharmaceutically acceptable carrier.

E52 is a method of treating a coronavirus infection in a patient, the method comprising administering a therapeutically effective amount of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a pharmaceutically acceptable salt thereof to a patient in need of treatment thereof.

E52a is a method of treating a coronavirus infection in a patient, the method comprising administering a therapeutically effective amount of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide to a patient in need of treatment thereof.

E53 is the method of E52 wherein the coronavirus infection is COVID-19.

E53a is the method of E52a wherein the coronavirus infection is COVID-19.

E54 is the method of E52 or E53 wherein (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a pharmaceutically acceptable salt thereof is administered orally.

E54a is the method of E52a or E53a wherein (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide is administered orally.

E55 is the method of E54 wherein 50 mg to 1500 mg of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a pharmaceutically acceptable salt thereof is administered each day.

E55a is the method of E54a wherein 50 mg to 1500 mg of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide is administered each day.

E56 is the method of E55 wherein 380 mg of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a pharmaceutically acceptable salt thereof is administered three times a day.

E56a is the method of E55a wherein 380 mg of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a pharmaceutically acceptable salt thereof is administered three times a day.

E57 is the method of E55 wherein 50 mg to 1500 mg of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a pharmaceutically acceptable salt thereof is administered each day as an oral suspension, capsule or tablet.

E57a is the method of E55a wherein 50 mg to 1500 mg of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a pharmaceutically acceptable salt thereof is administered each day as an oral suspension, capsule or tablet.

E58 is the method of E57 wherein a tablet is administered.

E58a is the method of E57a wherein a tablet is administered.

E59 is a compound of Formula I″

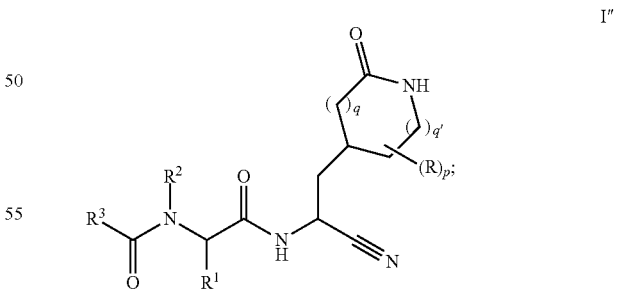

I″ or a solvate or hydrate thereof, or a pharmaceutically acceptable salt of said compound, solvate or hydrate thereof; wherein R at each occurrence is independently hydroxy or oxo;
q and q' are each independently selected from 0, 1 and 2;
p is 0, 1 or 2;
$R^1$ is selected from the group consisting of $C_1$-$C_6$ alkyl which is optionally substituted with a cyano or with one to five fluoro; $C_2$-$C_6$ alkynyl; and ($C_3$-$C_6$ cycloalkyl)-$C_1$-$C_3$ alkyl which is optionally substituted with one to two substituents selected from trifluoromethyl and $C_1$-$C_3$ alkyl or with one to five fluoro;

$R^2$ is hydrogen or $R^2$ and $R^1$ taken together with the nitrogen and carbon atoms to which they are attached are a pyrrolidine or piperidine ring which is optionally substituted with one to four $R^{2a}$;

$R^{2a}$ at each occurrence is independently selected from the group consisting of fluoro, hydroxy, $C_1$-$C_6$ alkyl optionally substituted with one to three fluoro and $C_1$-$C_6$ alkoxy optionally substituted with one to three fluoro; or two $R^{2a}$ groups when attached to adjacent carbons and taken together with the carbons to which they are attached are a fused $C_3$-$C_6$ cycloalkyl which is optionally substituted with one to four $R^{2b}$; or two $R^{2a}$ groups when attached to the same carbon and taken together with the carbon to which they are attached are a spiro $C_3$-$C_6$ cycloalkyl which is optionally substituted with one to four $R^{2b}$;

$R^{2b}$ at each occurrence is independently selected from fluoro, hydroxy, $C_1$-$C_3$ alkyl optionally independently substituted with one to three fluoro or hydroxy and $C_1$-$C_3$ alkoxy optionally independently substituted with one to three fluoro or hydroxy;

$R^3$ is selected from the group consisting of $C_1$-$C_8$ alkyl, $C_1$-$C_8$ alkoxy, ($C_1$-$C_6$ alkoxy)-$C_1$-$C_6$ alkyl, $C_2$-$C_6$ alkynyl, $C_2$-$C_6$ alkynyloxy, $C_3$-$C_{12}$ cycloalkyl optionally fused with a 5- to 6-membered heteroaryl or phenyl, ($C_3$-$C_{12}$ cycloalkyl)-$C_1$-$C_6$ alkyl, $C_3$-$C_{12}$ cycloalkoxy, ($C_3$-$C_{12}$ cycloalkoxy)-$C_1$-$C_6$ alkyl, 4- to 12-membered heterocycloalkyl which is optionally fused with a 5- to 6-membered heteroaryl or phenyl and wherein said heterocycloalkyl comprises one to four heteroatoms independently selected from N, O and S(O)$_n$, (4- to 12-membered heterocycloalkyl)-$C_1$-$C_6$ alkyl wherein said heterocycloalkyl moiety comprises one to four heteroatoms independently selected from N, O and S(O)$_n$, $C_6$-$C_{10}$ aryl optionally fused with a $C_4$-$C_6$ cycloalkyl or a 4- to 7-membered heterocycloalkyl, ($C_6$-$C_{10}$ aryl)-$C_1$-$C_6$ alkyl, 5- to 10-membered heteroaryl comprising one to five heteroatoms independently selected from N, O and S, which is optionally fused with a $C_5$-$C_6$ cycloalkyl; (5- to 10-membered heteroaryl)-$C_1$-$C_6$ alkyl wherein the heteroaryl moiety comprises one to five heteroatoms independently selected from N, O and S; ($C_6$-$C_{10}$ aryl)-(5- to 10-membered heteroaryl)- wherein the heteroaryl moiety comprises one to five heteroatoms independently selected from N, O and S, (5- to 10-membered heteroaryloxy)-$C_1$-$C_6$ alkyl wherein the heteroaryl moiety comprises one to five heteroatoms independently selected from N, O and S; (5- to 6-membered heteroaryl)-(5- to 6-membered heteroaryl)- wherein each heteroaryl moiety comprises one to four heteroatoms independently selected from N, O and S; (4- to 7-membered heterocycloalkyl)-(5- to 6-membered heteroaryl)- wherein the heterocycloalkyl moiety comprises one to three heteroatoms independently selected from N, O and S(O)$_n$ and the heteroaryl moiety comprises one to four heteroatoms independently selected from N, O and S; (5- to 6-membered heteroaryl)-(4- to 7-membered heterocycloalkyl)- wherein the heterocycloalkyl moiety comprises one to three heteroatoms independently selected from N, O and S(O)$_n$ and the heteroaryl moiety comprises one to four heteroatoms independently selected from N, O and S; wherein each $R^3$ group is optionally substituted with one to five $R^4$;

$R^4$ at each occurrence is independently selected from the group consisting of oxo, halo, hydroxy, cyano, phenyl, benzyl, amino, ($C_1$-$C_6$ alkyl)amino optionally substituted with one to five fluoro, di($C_1$-$C_6$ alkyl)amino optionally substituted with one to ten fluoro, $C_1$-$C_6$ alkyl optionally substituted with one to five fluoro, (5- to 6-membered heteroaryl)amino- wherein the heteroaryl moiety comprises one to four heteroatoms independently selected from N, O and S; (4- to 7-membered heterocycloalkyl)amino- wherein the heterocycloalkyl moiety comprises one to three heteroatoms independently selected from N, O and S(O)$_n$, $C_1$-$C_6$ alkoxy optionally substituted with one to five fluoro, $C_1$-$C_3$ alkoxy-$C_1$-$C_3$ alkyl optionally substituted with one to five fluoro, $C_3$-$C_6$ cycloalkyl optionally substituted with one to three fluoro or $C_1$-$C_3$ alkyl, $C_1$-$C_6$ alkyl-C(O)NH-optionally substituted with one to five fluoro, $C_1$-$C_6$ alkyl-OC(O)NH— optionally substituted with one to five fluoro or with one $R^5$, $C_1$-$C_6$ alkyl-NHC(O)NH— optionally substituted with one to five fluoro or with one $R^5$, $C_1$-$C_6$ alkyl-S(O)$_2$NH— optionally substituted with one to five fluoro or with one $R^5$, $C_1$-$C_6$ alkyl-C(O)— optionally substituted with one to five fluoro or with one $R^5$, $C_1$-$C_6$ alkyl-S(O)$_n$— optionally substituted with one to five fluoro or with one $R^5$;

$R^5$ is selected from phenyl, phenoxy, $C_3$-$C_6$ cycloalkyl, $C_3$-$C_6$ cycloalkoxy, 4- to 7-membered heterocycloalkyl- wherein the heterocycloalkyl moiety comprises one to three heteroatoms independently selected from N, O and S(O)$_n$ and 5- to 6-membered heteroaryl- wherein the heteroaryl moiety comprises one to four heteroatoms independently selected from N, O and S; wherein each $R^5$ is optionally independently substituted with one to three halo, $C_1$-$C_3$ alkyl and $C_1$-$C_3$ alkoxy; and n at each occurrence is independently selected from 0, 1 and 2.

E60 is the compound of E59 which is (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a solvate or hydrate thereof, or a pharmaceutically acceptable salt of said compound, solvate or hydrate.

E61 is the compound (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide having the structure

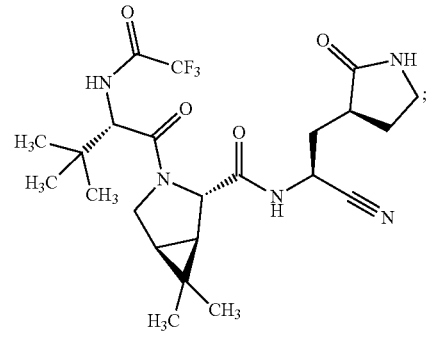 [SMILES: CC(C)(C)[C@H](NC(=O)C(F)(F)F)C(=O)N1C[C@H]2[C@@H]([C@H]1C(=O)N[C@H](C#N)C[C@@H]1CCNC1=O)C2(C)C]

or a solvate or hydrate thereof.

E62 is the compound of E61 which is crystalline (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide.

E63 is the compound of E62 which is crystalline (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, Solid Form 1.

E64 is the compound of E62 which is crystalline (1R,2S,5S)—N-{(1S)-1-Cyano-2-[(3S)-2-oxopyrrolidin-3-yl]

ethyl}-6,6-dimethyl-3-[3-methyl-N-(trifluoroacetyl)-L-valyl]-3-azabicyclo[3.1.0]hexane-2-carboxamide, Solid Form 4.

E65 is the compound of E61 which is amorphous (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide.

E66 is the compound of E61 which is (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl solvate.

E67 is the compound of E66 which is crystalline (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl solvate.

E68 is the compound of E67 which is crystalline (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl solvate, Solid Form 2.

E69 is a method of treating a coronavirus infection in a patient, the method comprising administering a therapeutically effective amount of a compound according to any one of E61 to E68 to a patient in need of treatment thereof.

E70 is the method of E69 wherein the coronavirus infection is COVID-19.

E71 is the method of E70 wherein ritonavir is also administered to the patient.

E72 is the method of E71 wherein the compound of any one of E61 to E68 and ritonavir are administered to the patient orally.

E73 is the method of E72 wherein about 10 mg to about 1500 mg per day of the compound of any one of E61 to E68 and about 10 mg to about 1000 mg per day of ritonavir are administered.

E74 is the method of E73 wherein about 50 mg of the compound of any one of E61 to E68 and about 100 mg of ritonavir are each administered to the patient twice a day.

E75 is a pharmaceutical composition comprising a therapeutically effective amount of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a solvate or hydrate thereof, or a pharmaceutically acceptable salt of said compound, solvate or hydrate together with a pharmaceutically acceptable carrier.

E75a is a pharmaceutical composition comprising a therapeutically effective amount of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide; or a solvate or hydrate thereof together with a pharmaceutically acceptable carrier.

E76 is the pharmaceutical composition of E75a comprising the compound according to any one of E62 to E68.

E77 is the method of E69 or E70 wherein about 100 mg, 150 mg, 200 mg, 250 mg, 300 mg, 350 mg, 400 mg, 450 mg, 500 mg, 550 mg, 600 mg, 650 mg, 700 mg or 750 mg of the compound according to any one of E61 to E68 is administered orally to the patient twice a day.

E78 is the method of E77 wherein ritonavir is co-administered orally to the patient twice a day.

E79 is the method of E78 wherein about 300 mg of the compound according to any one of E61 to E68 and about 100 mg of ritonavir are co-administered to the patient twice a day.

E80 is the compound of E63 which is characterized by a $^{19}$F peak with a chemical shift at −73.3±0.1 ppm and $^{13}$C peaks with chemical shifts at 31.0±0.1 ppm, 27.9±0.1 ppm and 178.9±0.2 ppm.

E81 is the compound of E64 which is characterized by one or more peaks selected from the group consisting of a $^{19}$F peak with chemical shift at −73.6±0.1 ppm and $^{13}$C peaks at 26.9±0.1 ppm, 21.6±0.1 ppm and 41.5±0.1 ppm.

E82 is the compound N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide having the structure

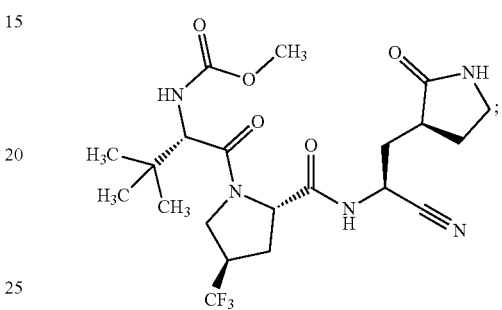

or a solvate or hydrate thereof.

E83 is the compound of E82 which is N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide.

E84 is a pharmaceutical comprising a therapeutically effective amount of N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide; or a solvate or hydrate thereof together with a pharmaceutically acceptable carrier.

E85 is a method of treating a coronavirus infection in a patient, the method comprising administering a therapeutically effective amount of a compound of E82 or E83 to a patient in need of treatment thereof.

E86 is the method of E85 wherein the coronavirus infection is COVID-19.

E87 is the method of E85 or E86 wherein 10 mg to 1500 mg per day of the compound of E82 or E83 is administered.

E88 is the method of any one of E85 to E87 wherein the compound is administered orally.

E89 is the method of E88 wherein 200 mg of the compound is administered twice a day.

E90 is a method of targeting SARS-CoV-2 inhibition a compound of any one of E1 to E30, E45 to E46, E50, E50a, E59 to E68 and E80 to E83 as a means of treating indications caused by SARS-CoV-2-related viral infections.

E91 is a method of identifying cellular or viral pathways interfering with the functioning of the members of which could be used for treating indications caused by SARS-CoV-2 infections by administering a SARS-CoV-2 protease inhibitor compound of any one of E1 to E30, E45 to E46, E50, E50a, E59 to E68 and E80 to E83.

E92 is a method of using a SARS-CoV-2 protease inhibitor compound of any one of E1 to E30, E45 to E46, E50, E50a, E59 to E68 and E80 to E83 as tools for understanding mechanism of action of other SARS-CoV-2 inhibitors.

E93 is a method of using a SARS-CoV-2 3C-like protease inhibitor compound of any one of E1 to E30, E45 to E46, E50, E50a, E59 to E68 and E80 to E83 for carrying out gene-profiling experiments for monitoring the up- or down-regulation of genes for the purpose of identifying inhibitors for treating indications caused by SARS-CoV-2 infections such as COVID-19.

E94 is a pharmaceutical composition for the treatment of COVID-19 in a mammal containing an amount of a SARS-CoV-2 3C-like protease inhibitor compound of any one of E1 to E30, E45 to E46, E50, E50a, E59 to E68 and E80 to E83 that is effective in treating COVID-19 together with a pharmaceutically acceptable carrier.

E95 is a method of treating MERS in a patient, the method comprising administering a therapeutically effective amount of a compound of any one of E1 to E30, E45 to E46, E50, E50a, E59 to E68 and E80 to E83 to a patient in need thereof.

E96 is a method of treating MERS in a patient, the method comprising administering a pharmaceutical composition of any one of E31 to E35, E51, E51a, E75, E75a, E84 and E94 to a patient in need thereof.

E97 is a method of inhibiting or preventing MERS viral replication comprising contacting the SARS-CoV-2 coronavirus 3CL protease with a therapeutically effective amount of a compound of any one of E1 to E30, 45-46, 50, 50a, 59-68 and 80-83.

E98 is a method of inhibiting or preventing MERS viral replication in a patient comprising administering to the patient in need of inhibition of or prevention of MERS viral replication a therapeutically effective amount of a compound of any one of E1 to E30, 45-46, 50, 50a, 59-68 and 80-83.

E99 Use of a compound of any one of E1 to E30, 45-46, 50, 50a, 59-68 and 80-83 for the treatment of a coronavirus infection.

E100 The use of E99 wherein the coronavirus infection is COVID-19.

E101 Use of a compound of any one of E1 to E30, 45-46, 50, 50a, 59-68 and 80-83 in the preparation of a medicament.

E102 is a compound of any one of embodiments E1 to E30, or a pharmaceutically acceptable salt thereof, for use as a medicament.

E103 is a compound of any one of embodiments E1 to E30, or a pharmaceutically acceptable salt thereof, for use in a method of treatment, wherein the method is as described in any one of embodiments E36 to E41.

DETAILED DESCRIPTION OF THE INVENTION

Figure 1:
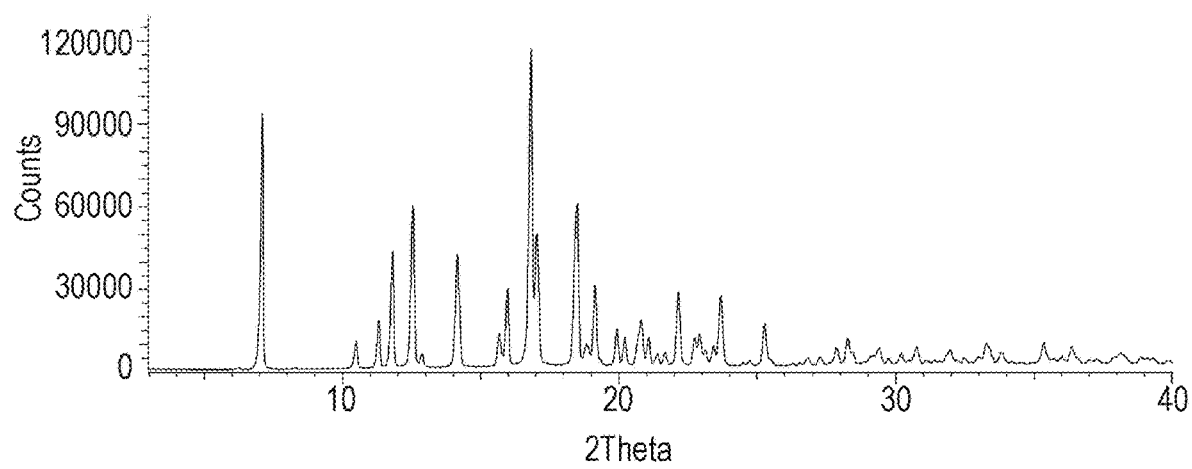
FIG. 1: Powder X-ray Diffraction Pattern of 13, methyl tert-butyl ether solvate, Solid Form 2, from Alternate Synthesis of Example 13, methyl tert-butyl ether solvate; Generation of Solid Form 2

For the purposes of the present invention, as described and claimed herein, the following terms are defined as follows:

As used herein, the terms "comprising" and "including" are used in their open, non-limiting sense. The term "treating", as used herein, unless otherwise indicated, means reversing, alleviating, inhibiting the progress of, or preventing the disorder or condition to which such term applies, or one or more symptoms of such disorder or condition. In the methods of treating COVID-19 it is to be understood that COVID-19 is the disease caused in patients by infection with the SARS-CoV-2 virus. The SARS-CoV-2 virus is to be understood to encompass the initially discovered strain of the virus as well as mutant strains which emerge, such as but not limited to, strains such as B.1.1.7 (UK variant), B.1.351 (South African variant), P.1 (Brazilian variant) and B.1.427/B.1.429 (Califonia variants). The term "treatment", as used herein, unless otherwise indicated, refers to the act of treating as "treating" is defined immediately above.

The term "patient" refers to warm-blooded animals such as, for example, guinea pigs, mice, rats, gerbils, cats, rabbits, dogs, cattle, goats, sheep, horses, monkeys, chimpanzees, and humans. With respect to the treatment of COVID-19 the methods of the invention are particularly useful for the treatment of a human patient.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "alkyl" as used herein refers to a linear or branched-chain saturated hydrocarbyl substituent (i.e., a substituent obtained from a hydrocarbon by removal of a hydrogen); in one embodiment containing from one to eight carbon atoms, in another one to six carbon atoms and in yet another one to three carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl, heptyl, octyl and the like. In another embodiment containing one to three carbons and consisting of methyl, ethyl, n-propyl and isopropyl.

The term "alkynyl" as used herein refers to a linear or branched-chain saturated hydrocarbyl substituent that contains a carbon-carbon triple bond (i.e., a substituent obtained from a triple bond-containing hydrocarbon by removal of a hydrogen); in one embodiment containing from two to six carbon atoms. Non-limiting examples of such substituents include prop-2-yn-1-yl, but-3-yn-1-yl, pent-4-yn-1-yl and hex-5-yn-1-yl.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like. In another embodiment having one to three carbons and consisting of methoxy, ethoxy, n-propoxy and isopropoxy. An alkoxy group which is attached to an alkyl group is referred to as an alkoxyalkyl. An example of an alkoxyalkyl group is methoxymethyl.

The term "alkynyloxy" refers to a linear or branched-chain saturated hydrocarbyl substituent containing a carbon-carbon triple bond attached to an oxygen radical (i.e., a substituent obtained from a triple bond-containing hydrocarbon alcohol by removal of the hydrogen from the OH); in one embodiment containing from three to six carbon atoms. Non-limiting examples of such substituents include propynyloxy, butynyloxy and pentynyloxy and the like.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_8$ alkyl" or "$C_{1-8}$ alkyl" refers to an alkyl substituent containing from 1 to 8 carbon atoms, "$C_1$-$C_6$ alkyl" or "$C_{1-6}$ alkyl" refers to an alkyl substituent containing from 1 to 6 carbon atoms, "$C_1$-$C_3$ alkyl" or "$C_{1-3}$ alkyl" refers to an alkyl substituent containing from 1 to 3 carbon atoms. Illustrating further, $C_3$-$C_6$ cycloalkyl or $C_{3-6}$-cycloalkyl refers to a saturated cycloalkyl group containing from 3 to 6 carbon ring atoms.

The term "cycloalkyl" refers to a carbocyclic substituent obtained by removing a hydrogen from a saturated carbocyclic molecule, for example one having three to seven carbon atoms. The term "cycloalkyl" includes monocyclic saturated carbocycles. The term "$C_3$-$C_7$ cycloalkyl" means a radical of a three- to seven-membered ring system which includes the groups cyclopropyl, cyclobutyl, cyclopentyl, cyclohexyl, and cycloheptyl. The term "$C_3$-$C_6$ cycloalkyl" means a radical of a three- to six-membered ring system which includes the groups cyclopropyl, cyclobutyl, cyclopentyl and cyclohexyl. The cycloalkyl groups can also be bicyclic or spirocyclic carbocycles. For example, the term "$C_3$-$C_{12}$ cycloalkyl" includes monocyclic carbocycles and bicyclic and spirocyclic cycloalkyl moieties such as bicyclopentyl, bicyclohexyl, bicycloheptyl, bicyclooctyl, bicyclononyl, spiropentyl, spirohexyl, spiroheptyl, spirooctyl and spirononyl.

The term "$C_3$-$C_6$ cycloalkoxy" refers to a three- to six-membered cycloalkyl group attached to an oxygen radical. Examples include cyclopropoxy, cyclobutoxy, cyclopentoxy and cyclohexoxy.

The term "aryl" refers to a carbocyclic aromatic system. The term "$C_6$-$C_{10}$ aryl" refers to carbocyclic aromatic systems with 3 to 10 atoms and includes phenyl and naphthyl.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 6-membered heterocycloalkyl" refers to a heterocycloalkyl containing from 4 to 6 atoms, including one to three heteroatoms, in the cyclic moiety of the heterocycloalkyl. Likewise, the phrase "5- to 6-membered heteroaryl" refers to a heteroaryl containing 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore, the phrases "5-membered heteroaryl" and "6-membered heteroaryl" refer to a five-membered heteroaromatic ring system and a six-membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol. The terms cyano and nitrile refer to a —CN group. The term "oxo" means an oxygen which is attached to a carbon by a double bond (i.e., when $R^4$ is oxo then $R^4$ together with the carbon to which it is attached are a C═O moiety).

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms or 4 to 12 atoms, wherein at least one of the ring atoms is a heteroatom (i.e., oxygen, nitrogen, or sulfur), with the remaining ring atoms being independently selected from the group consisting of carbon, oxygen, nitrogen, and sulfur. The sulfur may be oxidized [i.e., S(O) or S(O)$_2$] or not. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom. It is to be understood that a heterocyclic group may be monocyclic, bicyclic, polycyclic or spirocyclic.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring. In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2 (1H)-onyl, pyridazin-2(1H)-onyl, pyrimidin-2(1H)-onyl, pyrazin-2(1H)-onyl, imidazo[1,2-a]pyridinyl, and pyrazolo [1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), and morpholinyl.

The term "heteroaryl" can also include, when specified as such, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo [1,5-a]pyridinyl, 4,5,6,7-tetrahydro-1H-indazolyl and 4,5,6, 7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I", "Formula I'" or "Formula I''" may be hereinafter referred to as a "compound (s) of the invention," "the present invention," and "compound(s) of Formula I, I' or I''. Such terms are also defined to include all forms of the compound of Formula I, I' and I'' including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes.

Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (—), a solid wedge ( ), or a dotted wedge ( ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I, I' and I'' may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I, I' and I'' can exist as enantiomers and diastereomers or as racemates and mixtures thereof. The use of a solid line to depict bonds to one or more asymmetric carbon atoms in a compound of Formula I, I' and I'' and the use of a solid or dotted wedge to depict bonds to other asymmetric carbon atoms in the same compound is meant to indicate that a mixture of diastereomers is present.

Stereoisomers of Formula I, I' and I" include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention such as those of Formula I, I' and I" may exhibit the phenomenon of tautomerism; such tautomers are also regarded as compounds of the invention. All such tautomeric forms, and mixtures thereof, are included within the scope of compounds of Formula I, I' and I". Tautomers exist as mixtures of a tautomeric set in solution. In solid form, usually one tautomer predominates. Even though one tautomer may be described, the present invention includes all tautomers of the compounds of Formula I, I' and I" and salts thereof.

The phrase "pharmaceutically acceptable salts(s)", as used herein, unless otherwise indicated, includes salts of acidic or basic groups which may be present in the compounds described herein. The compounds used in the methods of the invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, hexylresorcinate, hydrabamine, hydrobromide, hydrochloride, iodide, isethionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts.

With respect to the compounds of the invention used in the methods of the invention, if the compounds also exist as tautomeric forms then this invention relates to those tautomers and the use of all such tautomers and mixtures thereof.

The subject invention also includes compounds and methods of treatment of coronavirus infections such as COVID-19 and methods of inhibiting SARS-CoV-2 with isotopically labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Compounds of the present invention, prodrugs thereof, and pharmaceutically acceptable salts of said compounds or of said prodrugs which contain the aforementioned isotopes and/or isotopes of other atoms are with the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds used in the methods of this invention and prodrugs thereof can generally be prepared by carrying out the procedures for preparing the compounds disclosed in the art by substituting a readily available isotopically labelled reagent for a non-isotopically labelled reagent.

This invention also encompasses methods using pharmaceutical compositions and methods of treating coronavirus infections such as COVID-19 infections through administering prodrugs of compounds of the invention. Compounds having free amino, amido or hydroxy groups can be converted into prodrugs. Prodrugs include compounds wherein an amino acid residue, or a polypeptide chain of two or more (e.g., two, three or four) amino acid residues is covalently joined through an ester bond to a hydroxy of compounds used in the methods of this invention. The amino acid residues include but are not limited to the 20 naturally occurring amino acids commonly designated by three letter symbols and also include 4-hydroxyproline, hydroxylysine, desmosine, isodesmosine, 3-methylhistidine, norvalin, beta-alanine, gamma-aminobutyric acid, citrulline, homocysteine, homoserine, ornithine and methionine sulfone. Additional types of prodrugs are also encompassed. For instance, free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem., 1996, 29, 10. Free amines can also be derivatized as amides, sulfonamides or phosphonamides. All of these prodrug moieties may incorporate groups including but not limited to ether, amine and carboxylic acid functionalities.

The compounds of the present invention can be used in the methods of the invention in combination with other drugs. For example, dosing a SARS-CoV-2 coronavirus-infected patient (i.e., a patient with COVID-19) with the SARS-CoV-2 coronavirus 3CL protease inhibitor of the invention and an interferon, such as interferon alpha, or a pegylated interferon, such as PEG-Intron or Pegasus, may provide a greater clinical benefit than dosing either the interferon, pegylated interferon or the SARS-CoV-2 coronavirus inhibitor alone. Other additional agents that can be used in the methods of the present invention include dexamethasone, azithromycin and remdesivir. Examples of greater clinical benefits could include a larger reduction in COVID-19 symptoms, a faster time to alleviation of symptoms, reduced lung pathology, a larger reduction in the amount of SARS-CoV-2 coronavirus in the patient (viral load), and decreased mortality.

The SARS-CoV-2 coronavirus infects cells which express P-glycoprotein. Some of the SARS-CoV-2 coronavirus 3CL protease inhibitors of the invention are P-glycoprotein substrates. Compounds which inhibit the SARS-CoV-2 coronavirus which are also P-glycoprotein substrates may be dosed with a P-glycoprotein inhibitor. Examples of P-glycoprotein inhibitors are verapamil, vinblastine, ketoconazole, nelfinavir, ritonavir or cyclosporine. The P-glycoprotein inhibitors act by inhibiting the efflux of the SARS-CoV-2 coronavirus inhibitors of the invention out of the cell. The inhibition of the P-glycoprotein-based efflux will prevent reduction of intracellular concentrations of the SARS-CoV-2 coronavirus inhibitor due to P-glycoprotein efflux. Inhibition of the P-glycoprotein efflux will result in larger intracellular concentrations of the SARS-CoV-2 coronavirus inhibitors. Dosing a SARS-CoV-2 coronavirus-infected patient with the SARS-CoV-2 coronavirus 3CL protease inhibitors of the invention and a P-glycoprotein inhibitor may lower the amount of SARS-CoV-2 coronavirus 3CL protease inhibitor required to achieve an efficacious dose by increasing the intracellular concentration of the SARS-CoV-2 coronavirus 3CL protease inhibitor.

Among the agents that may be used to increase the exposure of a mammal to a compound of the present invention are those that can act as inhibitors of at least one isoform of the cytochrome P450 (CYP450) enzymes. The isoforms of CYP450 that may be beneficially inhibited include, but are not limited to CYP1A2, CYP2D6, CYP2C9, CYP2C19 and CYP3A4. The compounds used in the methods of the invention include compounds that may be CYP3A4 substrates and are metabolized by CYP3A4. Dosing a SARS-CoV-2 coronavirus-infected patient with a SARS-CoV-2 coronavirus inhibitor which is a CYP3A4 substrate, such as SARS-CoV-2 coronavirus 3CL protease inhibitor, and a CYP3A4 inhibitor, such as ritonavir, nelfinavir or delavirdine, will reduce the metabolism of the SARS-CoV-2 coronavirus inhibitor by CYP3A4. This will result in reduced clearance of the SARS-CoV-2 coronavirus inhibitor and increased SARS-CoV-2 coronavirus inhibitor plasma concentrations. The reduced clearance and higher plasma concentrations may result in a lower efficacious dose of the SARS-CoV-2 coronavirus inhibitor.

Additional therapeutic agents that can be used in combination with the SARS-CoV-2 inhibitors in the methods of the present invention include the following:

PLpro inhibitors, Apilomod, EIDD-2801, Ribavirin, Valganciclovir, β-Thymidine, Aspartame, Oxprenolol, Doxycycline, Acetophenazine, Iopromide, Riboflavin, Reproterol, 2,2'-Cyclocytidine, Chloramphenicol, Chlorphenesin carbamate, Levodropropizine, Cefamandole, Floxuridine, Tigecycline, Pemetrexed, L(+)-Ascorbic acid, Glutathione, Hesperetin, Ademetionine, Masoprocol, Isotretinoin, Dantrolene, Sulfasalazine Anti-bacterial, Silybin, Nicardipine, Sildenafil, Platycodin, Chrysin, Neohesperidin, Baicalin, Sugetriol-3,9-diacetate, (−)-Epigallocatechin gallate, Phaitanthrin D, 2-(3,4-Dihydroxyphenyl)-2-[[2-(3,4-dihydroxyphenyl)-3,4-dihydro-5,7-dihydroxy-2H-1-benzopyran-3-yl]oxy]-3,4-dihydro-2H-1-benzopyran-3,4,5,7-tetrol, 2,2-di(3-indolyl)-3-indolone, (S)-(1 S,2R,4aS,5R,8aS)-1-Formamido-1,4a-dimethyl-6-methylene-5-((E)-2-(2-oxo-2,5-dihydrofuran-3-yl)ethenyl) decahydronaphthalen-2-yl-2-amino-3-phenylpropanoate, Piceatannol, Rosmarinic acid, and Magnolol.

3CLpro inhibitors, Lymecycline, Chlorhexidine, Alfuzosin, Cilastatin, Famotidine, Almitrine, Progabide, Nepafenac, Carvedilol, Amprenavir, Tigecycline, Montelukast, Carminic acid, Mimosine, Flavin, Lutein, Cefpiramide, Phenethicillin, Candoxatril, Nicardipine, Estradiol valerate, Pioglitazone, Conivaptan, Telmisartan, Doxycycline, Oxytetracycline, (1 S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl5-((R)-1,2-dithiolan-3-yl) pentanoate, Betulonal, Chrysin-7-O-β-glucuronide, Andrographiside, (1 S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 2-nitrobenzoate, 2β-Hydroxy-3,4-seco-friedelolactone-27-oic acid (S)-(1 S,2R,4aS,5R,8aS)-1-Formamido-1,4a-dimethyl-6-methylene-5-((E)-2-(2-oxo-2,5-dihydrofuran-3-yl)ethenyl) decahydronaphthalen-2-yl-2-amino-3-phenylpropanoate, Isodecortinol, Cerevisterol, Hesperidin, Neohesperidin, Andrograpanin, 2-((1R,5R,6R,8aS)-6-Hydroxy-5-(hydroxymethyl)-5,8a-dimethyl-2-methylenedecahydronaphthalen-1-yl)ethyl benzoate, Cosmosiin, Cleistocaltone A, 2,2-Di(3-indolyl)-3-indolone, Biorobin, Gnidicin, Phyllaemblinol, Theaflavin 3,3'-di-O-gallate, Rosmarinic acid, Kouitchenside I, Oleanolic acid, Stigmast-5-en-3-ol, Deacetylcentapicrin, and Berchemol.

RdRp inhibitors, Valganciclovir, Chlorhexidine, Ceftibuten, Fenoterol, Fludarabine, Itraconazole, Cefuroxime, Atovaquone, Chenodeoxycholic acid, Cromolyn, Pancuronium bromide, Cortisone, Tibolone, Novobiocin, Silybin, Idarubicin Bromocriptine, Diphenoxylate, Benzylpenicilloyl G, Dabigatran etexilate, Betulonal, Gnidicin, 2β,30β-Dihydroxy-3,4-seco-friedelolactone-27-Iactone, 14-Deoxy-11,12-didehydroandrographolide, Gniditrin, Theaflavin 3,3'-di-O-gallate, (R)-((1R,5aS,6R,9aS)-1,5a-Dimethyl-7-methylene-3-oxo-6-((E)-2-(2-oxo-2,5-dihydrofuran-3-yl) ethenyl)decahydro-1H-benzo[c]azepin-1-yl)methyl2-amino-3-phenylpropanoate, 2β-Hydroxy-3,4-seco-friedelolactone-27-oic acid, 2-(3,4-Dihydroxyphenyl)-2-[[2-(3,4-dihydroxyphenyl)-3,4-dihydro-5,7-dihydroxy-2H-1-benzopyran-3-yl]oxy]-3,4-dihydro-2H-1-benzopyran-3,4,5,7-tetrol, Phyllaemblicin B, 14-hydroxycyperotundone, Andrographiside, 2-((1R,5R,6R,8aS)-6-Hydroxy-5-(hydroxymethyl)-5,8a-dimethyl-2-methylenedecahydro naphthalen-1-yl)ethyl benzoate, Andrographolide, Sugetriol-3,9-diacetate, Baicalin, (1 S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 5-((R)-1,2-dithiolan-3-yl)pentanoate, 1,7-Dihydroxy-3-methoxyxanthone, 1,2,6-Trimethoxy-8-[(6-O-β-D-xylopyranosyl-β-D-glucopyranosyl)oxy]-9H-xanthen-9-one, and 1,8-Dihydroxy-6-methoxy-2-[(6-O-β-D-xylopyranosyl-β-D-glucopyranosyl)oxy]-9H-xanthen-9-one, 8-(β-D-Glucopyranosyloxy)-1,3,5-trihydroxy-9H-xanthen-9-one, Additional therapeutic agents that can be used in the methods of the invention include Diosmin, Hesperidin, MK-3207, Venetoclax, Dihydroergocristine, Bolazine, R428, Ditercalinium, Etoposide, Teniposide, UK-432097, Irinotecan, Lumacaftor, Velpatasvir, Eluxadoline, Ledipasvir, Lopinavir/Ritonavir+Ribavirin, Alferon, and prednisone. Other additional agents useful in the methods of the present invention include dexamethasone, azithromycin and remdesivir as well as boceprevir, umifenovir and favipiravir.

Other additional agents that can be used in the methods of the present invention include α-ketoamides compounds designated as 11 r, 13a and 13b, shown below, as described in Zhang, L.; Lin, D.; Sun, X.; Rox, K.; Hilgenfeld, R.; X-ray Structure of Main Protease of the Novel Coronavirus SARS-CoV-2 Enables Design of α-Ketoamide Inhibitors; bioRxiv preprint doi: https://doi.org/10.1101/2020.02.17.952879

11r

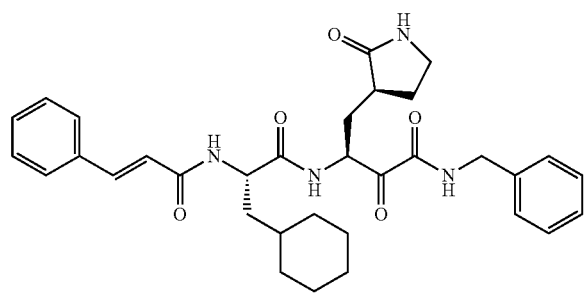

13a

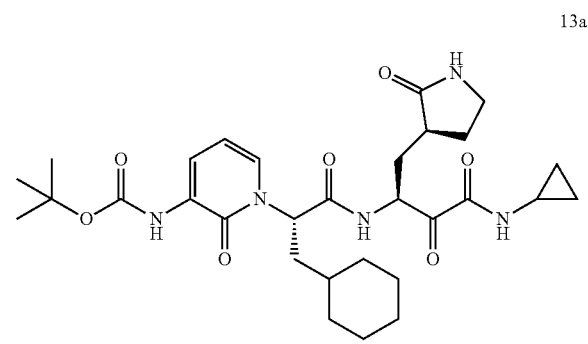

13b

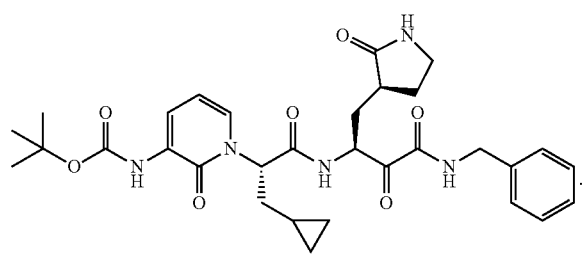

Additional agents that can be used in the methods of the present invention include RIG 1 pathway activators such as those described in U.S. Pat. No. 9,884,876.

Other additional therapeutic agents include protease inhibitors such as those described in Dai W, Zhang B, Jiang X-M, et al. Structure-based design of antiviral drug candidates targeting the SARS-CoV-2 main protease. Science. 2020; 368(6497):1331-1335 including compounds such as the compound shown below and a compound designated as DC402234

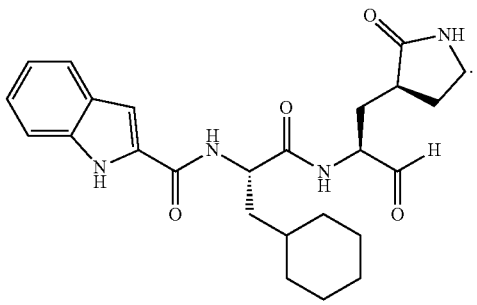 [SMILES: O=C[C@H](C[C@@H]1CCNC1=O)NC(=O)[C@H](CC1CCCCC1)NC(=O)c1cc2ccccc2[nH]1]

Another embodiment of the present invention is a method of treating COVID-19 in a patient wherein in addition to administering a compound of the present invention is (i.e. a compound of Formula I, I' or I" or a solvate or hydrate thereof or a pharmaceutically acceptable salt of the compound or solvate or hydrate thereof) an additional agents is administered and the additional agent is selected from antivirals such as remdesivir, galidesivir, favilavir/avifavir, molnupiravir (MK-4482/EIDD 2801), AT-527, AT-301, BLD-2660, favipiravir, camostat, SLV213 emtrictabine/tenofivir, clevudine, dalcetrapib, boceprevir and ABX464, glucocorticoids such as dexamethasone and hydrocortisone, convalescent plasma, a recombinant human plasma such as gelsolin (Rhu-p65N), monoclonal antibodies such as regdanvimab (Regkirova), ravulizumab (Ultomiris), VIR-7831/VIR-7832, BRII-196/BRII-198, COVI-AMG/COVI DROPS (STI-2020), bamlanivimab (LY-CoV555), mavrilimab, leronlimab (PRO140), AZD7442, lenzilumab, infliximab, adalimumab, JS 016, STI-1499 (COVIGUARD), lanadelumab (Takhzyro), canakinumab (Ilaris), gimsilumab and otilimab, antibody cocktails such as casirivimab/imdevimab (REGN-Cov2), recombinant fusion protein such as MK-7110 (CD24Fc/SACCOVID), anticoagulants such as heparin and apixaban, IL-6 receptor agonists such as tocilizumab (Actemra) and sarilumab (Kevzara), PIKfyve inhibitors such as apilimod dimesylate, RIPK1 inhibitors such as DNL758, DC402234, VIP receptor agonists such as PB1046, SGLT2 inhibitors such as dapaglifozin, TYK inhibitors such as abivertinib, kinase inhibitors such as ATR-002, bemcentinib, acalabrutinib, losmapimod, baricitinib and tofacitinib, H2 blockers such as famotidine, anthelmintics such as niclosamide, furin inhibitors such as diminazene.

The term "SARS-CoV-2 inhibiting agent" means any SARS-CoV-2-related coronavirus 3C-like protease inhibitor compound described herein or a pharmaceutically acceptable salt, hydrate, prodrug, active metabolite or solvate thereof or a compound which inhibits replication of SARS-CoV-2 in any manner.

The term "interfering with or preventing" SARS-CoV-2-related coronavirus ("SARS-CoV-2") viral replication in a cell means to reduce SARS-CoV-2 replication or production of SARS-CoV-2 components necessary for progeny virus in a cell treated with a compound of this invention as compared to a cell not being treated with a compound of this invention. Simple and convenient assays to determine if SARS-CoV-2 viral replication has been reduced include an ELISA assay for the presence, absence, or reduced presence of anti-SARS-CoV-2 antibodies in the blood of the subject (Nasoff, et al., PNAS 88:5462-5466, 1991), RT-PCR (Yu, et al., in Viral Hepatitis and Liver Disease 574-577, Nishioka, Suzuki and Mishiro (Eds.); Springer-Verlag, Tokyo, 1994). Such methods are well known to those of ordinary skill in the art.

Alternatively, total RNA from transduced and infected "control" cells can be isolated and subjected to analysis by dot blot or northern blot and probed with SARS-CoV-2-specific DNA to determine if SARS-CoV-2 replication is reduced. Alternatively, reduction of SARS-CoV-2 protein expression can also be used as an indicator of inhibition of SARS-CoV-2 replication. A greater than fifty percent reduction in SARS-CoV-2 replication as compared to control cells typically quantitates a prevention of SARS-CoV-2 replication.

If a SARS-CoV-2 inhibitor compound used in the method of the invention is a base, a desired salt may be prepared by any suitable method known to the art, including treatment of the free base with an inorganic acid (such as hydrochloric acid, hydrobromic acid, sulfuric acid, nitric acid, phosphoric acid, and the like), or with an organic acid (such as acetic acid, maleic acid, succinic acid, mandelic acid, fumaric acid, malonic acid, pyruvic acid, oxalic acid, glycolic acid, salicylic acid, pyranosidyl acid (such as glucuronic acid or galacturonic acid), alpha-hydroxy acid (such as citric acid or tartaric acid), amino acid (such as aspartic acid or glutamic acid), aromatic acid (such as benzoic acid or cinnamic acid), sulfonic acid (such as p-toluenesulfonic acid or ethanesulfonic acid), and the like.

If a SARS-CoV-2 inhibitor compound used in the method of the invention is an acid, a desired salt may be prepared by any suitable method known to the art, including treatment of the free acid with an inorganic or organic base [such as an amine (primary, secondary, or tertiary)], an alkali metal hydroxide, or alkaline earth metal hydroxide. Illustrative examples of suitable salts include organic salts derived from amino acids (such as glycine and arginine), ammonia, primary amines, secondary amines, tertiary amines, and cyclic amines (such as piperidine, morpholine, and piperazine), as well as inorganic salts derived from sodium, calcium, potassium, magnesium, manganese, iron, copper, zinc, aluminum and lithium.

In the case of SARS-CoV-2 inhibitor compounds, prodrugs, salts, or solvates that are solids, it is understood by those skilled in the art that the compound, prodrugs, salts, and solvates used in the method of the invention, may exist in different polymorph or crystal forms, all of which are intended to be within the scope of the present invention and specified formulas. In addition, the compound, salts, prodrugs and solvates used in the method of the invention may exist as tautomers, all of which are intended to be within the broad scope of the present invention.

Solubilizing agents may also be used with the compounds of the invention to increase the compounds' solubility in water of physiologically acceptable solutions. These solubilizing agents include cyclodextrins, propylene glycol, diethylacetamide, polyethylene glycol, Tween, ethanol and micelle-forming agents. Offered solubilizing agents are cyclodextrins, particularly beta-cyclodextrins and in particular hydroxypropyl beta-cyclodextrin and sulfobutylether beta-cyclodextrin.

In some cases, the SARS-CoV-2 inhibitor compounds, salts, prodrugs and solvates used in the method of the invention may have chiral centers. When chiral centers are present, the compound, salts, prodrugs and solvates may exist as single stereoisomers, racemates, and/or mixtures of enantiomers and/or diastereomers. All such single stereoisomers, racemates, and mixtures thereof are intended to be within the broad scope of the present invention.

As generally understood by those skilled in the art, an optically pure compound is one that is enantiomerically pure. As used herein, the term "optically pure" is intended to mean a compound comprising at least a sufficient activity. Preferably, an optically pure amount of a single enantiomer to yield a compound having the desired pharmacologically pure compound of the invention comprises at least 90% of a single isomer (80% enantiomeric excess), more preferably at least 95% (90% e.e.), even more preferably at least 97.5% (95% e.e.), and most preferably at least 99% (98% e.e.).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. In a preferred embodiment of the present invention, "treating" or "treatment" means at least the mitigation of a disease condition in a human, that is alleviated by the inhibition of the activity of the SARS-CoV-2 3C-like protease which is the main protease of SARS-CoV-2, the causative agent for COVID-19. For patients suffering from COVID-19, fever, fatigue, and dry cough are the main manifestations of the disease, while nasal congestion, runny nose, and other symptoms of the upper respiratory tract are rare. Beijing Centers for Diseases Control and Prevention indicated that the typical case of COVID-19 has a progressive aggravation process. COVID-19 can be classified into light, normal, severe, and critical types based on the severity of the disease. National Health Commission of the People's Republic of China. Diagnosis and Treatment of Pneumonia Caused by 2019-nCoV (Trial Version 4). Available online: http://www.nhc.gov.cn/jkj/s3577/202002/573340613ab243b3a7f61df260551dd4/files/c7 91e5a7ea5149f680fdcb34dac0f54e.pdf: (1) Mild cases—the clinical symptoms were mild, and no pneumonia was found on the chest computed tomography (CT); (2) normal cases-fever, respiratory symptoms, and patients found to have imaging manifestations of pneumonia; (3) severe cases-one of the following three conditions: Respiratory distress, respiratory rate ≥30 times/min (in resting state, refers to oxygen saturation ≤93%), partial arterial oxygen pressure (PaO2)/oxygen absorption concentration (FiO2) ≤300 mmHg (1 mm Hg=0.133 kPa); (4) critical cases—one of the following three conditions: Respiratory failure and the need for mechanical ventilation, shock, or the associated failure of other organs requiring the intensive care unit. The current clinical data shows that the majority of deaths occurred in the older patients. However, severe cases have been documented in young adults who have unique factors, particularly those with chronic diseases, such as diabetes or hepatitis B. Those with a long-term use of hormones or immunosuppressants, and decreased immune function, are likely to get severely infected.

Methods of treatment for mitigation of a coronavirus disease condition such as COVID-19 include the use of one or more of the compounds of the invention in any conventionally acceptable manner. According to certain preferred embodiments of the invention, the compound or compounds used in the methods of the present invention are administered to a mammal, such as a human, in need thereof. Preferably, the mammal in need thereof is infected with a coronavirus such as the causative agent of COVID-19, namely SARS-CoV-2.

The present invention also includes prophylactic methods, comprising administering an effective amount of a SARS-CoV-2 inhibitor of the invention, or a pharmaceutically acceptable salt, prodrug, pharmaceutically active metabolite, or solvate thereof to a mammal, such as a human at risk for infection by SARS-CoV-2. According to certain preferred embodiments, an effective amount of one or more compounds of the invention, or a pharmaceutically acceptable salt, prodrug, pharmaceutically active metabolite, or solvate thereof is administered to a human at risk for infection by SARS-CoV-2, the causative agent for COVID-19. The prophylactic methods of the invention include the use of one or more of the compounds in the invention in any conventionally acceptable manner.

Certain of the compounds used in the methods of the invention, for example dexamethasone, azithromycin and remdesivir are known and can be made by methods known in the art.

Recent evidence indicates that a new coronavirus SARS-CoV-2 is the causative agent of COVID-19. The nucleotide sequence of the SARS-CoV-2 coronavirus as well as the recently determined L- and S-subtypes have recently been determined and made publicly available.

The activity of the inhibitor compounds as inhibitors of SARS-CoV-2 viral activity may be measured by any of the suitable methods available in the art, including in vivo and in vitro assays. The activity of the compounds of the present invention as inhibitors of coronavirus 3C-like protease activity (such as the 3C-like protease of the SARS-CoV-2 coronavirus) may be measured by any of the suitable methods known to those skilled in the art, including in vivo and in vitro assays. Examples of suitable assays for activity measurements include the antiviral cell culture assays described herein as well as the antiprotease assays described herein, such as the assays described in the Experimental section.

Administration of the SARS-CoV-2 inhibitor compounds and their pharmaceutically acceptable prodrugs, salts, active metabolites, and solvates may be performed according to any of the accepted modes of administration available to those skilled in the art. Illustrative examples of suitable modes of administration include oral, nasal, pulmonary, parenteral, topical, intravenous, injected, transdermal, and rectal. Oral, intravenous, subcutaneous and nasal deliveries are preferred.

A SARS-CoV-2-inhibiting agent may be administered as a pharmaceutical composition in any suitable pharmaceutical form. Suitable pharmaceutical forms include solid, semi-solid, liquid, or lyophilized formulations, such as tablets, powders, capsules, suppositories, suspensions, liposomes, and aerosols. The SARS-CoV-2-inhibiting agent may be prepared as a solution using any of a variety of methodologies. For example, SARS-CoV-2-inhibiting agent can be dissolved with acid (e.g., 1 M HCl) and diluted with a sufficient volume of a solution of 5% dextrose in water (D5W) to yield the desired final concentration of SARS-CoV-2-inhibiting agent (e.g., about 15 mM). Alternatively, a solution of D5W containing about 15 mM HCl can be used to provide a solution of the SARS-CoV-2-inhibiting agent at the appropriate concentration. Further, the SARS-CoV-2-inhibiting agent can be prepared as a suspension using, for example, a 1% solution of carboxymethylcellulose (CMC).

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling and dissolving the ingredients as appropriate, to give the desired products for intravenous, oral, parenteral, topical, intravaginal, intranasal, intrabronchial, intraocular, intraaural, and/or rectal administration.

Typically, a compound of the invention is administered in an amount effective to treat a condition as described herein.

The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable patients according to the present invention include mammalian patients. Mammals according to the present invention include, but are not limited to, canine, feline, bovine, caprine, equine, ovine, porcine, rodents, lagomorphs, primates, and the like, and encompass mammals in utero. In one embodiment, humans are suitable patients. Human patients may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The pharmaceutically acceptable carrier encompasses any suitable dosage form that is acceptable for administration to a patient. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention.

In another embodiment, the oral administration may be in a powder or granule form. In another embodiment, the oral dose form is sub-lingual, such as, for example, a lozenge. In such solid dosage forms, the compounds of the invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. Two or more compounds may be administered simultaneously, concurrently or sequentially. Additionally, simultaneous administration may be carried out by mixing the compounds prior to administration or by administering the compounds at the same point in time but at different anatomic sites or using different routes of administration. The phrases "concurrent administration," "co-administration," "simultaneous administration," and "administered simultaneously" mean that the compounds are administered in combination.

The present invention includes the use of a combination of a compound of the invention and one or more additional therapeutic agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the invention or a pharmaceutically acceptable salt of the compound; (b) a second therapeutic agent; and (c) a pharmaceutically acceptable carrier. Pharmaceutical compositions of the invention may also include suitable excipients, diluents, vehicles, and carriers, as well as other pharmaceutically active agents, depending upon the intended use. Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition may contain at least a therapeutically effective amount of a SARS-CoV-2-inhibiting agent and preferably is made up of one or more pharmaceutical dosage units. The selected dose may be administered to a mammal, for example, a human patient, in need of treatment mediated by inhibition of SARS-CoV-2 related coronavirus activity, by any known or suitable method of administering the dose, including topically, for example, as an ointment or cream; orally; rectally, for example, as a suppository; parenterally by injection; intravenously; or continuously by intravaginal, intranasal, intrabronchial, intraaural, or intraocular infusion.

The phrases "therapeutically effective amount" and "effective amount" are intended to mean the amount of an inventive agent that, when administered to a mammal in need of treatment, is sufficient to effect treatment for injury or disease conditions alleviated by the inhibition of SARS-CoV-2 viral replication. The amount of a given SARS-CoV-2-inhibiting agent used in the method of the invention that will be therapeutically effective will vary depending upon factors such as the particular SARS-CoV-2-inhibiting agent, the disease condition and the severity thereof, the identity and characteristics of the mammal in need thereof, which amount may be routinely determined by those skilled in the art.

It will be appreciated that the actual dosages of the SARS-CoV-2-inhibiting agents used in the pharmaceutical compositions of this invention will be selected according to the properties of the particular agent being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.01 to about 1000 mg/kg body weight, preferably from about 0.1 to about 500 mg/kg body weight, and even more preferably from about 1 to about 500 mg/kg body weight, with courses of treatment repeated at appropriate intervals. For intravenous dosing a dose of up to 5 grams per day may be employed. Intravenous administration can occur for intermittent periods during a day or continuously over a 24-hour period.

The terms "cytochrome P450-inhibiting amount" and "cytochrome P450 enzyme activity-inhibiting amount", as used herein, refer to an amount of a compound required to decrease the activity of cytochrome P450 enzymes or a particular cytochrome P450 enzyme isoform in the presence of such compound. Whether a particular compound decreases cytochrome P450 enzyme activity, and the amount of such a compound required to do so, can be determined by methods know to those of ordinary skill in the art and the methods described herein.

Protein functions required for coronavirus replication and transcription are encoded by the so-called "replicase" gene. Two overlapping polyproteins are translated from this gene and extensively processed by viral proteases. The C-proximal region is processed at eleven conserved interdomain junctions by the coronavirus main or "3C-like" protease. The name "3C-like" protease derives from certain similarities between the coronavirus enzyme and the well-known picornavirus 3C proteases. These include substrate preferences, use of cysteine as an active site nucleophile in catalysis, and similarities in their putative overall polypeptide folds. A comparison of the amino acid sequence of the SARS-CoV-2-associated coronavirus 3C-like protease to that of other known coronaviruses such as SARS-CoV shows the amino acid sequences have approximately 96% shared homology.

Amino acids of the substrate in the protease cleavage site are numbered from the N to the C terminus as follows: -P3-P2-P1-P1'-P2'-P3', with cleavage occurring between the P1 and P1' residues (Schechter & Berger, 1967). Substrate specificity is largely determined by the P2, P1 and P1' positions. Coronavirus main protease cleavage site specificities are highly conserved with a requirement for glutamine at P1 and a small amino acid at P1' [*Journal of General Virology,* 83, pp. 595-599 (2002)].

The compounds of the present invention can be prepared according to the methods set forth in Reaction Schemes 1 to 3 below.

The schemes provided below further illustrate and exemplify the compounds of the present invention and methods of preparing such compounds. It is to be understood that the scope of the present invention is not limited in any way by the scope of the following examples and preparations. In the following examples molecules with a single chiral center may exist as a single enantiomer or a racemic mixture. Those molecules with two or more chiral centers may exist as a single enantiomer, a racemic or otherwise mixture of two enantiomers, or as various mixtures of diastereomers. Such enantiomers, racemates, and diastereomers may be obtained and/or separated by methods known to those skilled in the art. It will be appreciated by one skilled in the art that certain synthetic manipulations may epimerize or racemize a stereocenter, and synthetic conditions may be selected to either promote or discourage such epimerization or racemization.

Scheme 1 illustrates a synthetic sequence for the preparation of compounds of Formula I as shown, wherein the N—BOC methyl ester of Formula 1 (WO 2005/113580) is converted to a primary amide of Formula 3 (N—BOC being N-tert-butoxycarbonyl). This may be accomplished directly, for example by treatment with ammonia ($NH_3$) in a sealed vessel in a solvent such as methanol or ethanol, for example, optionally in the presence of additives such as calcium chloride ($CaCl_2$)) or magnesium dimethoxide, $Mg(OMe)_2$.

Scheme 1

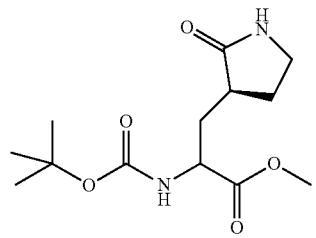

1

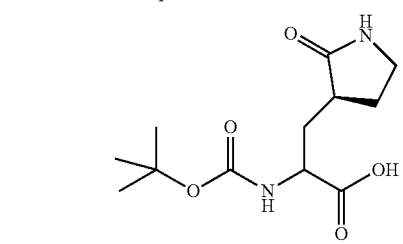

2

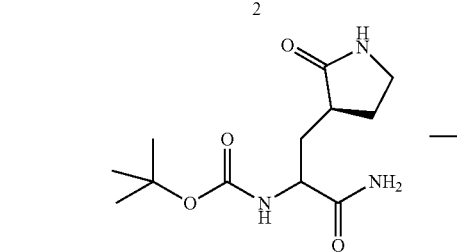

3

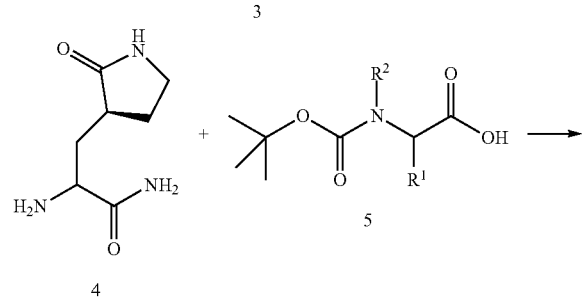

4

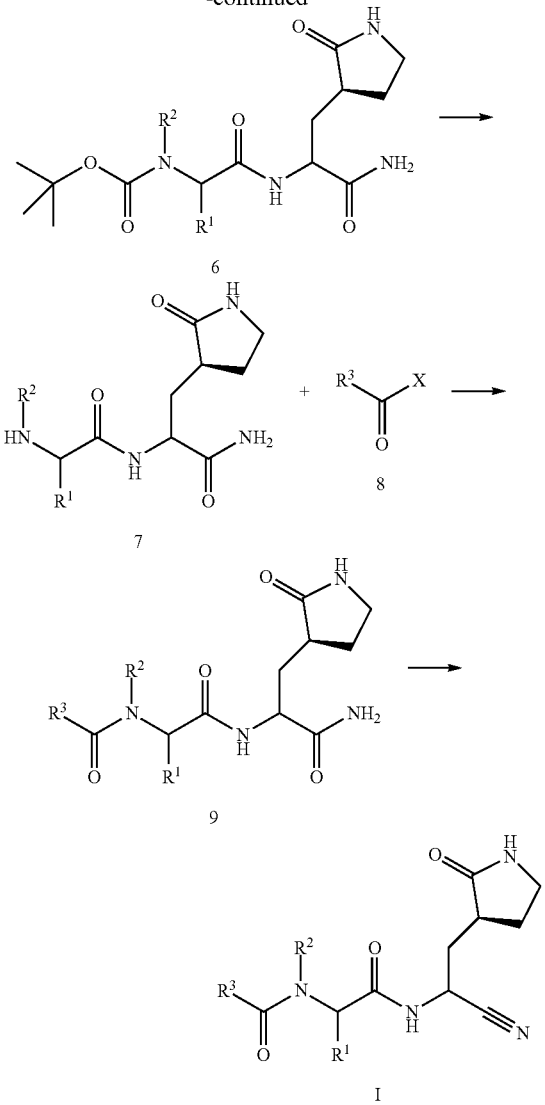

The transformation of the compound of Formula 1 to the compound of Formula 3 may also be carried out by prior conversion to the carboxylic acid of Formula 2 (WO 2005/113580). In this case the compound of Formula 2 may be converted to the compound of Formula 3 using methods well known to those skilled in the art. For example, the compound of Formula 2 may be treated with a reagent such as 0-(7-azabenzotriazol-1-yl)-N,N,N',N'-tetramethyluronium hexafluorophosphate (HATU), isobutyl chloroformate, 1-[3-(dimethylamino)propyl]-3-ethylcarbodiimide hydrochloride (EDCI) and hydroxybenzotriazole (HOBt), or 1,1'-carbonyldiimidazole (CDI), optionally in the presence of a base such as N,N-diisopropylethylamine (DIEA), 4-methylmorpholine (NMM), or triethylamine (TEA), followed by treatment with $NH_3$ administered as a gas or a solution in a reaction compatible solvent, or with a salt of $NH_3$ such as ammonium acetate or ammonium chloride in the presence of a base such as N,N-diisopropylethylamine, 4-methylmorpholine, or triethylamine. Suitable solvents include, but are not limited to, dichloromethane ($CH_2Cl_2$), N,N-dimethylformamide (DMF), tetrahydrofuran (THF), or acetonitrile ($CH_3CN$).

The compound of Formula 3 may be N-deprotected to provide an amine of Formula 4 using methods well known to those skilled in the art for effecting such deprotections. Frequently acidic reagents such as hydrogen chloride, methanesulfonic acid, or trifluoroacetic acid are used, typically in a reaction compatible solvent such as $CH_2Cl_2$, 1,4-dioxane, 1,2-dichloroethane, or $CH_3CN$. One skilled in the art will appreciate that the compound of Formula 4 will frequently be obtained as an acid addition salt. The compound of Formula 4 may then be transformed into a compound of Formula 6 by treatment with an N-protected amino acid compound of Formula 5 under appropriate conditions. Such methods are well known to those skilled in the art, and in general standard peptide coupling conditions may be selected.

The compound of Formula 6 may be N-deprotected to provide an amine of Formula 7 using methods well known to those skilled in the art for effecting such deprotections. Frequently acidic reagents such as hydrogen chloride, methanesulfonic acid, or trifluoroacetic acid are used, typically in a reaction compatible solvent such as $CH_2Cl_2$, 1,4-dioxane, 1,2-dichloroethane, or $CH_3CN$. One skilled in the art will appreciate that the compound of Formula 7 will frequently be obtained as an acid addition salt. The compound of Formula 7 may then be transformed into a compound of Formula 9 by treatment with a carboxylic acid compound of Formula 8 under appropriate conditions. Such methods are well known to those skilled in the art. For example, when X=a chlorine atom, the carboxylic acid compound is known as an acid chloride and the reaction is conducted in the presence of a base to consume the hydrogen halide HX produced as a by-product of the reaction. Examples of suitable bases include, but are not limited to, tertiary amines such as 4-methylmorpholine, 2,6-dimethylpyridine, or N,N-diisopropylethylamine, or inorganic bases such as magnesium oxide (MgO), sodium carbonate ($Na_2CO_3$), or potassium bicarbonate ($KHCO_3$). Suitable solvents include, but are not limited to, $CH_2Cl_2$, DMF, THF, or $CH_3CN$. When X=OH, it is customary to use a reagent or combination of reagents to facilitate the reaction of the carboxylic acid compound of Formula 8. One skilled in the art may choose to use, for example, a carbodiimide reagent such as 1-[3-(dimethylamino)propyl]-3-ethylcarbodiimide hydrochloride (EDCI) or N,N'-dicyclohexyl carbodiimide (DCC), optionally in the presence of an auxiliary nucleophile such as hydroxybenzotriazole (HOBt) or 2-hydroxypyridine-N-oxide (HOPO). Further, when X=OH, one skilled in the art may choose to use reagents that are suitable for the formation of mixed carboxyl/carbonic anhydrides, such as CDI, isobutyl or ethyl chloroformate, frequently in the presence of a base such as described above. Suitable solvents include, but are not limited to, $CH_2Cl_2$, THF, or $CH_3CN$. Another approach commonly used by those skilled in the art when X=OH is to treat the carboxylic acid compound of Formula 8 with a carboxylic acid chloride, for example such as $Me_3CCOCl$, in the presence of a base such as described above to generate a mixed carboxylic anhydride of the Formula $R_3C(O)O(O)CCMe_3$. Suitable solvents include, but are not limited to, $CH_2Cl_2$, THF, or $CH_3CN$. In many cases it is possible to use a symmetric anhydride of the desired carboxylic acid compound of Formula 8 to effect the reaction, optionally in the presence of a base such as described above, in which case X=O(O)$CR_3$ and the carboxylic acid compound of Formula 8 is therefore $R_3C(O)O(O)CR_3$. Suitable solvents include, but are not limited to, $CH_2Cl_2$, THF, or $CH_3CN$.

The compound of Formula 9 may be transformed into the compound of Formula I by treatment under dehydrating conditions well known to those skilled in the art. Frequently this dehydration step may be accomplished using an excess of trifluoroacetic anhydride or phosphorus oxychloride, generally in the presence of a base such as pyridine, N,N-diisopropylethylamine, 4-methylmorpholine, or triethylamine.

One skilled in the art will know that the N—BOC protected amino acids of Formula 5 are known in the chemical literature, are commercially available, and may be prepared from the corresponding known and commercially available amino acids by one skilled in the art using well established procedures for the synthesis of N-protected amino acids. Likewise, one skilled in the art will understand that the carboxylic acid compounds of Formula 8 may be known in the chemical literature, and/or are commercially available, and/or may be prepared by published methods or by analogy to published methods.

One skilled in the art will appreciate that the bond-forming steps in Scheme 1 may be conducted in a different order with appropriate considerations, for example as shown in Scheme 2.

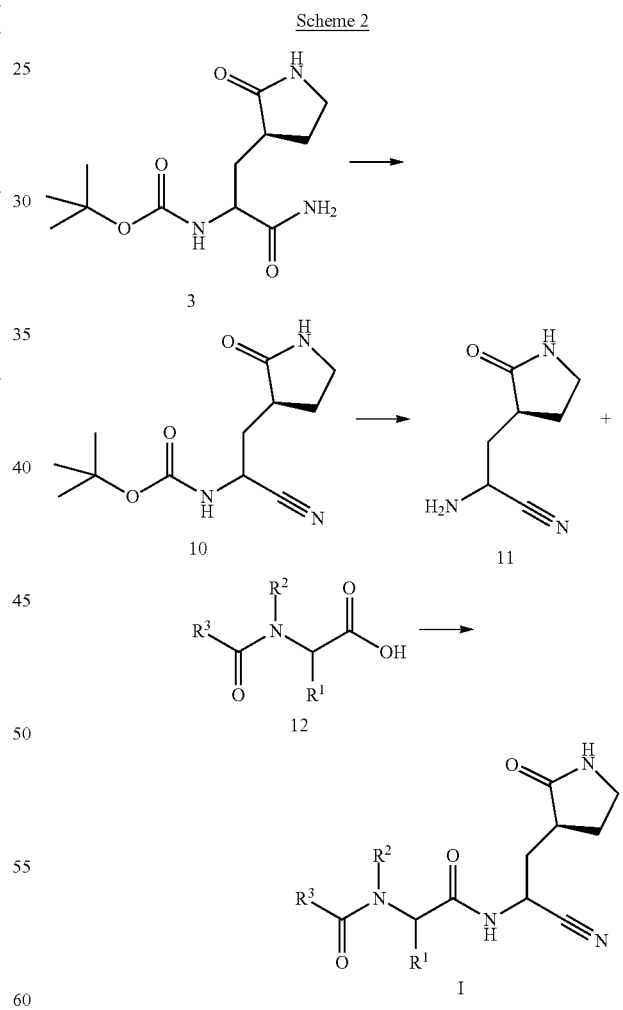

Scheme 2

In Scheme 2, the compound of Formula 3 is converted into the compound of Formula 10 by treatment under dehydrating conditions well known to those skilled in the art. Frequently this dehydration step may be accomplished using an excess of trifluoroacetic anhydride or phosphorus oxychloride, generally in the presence of a base such as pyridine, N,N-diisopropylethylamine, 4-methylmorpholine, or triethylamine. The compound of Formula 10 is N-deprotected to provide an amine of Formula 11 using methods well known to those skilled in the art for effecting such deprotections. Frequently, acidic reagents such as hydrogen chloride, methanesulfonic acid, or trifluoroacetic acid are used, typically in a reaction-compatible solvent such as $CH_2Cl_2$, 1,4-dioxane, 1,2-dichloroethane, or $CH_3CN$. One skilled in the art will appreciate that the compound of Formula 11 will frequently be obtained as an acid addition salt. The compound of Formula 11 may then be transformed into a compound of Formula I by treatment with a compound of Formula 12 under appropriate conditions. Such methods are well known to those skilled in the art, and in general standard peptide coupling conditions may be selected. Compounds of Formula 12 are exceptionally well known in the chemical literature, and one skilled in the art may choose to prepare any given compound of Formula 12 using methods analogous to those described in the chemical literature.

One skilled in the art will appreciate that the bond-forming steps in Schemes 1 and 2 may be conducted in still further different orders with appropriate considerations, for example as shown in Scheme 3.

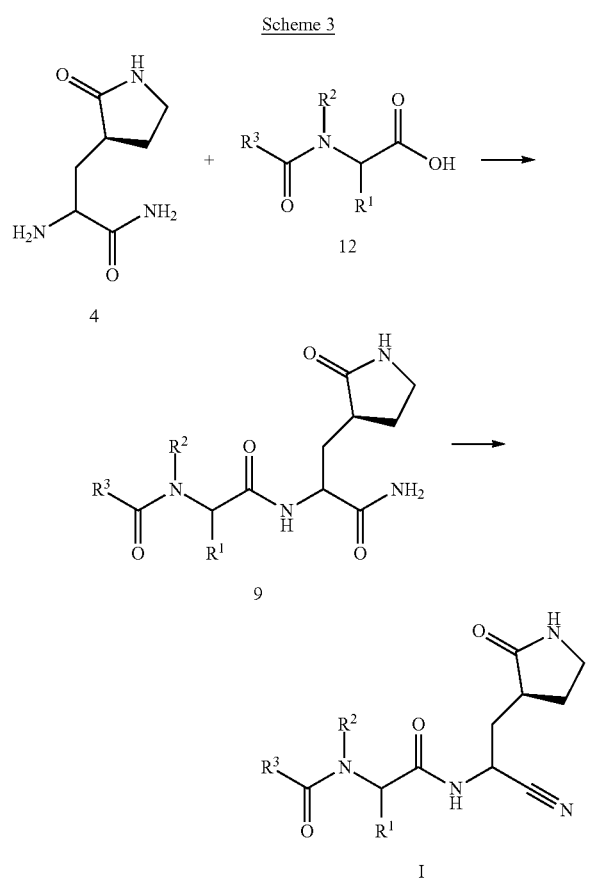

Scheme 3

In Scheme 3, the compound of Formula 4 may then be transformed into a compound of Formula 9 by treatment with a compound of Formula 12 under appropriate conditions. Such methods are well known to those skilled in the art, and in general standard peptide coupling conditions may be selected. Compounds of Formula 12 are exceptionally well known in the chemical literature, and one skilled in the art may choose to prepare any given compound of Formula 12 using methods analogous to those described in the chemical literature. The compound of Formula 9 is then converted into the compound of Formula I by treatment under dehydrating conditions well known to those skilled in the art. Frequently this dehydration step may be accomplished using an excess of trifluoroacetic anhydride or phosphorus oxychloride, generally in the presence of a base such as pyridine, N,N-diisopropylethylamine, 4-methylmorpholine, or triethylamine.

One skilled in the art will recognize that still further permutations of the bond-forming steps and functional group manipulations in Schemes 1, 2 and 3 may be applied with appropriate considerations. Such permutations in the selection of step order are well known in the chemical literature and one skilled in the art may consult the chemical literature for further guidance if desired. One skilled in the art will recognize that other selections of protecting groups and reagents for effecting the various transformations may be made.

EXAMPLES

Experimental Procedures

The following illustrate the synthesis of various compounds of the present invention. Additional compounds within the scope of this invention may be prepared using the methods illustrated in these Examples, either alone or in combination with techniques generally known in the art. All starting materials in these Preparations and Examples are either commercially available or can be prepared by methods known in the art or as described herein.

All reactions were carried out using continuous stirring under an atmosphere of nitrogen or argon gas unless otherwise noted. When appropriate, reaction apparatuses were dried under dynamic vacuum using a heat gun, and anhydrous solvents (Sure-Seal™ products from Aldrich Chemical Company, Milwaukee, Wis. or DriSolv™ products from EMD Chemicals, Gibbstown, N.J.) were employed. In some cases, commercial solvents were passed through columns packed with 4 Å molecular sieves, until the following QC standards for water were attained: a)<100 ppm for dichloromethane, toluene, N,N-dimethylformamide, and tetrahydrofuran; b)<180 ppm for methanol, ethanol, 1,4-dioxane, and diisopropylamine. For very sensitive reactions, solvents were further treated with metallic sodium, calcium hydride, or molecular sieves and distilled just prior to use. Other commercial solvents and reagents were used without further purification. For syntheses referencing procedures in other Examples or Methods, reaction conditions (reaction time and temperature) may vary. Products were generally dried under vacuum before being carried on to further reactions or submitted for biological testing.

When indicated, reactions were heated by microwave irradiation using Biotage Initiator or Personal Chemistry Emrys Optimizer microwaves. Reaction progress was monitored using thin-layer chromatography (TLC), liquid chromatography-mass spectrometry (LCMS), high-performance liquid chromatography (HPLC), and/or gas chromatography-mass spectrometry (GCMS) analyses. TLC was performed on pre-coated silica gel plates with a fluorescence indicator (254 nm excitation wavelength) and visualized under UV light and/or with 12, $KMnO_4$, $CoCl_2$, phosphomolybdic acid, and/or ceric ammonium molybdate stains. LCMS data were acquired on an Agilent 1100 Series instrument with a Leap Technologies autosampler, Gemini C18 columns, acetonitrile/water gradients, and either trifluoroacetic acid, formic acid, or ammonium hydroxide modifiers. The column eluate was analyzed using a Waters ZQ mass spectrometer scanning in both positive and negative ion modes from 100 to 1200 Da. Other similar instruments were also used. HPLC data were generally acquired on an Agilent 1100 Series instrument, using the columns indicated, acetonitrile/water gradients, and either trifluoroacetic acid or ammonium hydroxide modifiers. GCMS data were acquired using a Hewlett Packard 6890 oven with an HP 6890 injector, HP-1 column (12 m×0.2 mm×0.33 µm), and helium carrier gas. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC), generally using Berger or Thar instruments; columns such as ChiralPAK-AD, -AS, -IC, Chiralcel-OD, or -OJ columns; and $CO_2$ mixtures with methanol, ethanol, 2-propanol, or acetonitrile, alone or modified using trifluoroacetic acid or propan-2-amine. UV detection was used to trigger fraction collection. For syntheses referencing procedures in other Examples or Methods, purifications may vary: in general, solvents and the solvent ratios used for eluents/gradients were chosen to provide appropriate $R_f$s or retention times.

Mass spectrometry data are reported from LCMS analyses. Mass spectrometry (MS) was performed via atmospheric pressure chemical ionization (APCI), electrospray ionization (ESI), electron impact ionization (EI) or electron scatter ionization (ES) sources. Proton nuclear magnetic spectroscopy ($^1$H NMR) chemical shifts are given in parts per million downfield from tetramethylsilane and were recorded on 300, 400, 500, or 600 MHz Varian, Bruker, or Jeol spectrometers. Chemical shifts are expressed in parts per million (ppm, δ) referenced to the deuterated solvent residual peaks (chloroform, 7.26 ppm; $CD_2HOD$, 3.31 ppm; acetonitrile-$d_2$, 1.94 ppm; dimethyl sulfoxide-$d_5$, 2.50 ppm; DHO, 4.79 ppm). The peak shapes are described as follows: s, singlet; d, doublet; t, triplet; q, quartet; quin, quintet; m, multiplet; br s, broad singlet; app, apparent. Analytical SFC data were generally acquired on a Berger analytical instrument as described above. Optical rotation data were acquired on a PerkinElmer model 343 polarimeter using a 1 dm cell. Microanalyses were performed by Quantitative Technologies Inc. and were within 0.4% of the calculated values.

Unless otherwise noted, chemical reactions were performed at room temperature (about 23 degrees Celsius).

Unless noted otherwise, all reactants were obtained commercially and used without further purification, or were prepared using methods known in the literature.

The terms "concentrated", "evaporated", and "concentrated in vacuo" refer to the removal of solvent at reduced pressure on a rotary evaporator with a bath temperature less than 60° C. The abbreviations "min" and "h" stand for "minutes" and "hours," respectively. The term "TLC" refers to thin-layer chromatography, "room temperature or ambient temperature" means a temperature between 18 to 25° C., "GCMS" refers to gas chromatography-mass spectrometry, "LCMS" refers to liquid chromatography-mass spectrometry, "UPLC" refers to ultra-performance liquid chromatography, "HPLC" refers to high-performance liquid chromatography, and "SFC" refers to supercritical fluid chromatography.

Hydrogenation may be performed in a Parr shaker under pressurized hydrogen gas, or in a Thales-nano H-Cube flow hydrogenation apparatus at full hydrogen and a flow rate between 1-2 mL/min at specified temperature.

HPLC, UPLC, LCMS, GCMS, and SFC retention times were measured using the methods noted in the procedures.

In some examples, chiral separations were carried out to separate enantiomers or diastereomers of certain compounds of the invention (in some examples, the separated enantiomers are designated as ENT-1 and ENT-2, according to their order of elution; similarly, separated diastereomers are designated as DIAST-1 and DIAST-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, the indicated stereochemistry represents just one of the two enantiomers that make up the racemic mixture.

The compounds and intermediates described below were named using the naming convention provided with ACD/ChemSketch 2019.1.1, File Version C05H41, Build 110712 (Advanced Chemistry Development, Inc., Toronto, Ontario, Canada). The naming convention provided with ACD/ChemSketch 2019.1.1 is well known by those skilled in the art and it is believed that the naming convention provided with ACD/ChemSketch 2019.1.1 generally comports with the IUPAC (International Union for Pure and Applied Chemistry) recommendations on Nomenclature of Organic Chemistry and the CAS Index rules.

Example 1

(1R,2S,5S)—N-{(1S)-1-Cyano-2-[(3S)-2-oxopyrrolidin-3-yl]ethyl}-6,6-dimethyl-3-[N-(trifluoroacetyl)-L-valyl]-3-azabicyclo[3.1.0]hexane-2-carboxamide (1)

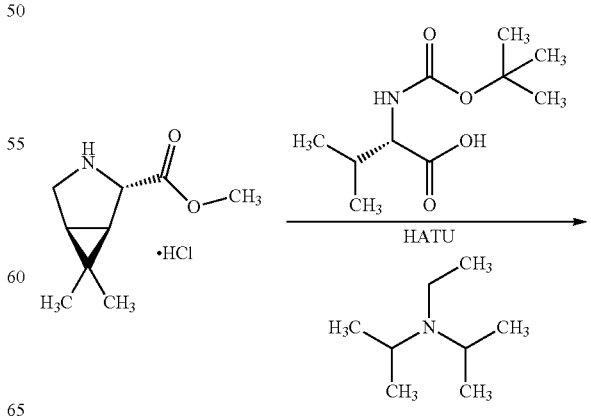

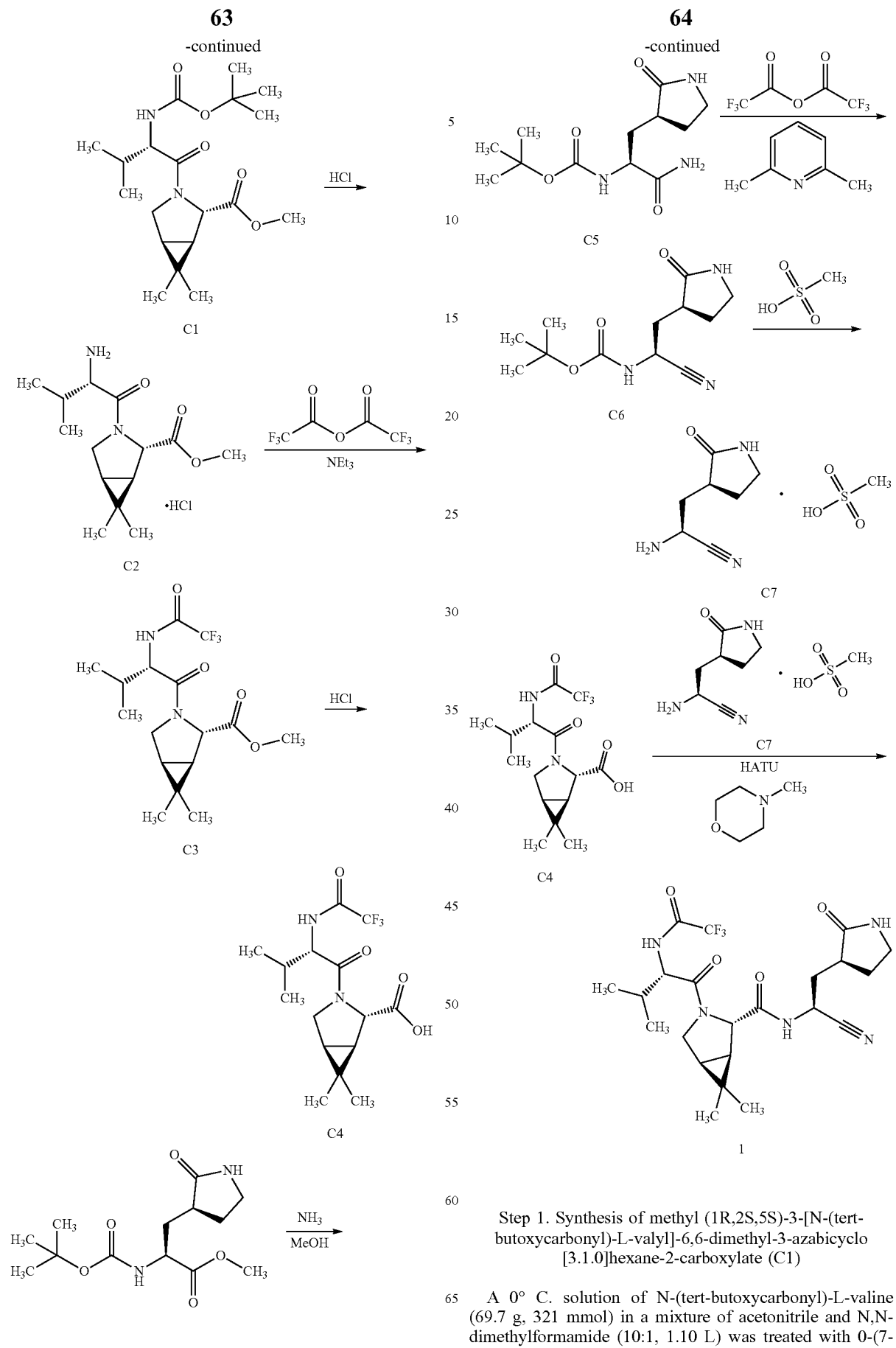
Step 1. Synthesis of methyl (1R,2S,5S)-3-[N-(tert-butoxycarbonyl)-L-valyl]-6,6-dimethyl-3-azabicyclo[3.1.0]hexane-2-carboxylate (C1)
A 0° C. solution of N-(tert-butoxycarbonyl)-L-valine (69.7 g, 321 mmol) in a mixture of acetonitrile and N,N-dimethylformamide (10:1, 1.10 L) was treated with O-(7- azabenzotriazol-1-yl)-N,N,N',N'-tetramethyluronium hexafluorophosphate (HATU; 122 g, 321 mmol), followed by N,N-diisopropylethylamine (127 mL, 729 mmol). After the reaction mixture had been stirred for 5 minutes, methyl (1R,2S,5S)-6,6-dimethyl-3-azabicyclo[3.1.0]hexane-2-carboxylate, hydrochloride salt (60.0 g, 292 mmol) was added, and stirring was continued at 0° C. for 1 hour. The reaction mixture was then diluted with aqueous citric acid solution (1 N; 50 mL) and water (100 mL), stirred for 2 minutes, and concentrated in vacuo to approximately one-half of the initial volume. The resulting mixture was partitioned between ethyl acetate and water, and the aqueous layer was extracted three times with ethyl acetate. The combined organic layers were then washed three times with water and once with saturated aqueous sodium chloride solution, dried over sodium sulfate, filtered, and concentrated in vacuo. The residue was stirred in a minimal amount of ethyl acetate, and then filtered; the insoluble material was washed with ethyl acetate until it was white. The combined filtrates were concentrated under reduced pressure and then subjected to silica gel chromatography (Eluent: 1:1 ethyl acetate/heptane), affording C1 as a yellow oil. Yield: 109 g, quantitative. LCMS m/z 369.3 [M+H]$^+$. $^1$H NMR (400 MHz, chloroform-d) δ 5.08 (d, J=9.6 Hz, 1H), 4.45 (s, 1H), 4.11 (dd, J=9.7, 7.8 Hz, 1H), 3.95 (d, half of AB quartet, J=10.1 Hz, 1H), 3.86 (dd, component of ABX system, J=10.2, 4.8 Hz, 1H), 3.74 (s, 3H), 2.04-1.93 (m, 1H), 1.50-1.41 (m, 2H), 1.40 (s, 9H), 1.04 (s, 3H), 1.00 (d, J=6.8 Hz, 3H), 0.95 (d, J=6.8 Hz, 3H), 0.93 (s, 3H).

Step 2. Synthesis of methyl (1R,2S,5S)-6,6-dimethyl-3-L-valyl-3-azabicyclo[3.1.0]hexane-2-carboxylate, hydrochloride salt (C2)

A solution of hydrogen chloride in 1,4-dioxane (4 M; 15 mL, 60 mmol) was added to a 0° C. solution of C1 (1.00 g, 2.71 mmol) in ethyl acetate (50 mL). The reaction mixture was stirred at 0° C. for 2 hours, whereupon additional hydrogen chloride in 1,4-dioxane solution (4 M; 10 mL, 40 mmol) was added, and stirring was continued at 0° C. for 3 hours, then at room temperature for 1 hour. The reaction mixture was then treated with a solution of hydrogen chloride in 1,4-dioxane (4 M; 10 mL, 40 mmol) and methanol (15 mL) and allowed to stir overnight at room temperature. Concentration in vacuo afforded C2 as a gum; this material was used in further chemistry without additional purification, and the reaction was assumed to be quantitative. LCMS m/z 269.3 [M+H]$^+$. $^1$H NMR (400 MHz, DMSO-d$_6$) δ 8.24 (br s, 3H), 4.27 (s, 1H), 3.81-3.61 (m, 3H), 3.67 (s, 3H), 2.21-2.06 (m, 1H), 1.63-1.55 (m, 1H), 1.49 (d, component of AB quartet, J=7.6 Hz, 1H), 1.09-0.88 (m, 12H).

Step 3. Synthesis of methyl (1R,2S,5S)-6,6-dimethyl-3-[N-(trifluoroacetyl)-L-valyl]-3-azabicyclo[3.1.0]hexane-2-carboxylate (C3)

Triethylamine (1.55 mL, 11.1 mmol) was added to a 0° C. solution of C2 (1.0 g, 3.3 mmol) in dichloromethane (37 mL), followed by drop-wise addition of trifluoroacetic anhydride (0.57 mL, 4.0 mmol) over 30 minutes. The reaction mixture was stirred at 0° C. for 30 minutes, whereupon it was diluted with dichloromethane (100 mL), washed sequentially with 10% aqueous potassium bisulfate solution (50 mL) and saturated aqueous sodium chloride solution (30 mL), dried over sodium sulfate, filtered, and concentrated in vacuo to provide C3 as a light-yellow oil. Yield: 1.2 g, 3.3 mmol, quantitative. LCMS m/z 365.2 [M+H]$^+$. $^1$H NMR (400 MHz, chloroform-d) δ 7.04 (br d, J=8.8 Hz, 1H), 4.54 (dd, J=8.9, 6.3 Hz, 1H), 4.46 (s, 1H), 3.91 (dd, J=10.1, 5.0 Hz, 1H), 3.80-3.73 (m, 1H), 3.76 (s, 3H), 2.25-2.13 (m, 1H), 1.55-1.47 (m, 2H), 1.09-1.03 (m, 6H), 0.94 (d, J=6.8 Hz, 3H), 0.92 (s, 3H).

Step 4. Synthesis of (1R,2S,5S)-6,6-dimethyl-3-[N-(trifluoroacetyl)-L-valyl]-3-azabicyclo[3.1.0]hexane-2-carboxylic acid (C4)

Concentrated hydrochloric acid (0.57 mL, 6.6 mmol) was added to a solution of C3 (1.25 g, 3.43 mmol) in a mixture of acetic acid (40.8 mL) and water (8.2 mL). The reaction mixture was heated at 55° C. for 3 days, whereupon it was partitioned between water (50 mL) and ethyl acetate (100 mL). The aqueous layer was extracted with ethyl acetate (2×50 mL), and the combined organic layers were washed with saturated aqueous sodium chloride solution (50 mL), dried over sodium sulfate, filtered, and concentrated in vacuo to afford C4 as a white foam. Yield: 1.00 g, 2.85 mmol, 83%. LCMS m/z 351.2 [M+H]$^+$. $^1$H NMR (400 MHz, chloroform-d), characteristic peaks: δ 4.56-4.44 (m, 2H), 2.24-2.12 (m, 1H), [1.66 (d, component of AB quartet, J=7.5 Hz) and 1.59-1.47 (m), total 2H], 1.10-1.01 (m, 6H), 0.96-0.91 (m, 6H).

Step 5. Synthesis of tert-butyl {(2S)-1-amino-1-oxo-3-[(3S)-2-oxopyrrolidin-3-yl]propan-2-yl}carbamate (C5)

A solution of ammonia in methanol (7.0 M; 150 mL, 1.0 mol) was added to a 0° C. solution of methyl N-(tert-butoxycarbonyl)-3-[(3S)-2-oxopyrrolidin-3-yl]-L-alaninate (5.00 g, 17.5 mmol) in methanol (25 mL). After the reaction mixture had been stirred at room temperature for 3 days, it was concentrated in vacuo; the residue was diluted and reconcentrated sequentially with a mixture of ethyl acetate and heptane (1:1, 4×50 mL) followed by heptane (50 mL) to provide C5 as a solid (5.27 g, assumed quantitative) that contained residual solvent. A portion of this material was used in the following step. LCMS m/z 216.2 [(M-2-methylprop-1-ene)+H]$^+$. $^1$H NMR (400 MHz, methanol-d$_4$) δ 4.16-3.96 (m, 1H), 3.40-3.27 (m, 2H, assumed; partially obscured by solvent peak), 2.55-2.42 (m, 1H), 2.35 (dddd, J=12.2, 8.6, 6.8, 3.3 Hz, 1H), 2.03 (dd, J=14.0, 11.0, 4.4 Hz, 1H), 1.93-1.81 (m, 1H), 1.74 (ddd, J=14.2, 10.1, 4.3 Hz, 1H), 1.45 (s, 9H).

Step 6. Synthesis of tert-butyl {(1S)-1-cyano-2-[(3S)-2-oxopyrrolidin-3-yl]ethyl}carbamate (C6)

2,6-Dimethylpyridine (2 mL, 17 mmol) and trifluoroacetic anhydride (0.94 mL, 6.6 mmol) were added to a 0° C. solution of C5 (from the previous step; 1.0 g, 53.3 mmol) in dichloromethane (12 mL). The reaction mixture was stirred at room temperature for 1.5 hours, whereupon it was treated with hydrochloric acid (1 M; 30 mL) and dichloromethane (60 mL). The organic layer was washed sequentially with saturated aqueous sodium chloride solution (30 mL) and saturated aqueous sodium bicarbonate solution (30 mL), dried over sodium sulfate, and concentrated in vacuo; chromatography on silica gel (Gradient: 40% to 100% ethyl acetate in heptane) afforded C6 as a solid. Yield: 737 mg, 2.91 mmol, 88% over 2 steps. LCMS m/z 254.3 [M+H]$^+$. $^1$H NMR (400 MHz, methanol-d$_4$) δ 4.72 (dd, J=9.3, 6.8 Hz, 1H), 3.39-3.27 (m, 2H, assumed; partially obscured by solvent peak), 2.57-2.46 (m, 1H), 2.36 (dddd, J=12.2, 8.6, 6.3, 3.4 Hz, 1H), 2.21 (ddd, J=13.8, 9.3, 5.6 Hz, 1H), 1.92-1.79 (m, 2H), 1.47 (s, 9H).

Step 7. Synthesis of (2S)-2-amino-3-[(3S)-2-oxopyrrolidin-3-yl]propanenitrile, methanesulfonate salt (C7)

To a solution of C6 (317 mg, 1.25 mmol) in 1,1,1,3,3,3-hexafluoropropan-2-ol (3 mL) was added methanesulfonic acid (81.2 µL, 1.25 mmol). After the reaction mixture had been stirred at room temperature for 45 minutes, it was concentrated in vacuo, then repeatedly taken up in a mixture of solvents and reconcentrated: acetonitrile and ethyl acetate (1:1, 2×10 mL) followed by ethyl acetate and heptane (1:1, 2×10 mL). The resulting C7 was obtained as a glass (423 mg), which was free of the nitrile epimer via $^1$H and $^{13}$C NMR analysis. A portion of this material was used in further reactions without additional purification. LCMS m/z 154.2 [M+H]$^+$. $^1$H NMR (400 MHz, methanol-d$_4$) δ 4.78 (t, J=7.3 Hz, 1H), 3.42-3.36 (m, 2H), 2.82-2.68 (m, 1H), 2.70 (s, 3H), 2.50-2.39 (m, 1H), 2.20 (t, J=7.3 Hz, 1H), 2.07-1.80 (m, 2H).

Step 8. Synthesis of (1R,2S,5S)—N-{(1S)-1-cyano-2-[(3S)-2-oxopyrrolidin-3-yl]ethyl}-6,6-dimethyl-3-[N-(trifluoroacetyl)-L-valyl]-3-azabicyclo[3.1.0]hexane-2-carboxamide (1)

A mixture of C7 (from the previous step; 98.8 mg, 50.292 mmol) and C$_4$ (100 mg, 0.285 mmol) in acetonitrile (1.5 mL) was cooled to 0° C. O-(7-Azabenzotriazol-1-yl)-N,N,N',N'-tetramethyluronium hexafluorophosphate (HATU, 97%; 112 mg, 0.286 mmol) was added, followed by a solution of 4-methylmorpholine (94.0 µL, 0.855 mmol) in acetonitrile (0.5 mL), and the reaction mixture was stirred at 0° C. for approximately 2 hours. Saturated aqueous sodium bicarbonate solution (30 mL) was then added to the 0° C. reaction mixture, followed by dichloromethane (50 mL), and the organic layer was washed with hydrochloric acid (1 M; 30 mL). The combined aqueous layers were extracted with dichloromethane (60 mL), whereupon the combined organic layers were dried over sodium sulfate, concentrated in vacuo, and subjected to silica gel chromatography (Gradient: 0% to 20% methanol in ethyl acetate). As the resulting material was judged by NMR and LCMS to be contaminated with an epimer of the product, it was then purified via reversed-phase HPLC (Column: Waters Sunfire C18, 19×100 mm, 5 µm; Mobile phase A: water containing 0.05% trifluoroacetic acid (v/v); Mobile phase B: acetonitrile containing 0.05% trifluoroacetic acid (v/v); Gradient: 5% to 95% B over 8.54 minutes, then 95% B for 1.46 minutes; Flow rate: 25 mL/minute) to afford (1R,2S,5S)—N-{(1S)-1-cyano-2-[(3S)-2-oxopyrrolidin-3-yl]ethyl}-6,6-dimethyl-3-[N-(trifluoroacetyl)-L-valyl]-3-azabicyclo[3.1.0]hexane-2-carboxamide (1). Yield: 14.6 mg, 30.1 µmol, 11%. LCMS m/z 486.5 [M+H]$^+$. Retention time: 2.33 minutes (Analytical conditions. Column: Waters Atlantis C18, 4.6×50 mm, 5 µm; Mobile phase A: water containing 0.05% trifluoroacetic acid (v/v); Mobile phase B: acetonitrile containing 0.05% trifluoroacetic acid (v/v). Gradient: 5% to 95% B over 4.0 minutes, then 95% B for 1.0 minute. Flow rate: 2 mL/minute).

Alternate Synthesis of C$_4$ (1R,2S,5S)-6,6-Dimethyl-3-[N-(trifluoroacetyl)-L-valyl]-3-azabicyclo[3.1.0]hexane-2-carboxylic acid (C4)

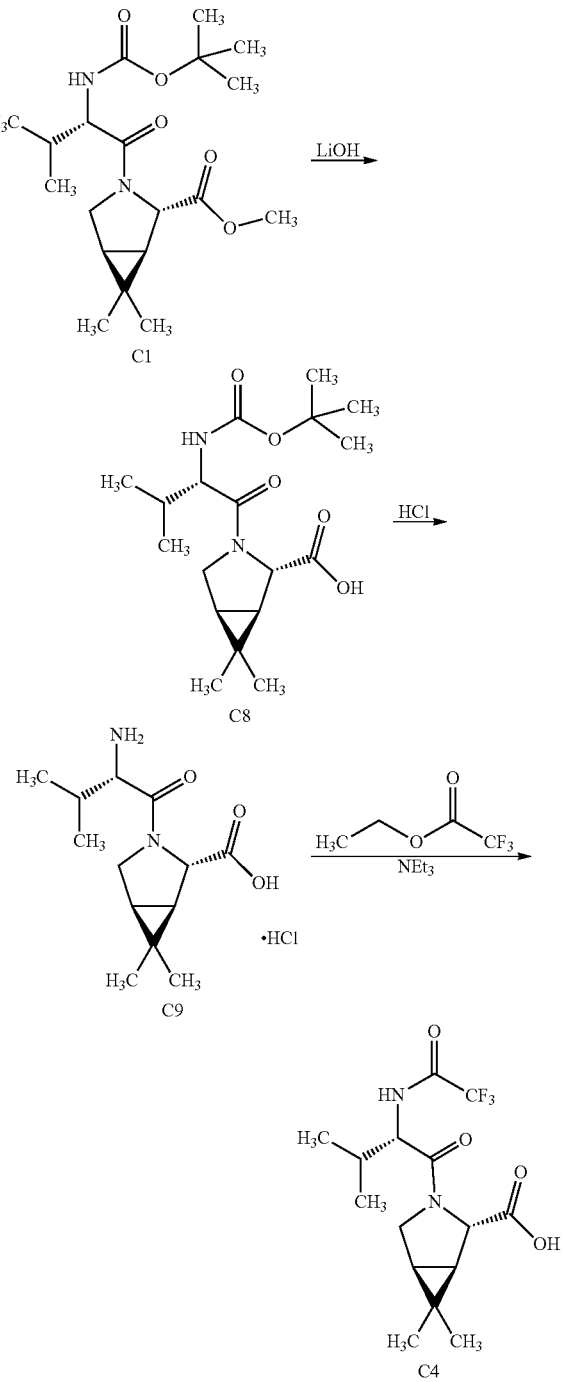

Step 1. Synthesis of (1R,2S,5S)-3-[N-(tert-butoxycarbonyl)-L-valyl]-6,6-dimethyl-3-azabicyclo[3.1.0]hexane-2-carboxylic acid (C8)

An aqueous solution of lithium hydroxide (2.0 M; 436 mL, 872 mmol) was added to a solution of C1 (107 g, 290 mmol) in tetrahydrofuran (730 mL). After the resulting mixture had been stirred at room temperature for approximately 2 hours, it was diluted with water and ethyl acetate, then treated with 1 M aqueous sodium hydroxide solution. The aqueous layer was washed with ethyl acetate, and the combined organic layers were extracted three times with 1 M aqueous sodium hydroxide solution, until LCMS analysis indicated that C8 had been completely removed from the organic layer. Acidification of the combined aqueous layers to pH 2 was carried out by addition of concentrated hydrochloric acid, whereupon the mixture was extracted three times with ethyl acetate. The combined organic layers were washed with saturated aqueous sodium chloride solution, dried over sodium sulfate, filtered, and concentrated; trituration of the residue with heptane afforded C8 as a white solid. Yield: 92.8 g, 262 mmol, 90%. LCMS m/z 355.3 [M+H]$^+$. $^1$H NMR (400 MHz, methanol-$d_4$) δ 4.32 (s, 1H), 4.05 (d, half of AB quartet, J=10.5 Hz, 1H), 4.01 (d, J=9.0 Hz, 1H), 3.88 (dd, component of ABX system, J=10.4, 5.3 Hz, 1H), 2.03-1.91 (m, 1H), 1.57 (dd, component of ABX system, J=7.5, 5.2 Hz, 1H), 1.50 (d, half of AB quartet, J=7.5 Hz, 1H), 1.41 (s, 9H), 1.08 (s, 3H), 0.99 (d, J=6.8 Hz, 3H), 0.97-0.94 (m, 6H).

Step 2. Synthesis of (1R,2S,5S)-6,6-dimethyl-3-L-valyl-3-azabicyclo[3.1.0]hexane-2-carboxylic acid, hydrochloride salt (C9)

To a solution of C8 (82.8 g, 234 mmol) in dichloromethane (230 mL) was added a solution of hydrogen chloride in 1,4-dioxane (4.0 M; 409 mL, 1.64 mol). The reaction mixture was stirred overnight at room temperature, whereupon it was concentrated in vacuo, providing C9 as a white foam. This material was used directly in the following step. LCMS m/z 255.3 [M+H]$^+$. $^1$H NMR (400 MHz, methanol-$d_4$) δ 4.42 (s, 1H), 4.05 (d, J=4.8 Hz, 1H), 3.89 (dd, component of ABX system, J=10.5, 5.2 Hz, 1H), 3.74 (d, half of AB quartet, J=10.5 Hz, 1H), 2.36-2.25 (m, 1H), 1.62 (dd, component of ABX system, J=7.5, 5.1 Hz, 1H), 1.57 (d, half of AB quartet, J=7.6 Hz, 1H), 1.16 (d, J=7.0 Hz, 3H), 1.10 (s, 3H), 1.04 (d, J=6.9 Hz, 3H), 1.01 (s, 3H).

Step 3. Synthesis of (1R,2S,5S)-6,6-dimethyl-3-[N-(trifluoroacetyl)-L-valyl]-3-azabicyclo[3.1.0]hexane-2-carboxylic acid (C4)

A solution of C9 (from the previous step, 5234 mmol) in methanol (230 mL) was cooled to 0° C., treated with triethylamine (66.7 mL, 479 mmol), and stirred for 5 minutes, whereupon ethyl trifluoroacetate (36.1 mL, 303 mmol) was slowly added. After the reaction mixture had been allowed to stir at room temperature for 90 minutes, it was concentrated in vacuo. The residue was diluted with water, 1 M aqueous sodium hydroxide solution, and ethyl acetate, and the resulting organic layer was extracted twice with 1 M aqueous sodium hydroxide solution. The combined aqueous layers were acidified to pH 2 by addition of 1 M hydrochloric acid, then extracted three times with ethyl acetate. The combined organic layers were washed with water and with saturated aqueous sodium chloride solution, dried over sodium sulfate, filtered, and concentrated in vacuo, affording C4 as a white foam. Yield: 73.4 g, 210 mmol, 90% over 2 steps. LCMS m/z 351.3 [M+H]$^+$. $^1$H NMR (400 MHz, DMSO-$d_6$) δ 12.65 (v br s, 1H), 9.82 (d, J=7.7 Hz, 1H), 4.16 (dd, J=9.9, 7.9 Hz, 1H), 4.12 (s, 1H), 3.86 (d, half of AB quartet, J=10.4 Hz, 1H), 3.81 (dd, component of ABX system, J=10.5, 5.0 Hz, 1H), 2.18-2.05 (m, 1H), 1.54 (dd, component of ABX system, J=7.7, 4.6 Hz, 1H), 1.42 (d, half of AB quartet, J=7.5 Hz, 1H), 1.02 (s, 3H), 0.95 (d, J=6.7 Hz, 3H), 0.89 (d, J=6.6 Hz, 3H), 0.84 (s, 3H).

Alternate Synthesis of Example 1 (1R,2S,5S)—N-{(1S)-1-Cyano-2-[(3S)-2-oxopyrrolidin-3-yl]ethyl}-6,6-dimethyl-3-[N-(trifluoroacetyl)-L-valyl]-3-azabicyclo[3.1.0]hexane-2-carboxamide (1)

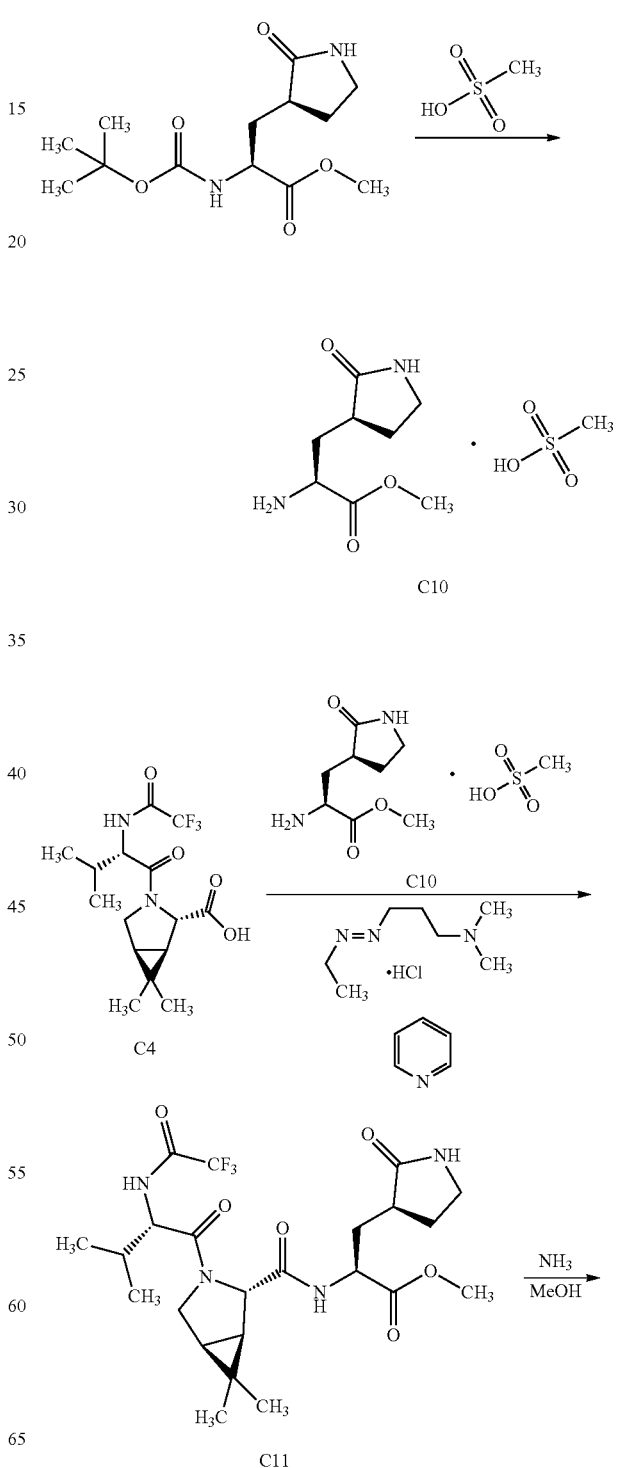

-continued

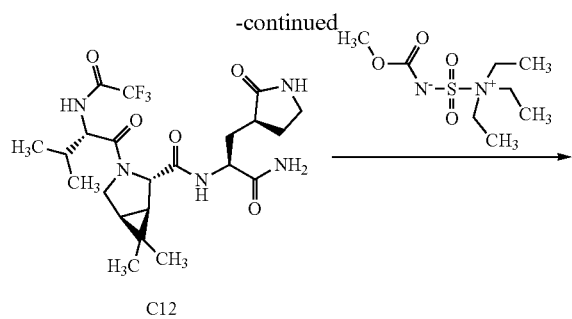

C12

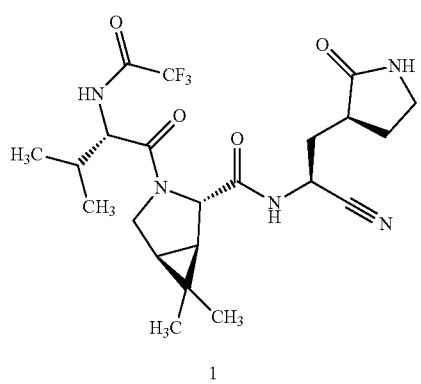

1

Step 1. Synthesis of methyl 3-[(3S)-2-oxopyrrolidin-3-yl]-L-alaninate, methanesulfonate salt (C10)

To a solution of methyl N-(tert-butoxycarbonyl)-3-[(3S)-2-oxopyrrolidin-3-yl]-L-alaninate (10.1 g, 35.3 mmol) in 1,1,1,3,3,3-hexafluoropropan-2-ol (70 mL) was added methanesulfonic acid (2.30 mL, 35.4 mmol). After the reaction mixture had been stirred at room temperature for 70 minutes, LCMS analysis indicated that the starting material had been converted to C10: LCMS m/z 187.2 [M+H]$^+$. The reaction mixture was concentrated in vacuo, and the residue was redissolved twice, followed by concentration under reduced pressure, in a mixture of acetonitrile and ethyl acetate (1:1, 2×20 mL). The resulting material was taken up in a mixture of acetonitrile and ethyl acetate (1:1, 30 mL), concentrated, then twice redissolved in ethyl acetate (2×40 mL) and concentrated. The residue was triturated with ethyl acetate (60 mL) to afford C10. Yield: 9.87 g, 35.0 mmol, 99%. $^1$H NMR (400 MHz, methanol-d$_4$) δ 4.22 (dd, J=9.7, 3.6 Hz, 1H), 3.86 (s, 3H), 3.41-3.36 (m, 2H), 2.84-2.74 (m, 1H), 2.70 (s, 3H), 2.41 (dddd, J=12.3, 8.6, 5.1, 3.6 Hz, 1H), 2.25 (ddd, J=15.1, 4.5, 3.6 Hz, 1H), 1.98 (ddd, J=15.1, 9.6, 9.6 Hz, 1H), 1.87 (dddd, J=12.6, 10.9, 9.2, 9.2 Hz, 1H).

Step 2. Synthesis of methyl N-({(1R,2S,5S)-6,6-dimethyl-3-[N-(trifluoroacetyl)-L-valyl]-3-azabicyclo[3.1.0]hexan-2-yl}carbonyl)-3-[(3S)-2-oxopyrrolidin-3-yl]-L-alaninate (C11)

To a 0° C. solution of C10 (2.76 g, 9.78 mmol) and C4 (3.43 g, 9.79 mmol) in acetonitrile (40 mL) was added 1-[3-(dimethylamino)propyl]-3-ethylcarbodiimide hydrochloride (1.88 g, 9.81 mmol), followed by drop-wise addition of pyridine (2.37 mL, 29.3 mmol). The reaction mixture was stirred at 0° C. for 2.25 hours, whereupon it was treated with hydrochloric acid (1 M; 50 mL) and extracted with ethyl acetate (150 mL). The organic layer was washed sequentially with saturated aqueous sodium chloride solution (50 mL), saturated aqueous sodium bicarbonate solution (50 mL), and saturated aqueous sodium chloride solution (50 mL), dried over sodium sulfate, filtered, and concentrated in vacuo. The residue was taken up in methyl tert-butyl ether (30 mL) and concentrated under reduced pressure, and the resulting glass was stirred with methyl tert-butyl ether (50 mL) at room temperature overnight. After filtration, the filter cake was washed with methyl tert-butyl ether (3×6 mL) to afford C11 as a solid, which by $^1$H NMR analysis contained substantial residual methyl tert-butyl ether. A portion of this material was used in the following step. Yield: 3.74 g; corrected for residual methyl tert-butyl ether: 2.94 g, 5.67 mmol, 58%. LCMS m/z 519.5 [M+H]$^+$. $^1$H NMR (400 MHz, methanol-d$_4$) δ 4.55 (dd, J=12.0, 3.8 Hz, 1H), 4.34 (s, 1H), 4.29 (d, J=9.6 Hz, 1H), 3.97 (d, J=3.1 Hz, 2H), 3.74 (s, 3H), 3.37-3.23 (m, 2H, assumed; partially obscured by solvent peak), 2.73-2.62 (m, 1H), 2.32 (dddd, J=12.4, 8.8, 6.7, 2.4 Hz, 1H), 2.21-2.10 (m, 2H), 1.86-1.74 (m, 2H), 1.60 (dt, component of ABX2 system, J=7.7, 3.1 Hz, 1H), 1.49 (d, half of AB quartet, J=7.6 Hz, 1H), 1.09 (s, 3H), 1.02 (d, J=6.9 Hz, 3H), 0.99-0.95 (m, 6H).

Step 3. Synthesis of (1R,2S,5S)—N-{(2S)-1-amino-1-oxo-3-[(3S)-2-oxopyrrolidin-3-yl]propan-2-yl}-6,6-dimethyl-3-[N-(trifluoroacetyl)-L-valyl]-3-azabicyclo[3.1.0]hexane-2-carboxamide (C12)

A solution of ammonia in methanol (7.0 M; 5 mL, 40 mmol) was added to a solution of C11 (from the previous step: 205 mg, 0.311 mmol) in methanol (1 mL). The resulting solution was stirred at room temperature for 1.5 hours, whereupon a solution of ammonia in methanol (7.0 M; 5 mL, 40 mmol) was again added, and stirring was continued overnight. The reaction mixture was then treated for a third time with the same quantity of ammonia in methanol; after a further 8 hours of reaction, it was concentrated in vacuo. The residue was diluted and reconcentrated sequentially with ethyl acetate (2×20 mL) and a mixture of ethyl acetate and heptane (1:1, 2×20 mL). The resulting material was dissolved in dichloromethane (50 mL), washed with hydrochloric acid (1 M; 30 mL) and with saturated aqueous sodium chloride solution (30 mL), dried over sodium sulfate, filtered, and concentrated in vacuo to provide C12 as a solid. Yield: 87 mg, 0.17 mmol, 55%. LCMS m/z 504.5 [M+H]$^+$. $^1$H NMR (400 MHz, methanol-d$_4$) δ 8.68 (d, J=7.9 Hz, <1H, incompletely exchanged with solvent), 4.44 (ddd, J=11.9, 7.9, 4.0 Hz, 1H), 4.37-4.26 (m, 2H), 4.01 (dd, component of ABX system, J=10.3, 5.1 Hz, 1H), 3.94 (d, half of AB quartet, J=10.2 Hz, 1H), 3.39-3.24 (m, 2H, assumed; largely obscured by solvent peak), 2.72-2.62 (m, 1H), 2.38-2.28 (m, 1H), 2.21-2.08 (m, 2H), 1.90-1.72 (m, 2H), 1.58 (dd, component of ABX system, J=7.5, 5 Hz, 1H), 1.54 (d, half of AB quartet, J=7.7 Hz, 1H), 1.08 (s, 3H), 1.02 (d, J=6.7 Hz, 3H), 0.97 (d, J=6.7 Hz, 3H), 0.96 (s, 3H).

Step 4. Synthesis of (1R,2S,5S)—N-{(1S)-1-cyano-2-[(3S)-2-oxopyrrolidin-3-yl]ethyl}-6,6-dimethyl-3-[N-(trifluoroacetyl)-L-valyl]-3-azabicyclo[3.1.0]hexane-2-carboxamide (1)

Methyl N-(triethylammoniosulfonyl)carbamate, inner salt (Burgess reagent; 88.4 mg, 0.371 mmol) was added to a solution of C12 (85.0 mg, 0.17 mmol) in dichloromethane (4.0 mL), and the reaction mixture was stirred at room temperature. After 3 hours, methyl N-(triethylammoniosulfonyl)carbamate, inner salt (Burgess reagent; 20 mg, 84 μmol) was again added; 30 minutes later, the reaction mixture was diluted with ethyl acetate (60 mL), washed sequentially with hydrochloric acid (1 M; 30 mL), saturated aqueous sodium bicarbonate solution (30 mL), and saturated aqueous sodium chloride solution (30 mL), dried over sodium sulfate, filtered, and concentrated in vacuo. The residue was taken up in heptane and reconcentrated before being purified via silica gel chromatography (Gradient: 0% to 5% methanol in ethyl acetate). (1R,2S,5S)—N-{(1S)-1-Cyano-2-[(3S)-2-oxopyrrolidin-3-yl]ethyl}-6,6-dimethyl-3-[N-(trifluoroacetyl)-L-valyl]-3-azabicyclo[3.1.0]hexane-2-carboxamide (1) was isolated as a solid. Yield: 35 mg, 72 μmol, 42%. LCMS m/z 486.5 [M+H]$^+$. $^1$H NMR (400 MHz, methanol-d$_4$) δ 5.04 (dd, J=10.7, 5.4 Hz, 1H), 4.28 (d, J=9.6 Hz, 1H), 4.25 (s, 1H), 4.03-3.94 (m, 2H), 3.35-3.23 (m, 2H, assumed; largely obscured by solvent peak), 2.72-2.62 (m, 1H), 2.37-2.26 (m, 2H), 2.19-2.08 (m, 1H), 1.93-1.75 (m, 2H), 1.64 (ddd, J=7.6, 4.2, 2.1 Hz, 1H), 1.41 (d, J=7.6 Hz, 1H), 1.09 (s, 3H), 1.02 (d, J=6.8 Hz, 3H), 1.00-0.95 (m, 6H).

Example 2

N-{(1S)-1-Cyano-2-[(3S)-2-oxopyrrolidin-3-yl]ethyl}-4-methyl-N$^2$-(pyrrolidin-1-ylacetyl)-L-leucinamide, trifluoroacetate salt (2)

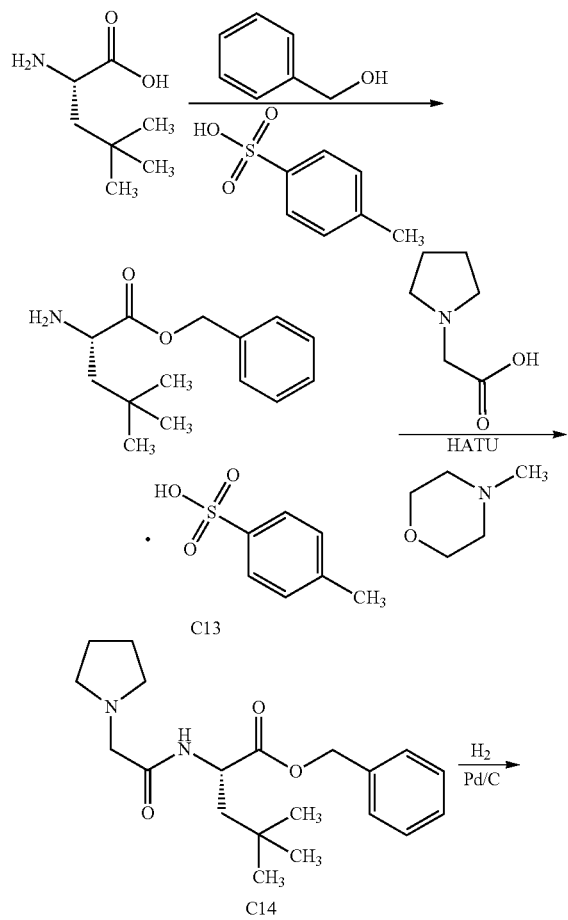

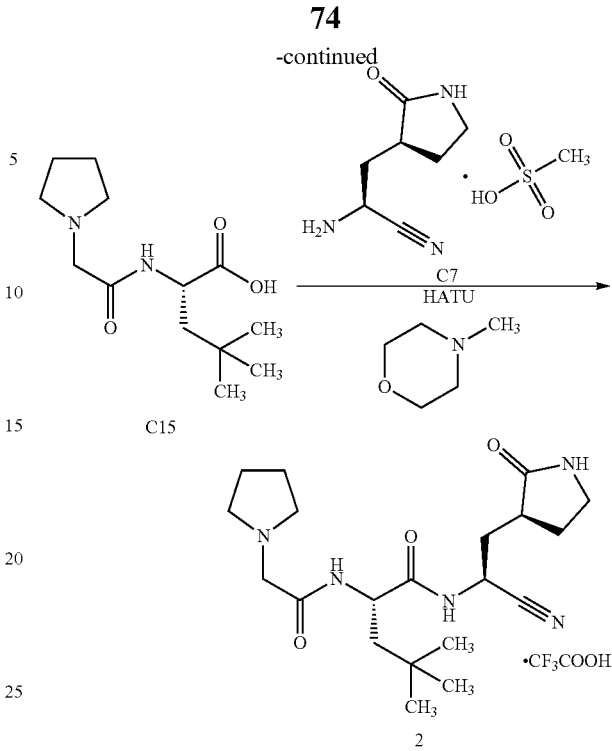

Step 1. Synthesis of benzyl 4-methyl-L-leucinate, p-toluenesulfonic acid salt (C13)

A suspension of 4-methyl-L-leucine (9.5 g, 65 mmol), benzyl alcohol (28.3 g, 262 mmol), and p-toluenesulfonic acid monohydrate (14.9 g, 78.3 mmol) in toluene (200 mL) was heated at reflux overnight; a Dean-Stark trap was employed to azeotropically remove the resulting water. The reaction mixture was then concentrated in vacuo, whereupon the residue was diluted with diethyl ether (200 mL) and ethyl acetate (100 mL). The resulting suspension was stirred for 1.5 hours and filtered; the filter cake was washed with diethyl ether to provide C13 as a white solid. Yield: 24.9 g, 61.1 mmol, 94%. LCMS m/z 236.3 [M+H]$^+$. $^1$H NMR (400 MHz, DMSO-d$_6$) δ 8.30 (br s, 3H), 7.47 (d, J=8.1 Hz, 2H), 7.44-7.36 (m, 5H), 7.11 (d, J=7.8 Hz, 2H), 5.23 (AB quartet, J$_{AB}$=12.3 Hz, Δv$_{AB}$=13.7 Hz, 2H), 4.02 (dd, J=7.3, 4.5 Hz, 1H), 2.29 (s, 3H), 1.81 (dd, J=14.5, 7.3 Hz, 1H), 1.57 (dd, J=14.5, 4.6 Hz, 1H), 0.90 (s, 9H).

Step 2. Synthesis of benzyl 4-methyl-N-(pyrrolidin-1-ylacetyl)-L-leucinate (C14)

A 0° C. mixture of C13 (800 mg, 1.96 mmol) and pyrrolidin-1-ylacetic acid (254 mg, 1.97 mmol) in N,N-dimethylformamide (4 mL) was treated with 0-(7-azabenzotriazol-1-yl)-N,N,N',N'-tetramethyluronium hexafluorophosphate (HATU; 746 mg, 1.96 mmol), followed by a solution of 4-methylmorpholine (0.496 mL, 4.51 mmol) in dichloromethane (1 mL). After the reaction mixture had been stirred at 0° C. for 2 hours, saturated aqueous sodium bicarbonate solution (30 mL) was added at 0° C.; the resulting mixture was extracted with ethyl acetate (2×60 mL), and the combined organic layers were dried over sodium sulfate, filtered, and concentrated in vacuo. Purification via silica gel chromatography was carried out twice (Gradient: 0% to 20% ethyl acetate in heptane, followed by a second chromatographic purification using 0% to 10% ethyl acetate in heptane), to afford C14 as a gum (761 mg). This material was used directly in the following step. LCMS m/z 347.4 [M+H]+. 1H NMR (400 MHz, methanol-$d_4$) δ 7.40-7.29 (m, 5H), 5.16 (AB quartet, $J_{AB}$=12.2 Hz, $\Delta v_{AB}$=11.1 Hz, 2H), 4.56 (dd, J=9.0, 3.1 Hz, 1H), 3.76 (AB quartet, $J_{AB}$=15.6 Hz, $\Delta v_{AB}$=13.6 Hz, 2H), 3.17-3.06 (m, 4H), 2.03-1.93 (m, 4H), 1.81 (dd, J=14.5, 3.1 Hz, 1H), 1.60 (dd, J=14.5, 9.0 Hz, 1H), 0.95 (s, 9H).

Step 3. Synthesis of 4-methyl-N-(pyrrolidin-1-ylacetyl)-L-leucine (C15)

To a solution of C14 (from the previous step; 760 mg, ≤1.96 mmol) in methanol (5 mL) was added palladium on carbon (76.0 mg). The reaction mixture was stirred at room temperature under hydrogen (50 psi) overnight, whereupon LCMS analysis indicated conversion to C15: LCMS m/z 257.4 [M+H]+. The reaction mixture was filtered twice through a 0.15 μm filter, and the filtrate was concentrated in vacuo. The residue was twice dissolved in a mixture of ethyl acetate and heptane (1:1, 2×20 mL), followed by concentration under reduced pressure; this provided C15 as a solid (646 mg). Portions of this material were used in subsequent chemistry without further purification. 1H NMR (400 MHz, DMSO-$d_6$) δ 8.46 (d, J=8.3 Hz, 1H), 4.31 (ddd, J=8.9, 8.6, 3.0 Hz, 1H), 3.74-3.60 (m, 2H), 3.00 br (s, 4H), 1.90-1.79 (m, 4H), 1.70 (dd, component of ABX system, J=14.3, 3.0 Hz, 1H), 1.56 (dd, component of ABX system, J=14.3, 9.2 Hz, 1H), 0.90 (s, 9H).

Step 4. Synthesis of N-{(1S)-1-cyano-2-[(3S)-2-oxopyrrolidin-3-yl]ethyl}-4-methyl-N²-(pyrrolidin-1-ylacetyl)-L-leucinamide, trifluoroacetate salt (2)

A mixture of C15 (from the previous step; 30 mg, 591 μmol) and C7 (from Step 7 of Example 1; 35.3 mg, 50.104 mmol) in N,N-dimethylformamide (1 mL) was cooled to 0° C. and treated with 0-(7-azabenzotriazol-1-yl)-N,N,N',N'-tetramethyluronium hexafluorophosphate (HATU, 97%; 39.9 mg, 0.102 mmol), followed by a solution of 4-methylmorpholine (28.0 μL, 0.255 mmol) in dichloromethane (0.25 mL). After the reaction mixture had been stirred at 0° C. for about 1.5 hours, it was diluted with saturated aqueous sodium bicarbonate solution (3 mL) at 0° C. and extracted with dichloromethane (4×4 mL). The combined organic layers were concentrated in vacuo and purified via reversed-phase HPLC (Column: Waters Sunfire C18, 19×100 mm, 5 μm; Mobile phase A: water containing 0.05% trifluoroacetic acid (v/v); Mobile phase B: acetonitrile containing 0.05% trifluoroacetic acid (v/v); Gradient: 5% to 25% B over 8.5 minutes, then 25% to 95% acetonitrile over 0.5 minutes, then 95% B for 1.0 minute; Flow rate: 25 mL/minute) to afford N-{(1S)-1-cyano-2-[(3S)-2-oxopyrrolidin-3-yl]ethyl}-4-methyl-N²-(pyrrolidin-1-ylacetyl)-L-leucinamide, trifluoroacetate salt (2) as a gum. Yield: 8.1 mg, 16 μmol, 18% over 3 steps. LCMS m/z 392.6 [M+H]+. Retention time: 1.47 minutes (Analytical conditions. Column: Waters Atlantis C18, 4.6×50 mm, 5 μm; Mobile phase A: water containing 0.05% trifluoroacetic acid (v/v); Mobile phase B: acetonitrile containing 0.05% trifluoroacetic acid (v/v). Gradient: 5% to 95% B over 4.0 minutes, then 95% B for 1.0 minute. Flow rate: 2 mL/minute).

Example 3

N-{(1S)-1-Cyano-2-[(3S)-2-oxopyrrolidin-3-yl]ethyl}-N²-(2,6-dichlorobenzoyl)-4-methyl-L-leucinamide (3)

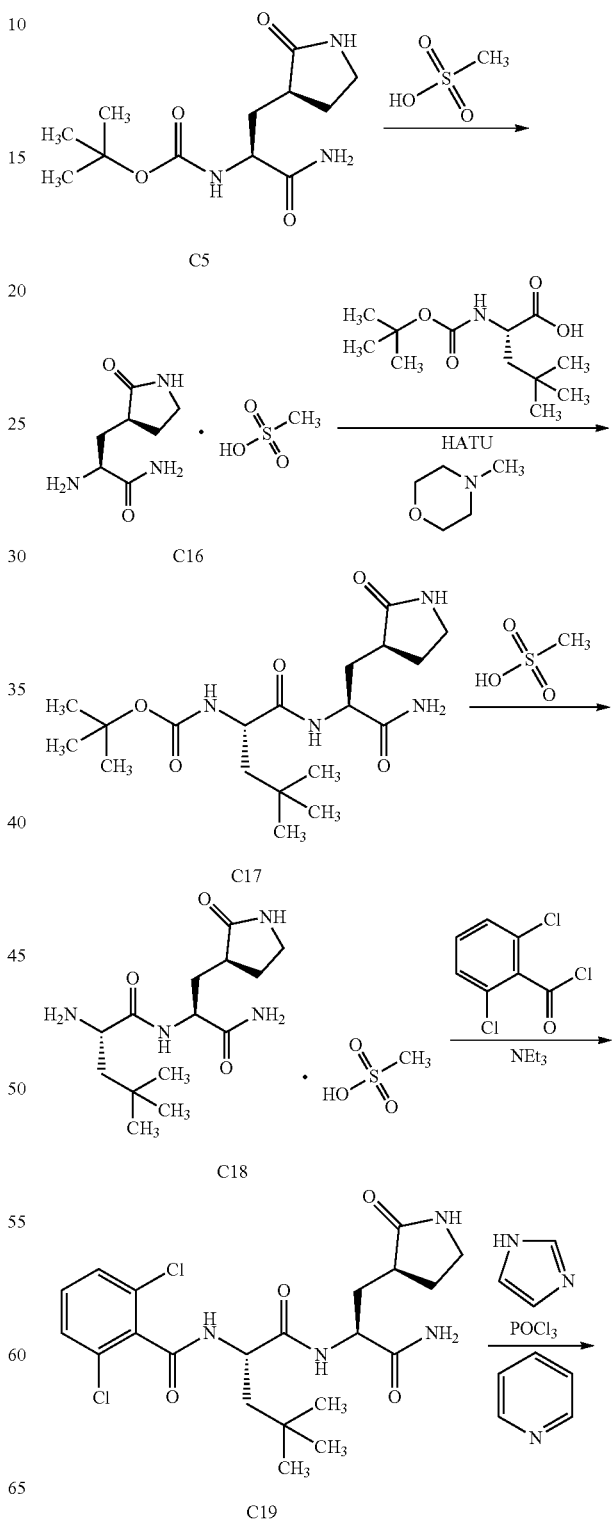

-continued

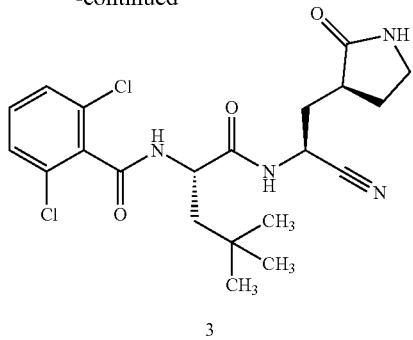

3

Step 1. Synthesis of 3-[(3S)-2-oxopyrrolidin-3-yl]-L-alaninamide, methanesulfonate salt, (C16)

To a solution of C5 (6.13 g, 519 mmol) in 1,1,1,3,3,3-hexafluoropropan-2-ol (40 mL) was added methanesulfonic acid (1.83 g, 19 mmol). The reaction mixture was stirred at room temperature for 1 hour, whereupon it was concentrated in vacuo, resuspended in a mixture of toluene and heptane, and concentrated once more, providing a hygroscopic glass (7.47 g). A portion of this material (6.47 g) was diluted and reconcentrated sequentially with the following: a mixture of dichloromethane and ethanol (2:3, 2×50 mL); ethyl acetate and ethanol (2:3, 50 mL); ethyl acetate, heptane, and dichloromethane (4:4:1, 2×50 mL). The resulting material was dissolved in a mixture of acetonitrile and water (1:1, 22 mL) and lyophilized for 2 days to afford C16 as a glass. Yield: 3.23 g, 12.1 mmol, 73% over 2 steps. LCMS m/z 172.2 [M+H]$^+$. $^1$H NMR (400 MHz, methanol-$d_4$) δ 4.03 (dd, J=9.1, 4.6 Hz, 1H), 3.43-3.35 (m, 2H), 2.82-2.72 (m, 1H), 2.71 (s, 3H), 2.49-2.38 (m, 1H), 2.12-1.96 (m, 2H), 1.94-1.81 (m, 1H).

Step 2. Synthesis of N-(tert-butoxycarbonyl)-4-methyl-L-leucyl-3-[(3S)-2-oxopyrrolidin-3-yl]-L-alaninamide (C17)

A 0° C. solution of C16 (1.34 g, 5.02 mmol) and N-(tert-butoxycarbonyl)-4-methyl-L-leucine (1.28 g, 5.22 mmol) in N,N-dimethylformamide (7.0 mL) was treated with 0-(7-azabenzotriazol-1-yl)-N,N,N',N'-tetramethyluronium hexafluorophosphate (HATU, 97%; 2.04 g, 5.20 mmol), followed by a solution of 4-methylmorpholine (1.43 mL, 13.0 mmol) in dichloromethane (3 mL). After the reaction mixture had been stirred at 0° C. for 2.25 hours, it was quenched at 0° C. by addition of hydrochloric acid (1 M; 30 mL) and then diluted with dichloromethane (50 mL). The organic layer was washed with saturated aqueous sodium bicarbonate solution (30 mL), and the combined aqueous layers were extracted with dichloromethane (60 mL). The combined organic layers were dried over sodium sulfate, filtered, concentrated in vacuo, and suspended/concentrated with heptane (3×10 mL). Purification of the residue via silica gel chromatography (Gradient: 0% to 20% methanol in ethyl acetate) afforded C17 as a solid. Yield: 1.42 g, 3.56 mmol, 71%. LCMS m/z 399.4 [M+H]$^+$. $^1$H NMR (400 MHz, methanol-$d_4$) δ 6.83 (d, J=7.4 Hz, <1H, incompletely exchanged with solvent), 4.43 (dd, J=11.2, 4.2 Hz, 1H), 4.11-4.05 (m, 1H), 3.38-3.24 (m, 2H, assumed; partially obscured by solvent peak), 2.52-2.41 (m, 1H), 2.40-2.30 (m, 1H), 2.13 (ddd, J=14.0, 11.2, 4.5 Hz, 1H), 1.91-1.75 (m, 2H), 1.71 (dd, component of ABX system, J=14.4, 3.2 Hz, 1H), 1.51 (dd, component of ABX system, J=14.4, 9.3 Hz, 1H), 1.45 (s, 9H), 0.97 (s, 9H).

Step 3. Synthesis of 4-methyl-L-leucyl-3-[(3S)-2-oxopyrrolidin-3-yl]-L-alaninamide, methanesulfonate salt (C18)

Methanesulfonic acid (32.6 µL, 0.502 mmol) was added to a solution of C17 (200 mg, 0.502 mmol) in 1,1,1,3,3,3-hexafluoropropan-2-ol (1.5 mL). The reaction mixture was stirred at room temperature for 40 minutes, whereupon it was concentrated in vacuo, dissolved in ethyl acetate and concentrated once more, providing C18 as a solid (238 mg). Most of this material was used in the following step. LCMS m/z 299.4 [M+H]$^+$. $^1$H NMR (400 MHz, methanol-$d_4$) δ 4.53 (dd, J=10.3, 5.0 Hz, 1H), 3.91 (dd, J=7.6, 5.5 Hz, 1H), 3.41-3.27 (m, 2H, assumed; partially obscured by solvent peak), 2.70 (s, 3H), 2.57-2.47 (m, 1H), 2.41 (dddd, J=12.0, 8.6, 7.0, 3.2 Hz, 1H), 2.15 (ddd, J=14.0, 10.3, 5.0 Hz, 1H), 2.01 (dd, J=14.4, 7.5 Hz, 1H), 1.96-1.85 (m, 1H), 1.78 (ddd, J=14.1, 9.1, 5.0 Hz, 1H), 1.59 (dd, J=14.3, 5.5 Hz, 1H), 1.01 (s, 9H).

Step 4. Synthesis of N-(2,6-dichlorobenzoyl)-4-methyl-L-leucyl-3-[(3S)-2-oxopyrrolidin-3-yl]-L-alaninamide (C19)

A 0° C. suspension of C18 (from the previous step: 234 mg, 50.49 mmol) in dichloromethane (2 mL) was treated with triethylamine (170 µL, 1.2 mmol) followed by dropwise addition of a solution of 2,6-dichlorobenzoyl chloride (130 mg, 0.621 mmol) in dichloromethane (0.2 mL). The reaction mixture was stirred at room temperature for 1 hour, whereupon it was diluted with dichloromethane (60 mL), then washed with hydrochloric acid (1 M; 30 mL) followed by saturated aqueous sodium bicarbonate solution (30 mL). The organic layer was dried over sodium sulfate, filtered, concentrated in vacuo, and subjected to chromatography on silica gel (Gradient: 0% to 30% methanol in ethyl acetate) to afford C19. Yield: 120 mg, 0.255 mmol, 52% over 2 steps. LCMS m/z 471.4 (dichloro isotope pattern observed) [M+H]$^+$. $^1$H NMR (400 MHz, methanol-$d_4$) δ 8.45 (d, J=7.9 Hz, <1H, incompletely exchanged with solvent), 7.45-7.35 (m, 3H), 4.59 (dd, J=7.8, 4.5 Hz, 1H), 4.52-4.44 (m, 1H), 3.37-3.24 (m, 2H, assumed; partially obscured by solvent peak), 2.65-2.55 (m, 1H), 2.37 (dddd, J=12.5, 8.8, 6.6, 2.8 Hz, 1H), 2.19 (ddd, J=13.9, 11.3, 4.5 Hz, 1H), 1.91-1.72 (m, 3H), 1.66 (dd, component of ABX system, J=14.4, 7.8 Hz, 1H), 1.03 (s, 9H).

Step 5. Synthesis of N-{(1S)-1-cyano-2-[(3S)-2-oxopyrrolidin-3-yl]ethyl}-N²-(2,6-dichlorobenzoyl)-4-methyl-L-leucinamide (3)

A solution of C19 (90 mg, 0.19 mmol) and 1H-imidazole (33.8 mg, 0.496 mmol) in pyridine (1 mL) was cooled in an acetonitrile/dry ice bath (−35° C.). To this was added phosphorus oxychloride (0.100 mL, 1.07 mmol), and the reaction mixture was stirred at −30° C. to −20° C. After 30 minutes, pyridine (2 mL) was added to facilitate stirring; after 1 hour, dichloromethane (2 mL) was added for the same reason. At 2 hours of reaction, phosphorus oxychloride (0.100 mL, 1.07 mmol) was again added, and stirring was continued for 30 minutes at −30° C., whereupon the reaction mixture was warmed to 0° C. and stirred for an additional 40 minutes. It was then treated with hydrochloric acid (1 M; 30 mL) and extracted with dichloromethane (2×60 mL). The combined organic layers were dried over sodium sulfate, filtered, concentrated in vacuo, and subjected to silica gel chromatography (Gradient: 0% to 15% methanol in ethyl acetate) to provide a solid (67 mg). This material was combined with the product (12 mg) from a similar reaction carried out using C19 (30 mg, 64 µmol) and twice taken up in ethyl acetate (2×3 mL) followed by concentration under reduced pressure. The residue was stirred with a mixture of ethyl acetate and heptane (1:3, 4 mL) at room temperature for 40 minutes and filtered; the filter cake was washed with a mixture of ethyl acetate and heptane (1:3, 5×2 mL), to provide N-{(1S)-1-cyano-2-[(3S)-2-oxopyrrolidin-3-yl]ethyl}-$N^2$-(2,6-dichlorobenzoyl)-4-methyl-L-leucinamide (3) as a solid. Combined yield: 70 mg, 0.15 mmol, 59%. LCMS m/z 453.3 (dichloro isotope pattern observed) [M+H]$^+$. $^1$H NMR (400 MHz, methanol-d$_4$) δ 7.45-7.34 (m, 3H), 5.05 (dd, J=10.7, 5.4 Hz, 1H), 4.56 (dd, J=7.0, 5.7 Hz, 1H), 3.37-3.23 (m, 2H, assumed; partially obscured by solvent peak), 2.70-2.59 (m, 1H), 2.42-2.29 (m, 2H), 1.95-1.77 (m, 3H), 1.67 (dd, component of ABX system, J=14.4, 7.0 Hz, 1H), 1.04 (s, 9H).

Example 4

N-[(2S)-1-({(1S)-1-Cyano-2-[(3S)-2-oxopyrrolidin-3-yl]ethyl}amino)-4-methyl-1-oxopentan-2-yl]-4-methoxy-1H-indole-2-carboxamide (4)

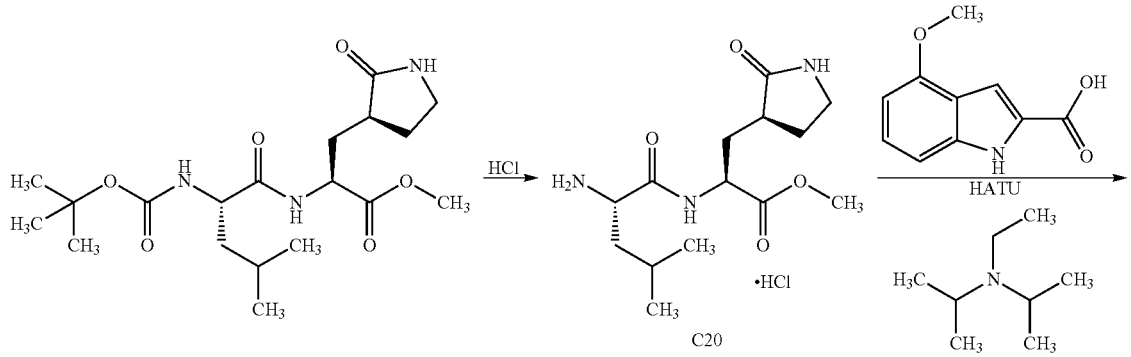

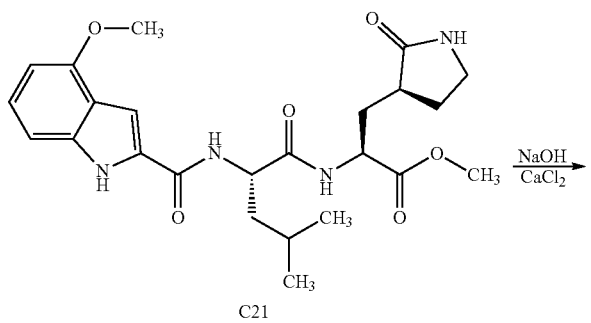

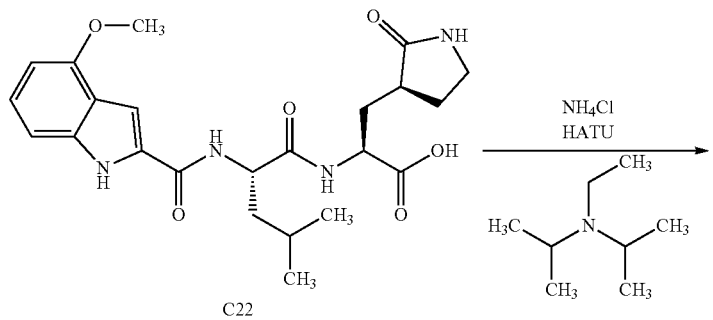

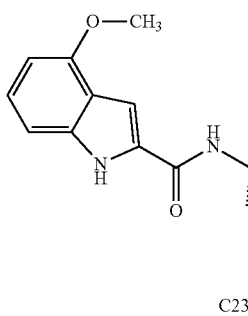
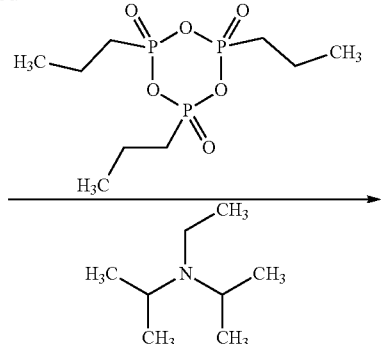

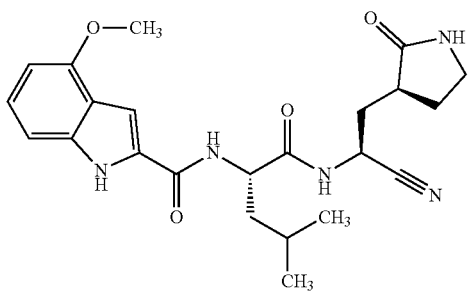

Step 1. Synthesis of methyl L-leucyl-3-[(3S)-2-oxopyrrolidin-3-yl]-L-alaninate, hydrochloride salt (C20)

A solution of methyl N-(tert-butoxycarbonyl)-L-leucyl-3-[(3S)-2-oxopyrrolidin-3-yl]-L-alaninate (see Prior, A. M., et al., Bioorg. Med. Chem. Lett. 2013, 23, 6317-6320; 2.0 g, 5.0 mmol) in a mixture of methanol (2 mL) and a solution of hydrogen chloride in ethyl acetate (4 M; 20 mL) was stirred at 25° C. for 1 hour. Concentration in vacuo afforded C20 as a white solid (1.92 g, assumed quantitative). $^1$H NMR (400 MHz, DMSO-$d_6$), characteristic peaks: δ 9.09-8.98 (m, 1H), 8.39 (br s, 3H), 7.69 (s, 1H), 4.44-4.31 (m, 1H), 3.22-3.07 (m, 2H), 2.5-2.38 (m, 1H, assumed; partially obscured by solvent peak), 2.24-2.11 (m, 1H), 2.11-1.99 (m, 1H), 1.78-1.48 (m, 5H), 0.92 (d, J=6.5 Hz, 3H), 0.89 (d, J=6.5 Hz, 3H).

Step 2. Synthesis of methyl N-(4-methoxy-1H-indole-2-carbonyl)-L-leucyl-3-[(3S)-2-oxopyrrolidin-3-yl]-L-alaninate (C21)

O-(7-Azabenzotriazol-1-yl)-N,N,N',N'-tetramethyluronium hexafluorophosphate (HATU; 494 mg, 1.30 mmol) and N,N-diisopropylethylamine (388 mg, 3.00 mmol) were added to a 0° C. solution of C20 (from a smaller-scale experiment similar to Step 1; 336 mg, 50.840 mmol) and 4-methoxy-1H-indole-2-carboxylic acid (159 mg, 0.832 mmol) in N,N-dimethylformamide (6 mL). The solution was stirred at 0° C. for 1.5 hours, whereupon it was poured into water/ice (10 mL) and extracted with ethyl acetate (3×10 mL). The combined organic layers were washed with saturated aqueous sodium chloride solution, dried over sodium sulfate, filtered, and concentrated in vacuo. Silica gel chromatography (Eluent: 10:1 dichloromethane/methanol) provided $C_{21}$ as a yellow oil. Yield: 380 mg, 0.804 mmol, 97%. LCMS m/z 473.2 [M+H]$^+$. $^1$H NMR (400 MHz, DMSO-$d_6$) δ 11.59-11.53 (m, 1H), 8.53 (d, J=8.0 Hz, 1H), 8.37 (d, J=8.0 Hz, 1H), 7.65 (s, 1H), 7.37-7.33 (m, 1H), 7.09 (dd, J=8, 8 Hz, 1H), 7.00 (d, component of AB quartet, J=8.2 Hz, 1H), 6.50 (d, J=7.6 Hz, 1H), 4.56-4.47 (m, 1H), 4.40-4.31 (m, 1H), 3.88 (s, 3H), 3.62 (s, 3H), 3.18-3.05 (m, 2H), 2.41-2.29 (m, 1H), 2.15-2.03 (m, 2H), 1.78-1.49 (m, 5H), 0.93 (d, J=6.3 Hz, 3H), 0.89 (d, J=6.4 Hz, 3H).

Step 3. Synthesis of N-(4-methoxy-1H-indole-2-carbonyl)-L-leucyl-3-[(3S)-2-oxopyrrolidin-3-yl]-L-alanine (C22)

To a stirring mixture of calcium chloride (0.887 g, 7.99 mmol) and sodium hydroxide (0.168 g, 4.20 mmol) in 2-propanol (7 mL) and water (3 mL) was added C21 (1.8 g, 3.8 mmol). The reaction mixture was stirred at 20° C. for 6 hours, whereupon it was concentrated in vacuo, diluted with water (4 mL), adjusted to pH 4 by addition of 1 M hydrochloric acid, and extracted with ethyl acetate (3×10 mL). The combined organic layers were washed with saturated aqueous sodium chloride solution, dried over sodium sulfate, filtered, and concentrated in vacuo. Silica gel chromatography (Eluent: 10:1:0.1 dichloromethane/methanol/acetic acid) afforded C22 as a yellow solid. Yield: 1.76 g, 3.84 mmol, 100%. LCMS m/z 459.2 [M+H]$^+$. $^1$H NMR (400 MHz, chloroform-d), characteristic peaks: δ 6.51-6.43 (m, 1H), 4.80-4.66 (m, 1H), 4.60-4.45 (m, 1H), 3.92 (s, 3H), 3.36-3.18 (m, 2H), 2.59-2.44 (m, 1H).

Alternate Step 3. Synthesis of N-(4-methoxy-1H-indole-2-carbonyl)-L-leucyl-3-[(3S)-2-oxopyrrolidin-3-yl]-L-alanine (C22)

A solution of C21 (20 mg, 42 μmol) in tetrahydrofuran (0.4 mL) was treated with an aqueous solution containing lithium hydroxide (14.2 mg, 0.593 mmol). After the reaction mixture had been stirred at room temperature for 2.5 hours, it was diluted with ethyl acetate and washed with 10% aqueous potassium bisulfate solution. The organic layer was then dried over sodium sulfate, filtered, and concentrated in vacuo, providing C22 as a white solid. Yield: 20 mg, quantitative. LCMS m/z 459.2 [M+H]$^+$. $^1$H NMR (400 MHz, methanol-d$_4$) δ 7.27 (s, 1H), 7.14 (dd, component of ABX system, J=8, 8 Hz, 1H), 7.02 (d, component of AB quartet, J=8.3 Hz, 1H), 6.50 (d, J=7.7 Hz, 1H), 4.66 (dd, J=9.0, 5.9 Hz, 1H), 4.52 (dd, J=11.7, 3.9 Hz, 1H), 3.92 (s, 3H), 3.30-3.18 (m, 2H), 2.65-2.52 (m, 1H), 2.38-2.26 (m, 1H), 2.21 (ddd, J=14.0, 11.7, 4.1 Hz, 1H), 1.90-1.70 (m, 5H), 1.02 (d, J=6.3 Hz, 3H), 0.99 (d, J=6.3 Hz, 3H).

Step 4. Synthesis of N-(4-methoxy-1H-indole-2-carbonyl)-L-leucyl-3-[(3S)-2-oxopyrrolidin-3-yl]-L-alaninamide (C23)

To a 0° C. solution of C22 (1.76 g, 3.84 mmol) and ammonium chloride (0.246 g, 4.60 mmol) in N,N-dimethylformamide (15 mL) were added O-(7-azabenzotriazol-1-yl)-N,N,N',N'-tetramethyluronium hexafluorophosphate (HATU; 1.90 g, 5.00 mmol) and N,N-diisopropylethylamine (1.49 g, 11.5 mmol). After the reaction mixture had been stirred at 0° C. for 1.5 hours, N,N-diisopropylethylamine (2.3 g, 18 mmol) was used to adjust the pH to 8. The reaction mixture was stirred for an additional 30 minutes, whereupon it was poured into a mixture of hydrochloric acid (1 M; 20 mL, 20 mmol) and ice. The resulting mixture was extracted with ethyl acetate (3×10 mL); the combined organic layers were washed sequentially with hydrochloric acid (1 M; 10 mL) and saturated aqueous sodium chloride solution (10 mL), dried over sodium sulfate, filtered, concentrated in vacuo, and purified via silica gel chromatography (Eluent: 10:1 dichloromethane/methanol), affording C23 as a yellow solid. Yield: 1.09 g, 2.38 mmol, 62%. LCMS m/z 458.0 [M+H]$^+$. $^1$H NMR (400 MHz, DMSO-d$_6$) δ 11.62-11.55 (m, 1H), 8.42 (d, J=7.9 Hz, 1H), 8.04 (d, J=8.4 Hz, 1H), 7.60 (br s, 1H), 7.38-7.26 (m, 2H), 7.10 (dd, component of ABX system, J=8, 8 Hz, 1H), 7.06 (br s, 1H), 7.00 (d, component of AB quartet, J=8.2 Hz, 1H), 6.51 (d, J=7.7 Hz, 1H), 4.54-4.41 (m, 1H), 4.34-4.22 (m, 1H), 3.88 (s, 3H), 3.17-3.01 (m, 2H), 2.31-1.95 (m, 3H), 1.76-1.45 (m, 5H), 0.92 (d, J=6.1 Hz, 3H), 0.88 (d, J=6.3 Hz, 3H).

Step 5. Synthesis of N-[(2S)-1-({(1S)-1-cyano-2-[(3S)-2-oxopyrrolidin-3-yl]ethyl}amino)-4-methyl-1-oxopentan-2-yl]-4-methoxy-1H-indole-2-carboxamide (4)

To a 0° C. mixture of C23 (500 mg, 1.09 mmol) and N,N-diisopropylethylamine (565 mg, 4.37 mmol) in tetrahydrofuran (8 mL) was added 2,4,6-tripropyl-1,3,5,2,4,6-trioxatriphosphinane 2,4,6-trioxide (50% solution by weight in ethyl acetate; 2.78 g, 4.37 mmol). After the reaction mixture had been stirred at 50° C. for 3 hours, it was concentrated in vacuo, diluted with water (5 mL), and extracted with ethyl acetate (3×5 mL). The combined organic layers were washed with saturated aqueous sodium chloride solution, dried over sodium sulfate, filtered, and concentrated in vacuo; silica gel chromatography (Eluent: 10:1 dichloromethane/methanol) followed by reversed-phase HPLC purification (Column: YMC-Actus Triart C18, 50×250 mm, 7 μm; Mobile phase A: water containing 0.225% formic acid; Mobile phase B: acetonitrile; Gradient: 18% to 58% B; Flow rate: 25 mL/minute) afforded N-[(2S)-1-({(1S)-1-cyano-2-[(3S)-2-oxopyrrolidin-3-yl]ethyl}amino)-4-methyl-1-oxopentan-2-yl]-4-methoxy-1H-indole-2-carboxamide (4) as a yellow solid. Yield: 130 mg, 0.296 mmol, 27%. LCMS m/z 440.2 [M+H]$^+$. $^1$H NMR (400 MHz, DMSO-d$_6$) δ 11.58 (br s, 1H), 8.90 (d, J=8.0 Hz, 1H), 8.47 (d, J=7.7 Hz, 1H), 7.71 (br s, 1H), 7.38-7.35 (m, 1H), 7.09 (dd, component of ABX system, J=8, 8 Hz, 1H), 7.00 (d, component of AB quartet, J=8.2 Hz, 1H), 6.51 (d, J=7.7 Hz, 1H), 5.02-4.93 (m, 1H), 4.49-4.40 (m, 1H), 3.88 (s, 3H), 3.19-3.05 (m, 2H), 2.41-2.29 (m, 1H), 2.20-2.06 (m, 2H), 1.85-1.62 (m, 4H), 1.58-1.47 (m, 1H), 0.94 (d, J=6.3 Hz, 3H), 0.89 (d, J=6.3 Hz, 3H).

Alternate Synthesis of Example 4

N-[(2S)-1-({(1S)-1-Cyano-2-[(3S)-2-oxopyrrolidin-3-yl]ethyl}amino)-4-methyl-1-oxopentan-2-yl]-4-methoxy-1H-indole-2-carboxamide (4)

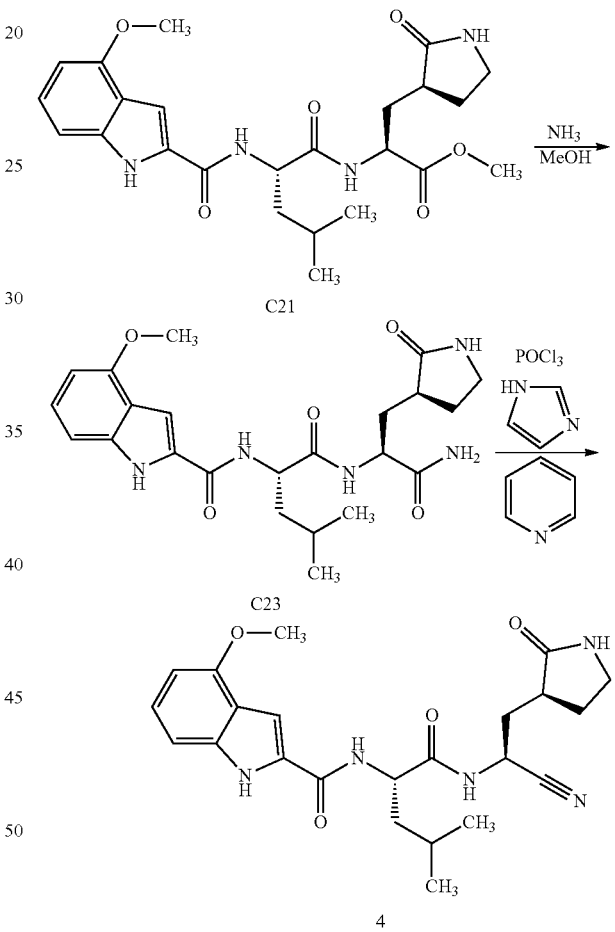

Step 1. Synthesis of N-[(4-methoxy-1H-indol-2-yl)carbonyl]-L-leucyl-3-[(3S)-2-oxopyrrolidin-3-yl]-L-alaninamide (C23)

A solution of ammonia in methanol (7.0 M; 21 mL, 150 mmol) was added to a solution of C21 (500 mg, 1.06 mmol) in methanol (2.0 mL). After the reaction mixture had been stirred at room temperature for 6 hours, a solution of ammonia in methanol (7.0 M; 7.0 mL, 49 mmol) was again added, and stirring was continued overnight. A solution of ammonia in methanol (7.0 M; 7.0 mL, 49 mmol) was again added, and stirring was continued for 24 hours, whereupon a final treatment with a solution of ammonia in methanol (7.0 M; 7.0 mL, 49 mmol) was carried out. The reaction mixture was stirred for one more day, at which point it was concentrated in vacuo. The residue was combined with the product of a similar reaction (350 mg of the 512 mg isolated) carried out using C21 (500 mg, 1.06 mmol), and the mixture was repeatedly dissolved in ethyl acetate (5×10 mL) and concentrated under reduced pressure, providing C23 (835 mg). This material was used directly in the following step. LCMS m/z 458.4 [M+H]$^+$. $^1$H NMR (400 MHz, methanol-d$_4$) δ 7.29 (d, J=0.9 Hz, 1H), 7.15 (dd, component of ABX system, J=8, 8 Hz, 1H), 7.03 (br d, component of AB quartet, J=8.3 Hz, 1H), 6.51 (d, J=7.7 Hz, 1H), 4.59 (dd, J=9.7, 5.0 Hz, 1H), 4.45 (dd, J=11.3, 4.2 Hz, 1H), 3.93 (s, 3H), 3.34-3.19 (m, 2H, assumed; partially obscured by solvent peak), 2.57-2.47 (m, 1H), 2.31 (dddd, J=12.6, 8.5, 6.8, 2.8 Hz, 1H), 2.15 (ddd, J=14.0, 11.4, 4.6 Hz, 1H), 1.88-1.67 (m, 5H), 1.02 (d, J=6.1 Hz, 3H), 0.98 (d, J=6.1 Hz, 3H).

Step 2. Synthesis of N-[(2S)-1-({(1S)-1-cyano-2-[(3S)-2-oxopyrrolidin-3-yl]ethyl}amino)-4-methyl-1-oxopentan-2-yl]-4-methoxy-1H-indole-2-carboxamide (4)

A solution of C23 (from the previous step; 835 mg, ≤1.78 mmol) and 1H-imidazole (323 mg, 4.74 mmol) in a mixture of pyridine (4 mL) and dichloromethane (4 mL) was cooled to −35° C. using an acetonitrile/dry ice bath, whereupon phosphorus oxychloride (0.956 mL, 10.2 mmol) was added in a drop-wise manner over 5 minutes. The reaction was stirred at a temperature between −30° C. and −20° C. for about 1.5 hours, then treated with hydrochloric acid (1 M; 50 mL) and stirred for 1 hour. After extraction with dichloromethane (3×60 mL), the resulting organic layers were combined, dried over sodium sulfate, filtered, and concentrated in vacuo. The residue was combined with purified 4 from a different batch (75 mg, 0.17 mmol) and subjected to silica gel chromatography (Gradient: 0% to 5% methanol in ethyl acetate) to provide 4 as a solid (800 mg). This material was combined with the product (80 mg) from a similar reaction carried out using C23 (161 mg, 0.352 mmol); the resulting material was stirred in diethyl ether (25 mL) for 3 days, whereupon it was filtered. The filter cake was washed with a mixture of diethyl ether and heptane (1:1, 4×2 mL) to afford N-[(2S)-1-({(1S)-1-cyano-2-[(3S)-2-oxopyrrolidin-3-yl]ethyl}amino)-4-methyl-1-oxopentan-2-yl]-4-methoxy-1H-indole-2-carboxamide (4) as a solid. Combined yield: 519 mg, 1.18 mmol, approximately 50% over 2 steps. LCMS m/z 440.5 [M+H]$^+$. $^1$H NMR (400 MHz, DMSO-d$_6$) δ 11.57 (d, J=2.3 Hz, 1H), 8.90 (d, J=8.1 Hz, 1H), 8.46 (d, J=7.7 Hz, 1H), 7.70 (s, 1H), 7.37 (d, J=2.3 Hz, 1H), 7.10 (dd, component of ABX system, J=8, 8 Hz, 1H), 7.00 (d, component of AB quartet, J=8.2 Hz, 1H), 6.51 (d, J=7.7 Hz, 1H), 5.03-4.92 (m, 1H), 4.51-4.39 (m, 1H), 3.88 (s, 3H), 3.19-3.05 (m, 2H), 2.42-2.30 (m, 1H), 2.20-2.06 (m, 2H), 1.80 (ddd, J=13.2, 9.3, 6.7 Hz, 1H), 1.75-1.63 (m, 3H), 1.58-1.47 (m, 1H), 0.94 (d, J=6.2 Hz, 3H), 0.89 (d, J=6.2 Hz, 3H).

Examples 5 and 6

N-[(2S)-1-({(1S)-1-Cyano-2-[(3S)-2-oxopyrrolidin-3-yl]ethyl}amino)-4-methyl-1-oxopentan-2-yl]-4-methoxy-3-(trifluoromethyl)-1H-indole-2-carboxamide (5) and N-[(2S)-1-({(1S)-1-Cyano-2-[(3S)-2-oxopyrrolidin-3-yl]ethyl}amino)-4-methyl-1-oxopentan-2-yl]-4-methoxy-7-(trifluoromethyl)-1H-indole-2-carboxamide (6)

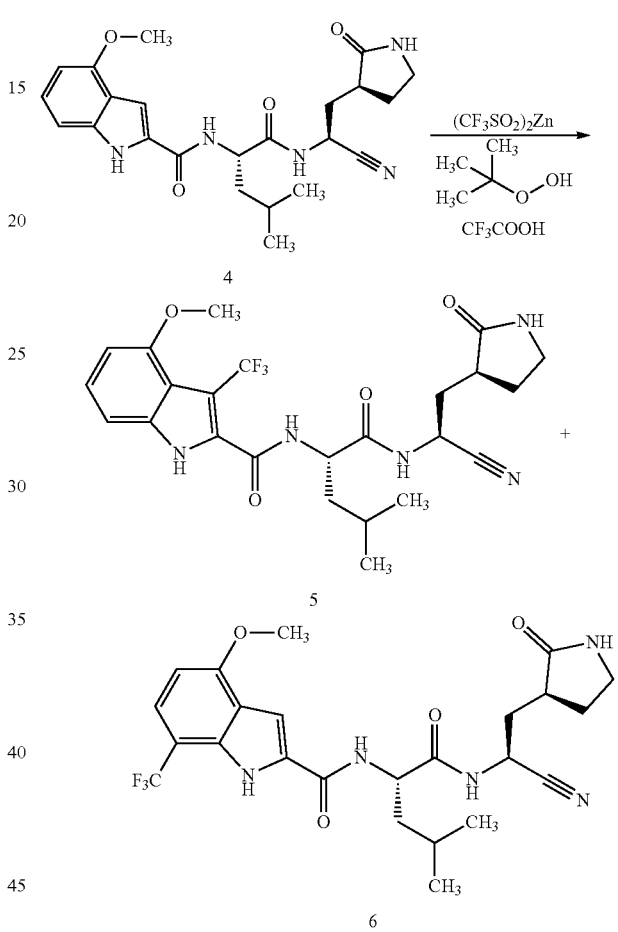

To a pressure release vial containing zinc(II) trifluoromethanesulfinate (98%, 2.44 mg, 7.21 µmol) were sequentially added a solution of 4 (0.79 mg, 1.8 µmol) in dimethyl sulfoxide (60 µL), trifluoroacetic acid (0.56 µL, 7.3 µmol), and tert-butyl hydroperoxide (70% in water; 1.25 uL, 9.03 µmol). The vial was capped and heated to 50° C. overnight, whereupon the reaction mixture was cooled and diluted with acetonitrile and a 1% solution of formic acid in water, to a volume of approximately 2 to 3 mL. The final solvent composition was such that the resulting mixture appeared clear, generally about 20% to 30% acetonitrile. The entire mixture was subjected to reversed-phase HPLC (Column: Phenomenex Luna C18, 10×250 mm, 10 µm; Mobile phase A: 0.5% acetic acid in water; Mobile phase B: 9:1 acetonitrile/methanol; Gradient: 15% B for 5 minutes, then 15% to 70% B linear gradient over 84 minutes, then 70% to 95% B over 1 minute, then 95% B for 9 minutes; Flow rate: 2 mL/min). The eluate was passed through a UV/VIS detector and then was split at approximately 15:1 between a fraction collector and an ion trap mass spectrometer. Fractions were collected every 20 seconds and those potentially containing products of interest were evaluated by UHPLC-UV-HRMS before pooling. The two products eluted at approximately 71 and 75 minutes. The first-eluting product was 5 {N-[(2S)-1-({(1S)-1-cyano-2-[(3S)-2-oxopyrrolidin-3-yl]ethyl}amino)-4-methyl-1-oxopentan-2-yl]-4-methoxy-3-(trifluoromethyl)-1H-indole-2-carboxamide}, and the second-eluting was 6 {N-[(2S)-1-({(1S)-1-cyano-2-[(3S)-2-oxopyrrolidin-3-yl]ethyl}amino)-4-methyl-1-oxopentan-2-yl]-4-methoxy-7-(trifluoromethyl)-1H-indole-2-carboxamide}.

5—Yield: 0.101 mg, 0.199 μmol, 11%. High-resolution MS m/z 508.2171 [M+H]$^+$; calculated for $C_{24}H_{29}F_3N_5O_4$, 508.2172. $^1$H NMR (600 MHz, DMSO-$d_6$) δ 12.22 (br s, 1H), 9.01 (d, J=7.6 Hz, 1H), 8.96 (d, J=7.9 Hz, 1H), 7.73 (s, 1H), 7.21 (dd, J=8, 8 Hz, 1H), 7.08 (d, J=8.2 Hz, 1H), 6.69 (d, J=7.8 Hz, 1H), 5.03-4.95 (m, 1H), 4.49-4.40 (m, 1H), 3.87 (s, 3H), 3.22-3.08 (m, 2H), 2.43-2.34 (m, 1H), 2.23-2.10 (m, 2H), 1.82 (ddd, J=13.7, 9.3, 6.8 Hz, 1H), 1.78-1.66 (m, 2H), 1.62 (ddd, J=14.6, 9.7, 5.2 Hz, 1H), 1.49 (ddd, J=13.8, 8.8, 5.5 Hz, 1H), 0.97-0.88 (m, 6H). Retention time: 8.43 minutes (Analytical conditions. Column: Phenomenex Kinetex XB-C18, 2.1×100 mm, 2.6 μm; Mobile phase A: water containing 0.1% formic acid; Mobile phase B: acetonitrile; Gradient: 5% B for 0.5 minutes, then 5% to 70% B over 10.5 minutes, then 70% to 95% B over 2 minutes; Flow rate: 0.4 mL/min).

6—Yield: 14.7 μg, 0.029 μmol, 1.6%. High-resolution MS m/z 508.2178 [M+H]$^+$; calculated for $C_{24}H_{29}F_3N_5O_4$, 508.2172. $^1$H NMR (600 MHz, DMSO-$d_6$) δ 11.47 (brs, 1H), 9.00 (d, J=7.9 Hz, 1H), 8.79 (d, J=7.8 Hz, 1H), 7.70 (s, 1H), 7.55 (d, J=8.2 Hz, 1H), 7.35 (s, 1H), 6.72 (d, J=8.3 Hz, 1H), 5.02-4.94 (m, 1H), 4.56-4.48 (m, 1H), 3.97 (s, 3H), 3.18-3.05 (m, 2H), 2.39-2.30 (m, 1H), 2.18-2.08 (m, 2H), 1.86-1.77 (m, 1H), 1.75-1.64 (m, 3H), 1.61-1.52 (m, 1H), 0.95 (d, J=6.1 Hz, 3H), 0.90 (d, J=6.1 Hz, 3H). Retention time: 8.92 minutes (Analytical conditions identical to those used for 5).

Alternate Synthesis of Example 6

N-[(2S)-1-({(1S)-1-Cyano-2-[(3S)-2-oxopyrrolidin-3-yl]ethyl}amino)-4-methyl-1-oxopentan-2-yl]-4-methoxy-7-(trifluoromethyl)-1H-indole-2-carboxamide (6)

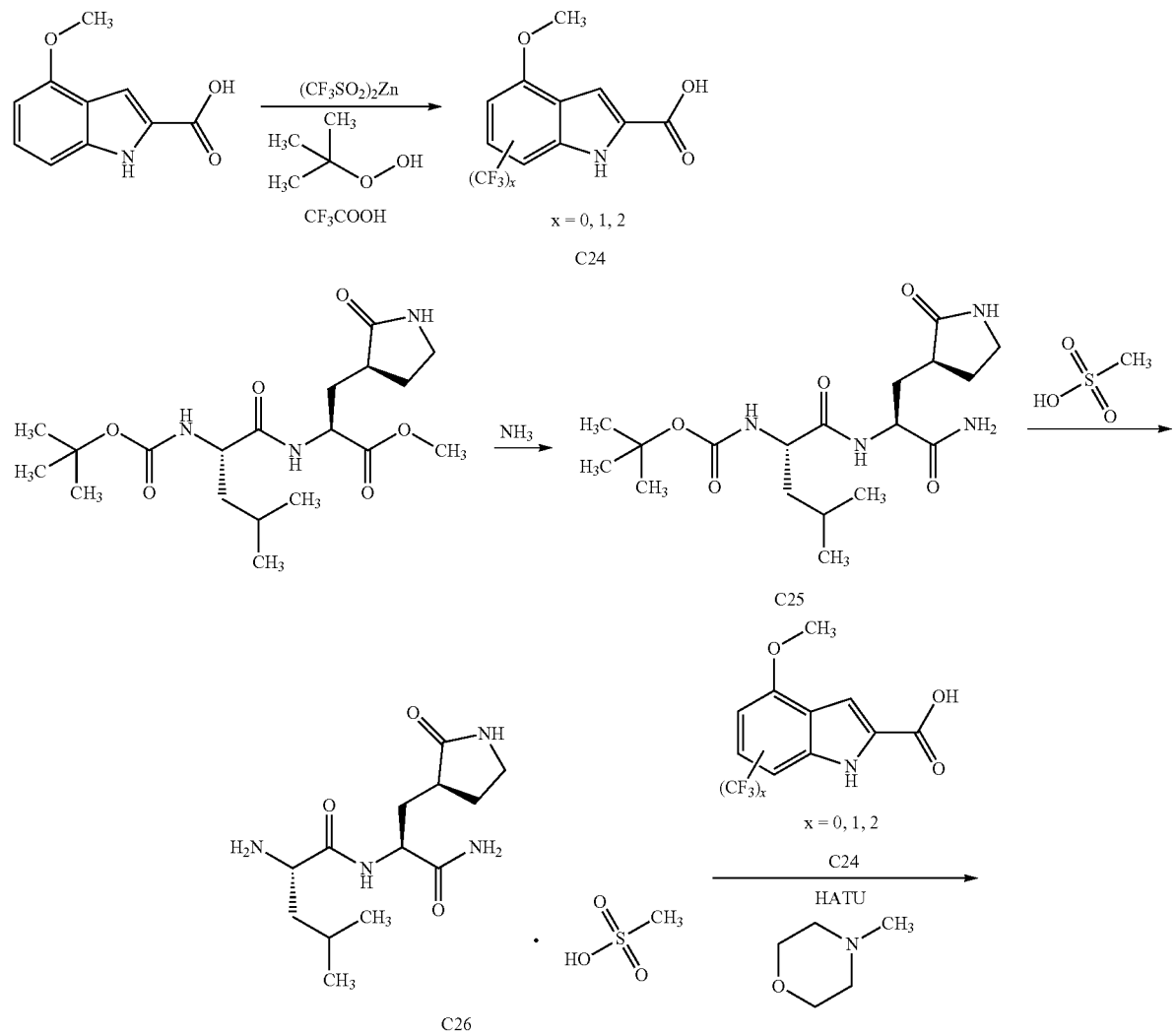

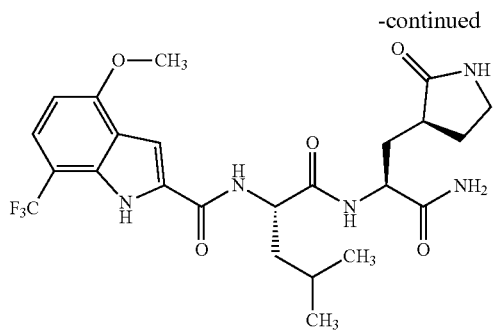 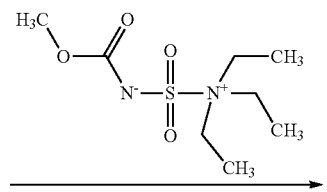

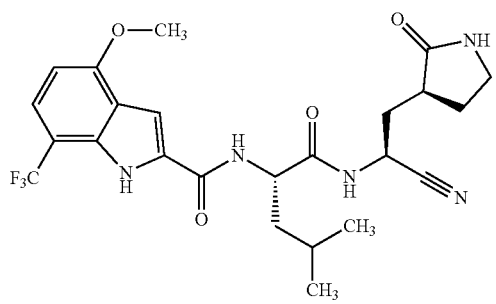

Step 1. Synthesis of trifluoromethylated 4-methoxy-1H-indole-2-carboxylic acid (C24)

A mixture of 4-methoxy-1H-indole-2-carboxylic acid (100 mg, 0.523 mmol) and zinc(II) trifluoromethanesulfinate (120 mg, 0.362 mmol) was treated with dimethyl sulfoxide (1.5 mL) followed by trifluoroacetic acid (56 μL, 0.727 mmol). After the reaction mixture had been cooled to 0° C., tert-butyl hydroperoxide (70% in water; 143 μL, 1.03 mmol) was added, and stirring was continued at 0° C. for 20 minutes, then at room temperature for 25 minutes. The reaction mixture was subsequently heated at 52° C. for 2 hours, whereupon it was cooled to room temperature and treated in a drop-wise manner with aqueous sodium bicarbonate solution until bubbling had ceased. After the resulting mixture had been partitioned between aqueous sodium bicarbonate solution and ethyl acetate, the aqueous layer was extracted once with ethyl acetate and the organic layers were discarded. The aqueous layer was then acidified to pH 7 with 1 M hydrochloric acid; ethyl acetate was added, and the mixture was stirred while the pH was adjusted to 1 by addition of 1 M hydrochloric acid. After the biphasic mixture had been stirred for 10 minutes, the organic layer was washed with saturated aqueous sodium chloride solution, dried over magnesium sulfate, filtered, and concentrated in vacuo. By LCMS analysis, the residue (115 mg) contained a mixture of starting material and mono-trifluoromethylated products, as well as a small amount of di-trifluoromethylated material. The bulk of this mixture was used in Step 4. Yield: 115 mg, <0.4 mmol. LCMS m/z 189.8, 257.8, 325.8 (minor) [M−H]⁻. $^1$H NMR (400 MHz, methanol-$d_4$), characteristic peaks from the three major components: δ 7.07 (br d, J=8.4 Hz), 7.02 (br d, J=8.4 Hz), 6.81 (d, J=7.8 Hz), 6.66 (d, J=7.8 Hz), 6.51 (d, J=7.7 Hz), 4.06 (s, —OMe), 3.93 (s, —OMe), 3.92 (s, —OMe).

Step 2. Synthesis of N-(tert-butoxycarbonyl)-L-leucyl-3-[(3S)-2-oxopyrrolidin-3-yl]-L-alaninamide (C25)

To a 0° C. solution of methyl N-(tert-butoxycarbonyl)-L-leucyl-3-[(3S)-2-oxopyrrolidin-3-yl]-L-alaninate (see Prior, A. M., et al., Bioorg. Med. Chem. Lett. 2013, 23, 6317-6320; 1.5 g, 3.8 mmol) in methanol (5 mL) was added a solution of ammonia in methanol (7 M; 43 mL, 300 mmol). After the reaction vessel had been capped, the reaction mixture was stirred overnight at room temperature. A solution of ammonia in methanol (7 M; 10.7 mL, 74.9 mmol) was again added, and the reaction was allowed to continue at room temperature for 3 days, whereupon it was concentrated in vacuo. The residue was taken up twice in diethyl ether (40 mL) and concentrated under reduced pressure, affording C25 as a white solid. Yield: 1.46 g, 3.80 mmol, quantitative. LCMS m/z 385.4 [M+H]⁺. $^1$H NMR (400 MHz, chloroform-d) δ 8.29-8.17 (m, 1H), 7.23 (br s, 1H), 5.64 (br s, 1H), 5.32 (br s, 1H), 5.02 (d, J=6.1 Hz, 1H), 4.50-4.38 (m, 1H), 4.05 (ddd, J=10.3, 6.3, 4.5 Hz, 1H), 3.44-3.32 (m, 2H), 2.51-2.35 (m, 2H), 2.16-1.98 (m, 2H), 1.97-1.83 (m, 1H), 1.76-1.6 (m, 2H, assumed; partially obscured by water peak), 1.49-1.39 (m, 1H), 1.45 (s, 9H), 0.94 (d, J=6.4 Hz, 3H), 0.94 (d, J=6.3 Hz, 3H).

Step 3. Synthesis of L-leucyl-3-[(3S)-2-oxopyrrolidin-3-yl]-L-alaninamide, methanesulfonate salt (C26)

A solution of methanesulfonic acid (0.861 mL, 13.3 mmol) in 1,1,1,3,3,3-hexafluoropropan-2-ol (5 mL) was slowly added to a solution of C25 (5.1 g, 13 mmol) in 1,1,1,3,3,3-hexafluoropropan-2-ol (43 mL). After 30 minutes, LCMS analysis indicated conversion to C26: LCMS m/z 285.3 [M+H]⁺. The reaction mixture was concentrated in vacuo, then taken up in the following solvent mixtures and reconcentrated: a mixture of acetonitrile and ethyl acetate (1:1, 2×20 mL), then a mixture of ethyl acetate and heptane, (1:1, 2×20 mL). The resulting solid was azeotroped twice with a mixture of acetonitrile and ethyl acetate, then twice with a mixture of ethyl acetate and heptane, affording C26 as a white solid (6.05 g) that retained solvents by $^1$H NMR analysis. Yield: assumed quantitative. $^1$H NMR (600 MHz, methanol-d$_4$) δ4.50 (dd, J=10.7, 4.9 Hz, 1H), 3.91 (dd, J=8.6, 5.5 Hz, 1H), 3.39-3.28 (m, 2H, assumed; partially obscured by solvent peak), 2.70 (s, 3H), 2.53-2.46 (m, 1H), 2.43-2.36 (m, 1H), 2.14 (ddd, J=14.0, 10.7, 5.0 Hz, 1H), 1.95-1.86 (m, 1H), 1.82-1.71 (m, 3H), 1.70-1.64 (m, 1H), 1.02 (d, J=6.3 Hz, 3H), 1.01 (d, J=6.1 Hz, 3H).

Step 4. Synthesis of N-{[4-methoxy-7-(trifluoromethyl)-1H-indol-2-yl]carbonyl}-L-leucyl-3-[(3S)-2-oxopyrrolidin-3-yl]-L-alaninamide (C27)

A solution of C24 (from Step 1; 101 mg, <0.35 mmol) and C26 (from the previous step; 204 mg, ≤0.438 mmol) in acetonitrile (1.7 mL) and N,N-dimethylformamide (1 mL) was cooled to 0° C. and treated with 0-(7-azabenzotriazol-1-yl)-N,N,N',N'-tetramethyluronium hexafluorophosphate (HATU; 163 mg, 0.429 mmol) followed by 4-methylmorpholine (0.129 mL, 1.17 mmol). The reaction mixture was stirred at 0° C. for 40 minutes, whereupon a 1:1 mixture of aqueous sodium bicarbonate solution and ice was slowly added until a cloudy precipitate formed. Ethyl acetate was then added, and the biphasic mixture was stirred for 5 minutes. The aqueous layer was extracted once with ethyl acetate, and the combined organic layers were washed with saturated aqueous sodium chloride solution, dried over magnesium sulfate, filtered, and concentrated in vacuo. Purification via silica gel chromatography was carried out twice (Gradient #1: 0% to 10% methanol in dichloromethane; Gradient #2: 5% to 10% methanol in dichloromethane) to afford C27. The regiochemistry of this material was confirmed by 2D NMR experiments. Yield: 19 mg, 36 μmol, approximately 10%. LCMS m/z 526.5 [M+H]$^+$. $^1$H NMR (400 MHz, methanol-d$_4$) δ 7.53 (br d, J=8.2 Hz, 1H), 7.41 (s, 1H), 6.68 (d, J=8.3 Hz, 1H), 4.60 (dd, J=9.5, 5.1 Hz, 1H), 4.45 (dd, J=11.4, 4.2 Hz, 1H), 4.01 (s, 3H), 3.3-3.21 (m, 2H, assumed; partially obscured by solvent peak), 2.60-2.49 (m, 1H), 2.36-2.26 (m, 1H), 2.15 (ddd, J=14.1, 11.5, 4.6 Hz, 1H), 1.89-1.68 (m, 5H), 1.03 (d, J=6.1 Hz, 3H), 0.99 (d, J=6.2 Hz, 3H).

Step 5. Synthesis of N-[(2S)-1-({(1S)-1-cyano-2-[(3S)-2-oxopyrrolidin-3-yl]ethyl}amino)-4-methyl-1-oxopentan-2-yl]-4-methoxy-7-(trifluoromethyl)-1H-indole-2-carboxamide (6)

Methyl N-(triethylammoniosulfonyl)carbamate, inner salt (Burgess reagent; 17.2 mg, 72.2 μmol) was added to a solution of C27 (19 mg, 36 μmol) in a mixture of dichloromethane (0.5 mL) and acetonitrile (0.2 mL). After the reaction mixture had been stirred at room temperature for 1 hour, it was diluted with ethyl acetate and washed with a 1:1 mixture of aqueous sodium bicarbonate solution and ice. The aqueous layer was extracted with ethyl acetate, and the combined organic layers were washed with saturated aqueous sodium chloride solution, and passed through a solid-phase extraction cartridge packed with magnesium sulfate. Concentration of the filtrate in vacuo provided a residue, which was purified via reversed-phase HPLC (Column: Waters Sunfire C18, 19×100 mm, 5 μm; Mobile phase A: water containing 0.05% trifluoroacetic acid (v/v); Mobile phase B: acetonitrile containing 0.05% trifluoroacetic acid (v/v); Gradient: 25% to 65% B over 8.5 minutes, then 65% to 95% B over 0.5 minutes, then 95% B for 1.0 minute; Flow rate: 25 mL/minute) to afford N-[(2S)-1-({(1S)-1-cyano-2-[(3S)-2-oxopyrrolidin-3-yl]ethyl}amino)-4-methyl-1-oxopentan-2-yl]-4-methoxy-7-(trifluoromethyl)-1H-indole-2-carboxamide (6). Yield: 4.3 mg, 8.5 μmol, 24%. LCMS m/z 508.6 [M+H]$^+$. Retention time: 2.83 minutes (Column: Waters Atlantis C18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5% to 95% B over 4.0 minutes, then 95% B for 1.0 minute; Flow rate: 2 mL/minute).

Example 7

N-[(2S)-1-({(1S)-1-Cyano-2-[(3S)-2-oxopyrrolidin-3-yl]ethyl}amino)-4,4-dimethyl-1-oxopentan-2-yl]-3-methylimidazo[2,1-b][1,3]thiazole-2-carboxamide (7)

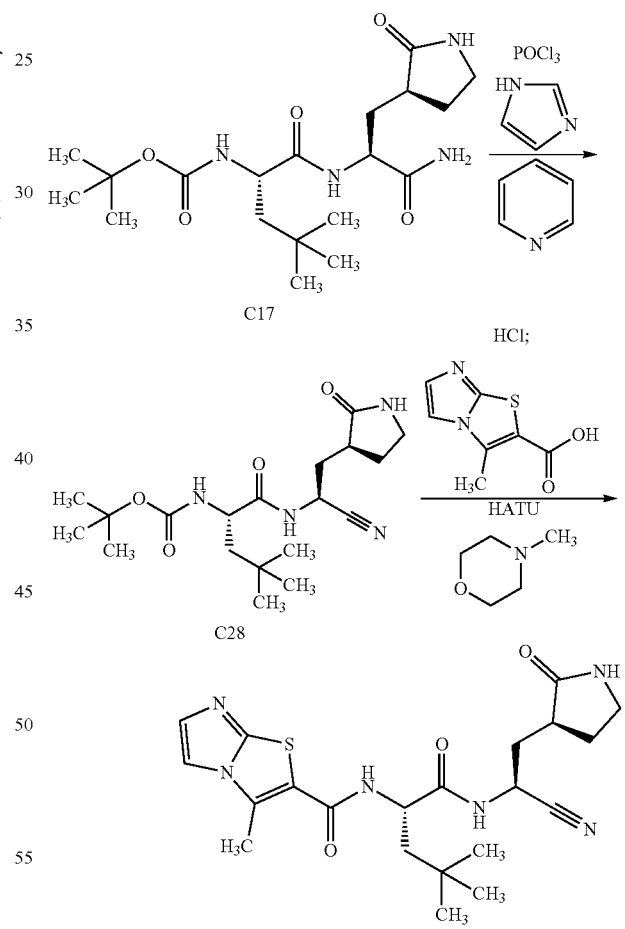

Step 1. Synthesis of N$^2$-(tert-butoxycarbonyl)-N-{(1S)-1-cyano-2-[(3S)-2-oxopyrrolidin-3-yl]ethyl}-4-methyl-L-leucinamide (C28)

A solution of C17 (560 mg, 1.41 mmol) and 1H-imidazole (249 mg, 3.65 mmol) in a mixture of pyridine (3 mL) and dichloromethane (3 mL) was cooled to −35° C. using an acetonitrile/dry ice bath. Phosphorus oxychloride (0.74 mL, 7.94 mmol) was added in a drop-wise manner, over 4 minutes, followed by additional dichloromethane (2 mL), and stirring was continued at −30° C. to −20° C. After 1 hour, the reaction mixture was diluted with dichloromethane (2 mL). After approximately 1.5 hours, hydrochloric acid (1 M; 30 mL) was added; the resulting mixture was stirred for 30 minutes, and then extracted with dichloromethane (2×60 mL). The combined organic layers were dried over sodium sulfate, filtered, and concentrated in vacuo, affording C28 as a solid. Yield: 492 mg, 1.29 mmol, 91%. LCMS m/z 381.4 [M+H]$^+$. $^1$H NMR (400 MHz, methanol-d$_4$) δ 5.03 (dd, J=10.4, 5.7 Hz, 1H), 4.09 (dd, J=8.7, 4.2 Hz, 1H), 3.39-3.25 (m, 2H, assumed; partially obscured by solvent peak), 2.64-2.52 (m, 1H), 2.40-2.27 (m, 2H), 1.97-1.78 (m, 2H), 1.70 (dd, component of ABX system, J=14.3, 4.1 Hz, 1H), 1.54 (dd, component of ABX system, J=14.3, 8.7 Hz, 1H), 1.45 (s, 9H), 1.00 (s, 9H).

Step 2. Synthesis of N-[(2S)-1-({(1S)-1-cyano-2-[(3S)-2-oxopyrrolidin-3-yl]ethyl}amino)-4,4-dimethyl-1-oxopentan-2-yl]-3-methylimidazo[2,1-b][1,3]thiazole-2-carboxamide (7)

A solution of hydrogen chloride in 1,4-dioxane (4.0 M; 0.3 mL, 1.2 mmol) was added to a solution of C28 (100 mg, 0.263 mmol) in a mixture of acetonitrile (1.5 mL) and methanol (1.0 mL). The reaction mixture was stirred at room temperature for 30 minutes, whereupon it was treated with 4-methylmorpholine (0.144 mL, 1.31 mmol). After solvents had been removed in vacuo, the residue was twice resuspended in a mixture of dichloromethane and heptane (1:1, 2×10 mL) and concentrated under reduced pressure. The residue was combined with 3-methylimidazo[2,1-b][1,3]thiazole-2-carboxylic acid (47.9 mg, 0.263 mmol) in N,N-dimethylformamide (3.3 mL), cooled to 0° C., and treated with 0-(7-azabenzotriazol-1-yl)-N,N,N',N'-tetramethyluronium hexafluorophosphate (HATU; 99.9 mg, 0.263 mmol) followed by a solution of 4-methylmorpholine (72 μL, 0.655 mmol) in dichloromethane (0.2 mL). After the reaction mixture had been stirred at 0° C. for approximately 2 hours, it was treated at 0° C. with hydrochloric acid (1 M; 30 mL), and the resulting mixture was extracted with dichloromethane (2×60 mL). The aqueous layer was then basified to pH 9 by addition of saturated aqueous sodium bicarbonate solution, whereupon it was extracted with dichloromethane (3×60 mL). The combined organic layers were washed with saturated aqueous ammonium chloride solution (50 mL), dried over sodium sulfate, filtered, and concentrated in vacuo. $^1$H NMR analysis of this material indicated the presence of a minor epimer, presumed to arise from partial racemization at the center bearing the nitrile. The major product was isolated using silica gel chromatography (Gradient: 0% to 20% methanol in ethyl acetate), providing N-[(2S)-1-({(1S)-1-cyano-2-[(3S)-2-oxopyrrolidin-3-yl]ethyl}amino)-4,4-dimethyl-1-oxopentan-2-yl]-3-methylimidazo[2,1-b][1,3]thiazole-2-carboxamide (7) as a solid. Yield: 56 mg, 0.13 mmol, 49%. LCMS m/z 445.4 [M+H]$^+$. 1H NMR (400 MHz, methanol-d$_4$) δ 7.73 (d, J=1.6 Hz, 1H), 7.37 (d, J=1.6 Hz, 1H), 5.04 (dd, J=10.3, 5.9 Hz, 1H), 4.53 (dd, J=7.8, 5.0 Hz, 1H), 3.36-3.24 (m, 2H; assumed; partially obscured by solvent peak), 2.70 (s, 3H), 2.67-2.57 (m, 1H), 2.38-2.27 (m, 2H), 1.93 (ddd, J=14.0, 9.4, 6.0 Hz, 1H), 1.88-1.78 (m, 3H), 1.03 (s, 9H).

Examples 8 and 9

N-{1-Cyano-2-[(3S)-2-oxopyrrolidin-3-yl]ethyl}-N$^2$-[cyclohexyl(methoxy)acetyl]-4-methyl-L-leucinamide, DIAST-1 (8) and N-{1-Cyano-2-[(3S)-2-oxopyrrolidin-3-yl]ethyl}-N$^2$-[cyclohexyl(methoxy)acetyl]-4-methyl-L-leucinamide, DIAST-2 (9)

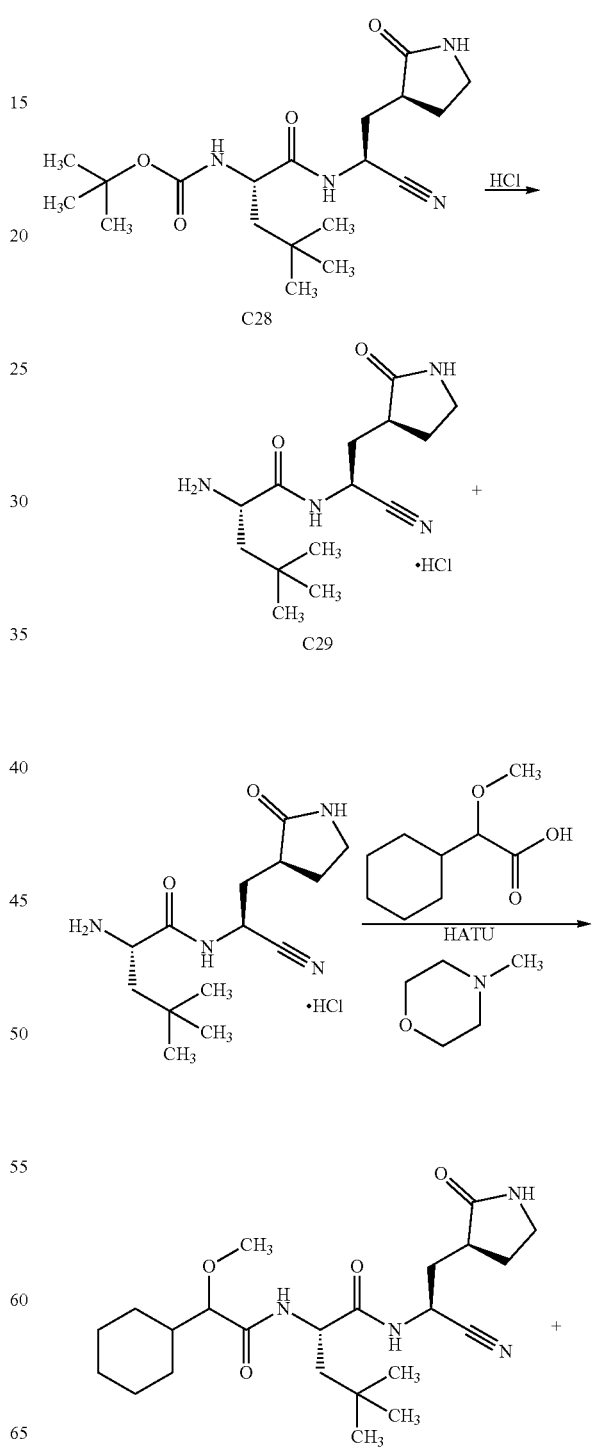

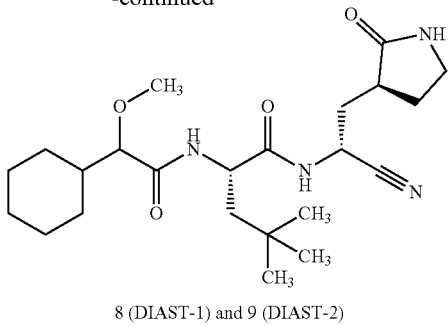

8 (DIAST-1) and 9 (DIAST-2)

Step 1. Synthesis of N-{1-cyano-2-[(3S)-2-oxopyrrolidin-3-yl]ethyl}-4-methyl-L-leucinamide (C29)

To a solution of C28 (114 mg, 0.300 mmol) in a mixture of acetonitrile (1 mL) and methanol (1 mL) was added a solution of hydrogen chloride in 1,4-dioxane (4 M; 0.4 mL, 1.6 mmol). The reaction mixture was stirred at room temperature for 30 minutes, whereupon 4-methylmorpholine (0.165 mL, 1.50 mmol) was added, bringing the pH to 7 to 8. After solvents were removed in vacuo, the residue was twice taken up in a mixture of ethyl acetate and heptane (1:1, 2×10 mL) and concentrated under reduced pressure to provide C29 as a solid (269 mg); by $^1$H NMR analysis, this consisted of a mixture of epimers, presumed to be at the center bearing the nitrile, in a ratio of 2-3 to 1. A portion of this material was used in the following step. LCMS m/z 281.3 [M+H]$^+$. $^1$H NMR (400 MHz, methanol-d$_4$), characteristic peaks: δ [5.11 (dd, J=8.8, 7.3 Hz, major) and 5.01 (dd, J=6.5, 6.5 Hz, minor), total 1H], [2.75-2.65 (m, minor) and 2.64-2.54 (m, major), total 1H], 2.48-2.38 (m, 1H), 2.30-2.20 (m, 1H), 2.06-1.83 (m, 3H), 1.64 (dd, J=14.1, 4.8 Hz, 1H), [1.04 (s, major), 1.01 (s, minor), total 9H].

Step 2. Synthesis of N-{1-cyano-2-[(3S)-2-oxopyrrolidin-3-yl]ethyl}-N$^2$-[cyclohexyl(methoxy)acetyl]-4-methyl-L-leucinamide, DIAST-1 (8) and N-{1-cyano-2-[(3S)-2-oxopyrrolidin-3-yl]ethyl}-N$^2$-[cyclohexyl(methoxy)acetyl]-4-methyl-L-leucinamide, DIAST-2 (9)

To a 0° C. solution of C29 (from the previous step; 83.4 mg, 593 μmol) and cyclohexyl(methoxy)acetic acid (17.2 mg, 99.9 μmol) in N,N-dimethylformamide (1 mL) was added O-(7-azabenzotriazol-1-yl)-N,N,N',N'-tetramethyluronium hexafluorophosphate (HATU; 38.0 mg, 0.100 mmol), followed by a solution of 4-methylmorpholine (30.8 μL, 0.280 mmol) in dichloromethane (0.2 mL). After the reaction mixture had been stirred at 0° C. for about 2 hours, it was diluted with saturated aqueous sodium bicarbonate solution (3 mL) at 0° C., and extracted with dichloromethane (4×4 mL). The combined organic layers were concentrated in vacuo; by LCMS analysis, the residue consisted of two components, assumed to correspond to the two epimers at the center bearing the nitrile. These diastereomers were separated via reversed-phase HPLC (Column: Waters XBridge C18, 19×100 mm, 5 μm; Mobile phase A: water; Mobile phase B: acetonitrile; Gradient: 5% to 95% B over 8.54 minutes, then 95% B for 1.46 minutes; Flow rate: 25 mL/minute). The first-eluting diastereomer was designated as 8 (N-{1-cyano-2-[(3S)-2-oxopyrrolidin-3-yl]ethyl}-N$^2$-[cyclohexyl(methoxy)acetyl]-4-methyl-L-leucinamide, DIAST-1), and the second-eluting diastereomer as 9 (N-{1-cyano-2-[(3S)-2-oxopyrrolidin-3-yl]ethyl}-N$^2$-[cyclohexyl(methoxy)acetyl]-4-methyl-L-leucinamide, DIAST-2).

8—Yield: 12.8 mg, 29.4 μmol, 32% over 2 steps. LCMS m/z 435.6 [M+H]$^+$. Retention time: 2.63 minutes (Analytical conditions. Column: Waters Atlantis C18, 4.6×50 mm, 5 μm; Mobile phase A: water containing 0.05% trifluoroacetic acid (v/v); Mobile phase B: acetonitrile containing 0.05% trifluoroacetic acid (v/v). Gradient: 5% to 95% B over 4.0 minutes, then 95% B for 1.0 minute. Flow rate: 2 mL/minute). 9—Yield: 10 mg, 23.0 μmol, 25% over 2 steps. LCMS m/z 435.6 [M+H]$^+$. Retention time: 2.72 minutes (Analytical conditions identical to those used for 8).

Example 10

N-[(2S)-1-({(1S)-1-Cyano-2-[(3S)-2-oxopyrrolidin-3-yl]ethyl}amino)-4,4-dimethyl-1-oxopentan-2-yl]-4-methoxy-1H-indole-2-carboxamide (10)

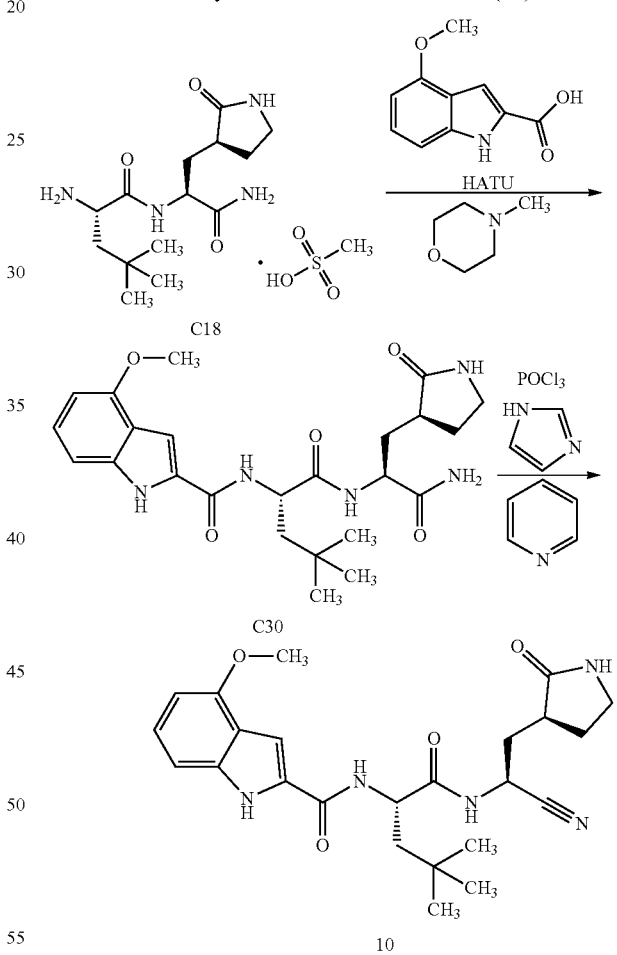

Step 1. Synthesis of N-[(4-methoxy-1H-indol-2-yl)carbonyl]-4-methyl-L-leucyl-3-[(3S)-2-oxopyrrolidin-3-yl]-L-alaninamide (C30)

To a 0° C. solution of C18 (200 mg, 50.46 mmol) and 4-methoxy-1H-indole-2-carboxylic acid (88.2 mg, 0.460 mmol) in acetonitrile (2 mL) was added O-(7-azabenzotriazol-1-yl)-N,N,N',N'-tetramethyluronium hexafluorophosphate (HATU; 175 mg, 0.460 mmol), followed by a solution of 4-methylmorpholine (0.127 mL, 1.16 mmol) in acetonitrile (0.2 mL). The reaction mixture was stirred at 0° C. for 2.5 hours, whereupon it was diluted with saturated aqueous sodium bicarbonate solution (30 mL) at 0° C., then extracted with dichloromethane (50 mL). The organic layer was washed with hydrochloric acid (1 M; 30 mL), and the aqueous layers were extracted with dichloromethane (60 mL). After the combined organic layers had been dried over sodium sulfate, filtered, and concentrated in vacuo, the residue was purified via silica gel chromatography (Gradient: 0% to 30% methanol in ethyl acetate) to provide C30 as a solid. Yield: 148 mg, 0.314 mmol, 68% over 2 steps. LCMS m/z 472.4 [M+H]$^+$. $^1$H NMR (400 MHz, methanol-d$_4$) δ 7.25 (d, J=0.9 Hz, 1H), 7.15 (dd, J=8, 8 Hz, 1H), 7.03 (br d, component of AB quartet, J=8.3 Hz, 1H), 6.51 (d, J=7.7 Hz, 1H), 4.65 (dd, J=9.2, 3.4 Hz, 1H), 4.44 (dd, J=11.2, 4.2 Hz, 1H), 3.93 (s, 3H), 3.29-3.15 (m, 2H), 2.54-2.44 (m, 1H), 2.29 (dddd, J=12.6, 8.6, 7.0, 2.7 Hz, 1H), 2.14 (ddd, J=14.0, 11.2, 4.6 Hz, 1H), 1.89 (dd, component of ABX system, J=14.5, 3.4 Hz, 1H), 1.85-1.74 (m, 3H), 1.02 (s, 9H).

Step 2. Synthesis of N-[(2S)-1-({(1S)-1-cyano-2-[(3S)-2-oxopyrrolidin-3-yl]ethyl}amino)-4,4-dimethyl-1-oxopentan-2-yl]-4-methoxy-1H-indole-2-carboxamide (10)

A solution of C30 (143 mg, 0.303 mmol) and 1H-imidazole (53.7 mg, 0.789 mmol) in a mixture of pyridine (1 mL) and dichloromethane (1 mL) was cooled in an acetonitrile/dry ice bath (−35° C.). Phosphorus oxychloride (0.159 mL, 1.71 mmol) was added in a drop-wise manner over 5 minutes, and the reaction mixture was stirred at −30° C. to −20° C. for 2 hours, whereupon it was treated with hydrochloric acid (1 M; 30 mL), stirred for 20 minutes, and extracted with dichloromethane (2×60 mL). The combined organic layers were dried over sodium sulfate, filtered, and concentrated in vacuo. Chromatography on silica gel (Gradient: 0% to 10% methanol in ethyl acetate) provided N-[(2S)-1-({(1S)-1-cyano-2-[(3S)-2-oxopyrrolidin-3-yl]ethyl}amino)-4,4-dimethyl-1-oxopentan-2-yl]-4-methoxy-1H-indole-2-carboxamide (10) as a solid. Yield: 68 mg, 0.15 mmol, 50%. LCMS m/z 454.5 [M+H]$^+$. $^1$H NMR (400 MHz, methanol-d$_4$) δ 7.24 (d, J=0.9 Hz, 1H), 7.14 (dd, J=8, 8 Hz, 1H), 7.02 (br d, component of AB quartet, J=8.3 Hz, 1H), 6.51 (d, J=7.7 Hz, 1H), 5.03 (dd, J=10.1, 6.0 Hz, 1H), 4.64 (dd, J=8.6, 4.3 Hz, 1H), 3.93 (s, 3H), 3.30-3.17 (m, 2H), 2.63-2.52 (m, 1H), 2.37-2.21 (m, 2H), 1.95-1.74 (m, 4H), 1.03 (s, 9H).

Example 11

N$^2$-[(4-Bromo-1-ethyl-3-methyl-1H-pyrazol-5-yl)carbonyl]-N-{(1S)-1-cyano-2-[(3S)-2-oxopyrrolidin-3-yl]ethyl}-4-methyl-L-leucinamide (11)

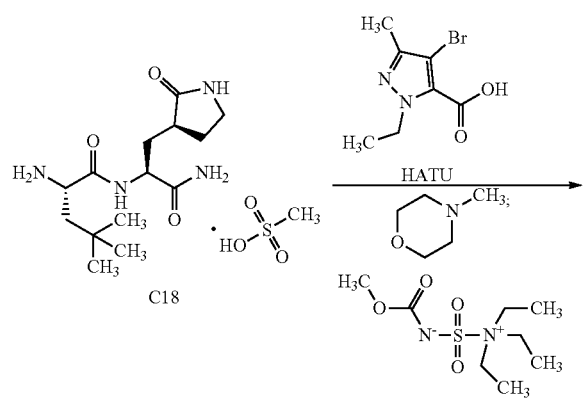

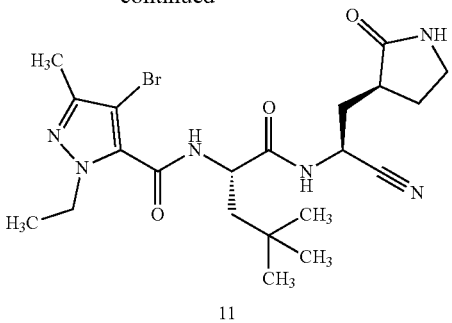

To a 0° C. slurry of C18 (43.4 mg, 50.10 mmol) and 4-bromo-1-ethyl-3-methyl-1H-pyrazole-5-carboxylic acid (23.3 mg, 0.100 mmol) in acetonitrile (1.0 mL) was added O-(7-azabenzotriazol-1-yl)-N,N,N',N'-tetramethyluronium hexafluorophosphate (HATU; 38.0 mg, 0.100 mmol), followed by a solution of 4-methylmorpholine (30 μL, 0.27 mmol) in acetonitrile (0.2 mL). After the reaction mixture had been stirred at 0° C. for approximately 80 minutes, methyl N-(triethylammoniosulfonyl)carbamate, inner salt (Burgess reagent; 71.5 mg, 0.300 mmol) was added, and stirring was continued. After approximately 2.75 hours, methyl N-(triethylammoniosulfonyl)carbamate, inner salt (Burgess reagent; 71.5 mg, 0.300 mmol) was again added, and the reaction was allowed to proceed for 1.5 hours, whereupon it was treated with saturated aqueous sodium bicarbonate solution (3 mL) at 0° C., and extracted with dichloromethane (2×8 mL). The combined organic layers were concentrated in vacuo, then dissolved in acetonitrile (4 mL) and concentrated again using a Genevac evaporator to provide the crude product (138 mg). A portion of this material (80 mg) was purified via reversed-phase HPLC (Column: Waters Sunfire C18, 19×100 mm, 5 μm; Mobile phase A: water containing 0.05% trifluoroacetic acid (v/v); Mobile phase B: acetonitrile containing 0.05% trifluoroacetic acid (v/v); Gradient: 5% to 95% B over 8.54 minutes, then 95% B for 1.46 minutes; Flow rate: 25 mL/minute) to afford N$^2$-[(4-bromo-1-ethyl-3-methyl-1H-pyrazol-5-yl)carbonyl]-N-{(1S)-1-cyano-2-[(3S)-2-oxopyrrolidin-3-yl]ethyl}-4-methyl-L-leucinamide (11). Yield: 24.7 mg, 49.8 μmol, 86% over 2 steps. LCMS m/z 495.5 (bromine isotope pattern observed) [M+H]$^+$. Retention time: 2.48 minutes (Analytical conditions. Column: Waters Atlantis C18, 4.6× 50 mm, 5 μm; Mobile phase A: water containing 0.05% trifluoroacetic acid (v/v); Mobile phase B: acetonitrile containing 0.05% trifluoroacetic acid (v/v). Gradient: 5% to 95% B over 4.0 minutes, then 95% B for 1.0 minute. Flow rate: 2 mL/minute).

Example 12

N-{(1S)-1-Cyano-2-[(3S)-2-oxopyrrolidin-3-yl]ethyl}-N²-[(3,3-difluorocyclobutyl)acetyl]-4-methyl-L-leucinamide (12)

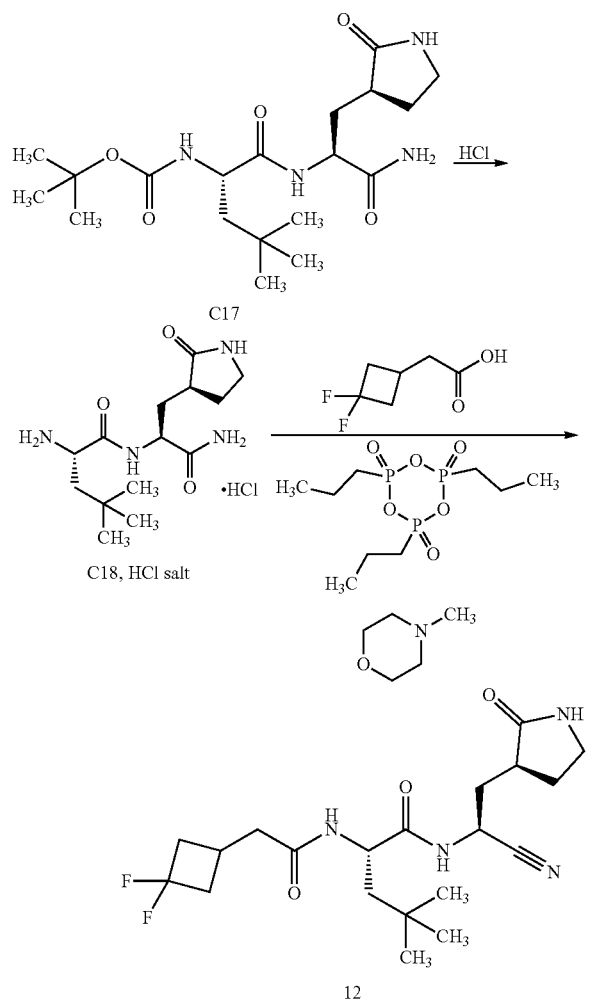

Step 1. Synthesis of 4-methyl-L-leucyl-3-[(3S)-2-oxopyrrolidin-3-yl]-L-alaninamide, hydrochloride salt (C18, HCl salt)

A solution of hydrogen chloride in 1,4-dioxane (4 M; 1.7 mL, 6.8 mmol) was added to a solution of C17 (260 mg, 0.652 mmol) in acetonitrile (3 mL). The reaction mixture was stirred at room temperature for 1.5 hours, whereupon it was concentrated in vacuo, then repeatedly dissolved in a mixture of dichloromethane and heptane (1:1, 3×10 mL) and re-concentrated, affording C18, HCl salt (242 mg) as a glass. A portion of this material was used in the following step. LCMS m/z 299.3 [M+H]⁺. ¹H NMR (400 MHz, methanol-d₄) δ 4.53 (dd, J=10.3, 5.0 Hz, 1H), 3.91 (dd, J=7.5, 5.4 Hz, 1H), 3.41 -3.26 (m, 2H, assumed; partially obscured by solvent peak), 2.57-2.47 (m, 1H), 2.41 (dddd, J=12.0, 8.7, 7.0, 3.1 Hz, 1H), 2.15 (ddd, J=13.9, 10.3, 4.9 Hz, 1H), 2.05-1.97 (m, 1H), 1.97-1.85 (m, 1H), 1.78 (ddd, J=14.1, 9.1, 5.0 Hz, 1H), 1.60 (dd, J=14.3, 5.4 Hz, 1H), 1.01 (s, 9H).

Step 2. Synthesis of N-{(1S)-1-cyano-2-[(3S)-2-oxopyrrolidin-3-yl]ethyl}-N²-[(3,3-difluorocyclobutyl)acetyl]-4-methyl-L-leucinamide (12)

A slurry of C18, HCl salt (from the previous step; 37.2 mg, 50.100 mmol) and (3,3-difluorocyclobutyl)acetic acid (15.8 mg, 0.105 mmol) in tetrahydrofuran (1.0 mL) was treated with 2,4,6-tripropyl-1,3,5,2,4,6-trioxatriphosphinane 2,4,6-trioxide trioxide (50% solution by weight in ethyl acetate; 65.5 μL, 0.110 mmol) and 4-methylmorpholine (27.5 μL, 0.250 mmol). After the reaction mixture had been stirred at room temperature overnight, it was heated at 50° C. for 4.5 hours, whereupon 2,4,6-tripropyl-1,3,5,2,4,6-trioxatriphosphinane 2,4,6-trioxide trioxide (50% solution by weight in ethyl acetate; 2.2 equivalents) and 4-methylmorpholine (5 equivalents) were again added. After the reaction mixture had been stirred at 50° C. for 3 additional days, it was treated with saturated aqueous sodium bicarbonate solution (3 mL) and extracted with dichloromethane (4×4 mL). The combined organic layers were concentrated in vacuo and purified via reversed-phase HPLC (Column: Waters XBridge C18, 19×100 mm, 5 μm; Mobile phase A: water; Mobile phase B: acetonitrile; Gradient: 20% to 40% B over 8.5 minutes, then 40% to 95% B over 0.5 minutes, then 95% B for 1.0 minute; Flow rate: 25 mL/minute) to afford N-{(1S)-1-cyano-2-[(3S)-2-oxopyrrolidin-3-yl]ethyl}-N²-[(3,3-difluorocyclobutyl)acetyl]-4-methyl-L-leucinamide (12). Yield: 10.1 mg, 24.5 μmol, 24% over 2 steps. LCMS m/z 413.5 [M+H]⁺. Retention time: 1.96 minutes (Analytical conditions. Column: Waters Atlantis C18, 4.6× 50 mm, 5 μm; Mobile phase A: water containing 0.05% trifluoroacetic acid (v/v); Mobile phase B: acetonitrile containing 0.05% trifluoroacetic acid (v/v). Gradient: 5% to 95% B over 4.0 minutes, then 95% B for 1.0 minute. Flow rate: 2 mL/minute).

Example 13

(1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13)

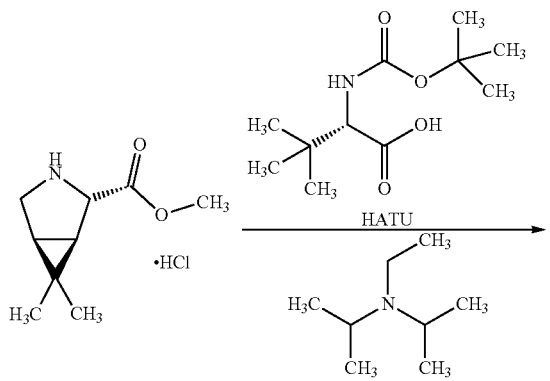

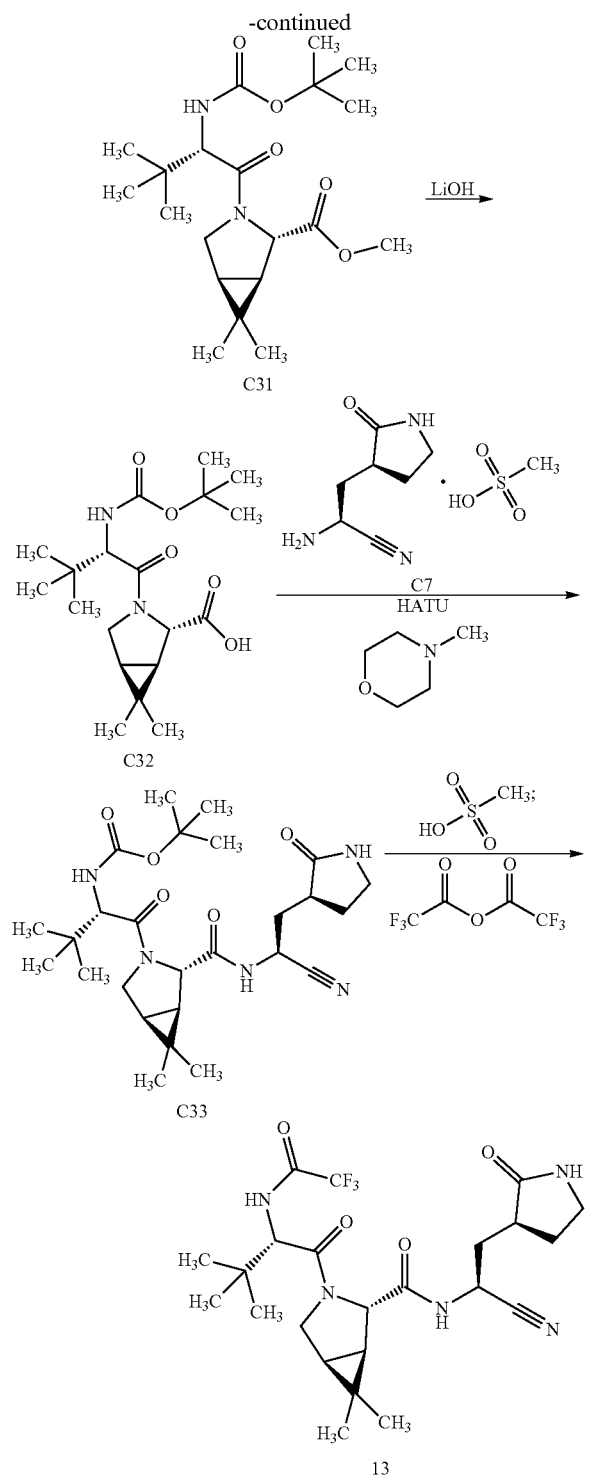

Step 1. Synthesis of methyl (1R,2S,5S)-3-[N-(tert-butoxycarbonyl)-3-methyl-L-valyl]-6,6-dimethyl-3-azabicyclo[3.1.0]hexane-2-carboxylate (C31)

O-(7-Azabenzotriazol-1-yl)-N,N,N',N'-tetramethyluronium hexafluorophosphate (HATU; 7.92 g, 20.8 mmol) was added to a 0° C. mixture of N-(tert-butoxycarbonyl)-3-methyl-L-valine (4.38 g, 18.9 mmol) and methyl (1R,2S,5S)-6,6-dimethyl-3-azabicyclo[3.1.0]hexane-2-carboxylate, hydrochloride salt (3.9 g, 19 mmol) in N,N-dimethylformamide (95 mL). After the reaction mixture had been stirred for 5 minutes, N,N-diisopropylethylamine (8.25 mL, 47.4 mmol) was added; stirring was continued at 0° C. for 2 hours, whereupon aqueous citric acid solution (1 N, 20 mL) and water (40 mL) were added. The resulting mixture was stirred for 2 minutes, and then diluted with ethyl acetate (250 mL). The organic layer was washed with water (3×150 mL) and with saturated aqueous sodium chloride solution, dried over sodium sulfate, filtered, and concentrated in vacuo. Purification via silica gel chromatography (Gradient: 0% to 100% ethyl acetate in heptane) afforded C31 as an oil. Yield: 3.60 g, 9.41 mmol, 50%. $^1$H NMR (400 MHz, methanol-$d_4$) δ 6.42 (d, J=9.7 Hz, <1H; incompletely exchanged with solvent), 4.35 (s, 1H), 4.21 (d, J=9.7 Hz, 1H), 4.02 (d, half of AB quartet, J=10.4 Hz, 1H), 3.91 (dd, component of ABX system, J=10.3, 5.3 Hz, 1H), 3.73 (s, 3H), 1.57 (dd, component of ABX system, J=7.5, 5.1 Hz, 1H), 1.47 (d, half of AB quartet, J=7.5 Hz, 1H), 1.41 (s, 9H), 1.07 (s, 3H), 1.02 (s, 9H), 0.93 (s, 3H).

Step 2. Synthesis of (1R,2S,5S)-3-[N-(tert-butoxycarbonyl)-3-methyl-L-valyl]-6,6-dimethyl-3-azabicyclo[3.1.0]hexane-2-carboxylic acid (C32)

Aqueous lithium hydroxide solution (1.0 M; 14.7 mmol, 14.7 mL) was added in a drop-wise manner to a 0° C. solution of C31 (3.60 g, 9.41 mmol) in a mixture of tetrahydrofuran and methanol (1:1, 30 mL). After the reaction mixture had been stirred at 0° C. for 1 hour, it was allowed to warm to room temperature and stirred for 1 hour, whereupon LCMS analysis indicated conversion to C32: LCMS m/z 367.3 [M−H]$^-$. Adjustment to pH 3 was carried out via addition of 1 M hydrochloric acid, after which the mixture was diluted with water (30 mL). The aqueous layer was extracted with ethyl acetate (2×75 mL), and the combined organic layers were dried over sodium sulfate, filtered, and concentrated under reduced pressure to provide C32 as an off-white solid. Yield: 3.10 g, 8.41 mmol, 89%. $^1$H NMR (400 MHz, methanol-$d_4$) δ 6.39 (d, J=9.7 Hz, approximately 0.5H; incompletely exchanged with solvent), 4.33 (s, 1H), [4.21 (d, J=9.6 Hz) and 4.21 (s), total 1H], 4.01 (d, half of AB quartet, J=10.5 Hz, 1H), 3.91 (dd, component of ABX system, J=10.4, 5.2 Hz, 1H), 1.56 (dd, component of ABX system, J=7.5, 5.0 Hz, 1H), 1.50 (d, half of AB quartet, J=7.6 Hz, 1H), 1.42 (s, 9H), 1.07 (s, 3H), 1.02 (s, 9H), 0.93 (s, 3H).

Step 3. Synthesis of tert-butyl {(2S)-1-[(1R,2S,5S)-2-({(1S)-1-cyano-2-[(3S)-2-oxopyrrolidin-3-yl]ethyl}carbamoyl)-6,6-dimethyl-3-azabicyclo[3.1.0]hexan-3-yl]-3,3-dimethyl-1-oxobutan-2-yl}carbamate (C33)

A 0° C. mixture of C7 (31.9 mg, 594 µmol) and C32 (34 mg, 92 µmol) in acetonitrile (1 mL) was treated with O-(7-azabenzotriazol-1-yl)-N,N,N',N'-tetramethyluronium hexafluorophosphate (HATU, 97%; 36.2 mg, 92.3 µmol) followed by a solution of 4-methylmorpholine (25 µL, 0.23 mmol) in acetonitrile (0.25 mL). After the reaction mixture had been stirred at 0° C. for approximately 1 hour, it was diluted with saturated aqueous sodium bicarbonate solution (3 mL) at 0° C., and extracted with dichloromethane (4×4 mL). The combined organic layers were concentrated in vacuo to provide C33 as a gum (48 mg). Most of this material was used in the following step. LCMS m/z 504.6 [M+H]$^+$.

Step 4. Synthesis of (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13)

A stock solution of methanesulfonic acid (60 μL) in 1,1,1,3,3,3-hexafluoropropan-2-ol (940 μL) was prepared. To a solution of C33 (from the previous step; 47 mg, 590 μmol) in 1,1,1,3,3,3-hexafluoropropan-2-ol (1 mL) was added a portion of the methanesulfonic acid stock solution (0.1 mL; 100 μmol). After the reaction mixture had been stirred at room temperature for 1 hour, it was concentrated in vacuo, then taken up in the following solvent mixtures and reconcentrated: a mixture of acetonitrile and ethyl acetate (1:1, 2×10 mL), and then a mixture of ethyl acetate and heptane (1:1, 2×10 mL). The residue was dissolved in dichloromethane (1 mL) and treated with 4-methylmorpholine (30.8 μL, 0.280 mmol), followed by trifluoroacetic anhydride (0.143 mL, 1.01 mmol). The reaction mixture was stirred at room temperature for 40 minutes, whereupon it was treated with 4-methylmorpholine (30.8 μL, 0.280 mmol) followed by trifluoroacetic anhydride (0.143 mL, 1.01 mmol); after 30 minutes, 4-methylmorpholine (30.8 μL, 0.280 mmol) was again added, followed by trifluoroacetic anhydride (0.143 mL, 1.01 mmol). After an additional 15 minutes of stirring, the reaction mixture was treated with hydrochloric acid (1 M; 3 mL), and the resulting mixture was extracted with dichloromethane (3×4 mL); the combined organic layers were concentrated in vacuo and purified using reversed-phase HPLC (Waters Sunfire C18, 19×100 mm, 5 μm; Mobile phase A: water containing 0.05% trifluoroacetic acid (v/v); Mobile phase B: acetonitrile containing 0.05% trifluoroacetic acid (v/v). Gradient: 20% to 60% B over 8.5 minutes, then 60% to 95% B over 0.5 minutes, then 95% B for 1 minute; Flow rate: 25 mL/minute) to afford (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13). Yield: 7.5 mg, 15 μmol, 17% over 2 steps. LCMS m/z 500.5 [M+H]$^+$. Retention time: 2.66 minutes (Analytical conditions. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B over 4.0 minutes, then 95% B for 1.0 minute; Flow rate: 2 mL/minute).

Alternate Synthesis of Example 13, Methyl Tert-Butyl Ether Solvate; Generation of 13, Methyl Tert-Butyl Ether Solvate, Solid Form 2

(1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate), Solid Form 2

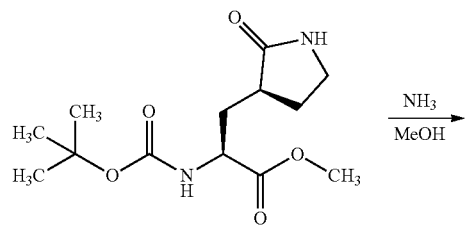

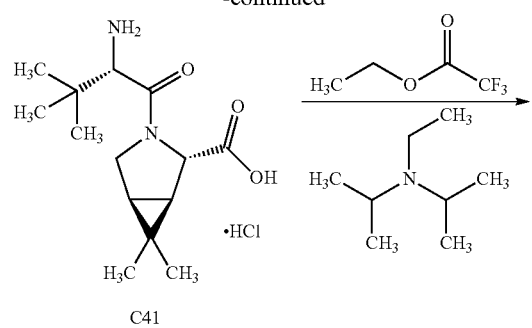

C41

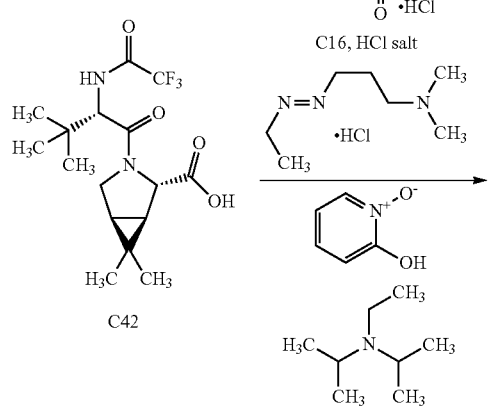

C16, HCl salt

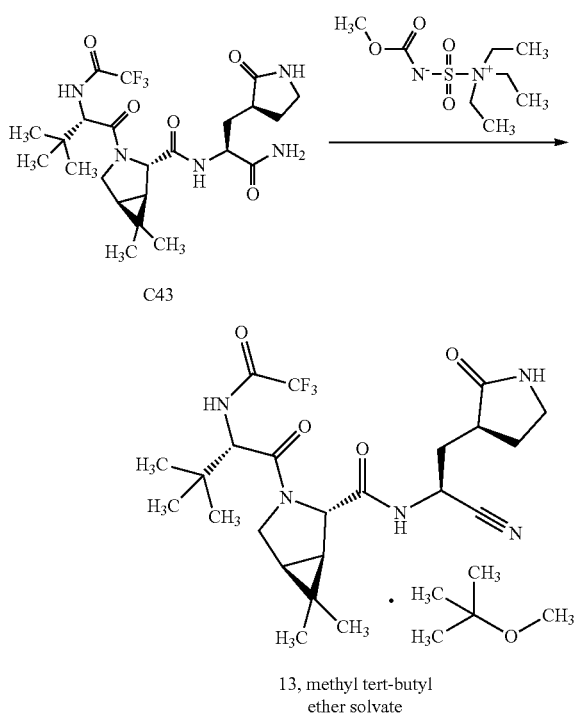

C43

13, methyl tert-butyl ether solvate

Step 1. Synthesis of tert-butyl {(2S)-1-amino-1-oxo-3-[(3S)-2-oxopyrrolidin-3-yl]propan-2-yl}carbamate (C5)

This experiment was carried out in 2 parallel batches. A solution of ammonia in methanol (7 M; 2.4 L, 17 mol) was added to methyl N-(tert-butoxycarbonyl)-3-[(3S)-2-oxopyrrolidin-3-yl]-L-alaninate (600 g, 2.10 mol) and the reaction mixture was stirred at 25° C. for 40 hours. Concentration in vacuo and combination of the 2 batches provided C5 as a yellow solid. Combined yield: 1.10 kg, 4.05 mol, 96%. $^1$H NMR (400 MHz, DMSO-$d_6$) δ 7.63 (br s, 1H), 7.29 (br s, 1H), 7.01 (br s, 1H), 6.89 (d, J=8.5 Hz, 1H), 3.96-3.85 (m, 1H), 3.22-3.06 (m, 2H, assumed; partially obscured by water peak), 2.28-2.08 (m, 2H), 1.89 (ddd, J=14.6, 10.8, 4.0 Hz, 1H), 1.74-1.60 (m, 1H), 1.56-1.43 (m, 1H), 1.36 (s, 9H).

Step 2. Synthesis of 3-[(3S)-2-oxopyrrolidin-3-yl]-L-alaninamide, hydrochloride salt (C16, HCl salt)

This experiment was carried out in 3 parallel batches. To a 0° C. solution of C5 (840 g, 3.10 mol) in dichloromethane (2.0 L) was added a solution of hydrogen chloride in 1,4-dioxane (4 M; 2 L, 8 mol). The reaction mixture was stirred at 25° C. for 2 hours, whereupon it was concentrated in vacuo; combination of the 3 batches afforded C16, HCl salt as a white solid. Combined yield: 1.20 kg, 5.78 mol, 62%. MS m/z 172.1 [M+H]$^+$. $^1$H NMR (400 MHz, DMSO-$d_6$) δ 8.52-8.35 (br s, 3H), 8.12 (s, 1H), 7.95 (s, 1H), 7.57 (s, 1H), 3.88-3.76 (m, 1H), 3.24-3.10 (m, 2H), 2.59-2.5 (m, 1H, assumed; partially obscured by solvent peak), 2.35-2.24 (m, 1H), 2.01 (ddd, J=14.9, 9.2, 6.1 Hz, 1H), 1.80-1.68 (m, 2H).

Figure 10:
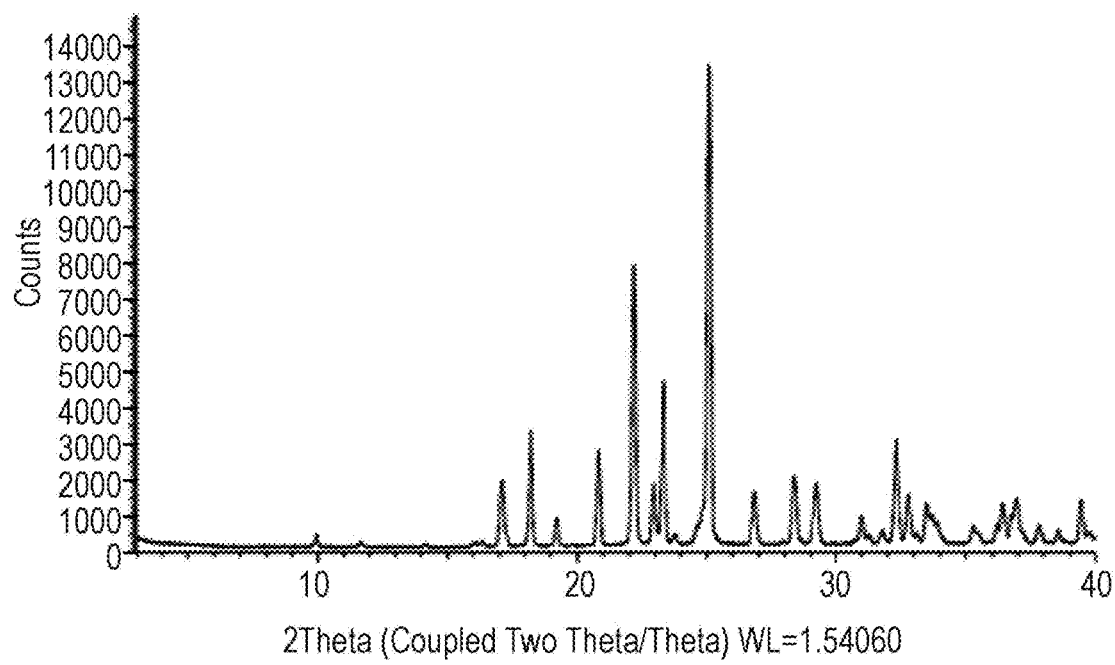
FIG. 10: Powder X-ray Diffraction Pattern of Intermediate C16, HCl salt.

A sample of C16, HCl salt was triturated in 2-propanol for 1.5 hours, whereupon it was collected via filtration and rinsed with 2-propanol. The collected solid was dried overnight under high vacuum to obtain a sample for powder X-ray diffraction study. The powder X-ray diffraction pattern for this material is given in FIG. 10; characteristic peaks are listed in Table Q.

Collection of Powder X-Ray Diffraction Data

The powder X-ray diffraction analysis was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu wavelength from 3.0 to 40.0 degrees 2-Theta using a step size of 0.020 degrees and a step time of 0.3 second. Samples were prepared by placing them in a silicon low background sample holder and rotated during collection.

The powder X-ray diffraction analysis was conducted using a Bruker AXS D8 Advance diffractometer equipped with a Cu radiation source. Diffracted radiation was detected by a LYNXEYE_EX detector with motorized slits. Both primary and secondary equipped with 2.5 soller slits. The X-ray tube voltage and amperage were set at 40 kV and 40 mA respectively. Data was collected in the Theta-Theta goniometer in a locked couple scan at Cu K-alpha (average) wavelength from 3.0 to 40.0 degrees 2-Theta with an increment of 0.02 degrees, using a scan speed of 0.5 seconds per step. Samples were prepared by placement in a silicon low background sample holder.

Data were collected with both instruments using Bruker DIFFRAC Plus software and analysis was performed by EVA DIFFRAC plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to +/−0.2° 2-Theta (USP-941).

TABLE Q

Selected powder X-ray diffraction peaks for C16, HCl salt

| Angle (°2 theta) | Rel. Intensity |
| --- | --- |
| 9.97 | 3 |
| 11.67 | 1 |
| 14.17 | 1 |
| 16.08 | 1 |
| 16.35 | 1 |
| 17.10 | 14 |
| 17.27 | 3 |
| 18.23 | 24 |
| 19.21 | 4 |
| 20.83 | 20 |
| 22.20 | 58 |
| 22.97 | 12 |
| 23.35 | 34 |
| 23.79 | 2 |
| 24.62 | 3 |
| 25.10 | 100 |
| 26.85 | 11 |
| 28.39 | 14 |
| 29.24 | 13 |
| 30.98 | 6 |
| 31.78 | 2 |
| 32.32 | 23 |
| 32.79 | 10 |
| 33.10 | 1 |
| 33.50 | 6 |
| 33.70 | 4 |
| 33.90 | 3 |
| 35.27 | 3 |
| 36.20 | 3 |
| 36.42 | 6 |
| 36.75 | 6 |
| 36.95 | 7 |
| 37.83 | 3 |
| 38.58 | 2 |
| 39.44 | 7 |
| 39.75 | 1 |

Alternate Synthesis of 3-[(3S)-2-oxopyrrolidin-3-yl]-L-alaninamide, hydrochloride salt, C16 HCl salt An alternate preparation of the compound C16, HCl salt is depicted in the reaction scheme below.

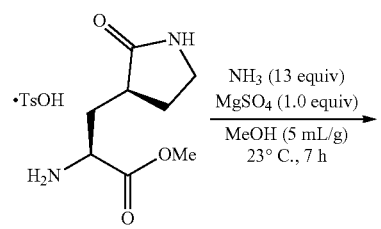

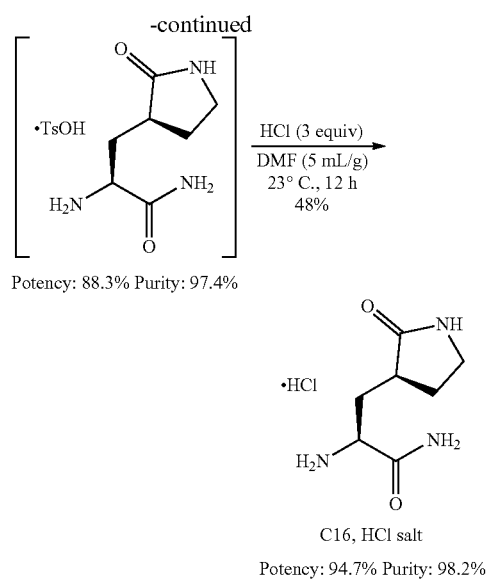

To a solution of ammonia in methanol (7.0 M; 100 mL, 725.4 mmol) was added methyl (S)-2-amino-3-((S)-2-oxopyrrolidin-3-yl)propanoate 4-methylbenzenesulfonate (20 g, 55.8 mmol) and magnesium sulfate (6.7 g, 55.8 mmol) at room temperature. After stirring the reaction mixture for 7 hours at room temperature, nitrogen was bubbled into the reaction for 1 hour to purge excess ammonia. Afterwards, the reaction was filtered through a pad of Celite® and then concentrated in vacuo and the resulting (S)-2-amino-3-((S)-2-oxopyrrolidin-3-yl)propanamide 4-methylbenzenesulfonate was used directly in the subsequent step without further purification. To a solution of dimethylformamide (50 mL, 647 mmol) was added a portion of (S)-2-amino-3-((S)-2-oxopyrrolidin-3-yl)propanamide 4-methylbenzenesulfonate (10 g, 25.9 mmol) and a solution of hydrogen chloride in 1,4-dioxane (4.0 M; 19.4 mL, 77.7 mmol). After stirring for 12 hours at room temperature the slurry was filtered and washed with dimethylformamide (15 mL, 190 mmol). The resulting solid was dried in a vacuum oven at 40° C. for 12 hours to afford 3-[(3S)-2-oxopyrrolidin-3-yl]-L-alaninamide, hydrochloride salt, C16 HCl salt (2.7 g, 12.4 mmol) as a tan solid (overall yield of 48%).

Step 3. Synthesis of methyl (1R,2S,5S)-3-[N-(tert-butoxycarbonyl)-3-methyl-L-valyl]-6,6-dimethyl-3-azabicyclo[3.1.0]hexane-2-carboxylate (C31)

This experiment was carried out in 3 parallel batches. To a 0° C. solution of methyl (1R,2S,5S)-6,6-dimethyl-3-azabicyclo[3.1.0]hexane-2-carboxylate, hydrochloride salt (237 g, 1.15 mol) and N-(tert-butoxycarbonyl)-3-methyl-L-valine (293 g, 1.27 mol) in a mixture of N,N-dimethylformamide (400 mL) and acetonitrile (3.6 L) was added O-(7-azabenzotriazol-1-yl)-N,N,N',N'-tetramethyluronium hexafluorophosphate (HATU; 481 g, 1.26 mol), followed by drop-wise addition of N,N-diisopropylethylamine (601 mL, 3.45 mol). The reaction mixture was then allowed to warm to 25° C. and was stirred for 16 hours, whereupon it was poured into a mixture of ice water (1 L) and hydrochloric acid (0.5 M; 1 L), of pH approximately 5, and stirred for 6 minutes. The resulting mixture was extracted with ethyl acetate (2 L), and the organic layer was washed with water (2 L), dried over sodium sulfate, filtered, and concentrated in vacuo. The residue was purified using silica gel chromatography (Gradient: 0% to 50% ethyl acetate in petroleum ether), affording, after combination of the 3 batches, C31 as a colorless oil. Combined yield: 1.17 kg, 3.06 mol, 89%. LCMS m/z 383.3 [M+H]$^+$. $^1$H NMR (400 MHz, chloroform-d) δ 5.10 (d, J=10.2 Hz, 1H), 4.46 (s, 1H), 4.20 (d, J=10.3 Hz, 1H), 3.98 (d, half of AB quartet, J=10.2 Hz, 1H), 3.89-3.82 (m, 1H), 3.74 (s, 3H), 1.48-1.41 (m, 2H), 1.38 (s, 9H), 1.03 (s, 3H), 1.01 (s, 9H), 0.89 (s, 3H).

Step 4. Synthesis of (1R,2S,5S)-3-[N-(tert-butoxycarbonyl)-3-methyl-L-valyl]-6,6-dimethyl-3-azabicyclo[3.1.0]hexane-2-carboxylic acid (C32)

This experiment was carried out in 3 parallel batches. To a solution of C31 (668 g, 1.75 mol) in tetrahydrofuran (2.5 L) was added lithium hydroxide monohydrate (220 g, 5.24 mol) and water (500 mL). After the reaction mixture had been stirred at 25° C. for 2 hours, it was concentrated in vacuo to remove most of the tetrahydrofuran; the residue was then adjusted to pH 2 by addition of 1 M hydrochloric acid. The resulting mixture was extracted with ethyl acetate (2×500 mL), and the combined organic layers were washed with saturated aqueous sodium chloride solution (500 mL), dried over sodium sulfate, filtered, and concentrated in vacuo to provide C32 as a white solid (2.0 kg) after combination of the 3 batches. This material was used directly in the following step. LCMS m/z 313.2 [(M-2-methylprop-1-ene)+H]$^+$. $^1$H NMR (400 MHz, chloroform-d) δ 5.14 (d, J=10.2 Hz, 1H), 4.46 (s, 1H), 4.24 (d, J=10.2 Hz, 1H), 4.06 (d, half of AB quartet, J=10.5 Hz, 1H), 3.82 (dd, component of ABX system, J=10.5, 5.5 Hz, 1H), 1.75 (d, J=7.7 Hz, 1H), 1.49 (dd, J=7.7, 5.4 Hz, 1H), 1.40 (s, 9H), 1.06 (s, 3H), 1.00 (s, 9H), 0.89 (s, 3H).

Step 5. Synthesis of (1R,2S,5S)-6,6-dimethyl-3-(3-methyl-L-valyl)-3-azabicyclo[3.1.0]hexane-2-carboxylic acid, hydrochloride salt (C41)

This experiment was carried out in 2 parallel batches. A solution of hydrogen chloride in 1,4-dioxane (4 M; 4.0 L, 16 mol) was added to a solution of C32 (from the previous step; 1.00 kg, 52.62 mol) in dichloromethane (1.0 L), and the reaction mixture was stirred at 25° C. for 16 hours. Removal of solvents in vacuo at 50° C. afforded C41 as a white solid (1.8 kg) after combination of the 2 batches. This material was used directly in the following step. $^1$H NMR (400 MHz, methanol-d$_4$) δ4.42 (s, 1H), 4.00 (s, 1H), 3.94 (dd, component of ABX system, J=10.7, 5.4 Hz, 1H), 3.80 (d, half of AB quartet, J=10.7 Hz, 1H), 1.62 (dd, component of ABX system, J=7.7, 5.2 Hz, 1H), 1.56 (d, half of AB quartet, J=7.6 Hz, 1H), 1.15 (s, 9H), 1.09 (s, 3H), 1.03 (s, 3H).

Step 6. Synthesis of (1R,2S,5S)-6,6-dimethyl-3-[3-methyl-N-(trifluoroacetyl)-L-valyl]-3-azabicyclo[3.1.0]hexane-2-carboxylic acid (C42)

This experiment was carried out in 3 parallel batches. To a 0° C. solution of C41 (from the previous step; 600 g, ≤1.75 mol) in methanol (2 L) was added triethylamine (1.64 L, 11.8 mol), followed by ethyl trifluoroacetate (699 g, 4.92 mol), whereupon the reaction mixture was allowed to warm to 25° C., and was stirred for 16 hours. It was then concentrated in vacuo at 50° C., and the residue was diluted with ethyl acetate (3 L) and adjusted to a pH of 3 to 4 by addition of 2 M hydrochloric acid. After extraction of the aqueous layer with ethyl acetate (1 L), the combined organic layers were washed with saturated aqueous sodium chloride solution (3 L), dried over sodium sulfate, filtered, and concentrated under reduced pressure. The 3 batches were combined at this point, treated with a mixture of petroleum ether and ethyl acetate (5:1, 3 L), and stirred at 25° C. for 2 hours. Filtration afforded C42 as a white solid. Combined yield: 1.90 kg, 5.21 mol, 99% over 3 steps. LCMS m/z 365.1 [M+H]$^+$. $^1$H NMR (400 MHz, methanol-d$_4$) δ 8.88 (d, J=8.8 Hz, <1H; incompletely exchanged), [4.60 (d, J=8.9 Hz) and 4.59 (s), total 1H], 4.35 (s, 1H), 3.96 (dd, component of ABX system, J=10.5, 5.1 Hz, 1H), 3.90 (d, half of AB quartet, J=10.4 Hz, 1H), 1.58 (dd, component of ABX system, J=7.6, 4.9 Hz, 1H), 1.52 (d, half of AB quartet, J=7.6 Hz, 1H), 1.08 (s, 12H), 0.92 (s, 3H).

Step 7. Synthesis of (1R,2S,5S)—N-{(2S)-1-amino-1-oxo-3-[(3S)-2-oxopyrrolidin-3-yl]propan-2-yl}-6,6-dimethyl-3-[3-methyl-N-(trifluoroacetyl)-L-valyl]-3-azabicyclo[3.1.0]hexane-2-carboxamide (C43)

This experiment was carried out in 4 parallel batches. 2-Hydroxypyridine 1-oxide (33.9 g, 305 mmol) was added to a solution of C42 (445 g, 1.22 mol) and C16, HCl salt (256 g, 1.23 mol) in butan-2-one (2.5 L), and the mixture was cooled to 0° C. N,N-Diisopropylethylamine (638 mL, 3.66 mol) was then added, followed by drop-wise addition of 1-[3-(dimethylamino)propyl]-3-ethylcarbodiimide hydrochloride (351 g, 1.83 mol). The reaction mixture was stirred at 25° C. for 16 hours, whereupon it was diluted with ethyl acetate (1 L) and treated with a mixture of hydrochloric acid (1 M; 1.5 L, 1.5 mol) and saturated aqueous sodium chloride solution (1 L). The organic layer was washed with a mixture of aqueous sodium hydroxide solution (1 M; 1.5 L, 1.5 mol) and saturated aqueous sodium chloride solution (1 L), dried over sodium sulfate, filtered, and concentrated in vacuo. Combination of the 4 batches provided C43 as a white solid (2.3 kg). Combined yield: 2.1 kg (corrected for residual ethyl acetate), 4.1 mol, 84%. LCMS m/z 518.3 [M+H]$^+$. $^1$H NMR (400 MHz, DMSO-d$_6$) δ 9.41 (br d, J=7.7 Hz, 1H), 8.30 (d, J=8.8 Hz, 1H), 7.56 (s, 1H), 7.32 (br s, 1H), 7.04 (br s, 1H), 4.43 (br d, J=7.3 Hz, 1H), 4.35-4.25 (m, 1H), 4.28 (s, 1H), 3.89 (dd, J=10.3, 5.5 Hz, 1H), 3.67 (d, J=10.4 Hz, 1H), 3.17-3.09 (m, 1H), 3.07-2.98 (m, 1H), 2.46-2.35 (m, 1H), 2.19-2.10 (m, 1H), 1.99-1.89 (m, 1H), 1.70-1.58 (m, 1H), 1.55-1.44 (m, 2H), 1.38 (d, half of AB quartet, J=7.6 Hz, 1H), 1.01 (s, 3H), 0.98 (s, 9H), 0.84 (s, 3H).

Step 8. Synthesis of (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate), Solid Form 2

This experiment was carried out in 3 parallel batches. Methyl N-(triethylammoniosulfonyl)carbamate, inner salt (Burgess reagent; 552 g, 2.32 mol) was added to a solution of C43 (600 g, 1.16 mol) in ethyl acetate (3 L). After the reaction mixture had been stirred at 25° C. for 3 hours, it was treated with additional methyl N-(triethylammoniosulfonyl)carbamate, inner salt (Burgess reagent; 27.6 g, 116 mmol) and the reaction mixture was stirred for 1 hour. It was then filtered; the filter cake was washed with ethyl acetate (2×500 mL), and the combined filtrates were washed sequentially with aqueous sodium bicarbonate solution (1 M; 2 L), saturated aqueous sodium chloride solution (2 L), hydrochloric acid (1 M; 2 L), and saturated aqueous sodium chloride solution (2 L). The organic layer was then dried over sodium sulfate, filtered, and concentrated in vacuo. The residue was treated with a mixture of ethyl acetate and methyl tert-butyl ether (1:10, 2.5 L) and heated to 50° C.; after stirring for 1 hour at 50° C., it was cooled to 25° C. and stirred for 2 hours. The solid was collected via filtration, and the 3 batches were combined in ethyl acetate (8 L) and filtered through silica gel (3.0 kg); the silica gel was then washed with ethyl acetate (2×2 L). After the combined eluates had been concentrated in vacuo, the residue was taken up in ethyl acetate (900 mL) and methyl tert-butyl ether (9 L). This mixture was heated to 50° C. for 1 hour, cooled to 25° C., and stirred for 2 hours. Filtration afforded (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate) as a white solid. The powder X-ray diffraction pattern for this material, designated as Solid Form 2, is given in FIG. 1; characteristic peaks are listed in Table A. Combined yield: 1.41 kg, 2.82 mol, 81%. LCMS m/z 500.3 [M+H]$^+$. $^1$H NMR (400 MHz, DMSO-$d_6$) δ 9.42 (d, J=8.4 Hz, 1H), 9.03 (d, J=8.6 Hz, 1H), 7.68 (s, 1H), 4.97 (ddd, J=10.9, 8.5, 5.1 Hz, 1H), 4.41 (d, J=8.5 Hz, 1H), 4.16 (s, 1H), 3.91 (dd, J=10.4, 5.5 Hz, 1H), 3.69 (d, J=10.4 Hz, 1H), 3.18-3.10 (m, 1H), 3.08-2.99 (m, 1H), 2.46-2.34 (m, 1H), 2.20-2.03 (m, 2H), 1.78-1.65 (m, 2H), 1.57 (dd, J=7.6, 5.4 Hz, 1H), 1.32 (d, J=7.6 Hz, 1H), 1.03 (s, 3H), 0.98 (s, 9H), 0.85 (s, 3H).

Collection of Powder X-Ray Diffraction Data

Powder X-ray diffraction analysis was conducted using a Bruker AXS D8 Endeavor diffractometer equipped with a Cu radiation source (K-α average). The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected in the Theta-Theta goniometer at the Cu wavelength from 3.0 to 40.0 degrees 2-Theta using a step size of 0.00998 degrees and a step time of 1.0 second. The antiscatter screen was set to a fixed distance of 1.5 mm. Samples were rotated at 15/minute during collection. Samples were prepared by placing them in a silicon low-background sample holder and rotated during collection. Data were collected using Bruker DIFFRAC Plus software and analysis was performed by EVA DIFFRAC Plus software. Using the peak search algorithm in the EVA software, peaks selected with a threshold value of 1 were used to make preliminary peak assignments. To ensure validity, adjustments were manually made; the output of automated assignments was visually checked and peak positions were adjusted to the peak maximum. Peaks with relative intensity of 3% were generally chosen. The peaks which were not resolved or were consistent with noise were not selected. A typical error associated with the peak position from PXRD stated in USP is up to +/−0.2° 2-Theta (USP-941).

TABLE A

Selected powder X-ray diffraction peaks for 13, methyl tert-butyl ether solvate, Solid Form 2, from Alternate Synthesis of Example 13, methyl tert-butyl ether solvate; Generation of 13, methyl tert-butyl ether solvate, Solid Form 2

| Angle (°2-theta) +/− 0.2° 2-Theta | Relative Intensity (%) |
|---|---|
| 7.1 | 78 |
| 10.5 | 8 |
| 11.3 | 15 |
| 11.8 | 36 |
| 12.5 | 49 |
| 12.9 | 4 |
| 14.2 | 34 |
| 15.7 | 10 |
| 16.0 | 24 |
| 16.8 | 100 |
| 17.0 | 41 |
| 18.5 | 50 |
| 18.8 | 7 |
| 19.1 | 25 |
| 19.9 | 11 |
| 20.2 | 8 |
| 20.8 | 14 |
| 21.1 | 9 |
| 21.4 | 4 |
| 21.7 | 4 |
| 22.2 | 24 |
| 22.7 | 9 |
| 22.9 | 10 |
| 23.1 | 5 |
| 23.4 | 6 |
| 23.7 | 22 |
| 25.3 | 14 |
| 27.3 | 3 |
| 27.9 | 6 |
| 28.3 | 9 |
| 28.5 | 4 |
| 29.1 | 3 |
| 29.4 | 6 |
| 30.2 | 3 |
| 30.8 | 5 |
| 32.0 | 4 |
| 33.3 | 7 |
| 33.8 | 4 |
| 35.4 | 7 |
| 36.4 | 6 |
| 38.1 | 3 |

Alternate Synthesis of (1R,2S, 5S)-6,6-dimethyl-3-[3-methyl-N-(trifluoroacetyl)-L-valyl]-3-azabicyclo[3.1.0]hexane-2-carboxylic acid (C42)

Second Alternate Synthesis of Example 13, methyl tert-butyl ether solvate; Generation of 13, methyl tert-butyl ether solvate, Solid Form 2

(1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate), Solid Form 2

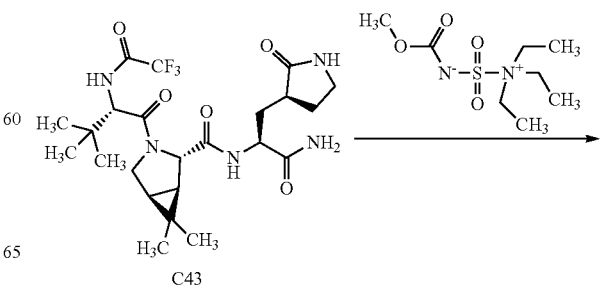

C43

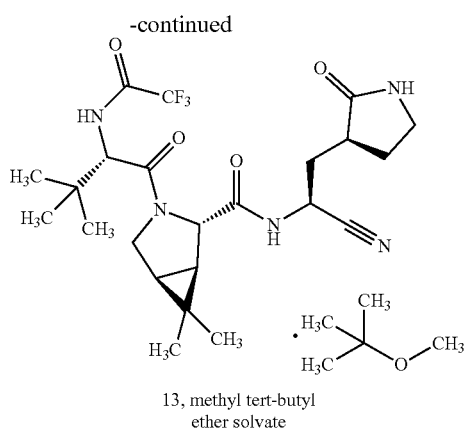

13, methyl tert-butyl ether solvate

Methyl N-(triethylammoniosulfonyl)carbamate, inner salt (Burgess reagent; 392 g, 1.64 mol) was added to a solution of C43 (415 g, 802 mmol) in ethyl acetate (2.0 L).

Figure 2:
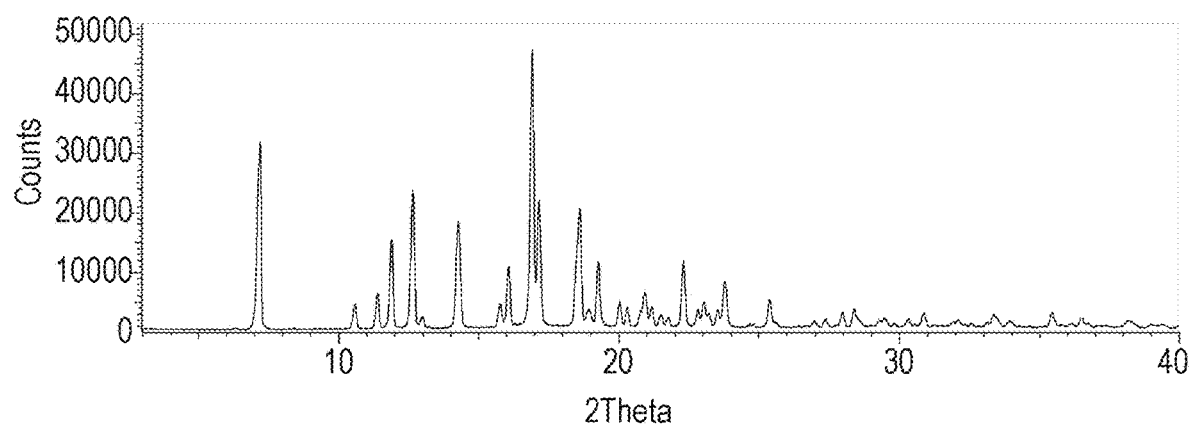
FIG. 2: Powder X-ray Diffraction Pattern of 13, methyl tert-butyl ether solvate, Solid Form 2, from Second Alternate Synthesis of Example 13, methyl tert-butyl ether solvate; Generation of Solid Form 2

The reaction mixture was stirred at 25° C. for 3 hours, whereupon methyl N-(triethylammoniosulfonyl)carbamate, inner salt (Burgess reagent; 86.0 g, 361 mmol) was again added. After the reaction mixture had been stirred for 1 hour, it was filtered, and the filtrate was washed sequentially with aqueous sodium bicarbonate solution (1 M; 1.5 L), saturated aqueous sodium chloride solution (1.5 L), hydrochloric acid (1 M; 1.5 L), and saturated aqueous sodium chloride solution (1.5 L), dried over sodium sulfate, filtered, and concentrated in vacuo. The residue was treated with a mixture of ethyl acetate and methyl tert-butyl ether (1:10, 2.5 L) and heated to 50° C.; after stirring for 1 hour at 50° C., it was cooled to 25° C. and stirred for 2 hours. Collection of the solid via filtration afforded (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate) as a crystalline white solid. The powder X-ray diffraction pattern for this material, designated as Solid Form 2, is given in FIG. 2; characteristic peaks are listed in Table B. Yield: 338 g, 575 mmol, 72%. LCMS m/z 500.3 [M+H]$^+$. $^1$H NMR (400 MHz, DMSO-d$_6$) δ 9.43 (d, J=8.4 Hz, 1H), 9.04 (d, J=8.6 Hz, 1H), 7.68 (s, 1H), 4.97 (ddd, J=10.9, 8.5, 5.0 Hz, 1H), 4.41 (d, J=8.5 Hz, 1H), 4.15 (s, 1H), 3.91 (dd, component of ABX system, J=10.4, 5.5 Hz, 1H), 3.69 (d, half of AB quartet, J=10.4 Hz, 1H), 3.18-3.10 (m, 1H), 3.08-2.98 (m, 1H), 2.46-2.34 (m, 1H), 2.20-2.02 (m, 2H), 1.77-1.65 (m, 2H), 1.57 (dd, J=7.6, 5.4 Hz, 1H), 1.32 (d, half of AB quartet, J=7.6 Hz, 1H), 1.02 (s, 3H), 0.98 (s, 9H), 0.85 (s, 3H); methyl tert-butyl ether peaks: 3.07 (s, 3H), 1.10 (s, 9H).

The method of collection of the powder X-ray diffraction data is described in Alternate Synthesis of Example 13, methyl tert-butyl ether solvate, Step 8.

TABLE B

Selected powder X-ray diffraction peaks for 13, methyl tert-butyl ether solvate, Solid Form 2, from Second Alternate Synthesis of Example 13, methyl tert-butyl ether solvate; Generation of 13, methyl tert-butyl ether solvate, Solid Form 2

| Angle (°2-theta) +/− 0.2° 2-Theta | Relative Intensity (%) |
|---|---|
| 7.2 | 66 |
| 10.6 | 9 |
| 11.4 | 12 |
| 11.9 | 32 |
| 12.6 | 49 |
| 13.0 | 4 |
| 14.3 | 37 |
| 15.8 | 8 |
| 16.1 | 22 |
| 16.9 | 100 |
| 17.2 | 46 |
| 18.6 | 42 |
| 18.9 | 6 |
| 19.3 | 23 |
| 20.0 | 9 |
| 20.3 | 6 |
| 20.8 | 6 |
| 20.9 | 12 |
| 21.2 | 7 |
| 21.5 | 4 |
| 21.8 | 3 |
| 22.3 | 24 |
| 22.8 | 6 |
| 23.0 | 9 |
| 23.2 | 5 |
| 23.5 | 6 |
| 23.8 | 17 |
| 25.4 | 10 |
| 27.4 | 3 |
| 28.0 | 6 |
| 28.4 | 7 |
| 29.5 | 4 |
| 30.3 | 3 |
| 30.9 | 5 |
| 32.1 | 3 |
| 33.4 | 5 |
| 33.5 | 3 |
| 35.5 | 6 |
| 36.5 | 3 |
| 38.2 | 3 |

Third Alternate Synthesis of Example 13

(1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13)

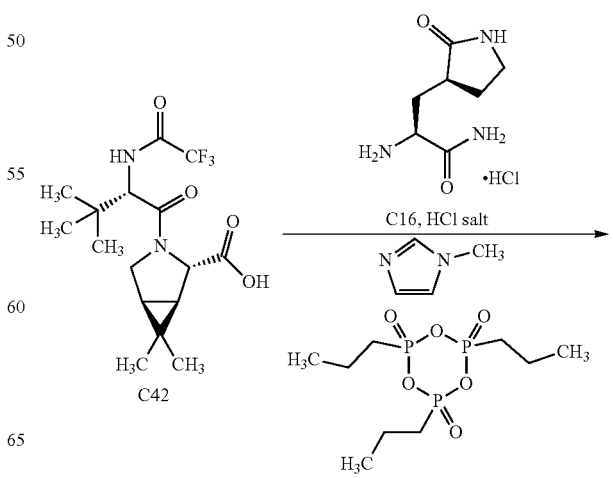

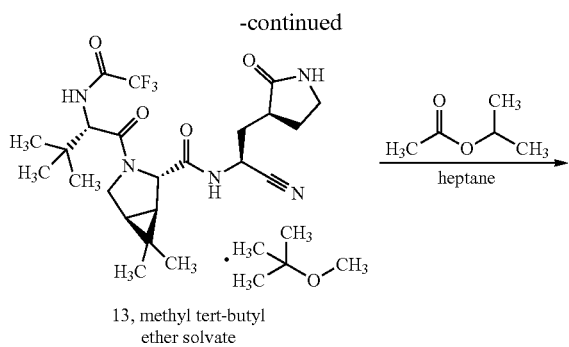

13, methyl tert-butyl
ether solvate

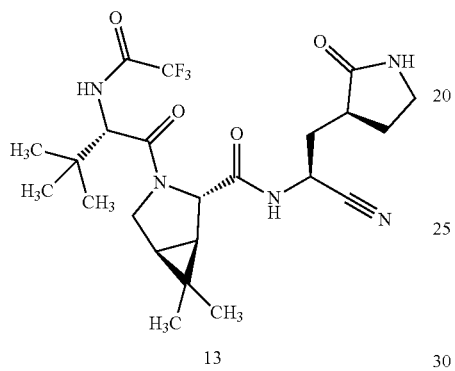

13

Step 1. Synthesis of (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate)

A 0° C. mixture of C42 (90.5 mass %, 5.05 g, 12.5 mmol) and C16, HCl salt (98.9 mass %, 3.12 g, 14.9 mmol) in acetonitrile (50 mL) was treated with 2,4,6-tripropyl-1,3,5,2,4,6-trioxatriphosphinane 2,4,6-trioxide (50% solution by weight in acetonitrile; 17 mL, 24.3 mmol) over approximately 10 minutes. 1-Methyl-1H-imidazole (4.0 mL, 50.2 mmol) was then added slowly, over approximately 15 minutes, and the reaction mixture was allowed to stir at 0° C. for 3.5 hours, whereupon it was warmed to 25° C. 2,4,6-Tripropyl-1,3,5,2,4,6-trioxatriphosphinane 2,4,6-trioxide (50% solution by weight in acetonitrile; 17 mL, 24.3 mmol) was added in one portion, and the reaction mixture was stirred at 45° C. for 16 hours. It was cooled to 25° C. at that point, and then treated over 10 minutes with an aqueous solution of sodium bicarbonate (1.14 M; 35 mL, 40 mmol). After addition of ethyl acetate (25 mL) and sufficient water to dissolve the resulting solids, the organic layer was washed twice with an aqueous solution of sodium bicarbonate (1.14 M; 25 mL, 28 mmol). After the organic layer had been washed with aqueous sodium chloride solution (14%, 2×20 mL), it was dried over sodium sulfate, filtered, and concentrated in vacuo. The residue was mixed with ethyl acetate (2.1 mL) and treated with methyl tert-butyl ether (19 mL); the resulting slurry was heated with stirring at 50° C. for 1 hour, cooled to 25° C. over 1 hour, and held at 25° C. for 1.5 hours. Solids were isolated via filtration, washed with methyl tert-butyl ether (2 mL/g), and dried in a vacuum oven overnight at 50° C. to afford (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate) as a crystalline white solid. The bulk of this material was progressed to the following step. Yield: 3.71 g, 6.31 mmol, 50%. $^1$H NMR (400 MHz, DMSO-$d_6$) δ 9.40 (d, J=8.4 Hz, 1H), 9.02 (d, J=8.6 Hz, 1H), 7.66 (s, 1H), 4.97 (ddd, J=10.7, 8.6, 5.1 Hz, 1H), 4.41 (d, J=8.4 Hz, 1H), 4.16 (s, 1H), 3.91 (dd, component of ABX system, J=10.3, 5.5 Hz, 1H), 3.69 (d, half of AB quartet, J=10.4 Hz, 1H), 3.18-3.10 (m, 1H), 3.09-2.99 (m, 1H), 2.46-2.35 (m, 1H), 2.20-2.04 (m, 2H), 1.78-1.64 (m, 2H), 1.56 (dd, J=7.4, 5.6 Hz, 1H), 1.32 (d, half of AB quartet, J=7.6 Hz, 1H), 1.03 (s, 3H), 0.98 (s, 9H), 0.85 (s, 3H); methyl tert-butyl ether peaks: 3.07 (s, 3H), 1.10 (s, 9H).

Step 2. Synthesis of (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13)

A mixture of propan-2-yl acetate (17 mL) and heptane (17 mL) was added to 13, methyl tert-butyl ether solvate (from the previous step; 3.41 g, 5.80 mmol), and stirring was carried out overnight at 20° C. Heptane (17 mL) was then added over 2 hours, and the mixture was stirred overnight at room temperature. The resulting slurry was filtered, and the collected solids were washed with a mixture of propan-2-yl acetate (1.36 mL) and heptane (3.73 mL) and dried at 50° C. under vacuum, affording (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13) as a crystalline solid. A portion of this batch was used as seed material in Recrystallization of Example 13; Generation of Solid Form 1 below. Yield: 2.73 g, 5.46 mmol, 94%.

Recrystallization of Example 13; Generation of Solid Form 1

(1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13), Solid Form 1

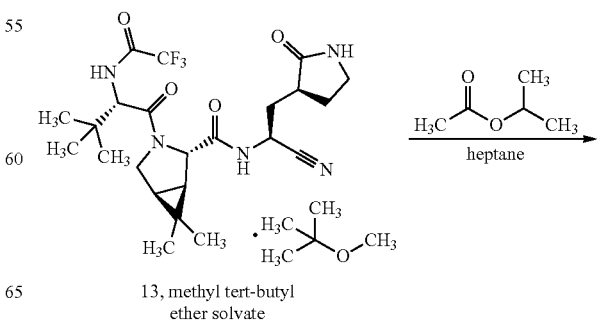

13, methyl tert-butyl
ether solvate

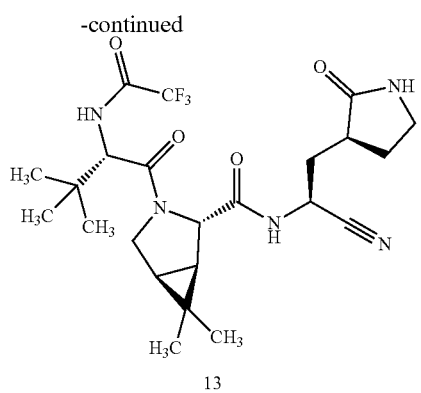

13

Figure 3:
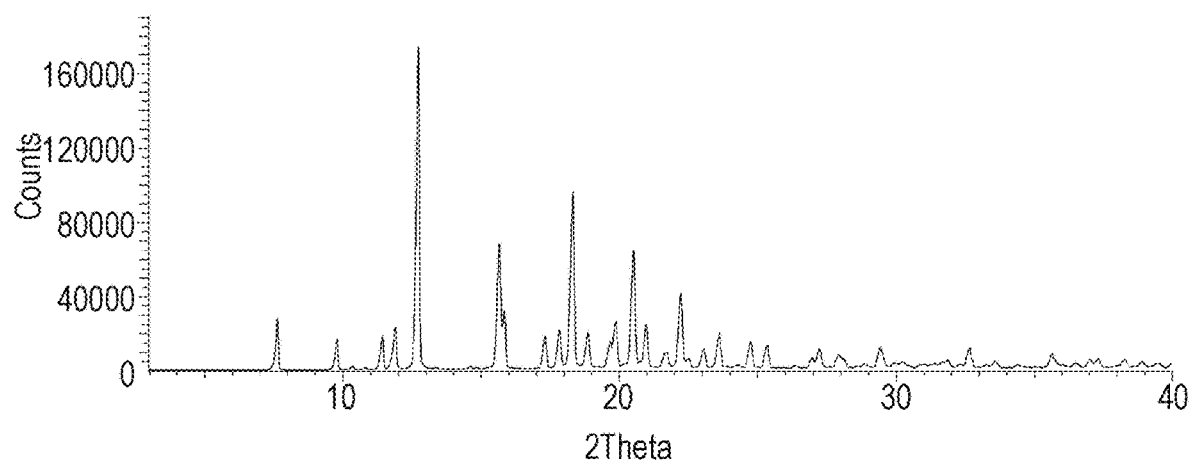
FIG. 3: Powder X-ray Diffraction Pattern of Example 13, Solid Form 1, from Recrystallization of Example 13; Generation of Solid Form 1

A mixture of 13, methyl tert-butyl ether solvate (from Alternate Synthesis of Example 13, methyl tert-butyl ether solvate; Generation of 13, methyl tert-butyl ether solvate, Solid Form 2; 60.1 g, 102 mmol) and propan-2-yl acetate (480 mL) was heated to 60° C. A sample of 13 (seed material, from Third Alternate Synthesis of Example 13, Step 2; 1.2 g, 2.4 mmol) was added; after 10 minutes, the seed material was still present in solid form. Heptane (360 mL) was slowly added to the stirring mixture, over 12 hours. Additional heptane (360 mL) was introduced over 4 hours, and the resulting mixture was stirred for 30 minutes. It was then cooled to 20° C., at a rate of 0.1 degrees/minute, whereupon it was stirred overnight. The solid was collected via filtration, and washed with a mixture of propan-2-yl acetate (72 mL) and heptane (168 mL). It was then dried under vacuum at 50° C. to provide (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13) as a white, crystalline solid. The powder X-ray diffraction pattern for this material, designated as Solid Form 1, is given in FIG. 3; characteristic peaks are listed in Table C. Yield: 47.8 g, 95.7 mmol, 94%.

The method of collection of the powder X-ray diffraction data is described in Alternate Synthesis of Example 13, methyl tert-butyl ether solvate, Step 8.

TABLE C

Selected powder X-ray diffraction peaks for 13, Solid Form 1

| Angle (°2-theta) +/− 0.2° 2-Theta | Relative Intensity (%) |
|---|---|
| 7.6 | 16 |
| 9.8 | 10 |
| 11.4 | 10 |
| 11.9 | 13 |
| 12.7 | 100 |
| 15.7 | 40 |
| 15.8 | 18 |
| 17.3 | 10 |
| 17.8 | 12 |
| 18.3 | 55 |
| 18.9 | 11 |
| 19.7 | 7 |
| 19.9 | 14 |
| 20.5 | 36 |
| 21.0 | 14 |
| 21.7 | 4 |
| 22.2 | 23 |
| 22.5 | 3 |
| 23.1 | 6 |
| 23.6 | 10 |
| 24.7 | 8 |
| 25.3 | 7 |
| 27.0 | 3 |

TABLE C-continued

Selected powder X-ray diffraction peaks for 13, Solid Form 1

| Angle (°2-theta) +/− 0.2° 2-Theta | Relative Intensity (%) |
|---|---|
| 27.2 | 6 |
| 27.9 | 4 |
| 28.1 | 3 |
| 29.5 | 7 |
| 32.6 | 6 |
| 35.7 | 4 |
| 37.0 | 3 |

Single-crystal X-ray Structural Determination of Example 13, Solid Form 1

Figure 4:
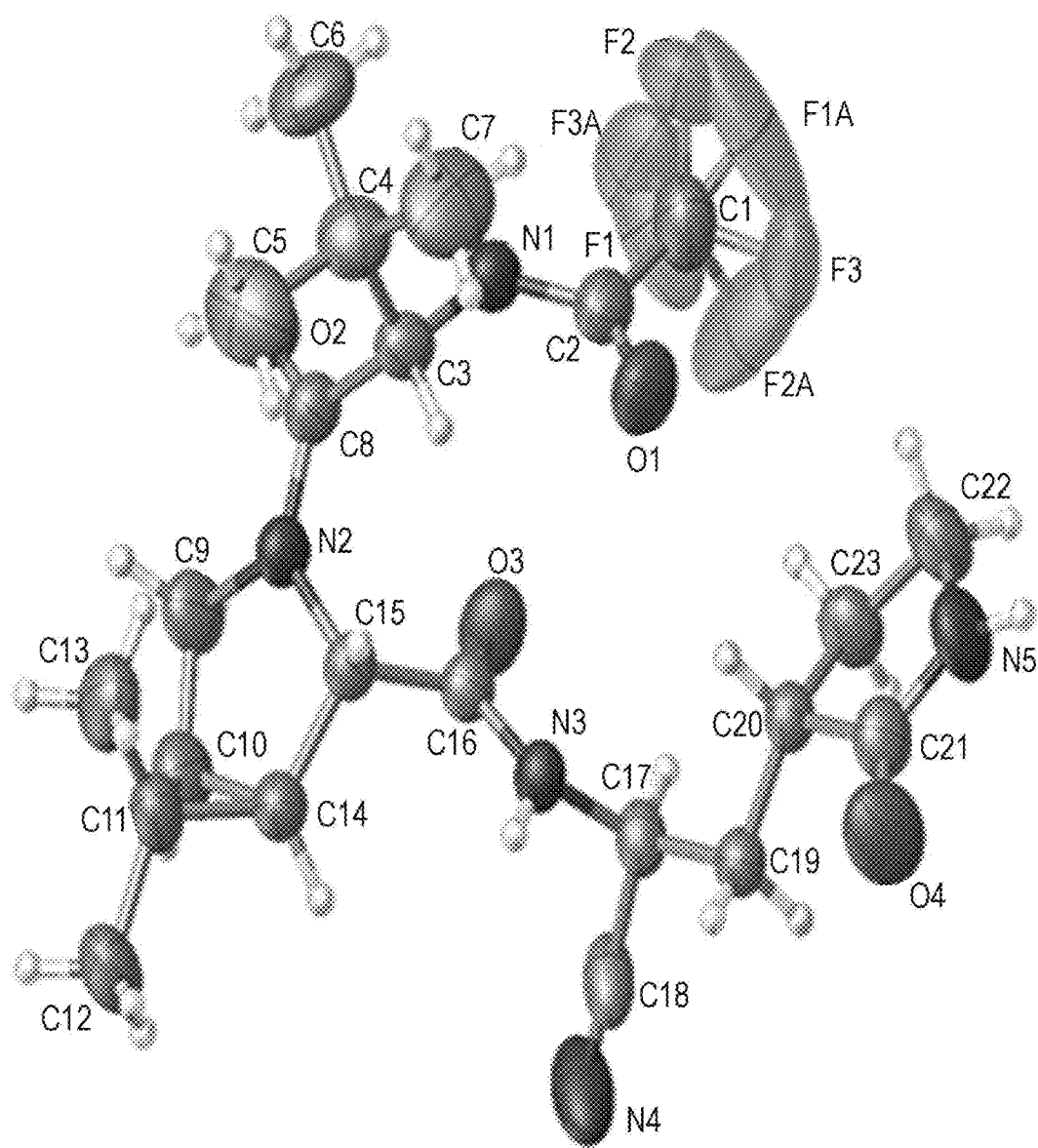
FIG. 4: Single-crystal X-ray Structural Determination of Example 13, Solid Form 1. ORTEP diagram drawn with displacement parameters at 50% probability
Figure 5:
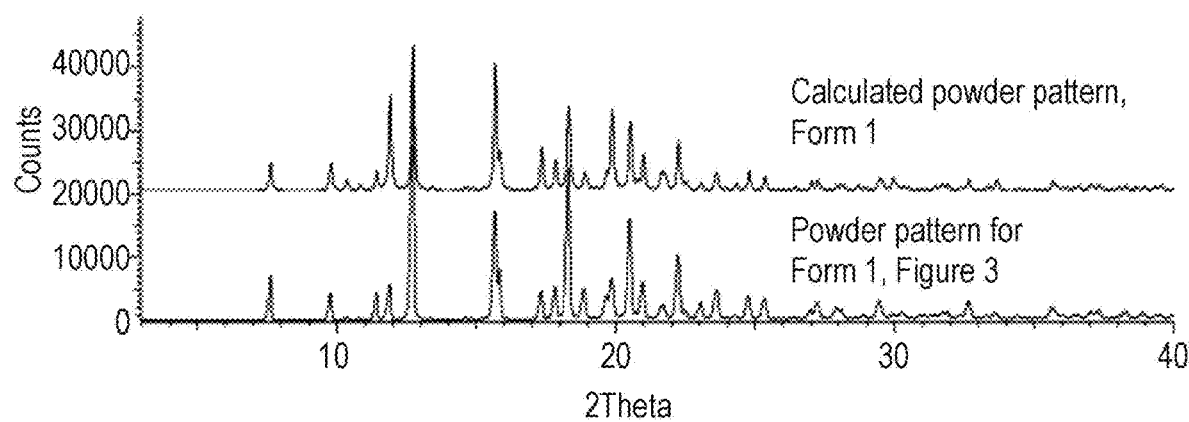
FIG. 5: Overlay of powder pattern obtained for Example 13, Solid Form 1, from Recrystallization of Example 13; Generation of Solid Form 1 (FIG. 3) and the calculated powder pattern, generated via Mercury software, from resolved X-ray single-crystal data of Form 1 (see Single-crystal X-ray Structural Determination of Example 13, Solid Form 1).

A sample of Example 13 was subjected to crystallization via diffusion, using ethyl acetate and hexane. The crystallization vessel was allowed to stand at room temperature while the solvent evaporated after 2.5 months, crystals of X-ray quality were present. One of these was used for the structural determination. An ORTEP diagram of the single-crystal data is shown in FIG. 4. Mercury software was used to calculate the powder pattern from the resolved crystal structure; comparison with the diffraction pattern from Recrystallization of Example 13; Generation of Solid Form 1 identified this material as being Solid Form 1 (see FIG. 5). Characteristic peaks for this calculated data are provided in Table D.

TABLE D

Powder pattern data for 13, Solid Form 1 calculated from Single-crystal X-ray Structural Determination of Example 13, Solid Form 1

| Angle (°2-theta) +/− 0.2° 2-Theta | Relative Intensity (%) |
|---|---|
| 7.6 | 22 |
| 9.8 | 21 |
| 10.4 | 9 |
| 10.8 | 4 |
| 11.4 | 16 |
| 11.9 | 75 |
| 12.7 | 89 |
| 14.6 | 3 |
| 15.7 | 100 |
| 15.9 | 30 |
| 17.4 | 34 |
| 17.9 | 24 |
| 18.3 | 67 |
| 18.9 | 12 |
| 19.7 | 15 |
| 19.9 | 63 |
| 20.5 | 53 |
| 20.8 | 9 |
| 21.0 | 28 |
| 21.6 | 14 |
| 21.7 | 14 |
| 22.2 | 40 |
| 22.5 | 7 |
| 23.1 | 5 |
| 23.6 | 15 |
| 24.3 | 5 |
| 24.8 | 15 |
| 25.4 | 10 |
| 26.4 | 3 |
| 27.0 | 9 |
| 27.3 | 8 |
| 27.9 | 3 |
| 28.1 | 5 |
| 28.7 | 5 |
| 29.5 | 9 |
| 30.0 | 9 |
| 30.1 | 4 |

TABLE D-continued

Powder pattern data for 13, Solid Form 1 calculated from Single-crystal X-ray Structural Determination of Example 13, Solid Form 1

| Angle (°2-theta) +/− 0.2° 2-Theta | Relative Intensity (%) |
|---|---|
| 30.3 | 3 |
| 31.5 | 4 |
| 31.7 | 5 |
| 31.9 | 4 |
| 32.7 | 8 |
| 33.4 | 3 |
| 33.6 | 8 |
| 35.7 | 8 |
| 36.6 | 3 |
| 36.6 | 3 |
| 37.0 | 4 |
| 37.3 | 4 |
| 38.3 | 3 |
| 39.4 | 3 |
| 39.6 | 4 |

Single Crystal X-Ray Analysis

Data collection was performed on a Bruker D8 Quest diffractometer at room temperature. Data collection consisted of omega and phi scans.

The structure was solved by intrinsic phasing using SHELX software suite in the orthorhombic class space group $P2_12_12_1$. The structure was subsequently refined by the full-matrix least squares method. All non-hydrogen atoms were found and refined using anisotropic displacement parameters.

The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned. The method calculates that the probability that the structure is correctly assigned is 100%. The Hooft parameter is reported as −0.01 with an esd (estimated standard deviation) of (3) and the Parson's parameter is reported as −0.01 with an esd of (2).

The final R-index was 3.3%. A final difference Fourier revealed no missing or misplaced electron density.

Pertinent crystal, data collection, and refinement information is summarized in Table E. Atomic coordinates, bond lengths, bond angles, and displacement parameters are listed in Tables F-H.

SOFTWARE AND REFERENCES

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Straver, and A. L. Spek, *J. Appl. Cryst.* 2008, 41, 96-103.

H. D. Flack, *Acta Cryst.* 1983, A39, 867-881.

TABLE E

Crystal data and structure refinement for Example 13, Solid Form 1.

| | |
|---|---|
| Empirical formula | $C_{23}H_{32}F_3N_5O_4$ |
| Formula weight | 499.53 |
| Temperature | 296(2) K |
| Wavelength | 1.54178 Å |
| Crystal system | Orthorhombic |
| Space group | $P2_12_12_1$ |
| Unit cell dimensions | a = 9.6836(2) Å  α = 90° |
| | b = 15.0522(4) Å  β = 90° |
| | c = 18.0272(5) Å  γ = 90° |
| Volume | 2627.64(11) Å$^3$ |
| Z | 4 |
| Density (calculated) | 1.263 Mg/m$^3$ |
| Absorption coefficient | 0.862 mm$^{-1}$ |
| F(000) | 1056 |
| Crystal size | 0.300 × 0.280 × 0.260 mm$^3$ |
| Theta range for data collection | 3.826 to 80.042° |
| Index ranges | −12 <= h <= 12, −18 <= k <= 19, −22 <= l <= 23 |
| Reflections collected | 79731 |
| Independent reflections | 5628 [$R_{int}$ = 0.0294] |
| Completeness to theta = 67.679° | 99.3% |
| Absorption correction | Empirical |
| Refinement method | Full-matrix least-squares on F$^2$ |
| Data/restraints/parameters | 5628/9/358 |
| Goodness-of-fit on F$^2$ | 1.040 |
| Final R indices [I > 2σ(I)] | R1 = 0.0326, wR2 = 0.0906 |
| R indices (all data) | R1 = 0.0346, wR2 = 0.0928 |
| Absolute structure parameter | −0.01(3) |
| Extinction coefficient | n/a |
| Largest diff. peak and hole | 0.112 and −0.121 e · Å$^{-3}$ |

TABLE F

Atomic coordinates (×10$^4$) and equivalent isotropic displacement parameters (Å$^2$ × 10$^3$) for Example 13, Solid Form 1. U(eq) is defined as one-third of the trace of the orthogonalized U$^{ij}$ tensor.

| | x | y | z | U(eq) |
|---|---|---|---|---|
| F(1) | 4585(8) | 3891(5) | 8183(8) | 174(4) |
| F(2) | 2984(6) | 4623(4) | 8601(2) | 135(2) |
| F(3) | 2988(7) | 4449(5) | 7471(2) | 133(3) |
| F(1A) | 2622(7) | 4494(8) | 8158(16) | 237(10) |
| F(2A) | 4140(20) | 3994(5) | 7406(4) | 167(6) |
| F(3A) | 4404(15) | 3963(8) | 8488(5) | 127(5) |
| N(1) | 5507(2) | 5598(1) | 8478(1) | 54(1) |
| N(2) | 8733(1) | 6526(1) | 8104(1) | 49(1) |
| N(3) | 7304(1) | 6456(1) | 6213(1) | 44(1) |
| N(4) | 9229(2) | 5659(2) | 4815(1) | 99(1) |
| N(5) | 2159(2) | 6087(2) | 5207(1) | 76(1) |
| O(1) | 4297(2) | 5900(1) | 7426(1) | 84(1) |
| O(2) | 8176(2) | 5753(1) | 9126(1) | 70(1) |
| O(3) | 7711(2) | 5377(1) | 7059(1) | 70(1) |
| O(4) | 3393(2) | 7171(1) | 4635(1) | 86(1) |
| C(1) | 3848(3) | 4543(2) | 8022(2) | 93(1) |
| C(2) | 4597(2) | 5424(2) | 7941(1) | 63(1) |
| C(3) | 6284(2) | 6425(1) | 8485(1) | 51(1) |
| C(4) | 5739(3) | 7084(2) | 9082(1) | 69(1) |
| C(5) | 6747(4) | 7872(2) | 9133(2) | 98(1) |
| C(6) | 5652(4) | 6670(2) | 9851(1) | 94(1) |
| C(7) | 4309(3) | 7402(3) | 8847(2) | 110(1) |
| C(8) | 7812(2) | 6195(1) | 8592(1) | 50(1) |
| C(9) | 10204(2) | 6319(2) | 8211(1) | 65(1) |
| C(10) | 10931(2) | 6770(2) | 7575(1) | 68(1) |
| C(11) | 10769(2) | 7754(2) | 7454(1) | 70(1) |
| C(12) | 11879(3) | 8175(2) | 6970(2) | 101(1) |
| C(13) | 10220(3) | 8359(2) | 8049(1) | 85(1) |
| C(14) | 9842(2) | 7109(1) | 7047(1) | 58(1) |
| C(15) | 8435(2) | 6868(1) | 7361(1) | 45(1) |
| C(16) | 7781(2) | 6149(1) | 6870(1) | 44(1) |
| C(17) | 6994(2) | 5848(1) | 5610(1) | 47(1) |
| C(18) | 8256(2) | 5732(2) | 5157(1) | 67(1) |
| C(19) | 5822(2) | 6180(1) | 5115(1) | 47(1) |
| C(20) | 4454(2) | 6159(1) | 5519(1) | 44(1) |

TABLE F-continued

Atomic coordinates (×10⁴) and equivalent isotropic displacement parameters ($Å^2 \times 10^3$) for Example 13, Solid Form 1. U(eq) is defined as one-third of the trace of the orthogonalized $U^{ij}$ tensor.

|       | x       | y       | z       | U(eq) |
|-------|---------|---------|---------|-------|
| C(21) | 3297(2) | 6544(1) | 5059(1) | 56(1) |
| C(22) | 2355(2) | 5356(2) | 5718(2) | 82(1) |
| C(23) | 3911(2) | 5237(1) | 5704(1) | 63(1) |

TABLE G

Bond lengths [Å] and angles [°] for Example 13, Solid Form 1.

| | |
|---|---|
| F(1)—C(1) | 1.248(7) |
| F(2)—C(1) | 1.342(5) |
| F(3)—C(1) | 1.305(4) |
| F(1A)—C(1) | 1.215(9) |
| F(2A)—C(1) | 1.414(8) |
| F(3A)—C(1) | 1.325(11) |
| N(1)—C(2) | 1.335(2) |
| N(1)—C(3) | 1.455(2) |
| N(1)—H(1X) | 0.906(18) |
| N(2)—C(8) | 1.348(2) |
| N(2)—C(15) | 1.4631(19) |
| N(2)—C(9) | 1.471(2) |
| N(3)—C(16) | 1.3527(19) |
| N(3)—C(17) | 1.452(2) |
| N(3)—H(3X) | 0.944(17) |
| N(4)—C(18) | 1.132(3) |
| N(5)—C(21) | 1.326(3) |
| N(5)—C(22) | 1.447(3) |
| N(5)—H(5X) | 0.91(2) |
| O(1)—C(2) | 1.209(2) |
| O(2)—C(8) | 1.222(2) |
| O(3)—C(16) | 1.214(2) |
| O(4)—C(21) | 1.218(2) |
| C(1)—C(2) | 1.518(4) |
| C(3)—C(8) | 1.531(2) |
| C(3)—C(4) | 1.554(3) |
| C(3)—H(3) | 0.9800 |
| C(4)—C(7) | 1.525(4) |
| C(4)—C(6) | 1.523(3) |
| C(4)—C(5) | 1.540(4) |
| C(5)—H(5A) | 0.9600 |
| C(5)—H(5B) | 0.9600 |
| C(5)—H(5C) | 0.9600 |
| C(6)—H(6A) | 0.9600 |
| C(6)—H(6B) | 0.9600 |
| C(6)—H(6C) | 0.9600 |
| C(7)—H(7A) | 0.9600 |
| C(7)—H(7B) | 0.9600 |
| C(7)—H(7C) | 0.9600 |
| C(9)—C(10) | 1.506(3) |
| C(9)—H(9A) | 0.9700 |
| C(9)—H(9B) | 0.9700 |
| C(10)—C(11) | 1.505(3) |
| C(10)—C(14) | 1.510(3) |
| C(10)—H(10) | 0.9800 |
| C(11)—C(13) | 1.505(4) |
| C(11)—C(14) | 1.511(3) |
| C(11)—C(12) | 1.522(3) |
| C(12)—H(12A) | 0.9600 |
| C(12)—H(12B) | 0.9600 |
| C(12)—H(12C) | 0.9600 |
| C(13)—H(13A) | 0.9600 |
| C(13)—H(13B) | 0.9600 |
| C(13)—H(13C) | 0.9600 |
| C(14)—C(15) | 1.520(2) |
| C(14)—H(14) | 0.9800 |
| C(15)—C(16) | 1.535(2) |
| C(15)—H(15) | 0.9800 |
| C(17)—C(18) | 1.480(2) |
| C(17)—C(19) | 1.528(2) |
| C(17)—H(17) | 0.9800 |
| C(19)—C(20) | 1.512(2) |
| C(19)—H(19A) | 0.9700 |
| C(19)—H(19B) | 0.9700 |
| C(20)—C(21) | 1.510(2) |
| C(20)—C(23) | 1.521(2) |
| C(20)—H(20) | 0.9800 |
| C(22)—C(23) | 1.518(3) |
| C(22)—H(22A) | 0.9700 |
| C(22)—H(22B) | 0.9700 |
| C(23)—H(23A) | 0.9700 |
| C(23)—H(23B) | 0.9700 |
| C(2)—N(1)—C(3) | 121.10(16) |
| C(2)—N(1)—H(1X) | 120.7(15) |
| C(3)—N(1)—H(1X) | 117.9(15) |
| C(8)—N(2)—C(15) | 126.62(13) |
| C(8)—N(2)—C(9) | 118.51(14) |
| C(15)—N(2)—C(9) | 112.66(14) |
| C(16)—N(3)—C(17) | 120.65(13) |
| C(16)—N(3)—H(3X) | 122.1(13) |
| C(17)—N(3)—H(3X) | 112.1(12) |
| C(21)—N(5)—C(22) | 114.42(16) |
| C(21)—N(5)—H(5X) | 126.1(19) |
| C(22)—N(5)—H(5X) | 119.3(19) |
| F(1)—C(1)—F(3) | 117.2(6) |
| F(1A)—C(1)—F(3A) | 103.3(11) |
| F(1)—C(1)—F(2) | 104.3(6) |
| F(3)—C(1)—F(2) | 101.7(4) |
| F(1A)—C(1)—F(2A) | 108.6(10) |
| F(3A)—C(1)—F(2A) | 91.8(7) |
| F(1A)—C(1)—C(2) | 122.6(7) |
| F(1)—C(1)—C(2) | 115.8(4) |
| F(3)—C(1)—C(2) | 109.1(3) |
| F(3A)—C(1)—C(2) | 116.3(6) |
| F(2)—C(1)—C(2) | 107.2(3) |
| F(2A)—C(1)—C(2) | 109.8(5) |
| O(1)—C(2)—N(1) | 126.8(2) |
| O(1)—C(2)—C(1) | 118.5(2) |
| N(1)—C(2)—C(1) | 114.65(19) |
| N(1)—C(3)—C(8) | 107.86(14) |
| N(1)—C(3)—C(4) | 112.12(15) |
| C(8)—C(3)—C(4) | 112.72(16) |
| N(1)—C(3)—H(3) | 108.0 |
| C(8)—C(3)—H(3) | 108.0 |
| C(4)—C(3)—H(3) | 108.0 |
| C(7)—C(4)—C(6) | 109.3(2) |
| C(7)—C(4)—C(5) | 110.5(2) |
| C(6)—C(4)—C(5) | 107.2(2) |
| C(7)—C(4)—C(3) | 108.5(2) |
| C(6)—C(4)—C(3) | 112.81(19) |
| C(5)—C(4)—C(3) | 108.52(19) |
| C(4)—C(5)—H(5A) | 109.5 |
| C(4)—C(5)—H(5B) | 109.5 |
| H(5A)—C(5)—H(5B) | 109.5 |
| C(4)—C(5)—H(5C) | 109.5 |
| H(5A)—C(5)—H(5C) | 109.5 |
| H(5B)—C(5)—H(5C) | 109.5 |
| C(4)—C(6)—H(6A) | 109.5 |
| C(4)—C(6)—H(6B) | 109.5 |
| H(6A)—C(6)—H(6B) | 109.5 |
| C(4)—C(6)—H(6C) | 109.5 |
| H(6A)—C(6)—H(6C) | 109.5 |
| H(6B)—C(6)—H(6C) | 109.5 |
| C(4)—C(7)—H(7A) | 109.5 |
| C(4)—C(7)—H(7B) | 109.5 |
| H(7A)—C(7)—H(7B) | 109.5 |
| C(4)—C(7)—H(7C) | 109.5 |
| H(7A)—C(7)—H(7C) | 109.5 |
| H(7B)—C(7)—H(7C) | 109.5 |
| O(2)—C(8)—N(2) | 121.60(16) |
| O(2)—C(8)—C(3) | 120.04(16) |
| N(2)—C(8)—C(3) | 118.28(13) |
| N(2)—C(9)—C(10) | 104.93(15) |
| N(2)—C(9)—H(9A) | 110.8 |
| C(10)—C(9)—H(9A) | 110.8 |
| N(2)—C(9)—H(9B) | 110.8 |
| C(10)—C(9)—H(9B) | 110.8 |
| H(9A)—C(9)—H(9B) | 108.8 |
| C(11)—C(10)—C(9) | 120.3(2) |
| C(11)—C(10)—C(14) | 60.18(13) |
| C(9)—C(10)—C(14) | 107.82(15) |

TABLE G-continued

Bond lengths [Å] and angles [°] for Example 13, Solid Form 1.

| | |
|---|---|
| C(11)—C(10)—H(10) | 118.0 |
| C(9)—C(10)—H(10) | 118.0 |
| C(14)—C(10)—H(10) | 118.0 |
| C(10)—C(11)—C(13) | 121.92(19) |
| C(10)—C(11)—C(14) | 60.07(14) |
| C(13)—C(11)—C(14) | 121.66(19) |
| C(10)—C(11)—C(12) | 114.8(2) |
| C(13)—C(11)—C(12) | 113.9(2) |
| C(14)—C(11)—C(12) | 114.14(18) |
| C(11)—C(12)—H(12A) | 109.5 |
| C(11)—C(12)—H(12B) | 109.5 |
| H(12A)—C(12)—H(12B) | 109.5 |
| C(11)—C(12)—H(12C) | 109.5 |
| H(12A)—C(12)—H(12C) | 109.5 |
| H(12B)—C(12)—H(12C) | 109.5 |
| C(11)—C(13)—H(13A) | 109.5 |
| C(11)—C(13)—H(13B) | 109.5 |
| H(13A)—C(13)—H(13B) | 109.5 |
| C(11)—C(13)—H(13C) | 109.5 |
| H(13A)—C(13)—H(13C) | 109.5 |
| H(13B)—C(13)—H(13C) | 109.5 |
| C(10)—C(14)—C(11) | 59.75(14) |
| C(10)—C(14)—C(15) | 108.04(15) |
| C(11)—C(14)—C(15) | 120.32(16) |
| C(10)—C(14)—H(14) | 118.0 |
| C(11)—C(14)—H(14) | 118.0 |
| C(15)—C(14)—H(14) | 118.0 |
| N(2)—C(15)—C(14) | 104.39(13) |
| N(2)—C(15)—C(16) | 111.18(13) |
| C(14)—C(15)—C(16) | 108.87(13) |
| N(2)—C(15)—H(15) | 110.7 |
| C(14)—C(15)—H(15) | 110.7 |
| C(16)—C(15)—H(15) | 110.7 |
| O(3)—C(16)—N(3) | 123.70(15) |
| O(3)—C(16)—C(15) | 122.40(14) |
| N(3)—C(16)—C(15) | 113.89(13) |
| N(3)—C(17)—C(18) | 108.50(13) |
| N(3)—C(17)—C(19) | 112.62(13) |
| C(18)—C(17)—C(19) | 109.24(14) |
| N(3)—C(17)—H(17) | 108.8 |
| C(18)—C(17)—H(17) | 108.8 |
| C(19)—C(17)—H(17) | 108.8 |
| N(4)—C(18)—C(17) | 178.6(2) |
| C(20)—C(19)—C(17) | 111.27(13) |
| C(20)—C(19)—H(19A) | 109.4 |
| C(17)—C(19)—H(19A) | 109.4 |
| C(20)—C(19)—H(19B) | 109.4 |
| C(17)—C(19)—H(19B) | 109.4 |
| H(19A)—C(19)—H(19B) | 108.0 |
| C(21)—C(20)—C(19) | 112.17(13) |
| C(21)—C(20)—C(23) | 102.32(14) |
| C(19)—C(20)—C(23) | 115.26(15) |
| C(21)—C(20)—H(20) | 108.9 |
| C(19)—C(20)—H(20) | 108.9 |
| C(23)—C(20)—H(20) | 108.9 |
| O(4)—C(21)—N(5) | 126.30(18) |
| O(4)—C(21)—C(20) | 125.79(17) |
| N(5)—C(21)—C(20) | 107.91(15) |
| N(5)—C(22)—C(23) | 102.06(17) |
| N(5)—C(22)—H(22A) | 111.4 |
| C(23)—C(22)—H(22A) | 111.4 |
| N(5)—C(22)—H(22B) | 111.4 |
| C(23)—C(22)—H(22B) | 111.4 |
| H(22A)—C(22)—H(22B) | 109.2 |
| C(22)—C(23)—C(20) | 103.82(18) |
| C(22)—C(23)—H(23A) | 111.0 |
| C(20)—C(23)—H(23A) | 111.0 |
| C(22)—C(23)—H(23B) | 111.0 |
| C(20)—C(23)—H(23B) | 111.0 |
| H(23A)—C(23)—H(23B) | 109.0 |

Symmetry transformations used to generate equivalent atoms.

TABLE H

Anisotropic displacement parameters (Å$^2$ × 10$^3$) for Example 13, Solid Form 1. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| F(1) | 105(3) | 87(3) | 329(14) | −12(6) | −36(6) | −6(2) |
| F(2) | 113(4) | 185(4) | 107(3) | 29(2) | 25(2) | −68(3) |
| F(3) | 138(4) | 170(5) | 91(2) | 18(3) | −44(2) | −92(4) |
| F(1A) | 55(3) | 183(9) | 470(30) | 64(16) | −24(9) | −39(4) |
| F(2A) | 317(18) | 99(4) | 86(4) | −28(3) | −12(6) | −34(7) |
| F(3A) | 185(11) | 94(6) | 103(4) | 17(3) | −12(4) | −63(6) |
| N(1) | 48(1) | 70(1) | 44(1) | 10(1) | −3(1) | −5(1) |
| N(2) | 42(1) | 64(1) | 42(1) | 7(1) | −7(1) | 0(1) |
| N(3) | 45(1) | 45(1) | 42(1) | 2(1) | −6(1) | −4(1) |
| N(4) | 46(1) | 140(2) | 110(2) | −65(1) | 7(1) | −2(1) |
| N(5) | 40(1) | 105(1) | 84(1) | 12(1) | −14(1) | −6(1) |
| O(1) | 75(1) | 118(1) | 59(1) | 14(1) | −21(1) | −4(1) |
| O(2) | 60(1) | 92(1) | 58(1) | 32(1) | −8(1) | 1(1) |
| O(3) | 92(1) | 51(1) | 67(1) | 12(1) | −19(1) | −3(1) |
| O(4) | 76(1) | 79(1) | 102(1) | 36(1) | −15(1) | 14(1) |
| C(1) | 86(2) | 113(2) | 79(2) | 7(2) | −14(1) | −34(2) |
| C(2) | 51(1) | 90(1) | 48(1) | 1(1) | −3(1) | −4(1) |
| C(3) | 47(1) | 62(1) | 43(1) | 11(1) | 0(1) | 1(1) |
| C(4) | 70(1) | 70(1) | 67(1) | −2(1) | 7(1) | 9(1) |
| C(5) | 111(2) | 67(1) | 117(2) | −14(1) | 17(2) | 0(1) |
| C(6) | 117(2) | 108(2) | 57(1) | −11(1) | 18(1) | 2(2) |
| C(7) | 81(1) | 138(2) | 111(2) | −8(2) | 10(2) | 46(2) |
| C(8) | 49(1) | 58(1) | 42(1) | 7(1) | −6(1) | 0(1) |
| C(9) | 44(1) | 88(1) | 65(1) | 16(1) | −11(1) | 4(1) |
| C(10) | 41(1) | 99(2) | 63(1) | 5(1) | −4(1) | −3(1) |
| C(11) | 57(1) | 95(1) | 56(1) | 11(1) | −11(1) | −27(1) |
| C(12) | 74(2) | 150(3) | 80(2) | 23(2) | −9(1) | −55(2) |
| C(13) | 93(2) | 91(2) | 72(1) | −3(1) | −13(1) | −32(1) |
| C(14) | 47(1) | 84(1) | 44(1) | 3(1) | −2(1) | −14(1) |
| C(15) | 43(1) | 54(1) | 39(1) | 5(1) | −4(1) | −3(1) |
| C(16) | 41(1) | 48(1) | 44(1) | 4(1) | −3(1) | 1(1) |
| C(17) | 39(1) | 52(1) | 51(1) | −5(1) | −6(1) | −2(1) |
| C(18) | 42(1) | 85(1) | 73(1) | −33(1) | −9(1) | 0(1) |
| C(19) | 41(1) | 58(1) | 41(1) | 1(1) | −4(1) | −5(1) |
| C(20) | 40(1) | 52(1) | 41(1) | 1(1) | −6(1) | −4(1) |
| C(21) | 46(1) | 62(1) | 58(1) | 4(1) | −9(1) | 6(1) |
| C(22) | 58(1) | 103(2) | 84(1) | 14(1) | 0(1) | −28(1) |
| C(23) | 60(1) | 64(1) | 66(1) | 19(1) | −4(1) | −12(1) |

Solid-state NMR analysis of the compound of Example 13, Forms 1 and 4 was conducted on a CPMAS probe positioned into a Bruker-BioSpin Avance III 500 MHz ($^1$H frequency) NMR spectrometer. A magic angle spinning rate of 15.0 kHz was used. Form 1 spectra were collected at ambient temperature (temperature uncontrolled) and Form 4 spectra were collected at 15° C.

$^{13}$C ssNMR spectra were collected using a proton decoupled cross-polarization magic angle spinning (CP-MAS) experiment. A phase modulated proton decoupling field of 80-100 kHz was applied during spectral acquisition. The cross-polarization contact time was set to 2 ms and the recycle delay to 3.5 seconds for Form 1 and Form 4. The number of scans was adjusted to obtain an adequate signal to noise ratio. The $^{13}$C chemical shift scale was referenced using a $^{13}$C CPMAS experiment on an external standard of crystalline adamantane, setting its up-field resonance to 29.5 ppm.

$^{19}$F ssNMR spectra were collected using a proton decoupled magic angle spinning (MAS) experiment. A phase modulated proton decoupling field of 80-100 kHz was applied during spectral acquisition. Spectra were collected with a recycle delay to 6 seconds for Form 1 and 5.25 seconds for Form 4. The number of scans was adjusted to obtain an adequate signal to noise ratio. The $^{19}$F chemical shift scale was referenced using a $^{19}$F MAS experiment on an external standard of trifluoroacetic acid (50%/50% v/v in H$_2$O), setting its resonance to −76.54 ppm.

Automatic peak picking was performed using Bruker-BioSpin TopSpin version 3.6 software. Generally, a threshold value of 4% relative intensity was used for preliminary peak selection. The output of the automated peak picking was visually checked to ensure validity and adjustments were manually made if necessary. Although specific solid-state NMR peak values are reported herein there does exist a range for these peak values due to differences in instruments, samples, and sample preparation. This is common practice in the art of solid-state NMR because of the variation inherent in peak positions. A typical variability for a $^{13}$C chemical shift x-axis value is on the order of plus or minus 0.2 ppm, unless otherwise stated, for a crystalline solid. The variability for the $^{19}$F chemical shift x-axis value is on the order of plus or minus 0.1 ppm. The solid-state NMR peak heights reported herein are relative intensities. Solid-state NMR intensities can vary depending on the actual setup of the experimental parameters and the thermal history of the sample.

$^{13}$C solid-state NMR of Example 13, Form 1 was obtained as described above and the following peak list of Example 13, Form 1 was determined. The variability for $^{13}$C chemical shift values is ±0.2 ppm, unless otherwise specified.

| $^{13}$C Chemical Shift (ppm) | Relative Intensity (%) |
| --- | --- |
| 178.9 | 24 |
| 172.3 | 21 |
| 172.1 | 25 |
| 169.6 | 21 |
| 156.7 | 14 |
| 123.5 | 10 |
| 122.6 ± 0.1 | 6 |
| 118.5 | 4 |
| 116.1 | 4 |
| 62.7 | 24 |
| 58.6 | 27 |
| 47.2 | 26 |
| 40.3 | 28 |
| 39.4 | 24 |
| 39.0 | 31 |
| 37.8 ± 0.1 | 48 |
| 37.4 ± 0.1 | 41 |
| 34.6 ± 0.1 | 33 |
| 33.0 ± 0.1 | 35 |
| 31.0 ± 0.1 | 31 |
| 27.9 ± 0.1 | 100 |
| 26.3 | 58 |
| 26.0 | 41 |
| 20.8 ± 0.1 | 49 |
| 13.0 ± 0.1 | 47 |

The $^{19}$F solid-state NMR of the compound of Example 13, Form 1 was obtained and the $^{19}$F solid-state NMR peak at a chemical shift of −73.3±0.1 ppm was determined.

Characteristic peaks for the compound of Example 13, Form 1 are the $^{19}$F peak with a chemical shift at −73.3±0.1 ppm in combination with the $^{13}$C peaks with chemical shifts at 31.0±0.1 ppm, 27.9±0.1 ppm and 178.9±0.2 ppm.

Alternate Recrystallization of Example 13; Generation of Solid Form 4

(1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13), Solid Form 4

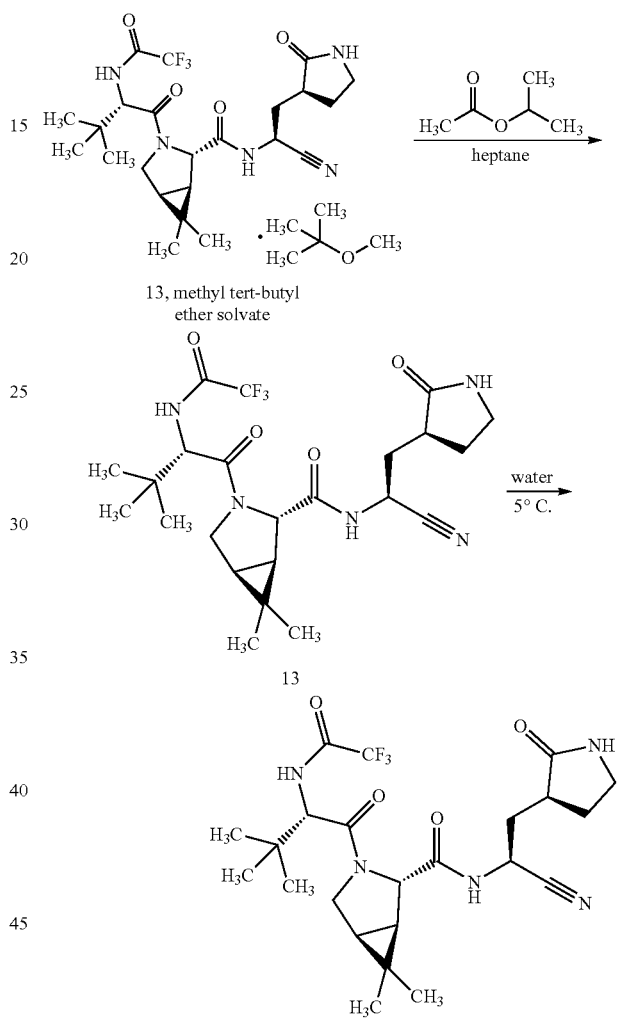

13, methyl tert-butyl ether solvate

13

Step 1. Recrystallization of (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13) from propan-2-yl acetate and heptane A mixture of propan-2-yl acetate (50 mL) and heptane (50 mL) was added to 13, methyl tert-butyl ether solvate, Solid Form 2 (from Second Alternate Synthesis of Example 13, methyl tert-butyl ether solvate; 10.02 g, 17.0 mmol) and the mixture was stirred at 20° C. and 3500 rpm overnight. Heptane (50 mL) was then slowly added, and stirring was continued for 30 minutes, whereupon the mixture was cooled to 10° C. over 30 minutes. After stirring for an additional 2 hours, the slurry was filtered; the filter cake was washed with a mixture of propan-2-yl acetate (4 mL) and heptane (16 mL) and subsequently dried at 55° C. under vacuum to afford (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13) as a crystalline solid. A portion of this material was used in the following recrystallization. Yield: 7.74 g, 15.5 mmol, 91%.

Figure 6:
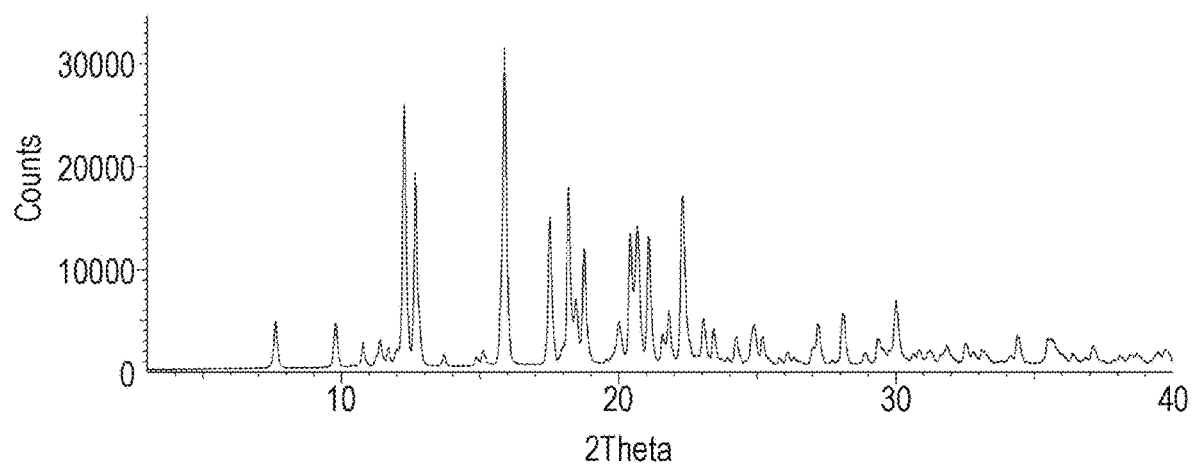
FIG. 6: Powder X-ray Diffraction Pattern of Example 13, Solid Form 4, from Alternate Recrystallization of Example 13; Generation of Solid Form 4

Step 2. Recrystallization of (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13) from Water A slurry of 13 (from the previous step; 1.0 g, 2.0 mmol) in water (12 mL) was stirred at 5° C. for 21 days, whereupon the solid was collected via filtration. It was then dried under vacuum for 10 minutes and air-dried in a thin layer on paper for 20 minutes, affording (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13) as a white, crystalline solid. The powder X-ray diffraction pattern for this material, designated as Solid Form 4, is given in FIG. 6; characteristic peaks are listed in Table J. Yield: 755 mg, 1.51 mmol, 76%. The method of collection of the powder X-ray diffraction data is described in Alternate Synthesis of Example 13, methyl tert-butyl ether solvate, Step 8.

TABLE J

Selected powder X-ray diffraction peaks for 13, Solid Form 4

| Angle (°2-theta) +/− 0.2° 2-Theta | Relative Intensity (%) |
|---|---|
| 7.6 | 15 |
| 9.8 | 14 |
| 10.8 | 7 |
| 11.2 | 4 |
| 11.4 | 4 |
| 11.4 | 8 |
| 11.7 | 5 |
| 12.0 | 6 |
| 12.3 | 82 |
| 12.7 | 61 |
| 13.7 | 4 |
| 14.9 | 3 |
| 15.1 | 5 |
| 15.9 | 100 |
| 17.5 | 47 |
| 18.0 | 5 |
| 18.2 | 57 |
| 18.5 | 21 |
| 18.8 | 37 |
| 20.0 | 12 |
| 20.4 | 43 |
| 20.7 | 44 |
| 21.1 | 42 |
| 21.6 | 9 |
| 21.8 | 16 |
| 22.3 | 53 |
| 23.1 | 14 |
| 23.4 | 11 |
| 24.2 | 9 |
| 24.9 | 12 |
| 25.2 | 8 |
| 26.1 | 4 |
| 27.0 | 5 |
| 27.2 | 15 |
| 28.1 | 17 |
| 28.9 | 4 |
| 29.4 | 9 |
| 29.5 | 4 |

TABLE J-continued

Selected powder X-ray diffraction peaks for 13, Solid Form 4

| Angle (°2-theta) +/− 0.2° 2-Theta | Relative Intensity (%) |
|---|---|
| 29.8 | 5 |
| 30.0 | 21 |
| 30.6 | 3 |
| 30.8 | 5 |
| 31.3 | 3 |
| 31.8 | 6 |
| 32.5 | 6 |
| 32.8 | 4 |
| 33.2 | 4 |
| 34.4 | 9 |
| 35.5 | 12 |
| 35.6 | 7 |
| 35.6 | 7 |
| 36.0 | 3 |
| 36.4 | 3 |
| 37.1 | 6 |
| 38.7 | 3 |
| 39.4 | 3 |
| 39.5 | 3 |
| 39.8 | 4 |

Single-Crystal X-Ray Structural Determination of Example 13, Solid Form 4

Figure 7:
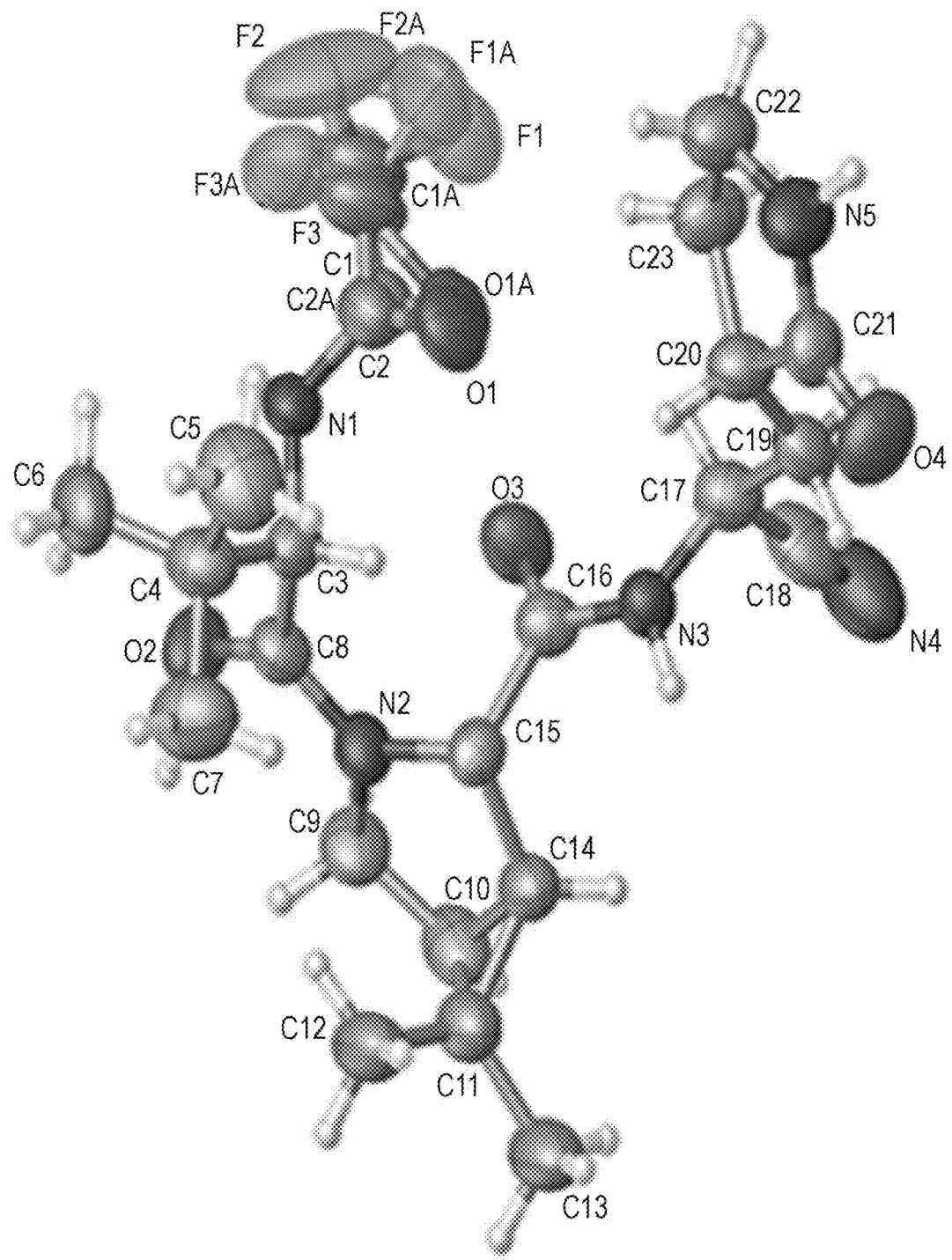
FIG. 7: Single-crystal X-ray Structural Determination of Example 13, Solid Form 4. ORTEP diagram drawn with displacement parameters at 50% probability
Figure 8:
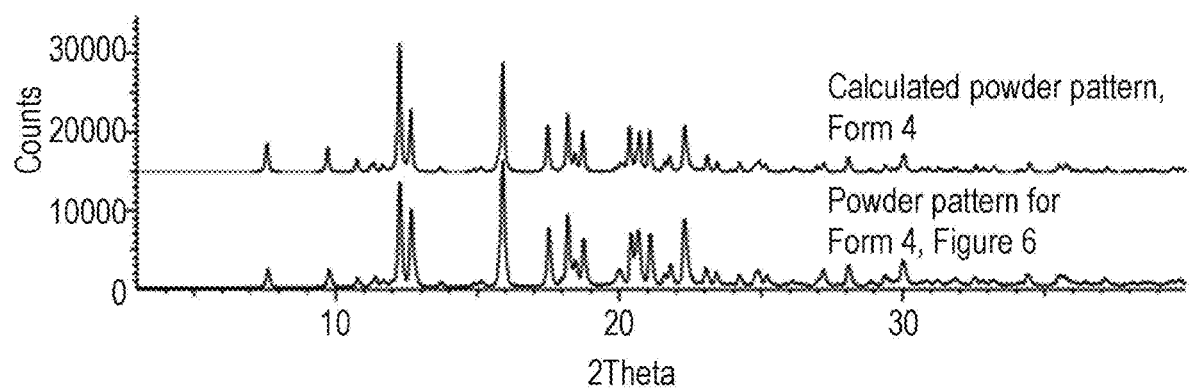
FIG. 8: Overlay of powder pattern obtained for Example 13, Solid Form 4, from Alternate Recrystallization of Example 13; Generation of Solid Form 4 (FIG. 6) and the calculated powder pattern, generated via Mercury software, from resolved X-ray single-crystal data of Form 4 (see Single-crystal X-ray Structural Determination of Example 13, Solid Form 4).

A sample of Example 13 was subjected to crystallization via diffusion at room temperature, using ethyl acetate and pentane; one of the resulting crystals was used for single-crystal X-ray structural determination. An ORTEP diagram of the single-crystal data is shown in FIG. 7. Mercury software was used to calculate the powder pattern from the resolved crystal structure; comparison with the diffraction pattern from Alternate Recrystallization of Example 13; Generation of Solid Form 4 identified this material as being Solid Form 4 (see FIG. 8). Characteristic peaks for this calculated data are provided in Table K.

TABLE K

Powder pattern data for 13, Solid Form 1 calculated from Single-crystal X-ray Structural Determination of Example 13, Solid Form 4

| Angle (°2-theta) +/− 0.2° 2-Theta | Relative Intensity (%) |
|---|---|
| 7.6 | 22 |
| 9.7 | 19 |
| 10.8 | 10 |
| 11.2 | 4 |
| 11.3 | 7 |
| 11.7 | 6 |
| 12.2 | 100 |
| 12.6 | 49 |
| 13.7 | 4 |
| 14.9 | 3 |
| 15.1 | 4 |
| 15.7 | 14 |
| 15.9 | 82 |
| 17.5 | 35 |
| 18.2 | 54 |
| 18.5 | 14 |
| 18.7 | 31 |
| 19.9 | 3 |
| 20.1 | 6 |
| 20.4 | 40 |
| 20.7 | 31 |
| 21.1 | 32 |
| 21.6 | 8 |
| 21.8 | 12 |
| 22.3 | 35 |
| 22.5 | 3 |
| 23.1 | 13 |

TABLE K-continued

Powder pattern data for 13, Solid Form 1 calculated from Single-crystal X-ray Structural Determination of Example 13, Solid Form 4

| Angle (°2-theta) +/− 0.2° 2-Theta | Relative Intensity (%) |
|---|---|
| 23.5 | 7 |
| 24.2 | 8 |
| 24.8 | 6 |
| 24.9 | 8 |
| 25.2 | 7 |
| 26.2 | 4 |
| 27.0 | 4 |
| 27.2 | 7 |
| 28.1 | 11 |
| 29.9 | 3 |
| 30.0 | 13 |
| 30.7 | 3 |
| 30.9 | 3 |
| 31.3 | 3 |
| 31.9 | 3 |
| 32.6 | 4 |
| 33.2 | 5 |
| 34.5 | 7 |
| 35.5 | 6 |
| 35.8 | 6 |
| 37.2 | 3 |
| 39.9 | 3 |

Single Crystal X-Ray Analysis

Data collection was performed on a Bruker D8 Venture diffractometer at −100 OC. Data collection consisted of omega and phi scans.

The structure was solved by intrinsic phasing using SHELX software suite in the orthorhombic class space group $P2_12_12_1$. The structure was subsequently refined by the full-matrix least squares method. All non-hydrogen atoms were found and refined using anisotropic displacement parameters.

The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The absolute stereochemistry was not determined, due to out-of-specification values of Hooft/Parsons/Flack parameters and standard deviations.

The final R-index was 6.3%. A final difference Fourier revealed no missing or misplaced electron density.

Pertinent crystal, data collection, and refinement information is summarized in Table L. Atomic coordinates, bond lengths, bond angles, and displacement parameters are listed in Tables M-P.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Straver, and A. L. Spek, *J. Appl. Cryst.* 2008, 41, 96-103.
H. D. Flack, *Acta Cryst.* 1983, A39, 867-881.

TABLE L

Crystal data and structure refinement for Example 13, Solid Form 4.

| | |
|---|---|
| Empirical formula | $C_{23}H_{32}F_3N_5O_4$ |
| Formula weight | 499.53 |
| Temperature | 173(2) K |
| Wavelength | 1.54178 Å |
| Crystal system | Orthorhombic |
| Space group | $P2_12_12_1$ |
| Unit cell dimensions | a = 9.2114(9) Å    α = 90° |
| | b = 15.1607(16) Å    β = 90° |
| | c = 18.191(2) Å    γ = 90° |
| Volume | 2540.5(5) Å$^3$ |
| Z | 4 |
| Density (calculated) | 1.306 Mg/m$^3$ |
| Absorption coefficient | 0.892 mm$^{-1}$ |
| F(000) | 1056 |
| Crystal size | 0.100 × 0.060 × 0.040 mm$^3$ |
| Theta range for data collection | 3.795 to 54.284° |
| Index ranges | −9 <= h <= 9, −15 <= k <= 15, −18 <= l <= 18 |
| Reflections collected | 15896 |
| Independent reflections | 3070 [$R_{int}$ = 0.1260] |
| Completeness to theta = 54.284° | 99.1% |
| Absorption correction | Empirical |
| Refinement method | Full-matrix least-squares on $F^2$ |
| Data/restraints/parameters | 3070/9/349 |
| Goodness-of-fit on $F^2$ | 1.067 |
| Final R indices [I > 2σ(I)] | R1 = 0.0625, wR2 = 0.1515 |
| R indices (all data) | R1 = 0.0696, wR2 = 0.1578 |
| Absolute structure parameter | 0.14(14) |
| Extinction coefficient | n/a |
| Largest diff. peak and hole | 0.280 and −0.220 e · Å$^{-3}$ |

TABLE M

Atomic coordinates (×10$^4$) and equivalent isotropic displacement parameters (Å$^2$ × 10$^3$) for Example 13, Solid Form 4. U(eq) is defined as one-third of the trace of the orthogonalized U$^{ij}$ tensor.

| | x | y | z | U(eq) |
|---|---|---|---|---|
| F(1) | 4306(16) | 6041(7) | 2387(4) | 174(5) |
| F(2) | 2770(10) | 5589(8) | 1525(8) | 181(5) |
| F(3) | 4932(11) | 6015(5) | 1280(6) | 114(3) |
| O(1) | 4026(8) | 4159(6) | 2397(4) | 80(2) |
| C(1) | 4115(14) | 5581(8) | 1775(8) | 105(3) |
| C(2) | 4561(14) | 4555(7) | 1871(9) | 65(3) |
| F(1A) | 3230(70) | 5710(30) | 2210(20) | 174(5) |
| F(2A) | 3400(40) | 5940(30) | 1470(40) | 181(5) |
| F(3A) | 4940(60) | 6060(30) | 1660(30) | 114(3) |
| O(1A) | 4410(40) | 4580(20) | 2430(20) | 80(2) |
| C(1A) | 4210(70) | 5320(30) | 1790(40) | 105(3) |
| C(2A) | 4840(70) | 4850(40) | 1940(40) | 65(3) |
| N(1) | 5533(5) | 4303(3) | 1395(2) | 57(1) |
| N(2) | 8573(4) | 3139(3) | 1925(2) | 53(1) |
| N(3) | 6772(4) | 3489(3) | 3714(2) | 51(1) |
| N(4) | 8394(7) | 4673(5) | 5053(4) | 103(2) |
| N(5) | 1220(5) | 3638(4) | 4615(3) | 80(2) |
| O(2) | 8305(4) | 3783(3) | 826(2) | 76(1) |
| O(3) | 7583(4) | 4429(3) | 2845(2) | 70(1) |
| O(4) | 2759(5) | 2668(3) | 5176(3) | 84(1) |
| O(3) | 6097(5) | 3407(4) | 1448(3) | 55(1) |
| O(4) | 5356(6) | 2775(4) | 886(4) | 66(2) |
| O(5) | 3799(7) | 2611(6) | 1123(5) | 100(2) |
| O(6) | 5336(8) | 3163(5) | 106(3) | 80(2) |
| O(7) | 6176(8) | 1903(5) | 876(5) | 94(2) |
| O(8) | 7747(6) | 3468(3) | 1378(3) | 55(1) |
| O(9) | 10166(5) | 3230(5) | 1885(3) | 68(2) |
| C(10) | 10729(6) | 2754(5) | 2548(4) | 73(2) |
| C(11) | 10341(7) | 1816(5) | 2669(3) | 73(2) |
| C(12) | 9762(8) | 1239(5) | 2060(4) | 89(2) |

TABLE M-continued

Atomic coordinates (×10⁴) and equivalent isotropic displacement parameters ($Å^2 \times 10^3$) for Example 13, Solid Form 4. U(eq) is defined as one-third of the trace of the orthogonalized $U^{ij}$ tensor.

|  | x | y | z | U(eq) |
|---|---|---|---|---|
| C(13) | 11307(8) | 1311(5) | 3196(4) | 96(2) |
| O(14) | 9439(6) | 2528(4) | 3023(3) | 62(2) |
| O(15) | 8090(5) | 2884(4) | 2660(3) | 51(1) |
| O(16) | 7471(5) | 3677(3) | 3070(3) | 49(1) |
| O(17) | 6277(6) | 4180(4) | 4192(3) | 61(2) |
| C(18) | 7465(7) | 4485(4) | 4670(4) | 78(2) |
| C(19) | 5031(6) | 3887(4) | 4683(3) | 62(2) |
| C(20) | 3625(6) | 3736(4) | 4274(3) | 59(2) |
| C(21) | 2506(6) | 3278(4) | 4745(3) | 61(1) |
| C(22) | 1247(7) | 4355(5) | 4095(4) | 80(2) |
| C(23) | 2822(6) | 4572(4) | 4041(4) | 71(2) |

TABLE N

Bond lengths [Å] and angles [°] for Example 13, Solid Form 4.

| | |
|---|---|
| F(1)—C(1) | 1.326(15) |
| F(2)—C(1) | 1.320(15) |
| F(3)—C(1) | 1.345(14) |
| O(1)—C(2) | 1.233(18) |
| C(1)—C(2) | 1.618(18) |
| C(2)—N(1) | 1.303(15) |
| F(1A)—C(1A) | 1.33(3) |
| F(1A)—F(2A) | 1.40(7) |
| F(2A)—C(1A) | 1.33(3) |
| F(2A)—F(3A) | 1.47(7) |
| F(3A)—C(1A) | 1.34(3) |
| F(3A)—C(2A) | 1.90(8) |
| O(1A)—C(2A) | 1.05(8) |
| O(1A)—C(1A) | 1.62(7) |
| C(1A)—C(2A) | 0.95(8) |
| C(2A)—N(1) | 1.45(6) |
| N(1)—C(3) | 1.458(7) |
| N(1)—H(1X) | 0.98(3) |
| N(2)—C(8) | 1.348(7) |
| N(2)—C(15) | 1.462(7) |
| N(2)—C(9) | 1.476(7) |
| N(3)—C(16) | 1.368(7) |
| N(3)—C(17) | 1.436(7) |
| N(3)—H(3X) | 0.98(3) |
| N(4)—C(18) | 1.140(9) |
| N(5)—C(21) | 1.326(8) |
| N(5)—C(22) | 1.441(9) |
| N(5)—H(5X) | 0.99(3) |
| O(2)—C(8) | 1.225(7) |
| O(3)—C(16) | 1.215(6) |
| O(4)—C(21) | 1.236(7) |
| C(3)—C(8) | 1.528(7) |
| C(3)—C(4) | 1.559(8) |
| C(3)—H(3) | 1.0000 |
| C(4)—C(5) | 1.518(9) |
| C(4)—C(7) | 1.522(9) |
| C(4)—C(6) | 1.537(9) |
| C(5)—H(5A) | 0.9800 |
| C(5)—H(5B) | 0.9800 |
| C(5)—H(5C) | 0.9800 |
| C(6)—H(6A) | 0.9800 |
| C(6)—H(6B) | 0.9800 |
| C(6)—H(6C) | 0.9800 |
| C(7)—H(7A) | 0.9800 |
| C(7)—H(7B) | 0.9800 |
| C(7)—H(7C) | 0.9800 |
| C(9)—C(10) | 1.497(9) |
| C(9)—H(9A) | 0.9900 |
| C(9)—H(9B) | 0.9900 |
| C(10)—C(11) | 1.483(10) |
| C(10)—C(14) | 1.509(8) |
| C(10)—H(10) | 1.0000 |
| C(11)—C(14) | 1.507(8) |
| C(11)—C(12) | 1.509(9) |
| C(11)—C(13) | 1.516(10) |

TABLE N-continued

Bond lengths [Å] and angles [°] for Example 13, Solid Form 4.

| | |
|---|---|
| C(12)—H(12A) | 0.9800 |
| C(12)—H(12B) | 0.9800 |
| C(12)—H(12C) | 0.9800 |
| C(13)—H(13A) | 0.9800 |
| C(13)—H(13B) | 0.9800 |
| C(13)—H(13C) | 0.9800 |
| C(14)—C(15) | 1.506(7) |
| C(14)—H(14) | 1.0000 |
| C(15)—C(16) | 1.525(7) |
| C(15)—H(15) | 1.0000 |
| C(17)—C(18) | 1.472(10) |
| C(17)—C(19) | 1.521(8) |
| C(17)—H(17) | 1.0000 |
| C(19)—C(20) | 1.511(8) |
| C(19)—H(19A) | 0.9900 |
| C(19)—H(19B) | 0.9900 |
| C(20)—C(21) | 1.509(8) |
| C(20)—C(23) | 1.528(8) |
| C(20)—H(20) | 1.0000 |
| C(22)—C(23) | 1.491(9) |
| C(22)—H(22A) | 0.9900 |
| C(22)—H(22B) | 0.9900 |
| C(23)—H(23A) | 0.9900 |
| C(23)—H(23B) | 0.9900 |
| F(2)—C(1)—F(1) | 114.1(13) |
| F(2)—C(1)—F(3) | 106.9(11) |
| F(1)—C(1)—F(3) | 103.3(11) |
| F(2)—C(1)—C(2) | 106.5(12) |
| F(1)—C(1)—C(2) | 112.4(11) |
| F(3)—C(1)—C(2) | 113.6(11) |
| O(1)—C(2)—N(1) | 130.4(10) |
| O(1)—C(2)—C(1) | 116.8(11) |
| N(1)—C(2)—C(1) | 112.6(11) |
| C(1A)—F(1A)—F(2A) | 59(2) |
| C(1A)—F(2A)—F(1A) | 58(2) |
| C(1A)—F(2A)—F(3A) | 57(2) |
| F(1A)—F(2A)—F(3A) | 85(4) |
| C(1A)—F(3A)—F(2A) | 56(2) |
| C(1A)—F(3A)—C(2A) | 28(3) |
| F(2A)—F(3A)—C(2A) | 84(4) |
| C(2A)—O(1A)—C(1A) | 34(4) |
| C(2A)—C(1A)—F(1A) | 125(8) |
| C(2A)—C(1A)—F(2A) | 171(9) |
| F(1A)—C(1A)—F(2A) | 63(4) |
| C(2A)—C(1A)—F(3A) | 112(7) |
| F(1A)—C(1A)—F(3A) | 94(5) |
| F(2A)—C(1A)—F(3A) | 67(4) |
| C(2A)—C(1A)—O(1A) | 38(5) |
| F(1A)—C(1A)—O(1A) | 89(4) |
| F(2A)—C(1A)—O(1A) | 149(5) |
| F(3A)—C(1A)—O(1A) | 131(7) |
| C(1A)—C(2A)—O(1A) | 108(8) |
| C(1A)—C(2A)—N(1) | 120(8) |
| O(1A)—C(2A)—N(1) | 121(5) |
| C(1A)—C(2A)—F(3A) | 41(4) |
| O(1A)—C(2A)—F(3A) | 129(5) |
| N(1)—C(2A)—F(3A) | 110(5) |
| C(2)—N(1)—C(3) | 118.3(7) |
| C(2A)—N(1)—C(3) | 130(3) |
| C(2)—N(1)—H(1X) | 120(4) |
| C(2A)—N(1)—H(1X) | 102(5) |
| C(3)—N(1)—H(1X) | 121(4) |
| C(8)—N(2)—C(15) | 127.0(4) |
| C(8)—N(2)—C(9) | 119.4(5) |
| C(15)—N(2)—C(9) | 111.8(4) |
| C(16)—N(3)—C(17) | 121.1(4) |
| C(16)—N(3)—H(3X) | 113(4) |
| C(17)—N(3)—H(3X) | 123(4) |
| C(21)—N(5)—C(22) | 114.3(5) |
| C(21)—N(5)—H(5X) | 120(4) |
| C(22)—N(5)—H(5X) | 125(4) |
| N(1)—C(3)—C(8) | 107.0(4) |
| N(1)—C(3)—C(4) | 111.9(4) |
| C(8)—C(3)—C(4) | 114.7(5) |
| N(1)—C(3)—H(3) | 107.7 |
| C(8)—C(3)—H(3) | 107.7 |
| C(4)—C(3)—H(3) | 107.7 |
| C(5)—C(4)—C(7) | 109.3(6) |

TABLE N-continued

Bond lengths [Å] and angles [°] for Example 13, Solid Form 4.

| | |
|---|---|
| C(5)—C(4)—C(6) | 108.2(5) |
| C(7)—C(4)—C(6) | 109.1(6) |
| C(5)—C(4)—C(3) | 109.2(5) |
| C(7)—C(4)—C(3) | 108.9(5) |
| C(6)—C(4)—C(3) | 112.1(5) |
| C(4)—C(5)—H(5A) | 109.5 |
| C(4)—C(5)—H(5B) | 109.5 |
| H(5A)—C(5)—H(5B) | 109.5 |
| C(4)—C(5)—H(5C) | 109.5 |
| H(5A)—C(5)—H(5C) | 109.5 |
| H(5B)—C(5)—H(5C) | 109.5 |
| C(4)—C(6)—H(6A) | 109.5 |
| C(4)—C(6)—H(6B) | 109.5 |
| H(6A)—C(6)—H(6B) | 109.5 |
| C(4)—C(6)—H(6C) | 109.5 |
| H(6A)—C(6)—H(6C) | 109.5 |
| H(6B)—C(6)—H(6C) | 109.5 |
| C(4)—C(7)—H(7A) | 109.5 |
| C(4)—C(7)—H(7B) | 109.5 |
| H(7A)—C(7)—H(7B) | 109.5 |
| C(4)—C(7)—H(7C) | 109.5 |
| H(7A)—C(7)—H(7C) | 109.5 |
| H(7B)—C(7)—H(7C) | 109.5 |
| O(2)—C(8)—N(2) | 120.8(5) |
| O(2)—C(8)—C(3) | 120.6(5) |
| N(2)—C(8)—C(3) | 118.5(5) |
| N(2)—C(9)—C(10) | 105.1(5) |
| N(2)—C(9)—H(9A) | 110.7 |
| C(10)—C(9)—H(9A) | 110.7 |
| N(2)—C(9)—H(9B) | 110.7 |
| C(10)—C(9)—H(9B) | 110.7 |
| H(9A)—C(9)—H(9B) | 108.8 |
| C(11)—C(10)—C(9) | 119.9(5) |
| C(11)—C(10)—C(14) | 60.5(4) |
| C(9)—C(10)—C(14) | 107.3(4) |
| C(11)—C(10)—H(10) | 118.2 |
| C(9)—C(10)—H(10) | 118.2 |
| C(14)—C(10)—H(10) | 118.2 |
| C(10)—C(11)—C(14) | 60.6(4) |
| C(10)—C(11)—C(12) | 122.2(6) |
| C(14)—C(11)—C(12) | 122.3(5) |
| C(10)—C(11)—C(13) | 115.9(6) |
| C(14)—C(11)—C(13) | 114.6(5) |
| C(12)—C(11)—C(13) | 112.2(6) |
| C(11)—C(12)—H(12A) | 109.5 |
| C(11)—C(12)—H(12B) | 109.5 |
| H(12A)—C(12)—H(12B) | 109.5 |
| C(11)—C(12)—H(12C) | 109.5 |
| H(12A)—C(12)—H(12C) | 109.5 |
| H(12B)—C(12)—H(12C) | 109.5 |
| C(11)—C(13)—H(13A) | 109.5 |
| C(11)—C(13)—H(13B) | 109.5 |
| H(13A)—C(13)—H(13B) | 109.5 |
| C(11)—C(13)—H(13C) | 109.5 |
| H(13A)—C(13)—H(13C) | 109.5 |
| H(13B)—C(13)—H(13C) | 109.5 |
| C(15)—C(14)—C(11) | 121.6(5) |
| C(15)—C(14)—C(10) | 108.5(5) |
| C(11)—C(14)—C(10) | 58.9(4) |
| C(15)—C(14)—H(14) | 117.6 |
| C(11)—C(14)—H(14) | 117.6 |
| C(10)—C(14)—H(14) | 117.6 |
| N(2)—C(15)—C(14) | 104.2(4) |
| N(2)—C(15)—C(16) | 110.6(4) |
| C(14)—C(15)—C(16) | 112.1(4) |
| N(2)—C(15)—H(15) | 109.9 |
| C(14)—C(15)—H(15) | 109.9 |
| C(16)—C(15)—H(15) | 109.9 |
| O(3)—C(16)—N(3) | 121.6(5) |
| O(3)—C(16)—C(15) | 122.9(5) |
| N(3)—C(16)—C(15) | 115.5(4) |
| N(3)—C(17)—C(18) | 110.5(4) |
| N(3)—C(17)—C(19) | 112.4(5) |
| C(18)—C(17)—C(19) | 107.8(5) |
| N(3)—C(17)—H(17) | 108.7 |
| C(18)—C(17)—H(17) | 108.7 |
| C(19)—C(17)—H(17) | 108.7 |
| N(4)—C(18)—C(17) | 176.2(8) |
| C(20)—C(19)—C(17) | 113.7(5) |
| C(20)—C(19)—H(19A) | 108.8 |
| C(17)—C(19)—H(19A) | 108.8 |
| C(20)—C(19)—H(19B) | 108.8 |
| C(17)—C(19)—H(19B) | 108.8 |
| H(19A)—C(19)—H(19B) | 107.7 |
| C(21)—C(20)—C(19) | 112.1(5) |
| C(21)—C(20)—C(23) | 102.0(5) |
| C(19)—C(20)—C(23) | 115.2(5) |
| C(21)—C(20)—H(20) | 109.1 |
| C(19)—C(20)—H(20) | 109.1 |
| C(23)—C(20)—H(20) | 109.1 |
| O(4)—C(21)—N(5) | 126.1(5) |
| O(4)—C(21)—C(20) | 125.2(5) |
| N(5)—C(21)—C(20) | 108.6(5) |
| N(5)—C(22)—C(23) | 103.1(5) |
| N(5)—C(22)—H(22A) | 111.1 |
| C(23)—C(22)—H(22A) | 111.1 |
| N(5)—C(22)—H(22B) | 111.1 |
| C(23)—C(22)—H(22B) | 111.1 |
| H(22A)—C(22)—H(22B) | 109.1 |
| C(22)—C(23)—C(20) | 105.6(5) |
| C(22)—C(23)—H(23A) | 110.6 |
| C(20)—C(23)—H(23A) | 110.6 |
| C(22)—C(23)—H(23B) | 110.6 |
| C(20)—C(23)—H(23B) | 110.6 |
| H(23A)—C(23)—H(23B) | 108.7 |

Symmetry transformations used to generate equivalent atoms.

TABLE P

Anisotropic displacement parameters (Å$^2$ × 10$^3$) for Example 13, Solid Form 4. The anisotropic displacement factor exponent takes the form: $-2\pi^2[h^2 a^{*2} U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| F(1) | 279(15) | 138(7) | 106(5) | −56(5) | −28(7) | 100(8) |
| F(2) | 69(5) | 172(9) | 302(12) | 75(9) | −10(7) | 44(5) |
| F(3) | 143(5) | 83(3) | 117(7) | −10(5) | −24(6) | 33(3) |
| O(1) | 77(5) | 91(6) | 74(3) | 1(4) | 29(3) | 9(4) |
| C(1) | 116(7) | 76(10) | 122(8) | 6(9) | 25(6) | 43(10) |
| C(2) | 65(7) | 68(9) | 63(6) | −13(7) | −5(5) | 18(6) |
| F(1A) | 279(15) | 138(7) | 106(5) | −56(5) | −28(7) | 100(8) |
| F(2A) | 69(5) | 172(9) | 302(12) | 75(9) | −10(7) | 44(5) |
| F(3A) | 143(5) | 83(3) | 117(7) | −10(5) | −24(6) | 33(3) |
| O(1A) | 77(5) | 91(6) | 74(3) | 1(4) | 29(3) | 9(4) |
| C(1A) | 116(7) | 76(10) | 122(8) | 6(9) | 25(6) | 43(10) |
| C(2A) | 65(7) | 68(9) | 63(6) | −13(7) | −5(5) | 18(6) |
| N(1) | 49(2) | 70(3) | 53(3) | −1(2) | 3(2) | 19(2) |
| N(2) | 38(2) | 75(3) | 45(3) | −2(2) | 3(2) | 2(2) |
| N(3) | 50(2) | 51(2) | 52(3) | 1(2) | 3(2) | 4(2) |
| N(4) | 60(3) | 130(5) | 119(5) | −49(4) | 0(4) | −10(3) |
| N(5) | 53(3) | 105(4) | 82(4) | 17(3) | 15(3) | 11(3) |
| O(2) | 51(2) | 114(3) | 62(3) | 25(2) | 12(2) | 6(2) |
| O(3) | 78(2) | 55(2) | 76(3) | 4(2) | 18(2) | 0(2) |
| O(4) | 82(3) | 83(3) | 86(3) | 30(3) | −2(2) | −11(2) |
| C(3) | 45(3) | 70(3) | 51(3) | 9(3) | 4(2) | 9(3) |
| C(4) | 48(3) | 70(4) | 79(4) | −5(3) | −7(3) | 5(3) |
| C(5) | 56(3) | 131(6) | 114(6) | −16(5) | 4(4) | −22(4) |
| C(6) | 76(4) | 107(5) | 59(4) | −15(4) | −9(3) | 12(4) |
| C(7) | 82(4) | 83(5) | 117(6) | −17(4) | −18(4) | 6(4) |
| C(8) | 44(3) | 60(3) | 60(4) | −2(3) | 6(3) | 7(2) |
| C(9) | 37(3) | 95(4) | 70(4) | −2(4) | 1(3) | 2(3) |
| C(10) | 41(3) | 105(5) | 73(4) | −24(4) | −8(3) | 5(3) |
| C(11) | 69(4) | 82(4) | 67(4) | −11(4) | −12(3) | 20(3) |
| C(12) | 85(4) | 96(5) | 87(5) | −24(4) | −17(4) | 34(4) |
| C(13) | 82(4) | 116(6) | 90(5) | −25(4) | −18(4) | 48(4) |
| C(14) | 55(3) | 74(4) | 57(3) | −6(3) | −6(3) | 16(3) |
| C(15) | 44(3) | 59(3) | 51(3) | 0(3) | −4(2) | 2(2) |
| C(16) | 39(2) | 48(3) | 59(3) | 2(3) | 3(2) | −4(2) |
| C(17) | 49(3) | 62(3) | 73(4) | −3(3) | 2(3) | 3(3) |
| C(18) | 57(4) | 85(4) | 92(5) | −26(4) | 26(4) | −8(3) |
| C(19) | 59(3) | 65(3) | 63(4) | 0(3) | 15(3) | 8(3) |

TABLE P-continued

Anisotropic displacement parameters (Å² × 10³) for Example 13, Solid Form 4. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(20) | 49(3) | 61(3) | 66(4) | 6(3) | 2(3) | 6(2) |
| C(21) | 58(3) | 72(4) | 53(3) | 6(3) | 6(3) | 2(3) |
| C(22) | 65(4) | 92(5) | 82(5) | 13(4) | 11(3) | 16(3) |
| C(23) | 62(3) | 74(4) | 77(4) | 21(3) | 7(3) | 5(3) |

$^{13}$C solid-state NMR peak list of PF-07321332-00 Form 4. The variability for $^{13}$C chemical shift values is ±0.2 ppm, unless otherwise stated.

| $^{13}$C Chemical Shift (ppm) | Relative Intensity (%) |
|---|---|
| 179.3 | 16 |
| 178.8 | 11 |
| 172.3 | 20 |
| 169.6 | 8 |
| 168.6 | 12 |
| 156.7 | 12 |
| 123.7 | 4 |
| 120.1 | 6 |
| 119.1 | 4 |
| 118.5 | 4 |
| 62.4 | 16 |
| 62.0 | 17 |
| 58.5 | 26 |
| 47.1 | 26 |
| 41.5 | 17 |
| 40.2 | 12 |
| 38.8 | 22 |
| 38.3 | 27 |
| 37.9 | 43 |
| 37.5 | 39 |
| 37.0 | 25 |
| 34.4 | 13 |
| 32.9 | 16 |
| 31.9 | 23 |
| 31.3 ± 0.1 | 16 |
| 29.7 | 18 |
| 27.9 ± 0.1 | 100 |
| 26.9 ± 0.1 | 36 |
| 26.2 | 28 |
| 25.9 | 18 |
| 21.6 ± 0.1 | 31 |
| 20.8 ± 0.1 | 22 |
| 12.9 ± 0.1 | 46 |

The $^{19}$F solid-state NMR of the compound of Example 13, Form 4 was obtained and a peak at −73.6±0.1 with a relative intensity of 100% was determined.

For the compound of Example 13, Form 4, six characteristic peaks were identified: $^{19}$F chemical shift at −73.6±0.1 ppm and $^{13}$C chemical shifts at 26.9±0.1 ppm, 21.6±0.1 ppm, 41.5±0.2 ppm, 27.9±0.1 ppm, and 12.9±0.1. The $^{19}$F peak with chemical shift at −73.6±0.1 ppm is characteristic of the compound of Example 13, Form 4. The $^{13}$C peaks at 26.9±0.1 ppm, 21.6±0.1 ppm and 41.5±0.1 ppm are each characteristic peaks of the compound of Example 13, Form 4. The $^{13}$C peaks at 27.9 ppm and 12.9 ppm are each characteristic of the compound of Example 13, Form 4 when taken in combination with one or more of the peaks selected from the $^{13}$C peaks at 21.6 ppm, 26.9 ppm and 41.5 ppm and the $^{19}$F peak at −73.6 ppm.

Fourth Alternate Synthesis of Example 13, methyl tert-butyl ether solvate (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate)

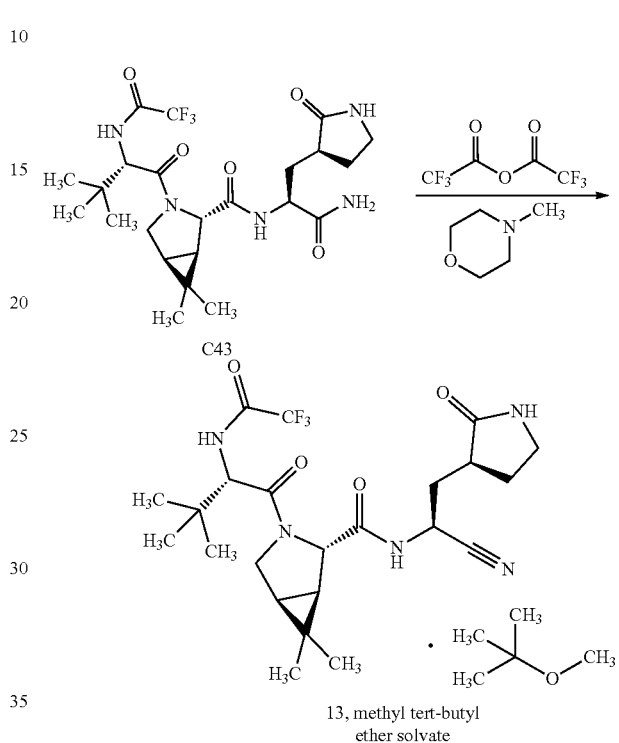

13, methyl tert-butyl ether solvate

To a 0° C. slurry of C43 (5.0 g, 9.7 mmol) in propan-2-yl acetate (7.6 mL/g, 38 mL) was charged 4-methylmorpholine (4.5 equivalents; 4.8 mL, 44 mmol). To the resulting slurry was charged trifluoroacetic anhydride (2.25 equivalents; 3.1 mL, 22 mmol) over 1 hour via a dosing pump. After stirring at 0° C. for at least 1 hour, the reaction mixture was warmed to about 20° C., quenched with water (8 mL/g, 40 mL), and stirred for at least 10 minutes. After decantation, the bottom (aqueous) layer was discarded and water (8 mL/g, 40 mL) was added to the organic layer. After stirring for at least 10 minutes, the layers were separated, and the bottom (aqueous) layer was discarded. The organic layer was concentrated under reduced pressure to approximately 4 mL/g (around 20 mL), whereupon the vacuum was broken using nitrogen and the solution was warmed to approximately 50° C. Methyl tert-butyl ether (12 mL/g, 60 mL) was slowly added over at least 4 hours via addition funnel, and the reaction mixture was maintained at 50° C. for at least 1 hour before being cooled to 25° C. over 1 hour. The resulting slurry was held at 25° C. overnight, then filtered, washed sequentially with a mixture of propan-2-yl acetate and methyl tert-butyl ether [1:3 (v/v); 2 mL/g] and with methyl tert-butyl ether (2 mL/g, 10 mL), and dried on the filter for at least 30 minutes. The solids were then transferred into a vacuum oven at 50° C. and dried for at least 8 hours, affording (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate) as an off-white solid. Yield: 3.4 g, 5.8 mmol, 60%.

Fifth Alternate Synthesis of Example 13, methyl tert-butyl ether solvate (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate)

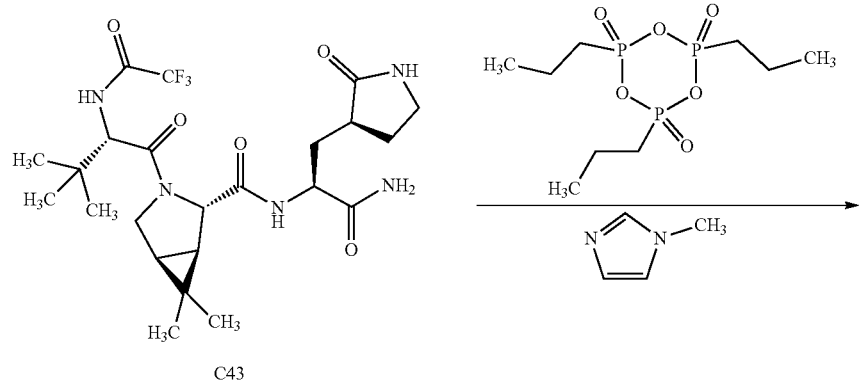

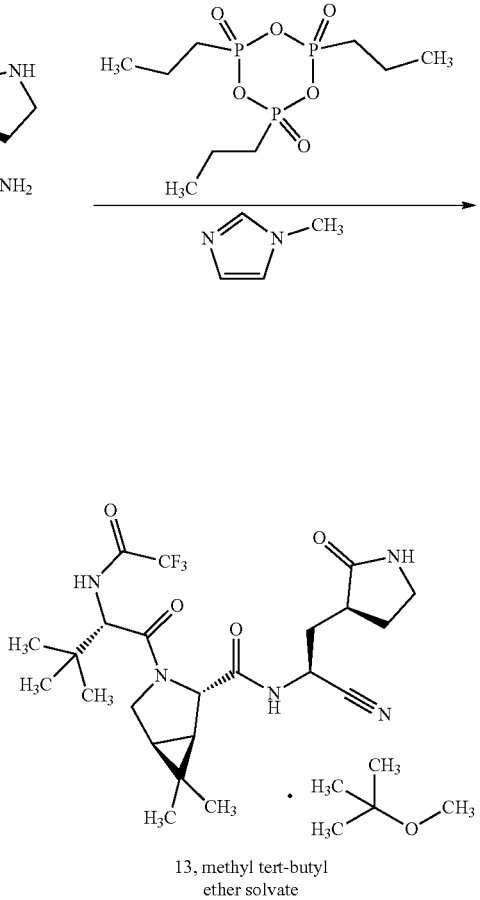

13, methyl tert-butyl ether solvate

To a room temperature slurry of C43 (4.0 g, 7.7 mmol) in acetonitrile (10 mL/g, 40 mL) was charged 1-methyl-1H-imidazole (4.6 equivalents; 2.84 mL, 35.6 mmol) and the resulting mixture was warmed to approximately 30° C. A solution of 2,4,6-tripropyl-1,3,5,2,4,6-trioxatriphosphinane 2,4,6-trioxide (50% solution by weight in acetonitrile; 2 equivalents; 10.8 mL) was added over at least 6 hours using a pump. After the reaction mixture had been stirred for at least 10 hours, it was cooled to 25° C. and carefully quenched by addition of saturated aqueous sodium bicarbonate solution (7 mL/g, 28 mL) (exothermic and off-gassing). Acetonitrile was then distilled off under reduced pressure; to the resulting mixture was added ethyl acetate (10 mL/g, 40 mL) and additional saturated aqueous sodium bicarbonate solution (5 mL/g, 20 mL). After phase split, the bottom (aqueous) layer was discarded and the organic layer was washed with saturated aqueous sodium bicarbonate solution (3.5 mL/g; 14 mL). The aqueous layer was again discarded, and the organic layer was concentrated under reduced pressure down to approximately 1 mL/g (4 mL). Methyl tert-butyl ether (9 mL/g; 36 mL) was charged and the resulting solution was warmed to 50° C., quickly resulting in a slurry. This slurry was held at 50° C. for at least 30 minutes, whereupon it was cooled to 25° C. over 1 hour and held at 25° C. for at least 8 hours. The slurry was then filtered, washed with a mixture of ethyl acetate and methyl tert-butyl ether [1:3 (v/v); 2 mL/g], and then washed with methyl tert-butyl ether (2 mL/g; 8 mL). The collected solid was dried on the filter for at least 30 minutes, transferred into a vacuum oven at around 50° C., and dried for at least 8 hours, affording (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide, methyl tert-butyl ether solvate (13, methyl tert-butyl ether solvate) as an off-white solid. Yield: 2.9 g, 4.9 mmol, 64%.

Formulation Examples for the Compound of Example 13

(1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide or a hydrate or solvate thereof or a pharmaceutically acceptable salt of the compound, hydrate or solvate is formulated to make a conventional immediate release film coated tablet for oral administration, with doses ranging from 100 to 250 mg. As an example, an immediate release formulation is described in Formulation Table and comprises conventional inactive excipients microcrystalline cellulose and lactose monohydrate (diluents), crospovidone (disintegrant), colloidal silicon dioxide (glidant), and sodium stearyl fumarate (lubricant). Immediate release tablets are film-coated using commercially available film-coat formulations including Opadry white and Opadry pink. All excipients used in the film-coated tablet are globally acceptable and are present at precedented levels. The formulation provided is an example of an immediate release tablet formulation, and as such, one skilled in the art would be able to use readily available routine techniques using alternate formulation excipients to make suitable tablets and achieve desired tablet quality attributes.

Formulation Examples: Representative Coated Tablet Formulations of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (referred to as the API below) immediate release tablets are manufactured using routine, standard batch processes for solid, oral immediate release tablets. Examples of standard batch processes which could be used to manufacture (1R, 2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide immediate release tablets include direct compression, dry granulation and wet granulation. Alternatively, a continuous operation manufacturing process could be used. Following tablet compression, the tablet cores are film-coated. Tablet film-coating can be performed via a continuous coating operation or using a conventional batch film-coating process.

Formulation Table: 100 mg, 150 mg and 250 mg (1R,2S,5S)-N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide tablet formulations

| Component | Role | 100 mg Tablet (% w/w) | 100 mg Tablet (mg/tablet) | 150 mg Tablet (% w/w) | 150 mg Tablet (mg/tablet) | 250 mg Tablet (% w/w) | 250 mg Tablet (mg/tablet) |
|---|---|---|---|---|---|---|---|
| API | Active | 20.00 | 100.00 | 20.00 | 150.00 | 25.00 | 250.00 |
| Microcrystalline cellulose | Diluent | 49.33 | 246.67 | 49.33 | 370.00 | 46.00 | 460.00 |
| Lactose Monohydrate | Diluent | 24.67 | 123.33 | 24.67 | 185.00 | 23.00 | 230.00 |
| Crospovidone | Disintegrant | 3.00 | 15.00 | 3.00 | 22.50 | 3.00 | 30.00 |
| Colloidal Silicon Dioxide | Glidant | 1.00 | 5.00 | 1.00 | 7.50 | 1.00 | 10.00 |
| Sodium stearyl fumarate (intra-granular) | Lubricant | 1.00 | 5.00 | 1.00 | 7.50 | 1.00 | 10.00 |
| Sodium stearyl fumarate (extra-granular) | Lubricant | 1.00 | 5.00 | 1.00 | 7.50 | 1.00 | 10.00 |
| Core total | | 100.00 | 500.00 | 100.00 | 750.00 | 100.00 | 1000.00 |
| Opadry White (YS-1-7027-SP) | Coating | 3.50 | 17.50 | — | — | — | — |
| Opadry Pink (058140011) | Coating | — | — | 3.00 | 22.50 | — | — |

Example 14
N-[(2S)-1-({(1S)-1-Cyano-2-[(3S)-2-oxopyrrolidin-3-yl]ethyl}amino)-5,5,5-trifluoro-1-oxopentan-2-yl]-4-methoxy-1H-indole-2-carboxamide (14)
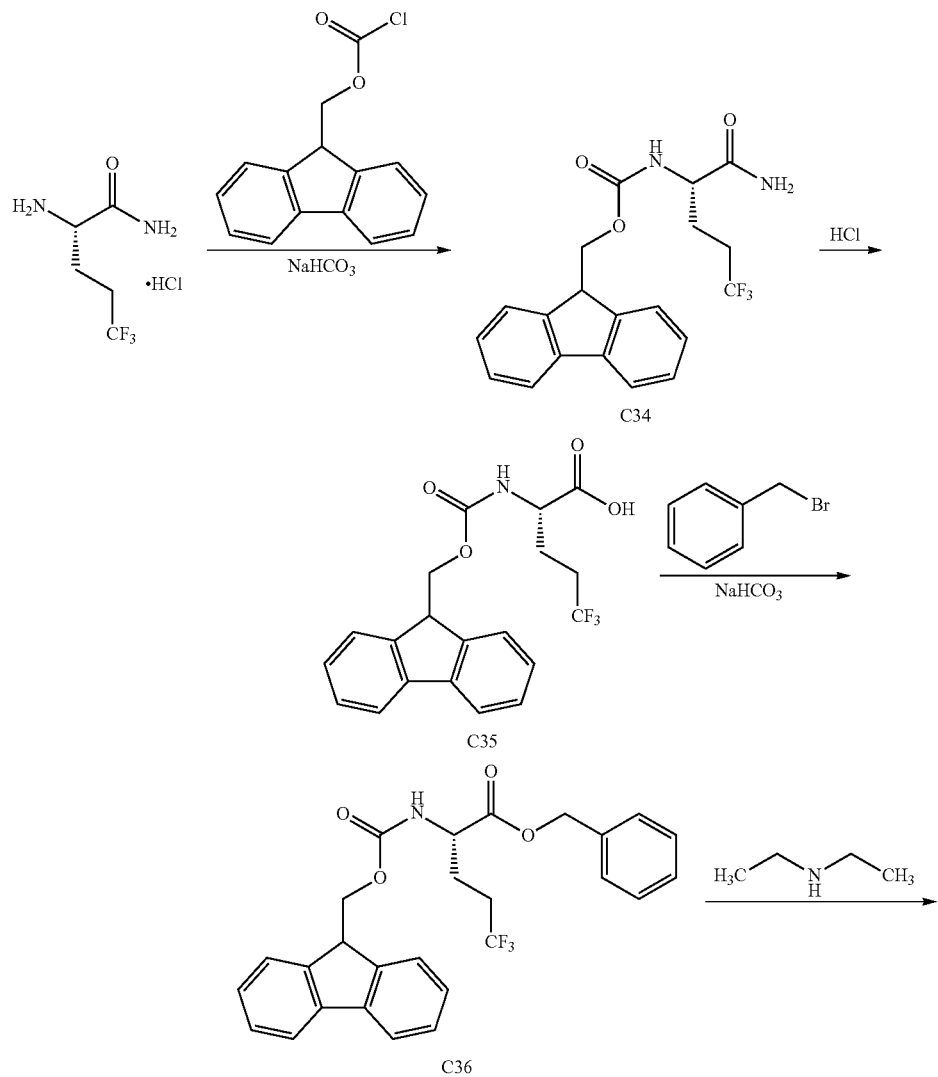
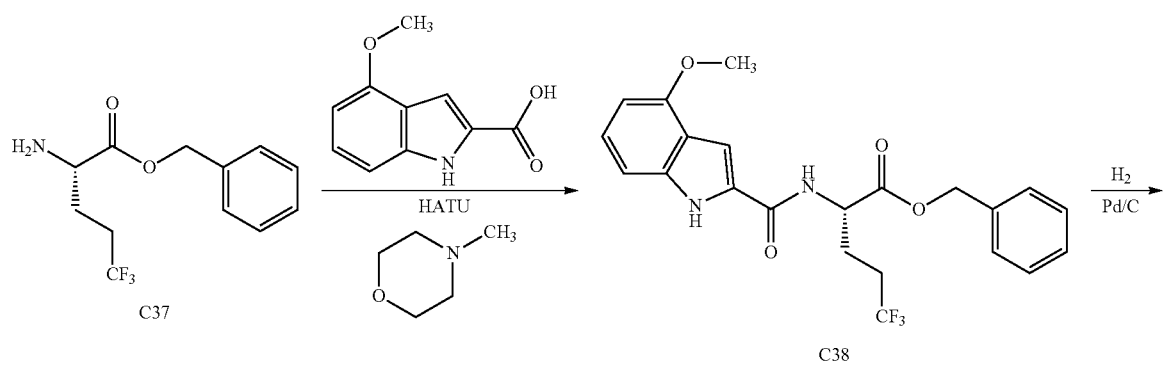

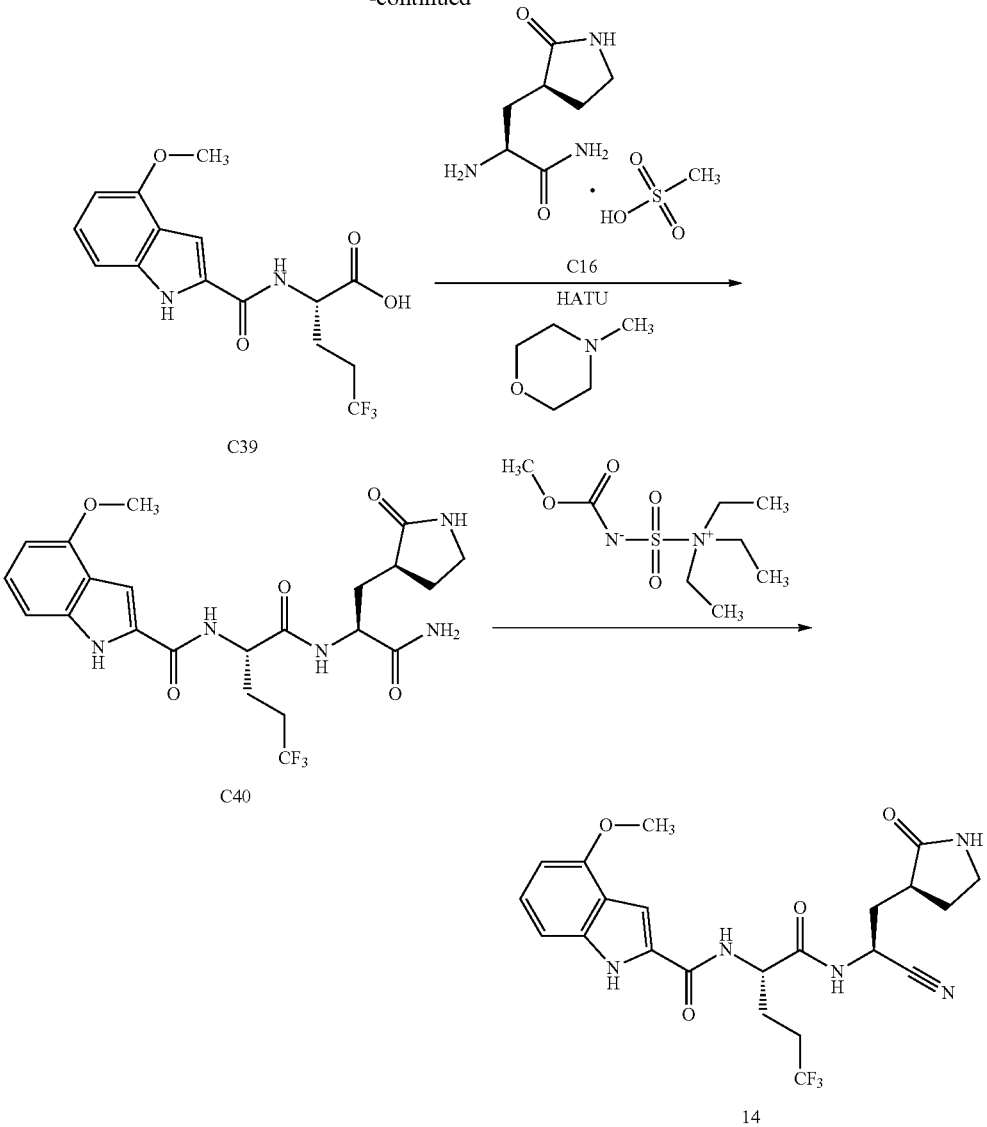

Step 1. Synthesis of 9H-fluoren-9-ylmethyl [(2S)-1-amino-5,5,5-trifluoro-1-oxopentan-2-yl]carbamate (C34)

Sodium bicarbonate (4.8 g, 57 mmol) was added to a solution of 5,5,5-trifluoro-L-norvalinamide, hydrochloride salt (this was synthesized using the method described for its enantiomer, in J. E. Starrett, PCT Int. Appl., 2010107997, Sep. 23, 2010; 4.0 g, 19 mmol) and 9H-fluoren-9-ylmethyl carbonochloridate (Fmoc chloride; 10.2 g, 39.4 mmol) in water (80 mL). The resulting slurry was stirred at 15° C. to 25° C. for 24 hours, whereupon it was partitioned between water and dichloromethane. The organic layer was washed sequentially with water and saturated aqueous sodium chloride solution, dried over sodium sulfate, filtered, and concentrated in vacuo, providing C34 as a solid. Yield: 6.2 g, 16 mmol, 83%. LCMS m/z 393.1 [M+H]$^+$. $^1$H NMR (400 MHz, DMSO-d$_6$) δ 7.9 (d, 2H), 7.7 (m, 2H), 7.5 (d, 1H), 7.4 (m, 5H), 7.1 (br s, 1H), 4.3 (m, 3H), 4.0 (m, 1H), 2.2 (m, 2H), 1.9 (m, 1H), 1.7 (m, 1H).

Step 2. Synthesis of N-[(9H-fluoren-9-ylmethoxy)carbonyl]-5,5,5-trifluoro-L-norvaline (C35)

To a solution of C34 (6.2 g, 16 mmol) in 1,4-dioxane (60 mL) was added hydrochloric acid (3 M; 10 mL, 30 mmol), and the reaction mixture was stirred at 80° C. for 16 hours. It was then partitioned between water and dichloromethane, and the organic layer was washed with water and with saturated aqueous sodium chloride solution, dried over sodium sulfate, filtered, and concentrated in vacuo. The residue was triturated with petroleum ether to afford C35 as a solid. Yield: 5.5 g, 14 mmol, 88%. LCMS m/z 392.1 [M−H]$^−$. $^1$H NMR (400 MHz, DMSO-d$_6$) δ 12.83 (br s, 1H), 7.89 (d, J=7.4 Hz, 2H), 7.77-7.67 (m, 3H), 7.46-7.38 (m, 2H), 7.36-7.28 (m, 2H), 4.38-4.28 (m, 2H), 4.26-4.19 (m, 1H), 4.06 (ddd, J=9, 9, 4.9 Hz, 1H), 2.43-2.15 (m, 2H), 2.01-1.89 (m, 1H), 1.89-1.75 (m, 1H).

Step 3. Synthesis of benzyl N-[(9H-fluoren-9-yl-methoxy)carbonyl]-5,5,5-trifluoro-L-norvalinate (C36)

A mixture of C35 (435 mg, 1.11 mmol), benzyl bromide (0.263 mL, 2.21 mmol), and sodium bicarbonate (464 mg, 5.52 mmol) in N,N-dimethylformamide (20 mL) was stirred for 15 hours at 25° C. After the reaction mixture had been diluted with water (30 mL) and extracted with ethyl acetate (3×30 mL), the combined organic layers were washed sequentially with saturated aqueous sodium chloride solution and 5% aqueous lithium chloride solution, dried over sodium sulfate, filtered, and concentrated in vacuo. Silica gel chromatography (Gradient: 0% to 100% ethyl acetate in petroleum ether) provided C36 as a white solid. Yield: 510 mg, 1.05 mmol, 95%. LCMS m/z 506.1 [M+Na$^+$].

Step 4. Synthesis of benzyl 5,5,5-trifluoro-L-norvalinate (C37)

Diethylamine (10 mL) was added to a 0° C. mixture of C36 (510 mg, 1.05 mmol) in acetonitrile (25 mL). After the reaction mixture had been stirred at 20° C. for 2 hours, it was concentrated under reduced pressure; chromatography on silica gel (Gradient: 0% to 10% methanol in dichloromethane) then afforded C37 as a colorless oil. Yield: 250 mg, 0.957 mmol, 91%. LCMS m/z 302.9 [M+CH$_3$CN+H]$^+$. $^1$H NMR (400 MHz, chloroform-d) δ 7.42-7.32 (m, 5H), 5.17 (s, 2H), 3.50 (dd, J=8.4, 5.0 Hz, 1H), 2.32-2.13 (m, 2H), 2.01 (dddd, J=13.7, 10.8, 5.2, 5.2 Hz, 1H), 1.76 (dddd, J=13.6, 10.8, 8.4, 5.3 Hz, 1H).

Step 5. Synthesis of benzyl 5,5,5-trifluoro-N-[(4-methoxy-1H-indol-2-yl)carbonyl]-L-norvalinate (C38)

To a 0° C. solution of C37 (250 mg, 0.957 mmol) and 4-methoxy-1H-indole-2-carboxylic acid (220 mg, 1.15 mmol) in N,N-dimethylformamide (10 mL) was added 0-(7-azabenzotriazol-1-yl)-N,N,N',N'-tetramethyluronium hexafluorophosphate (HATU; 437 mg, 1.15 mmol), followed by drop-wise addition of 4-methylmorpholine (194 mg, 1.92 mmol). Stirring was continued at 0° C. to 10° C. for 1 hour, whereupon the reaction mixture was diluted with water (20 mL) and aqueous citric acid solution (20 mL) and extracted with ethyl acetate (3×20 mL). The combined organic layers were washed sequentially with saturated aqueous sodium bicarbonate solution (30 mL), saturated aqueous sodium chloride solution, and aqueous lithium chloride solution (5%, 20 mL), then dried over sodium sulfate, filtered, and concentrated in vacuo. The residue was purified using silica gel chromatography (Gradient: 0% to 100% ethyl acetate in petroleum ether) to provide C38 as a white solid. Yield: 350 mg, 0.806 mmol, 84%. LCMS m/z 435.1 [M+H]$^+$. $^1$H NMR (400 MHz, chloroform-d) δ 9.09 (br s, 1H), 7.42-7.33 (m, 5H), 7.23 (dd, J=8, 8 Hz, 1H), 7.09 (d, J=2.3 Hz, 1H), 7.03 (d, J=8.3 Hz, 1H), 6.76 (br d, J=7.6 Hz, 1H), 6.53 (d, J=7.8 Hz, 1H), 5.25 (AB quartet, J$_{AB}$=12.1 Hz, Δv$_{AB}$=11.4 Hz, 2H), 4.94-4.87 (m, 1H), 3.96 (s, 3H), 2.35-2.14 (m, 2H), 2.14-1.96 (m, 2H).

Step 6. Synthesis of 5,5,5-trifluoro-N-[(4-methoxy-1H-indol-2-yl)carbonyl]-L-norvaline (C39)

A mixture of C38 (350 mg, 0.806 mmol) and palladium on carbon (10%, 85.7 mg, 80.5 μmol) in methanol (10 mL) was hydrogenated for 16 hours at 20° C. and 15 psi. The reaction mixture was then filtered, and the filter cake was washed with methanol (10 mL); the combined filtrates were concentrated in vacuo and subjected to silica gel chromatography (Eluent: ethyl acetate) to afford C39 as a white solid. Yield: 270 mg, 0.784 mmol, 97%. LCMS m/z 345.0 [M+H]$^+$. $^1$H NMR (400 MHz, DMSO-d$_6$) δ 11.62 (br s, 1H), 8.61 (d, J=7.9 Hz, 1H), 7.32 (d, J=2.2 Hz, 1H), 7.11 (dd, J=8, 8 Hz, 1H), 7.01 (d, half of AB quartet, J=8.2 Hz, 1H), 6.51 (d, J=7.6 Hz, 1H), 4.47 (ddd, J=8.5, 8.5, 4.8 Hz, 1H), 3.89 (s, 3H), 2.5-2.27 (m, 2H, assumed; partially obscured by solvent peak), 2.12-1.92 (m, 2H).

Step 7. Synthesis of 5,5,5-trifluoro-N-[(4-methoxy-1H-indol-2-yl)carbonyl]-L-norvalyl-3-[(3S)-2-oxopyrrolidin-3-yl]-L-alaninamide (C40)

A 0° C. mixture of C16 (58.2 mg, 0.218 mmol) and C39 (75.0 mg, 0.218 mmol) in N,N-dimethylformamide (4 mL) was treated with 0-(7-azabenzotriazol-1-yl)-N,N,N',N'-tetramethyluronium hexafluorophosphate (HATU; 99.4 mg, 0.261 mmol) and 4-methylmorpholine (44.1 mg, 0.436 mmol). After the reaction mixture had been stirred at 0° C. for 1 hour, it was diluted with water (20 mL) and aqueous citric acid solution (1 M; 20 mL), and extracted with ethyl acetate (3×30 mL). The combined organic layers were washed with saturated aqueous sodium bicarbonate solution (20 mL) and with saturated aqueous sodium chloride solution (3×20 mL), dried over sodium sulfate, filtered, and concentrated in vacuo. Chromatography on silica gel (Eluent: 10:1 ethyl acetate/methanol) provided C40 as a white solid. Yield: 72 mg, 0.145 mmol, 66%. LCMS m/z 498.2 [M+H]$^+$. $^1$H NMR (400 MHz, DMSO-d$_6$) δ 11.60 (br s, 1H), 8.52 (d, J=7.7 Hz, 1H), 8.20 (d, J=8.3 Hz, 1H), 7.61 (s, 1H), 7.42-7.33 (m, 2H), 7.14-7.05 (m, 2H), 7.00 (d, half of AB quartet, J=8.2 Hz, 1H), 6.51 (d, J=7.7 Hz, 1H), 4.58-4.46 (m, 1H), 4.32-4.22 (m, 1H), 3.89 (s, 3H), 3.18-3.02 (m, 2H), 2.45-2.21 (m, 3H), 2.18-2.07 (m, 1H), 2.06-1.88 (m, 3H), 1.73-1.59 (m, 1H), 1.59-1.48 (m, 1H).

Step 8. Synthesis of N-[(2S)-1-({(1S)-1-cyano-2-[(3S)-2-oxopyrrolidin-3-yl]ethyl}amino)-5,5,5-trifluoro-1-oxopentan-2-yl]-4-methoxy-1H-indole-2-carboxamide (14)

To a mixture of C40 (52 mg, 0.10 mmol) in dichloromethane (13 mL) was added methyl N-(triethylammoniosulfonyl)carbamate, inner salt (Burgess reagent; 37 mg, 0.16 mmol). The reaction mixture was stirred at room temperature for 1.5 hours, whereupon methyl N-(triethylammoniosulfonyl)carbamate, inner salt (Burgess reagent; 37 mg, 0.16 mmol) was again added, and stirring was continued for 16 hours. A final addition of methyl N-(triethylammoniosulfonyl)carbamate, inner salt (Burgess reagent; 24.9 mg, 0.105 mmol) was followed by stirring for 2 hours, whereupon the reaction mixture was diluted with water (20 mL) and extracted with dichloromethane (3×10 mL). The combined organic layers were washed with saturated aqueous sodium chloride solution (2×20 mL), dried over sodium sulfate, filtered, and concentrated in vacuo; preparative thin-layer chromatography (Eluent: 20:1 ethyl acetate/methanol) afforded N-[(2S)-1-({(1S)-1-cyano-2-[(3S)-2-oxopyrrolidin-3-yl]ethyl}amino)-5,5,5-trifluoro-1-oxopentan-2-yl]-4-methoxy-1H-indole-2-carboxamide (14) as a white solid. Yield: 17.4 mg, 36.3 μmol, 36%. This material was combined with the purified products from two other syntheses of 14 (3 mg and 4 mg) and subjected to supercritical fluid chromatography [Column: Chiral Technologies ChiralCel OD-H, 30×250 mm, 5 μm; Mobile phase: 7:3 carbon dioxide/(ethanol containing 0.1% ammonium hydroxide); Flow rate: 60 mL/minute] to provide N-[(2S)-1-({(1S)-1-cyano-2-[(3S)-2-oxopyrrolidin-3-yl]ethyl}amino)-5,5,5-trifluoro-1-oxopentan-2-yl]-4-methoxy-1H-indole-2-carboxamide (14) as a solid. Yield: 11.3 mg, 23.6 μmol, 46% for the supercritical fluid chromatography. LCMS m/z 480.2 [M+H]$^+$. $^1$H NMR (400 MHz, DMSO-d$_6$) δ 11.61 (br s, 1H), 8.96 (d, J=8.0 Hz, 1H), 8.61 (d, J=7.7 Hz, 1H), 7.71 (s, 1H), 7.37 (d, J=2.2 Hz, 1H), 7.11 (dd, J=8, 8 Hz, 1H), 7.01 (d, half of AB quartet, J=8.2 Hz, 1H), 6.51 (d, J=7.7 Hz, 1H), 5.03-4.94 (m, 1H), 4.51-4.43 (m, 1H), 3.89 (s, 3H), 3.19-3.07 (m, 2H), 2.43-2.28 (m, 3H), 2.20-2.08 (m, 2H), 2.06-1.92 (m, 2H), 1.86-1.76 (m, 1H), 1.76-1.64 (m, 1H).

Examples 15, 16, 17, 18, and 19

N-[(2S)-1-({(1S)-1-Cyano-2-[(3S)-2-oxopyrrolidin-3-yl]ethyl}amino)-4-methyl-1-oxopentan-2-yl]-7-fluoro-4-methoxy-1H-indole-2-carboxamide (15), N-[(2S)-1-({(1S)-1-Cyano-2-[(3S)-2-oxopyrrolidin-3-yl]ethyl}amino)-4-methyl-1-oxopentan-2-yl]-5-fluoro-4-methoxy-1H-indole-2-carboxamide (16), N-[(2S)-1-({(1S)-1-Cyano-2-[(3S)-2-oxopyrrolidin-3-yl]ethyl}amino)-4-methyl-1-oxopentan-2-yl]-3-fluoro-4-methoxy-1H-indole-2-carboxamide (17), N-[(2S)-1-({(1S)-1-Cyano-2-[(3S)-2-oxopyrrolidin-3-yl]ethyl}amino)-4-methyl-1-oxopentan-2-yl]-5,7-difluoro-4-methoxy-1H-indole-2-carboxamide (18), and N-[(2S)-1-({(1S)-1-Cyano-2-[(3S)-2-oxopyrrolidin-3-yl]ethyl}amino)-4-methyl-1-oxopentan-2-yl]-3,5-difluoro-4-methoxy-1H-indole-2-carboxamide (19)

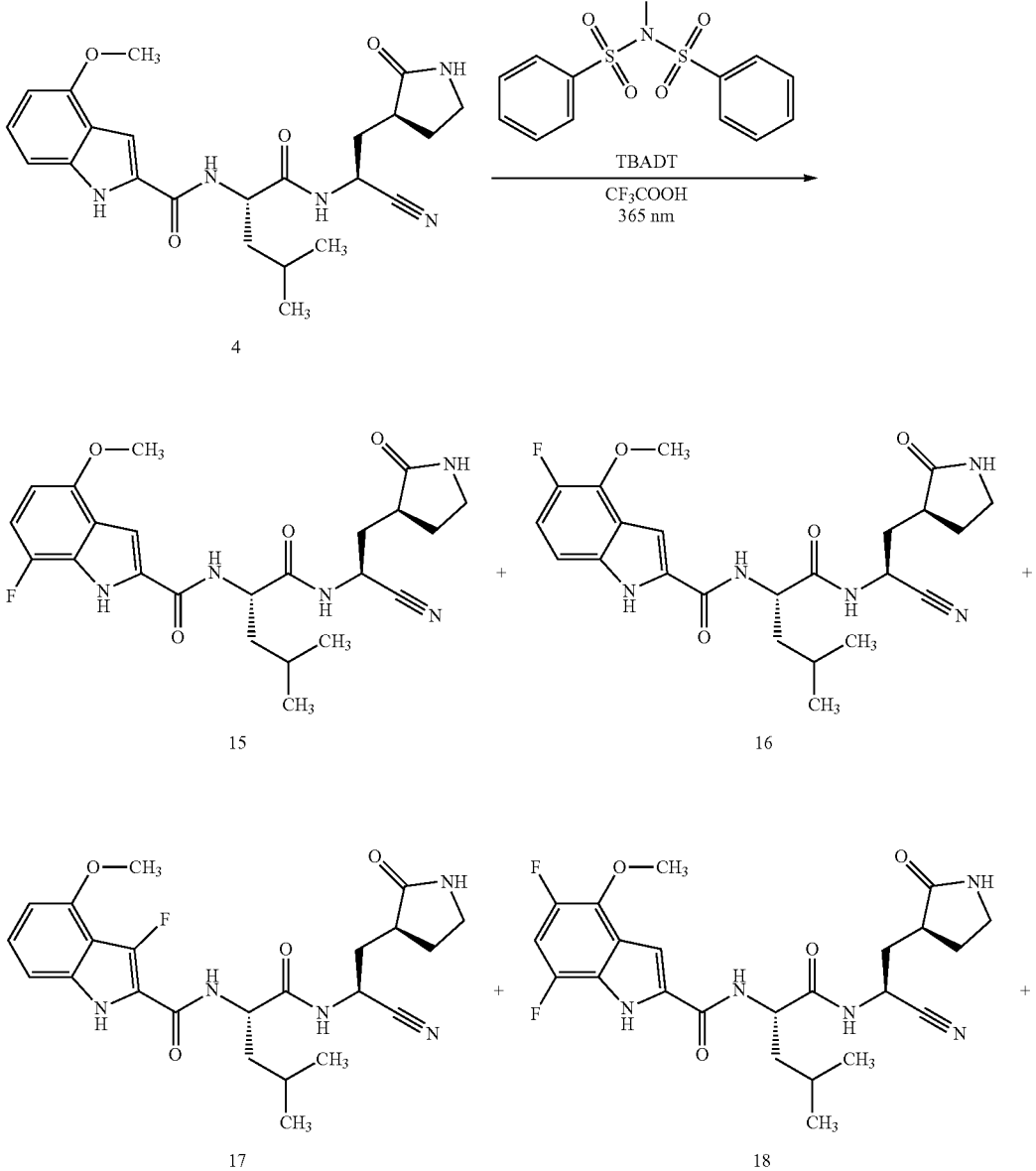

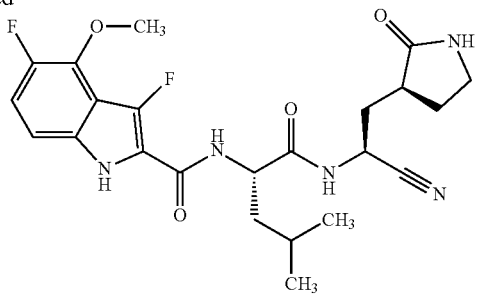

19

A mixture of 4 (10.0 mg, 22.8 μmol), tetra-n-butylammonium decatungstate (TBADT; 3.78 mg, 1.14 μmol), and N-fluoro-N-(phenylsulfonyl)benzenesulfonamide (8.61 mg, 27.3 μmol) was treated with acetonitrile (0.75 mL), water (0.5 mL), and trifluoroacetic acid (1.74 uL, 22.6 μmol) under argon. The reaction vial was then sealed, placed in an EvoluChem™ PhotoRedOx Box equipped with a fan, and irradiated with black light (PAR20-18W LG 365 nm, 100-240 VAC) at 25° C. for 16 hours. To the reaction mixture was added aqueous potassium phosphate solution (1 M, pH 7.45; 1 mL), followed by alternating aliquots of water and acetonitrile to maintain a clarified solution at a final volume of 18 mL. Aliquots (3 mL) of this mixture were applied to Biotage Isolute C18 solid phase extraction cartridges that had been preconditioned with methanol (3 mL) followed by water (3 mL). The cartridges were washed with water (3 mL) and with 20% acetonitrile in 20 mM aqueous ammonium acetate solution (3 mL), then eluted with acetonitrile (3 mL). After the eluates had been evaporated in a vacuum centrifuge, the residues were reconstituted in a mixture of 1% aqueous formic acid and acetonitrile, and combined to a total of 6 mL. This solution was divided in half, and each half was subjected to reversed-phase HPLC (Column: Phenomenex Luna C18, 10×250 mm, 10 μm; Mobile phase A: water containing 0.1% formic acid; Mobile phase B: acetonitrile; Gradient: 15% B for 5 minutes, then 15% to 70% B over 70 minutes, then 70% to 95% B over 15 minutes; Flow rate: 2 mL/min). Fractions were collected every 20 seconds, and like fractions of interest from the two separations were pooled and concentrated. These fractions were further purified via reversed-phase HPLC (Column: Agilent Polaris C18, 4.6×250 mm, 5 μm; Mobile phase A: water containing 10 mM ammonium acetate; Mobile phase B: acetonitrile; Gradient: 10% B for 5 minutes, then 10% to 35% B over 35 minutes, then 35% to 60% B over 15 minutes, then 60% to 95% B over 9 minutes; Flow rate: 0.8 mL/min). Fractions were collected every 20 seconds, affording N-[(2S)-1-({(1S)-1-cyano-2-[(3S)-2-oxopyrrolidin-3-yl]ethyl}amino)-4-methyl-1-oxopentan-2-yl]-7-fluoro-4-methoxy-1H-indole-2-carboxamide (15), N-[(2S)-1-({(1S)-1-cyano-2-[(3S)-2-oxopyrrolidin-3-yl]ethyl}amino)-4-methyl-1-oxopentan-2-yl]-5-fluoro-4-methoxy-1H-indole-2-carboxamide (16), N-[(2S)-1-({(1S)-1-cyano-2-[(3S)-2-oxopyrrolidin-3-yl]ethyl}amino)-4-methyl-1-oxopentan-2-yl]-3-fluoro-4-methoxy-1H-indole-2-carboxamide (17), N-[(2S)-1-({(1S)-1-cyano-2-[(3S)-2-oxopyrrolidin-3-yl]ethyl}amino)-4-methyl-1-oxopentan-2-yl]-5,7-difluoro-4-methoxy-1H-indole-2-carboxamide (18), and N-[(2S)-1-({(1S)-1-cyano-2-[(3S)-2-oxopyrrolidin-3-yl]ethyl}amino)-4-methyl-1-oxopentan-2-yl]-3,5-difluoro-4-methoxy-1H-indole-2-carboxamide (19).

| Example Number | Retention time, first HPLC purification (minutes) | Retention time, second HPLC purification (minutes) |
|---|---|---|
| 15 | 57.1 | 45.1 |
| 16 | 57.7 | 45.9 |
| 17 | 58.6 | 46.7 |
| 18 | 59.9 | 47.9 |
| 19 | 61.7 | 49.5 |

15—First separation, fraction numbers 172-174; Second separation, fraction numbers 136-137. Yield: 58 μg, 0.13 μmol, 0.6%. High-resolution MS m/z 458.2201 [M+H]$^+$; calculated for $C_{23}H_{29}FN_5O_4$, 458.2204. $^1$H NMR (600 MHz, DMSO-$d_6$) δ 12.05 (br s, 1H), 8.93 (d, J=7.9 Hz, 1H), 8.51 (d, J=7.6 Hz, 1H), 7.70 (s, 1H), 7.37 (d, J=2.3 Hz, 1H), 6.92 (dd, J=10.8, 8.6 Hz, 1H), 6.42 (dd, J=8.4, 2.5 Hz, 1H), 5.01-4.94 (m, 1H), 4.50-4.43 (m, 1H), 3.87 (s, 3H), 3.18-3.07 (m, 2H), 2.40-2.31 (m, 1H), 2.19-2.08 (m, 2H), 1.85-1.76 (m, 1H), 1.76-1.64 (m, 3H), 1.58-1.49 (m, 1H), 0.94 (d, J=6.3 Hz, 3H), 0.89 (d, J=6.3 Hz, 3H). Retention time: 7.90 minutes (Analytical conditions. Column: Phenomenex Kinetex XB-C18, 2.1×100 mm, 2.6 μm; Mobile phase A: water containing 0.1% formic acid; Mobile phase B: acetonitrile; Gradient: 5% B for 0.5 minutes, then 5% to 70% B over 10.5 minutes, then 70% to 95% B over 2 minutes; Flow rate: 0.4 mL/min).

16—First separation, fraction numbers 172-174; Second separation, fraction numbers 138-139. Yield: 153 μg, 0.33 μmol, 1.4%. High-resolution MS m/z 458.2201 [M+H]$^+$; calculated for $C_{23}H_{29}FN_5O_4$, 458.2204. $^1$H NMR (600 MHz, DMSO-$d_6$) δ 11.73 (br s, 1H), 8.95 (d, J=8.0 Hz, 1H), 8.61 (d, J=7.7 Hz, 1H), 7.70 (s, 1H), 7.49 (s, 1H), 7.09-7.03 (m, 2H), 5.01-4.94 (m, 1H), 4.51-4.43 (m, 1H), 4.06 (s, 3H), 3.18-3.07 (m, 2H), 2.40-2.31 (m, 1H), 2.19-2.08 (m, 2H), 1.80 (ddd, J=13.6, 9.2, 7.2 Hz, 1H), 1.76-1.65 (m, 3H), 1.58-1.50 (m, 1H), 0.94 (d, J=6.3 Hz, 3H), 0.89 (d, J=6.3 Hz, 3H). Retention time: 7.94 minutes (Analytical conditions identical to those used for 15).

17—First separation, fraction numbers 176-177; Second separation, fraction numbers 141-142. Yield: 22 μg, 0.048 μmol, 0.21%. High-resolution MS m/z 458.2199 [M+H]$^+$; calculated for $C_{23}H_{29}FN_5O_4$, 458.2204. $^1$H NMR (600 MHz, DMSO-$d_6$) δ 11.45 (s, 1H), 8.94 (d, J=7.8 Hz, 1H), 7.71 (s, 1H), 7.62 (br d, J=7.5 Hz, 1H), 7.16 (dd, J=8, 8 Hz, 1H), 6.95 (br d, J=8.3 Hz, 1H), 6.54 (d, J=7.8 Hz, 1H), 5.02-4.94 (m, 1H), 4.54-4.46 (m, 1H), 3.88 (s, 3H), 3.19-3.07 (m, 2H), 2.41-2.31 (m, 1H), 2.20-2.08 (m, 2H), 1.85-1.77 (m, 1H), 1.76-1.63 (m, 3H), 1.61-1.53 (m, 1H), 0.94 (d, J=6.3 Hz, 3H), 0.91 (d, J=6.3 Hz, 3H). Retention time: 8.06 minutes (Analytical conditions identical to those used for 15).

18—First separation, fraction numbers 180-181; Second separation, fraction number 145. Yield: 17 µg, 0.036 µmol, 0.16%. High-resolution MS m/z 476.2100 [M+H]+; calculated for $C_{23}H_{28}F_2N_5O_4$, 476.2109. $^1$H NMR (600 MHz, DMSO-$d_6$) δ 12.23 (s, 1H), 8.96 (d, J=8.0 Hz, 1H), 8.62 (d, J=7.6 Hz, 1H), 7.70 (s, 1H), 7.52-7.48 (m, 1H), 7.13 (dd, J=11, 11 Hz, 1H), 5.02-4.94 (m, 1H), 4.53-4.44 (m, 1H), 4.01 (s, 3H), 3.18-3.07 (m, 2H), 2.38-2.30 (m, 1H), 2.19-2.08 (m, 2H), 1.81 (ddd, J=13.6, 9.1, 7.0 Hz, 1H), 1.76-1.65 (m, 3H), 1.59-1.51 (m, 1H), 0.95 (d, J=6.2 Hz, 3H), 0.90 (d, J=6.3 Hz, 3H). Retention time: 8.20 minutes (Analytical conditions identical to those used for 15).

19—First separation, fraction numbers 185-187; Second separation, fraction numbers 150-151. Yield: 35 µg, 0.074 µmol, 0.32%. High-resolution MS m/z 476.2107 [M+H]+; calculated for $C_{23}H_{28}F_2N_5O_4$, 476.2109. $^1$H NMR (600 MHz, DMSO-$d_6$) δ 11.64 (s, 1H), 8.94 (d, J=7.9 Hz, 1H), 7.80 (br d, J=7 Hz, 1H), 7.71 (s, 1H), 7.16 (dd, component of ABX system, J=11.9, 9.1 Hz, 1H), 7.08 (br d, half of AB quartet, J=8.5 Hz, 1H), 5.02-4.94 (m, 1H), 4.55-4.47 (m, 1H), 3.99 (s, 3H), 3.19-3.08 (m, 2H), 2.41-2.32 (m, 1H), 2.19-2.10 (m, 2H), 1.81 (ddd, J=13.7, 9.0, 7.2 Hz, 1H), 1.77-1.63 (m, 3H), 1.57 (ddd, J=12.9, 8.4, 4.8 Hz, 1H), 0.94 (d, J=6.4 Hz, 3H), 0.91 (d, J=6.4 Hz, 3H). Retention time: 8.44 minutes (Analytical conditions identical to those used for 15).

Examples 20, 21, 22, and 23

N-[(2S)-1-({(1S)-1-Cyano-2-[(3S)-2-oxopyrrolidin-3-yl]ethyl}amino)-4,4-dimethyl-1-oxopentan-2-yl]-7-fluoro-4-methoxy-1H-indole-2-carboxamide (20), N-[(2S)-1-({(1S)-1-Cyano-2-[(3S)-2-oxopyrrolidin-3-yl]ethyl}amino)-4,4-dimethyl-1-oxopentan-2-yl]-5-fluoro-4-methoxy-1H-indole-2-carboxamide (21), N-[(2S)-1-({(1S)-1-Cyano-2-[(3S)-2-oxopyrrolidin-3-yl]ethyl}amino)-4,4-dimethyl-1-oxopentan-2-yl]-3-fluoro-4-methoxy-1H-indole-2-carboxamide (22), and N-[(2S)-1-({(1S)-1-Cyano-2-[(3S)-2-oxopyrrolidin-3-yl]ethyl}amino)-4,4-dimethyl-1-oxopentan-2-yl]-5,7-difluoro-4-methoxy-1H-indole-2-carboxamide (23)

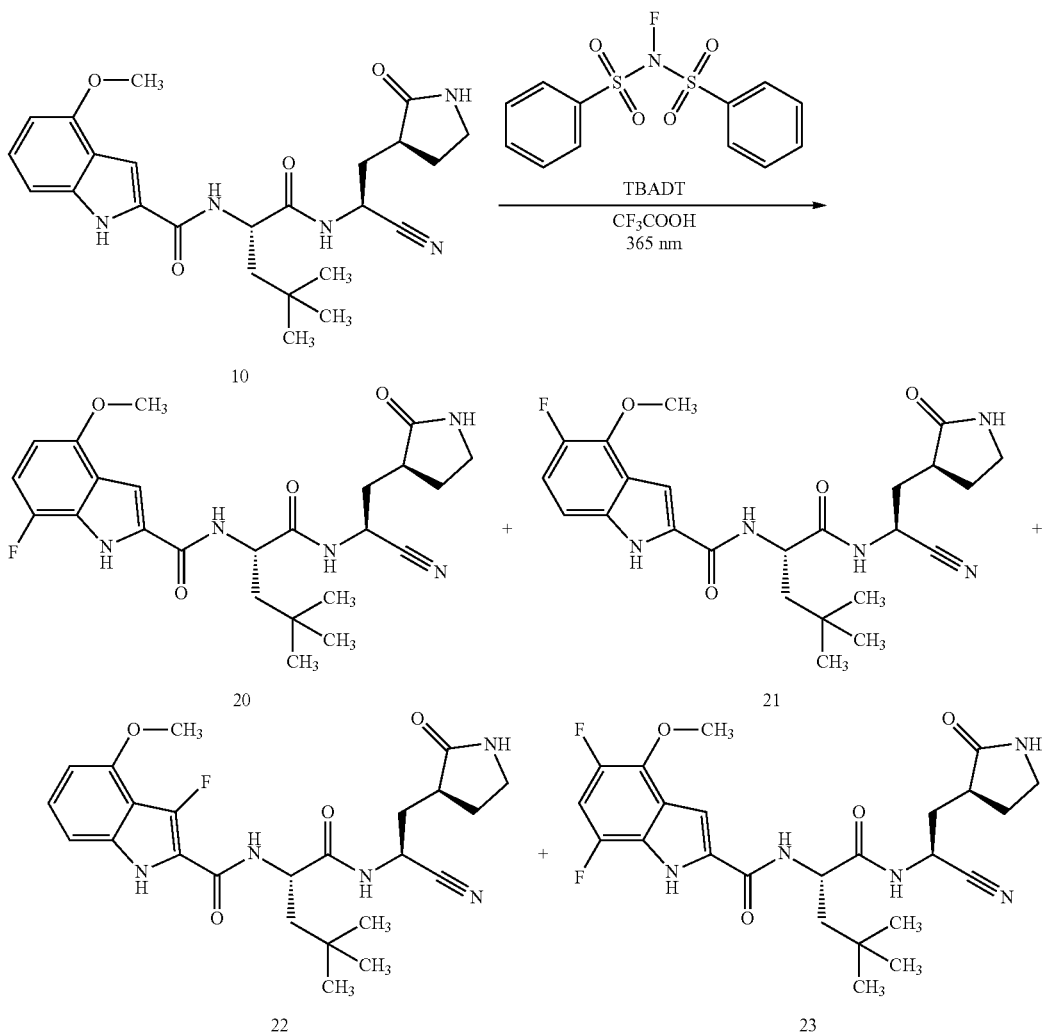

A mixture of 10 (10.0 mg, 22.0 µmol), tetra-n-butylammonium decatungstate (TBADT; 3.66 mg, 1.10 µmol), and N-fluoro-N-(phenylsulfonyl)benzenesulfonamide (8.34 mg, 26.4 µmol) was treated with acetonitrile (0.75 mL), water (0.5 mL), and trifluoroacetic acid (1.69 uL, 21.9 μmol) under argon. The reaction vial was then sealed, placed in an EvoluChem™ PhotoRedOx Box equipped with a fan, and irradiated with black light (PAR20-18W LG 365 nm, 100-240 VAC) at 25° C. for 16 hours. To the reaction mixture was added aqueous potassium phosphate solution (1 M, pH 7.45; 1 mL), followed by alternating aliquots of water and acetonitrile to maintain a clarified solution at a final volume of 18 mL. Aliquots (3 mL) of this mixture were applied to Biotage Isolute C18 solid phase extraction cartridges that had been preconditioned with methanol (3 mL) followed by aqueous ammonium acetate solution (10 mM; 3 mL). The cartridges were washed with aqueous ammonium acetate solution (10 mM; 3 mL) and with 20% acetonitrile in 20 mM ammonium acetate (3 mL), then eluted with acetonitrile (3 mL). After the eluates had been evaporated in a vacuum centrifuge, the residues were reconstituted in a mixture of 1% aqueous formic acid and acetonitrile, and combined to a total of 6 mL. This solution was divided in half, and each half was subjected to reversed-phase HPLC (Column: Phenomenex Luna C18, 10×250 mm, 10 μm; Mobile phase A: water containing 0.1% formic acid; Mobile phase B: acetonitrile; Gradient: 15% B for 5 minutes, then 15% to 70% B over 70 minutes, then 70% to 95% B over 15 minutes; Flow rate: 2 mL/min). Fractions were collected every 20 seconds, and like fractions of interest from the two separations were pooled and concentrated. These fractions were further purified via reversed-phase HPLC (Column: Agilent Polaris C18, 4.6×250 mm, 5 μm; Mobile phase A: water containing 10 mM ammonium acetate; Mobile phase B: acetonitrile; Gradient: 10% B for 5 minutes, then an immediate increase to 20% B, then 20% to 40% B over 35 minutes, then 40% to 60% B over 15 minutes, then 60% to 95% B over 9 minutes; Flow rate: 0.8 mL/min). Fractions were collected every 20 seconds, affording N-[(2S)-1-({(1S)-1-cyano-2-[(3S)-2-oxopyrrolidin-3-yl]ethyl}amino)-4,4-dimethyl-1-oxopentan-2-yl]-7-fluoro-4-methoxy-1H-indole-2-carboxamide (20), N-[(2S)-1-({(1S)-1-cyano-2-[(3S)-2-oxopyrrolidin-3-yl]ethyl}amino)-4,4-dimethyl-1-oxopentan-2-yl]-5-fluoro-4-methoxy-1H-indole-2-carboxamide (21), N-[(2S)-1-({(1S)-1-cyano-2-[(3S)-2-oxopyrrolidin-3-yl]ethyl}amino)-4,4-dimethyl-1-oxopentan-2-yl]-3-fluoro-4-methoxy-1H-indole-2-carboxamide (22), and N-[(2S)-1-({(1S)-1-cyano-2-[(3S)-2-oxopyrrolidin-3-yl]ethyl}amino)-4,4-dimethyl-1-oxopentan-2-yl]-5,7-difluoro-4-methoxy-1H-indole-2-carboxamide (23).

| Example Number | Retention time, first HPLC purification (minutes) | Retention time, second HPLC purification (minutes) |
| --- | --- | --- |
| 20 | 61.2 | 49.8 |
| 21 | 61.2 | 50.2 |
| 22 | 62.3 | 50.8 |
| 23 | 63.5 | 51.9 |

20—First separation, fraction numbers 183-185; Second separation, fraction numbers 150-151. Yield: 24 μg, 0.051 μmol, 0.23%. High-resolution MS m/z 472.2342 [M+H]$^+$; calculated for $C_{24}H_{31}FN_5O_4$, 472.2360. $^1$H NMR (600 MHz, DMSO-d$_6$) δ 12.05 (br s, 1H), 8.91 (d, J=8.0 Hz, 1H), 8.52 (d, J=8.0 Hz, 1H), 7.69 (s, 1H), 7.37-7.32 (m, 1H), 6.92 (dd, J=10.9, 8.4 Hz, 1H), 6.41 (dd, J=8.5, 2.7 Hz, 1H), 5.00-4.93 (m, 1H), 4.52 (ddd, J=8.5, 8.2, 3.7 Hz, 1H), 3.87 (s, 3H), 3.17-3.05 (m, 2H), 2.38-2.30 (m, 1H), 2.18-2.06 (m, 2H), 1.85-1.64 (m, 4H), 0.94 (s, 9H). Retention time: 8.32 minutes (Analytical conditions. Column: Phenomenex Kinetex XB-C18, 2.1×100 mm, 2.6 μm; Mobile phase A: water containing 0.1% formic acid; Mobile phase B: acetonitrile; Gradient: 5% B for 0.5 minutes, then 5% to 70% B over 10.5 minutes, then 70% to 95% B over 2 minutes; Flow rate: 0.4 mL/minute).

21—First separation, fraction numbers 183-185; Second separation, fraction numbers 152-153. Yield: 68 μg, 0.14 μmol, 0.64%. High-resolution MS m/z 472.2344 [M+H]$^+$; calculated for $C_{24}H_{31}FN_5O_4$, 472.2360. $^1$H NMR (600 MHz, DMSO-d$_6$) δ 11.72 (br s, 1H), 8.91 (d, J=8.1 Hz, 1H), 8.59 (d, J=8.0 Hz, 1H), 7.69 (s, 1H), 7.47 (d, J=2.2 Hz, 1H), 7.09-7.04 (m, 2H), 5.00-4.93 (m, 1H), 4.52 (ddd, J=8.5, 8.5, 3.8 Hz, 1H), 4.06 (br s, 3H), 3.17-3.05 (m, 2H), 2.39-2.31 (m, 1H), 2.18-2.06 (m, 2H), 1.84-1.77 (m, 1H), 1.78 (dd, J=13.9, 9.0 Hz, 1H), 1.74-1.64 (m, 2H), 0.94 (s, 9H). Retention time: 8.34 minutes (Analytical conditions identical to those used for 20).

22—First separation, fraction numbers 187-188; Second separation, fraction number 154. Yield: 5 μg, 0.011 μmol, 0.05%. High-resolution MS m/z 472.2354 [M+H]$^+$; calculated for $C_{24}H_{31}FN_5O_4$, 472.2360. $^1$H NMR (600 MHz, DMSO-d$_6$) δ 11.45 (s, 1H), 8.91 (d, J=7.9 Hz, 1H), 7.70 (s, 1H), 7.57 (dd, J=8.2, 3.6 Hz, 1H), 7.15 (dd, J=8, 8 Hz, 1H), 6.95 (br d, J=8.3 Hz, 1H), 6.54 (d, J=7.8 Hz, 1H), 5.00-4.94 (m, 1H), 4.56-4.49 (m, 1H), 3.88 (s, 3H), 3.18-3.07 (m, 2H), 2.40-2.32 (m, 1H), 2.17-2.09 (m, 2H), 1.84-1.77 (m, 1H), 1.76-1.65 (m, 3H), 0.95 (s, 9H). Retention time: 8.51 minutes (Analytical conditions identical to those used for 20).

23—First separation, fraction numbers 190-192; Second separation, fraction numbers 156-157. Yield: 21 μg, 0.043 μmol, 0.19%. High-resolution MS m/z 490.2258 [M+H]$^+$; calculated for $C_{24}H_{30}F_2N_5O_4$, 490.2266. $^1$H NMR (600 MHz, DMSO-d$_6$) δ 12.24 (s, 1H), 8.95 (d, J=8.0 Hz, 1H), 8.64 (d, J=8.0 Hz, 1H), 7.69 (s, 1H), 7.49-7.47 (m, 1H), 7.13 (dd, J=11.1, 11.1 Hz, 1H), 5.00-4.93 (m, 1H), 4.54 (ddd, J=8, 8, 4.1 Hz, 1H), 4.00 (s, 3H), 3.17-3.06 (m, 2H), 2.38-2.30 (m, 1H), 2.18-2.07 (m, 2H), 1.85-1.65 (m, 4H), 0.95 (s, 9H). Retention time: 8.65 minutes (Analytical conditions identical to those used for 20).

TABLE 1

Method of synthesis, structure, and physicochemical data for Examples 24-74.

| Ex. # | Method of synthesis; Non-commercial starting materials | Structure | 1H NMR (600 MHz, DMSO-d6) δ, Mass spectrum, observed ion m/z [M + H]+ or HPLC retention time; Mass spectrum m/z [M + H]+ (unless otherwise indicated) |
|---|---|---|---|
| 24 | Example 10; C18 | 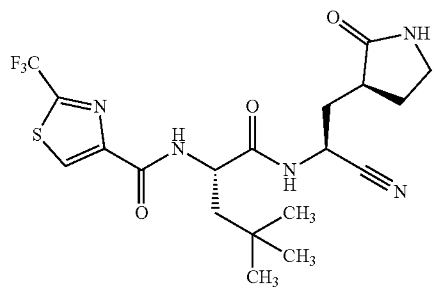 [SMILES: CC(C)(C)C[C@H](NC(=O)c1csc(C(F)(F)F)n1)C(=O)N[C@H](C#N)C[C@@H]1CCNC1=O] | 1H NMR (400 MHz, methanol-d4) δ 8.58 (s, 1H), 5.04 (dd, J = 9.9, 6.1 Hz, 1H), 4.64 (dd, J = 8.7, 4.1 Hz, 1H), 3.34-3.23 (m, 2H; assumed; partially obscured by solvent peak), 2.61-2.50 (m, 1H), 2.35-2.24 (m, 2H), 1.96-1.76 (m, 4H), 1.01 (s, 9H), 460.4 |
| 25 | Examples 8 and 9[1,2]; C28 | 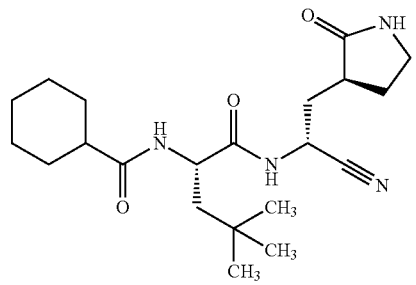 [SMILES: CC(C)(C)C[C@H](NC(=O)C1CCCCC1)C(=O)N[C@@H](C#N)C[C@@H]1CCNC1=O] or DIAST-1 | 2.29 minutes[3]; 391.4 |
| 26 | Examples 8 and 9[1,2]; C28 | 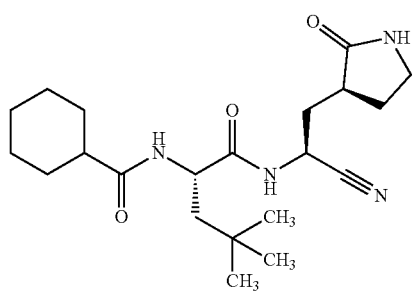 [SMILES: CC(C)(C)C[C@H](NC(=O)C1CCCCC1)C(=O)N[C@H](C#N)C[C@@H]1CCNC1=O] or | 2.69 minutes[3]; 391.4 |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
|  |  | DIAST-2 |  |
| 27 | Example 7; C28 | 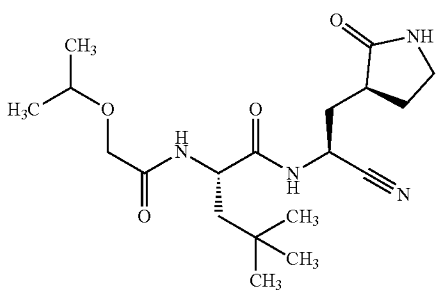 [SMILES: CC(C)OCC(=O)N[C@@H](CC(C)(C)C)C(=O)N[C@H](C#N)C[C@@H]1CCNC1=O] | 2.18 minutes[4]; 381.4 |
| 28 | Example 7; C28 | 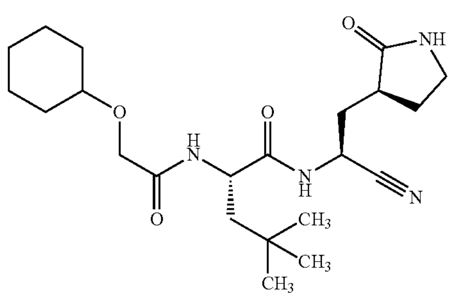 [SMILES: CC(C)(C)C[C@H](NC(=O)COC1CCCCC1)C(=O)N[C@H](C#N)C[C@@H]1CCNC1=O] | 2.61 minutes[4]; 421.5 |
| 29 | Example 7; C28 | 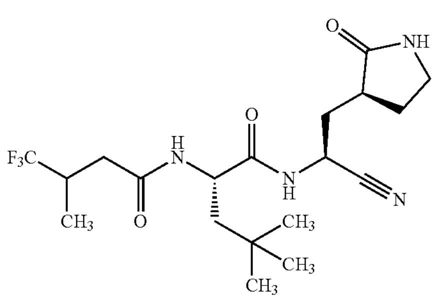 [SMILES: CC(CC(=O)N[C@@H](CC(C)(C)C)C(=O)N[C@H](C#N)C[C@@H]1CCNC1=O)C(F)(F)F] | 2.31 minutes[4]; 419.4 |

US 11,452,711 B2
159                                                                                  160
TABLE 1-continued
Method of synthesis, structure, and physicochemical data for Examples 24-74.
| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| 30 | Example 7[1]; C28 | 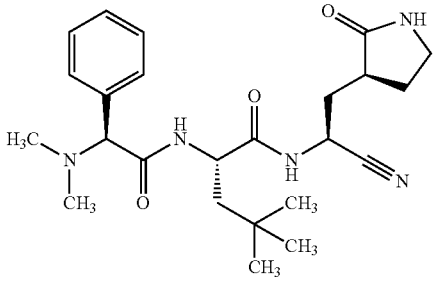 [SMILES: CN(C)[C@H](C(=O)N[C@@H](CC(C)(C)C)C(=O)N[C@H](C#N)C[C@@H]1CCNC1=O)c1ccccc1] | 1.59 minutes[4]; 442.55 |
| 31 | C29[6] | 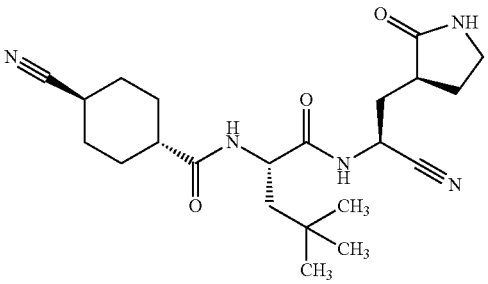 [SMILES: CC(C)(C)C[C@H](NC(=O)[C@H]1CC[C@H](C#N)CC1)C(=O)N[C@H](C#N)C[C@@H]1CCNC1=O] <br> or <br> 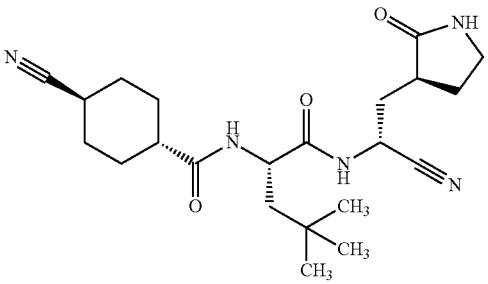 [SMILES: CC(C)(C)C[C@H](NC(=O)[C@H]1CC[C@H](C#N)CC1)C(=O)N[C@@H](C#N)C[C@@H]1CCNC1=O] | 2.06 minutes[4]; 416.5 |
| 32 | C29[6] | 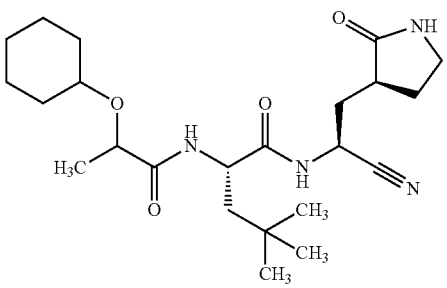 [SMILES: CC(OC1CCCCC1)C(=O)N[C@@H](CC(C)(C)C)C(=O)N[C@H](C#N)C[C@@H]1CCNC1=O] <br> or | 2.67 minutes[4]; 435.6 |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| | | (structure shown) | |
| 33 | Example 4[7] | (structure shown) | 11.40 (s, 1H), 9.60 (br s, 1H), 8.90 (d, J = 8.1 Hz, 1H), 8.44 (d, J = 7.9 Hz, 1H), 7.70 (s, 1H), 7.31 (s, 1H), 6.95 (dd, J = 8, 8 Hz, 1H), 6.85 (d, J = 8.2 Hz, 1H), 6.36 (d, J = 7.5 Hz, 1H), 5.02-4.93 (m, 1H), 4.50-4.41 (m, 1H), 3.17-3.07 (m, 2H), 2.41-2.31 (m, 1H), 2.19-2.08 (m, 2H), 1.80 (ddd, J = 13.6, 9.4, 6.8 Hz, 1H), 1.76-1.65 (m, 3H), 1.57-1.48 (m, 1H), 0.94 (d, J = 6.3 Hz, 3H), 0.89 (d, J = 6.3 Hz, 3H); high-resolution MS m/z 426.2139 [M + H]$^+$; calculated for $C_{22}H_{28}N_5O_4$, 426.2141 |
| 34 | Example 4[7] | (structure shown) | 11.34 (s, 1H), 8.91 (d, J = 8.1 Hz, 1H), 8.46 (d, J = 7.9 Hz, 1H), 7.69 (s, 1H), 7.29 (s, 1H), 6.95 (d, J = 8.6 Hz, 1H), 6.78 (d, J = 8.6 Hz, 1H), 5.02-4.93 (m, 1H), 4.50-4.41 (m, 1H), 3.91 (s, 3H), 3.18-3.06 (m, 2H, assumed; partially obscured by solvent peak), 2.39-2.31 (m, 1H), 2.20-2.07 (m, 2H), 1.84-1.65 (m, 4H), 1.58-1.49 (m, 1H), 0.94 (d, J = 6.2 Hz, 3H), 0.89 (d, J = 6.2 Hz, 3H); high-resolution MS m/z 456.2238 [M + H]$^+$; calculated for $C_{23}H_{30}N_5O_5$, 456.2247 |
| 35 | Example 11[8]; C18 | (structure shown) | 2.39 minutes[4]; 437.4 (chlorine isotope pattern observed) |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| 36 | Example 11; C18 | (structure) | $^1$H NMR (600 MHz, methanol-$d_4$) δ 7.45-7.40 (m, 2H), 7.34-7.27 (m, 3H), 4.98 (dd, J = 10.5, 5.6 Hz, 1H), 4.27 (dd, J = 8.4, 4.3 Hz, 1H), 3.70 (s, 1H), 3.28-3.23 (m, 1H), 3.20 (ddd, J = 9.5, 9.3, 7.1 Hz, 1H), 2.57-2.49 (m, 1H), 2.27 (ddd, J = 13.8, 10.5, 5.2 Hz, 1H), 2.21-2.13 (m, 1H), 2.17 (s, 6H), 1.85 (ddd, J = 13.8, 9.7, 5.7 Hz, 1H), 1.79-1.70 (m, 1H), 1.67 (dd, component of ABX system, J = 14.4, 4.3 Hz, 1H), 1.59 (dd, component of ABX system, J = 14.4, 8.4 Hz, 1H), 0.84 (s, 9H); 442.5 |
| 37 | Examples 5 and 6[9]; Example 10 | (structure) | 12.13 (s, 1H), 8.96 (br d, J = 7.6 Hz, 2H), 7.69 (s, 1H), 7.21 (dd, J = 8, 8 Hz, 1H), 7.08 (d, J = 8.2 Hz, 1H), 6.68 (d, J = 7.8 Hz, 1H), 5.00-4.92 (m, 1H), 4.52-4.45 (m, 1H), 3.86 (s, 3H), 3.20-3.15 (m, 1H), 3.14-3.08 (m, 1H), 2.43-2.34 (m, 1H), 2.23-2.13 (m, 2H), 1.85-1.78 (m, 1H), 1.78-1.68 (m, 2H), 1.59 (dd, J = 14.1, 6.6 Hz, 1H), 0.95 (s, 9H); high-resolution MS m/z 522.2321 [M + H]$^+$; calculated for $C_{25}H_{31}F_3N_5O_4$, 522.2328; retention time 7.18 minutes[10] |
| 38 | Examples 5 and 6[9]; Example 10 | (structure) | 11.41 (s, 1H), 8.96 (d, J = 7.7 Hz, 1H), 8.79 (d, J = 8.0 Hz, 1H), 7.65 (s, 1H), 7.55 (d, J = 8.2 Hz, 1H), 7.34 (s, 1H), 6.72 (d, J = 8.3 Hz, 1H), 5.01-4.94 (m, 1H), 4.62-4.55 (m, 1H), 3.97 (s, 3H), 3.17-3.11 (m, 1H), 3.11-3.04 (m, 1H), 2.38-2.30 (m, 1H), 2.18-2.07 (m, 2H), 1.86-1.78 (m, 1H), 1.77-1.64 (m, 3H), 0.95 (s, 9H); high-resolution MS m/z 522.2316 [M + H]$^+$; calculated for calculated for $C_{25}H_{31}F_3N_5O_4$, 522.2328; retention time 7.45 minutes[10] |
| 39 | Examples 5 and 6[9]; Example 10 | (structure) | 9.08 (br s, 1H), 9.03 (d, J = 8.0 Hz, 1H), 7.65 (s, 1H), 7.60 (d, J = 8.3 Hz, 1H), 6.84 (d, J = 8.2 Hz, 1H), 4.98-4.91 (m, 1H), 4.53-4.47 (m, 1H), 3.95 (s, 3H), 3.20-3.14 (m, 1H), 3.13-3.06 (m, 1H), 2.44-2.36 (m, 1H), 2.23-2.12 (m, 2H), 1.85 (dd, J = 13.9, 7.8 Hz, 1H), 1.80 (ddd, J = 13.6, 9.6, 6.5 Hz, 1H), 1.76-1.68 (m, 1H), 1.54 (dd, J = 13.9, 5.1 Hz, 1H), 0.95 (s, 9H); high-resolution MS m/z 590.2177 [M + H]$^+$; calculated for $C_{26}H_{30}F_6N_5O_4$, 590.2202; retention time 7.70 minutes[10] |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| 40 | Examples 5 and 6[9]; Example 10 | (structure) | 12.76 (br s, 1H), 9.19-9.10 (m, 1H), 9.06-9.00 (m, 1H), 7.69 (s, 1H), 7.49 (AB quartet, $J_{AB}$ = 8.6 Hz, $\Delta v_{AB}$ = 48.9 Hz, 2H), 5.01-4.93 (m, 1H), 4.54-4.47 (m, 1H), 3.85 (s, 3H), 3.21-3.15 (m, 1H), 3.15-3.07 (m, 1H), 2.43-2.35 (m, 1H), 2.22-2.13 (m, 2H), 1.86-1.78 (m, 1H), 1.78-1.70 (m, 2H), 1.59 (dd, component of ABX system, J = 14.1, 6.5 Hz, 1H), 0.96 (s, 9H); high-resolution MS m/z 590.2181 [M + H]$^+$; calculated for $C_{26}H_{30}F_6N_5O_4$, 590.2202; retention time 7.79 minutes[10] |
| 41 | Examples 5 and 6[9,11]; Example 10 | (structure) | 12.62 (s, 1H), 9.14 (d, J = 7.5 Hz, 1H), 9.03 (d, J = 7.8 Hz, 1H), 7.70 (s, 1H), 7.42 (s, 1H), 6.92 (s, 1H), 5.00-4.93 (m, 1H), 4.54-4.47 (m, 1H), 3.96 (s, 3H), 3.21-3.15 (m, 1H), 3.15-3.08 (m, 1H), 2.43-2.35 (m, 1H), 2.22-2.13 (m, 2H), 1.86-1.79 (m, 1H), 1.78-1.69 (m, 2H), 1.59 (dd, component of ABX system, J = 14.0, 6.4 Hz, 1H), 0.96 (s, 9H); high-resolution MS m/z 590.2175 [M + H]$^+$; calculated for $C_{26}H_{30}F_6N_5O_4$, 590.2202; retention time 7.84 minutes[10] |
| 42 | Examples 5 and 6[12]; Example 36 | (structure) | 8.92 (d, J = 8.0 Hz, 1H), 8.45 (d, J = 7.9 Hz, 1H), 7.71 (s, 2H), 7.67 (d, J = 7.6 Hz, 1H), 7.64-7.60 (m, 1H), 7.58-7.52 (m, 1H), 4.99-4.87 (m, 1H), 4.24-4.17 (m, 1H), 3.92 (s, 1H), 3.20-3.10 (m, 1H), 3.09-3.00 (m, 1H), 2.36-2.27 (m, 1H), 2.19-2.00 (m, 2H), 2.08 (s, 6H), 1.81-1.64 (m, 2H), 1.49 (d, J = 6.5 Hz, 2H), 0.74 (s, 9H); high-resolution MS m/z 510.2679 [M + H]$^+$; calculated for $C_{25}H_{35}F_3N_5O_3$, 510.2692; retention time 5.83 minutes[10] |
| 43 | Examples 5 and 6[12]; Example 36 | (structure) | 8.93 (d, J = 8.1 Hz, 1H), 8.42 (d, J = 8.1 Hz, 1H), 7.71 (s, 1H), 7.63 (AB quartet, $J_{AB}$ = 7.6 Hz, $\Delta v_{AB}$ = 48.8 Hz, 4H), 4.97-4.88 (m, 1H), 4.26-4.19 (m, 1H), 3.91 (s, 1H), 3.19-3.11 (m, 1H), 3.07-3.00 (m, 1H), 2.35-2.26 (m, 1H), 2.18-1.99 (m, 2H), 2.08 (s, 6H), 1.80-1.64 (m, 2H), 1.56-1.44 (m, 2H), 0.77 (s, 9H); high-resolution MS m/z 510.2676 [M + H]$^+$; calculated for $C_{25}H_{35}F_3N_5O_3$, 510.2692; retention time 5.92 minutes[10] |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| 44 | Alternate Synthesis of Example 6; C26 | 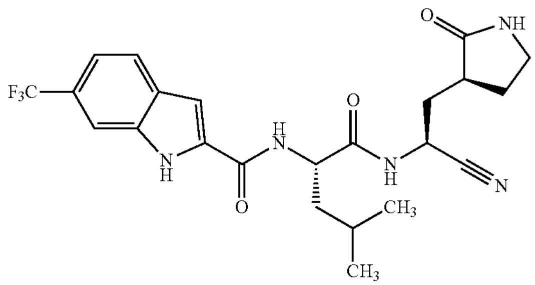 [SMILES: CC(C)C[C@H](NC(=O)c1cc2ccc(C(F)(F)F)cc2[nH]1)C(=O)N[C@H](C#N)C[C@@H]1CCNC1=O] | 2.85 minutes[4]; 478.6 |
| 45 | Alternate Synthesis of Example 6; C18 | 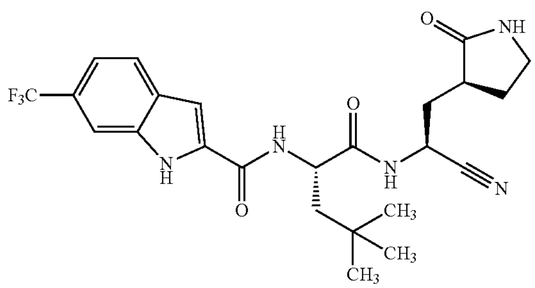 [SMILES: CC(C)(C)C[C@H](NC(=O)c1cc2ccc(C(F)(F)F)cc2[nH]1)C(=O)N[C@H](C#N)C[C@@H]1CCNC1=O] | 2.95 minutes[4]; 492.6 |
| 46 | Examples 5 and 6[13]; 4 | 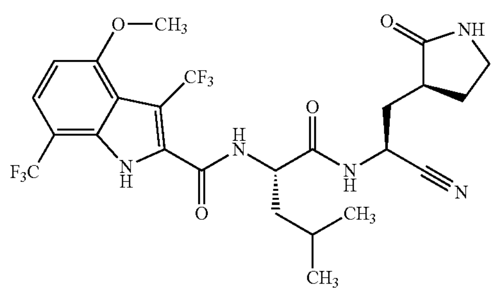 [SMILES: COc1ccc(C(F)(F)F)c2[nH]c(C(=O)N[C@@H](CC(C)C)C(=O)N[C@H](C#N)C[C@@H]3CCNC3=O)c(C(F)(F)F)c12] | 12.48 (s, 1H), 9.13 (d, J = 7.4 Hz, 1H), 8.97 (d, J = 7.7 Hz, 1H), 7.70 (s, 1H), 7.62 (d, J = 8.3 Hz, 1H), 6.86 (d, J = 8.3 Hz, 1H), 5.04-4.95 (m, 1H), 4.53-4.44 (m, 1H), 3.96 (s, 3H), 3.22-3.14 (m, 1H), 3.14-3.06 (m, 1H), 2.44-2.34 (m, 1H), 2.24-2.10 (m, 2H), 1.87-1.77 (m, 1H), 1.77-1.61 (m, 2H), 1.61-1.50 (m, 2H), 0.98-0.89 (m, 6H); high-resolution MS m/z 576.2055 [M + H]$^+$; calculated for $C_{25}H_{28}F_6N_5O_4$, 576.2045; retention time 6.70 minutes[14] |
| 47 | Examples 5 and 6[13]; 4 | 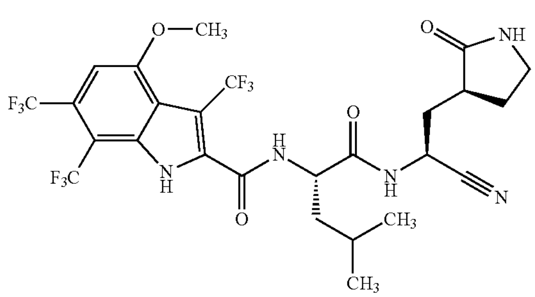 [SMILES: COc1cc(C(F)(F)F)c(C(F)(F)F)c2[nH]c(C(=O)N[C@@H](CC(C)C)C(=O)N[C@H](C#N)C[C@@H]3CCNC3=O)c(C(F)(F)F)c12] | 12.61 (s, 1H), 9.23 (d, J = 7.6 Hz, 1H), 9.01 (d, J = 7.9 Hz, 1H), 7.71 (s, 1H), 7.20 (s, 1H), 5.04-4.95 (m, 1H), 4.54-4.45 (m, 1H), 4.07 (s, 3H), 3.22-3.14 (m, 1H), 3.14-3.06 (m, 1H), 2.43-2.34 (m, 1H), 2.23-2.11 (m, 2H), 1.82 (ddd, J = 13.5, 9.0, 7.0 Hz, 1H), 1.78-1.61 (m, 2H), 1.61-1.49 (m, 2H), 0.99-0.89 (m, 6H); high-resolution MS m/z 644.1914 [M + H]$^+$; calculated for $C_{26}H_{27}F_9N_5O_4$, 644.1919; retention time 7.43 minutes[14] |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| 48 | Examples 5 and 6[13]; 4 | 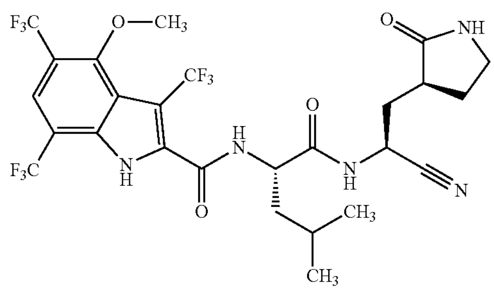 [SMILES: COc1c(C(F)(F)F)cc(C(F)(F)F)c2[nH]c(C(=O)N[C@@H](CC(C)C)C(=O)N[C@H](C#N)C[C@@H]3CCNC3=O)c(C(F)(F)F)c12] | 13.21 (s, 1H), 9.28 (d, J = 7.5 Hz, 1H), 9.05 (d, J = 7.8 Hz, 1H), 7.86 (s, 1H), 7.72 (s, 1H), 5.04-4.96 (m, 1H), 4.54-4.47 (m, 1H), 3.93 (s, 3H), 3.22-3.15 (m, 1H), 3.15-3.07 (m, 1H), 2.43-2.35 (m, 1H), 2.23-2.11 (m, 2H), 1.82 (ddd, J = 13.7, 9.0, 6.9 Hz, 1H), 1.78-1.63 (m, 2H), 1.61-1.51 (m, 2H), 0.98-0.91 (m, 6H); high-resolution MS m/z 644.1901 [M + H]$^+$; calculated for $C_{26}H_{27}F_9N_5O_4$, 644.1919; retention time 7.51 minutes[14] |
| 49 | Alternate Synthesis of Example 6; C26 | 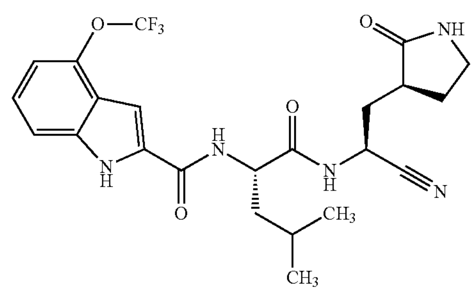 [SMILES: CC(C)C[C@H](NC(=O)c1cc2c(OC(F)(F)F)cccc2[nH]1)C(=O)N[C@H](C#N)C[C@@H]1CCNC1=O] | 2.95 minutes[4]; 494.4 |
| 50 | Alternate Synthesis of Example 6; C18 | 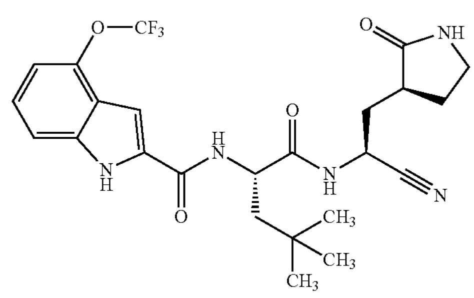 [SMILES: CC(C)(C)C[C@H](NC(=O)c1cc2c(OC(F)(F)F)cccc2[nH]1)C(=O)N[C@H](C#N)C[C@@H]1CCNC1=O] | 3.04 minutes[4]; 508.4 |
| 51 | Alternate Synthesis of Example 6; C18 | 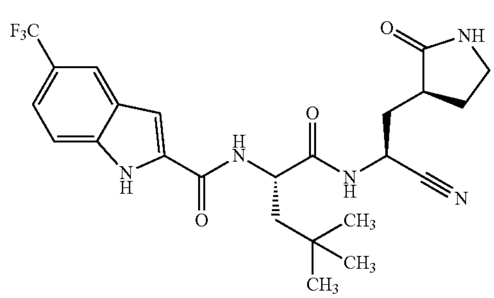 [SMILES: CC(C)(C)C[C@H](NC(=O)c1cc2cc(C(F)(F)F)ccc2[nH]1)C(=O)N[C@H](C#N)C[C@@H]1CCNC1=O] | 3.00 minutes[4]; 492.4 |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]+ or HPLC retention time; Mass spectrum m/z [M + H]+ (unless otherwise indicated) |
|---|---|---|---|
| 52 | Alternate Synthesis of Example 6; C18 | 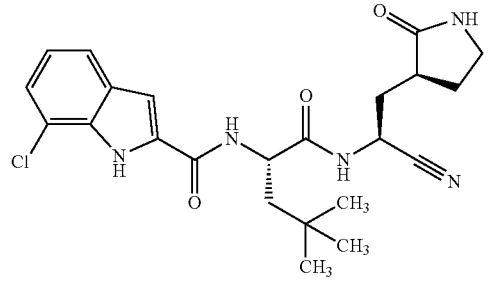 [SMILES: CC(C)(C)C[C@H](NC(=O)c1cc2cccc(Cl)c2[nH]1)C(=O)N[C@H](C#N)C[C@@H]1CCNC1=O] | 2.84 minutes[4]; 458.4 (chlorine isotope pattern observed) |
| 53 | Alternate Synthesis of Example 6; C18 | 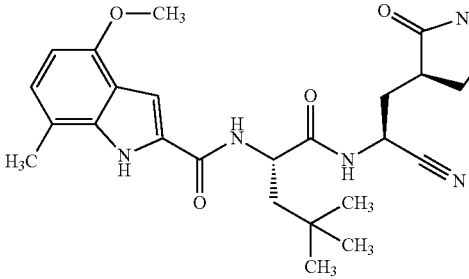 | 2.80 minutes[4]; 468.5 |
| 54 | Alternate Synthesis of Example 6; C18 | 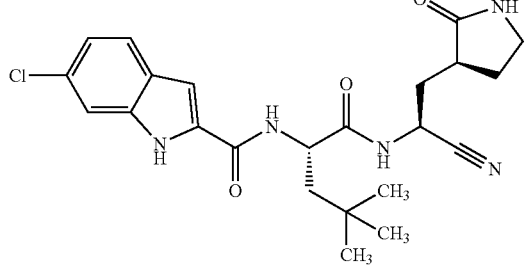 | 2.89 minutes[4]; 458.4 (chlorine isotope pattern observed) |
| 55 | Alternate Synthesis of Example 6; C18 | 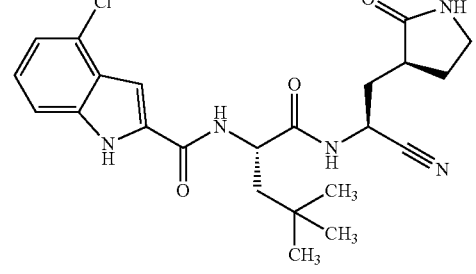 | 2.90 minutes[4]; 458.4 (chlorine isotope pattern observed) |
| 56 | Alternate Synthesis of Example 6; C18 | 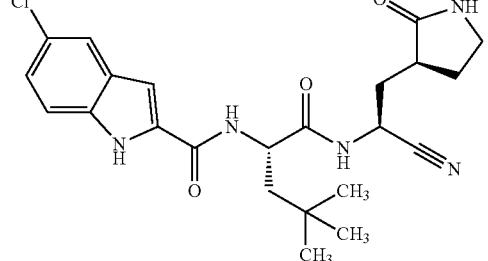 | 2.89 minutes[4]; 458.4 (chlorine isotope pattern observed) |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| 57 | Alternate Synthesis of Example 6; C18 | 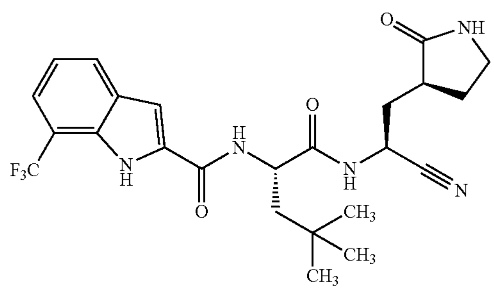 [SMILES: CC(C)(C)C[C@H](NC(=O)c1cc2cccc(C(F)(F)F)c2[nH]1)C(=O)N[C@H](C#N)C[C@@H]1CCNC1=O] | 2.95 minutes$^4$; 492.4 |
| 58 | Alternate Synthesis of Example 6; C18 | 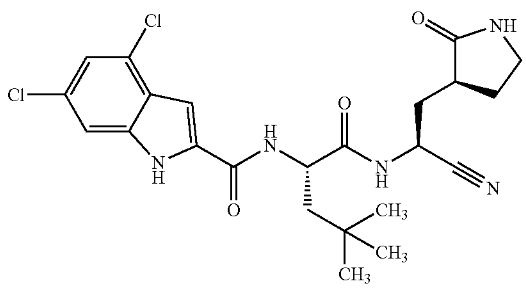 [SMILES: CC(C)(C)C[C@H](NC(=O)c1cc2c(Cl)cc(Cl)cc2[nH]1)C(=O)N[C@H](C#N)C[C@@H]1CCNC1=O] | 3.16 minutes$^4$; 492.3 (dichloro isotope pattern observed) |
| 59 | Alternate Synthesis of Example 6; C18 | 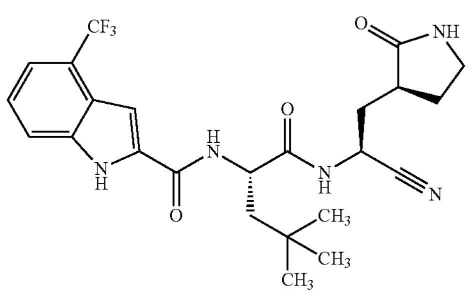 | 2.99 minutes$^4$; 492.4 |
| 60 | Alternate Synthesis of Example 6; C26 | 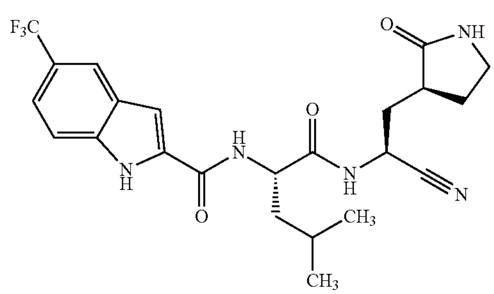 [SMILES: CC(C)C[C@H](NC(=O)c1cc2cc(C(F)(F)F)ccc2[nH]1)C(=O)N[C@H](C#N)C[C@@H]1CCNC1=O] | 2.91 minutes$^4$; 478.4 |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]+ or HPLC retention time; Mass spectrum m/z [M + H]+ (unless otherwise indicated) |
|---|---|---|---|
| 61 | Alternate Synthesis of Example 6; C26 | 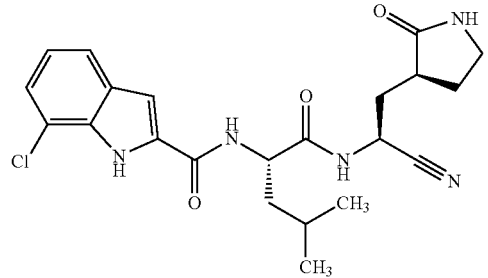 [SMILES: CC(C)C[C@H](NC(=O)c1cc2cccc(Cl)c2[nH]1)C(=O)N[C@H](C#N)C[C@@H]1CCNC1=O] | 2.74 minutes[4]; 444.4 (chlorine isotope pattern observed) |
| 62 | Alternate Synthesis of Example 6; C26 | 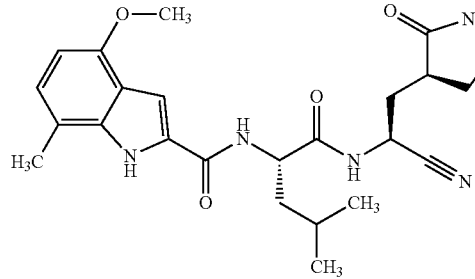 | 2.70 minutes[4]; 454.4 |
| 63 | Alternate Synthesis of Example 6; C26 | 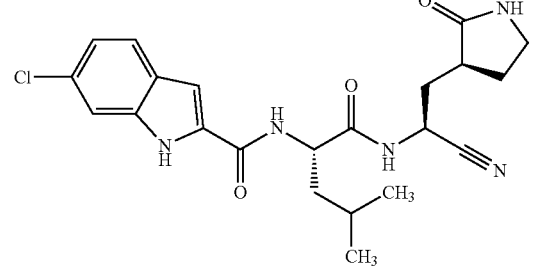 | 2.80 minutes[4]; 444.4 (chlorine isotope pattern observed) |
| 64 | Alternate Synthesis of Example 6; C26 | 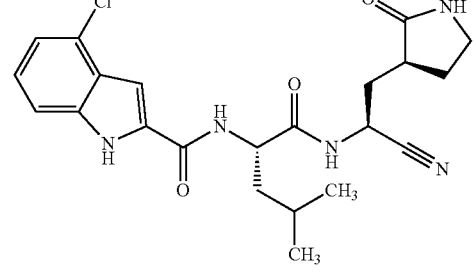 | 2.81 minutes[4]; 444.4 (chlorine isotope pattern observed) |
| 65 | Alternate Synthesis of Example 6; C26 | 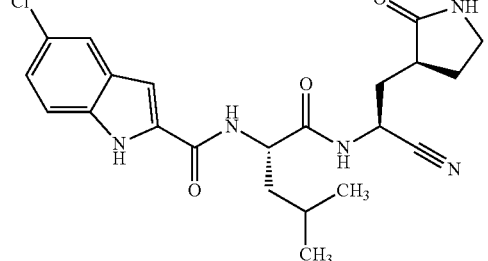 | 2.80 minutes[4]; 444.4 (chlorine isotope pattern observed) |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| 66 | Alternate Synthesis of Example 6; C26 | 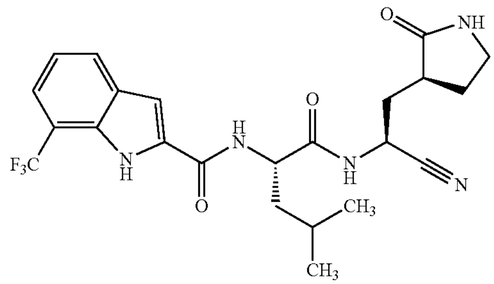 [SMILES: CC(C)C[C@H](NC(=O)c1cc2cccc(C(F)(F)F)c2[nH]1)C(=O)N[C@H](C#N)C[C@@H]1CCNC1=O] | 2.86 minutes$^4$; 478.4 |
| 67 | Alternate Synthesis of Example 6; C26 | 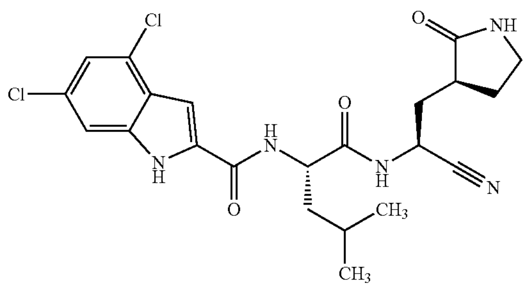 [SMILES: CC(C)C[C@H](NC(=O)c1cc2c(Cl)cc(Cl)cc2[nH]1)C(=O)N[C@H](C#N)C[C@@H]1CCNC1=O] | 3.08 minutes4; 478.3 (dichloro isotope pattern observed) |
| 68 | Alternate Synthesis of Example 6; C26 | 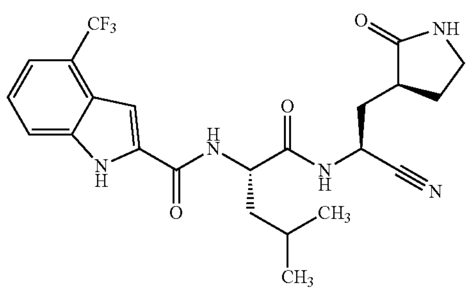 [SMILES: CC(C)C[C@H](NC(=O)c1cc2c(C(F)(F)F)cccc2[nH]1)C(=O)N[C@H](C#N)C[C@@H]1CCNC1=O] | 2.91 minutes$^4$; 478.4 |
| 69 | Examples 5 and 6$^{15}$; 7 | 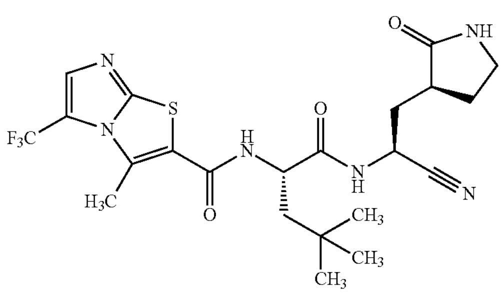 [SMILES: Cc1c(C(=O)N[C@@H](CC(C)(C)C)C(=O)N[C@H](C#N)C[C@@H]2CCNC2=O)sc2ncc(C(F)(F)F)n12] | 9.00 (d, J = 7.9 Hz, 1H), 8.83 (d, J = 7.9 Hz, 1H), 8.01 (s, 1H), 7.72 (s, 1H), 5.01-4.93 (m, 1H), 4.44 (ddd, J = 8, 8, 4.4 Hz, 1H), 3.20-3.14 (m, 1H), 3.14-3.08 (m, 1H), 2.66 (s, 3H), 2.42-2.34 (m, 1H), 2.20-2.08 (m, 2H), 1.81 (ddd, J = 13.5, 9.4, 6.7 Hz, 1H), 1.77-1.64 (m, 3H), 0.95 (s, 9H); high-resolution MS m/z 513.1873 [M + H]$^+$; calculated for $C_{22}H_{28}F_3N_6O_3S$, 513.1896; retention time 6.88 minutes$^{10}$ |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| 70 | Alternate Synthesis of Example 6; C18 | 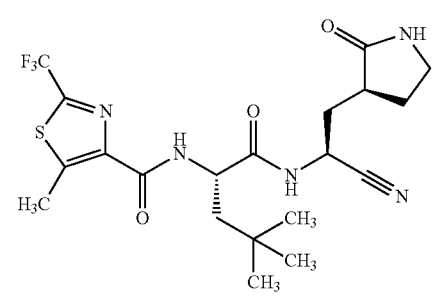 [SMILES: Cc1sc(C(F)(F)F)nc1C(=O)N[C@@H](CC(C)(C)C)C(=O)N[C@H](C#N)C[C@@H]1CCNC1=O] | 2.87 minutes[4]; 474.5 |
| 71 | Alternate Synthesis of Example 6; C18 | 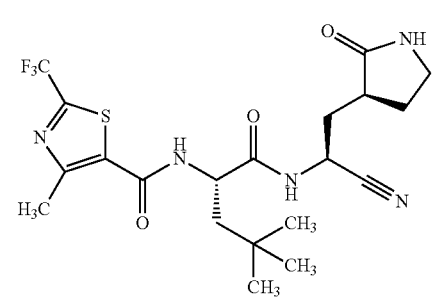 [SMILES: Cc1nc(C(F)(F)F)sc1C(=O)N[C@@H](CC(C)(C)C)C(=O)N[C@H](C#N)C[C@@H]1CCNC1=O] | 2.70 minutes[4]; 474.5 |
| 72 | Alternate Synthesis of Example 6; C26 | 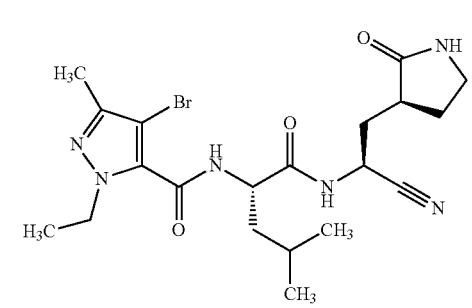 [SMILES: CCn1nc(C)c(Br)c1C(=O)N[C@@H](CC(C)C)C(=O)N[C@H](C#N)C[C@@H]1CCNC1=O] | 2.41 minutes[4]; 481.5 (bromine isotope pattern observed) |
| 73 | Alternate Synthesis of Example 6; C26 | 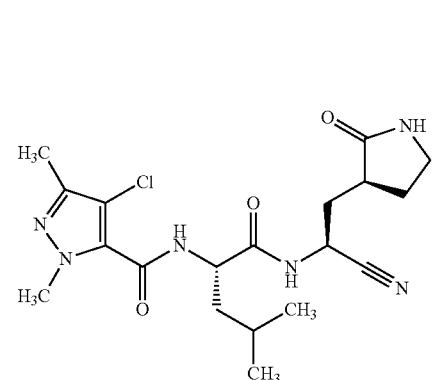 | 2.30 minutes[4]; 423.5 (chlorine isotope pattern observed) |

TABLE 1-continued

Method of synthesis, structure, and physicochemical data for Examples 24-74.

| Ex. # | Method of synthesis; Non-commercial starting materials | Structure | $^1$H NMR (600 MHz, DMSO-$d_6$) δ, Mass spectrum, observed ion m/z [M + H]$^+$ or HPLC retention time; Mass spectrum m/z [M + H]$^+$ (unless otherwise indicated) |
|---|---|---|---|
| 74 | 4[16] | (structure) | 12.20 (s, 1H), 8.99 (d, J = 7.9 Hz, 1H), 8.97 (d, J = 7.4 Hz, 1H), 7.70 (s, 1H), 7.24 (dd, J = 8, 8 Hz, 1H), 7.12 (d, half of AB quartet, J = 8.2 Hz, 1H), 6.69 (d, J = 7.8 Hz, 1H), 5.01-4.93 (m, 1H), 4.47-4.41 (m, 1H), 3.89 (s, 3H), 3.18-3.08 (m, 2H), 2.57 (s, 3H), 2.40-2.32 (m, 1H), 2.19-2.09 (m, 2H), 1.81 (ddd, J = 13.5, 9.3, 6.8 Hz, 1H), 1.7-1.63 (m, 2H), 1.59 (dd, J = 7.5, 6.8 Hz, 2H), 0.95 (d, J = 6.5 Hz, 3H), 0.91 (d, J = 6.5 Hz, 3H); high-resolution MS m/z 482.2391 [M + H]$^+$; calculated for $C_{25}H_{32}N_5O_5$, 482.2403; retention time 8.38 minutes[10] |

1. In this case, C28 was deprotected using methanesulfonic acid, rather than hydrogen chloride.

2. Epimers Example 25 and Example 26 were separated via supercritical fluid chromatography (Column: Chiral Technologies Chiralpak IB, 21×250 mm, 5 μm; Mobile phase: 9:1 carbon dioxide/methanol; Back pressure: 120 bar; Flow rate: 75 mL/minute). The first-eluting diastereomer was designated as Example 25, and the second-eluting diastereomer as Example 26.

3. Conditions for analytical HPLC. Column: Chiral Technologies Chiralpak IB, 4.6×100 mm, 5 μm; Mobile phase: 85:15 carbon dioxide/methanol; Back pressure: 120 bar; Flow rate: 1.5 mL/minute.

4. Conditions for analytical HPLC. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute.

5. $^1$H NMR of Example 30 before final purification: $^1$H NMR (400 MHz, methanol-$d_4$) δ 7.48-7.42 (m, 2H), 7.36-7.26 (m, 3H), 4.90 (dd, J=10.5, 5.7 Hz, 1H), 4.37 (dd, J=7.7, 4.9 Hz, 1H), 3.69 (s, 1H), 3.25 (ddd, J=9.9, 8.9, 2.5 Hz, 1H), 3.18 (ddd, J=9.6, 9.0, 7.1 Hz, 1H), 2.40-2.29 (m, 1H), 2.20 (s, 6H), 2.2-2.10 (m, 1H), 2.09-1.99 (m, 1H), 1.80-1.61 (m, 2H), 1.73 (dd, J=14.5, 5.0 Hz, 1H), 1.61 (dd, J=14.4, 7.8 Hz, 1H), 0.95 (s, 9H).

6. Amide coupling with the appropriate carboxylic acid was carried out using 2,4,6-tripropyl-1,3,5,2,4,6-trioxatriphosphinane 2,4,6-trioxide trioxide.

7. Example 4 (25 μM) was incubated with human cytochrome P450 3A5 (4 nmol) in potassium phosphate buffer (100 mM, pH 7.4; 40 mL) containing magnesium chloride (3.3 mM), and NADPH (1.3 mM). The incubation was carried out for 0.75 hours in a shaking water bath maintained at 37° C. The incubation was terminated by addition of an equal volume of acetonitrile, whereupon the mixture was spun in a centrifuge at 1700×g for 5 minutes, and the supernatant was subjected to vacuum centrifugation for approximately 1.5 hours. To this mixture was added formic acid (0.5 mL), acetonitrile (0.5 mL), and water to a final volume of 50 mL, and the resulting mixture was spun in a centrifuge at 40000×g for 30 minutes. The supernatant was subjected to reversed-phase HPLC (Column: Polaris C18, 4.6×250 mm; 5 μm; Mobile phase A: water containing 0.1% formic acid; Mobile phase B: methanol; Gradient: 15% B for 5 minutes, then 15% to 35% B over 75 minutes, then 35% to 95% B over 10 minutes; Flow rate: 0.8 mL/minute). Fractions were collected every 20 seconds. The first-eluting material, impure Example 33, eluted at 54.7 minutes, and Example 34 eluted at 55.3 minutes. The impure Example 33 was repurified using reversed-phase HPLC (Column: Phenomenex Kinetex XB-C18, 2.1×100 mm, 2.6 μm; Mobile phase A: water containing 0.5% acetic acid; Mobile phase B: 9:1 acetonitrile/methanol; Gradient: 10% B for 0.5 minutes, then 10% to 35% over 26.5 minutes, then 35% to 60% B over 3 minutes; Flow rate 0.5 mL/minute); fractions were collected every 15 seconds. In this system, Example 33 had a retention time of 12.7 minutes; additional Example 34 eluted at 13.5 minutes.

8. The requisite 4-chloro-1,3-dimethyl-1H-pyrazole-5-carboxylic acid may be prepared by hydrolysis of the commercially available ethyl ester.

9. The reaction mixture was diluted with acetonitrile and 1% aqueous formic acid, to a volume of approximately 2 mL; the final solvent composition was such that mixture appeared clear, with approximately 20% to 30% acetonitrile content. The components of this mixture were separated via reversed-phase HPLC (Column: Phenomenex Luna C18, 10×250 mm, 10 μm; Mobile phase A: water containing 0.1% formic acid; Mobile phase B: acetonitrile; Gradient: 15% B for 5 minutes, then 15% to 70% B over 70 minutes, then 70% to 95% B over 15 minutes; Flow rate: 2 mL/minute); fractions were collected every 20 seconds. Examples 37, 38, 39, 40, and 41 eluted at the retention times given below.

| Example | Retention time (minutes) |
|---------|--------------------------|
| 37 | 64.9 |
| 38 | 68.4 |
| 39 | 72.1 |
| 40 | 73.5 |
| 41 | 74.2 |

10. Conditions for analytical HPLC. Column: Phenomenex Kinetex XB-C18, 2.1×100 mm, 2.6 μm; Mobile phase A: water containing 0.1% formic acid; Mobile phase B: acetonitrile; Gradient: 5% B for 0.5 minutes, then 5% to 70% B over 10.5 minutes, then 70% to 95% B over 2 minutes; Flow rate: 0.4 mL/min.

11. The regiochemistry of Example 41 was not rigorously determined; other possible structures for this example are N-[(2S)-1-({(1S)-1-cyano-2-[(3S)-2-oxopyrrolidin-3-yl]ethyl}amino)-4,4-dimethyl-1-oxopentan-2-yl]-4-methoxy-5,6-bis(trifluoromethyl)-1H-indole-2-carboxamide and N-[(2S)-1-({(1S)-1-cyano-2-[(3S)-2-oxopyrrolidin-3-yl]ethyl}amino)-4,4-dimethyl-1-oxopentan-2-yl]-4-methoxy-6,7-bis(trifluoromethyl)-1H-indole-2-carboxamide.

12. The reaction mixture was purified using the conditions described in footnote 9. Example 42 eluted at 58.1 minutes and Example 43 eluted at 59.2 minutes.

13. The reaction mixture was diluted with a mixture of acetonitrile (0.3 mL) and 1% aqueous formic acid (0.7 mL). The resulting mixture was centrifuged, and the supernatant was subjected to reversed-phase HPLC (Column: Phenomenex Luna C18, 10×250 mm, 10 μm; Mobile phase A: water containing 0.1% formic acid; Mobile phase B: acetonitrile; Gradient: 2% to 10% B over 5.0 minutes, then 10% to 95% B over 95 minutes; Flow rate: 2 mL/minute); fractions were collected every 20 seconds. Examples 46, 47, and 48 eluted at the retention times given below. Example 5 was also isolated from this reaction, in fractions 189-190.

| Example | Fraction number |
|---------|-----------------|
| 46 | 207 |
| 47 | 225-226 |
| 48 | 231-232 |

14. Conditions for analytical HPLC. Column: Phenomenex Kinetex C18, 2.1×50 mm, 1.7 μm; Mobile phase A: water containing 0.1% formic acid; Mobile phase B: acetonitrile containing 0.1% formic acid; Gradient: 5% B for 0.5 minutes, then 5% to 50% B over 6.0 minutes, then 50% to 80% B over 1.5 minutes, then 80% to 95% B over 1.0 minute; Flow rate: 0.4 mL/min.

15. Only the indicated product was observed from this reaction.

16. A stock solution of Example 4 (5.56 mg, 12.7 μmol) and trifluoroacetic acid (4 μL, 50 μL) in dimethyl sulfoxide (420 μL) was prepared. One-sixth of this solution was treated with sodium 1,1-difluoroethanesulfinate 1.3 mg, 8.5 μmol), followed by tert-butyl hydroperoxide (70% in water; 1.4 μL, 10 μmol), and heated at 50° C. overnight. The reaction mixture was diluted with acetonitrile and 1% aqueous formic acid, to a volume of approximately 2-3 mL; the final solvent composition was such that mixture appeared clear, with approximately 20% to 30% acetonitrile content. The components of this mixture were separated via reversed-phase HPLC (Column: Phenomenex Luna C18, 10×250 mm, 10 μm; Mobile phase A: water containing 0.1% formic acid; Mobile phase B: acetonitrile; Gradient: 15% B for 5 minutes, then 15% to 40% B over 70 minutes, then 40% to 95% B over 15 minutes; Flow rate: 2 mL/minute); fractions were collected every 20 seconds. Example 74 eluted at 68.6 minutes.

Examples 75 and 76

(2S,4R)-4-tert-Butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide and (2R,4S)-4-tert-Butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide [75 (DIAST-1) and 76 (DIAST-2)

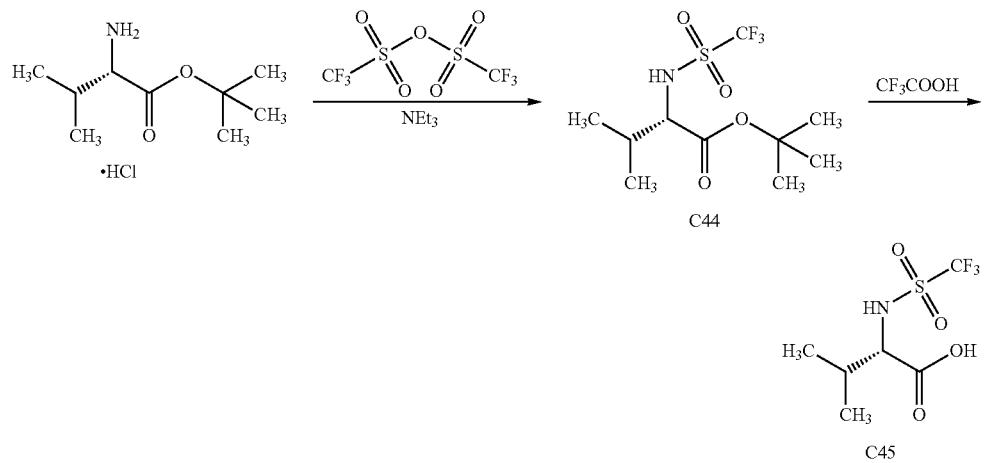

-continued
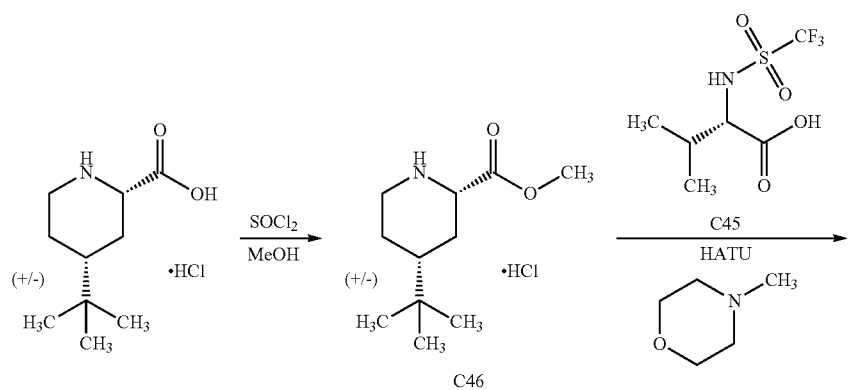
C46
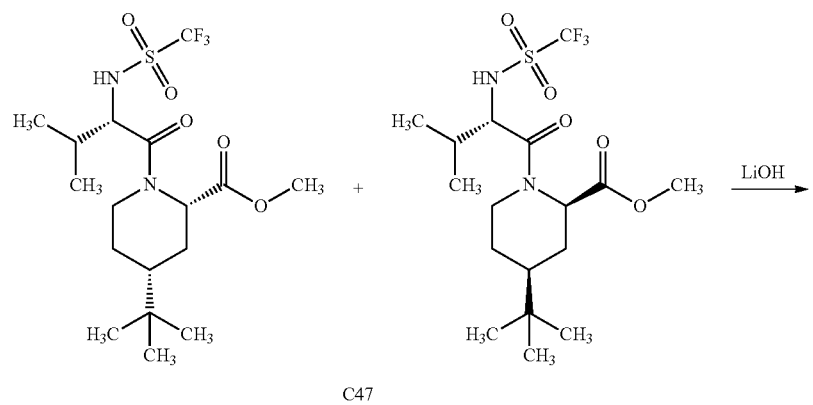
C47
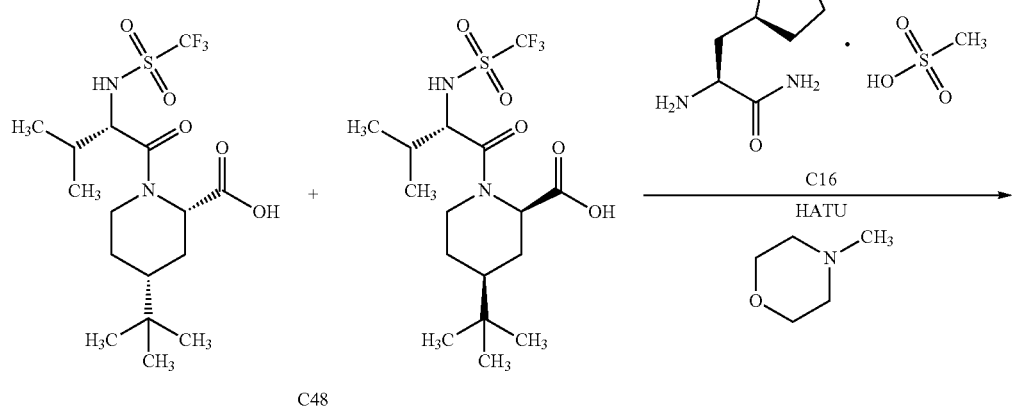
C48
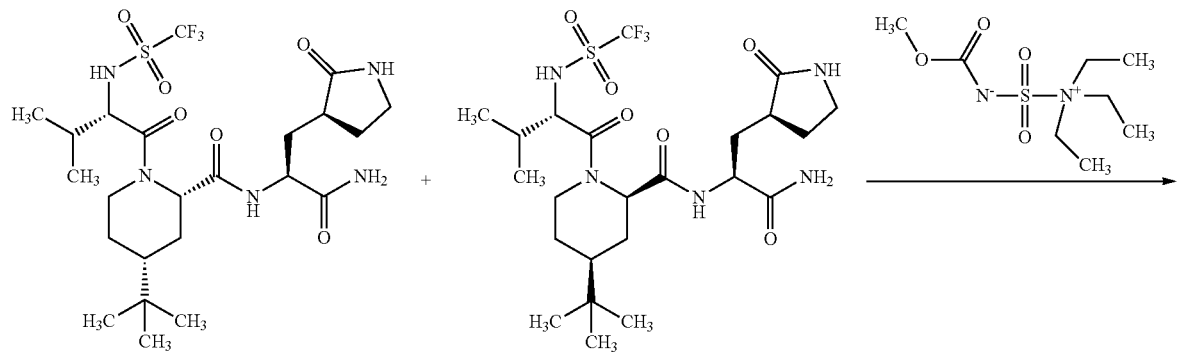
C49

-continued

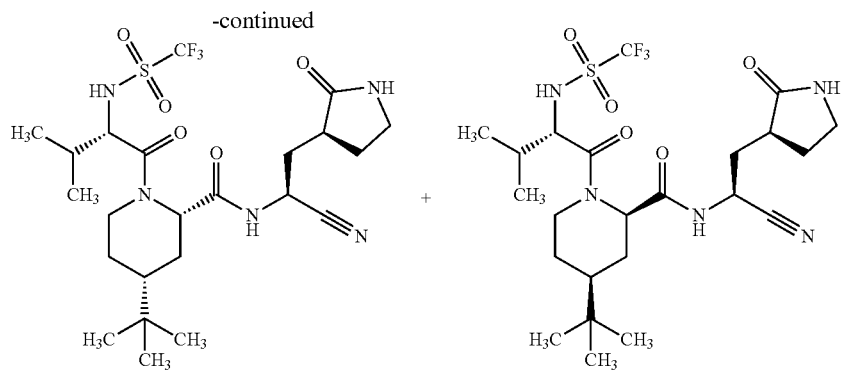

75 (DIAST-1) and 76 (DIAST-2)

Step 1. Synthesis of tert-butyl N-[(trifluoromethyl)sulfonyl]-L-valinate (C44)

A solution of trifluoromethanesulfonic anhydride (8.88 mL, 52.8 mmol) in dichloromethane (10 mL) was added to a −78° C. solution of tert-butyl L-valinate, hydrochloride salt (10.0 g, 47.7 mmol) and triethylamine (18.7 mL, 134 mmol) in dichloromethane (90 mL). The reaction mixture was stirred at −78° C. for 2 hours, whereupon it was poured into water and acidified to a pH of approximately 4 by addition of 1 M hydrochloric acid. The resulting mixture was extracted with dichloromethane, and the organic layer was washed with aqueous sodium bicarbonate solution and with saturated aqueous sodium chloride solution, dried over sodium sulfate, filtered, and concentrated in vacuo. The residue was combined with the products of two similar reactions carried out using tert-butyl L-valinate, hydrochloride salt (1.00 g, 4.77 mmol; 1.00 g, 4.77 mmol) and purified via chromatography on silica gel (Gradient: 0% to 20% ethyl acetate in petroleum ether), affording C44 as a white solid. Combined yield: 14.0 g, 45.9 mmol, 80%. $^1$H NMR (400 MHz, DMSO-$d_6$) δ 9.92 (d, J=8.8 Hz, 1H), 3.68 (dd, J=8.8, 6.2 Hz, 1H), 2.16-2.02 (m, 1H), 1.43 (s, 9H), 0.92 (d, J=6.9 Hz, 3H), 0.90 (d, J=6.9 Hz, 3H).

Step 2. Synthesis of N-[(trifluoromethyl)sulfonyl]-L-valine (C45)

To a solution of C44 (14.0 g, 45.9 mmol) in dichloromethane (85 mL) was added trifluoroacetic acid (85 mL). The reaction mixture was stirred at room temperature for 3 hours, whereupon it was concentrated in vacuo; the residue was washed with petroleum ether to provide C45 as a white solid. Yield: 10.9 g, 43.7 mmol, 95%. MS m/z 248.0 [M−H]$^−$. 1H NMR (400 MHz, DMSO-$d_6$) δ 9.86 (br d, J=8.3 Hz, 1H), 3.79-3.71 (m, 1H), 2.19-2.05 (m, 1H), 0.93 (d, J=6.8 Hz, 3H), 0.90 (d, J=6.8 Hz, 3H).

Step 3. Synthesis of methyl cis-4-tert-butylpiperidine-2-carboxylate, hydrochloride salt (C46)

To a 0° C. solution of cis-4-tert-butylpiperidine-2-carboxylic acid, hydrochloride salt (See R. T. Shuman et al., J. Org. Chem. 1990, 55, 738-741; 4.00 g, 18.0 mmol) in methanol (40 mL) was added thionyl chloride (6.44 g, 54.1 mmol). After the reaction mixture had been stirred at 25° C. for 16 hours, it was concentrated in vacuo to afford C46 as an off-white solid (4.50 g). A portion of this material was used in the following step. LCMS m/z 200.0 [M+H]$^+$. $^1$H NMR (400 MHz, DMSO-$d_6$) δ 9.46 (br s, 1H), 9.09 (br s, 1H), 4.11-3.96 (m, 1H), 3.76 (s, 3H), 3.4-3.21 (m, 1H, assumed; largely obscured by water peak), 2.93-2.77 (m, 1H), 2.07 (br d, J=10.8 Hz, 1H), 1.75 (br d, J=10.6 Hz, 1H), 1.51-1.32 (m, 3H), 0.84 (s, 9H).

Step 4. Synthesis of methyl (2S,4R)-4-tert-butyl-1-{N-[(trifluoromethyl)sulfonyl]-L-valyl}piperidine-2-carboxylate and methyl (2R,4S)-4-tert-butyl-1-{N-[(trifluoromethyl) sulfonyl]-L-valyl}piperidine-2-carboxylate (C47)

To a 25° C. mixture of C45 (300 mg, 1.20 mmol) and C46 (from the previous step; 341 mg, ≤1.36 mmol) in N,N-dimethylformamide (3 mL) was added 4-methylmorpholine (365 mg, 3.61 mmol). The resulting mixture was cooled to 0° C. and treated with O-(7-azabenzotriazol-1-yl)-N,N,N', N'-tetramethyluronium hexafluorophosphate (HATU; 549 mg, 1.44 mmol). After the reaction mixture had been sparged with nitrogen for 1 minute, it was stirred at 25° C. for 12 hours. LCMS analysis at this point indicated the presence of C47: LCMS m/z 431.1 [M+H]$^+$. The reaction mixture was partitioned between ethyl acetate (20 mL) and water (20 mL), and the aqueous layer was extracted with ethyl acetate (20 mL). The combined organic layers were washed with saturated aqueous sodium chloride solution (4×20 mL), dried over sodium sulfate, filtered, and concentrated in vacuo. Silica gel chromatography (Gradient: 0% to 20% ethyl acetate in petroleum ether) provided C47 as a yellow gum. $^1$H NMR analysis confirmed that this comprised a mixture of diastereomers. Yield: 320 mg, 0.743 mmol, 62%. $^1$H NMR (400 MHz, chloroform-d) δ 6.12-5.94 (m, 1H), [4.51 (dd, J=11.7, 6.3 Hz) and 4.32-4.18 (m), total 2H], [3.73 (s) and 3.71 (s), total 3H], [3.63-3.49 (m) and 3.48-3.39 (m), total 2H], 2.18-1.93 (m, 2H), 1.91-1.77 (m, 1H), 1.63-1.37 (m, 2H), 1.37-1.22 (m, 1H), 1.13-1.04 (m, 3H), [0.94 (d, J=6.8 Hz) and 0.91 (d, J=6.8 Hz), total 3H], 0.87 (s, 9H).

Step 5. Synthesis of (2S,4R)-4-tert-butyl-1-{N-[(trifluoromethyl)sulfonyl]-L-valyl}piperidine-2-carboxylic acid and (2R,4S)-4-tert-butyl-1-{N-[(trifluoromethyl)sulfonyl]-L-valyl}piperidine-2-carboxylic acid (C48)

A solution of C47 (314 mg, 0.729 mmol) in a mixture of methanol (2 mL) and tetrahydrofuran (2 mL) was treated with a solution of lithium hydroxide monohydrate (91.8 mg, 2.19 mmol) in water (1.4 mL), and the reaction mixture was stirred at 25° C. for 3 hours. After removal of solvent in vacuo, the residue was diluted with water (10 mL) and acidified to a pH of approximately 1 by addition of 1 M hydrochloric acid. The resulting mixture was extracted with ethyl acetate (2×20 mL), and the combined organic layers were washed with saturated aqueous sodium chloride solution (15 mL), dried over sodium sulfate, filtered, and concentrated in vacuo, affording C48 as a yellow glass. $^1$H NMR analysis confirmed that this comprised a mixture of diastereomers. Yield: 304 mg, quantitative. $^1$H NMR (400 MHz, DMSO-$d_6$) δ [9.82 (d, J=8.7 Hz) and 9.69 (br d, J=8.8 Hz), total 1H], [4.28 (dd, J=11.5, 6.4 Hz), 4.24-4.14 (m), and 4.05-3.96 (m), total 2H], [3.80-3.69 (m) and 3.6-3.2 (m, assumed, substantially obscured by water peak), total 2H], 2.06-1.90 (m, 2H), 1.80-1.65 (m, 1H), 1.41-1.17 (m, 3H), [0.96 (d, J=6.8 Hz) and 0.93 (d, J=6.5 Hz), total 3H], [0.89 (d, J=6.9 Hz) and 0.86-0.80 (m), total 12H].

Step 6. Synthesis of (2S,4R)—N-{(2S)-1-amino-1-oxo-3-[(3S)-2-oxopyrrolidin-3-yl]propan-2-yl}-4-tert-butyl-1-{N-[(trifluoromethyl)sulfonyl]-L-valyl}piperidine-2-carboxamide and (2R,4S)—N-{(2S)-1-amino-1-oxo-3-[(3S)-2-oxopyrrolidin-3-yl]propan-2-yl}-4-tert-butyl-1-{N-[(trifluoromethyl)sulfonyl]-L-valyl}piperidine-2-carboxamide (C49)

To a 25° C. mixture of C16 (120 mg, 0.449 mmol) and C48 (144 mg, 0.346 mmol) in N,N-dimethylformamide (3 mL) was added 4-methylmorpholine (100 mg, 0.989 mmol), whereupon the mixture was cooled to 0° C. and treated with O-(7-azabenzotriazol-1-yl)-N,N,N',N'-tetramethyluronium hexafluorophosphate (HATU; 151 mg, 0.397 mmol). The reaction mixture was sparged with nitrogen for 1 minute and then stirred at 25° C. for 12 hours. LCMS analysis indicated the presence of C49: LCMS m/z 570.3 [M+H]$^+$. The reaction mixture was then partitioned between ethyl acetate (20 mL) and water (20 mL), and the aqueous layer was saturated with solid sodium chloride and extracted with ethyl acetate (5×20 mL). The combined organic layers were dried over sodium sulfate, filtered, concentrated in vacuo, and subjected to silica gel chromatography (Gradient: 0% to 15% methanol in dichloromethane), providing C49 as a white solid. This material contained a mixture of diastereomers, by $^1$H NMR analysis. Yield: 190 mg, 0.334 mmol, 96%. $^1$H NMR (400 MHz, DMSO-$d_6$), characteristic peaks, integrations are approximate: δ [9.88 (d, J=8.6 Hz) and 9.82-9.68 (m), total 1H], [8.12 (d, J=8.8 Hz) and 8.09-7.98 (m), total 1H], [7.63 (s) and 7.57 (s), total 1H], [7.30 (br s) and 7.18 (br s), total 1H], [7.06 (br s) and 7.03 (br s), total 1H], [4.36 (dd, J=12.0, 6.1 Hz) and 4.32-4.08 (m), total 2H], 2.26-2.05 (m, 2H), 1.81-1.54 (m, 2H), 1.53-1.30 (m, 2H), 0.98-0.87 (m, 6H), 0.86-0.76 (m, 9H).

Step 7. Synthesis of (2S,4R)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide and (2R,4S)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide [75 (DIAST-1) and 76 (DIAST-2)]

A mixture of C49 (190.0 mg, 0.334 mmol) and methyl N-(triethylammoniosulfonyl)carbamate, inner salt (Burgess reagent; 238 mg, 1.00 mmol) in dichloromethane (10 mL) was stirred at 25° C. for 2 days, whereupon the reaction mixture was diluted with water (20 mL) and extracted with dichloromethane (2×20 mL). The combined organic layers were washed with saturated aqueous sodium chloride solution (10 mL), dried over sodium sulfate, filtered, and concentrated in vacuo. Chromatography on silica gel (Gradient: 0% to 8% methanol in dichloromethane) provided a white solid, which by LCMS analysis contained a roughly 3:1 mixture of products: LCMS m/z 552.2 [M+H]$^+$ and LCMS m/z 552.2 [M+H]$^+$. These diastereomers were separated via supercritical fluid chromatography [Column: Chiral Technologies Chiralpak IG, 30×250 mm, 10 µm; Mobile phase: 3:1 carbon dioxide/(ethanol containing 0.1% ammonium hydroxide); Flow rate: 70 mL/minute]. The first-eluting diastereomer, isolated as a white solid, was designated as 75, and the second-eluting diastereomer, also a white solid, was designated as 76 [(2S,4R)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide and (2R,4S)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide].

75—Yield: 26.2 mg, 47.5 µmol, 14%. $^1$H NMR (400 MHz, DMSO-$d_6$) δ 9.87 (d, J=8.8 Hz, 1H), 8.87 (d, J=8.4 Hz, 1H), 7.70 (s, 1H), 4.99-4.91 (m, 1H), 4.24 (dd, J=12.3, 6.0 Hz, 1H), 4.18 (dd, J=8.3, 8.3 Hz, 1H), 3.88-3.78 (m, 1H), 3.19-3.00 (m, 2H), 2.46-2.35 (m, 1H), 2.17-2.02 (m, 2H), 1.99-1.85 (m, 2H), 1.79-1.62 (m, 3H), 1.50-1.36 (m, 2H), 1.26-1.12 (m, 2H), 0.97-0.87 (m, 6H), 0.84 (s, 9H). Retention time: 1.30 minutes (Analytical conditions. Column: Chiral Technologies Chiralpak IG-3, 4.6×50 mm, 3 µm; Mobile phase A: carbon dioxide; Mobile phase B: ethanol containing 0.05% diethylamine; Gradient: 5% to 40% B over 2 minutes, then 40% B for 1.2 minutes; Flow rate: 4 mL/minute; Back pressure: 1500 psi).

76-Yield: 8.8 mg, 16 µmol, 5%. LCMS m/z 552.3 [M+H]$^+$. By $^1$H NMR analysis, this sample of 76 contained impurities. $^1$H NMR (400 MHz, DMSO-$d_6$), characteristic peaks, integrations are approximate: δ 9.76 (d, J=8.8 Hz, 1H), 8.59 (d, J=8.1 Hz, 1H), 7.72 (s, 1H), 5.02-4.90 (m, 1H), 0.94-0.86 (m, 6H), 0.82 (s, 9H). Retention time: 1.61 minutes (Analytical conditions identical to those used for 75).

Example 77
3-Methyl-N-(trifluoroacetyl)-L-valyl-(4R)—N-
{(1S)-1-cyano-2-[(3S)-2-oxopyrrolidin-3-yl]ethyl}-
4-(trifluoromethyl)-L-prolinamide (77)
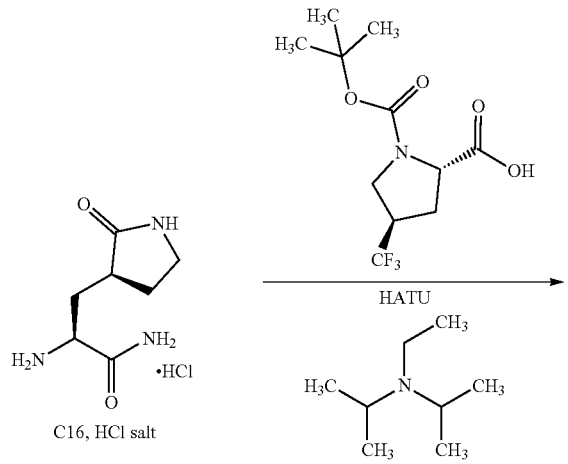
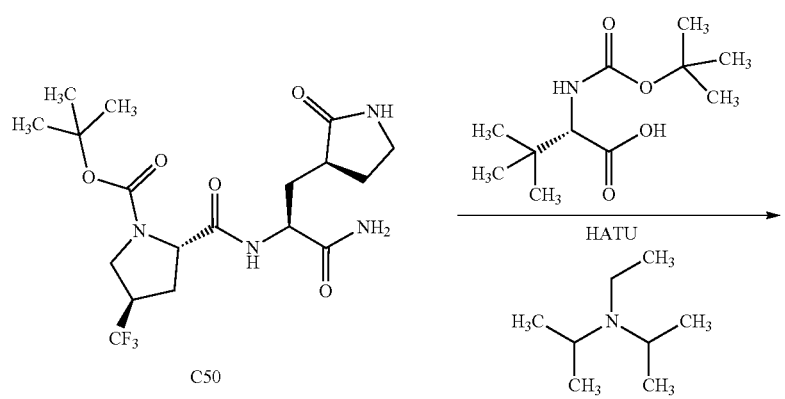
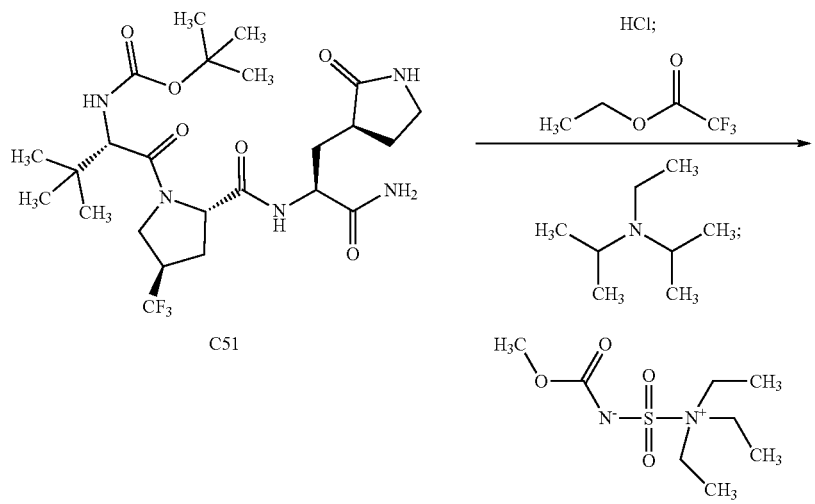

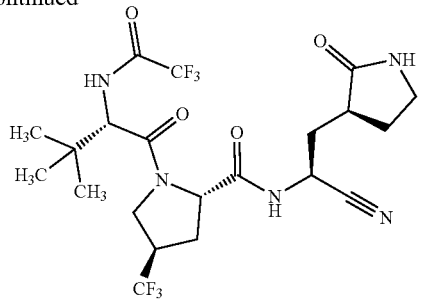

77

Step 1. Synthesis of (4R)-1-(tert-butoxycarbonyl)-4-(trifluoromethyl)-L-prolyl-3-[(3S)-2-oxopyrrolidin-3-yl]-L-alaninamide (C50)

To a −30° C. mixture of (4R)-1-(tert-butoxycarbonyl)-4-(trifluoromethyl)-L-proline (429 mg, 1.51 mmol) and C16, HCl salt (346 mg, 1.67 mmol) in N,N-dimethylformamide (7.8 mL) was added N,N-diisopropylethylamine (0.791 mL, 4.54 mmol), followed by 0-(7-azabenzotriazol-1-yl)-N,N,N′,N′-tetramethyluronium hexafluorophosphate (HATU; 633 mg, 1.66 mmol). The reaction mixture was allowed to warm to 0° C. over 1 hour, whereupon it was diluted with aqueous sodium bicarbonate solution (30 mL) and extracted with a mixture of 2-butanol and dichloromethane (9:1, 3 5×7 mL). The combined organic layers were concentrated in vacuo and purified via silica gel chromatography (Gradient: 0% to 100% methanol in dichloromethane), affording $C_{50}$ as an off-white foam. By $^1$H NMR analysis, this material existed as a mixture of rotamers, and contained impurities derived from the reagents employed; a portion of this sample was progressed to the following step. Yield: 613 mg, 1.40 mmol, 93%. LCMS m/z 459.3 [M+Na$^+$]. $^1$H NMR (400 MHz, DMSO-d$_6$), characteristic product peaks only: δ 8.33-8.18 (m, 1H), [7.65 (br s) and 7.59 (br s), total 1H], [7.39 (br s) and 7.27 br (s), total 1H], 7.05 (br s, 1H), 4.38-4.28 (m, 1H), 4.28-4.17 (m, 1H), 3.46-3.36 (m, 1H), 2.02-1.89 (m, 1H), 1.80-1.45 (m, 2H), [1.39 (s) and 1.32 (s), total 9H].

Step 2. Synthesis of N-(tert-butoxycarbonyl)-3-methyl-L-valyl-(4R)-4-(trifluoromethyl)-L-prolyl-3-[(3S)-2-oxopyrrolidin-3-yl]-L-alaninamide (C51)

A mixture of C50 (242 mg, 0.554 mmol) and a solution of hydrogen chloride in 1,4-dioxane (4 M; 2 mL, 8 mmol) was stirred at room temperature for 5 minutes, whereupon the reaction mixture was concentrated in vacuo to remove solvent and residual hydrogen chloride. The resulting deprotected material was combined with N-(tert-butoxycarbonyl)-3-methyl-L-valine (128 mg, 0.553 mmol) and O-(7-azabenzotriazol-1-yl)-N,N,N′,N′-tetramethyluronium hexafluorophosphate (HATU: 232 mg, 0.610 mmol) in N,N-dimethylformamide (2 mL), and then cooled to −30° C. N,N-Diisopropylethylamine (0.290 mL, 1.66 mmol) was added, and the reaction mixture was warmed to 0° C. over 1 hour. After addition of aqueous sodium bicarbonate solution, the resulting mixture was extracted three times with ethyl acetate; the combined organic layers were concentrated in vacuo and purified via silica gel chromatography (Gradient: 0% to 30% methanol in dichloromethane), affording C51 as a solid. Yield: 230 mg, 0.418 mmol, 75%. LCMS m/z 550.3 [M+H]$^+$.

Step 3. Synthesis of 3-methyl-N-(trifluoroacetyl)-L-valyl-(4R)—N-{(1S)-1-cyano-2-[(3S)-2-oxopyrrolidin-3-yl]ethyl}-4-(trifluoromethyl)-L-prolinamide (77)

A mixture of C51 (230 mg, 0.418 mmol) and a solution of hydrogen chloride in 1,4-dioxane (4 M; 2 mL, 8 mmol) was stirred at room temperature for 5 minutes, whereupon the reaction mixture was concentrated in vacuo to remove solvent and residual hydrogen chloride. The resulting deprotected material was combined with ethyl trifluoroacetate (595 mg, 4.19 mmol) and N,N-diisopropylethylamine (0.219 mL, 1.26 mmol) in methanol (1.0 mL). After the reaction mixture had been stirred at room temperature for 30 minutes, ethyl trifluoroacetate (60 mg, 0.422 mmol) was again added, and stirring was continued for 30 minutes. Aqueous sodium bicarbonate solution was then added, and the resulting mixture was extracted three times with ethyl acetate. The combined organic layers were dried over magnesium sulfate, filtered, concentrated in vacuo, and dissolved in dichloromethane (3 mL). To this was added ethyl N-(triethylammoniosulfonyl)carbamate, inner salt (Burgess reagent; 299 mg, 1.25 mmol), and the reaction mixture was stirred at room temperature for 2 hours, whereupon it was treated with additional methyl N-(triethylammoniosulfonyl)carbamate, inner salt (Burgess reagent; 100 mg, 0.420 mmol) and allowed to stir for a further 30 minutes. Dilute aqueous sodium carbonate solution was then added, and the mixture was extracted twice with ethyl acetate; the combined organic layers were dried over magnesium sulfate, filtered, and concentrated in vacuo. Purification via supercritical fluid chromatography (Column: Princeton Dinitrophenyl, 10×250 mm, 5 μm; Mobile phase: 9:1 carbon dioxide/methanol; Back pressure: 120 bar; Flow rate: 80 mL/minute) afforded material that was then slurried in heptane (2.0 mL) at 50° C. for 2 hours, cooled to room temperature, and collected via filtration, providing 3-methyl-N-(trifluoroacetyl)-L-valyl-(4R)—N-{(1S)-1-cyano-2-[(3S)-2-oxopyrrolidin-3-yl]ethyl}-4-(trifluoromethyl)-L-prolinamide (77) as a solid. Yield: 64 mg, 0.121 mmol, 29%. LCMS m/z 528.2 [M+H]$^+$. $^1$H NMR (400 MHz, DMSO-d$_6$) δ 9.46 (d, J=8.4 Hz, 1H), 9.05 (d, J=8.6 Hz, 1H), 7.67 (s, 1H), 4.96 (ddd, J=11.0, 8.5, 5.0 Hz, 1H), 4.56 (d, J=8.5 Hz, 1H), 4.37 (dd, J=7.5, 7.5 Hz, 1H), 3.98 (dd, component of ABX system, J=11.2, 7.5 Hz, 1H), 3.92 (dd, component of ABX system, J=11.3, 4.8 Hz, 1H), 3.46-3.35 (m, 1H), 3.19-3.10 (m, 1H), 3.09-3.00 (m, 1H), 2.5-2.38 (m, 1H, assumed; partially obscured by solvent peak), 2.38-2.28 (m, 1H), 2.21-2.04 (m, 3H), 1.78-1.65 (m, 2H), 0.99 (s, 9H).

Example 78
(1R,2S,5S)—N-{(1S)-1-Cyano-2-[(3S)-2-oxopyrrolidin-3-yl]ethyl}-6,6-dimethyl-3-[3-methyl-N-(methylcarbamoyl)-L-valyl]-3-azabicyclo[3.1.0]hexane-2-carboxamide (78)
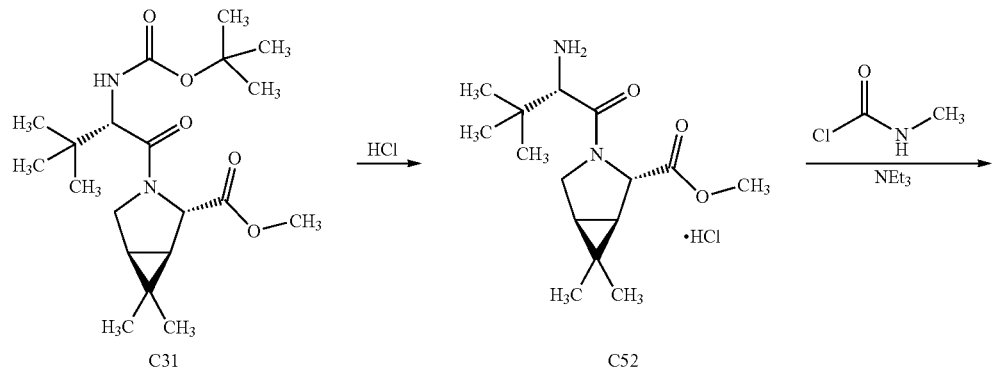
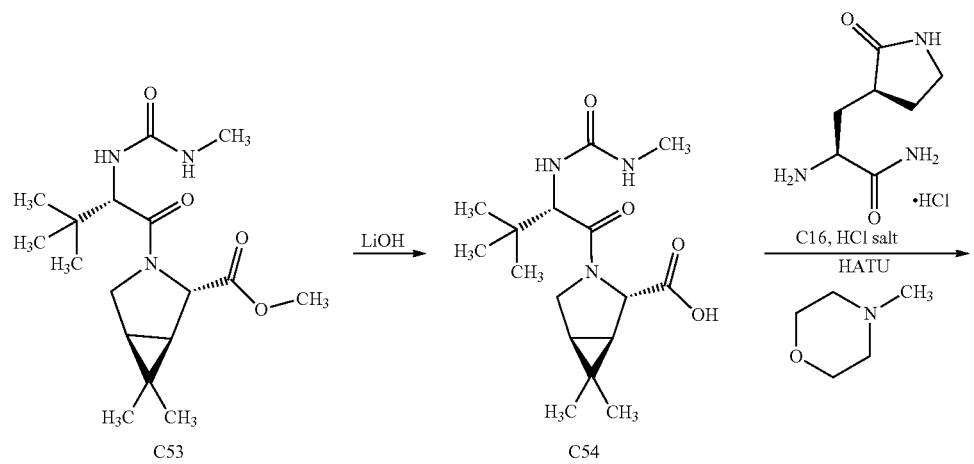
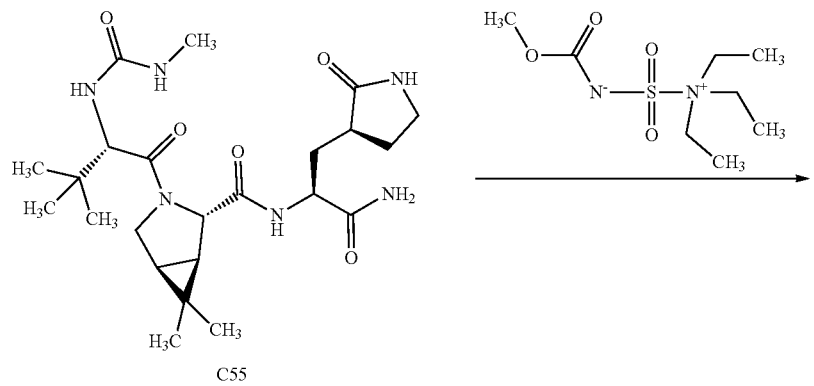

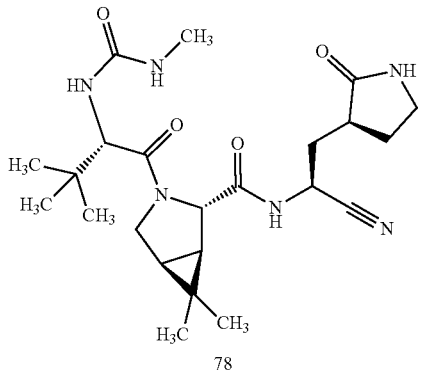

78

Step 1. Synthesis of methyl (1R,2S,5S)-6,6-dimethyl-3-(3-methyl-L-valyl)-3-azabicyclo[3.1.0]hexane-2-carboxylate, hydrochloride salt (C52)

To a 0° C. solution of C31 (1.00 g, 2.61 mmol) in dichloromethane (20 mL) was added, in a drop-wise manner, a solution of hydrogen chloride in ethyl acetate (4 M; 20 mL, 80 mmol). After the reaction mixture had been stirred at 25° C. overnight, it was concentrated in vacuo to afford C52 as a white gum. Yield: 700 mg, 2.20 mmol, 84%. LCMS m/z 283.1 [M+H]$^+$. $^1$H NMR (400 MHz, DMSO-d$_6$) δ 8.22 (br s, 3H), 4.25 (s, 1H), 3.87-3.77 (m, 2H), 3.72 (d, half of AB quartet, J=10.8 Hz, 1H), 3.67 (s, 3H), 1.59 (dd, component of ABX system, J=7.7, 5.3 Hz, 1H), 1.49 (d, half of AB quartet, J=7.7 Hz, 1H), 1.03 (s, 9H), 1.02 (s, 3H), 0.96 (s, 3H).

Step 2. Synthesis of methyl (1R,2S,5S)-6,6-dimethyl-3-[3-methyl-N-(methylcarbamoyl)-L-valyl]-3-azabicyclo[3.1.0]hexane-2-carboxylate (C53)

To a 0° C. solution of C52 (320 mg, 1.00 mmol) in dichloromethane (6 mL) were slowly added triethylamine (0.769 mL, 5.52 mmol) and methylcarbamyl chloride (188 mg, 2.01 mmol). The reaction mixture was allowed to warm to 20° C. and stir for 18 hours, whereupon it was treated in a drop-wise manner with saturated aqueous sodium carbonate solution (5 mL) and extracted with dichloromethane (2×5 mL). The combined organic layers were washed with saturated aqueous sodium chloride solution (2×20 mL), dried over sodium sulfate, filtered, and concentrated in vacuo. Silica gel chromatography (Gradient: 0% to 10% methanol in dichloromethane) provided C53 as a light-yellow gum. Yield: 190 mg, 0.560 mmol, 56%. LCMS m/z 339.9 [M+H]$^+$. $^1$H NMR (400 MHz, DMSO-d$_6$) δ 6.03 (d, J=9.4 Hz, 1H), 5.89 (br q, J=5 Hz, 1H), 4.20-4.14 (m, 2H), 3.91 (d, half of AB quartet, J=10.3 Hz, 1H), 3.79 (dd, component of ABX system, J=10.3, 5.3 Hz, 1H), 3.65 (s, 3H), 3.17 (d, J=5.3 Hz, 3H), 1.55-1.49 (m, 1H), 1.40 (d, half of AB quartet, J=7.4 Hz, 1H), 1.00 (s, 3H), 0.92 (s, 9H), 0.83 (s, 3H).

Step 3. Synthesis of (1R,2S,5S)-6,6-dimethyl-3-[3-methyl-N-(methylcarbamoyl)-L-valyl]-3-azabicyclo[3.1.0]hexane-2-carboxylic acid (C54)

To a 0° C. solution of C53 (190 mg, 0.560 mmol) in a mixture of tetrahydrofuran (2 mL), water (4 mL), and methanol (1 mL) was added lithium hydroxide monohydrate (82.0 mg, 1.95 mmol). After the reaction mixture had been stirred at 20° C. for 2 hours, it was diluted with ethyl acetate (10 mL); the aqueous layer was then cooled to 0° C. to 5° C. and acidified to pH 2 to 3 by addition of 1 M hydrochloric acid. The aqueous mixture was extracted with ethyl acetate (3×15 mL), and these combined ethyl acetate layers were dried over sodium sulfate, filtered, and concentrated in vacuo to provide C54 as a white solid. Yield: 120 mg, 0.369 mmol, 66%. LCMS m/z 348.3 [M+Na$^+$]. $^1$H NMR (400 MHz, DMSO-d$_6$), characteristic peaks: δ 6.04 (d, J=9.6 Hz, 1H), 5.89 (d, J=4.7 Hz, 1H), 4.17 (d, J=9.6 Hz, 1H), 4.09 (s, 1H), 3.87 (d, half of AB quartet, J=10.4 Hz, 1H), 3.77 (dd, component of ABX system, J=10.3, 5.4 Hz, 1H), 1.49 (dd, component of ABX system, J=7.6, 5.1 Hz, 1H), 1.38 (d, half of AB quartet, J=7.5 Hz, 1H), 1.00 (s, 3H), 0.92 (s, 9H), 0.82 (s, 3H).

Step 4. Synthesis of (1R,2S,5S)—N-{(2S)-1-amino-1-oxo-3-[(3S)-2-oxopyrrolidin-3-yl]propan-2-yl}-6,6-dimethyl-3-[3-methyl-N-(methylcarbamoyl)-L-valyl]-3-azabicyclo[3.1.0]hexane-2-carboxamide (C55)

To a 0° C. to 5° C. solution of C54 (120 mg, 0.369 mmol) and C16, HCl salt (75%, 107 mg, 0.387 mmol) in N,N-dimethylformamide (3.0 mL) were added O-(7-azabenzotriazol-1-yl)-N,N,N',N'-tetramethyluronium hexafluorophosphate (HATU; 154 mg, 0.405 mmol) and 4-methylmorpholine (0.144 mL, 1.31 mmol). After the reaction mixture had been allowed to warm from 0° C. to 20° C. over 1.5 hours, it was allowed to stir at 20° C. for 18 hours, whereupon it was diluted with water and treated with solid sodium sulfate to saturation. The resulting mixture was extracted with a mixture of 2-propanol and chloroform (1:4, 3×20 mL), and the combined organic layers were dried over sodium sulfate, filtered, and concentrated in vacuo. Silica gel chromatography (Gradient: 0% to 20% methanol in dichloromethane) provided C55 (240 mg) as a colorless glass. A portion of this material was used in the following step. LCMS m/z 479.2 [M+H]$^+$. By $^1$H NMR analysis, this material was contaminated with a byproduct derived from the HATU reagent. $^1$H NMR (400 MHz, DMSO-d$_6$), characteristic product peaks only: δ 8.21 (d, J=8.7 Hz, 1H), 7.53 (br s, 1H), 7.29 (br s, 1H), 7.03 (br s, 1H), 6.02 (d, J=9.6 Hz, 1H), 5.86 (q, J=4.6 Hz, 1H), 4.31-4.23 (m, 1H), 4.21 (s, 1H), 4.15 (d, J=9.6 Hz, 1H), 2.18-2.08 (m, 1H), 1.98-1.88 (m, 1H), 1.68-1.55 (m, 1H), 1.54-1.42 (m, 2H), 1.34 (d, half of AB quartet, J=7.6 Hz, 1H), 1.01 (s, 3H), 0.90 (s, 9H), 0.84 (s, 3H).

Step 5. Synthesis of (1R,2S,5S)—N-{(1S)-1-cyano-2-[(3S)-2-oxopyrrolidin-3-yl]ethyl}-6,6-dimethyl-3-[3-methyl-N-(methylcarbamoyl)-L-valyl]-3-azabicyclo[3.1.0]hexane-2-carboxamide (78)

To a solution of C55 (from the previous step; 190 mg, 50.292 mmol) in acetonitrile (12 mL) was added methyl N-(triethylammoniosulfonyl)carbamate, inner salt (Burgess reagent; 303 mg, 1.26 mmol). The reaction mixture was stirred at 20° C. for 22 hours, whereupon it was combined with a similar reaction carried out using C55 (from the previous step; 50 mg, 577 µmol). The resulting solution was concentrated in vacuo, diluted with water (10 mL), and extracted with ethyl acetate (3×10 mL). The combined organic layers were dried over sodium sulfate, filtered, and concentrated in vacuo; purification via reversed-phase HPLC (Column: Boston Prime C18, 30×150 mm, 5 µm; Mobile phase A: 0.225% formic acid in water; Mobile phase B: acetonitrile; Gradient: 23% to 46% B; Flow rate: 25 mL/minute) afforded (1R,2S,5S)—N-{(1S)-1-cyano-2-[(3S)-2-oxopyrrolidin-3-yl]ethyl}-6,6-dimethyl-3-[3-methyl-N-(methylcarbamoyl)-L-valyl]-3-azabicyclo[3.1.0]hexane-2-carboxamide (78) as a white solid. Combined yield: 25 mg, 54 µmol, 15% over 2 steps. LCMS m/z 461.2 [M+H]$^+$. $^1$H NMR (400 MHz, DMSO-$d_6$), characteristic peaks: δ 8.96 (d, J=8.6 Hz, 1H), 7.65 (s, 1H), 6.02 (d, J=9.5 Hz, 1H), 5.85 (q, J=4.5 Hz, 1H), 4.95 (ddd, J=10.8, 8.4, 5.1 Hz, 1H), 4.13 (d, J=9.6 Hz, 1H), 4.11 (s, 1H), 3.88-3.79 (m, 2H), 3.18-3.09 (m, 1H), 3.07-2.98 (m, 1H), 2.48-2.37 (m, 1H), 2.20-2.02 (m, 2H), 1.77-1.62 (m, 2H), 1.56-1.50 (m, 1H), 1.27 (d, half of AB quartet, J=7.6 Hz, 1H), 1.02 (s, 3H), 0.89 (s, 9H), 0.85 (s, 3H). $^1$H NMR (400 MHz, chloroform-d), characteristic peaks: δ 8.12 (d, J=7.6 Hz, 1H), 5.78 (br s, 1H), 5.04 (br d, J=9.4 Hz, 1H), 4.99-4.90 (m, 1H), 4.57-4.49 (m, 1H), 4.39 (d, J=9.7 Hz, 1H), 4.25 (s, 1H), 4.01 (d, half of AB quartet, J=10.2 Hz, 1H), 3.93 (br dd, component of ABX system, J=10.6, 4.9 Hz, 1H), 3.43-3.25 (m, 2H), 2.71 (d, J=4.8 Hz, 3H), 2.61-2.50 (m, 1H), 2.45-2.30 (m, 2H), 2.03-1.93 (m, 1H), 1.91-1.78 (m, 1H), 1.05 (s, 3H), 0.98 (s, 9H), 0.91 (s, 3H).

Example 79

Methyl {(2S)-1-[(1R,2S,5S)-2-({(1S)-1-cyano-2-[(3S)-2-oxopyrrolidin-3-yl]ethyl}carbamoyl)-6,6-dimethyl-3-azabicyclo[3.1.0]hexan-3-yl]-3,3-dimethyl-1-oxobutan-2-yl}carbamate (79)

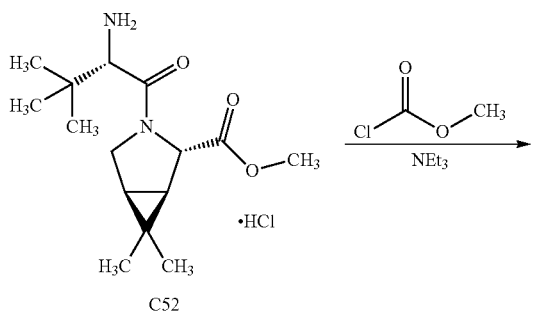

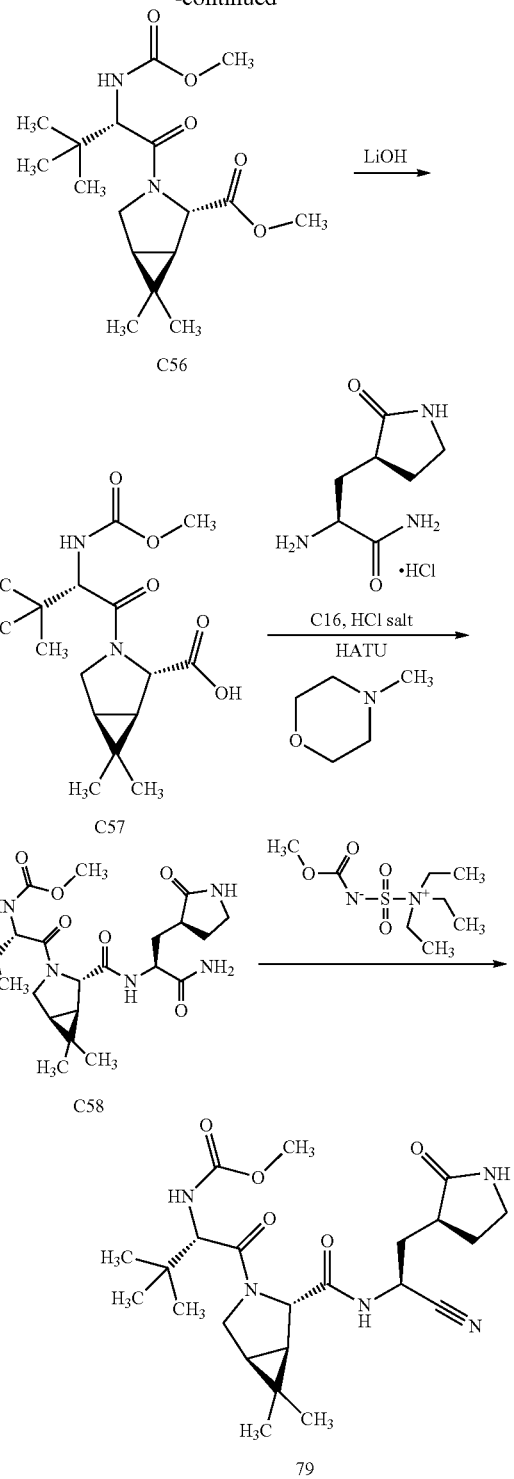

Step 1. Synthesis of methyl (1R,2S,5S)-3-[N-(methoxycarbonyl)-3-methyl-L-valyl]-6,6-dimethyl-3-azabicyclo[3.1.0]hexane-2-carboxylate (C56)

To a 0° C. solution of C52 (370 mg, 1.16 mmol) in dichloromethane (6 mL) were slowly added triethylamine (0.647 mL, 4.64 mmol) and methyl chloroformate (335 mg, 3.55 mmol). After the reaction mixture had been stirred at 20° C. for 16 hours, it was diluted in a drop-wise manner with saturated aqueous sodium carbonate solution (5 mL) and extracted with dichloromethane (2×20 mL). The combined organic layers were washed with saturated aqueous sodium chloride solution (2×20 mL), dried over sodium sulfate, filtered, and concentrated in vacuo; chromatography on silica gel (Gradient: 0% to 100% ethyl acetate in petroleum ether) provided C56 as a white gum. Yield: 115 mg, 0.338 mmol, 29%. LCMS m/z 341.1 [M+H]$^+$. $^1$H NMR (400 MHz, chloroform-d) δ 5.29 (br d, J=9.6 Hz, 1H), 4.46 (s, 1H), 4.23 (d, J=9.9 Hz, 1H), 3.94-3.86 (m, 2H), 3.74 (s, 3H), 3.63 (br s, 3H), 1.49-1.41 (m, 2H), 1.04 (s, 3H), 1.03 (s, 9H), 0.91 (s, 3H).

Step 2. Synthesis of (1R,2S,5S)-3-[N-(methoxycarbonyl)-3-methyl-L-valyl]-6,6-dimethyl-3-azabicyclo [3.1.0]hexane-2-carboxylic acid (C57)

To a solution of C56 (115 mg, 0.338 mmol) in a mixture of methanol (2.0 mL), tetrahydrofuran (2.0 mL), and water (2 mL) was added lithium hydroxide monohydrate (28.4 mg, 0.677 mmol). The reaction mixture was stirred at room temperature (22° C. to 25° C.) for 16 hours, then concentrated in vacuo. The aqueous residue was partitioned between water (5 mL) and ethyl acetate (20 mL), whereupon the organic layer was discarded and the aqueous layer was adjusted to a pH of 1 to 2 by addition of concentrated hydrochloric acid. The resulting mixture was extracted three times with ethyl acetate; the combined organic layers were dried over sodium sulfate, filtered, and concentrated in vacuo to provide C57 as a colorless gum. Yield: 100 mg, 0.306 mmol, 91%. LCMS m/z 327.2 [M+H]$^+$. $^1$H NMR (400 MHz, chloroform-d) δ 5.42 (d, J=9.9 Hz, 1H), 4.46 (s, 1H), 4.26 (d, J=10.0 Hz, 1H), 3.96 (d, half of AB quartet, J=10.5 Hz, 1H), 3.87 (dd, component of ABX system, J=10.3, 5.4 Hz, 1H), 3.64 (s, 3H), 1.68 (d, half of AB quartet, J=7.7 Hz, 1H), 1.50 (dd, component of ABX system, J=7.6, 5.3 Hz, 1H), 1.06 (s, 3H), 1.01 (s, 9H), 0.91 (s, 3H).

Step 3. Synthesis of methyl {(2S)-1-[(1R,2S,5S)-2-({(2S)-1-amino-1-oxo-3-[(3S)-2-oxopyrrolidin-3-yl] propan-2-yl}carbamoyl)-6,6-dimethyl-3-azabicyclo [3.1.0]hexan-3-yl]-3,3-dimethyl-1-oxobutan-2-yl}carbamate (C58)

To a 0° C. solution of C57 (100 mg, 0.306 mmol) and C16, HCl salt (75%, 84.8 mg, 0.306 mmol) in N,N-dimethylformamide (3 mL) was added O-(7-azabenzotriazol-1-yl)-N,N,N',N'-tetramethyluronium hexafluorophosphate (HATU; 140 mg, 0.368 mmol), followed by drop-wise addition of a solution of 4-methylmorpholine (93 mg, 0.919 mmol) in N,N-dimethylformamide (1 mL). The reaction mixture was then warmed to room temperature (25° C.) and stirred for 16 hours, whereupon water (10 mL) was added. After solid sodium sulfate had been added to saturation, the resulting mixture was extracted with a mixture of chloroform and 2-propanol (4:1, 3×10 mL). The combined organic layers were dried over sodium sulfate, filtered, concentrated in vacuo, and purified using silica gel chromatography (Gradient: 0% to 30% methanol in dichloromethane), affording C58 as a white solid. Yield: 93 mg, 0.19 mmol, 62%. LCMS m/z 480.0 [M+H]$^+$. $^1$H NMR (400 MHz, chloroform-d) δ 8.30 (br s, 1H), 7.18 (br s, 1H), 5.98 (br s, 1H), 5.64 (br s, 1H), 5.58-5.42 (m, 1H), 4.49-4.37 (m, 1H), 4.29 (d, J=10.0 Hz, 1H), 4.23 (s, 1H), 4.11 (dd, component of ABX system, J=10.3, 5.5 Hz, 1H), 3.93 (d, half of AB quartet, J=10.3 Hz, 1H), 3.64 (s, 3H), 3.43-3.29 (m, 2H), 2.55-2.33 (m, 2H), 2.15-1.81 (m, 3H), 1.54-1.47 (m, 1H), 1.45 (d, half of AB quartet, J=7.7 Hz, 1H), 1.03 (s, 3H), 1.01 (s, 9H), 0.88 (s, 3H).

Step 4. Synthesis of methyl {(2S)-1-[(1R,2S,5S)-2-({(1S)-1-cyano-2-[(3S)-2-oxopyrrolidin-3-yl] ethyl}carbamoyl)-6,6-dimethyl-3-azabicyclo[3.1.0] hexan-3-yl]-3,3-dimethyl-1-oxobutan-2-yl}carbamate (79)

To a suspension of C58 (93 mg, 0.19 mmol) in dichloromethane (5 mL) was added methyl N-(triethylammoniosulfonyl)carbamate, inner salt (Burgess reagent; 139 mg, 0.583 mmol), and the reaction mixture was stirred at 25° C. for 2 hours. It was then diluted with water (10 mL) and extracted with dichloromethane (3×10 mL); the combined organic layers were washed with saturated aqueous sodium chloride solution (2×10 mL), dried over sodium sulfate, filtered, and concentrated in vacuo. Silica gel chromatography (Gradient: 0% to 100% ethyl acetate in petroleum ether, followed by a gradient of 0% to 20% methanol in dichloromethane) afforded methyl {(2S)-1-[(1R,2S,5S)-2-({(1S)-1-cyano-2-[(3S)-2-oxopyrrolidin-3-yl]ethyl}carbamoyl)-6,6-dimethyl-3-azabicyclo[3.1.0]hexan-3-yl]-3,3-dimethyl-1-oxobutan-2-yl}carbamate (79) as a white solid. Yield: 7.0 mg, 15 μmol, 8%. LCMS m/z 462.2 [M+H]$^+$. $^1$H NMR (400 MHz, chloroform-d) δ 8.13 (br d, J=7.0 Hz, 1H), 5.68 (br s, 1H), 5.34 (br d, J=9.9 Hz, 1H), 4.95-4.85 (m, 1H), 4.26 (s, 1H), 4.23 (d, J=10.0 Hz, 1H), 3.94 (dd, component of ABX system, J=10.1, 4.5 Hz, 1H), 3.88 (d, half of AB quartet, J=10.3 Hz, 1H), 3.63 (s, 3H), 3.45-3.29 (m, 2H), 2.62-2.50 (m, 1H), 2.46-2.28 (m, 2H), 2.02-1.93 (m, 1H), 1.92-1.79 (m, 1H), 1.6-1.49 (m, 2H, assumed; partially obscured by water peak), 1.06 (s, 3H), 0.98 (s, 9H), 0.90 (s, 3H).

Example 80

N-(Trifluoroacetyl)-L-valyl-(4R)—N-{(1S)-1-cyano-2-[(3S)-2-oxopyrrolidin-3-yl]ethyl}-4-(trifluoromethyl)-L-prolinamide (80)

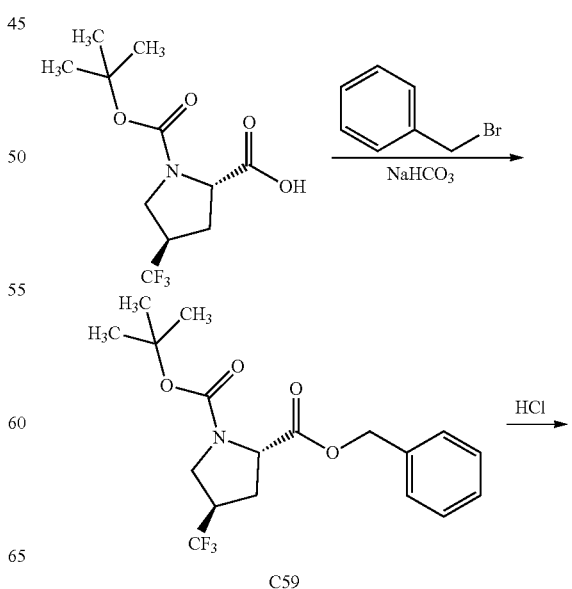

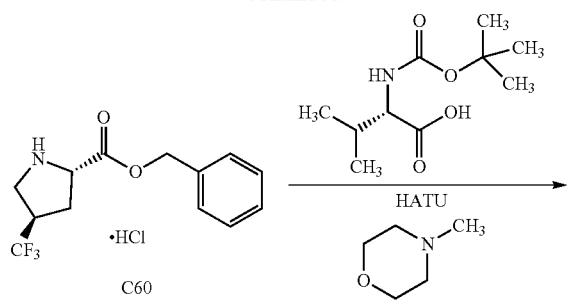

C60

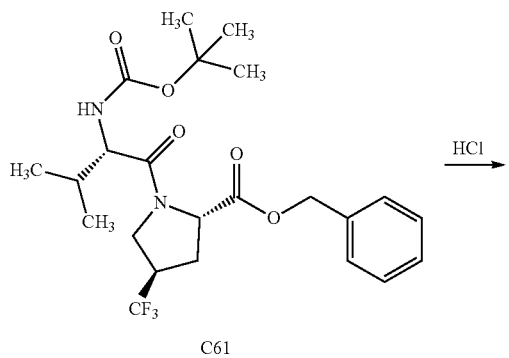

C61

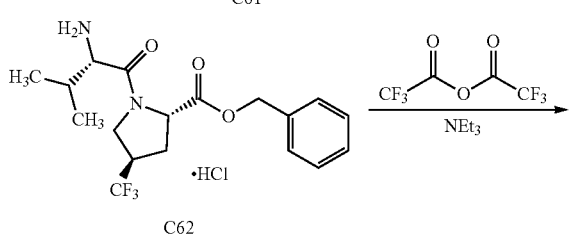

C62

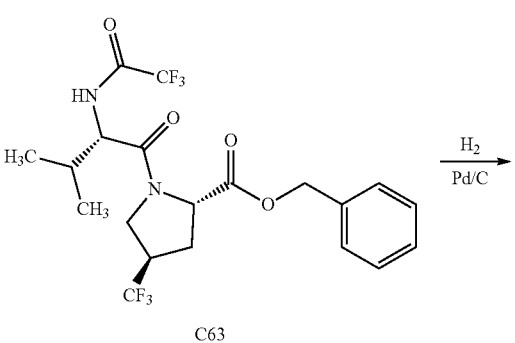

C63

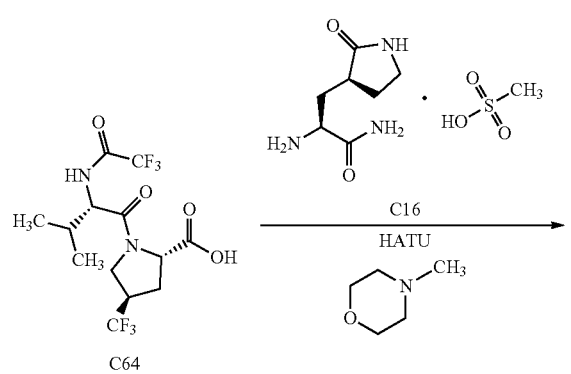

C64

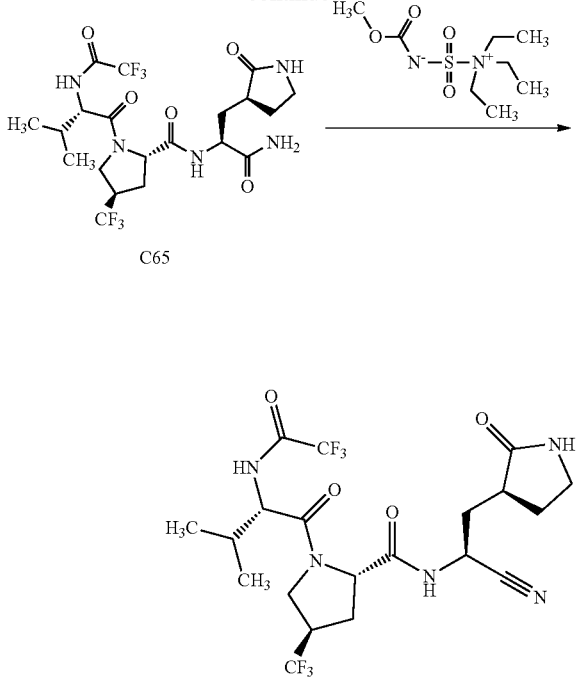

Step 1. Synthesis of 2-benzyl 1-tert-butyl (2S,4R)-4-(trifluoromethyl)pyrrolidine-1,2-dicarboxylate (C59)

A mixture of (4R)-1-(tert-butoxycarbonyl)-4-(trifluoromethyl)-L-proline (400 mg, 1.41 mmol), benzyl bromide (0.335 mL, 2.82 mmol), and sodium bicarbonate (593 mg, 7.06 mmol) in N,N-dimethylformamide (8 mL) was stirred for 15 hours at 25° C. After the reaction mixture had been diluted with water (30 mL) and extracted with ethyl acetate (3×30 mL), the combined organic layers were washed with saturated aqueous sodium chloride solution and with 5% aqueous lithium chloride solution, dried over sodium sulfate, filtered, and concentrated in vacuo. Silica gel chromatography (Gradient: 0% to 30% ethyl acetate in petroleum ether) provided C59 as a colorless oil. By $^1$H NMR analysis, this material existed as a mixture of rotamers. Yield: 355 mg, 0.951 mmol, 67%. $^1$H NMR (400 MHz, chloroform-d) δ 7.44-7.28 (m, 5H), 5.29-5.07 (m, 2H), [4.54 (br d, J=8.6 Hz) and 4.40 (br dd, J=8.5, 2 Hz), total 1H], 3.87-3.70 (m, 1H), [3.58 (dd, J=11.2, 7.4 Hz) and 3.49 (dd, J=11.0, 7.9 Hz), total 1H], 3.13-2.95 (m, 1H), 2.47-2.27 (m, 1H), 2.25-2.11 (m, 1H), [1.46 (s) and 1.33 (s), total 9H].

Step 2. Synthesis of benzyl (4R)-4-(trifluoromethyl)-L-prolinate, hydrochloride salt (C60)

To a 0° C. solution of C59 (200 mg, 0.536 mmol) in ethyl acetate (3 mL) was added a solution of hydrogen chloride in ethyl acetate (4 M; 6 mL, 24 mmol). After the reaction mixture had been stirred at room temperature (28° C.) for 3 hours, it was concentrated in vacuo to afford C60 as a white solid; this material was taken directly to the following step. LCMS m/z 274.0 [M+H]$^+$.

Step 3. Synthesis of benzyl N-(tert-butoxycarbonyl)-L-valyl-(4R)-4-(trifluoromethyl)-L-prolinate (C61)

O-(7-Azabenzotriazol-1-yl)-N,N,N',N'-tetramethyluronium hexafluorophosphate (HATU; 277 mg, 0.728 mmol) and 4-methylmorpholine (184 mg, 1.82 mmol) were added to a 0° C. mixture of C60 (from the previous step; 50.536 mmol) and N-(tert-butoxycarbonyl)-L-valine (158 mg, 0.727 mmol) in N,N-dimethylformamide (3 mL). The reaction mixture was stirred at 0° C. for 1 hour, whereupon it was poured into ice water (15 mL) and extracted with ethyl acetate (2×15 mL). The combined organic layers were washed sequentially with 1 M hydrochloric acid, saturated aqueous sodium bicarbonate solution, and saturated aqueous sodium chloride solution, dried over sodium sulfate, filtered, and concentrated in vacuo. Purification via silica gel chromatography (Gradient: 0% to 40% ethyl acetate in petroleum ether) provided C61 as a colorless gum. Yield: 230 mg, 0.487 mmol, 91% over 2 steps. LCMS m/z 495.0 [M+Na$^+$]. $^1$H NMR (400 MHz, chloroform-d), characteristic peaks: δ 7.40-7.30 (m, 5H), 5.17 (AB quartet, $J_{AB}$=12.3 Hz, $\Delta v_{AB}$=12.6 Hz, 2H), 4.21 (dd, J=9.3, 6.8 Hz, 1H), 4.00-3.86 (m, 2H), 3.18-3.04 (m, 1H), 2.36 (ddd, component of ABXY system, J=13.5, 9, 9 Hz, 1H), 2.20 (ddd, component of ABXY system, J=13.4, 7.4, 3.5 Hz, 1H), 2.05-1.94 (m, 1H), 1.42 (s, 9H), 0.98 (d, J=6.7 Hz, 3H), 0.91 (d, J=6.8 Hz, 3H).

Step 4. Synthesis of benzyl L-valyl-(4R)-4-(trifluoromethyl)-L-prolinate, hydrochloride salt (C62)

To a 0° C. solution of C61 (230 mg, 0.487 mmol) in ethyl acetate (2 mL) was added a solution of hydrogen chloride in ethyl acetate (4 M; 4 mL, 16 mmol). The reaction mixture was stirred at room temperature (28° C.) for 1 hour, whereupon LCMS analysis indicated conversion to C62: LCMS m/z 373.1 [M+H]$^+$. Concentration of the reaction mixture in vacuo provided C62 as a white solid, which was taken directly to the following step.

Step 5. Synthesis of benzyl N-(trifluoroacetyl)-L-valyl-(4R)-4-(trifluoromethyl)-L-prolinate (C63)

A solution of trifluoroacetic anhydride (154 mg, 0.733 mmol) in dichloromethane (0.5 mL) was added to a 0° C. suspension of C62 (from the previous step; 50.487 mmol) in dichloromethane (3 mL). After 3 minutes, a solution of triethylamine (148 mg, 1.46 mmol) in dichloromethane (0.5 mL) was added in a drop-wise manner, and stirring was continued at 25° C. for 3 hours. After dilution with dichloromethane (5 mL), the reaction mixture was washed with saturated aqueous sodium carbonate solution (10 mL) and with saturated aqueous sodium chloride solution (15 mL), dried, filtered, and concentrated in vacuo; silica gel chromatography (Gradient: 0% to 30% ethyl acetate in petroleum ether) afforded C63 as a colorless oil. Yield: 129 mg, 0.275 mmol, 56% over 2 steps. LCMS m/z 491.2 [M+Na$^+$].

Step 6. Synthesis of N-(trifluoroacetyl)-L-valyl-(4R)-4-(trifluoromethyl)-L-proline (C64)

To a 28° C. solution of C63 (129 mg, 0.275 mmol) in methanol (3 mL) was added palladium on carbon (10%, 29.3 mg, 27.5 μmol), whereupon the mixture was hydrogenated at 15 psi for 16 hours. Filtration provided a filter cake, which was washed with methanol (10 mL); the combined filtrates were concentrated in vacuo to afford C64 as a light-yellow solid. Yield: 80 mg, 0.21 mmol, 76%. LCMS m/z 401.0 [M+Na$^+$].

Step 7. Synthesis of N-(trifluoroacetyl)-L-valyl-(4R)-4-(trifluoromethyl)-L-prolyl-3-[(3S)-2-oxopyrrolidin-3-yl]-L-alaninamide (C65)

O-(7-Azabenzotriazol-1-yl)-N,N,N',N'-tetramethyluronium hexafluorophosphate (HATU; 88.5 mg, 0.233 mmol) and 4-methylmorpholine (64.2 mg, 0.635 mmol) were added to a 0° C. solution of C64 (80 mg, 0.21 mmol) and C16 (76.8 mg, 0.287 mmol) in N,N-dimethylformamide (3 mL). After the reaction mixture had been stirred at 0° C. for 2 hours, it was treated with water (10 mL) and aqueous citric acid solution (1 M; 10 mL, 10 mmol), then extracted with ethyl acetate (3×10 mL). The combined organic layers were washed sequentially with saturated aqueous sodium bicarbonate solution (15 mL) and saturated aqueous sodium chloride solution (15 mL), dried over sodium sulfate, filtered, and concentrated in vacuo. Purification via silica gel chromatography (Gradient: 0% to 10% methanol in dichloromethane) provided C65 as a white solid. Yield: 72 mg, 0.14 mmol, 67%. LCMS m/z 532.2 [M+H]$^+$.

Step 8. Synthesis of N-(trifluoroacetyl)-L-valyl-(4R)—N-{(1S)-1-cyano-2-[(3S)-2-oxopyrrolidin-3-yl]ethyl}-4-(trifluoromethyl)-L-prolinamide (80)

Methyl N-(triethylammoniosulfonyl)carbamate, inner salt (Burgess reagent; 96.9 mg, 0.407 mmol) was added to a mixture of C65 (72 mg, 0.14 mmol) in dichloromethane (5 mL), and the reaction mixture was stirred at room temperature overnight. After dilution with water (15 mL), the mixture was extracted with dichloromethane (3×15 mL), and the combined organic layers were washed with saturated aqueous sodium chloride solution (2×20 mL), dried over sodium sulfate, filtered, and concentrated in vacuo. Silica gel chromatography (Gradient: 0% to 10% methanol in dichloromethane) afforded N-(trifluoroacetyl)-L-valyl-(4R)—N-{(1S)-1-cyano-2-[(3S)-2-oxopyrrolidin-3-yl]ethyl}-4-(trifluoromethyl)-L-prolinamide (80) as a white solid. Yield: 30.9 mg, 60.2 μmol, 43%. LCMS m/z 536.1 [M+Na$^+$]. $^1$H NMR (400 MHz, DMSO-d$_6$), characteristic peaks: δ 9.89 (d, J=7.8 Hz, 1H), 9.06 (d, J=8.4 Hz, 1H), 7.69 (s, 1H), 4.96 (ddd, J=10.6, 8.4, 5.5 Hz, 1H), 4.38 (dd, J=7.9, 6.3 Hz, 1H), 4.28 (dd, J=9.8, 7.8 Hz, 1H), 4.07-3.94 (m, 2H), 3.20-3.00 (m, 2H), 2.5-2.41 (m, 1H, assumed; partially obscured by solvent peak), 2.38-2.28 (m, 1H), 2.19-2.02 (m, 4H), 1.78-1.61 (m, 2H), 0.92 (d, J=7 Hz, 3H), 0.90 (d, J=6.8 Hz, 3H).

Examples 81-84

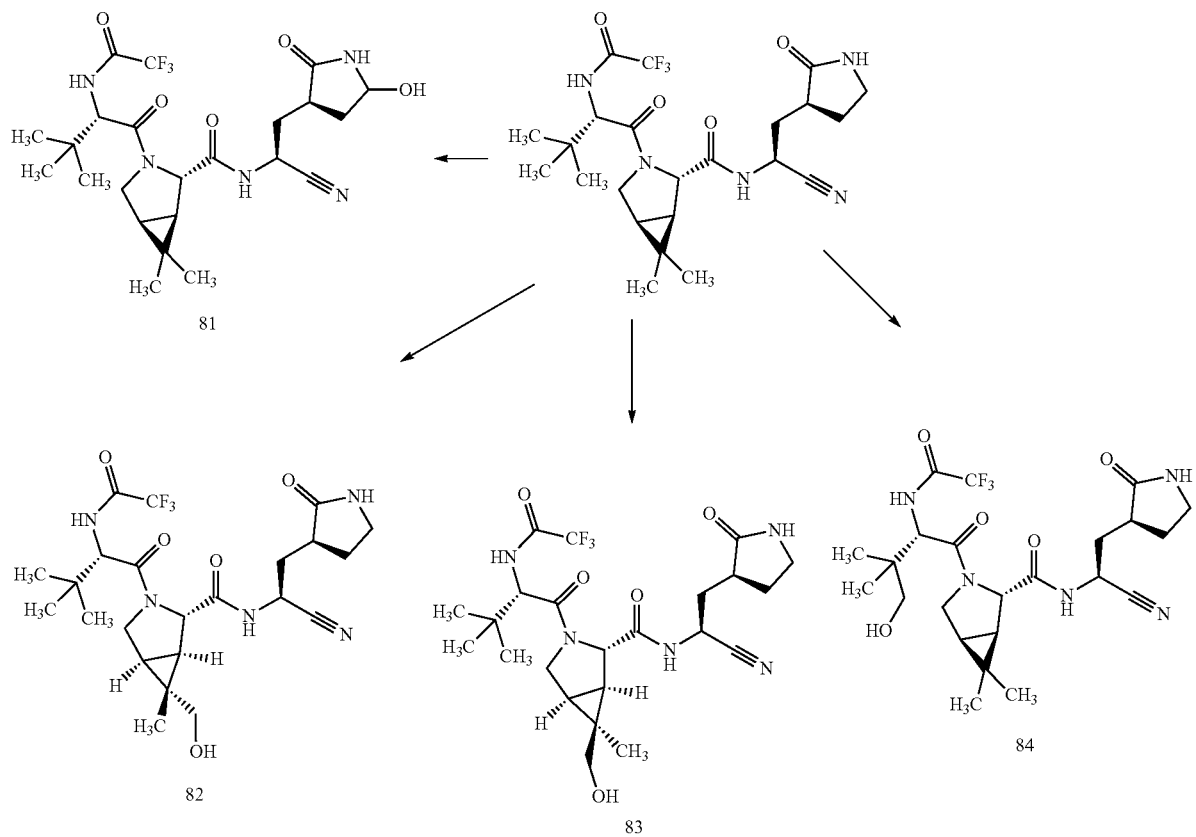

Example 81: (1R,2S,5S)—N-{(1S)-1-Cyano-2-[(3R)-5-hydroxy-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide Example 82: (1R,2S,5S,6R)—N-{(1S)-1-Cyano-2-[(3S)-2-oxopyrrolidin-3-yl]ethyl}-6-(hydroxymethyl)-6-methyl-3-[3-methyl-N-(trifluoroacetyl)-L-valyl]-3-azabicyclo[3.1.0]hexane-2-carboxamide Example 83: (1R,2S,5S,6S)—N-{(1S)-1-Cyano-2-[(3S)-2-oxopyrrolidin-3-yl]ethyl}-6-(hydroxymethyl)-6-methyl-3-[3-methyl-N-(trifluoroacetyl)-L-valyl]-3-azabicyclo[3.1.0]hexane-2-carboxamide Example 84: (1R,2S,5S)—N-{(1S)-1-Cyano-2-[(3S)-2-oxopyrrolidin-3-yl]ethyl}-3-[3-(hydroxymethyl)-N-(trifluoroacetyl)-L-valyl]-6,6-dimethyl-3-azabicyclo[3.1.0]hexane-2-carboxamide The compounds of Examples 81-84 were obtained by biotransformation pathways, both in vitro and in vivo, from (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (the compound of Example 13) as follows. In in vitro studies, (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide was incubated with mouse, rat, hamster, rabbit, monkey or human liver microsomes (see Table M1 below) or with rat, monkey or human hepatocytes (see Table M2 below). Alternatively, in in vivo studies (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide was administered to rat and monkey. Samples of rat plasma, urine and bile and monkey plasma were obtained. The resulting metabolites were then analyzed using HPLC/MS and the resulting oxidative metabolite compounds of Examples 81-84 were detected and obtained. In addition to the compounds of Examples 81-84 an additional metabolite, (1R,2S,5S)-6,6-dimethyl-3-[3-methyl-N-(trifluoroacetyl)-L-valyl]-3-azabicyclo[3.1.0]hexane-2-carboxylic acid, resulting from hydrolytic cleavage, was observed in the in vivo studies.

TABLE M1

Compounds obtained from liver microsomes

| Example | Mouse | Rat | Hamster | Rabbit | Monkey | Human |
|---------|-------|-----|---------|--------|--------|-------|
| 81 | +++ | +++ | +++ | +++ | +++ | +++ |
| 82 | + | + | + | ++ | t | + |
| 83 | + | + | + | + | t | + |
| 84 | + | t | − | t | t | + |

TABLE M2

Compounds of Examples 81-84 obtained from Hepatocytes

| Example | Mouse | Rat | Hamster |
|---|---|---|---|
| 81 | +++ | +++ | +++ |
| 82 | + | t | t |
| 83 | t | t | t |
| 84 | + | t | − |

TABLE M3

Compounds of Examples 81-84 obtained in vivo in the Rat or Monkey

| Example | Rat Plasma | Rat Urine | Rat Bile | Monkey Plasma |
|---|---|---|---|---|
| 81 | + | t | t | ++ |
| 82 | + | t | t | t |
| 83 | t | − | − | t |
| 84 | + | − | − | + |

In tables M1, M2 and M3 the following abbreviations are used: −=not detected; +=detected by mass spectrometry and minor UV peak; ++=detected by mass spectrometry and moderate UV peak; +++=detected by mass spectrometry and major UV peak; t=trace, detected by mass spectrometry only Examples 82, 83, 84, and 81

(1R,2S,5S,6R)—N-{(1S)-1-Cyano-2-[(3S)-2-oxopyrrolidin-3-yl]ethyl}-6-(hydroxymethyl)-6-methyl-3-[3-methyl-N-(trifluoroacetyl)-L-valyl]-3-azabicyclo[3.1.0]hexane-2-carboxamide (82), (1R,2S,5S,6S)—N-{(1S)-1-Cyano-2-[(3S)-2-oxopyrrolidin-3-yl]ethyl}-6-(hydroxymethyl)-6-methyl-3-[3-methyl-N-(trifluoroacetyl)-L-valyl]-3-azabicyclo[3.1.0]hexane-2-carboxamide (83), (1R,2S,5S)—N-{(1S)-1-Cyano-2-[(3S)-2-oxopyrrolidin-3-yl]ethyl}-3-[3-(hydroxymethyl)-N-(trifluoroacetyl)-L-valyl]-6,6-dimethyl-3-azabicyclo[3.1.0]hexane-2-carboxamide (84), and (1R,2S,5S)—N-{(1S)-1-Cyano-2-[(3R)-5-hydroxy-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (81)

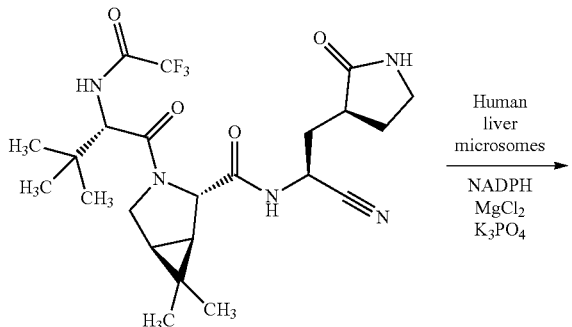

13

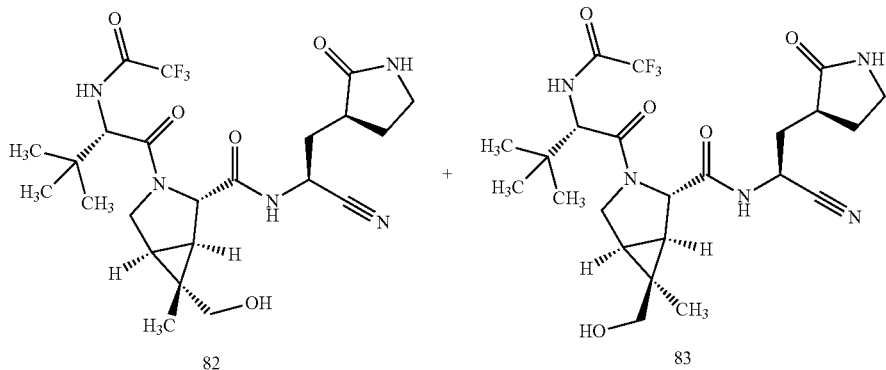

82

83

+

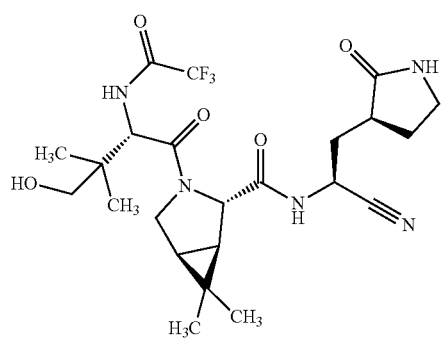

84

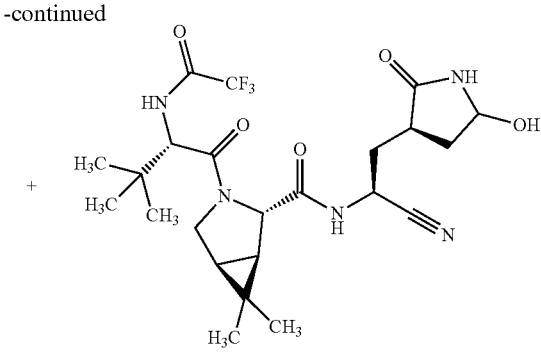

81

Example 13 (25 μM) was combined with human liver microsomes (2 mg/mL) in potassium phosphate buffer (100 mM, pH 7.4; 40 mL) containing magnesium chloride (3.3 mM) and NADPH (1.3 mM). The incubation was carried out for 55 minutes in a shaking water bath maintained at 37° C. The reaction was terminated by addition of an equal volume of acetonitrile, whereupon the mixture was spun in a centrifuge at 1800×g for 5 minutes, and the supernatant was subjected to vacuum centrifugation for approximately 1.5 hours. To the residue were added formic acid (0.5 mL), acetonitrile (0.5 mL), and water to a final volume of 50 mL, and the resulting mixture was spun in a centrifuge at 40000×g for 30 minutes. The supernatant was applied to an HPLC column (Polaris C18, 4.6×250 mm; 5 μm) at 1 mL/min using a Jasco HPLC pump. After application, the column was moved to a Waters Acquity HPLC-UV system coupled with a Thermo LTQ mass spectrometer and CTC Analytics fraction collector and subjected to reversed-phase HPLC separation (Mobile phase A: water containing 0.1% formic acid (v/v); Mobile phase B: acetonitrile; Gradient: 2% for 5 minutes, then raised to 15% B followed by 15% to 60% B over 80 minutes, then 60% to 95% B over 5 minutes; Flow rate: 0.8 mL/min). Fractions were collected every 20 seconds, affording (1R,2S,5S,6R)—N-{(1S)-1-cyano-2-[(3S)-2-oxopyrrolidin-3-yl]ethyl}-6-(hydroxymethyl)-6-methyl-3-[3-methyl-N-(trifluoroacetyl)-L-valyl]-3-azabicyclo[3.1.0]hexane-2-carboxamide (82), (1R,2S,5S,6S)—N-{(1S)-1-cyano-2-[(3S)-2-oxopyrrolidin-3-yl]ethyl}-6-(hydroxymethyl)-6-methyl-3-[3-methyl-N-(trifluoroacetyl)-L-valyl]-3-azabicyclo[3.1.0]hexane-2-carboxamide (83), (1R,2S,5S)—N-{(1S)-1-cyano-2-[(3S)-2-oxopyrrolidin-3-yl]ethyl}-3-[3-(hydroxymethyl)-N-(trifluoroacetyl)-L-valyl]-6,6-dimethyl-3-azabicyclo[3.1.0]hexane-2-carboxamide (84), and (1R,2S,5S)—N-{(1S)-1-cyano-2-[(3R)-5-hydroxy-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (81).

| Example Number | Retention time, HPLC purification (minutes) |
| --- | --- |
| 82 | 37.2 |
| 83 | 39.3 |
| 84 | 46.6 |
| 81 | 50.5 |

82—Yield: 60 μg, 0.12 μmol, 12%. High-resolution MS m/z 516.2424 [M+H]$^+$; calculated for $C_{23}H_{33}F_3N_5O_5$, 516.2434. $^1$H NMR (600 MHz, DMSO-$d_6$), characteristic peaks: δ 9.42 (br d, J=7.9 Hz, 1H), 9.03 (d, J=8.5 Hz, 1H), 7.66 (s, 1H), 5.01-4.93 (m, 1H), 4.69-4.63 (m, 1H), 4.43 (d, J=8.3 Hz, 1H), 4.15 (s, 1H), 3.94 (dd, component of ABX system, J=10.2, 5.4 Hz, 1H), 3.68 (d, half of AB quartet, J=10.4 Hz, 1H), 3.21-3.17 (m, 2H), 3.17-3.11 (m, 1H), 3.07-3.00 (m, 1H), 1.69-1.65 (m, 1H), 1.44 (d, J=7.8 Hz, 1H), 0.98 (s, 9H), 0.84 (s, 3H).

83—Yield: 30 μg, 0.058 μmol, 6%. High-resolution MS m/z 516.2425 [M+H]$^+$; calculated for $C_{23}H_{33}F_3N_5O_5$, 516.2434. $^1$H NMR (600 MHz, DMSO-$d_6$), characteristic peaks: δ 9.37 (d, J=7.0 Hz, 1H), 9.04 (d, J=8.5 Hz, 1H), 7.65 (s, 1H), 5.00-4.94 (m, 1H), 4.54-4.49 (m, 1H), 4.40 (d, J=8.1 Hz, 1H), 4.28 (s, 1H), 3.93 (dd, component of ABX system, J=10.2, 5.8 Hz, 1H), 3.74 (d, half of AB quartet, J=10.6 Hz, 1H), 3.3-3.20 (m, 1H, assumed; partially obscured by water peak), 3.17-3.11 (m, 1H), 3.07-3.00 (m, 1H), 1.75-1.63 (m, 2H), 1.38 (d, half of AB quartet, J=7.3 Hz, 1H), 1.06 (s, 3H), 0.98 (s, 9H).

84—Yield: 40 μg, 0.078 μmol, 8%. High-resolution MS m/z 516.2423 [M+H]$^+$; calculated for $C_{23}H_{33}F_3N_5O_5$, 516.2434. $^1$H NMR (600 MHz, DMSO-$d_6$), characteristic peaks: δ 9.61-9.51 (m, 1H), 9.00 (d, J=8.3 Hz, 1H), 7.68 (s, 1H), 5.02-4.92 (m, 1H), 4.51-4.43 (m, 1H), 4.16 (s, 1H), 3.92 (br dd, J=10.0, 5.6 Hz, 1H), 3.78 (d, J=10.6 Hz, 1H), 3.51 (d, J=10.1 Hz, 1H), 3.18-3.10 (m, 1H), 3.10-3.03 (m, 1H), 1.73-1.67 (m, 2H), 1.60-1.54 (m, 1H), 1.31 (d, J=7.6 Hz, 1H), 1.03 (s, 3H), 1.01 (s, 3H), 0.88 (br s, 6H).

81—Yield: 130 μg, 0.252 μmol, 25%. This material was determined to exist as an interconverting mixture of stereoisomers around the carbinolamine moiety of the pyrrolidone (see Examples 81 and 82). High-resolution MS m/z 516.2428 [M+H]$^+$; calculated for $C_{23}H_{33}F_3N_5O_5$, 516.2434. $^1$H NMR (600 MHz, DMSO-$d_6$) δ [9.40 (d, J=8.4 Hz) and 9.38 (d, J=8.2 Hz), total 1H], [8.99 (d, J=8.5 Hz) and 8.92 (d, J=7.6 Hz), total 1H], [8.37 (s) and 8.25 (s), total 1H], [5.83 (br s) and 5.70 (br s), total 1H], 5.04-4.92 (m, 2H), 4.44-4.38 (m, 1H), [4.19 (s) and 4.15 (s), total 1H], 3.91 (dd, J=10.2, 5.5 Hz, 1H), [3.69 (d, J=10 Hz) and 3.68 (d, J=10.2 Hz), total 1H], [2.65-2.57 (m), 2.43-2.30 (m), and 2.21-2.13 (m), total 2H], [2.08 (ddd, J=13.7, 8.4, 6.2 Hz), 2.00-1.90 (m), and 1.87-1.79 (m), total 2H], [1.78-1.70 (m) and 1.51-1.44 (m), total 1H], 1.60-1.53 (m), [1.32 (d, J=7.6 Hz) and 1.29 (d, J=7.6 Hz), total 1H], 1.03 (s, 3H), [0.99 (s) and 0.98 (s), total 9H], [0.85 (s) and 0.84 (s), total 3H].

Examples 81 and 85

(1R,2S,5S)—N-{(1S)-1-Cyano-2-[(3R)-5-hydroxy-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (81) and (1R,2S,5S)—N-{(1S)-1-Cyano-2-[(3R)-2,5-dioxopyrrolidin-3-yl]ethyl}-6,6-dimethyl-3-[3-methyl-N-(trifluoroacetyl)-L-valyl]-3-azabicyclo[3.1.0]hexane-2-carboxamide (85)

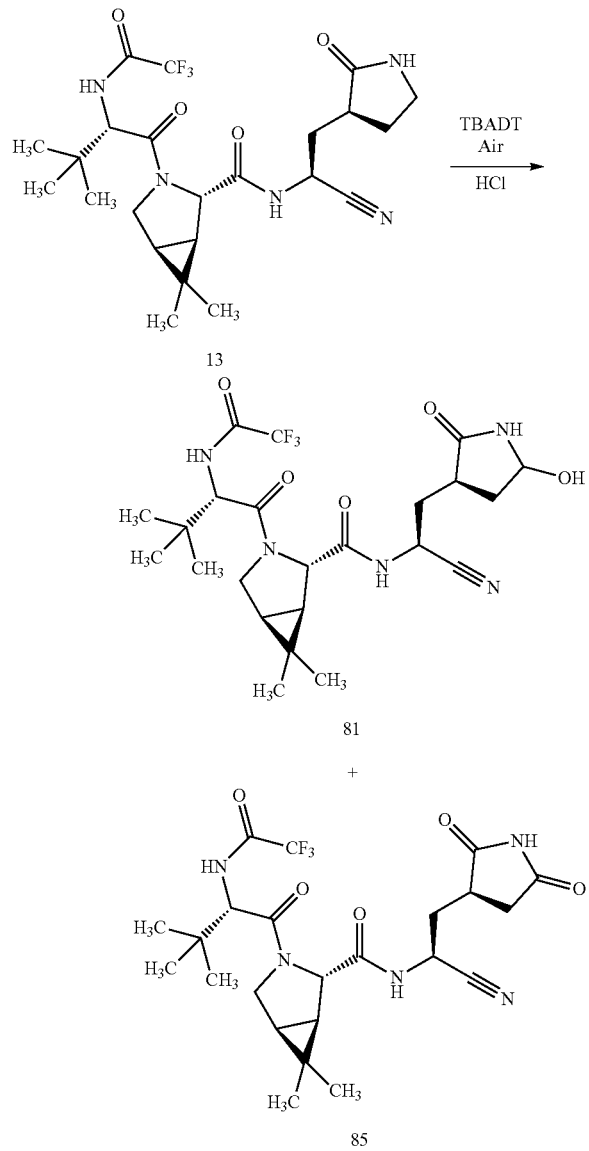

A mixture of Example 13 (1.0 mg, 2.0 μmol) and tetra-n-butylammonium decatungstate (TBADT; 0.33 mg, 0.10 μmol) was treated with acetonitrile (0.15 mL) and hydrochloric acid (1.0 M; 0.05 mL, 50 μmol). A syringe needle (18 gauge) was inserted through the Teflon cap of the vial, and the air-accessible reaction mixture was placed in an EvoluChem™ PhotoRedOx Box equipped with a fan and irradiated with black light (PAR20-18W LG 365 nm, 100-240 VAC) at 25° C. for 16 hours. To the reaction mixture was added aqueous potassium phosphate solution (1 M, pH 7.5; 0.5 mL), then water (to a volume of approximately 6 mL), followed by addition of aqueous formic acid (1%, 2 mL) and sufficient acetonitrile to maintain a solution. The resulting solution was divided in half and applied to two 5 g Biotage Isolute C18 solid phase extraction cartridges. The cartridges were washed with aqueous ammonium acetate solution (10 mM; 3 mL) and with 20% acetonitrile in 10 mM aqueous ammonium acetate solution (3 mL), then eluted with acetonitrile (3 mL). Solvents were removed using a Genevac evaporator, and the two residues were reconstituted in a mixture of acetonitrile and 1% aqueous formic acid and combined to a total of 2 mL of solution. This material was subjected to reversed-phase HPLC (Column: Phenomenex Luna C18, 10×250 mm, 10 μm; Mobile phase A: water containing 0.1% formic acid (v/v); Mobile phase B: acetonitrile; Gradient: 2% to 15% B over 5 minutes, then 15% to 60% B over 80 minutes, then 60% to 95% B over 5 minutes; Flow rate: 2 mL/min). Fractions were collected every 20 seconds; the first-eluting compound was (1R,2S,5S)—N-{(1S)-1-cyano-2-[(3R)-5-hydroxy-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (81), and the second-eluting compound was (1R,2S,5S)—N-{(1S)-1-cyano-2-[(3R)-2,5-dioxopyrrolidin-3-yl]ethyl}-6,6-dimethyl-3-[3-methyl-N-(trifluoroacetyl)-L-valyl]-3-azabicyclo[3.1.0]hexane-2-carboxamide (85).

Yield of 81: 0.122 mg, 0.237 μmol, 12%. This material was determined to exist as an interconverting mixture of stereoisomers around the carbinolamine moiety of the pyrrolidone, and eluted as a double peak on HPLC. High-resolution MS m/z 516.2413 [M+H]$^+$; calculated for $C_{23}H_{33}F_3N_5O_5$, 516.2434. $^1$H NMR (600 MHz, DMSO-$d_6$) δ 9.44-9.34 (m, 1H), [8.99 (d, J=8.5 Hz) and 8.92 (d, J=7.6 Hz), total 1H], [8.37 (s) and 8.25 (s), total 1H], [5.83 (br s) and 5.70 (br s), total 1H], 5.05-4.91 (m, 2H), 4.44-4.37 (m, 1H), [4.19 (s) and 4.15 (s), total 1H], 3.91 (dd, J=10.3, 5.5 Hz, 1H), [3.69 (d, J=10.1 Hz) and 3.68 (d, J=10.3 Hz), total 1H], [2.65-2.57 (m), 2.43-2.30 (m), and 2.17 (ddd, J=14.9, 10.7, 4.7 Hz), total 2H], [2.08 (ddd, J=14.1, 8.5, 6.2 Hz), 2.01-1.90 (m), and 1.83 (ddd, J=13.7, 10.1, 5.7 Hz), total 2H], [1.78-1.70 (m) and 1.51-1.44 (m), total 1H], 1.60-1.53 (m, 1H), [1.32 (d, J=7.6 Hz) and 1.29 (d, J=7.6 Hz), total 1H], 1.03 (s, 3H), [0.99 (s) and 0.98 (s), total 9H], [0.85 (s) and 0.84 (s), total 3H]. Retention time: 7.7 minutes (Analytical conditions. Column: Phenomenex Kinetex XB-C18, 2.1×100 mm, 2.6 μm; Mobile phase A: water containing 0.1% formic acid (v/v); Mobile phase B: acetonitrile; Gradient: 5% B for 0.5 minutes, then 5% to 70% B over 10.5 minutes, then 70% to 95% B over 2 minutes; Flow rate: 0.4 mL/minute).

Yield of 85: 0.104 mg, 0.203 μmol, 10%. High-resolution MS m/z 514.2259 [M+H]$^+$; calculated for $C_{23}H_{31}F_3N_5O_5$, 514.2277. $^1$H NMR (600 MHz, DMSO-$d_6$) δ 11.17 (br s, 1H), 9.40 (br s, 1H), 9.08 (d, J=8.9 Hz, 1H), 5.06-4.98 (m, 1H), 4.42-4.36 (m, 1H), 4.13 (s, 1H), 3.91 (dd, J=10.3, 5.6 Hz, 1H), 3.70 (d, half of AB quartet, J=10.4 Hz, 1H), 3.00-2.93 (m, 1H), 2.60 (dd, component of ABX system, J=18.0, 5.9 Hz, 1H), 2.46 (dd, component of ABX system, J=18.1, 9.1 Hz, 1H), 2.25-2.18 (m, 1H), 2.04-1.97 (m, 1H), 1.60-1.55 (m, 1H), 1.35 (d, half of AB quartet, J=7.6 Hz, 1H), 1.03 (s, 3H), 0.95 (s, 9H), 0.86 (s, 3H). Retention time: 8.3 minutes (Analytical conditions identical to those used for 81).

Example 86

(1R,2S,5S)—N-{(1S)-1-Cyano-2-[(3S)-2-oxopyrrolidin-3-yl]ethyl}-6,6-dimethyl-3-[5,5,5-trifluoro-2-(2,2,2-trifluoroacetamido)pentanoyl]-3-azabicyclo[3.1.0]hexane-2-carboxamide (86)

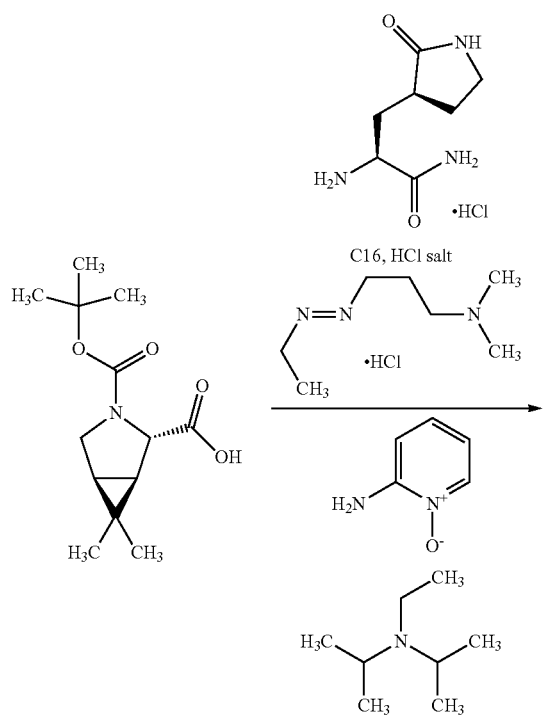

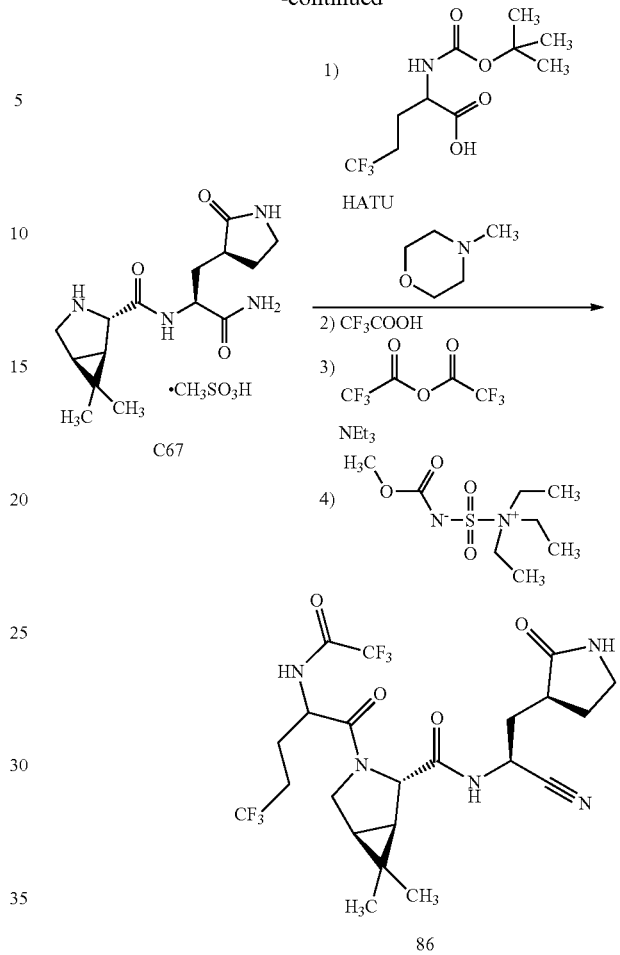

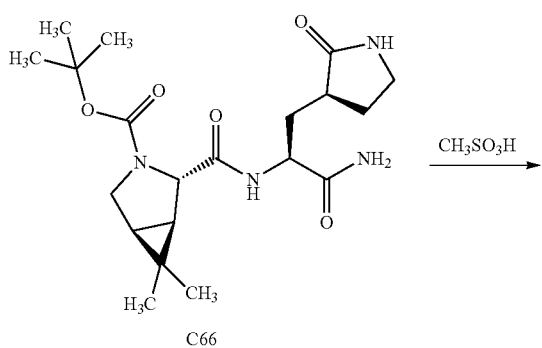

Step 1. Synthesis of tert-butyl (1R,2S,5S)-2-({(2S)-1-amino-1-oxo-3-[(3S)-2-oxopyrrolidin-3-yl]propan-2-yl}carbamoyl)-6,6-dimethyl-3-azabicyclo[3.1.0]hexane-3-carboxylate (C66)

To a 0° C. slurry of (1R,2S,5S)-3-(tert-butoxycarbonyl)-6,6-dimethyl-3-azabicyclo[3.1.0]hexane-2-carboxylic acid (5.25 g, 20.6 mmol), C16, HCl salt (4.70 g, 22.6 mmol), and 2-hydroxypyridine 1-oxide (571 mg, 5.14 mmol) in butan-2-one (108 mL) was added N,N-diisopropylethylamine (7.97 g, 61.7 mmol) followed by 1-[3-(dimethylamino)propyl]-3-ethylcarbodiimide hydrochloride (4.73 g, 24.7 mmol). After the reaction mixture had been stirred at 0° C. for 20 minutes, it was allowed to warm gradually to room temperature, and then stirred at room temperature overnight, whereupon LCMS analysis indicated the presence of C66: LCMS m/z 407.1 [M−H]⁻. The reaction mixture was diluted with ethyl acetate (100 mL), and washed sequentially with the following: a mixture of water (50 mL) and saturated aqueous sodium chloride solution (20 mL), saturated aqueous sodium chloride solution (70 mL), twice with a mixture of hydrochloric acid (1 M; 50 mL) and saturated aqueous sodium chloride solution (20 mL), and finally with saturated aqueous sodium chloride solution (70 mL). Each aqueous layer was extracted with ethyl acetate (100 mL), and the combined organic layers were dried over sodium sulfate and filtered. The collected sodium sulfate was washed with ethyl acetate (2×50 mL), and the combined filtrates were concentrated in vacuo, diluted with heptane (50 mL), and concentrated under reduced pressure to afford C66 as a colorless glass (6.69 g). By $^1$H NMR analysis, some solvents were present; the purity was estimated at approximately 85% by weight. $^1$H NMR analysis also indicated that this material exists as a mixture of rotamers. Yield, adjusted for the presence of solvents: 5.7 g, 14 mmol, 68%. $^1$H NMR (400 MHz, DMSO-$d_6$), characteristic peaks: δ 8.23-8.13 (m, 1H), [7.63 (br s) and 7.59 (br s), total 1H], [7.36 (br s) and 7.23 (br s), total 1H], 7.08-7.00 (m, 1H), 4.31-4.19 (m, 1H), [4.03 (s) and 3.99 (s), total 1H], [3.58 (dd, J=10.8, 4.6 Hz) and 3.49 (dd, J=10.8, 3.9 Hz), total 1H], [3.27 (d, J=10.9 Hz) and 3.26 (d, J=10.7 Hz), total 1H], 3.22-3.00 (m, 2H), 2.38-2.09 (m, 2H), 1.79-1.43 (m, 2H), [1.36 (s) and 1.29 (s), total 9H], 1.00 (s, 3H), 0.89 (s, 3H).

Step 2. Synthesis of (1R,2S,5S)—N-{(2S)-1-amino-1-oxo-3-[(3S)-2-oxopyrrolidin-3-yl]propan-2-yl}-6,6-dimethyl-3-azabicyclo[3.1.0]hexane-2-carboxamide, methanesulfonate salt (C67)

Methanesulfonic acid (0.920 mL, 14.2 mmol) was added to a solution of C66 (approximately 85% by weight, from the previous step; 6.68 g, 14 mmol) in 1,1,1,3,3,3-hexafluoropropan-2-ol (30 mL). The reaction mixture was stirred at room temperature for 3 hours, whereupon it was concentrated in vacuo. The residue was sequentially taken up in the following solvent systems, followed by reconcentration: acetonitrile/ethyl acetate (1:1, 2×10 mL) and ethyl acetate/heptane (1:1, 2×10 mL), to provide C67 as a glass (7.18 g). A portion of this material was taken to the following step. LCMS m/z 309.3 [M+H]$^+$. $^1$H NMR (400 MHz, methanol-$d_4$) δ4.51 (dd, J=10.8, 4.7 Hz, 1H), 4.21 (br s, 1H), 3.73 (dd, J=12.4, 6.3 Hz, 1H), 3.41-3.22 (m, 3H), 2.70 (s, 3H), 2.58-2.47 (m, 1H), 2.42-2.32 (m, 1H), 2.16 (ddd, J=14.0, 10.8, 4.8 Hz, 1H), 1.97 (br d, J=7.9 Hz, 1H), 1.95-1.84 (m, 1H), 1.84-1.75 (m, 2H), 1.15 (s, 6H).

Step 3. Synthesis of (1R,2S,5S)—N-{(1S)-1-cyano-2-[(3S)-2-oxopyrrolidin-3-yl]ethyl}-6,6-dimethyl-3-[5,5,5-trifluoro-2-(2,2,2-trifluoroacetamido)pentanoyl]-3-azabicyclo[3.1.0]hexane-2-carboxamide (86)

To a solution of 2-[(tert-butoxycarbonyl)amino]-5,5,5-trifluoropentanoic acid (59.0 mg, 0.218 mmol) in a mixture of acetonitrile (0.60 mL) and N,N-dimethylformamide (0.40 mL) was added O-(7-azabenzotriazol-1-yl)-N,N,N',N'-tetramethyluronium hexafluorophosphate (HATU; 82.7 mg, 0.218 mmol) followed by 4-methylmorpholine (54.4 µL, 0.495 mmol). After the reaction mixture had been stirred for 20 minutes, C67 (from the previous step; 100 mg, 50.19 mmol) was added as a solid. The reaction mixture was allowed to stir for 1.5 hours, whereupon it was partitioned between ethyl acetate and saturated aqueous sodium bicarbonate solution. The aqueous layer was extracted with ethyl acetate, and the combined organic layers were dried over magnesium sulfate, filtered, and concentrated using a stream of nitrogen. The residue was dissolved in dichloromethane (0.70 mL), treated with trifluoroacetic acid (0.175 mL), and stirred at room temperature. After 2 hours, trifluoroacetic acid (0.10 mL) was again added; stirring was continued for an additional 3 hours, whereupon the reaction mixture was concentrated under a stream of nitrogen, and then in vacuo. This material was dissolved in dichloromethane (0.75 mL), cooled in an ice bath, and treated with triethylamine (54.8 µL, 0.393 mmol); trifluoroacetic anhydride (41.2 µL, 0.292 mmol) was added in a drop-wise manner, and the reaction mixture was allowed to stir at 0° C. for 3 hours. Volatiles were removed using a Genevac evaporator, and the residue was dissolved in dichloromethane (0.90 mL), treated with methyl N-(triethylammoniosulfonyl)carbamate, inner salt (Burgess reagent; 132 mg, 0.554 mmol), and stirred at room temperature for 2.5 hours. The reaction mixture was then concentrated under a stream of nitrogen, diluted with ethyl acetate, and washed with saturated aqueous sodium bicarbonate solution. The aqueous layer was extracted with ethyl acetate, and the combined organic layers were dried over magnesium sulfate, filtered, and concentrated under a stream of nitrogen. Purification via reversed-phase HPLC (Column: Waters Sunfire C18, 19×100 mm, 5 µm; Mobile phase A: 0.05% trifluoroacetic acid in water; Mobile phase B: 0.05% trifluoroacetic acid in acetonitrile; Gradient: 5% to 95% B over 8.54 minutes, followed by 95% B for 1.46 minutes; Flow rate: 25 mL/minute) afforded (1R,2S,5S)—N-{(1S)-1-cyano-2-[(3S)-2-oxopyrrolidin-3-yl]ethyl}-6,6-dimethyl-3-[5,5,5-trifluoro-2-(2,2,2-trifluoroacetamido)pentanoyl]-3-azabicyclo[3.1.0]hexane-2-carboxamide (86). Yield: 14 mg, 26 µmol, 14% over 2 steps. LCMS m/z 540.6 [M+H]$^+$. Retention time: 2.60 minutes (Analytical conditions. Column: Waters Atlantis dC18, 4.6×50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 87

(1R,2S,5S)—N-{(1S)-1-Cyano-2-[(3S)-2-oxopyrrolidin-3-yl]ethyl}-3-[(2S)-2-cyclohexyl-2-{[(trifluoromethyl)sulfonyl]amino}acetyl]-6,6-dimethyl-3-azabicyclo[3.1.0]hexane-2-carboxamide (87)

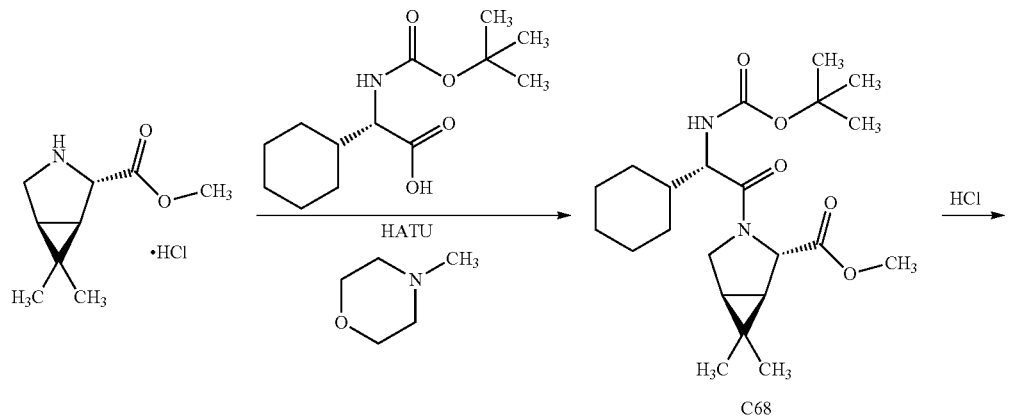

C68

-continued
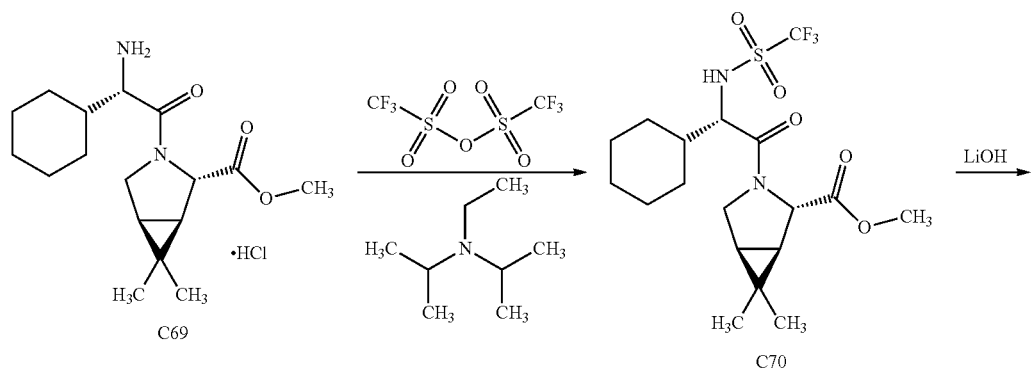
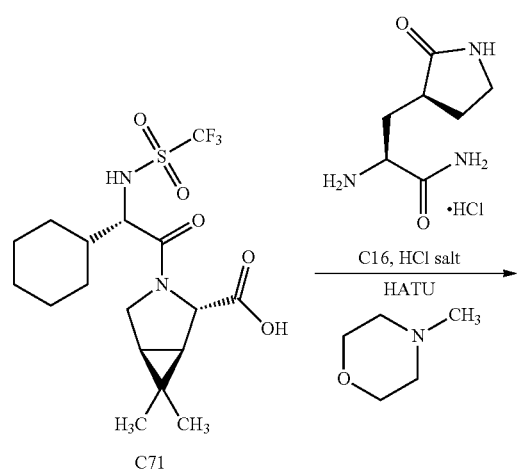
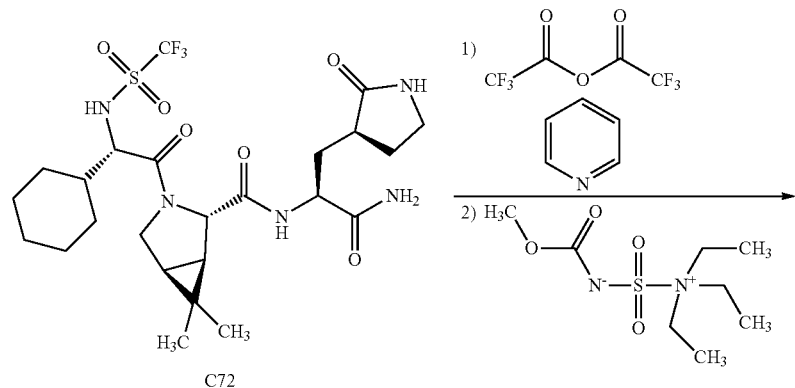
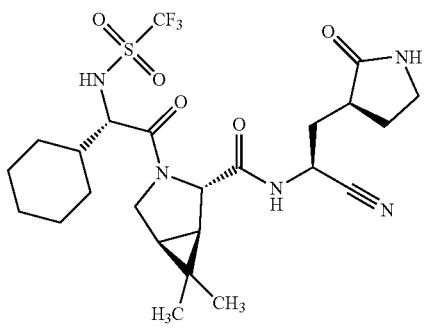

Step 1. Synthesis of methyl (1R,2S,5S)-3-{(2S)-2-[(tert-butoxycarbonyl)amino]-2-cyclohexylacetyl}-6,6-dimethyl-3-azabicyclo[3.1.0]hexane-2-carboxylate (C68)

To a 0° C. solution of methyl (1R,2S,5S)-6,6-dimethyl-3-azabicyclo[3.1.0]hexane-2-carboxylate, hydrochloride salt (300 mg, 1.46 mmol) and (2S)-[(tert-butoxycarbonyl)amino](cyclohexyl)acetic acid (394 mg, 1.53 mmol) in N,N-dimethylformamide (5 mL) was added O-(7-azabenzotriazol-1-yl)-N,N,N',N'-tetramethyluronium hexafluorophosphate (HATU; 610 mg, 1.60 mmol), followed by drop-wise addition of 4-methylmorpholine (443 mg, 4.38 mmol). The reaction mixture was stirred at 0° C. for 10 minutes, then at room temperature (20° C.) for 2 hours, whereupon it was poured into ice water (30 mL) and extracted with ethyl acetate (3×40 mL). The combined organic layers were washed sequentially with water (40 mL), hydrochloric acid (1 M; 40 mL), saturated aqueous sodium bicarbonate solution (40 mL), and saturated aqueous sodium chloride solution, then dried over sodium sulfate, filtered, and concentrated in vacuo to provide C68 as a white foam. Yield: 580 mg, 1.42 mmol, 97%. LCMS m/z 409.3 [M+H]$^+$. $^1$H NMR (400 MHz, DMSO-$d_6$) δ 7.03 (d, J=8.5 Hz, 1H), 4.17 (s, 1H), 4.00 (d, J=10.4 Hz, 1H), 3.88 (dd, J=9, 9 Hz, 1H), 3.75 (dd, J=10.3, 5.3 Hz, 1H), 3.64 (s, 3H), 1.83-1.47 (m, 8H), 1.46-1.28 (m, 2H), 1.33 (s, 9H), 1.18-1.06 (m, 3H), 1.00 (s, 3H), 0.86 (s, 3H).

Step 2. Synthesis of methyl (1R,2S,5S)-3-[(2S)-2-amino-2-cyclohexylacetyl]-6,6-dimethyl-3-azabicyclo[3.1.0]hexane-2-carboxylate, hydrochloride salt (C69)

A solution of hydrogen chloride in 1,4-dioxane (4 M; 15 mL) was added in a drop-wise manner to a 5° C. solution of C68 (580 mg, 1.42 mmol) in 1,4-dioxane (3 mL). After the reaction mixture had been stirred at room temperature (20° C.) for 1.5 hours, it was concentrated in vacuo. The residue was co-evaporated with dichloromethane to afford C69 as a light-yellow foam (490 mg), the bulk of which was used in the following experiment. $^1$H NMR (400 MHz, DMSO-$d_6$) δ 8.22 (br s, 3H), 4.26 (s, 1H), 3.99-3.90 (m, 1H), 3.76 (dd, component of ABX system, J=10.7, 5.1 Hz, 1H), 3.71 (d, half of AB quartet, J=10.6 Hz, 1H), 3.66 (s, 3H), 1.83-1.60 (m, 6H), 1.59 (dd, J=7.6, 5.1 Hz, 1H), 1.49 (d, half of AB quartet, J=7.6 Hz, 1H), 1.27-1.02 (m, 5H), 1.03 (s, 3H), 0.94 (s, 3H).

Step 3. Synthesis of methyl (1R,2S,5S)-3-[(2S)-2-cyclohexyl-2-{[(trifluoromethyl)sulfonyl]amino}acetyl]-6,6-dimethyl-3-azabicyclo[3.1.0]hexane-2-carboxylate (C70)

To a −10° C. solution of C69 (from the previous step; 480 mg, ≤1.39 mmol) in dichloromethane (10 mL) was added N,N-diisopropylethylamine (630 mg, 4.87 mmol), followed by drop-wise addition of trifluoromethanesulfonic anhydride (0.328 mL, 1.95 mmol). The reaction mixture was stirred at −10° C. for 1 hour, then at room temperature (20° C.) for 1 hour, whereupon it was diluted with saturated aqueous sodium chloride solution (50 mL) and extracted with dichloromethane (3×30 mL). The combined organic layers were dried over sodium sulfate, filtered, concentrated in vacuo, and purified via silica gel chromatography (Eluent: 1:4 ethyl acetate/petroleum ether), providing $C_{70}$ as a light-yellow oil. Yield: 124 mg, 0.282 mmol, 20% over 2 steps. LCMS m/z 441.1 [M+H]$^+$.

Step 4. Synthesis of (1R,2S,5S)-3-[(2S)-2-cyclohexyl-2-{[(trifluoromethyl)sulfonyl]amino}acetyl]-6,6-dimethyl-3-azabicyclo[3.1.0]hexane-2-carboxylic acid (C71)

To a solution of C70 (120 mg, 0.272 mmol) in a mixture of water (2 mL), methanol (2 mL), and tetrahydrofuran (2 mL) was added lithium hydroxide monohydrate (28.6 mg, 0.682 mmol). After the reaction mixture had been stirred at room temperature (20° C.) for 18 hours at room temperature, LCMS indicated that the reaction was complete: LCMS m/z 427.2 [M+H]$^+$. The reaction mixture was concentrated in vacuo to remove organic solvents. The residue was diluted with water (5 mL) and then acidified to a pH of 2 to 3 by addition of 1 M hydrochloric acid; the resulting mixture was extracted with ethyl acetate (2×30 mL). The combined organic layers were dried over sodium sulfate, filtered, and concentrated in vacuo, providing C71 as a light-yellow solid. Yield: 92.0 mg, 0.216 mmol, 79%.

Step 5. Synthesis of (1R,2S,5S)—N-{(2S)-1-amino-1-oxo-3-[(3S)-2-oxopyrrolidin-3-yl]propan-2-yl}-3-[(2S)-2-cyclohexyl-2-{[(trifluoromethyl)sulfonyl]amino}acetyl]-6,6-dimethyl-3-azabicyclo[3.1.0]hexane-2-carboxamide (C72)

To a 0° C. solution of C71 (92.0 mg, 0.216 mmol) and C16, HCl salt (72%, 68.8 mg, 0.238 mmol) in N,N-dimethylformamide (3 mL) was added O-(7-azabenzotriazol-1-yl)-N,N,N',N'-tetramethyluronium hexafluorophosphate (HATU; 98.4 mg, 0.259 mmol), followed by 4-methylmorpholine (76.4 mg, 0.755 mmol). The reaction mixture was then stirred at 20° C. for 2 hours, whereupon it was poured into ice water (10 mL) and extracted with a mixture of chloroform and 2-propanol (4:1, 4×20 mL). The combined organic layers were dried over sodium sulfate, filtered, concentrated in vacuo, and purified via chromatography on silica gel (Gradient: 0% to 10% methanol in dichloromethane), affording C72 as a colorless glass. Yield: 100 mg, 0.173 mmol, 80%. LCMS m/z 580.2 [M+H]$^+$.

Step 6. Synthesis of (1R,2S,5S)—N-{(1S)-1-cyano-2-[(3S)-2-oxopyrrolidin-3-yl]ethyl}-3-[(2S)-2-cyclohexyl-2-{[(trifluoromethyl)sulfonyl]amino}acetyl]-6,6-dimethyl-3-azabicyclo[3.1.0]hexane-2-carboxamide (87)

A solution of trifluoroacetic anhydride (47.1 mg, 0.224 mmol) in dichloromethane (1 mL) was added in a drop-wise manner to a 0° C. solution of C72 (100 mg, 0.173 mmol) and pyridine (41.7 µL, 0.516 mmol) in dichloromethane (3 mL). After the mixture had been stirred for 20 hours at room temperature (10° C. to 20° C.), it was concentrated in vacuo and re-dissolved in dichloromethane (3 mL). Methyl N-(triethylammoniosulfonyl)carbamate, inner salt (Burgess reagent; 103 mg, 0.432 mmol) was added, and the reaction mixture was stirred at room temperature (20° C.) for 20 hours. It was then was diluted with saturated aqueous sodium chloride solution (10 mL) and extracted with dichloromethane (3×20 mL); the combined organic layers were dried over sodium sulfate, filtered, concentrated in vacuo, and subjected to supercritical fluid chromatography [Column: Chiral Technologies Chiralcel OD, 30×250 mm, 10

μm; Mobile phase: 4:1 carbon dioxide/(ethanol containing 0.1% ammonium hydroxide); Flow rate: 60 mL/minute]. Fractions containing 87 were concentrated in vacuo below 40° C. to remove the alcohol co-solvent. The residue was diluted with ethyl acetate (50 mL) and dichloromethane (5 mL) and washed sequentially with hydrochloric acid (1 M; 20 mL), saturated aqueous sodium bicarbonate solution (20 mL), and saturated aqueous sodium chloride solution. The resulting organic layer was dried over sodium sulfate, filtered, and concentrated in vacuo before being mixed with water (20 mL) and acetonitrile (5 mL); this mixture was lyophilized to afford (1R,2S,5S)—N-{(1S)-1-cyano-2-[(3S)-2-oxopyrrolidin-3-yl]ethyl}-3-[(2S)-2-cyclohexyl-2-{[(trifluoromethyl)sulfonyl]amino}acetyl]-6,6-dimethyl-3-azabicyclo[3.1.0]hexane-2-carboxamide (87) as a white solid. Yield: 27.6 mg, 49.1 μmol, 28%. LCMS m/z 562.2 [M+H]⁺. ¹H NMR (400 MHz, DMSO-d₆), characteristic peaks: δ 9.93 (d, J=8.3 Hz, 1H), 9.10 (d, J=8.7 Hz, 1H), 7.70 (s, 1H), 5.03-4.94 (m, 1H), 4.15 (s, 1H), 3.88-3.78 (m, 2H), 3.55 (d, J=10.2 Hz, 1H), 3.20-3.11 (m, 1H), 3.10-3.00 (m, 1H), 2.19-2.08 (m, 1H), 2.06-1.95 (m, 1H), 1.85-1.53 (m, 9H), 1.33 (d, half of AB quartet, J=7.7 Hz, 1H), 1.03 (s, 3H), 0.89 (s, 3H).

Examples 88 and 89

(1R,2S,5S)—N-{(1S)-1-Cyano-2-[(3S)-2-oxopyrrolidin-3-yl]ethyl}-3-[3-cyclobutyl-N-(trifluoroacetyl)-L-alanyl]-6,6-dimethyl-3-azabicyclo[3.1.0]hexane-2-carboxamide and (1R,2S,5S)—N-{(1S)-1-Cyano-2-[(3S)-2-oxopyrrolidin-3-yl]ethyl}-3-[3-cyclobutyl-N-(trifluoroacetyl)-D-alanyl]-6,6-dimethyl-3-azabicyclo[3.1.0]hexane-2-carboxamide (88 and 89)

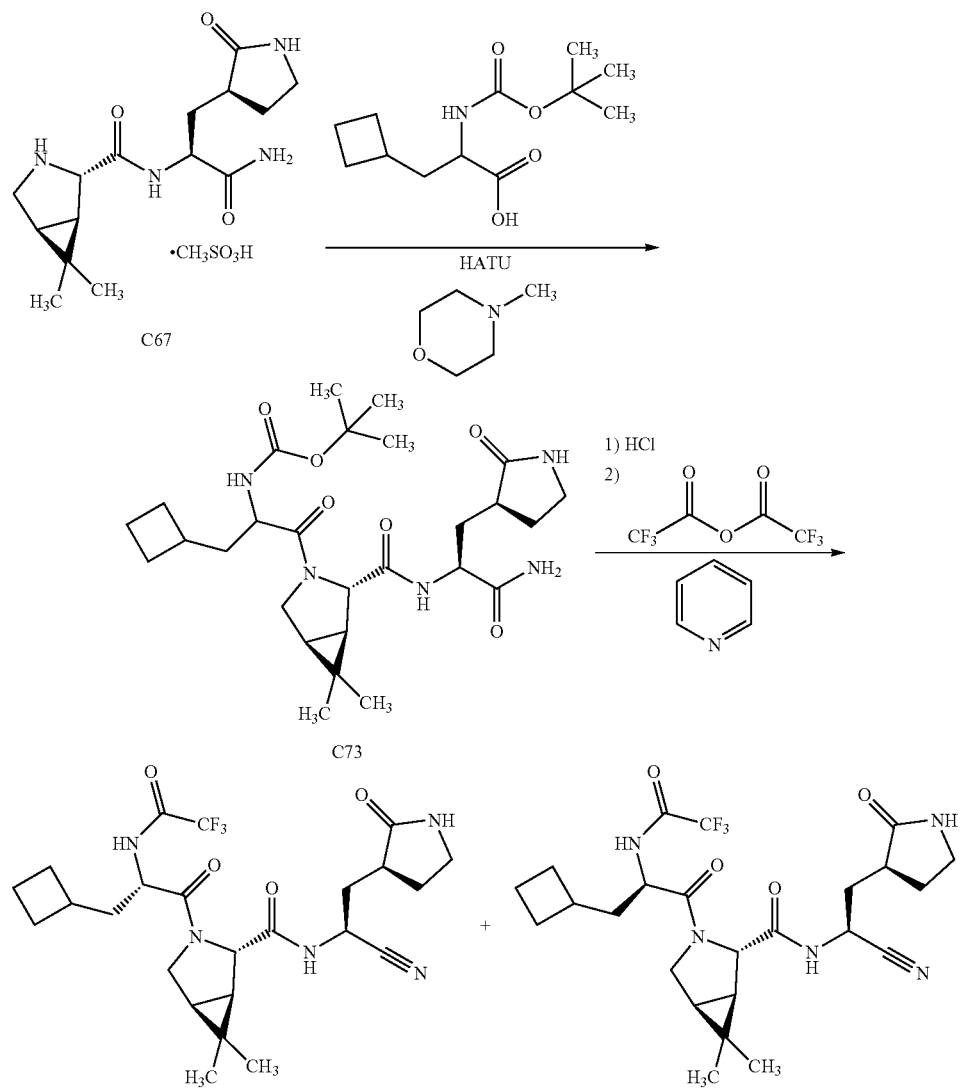

88 (DIAST-1) and 89 (DIAST-2)

Step 1. Synthesis of tert-butyl {1-[(1R,2S,5S)-2-({(2S)-1-amino-1-oxo-3-[(3S)-2-oxopyrrolidin-3-yl]propan-2-yl}carbamoyl)-6,6-dimethyl-3-azabicyclo[3.1.0]hexan-3-yl]-3-cyclobutyl-1-oxopropan-2-yl}carbamate (C73)

A 0° C. solution of C67 (150 mg, 0.371 mmol) and N-(tert-butoxycarbonyl)-3-cyclobutylalanine (99.2 mg, 0.408 mmol) in N,N-dimethylformamide (3 mL) was treated with O-(7-azabenzotriazol-1-yl)-N,N,N',N'-tetramethyluronium hexafluorophosphate (HATU; 169 mg, 0.444 mmol). 4-Methylmorpholine (131 mg, 1.30 mmol) was then added in a drop-wise manner, whereupon the reaction mixture was allowed to warm to 25° C. and stir overnight. Ice water (10 mL) was added, and the resulting mixture was extracted with a mixture of chloroform and 2-propanol (4:1, 4×20 mL); the combined organic layers were dried over sodium sulfate, filtered, and concentrated in vacuo. Chromatography on silica gel (Gradient: 0% to 10% methanol in dichloromethane) was carried out twice, providing C73 as a white solid, which comprised a mixture of two diastereomers. Yield: 106 mg, 0.199 mmol, 54%. LCMS m/z 534.2 [M+H]$^+$. $^1$H NMR (400 MHz, chloroform-d) δ [8.59 (d, J=5.5 Hz) and 7.85 (d, J=7.7 Hz), total 1H], 7.20-7.06 (m, 1H), [5.78 (br s) and 5.67 (br s), total 1H], [5.51 (br s) and 5.40 br (s), total 1H], 5.22-5.12 (m, 1H), [4.49-4.39 (m) and 4.38-4.23 (m), total 3H], 4.17-4.06 (m, 1H), [3.83 (d, J=10.4 Hz) and 3.50 (d, J=10.5 Hz), total 1H], 3.42-3.28 (m, 2H), 2.50-2.30 (m, 3H), 2.23-2.00 (m, 4H), 2.00-1.77 (m, 4H), 1.73-1.44 (m, 5H), [1.40 (s) and 1.39 (s), total 9H], [1.07 (s) and 1.03 (s), total 3H], [0.98 (s) and 0.92 (s), total 3H].

Step 2. Synthesis of (1R,2S,5S)—N-{(1S)-1-cyano-2-[(3S)-2-oxopyrrolidin-3-yl]ethyl}-3-[3-cyclobutyl-N-(trifluoroacetyl)-L-alanyl]-6,6-dimethyl-3-azabicyclo[3.1.0]hexane-2-carboxamide and (1R,2S,5S)—N-{(1S)-1-cyano-2-[(3S)-2-oxopyrrolidin-3-yl]ethyl}-3-[3-cyclobutyl-N-(trifluoroacetyl)-D-alanyl]-6,6-dimethyl-3-azabicyclo[3.1.0]hexane-2-carboxamide [88 (DIAST-1) and 89 (DIAST-2)]

A solution of hydrogen chloride in 1,4-dioxane (4 M; 5 mL, 20 mmol) was added in a drop-wise manner to a 0° C. solution of C73 (106 mg, 0.199 mmol) in dichloromethane (5 mL). The reaction mixture was stirred at 0° C. for 15 minutes and then at 25° C. for 2 hours, whereupon it was concentrated in vacuo to provide the deprotected material as a white solid: LCMS m/z 434.2 [M+H]$^+$. This was dissolved in dichloromethane (3 mL), cooled in an ice bath, and treated with pyridine (79.9 mg, 1.01 mmol) and a solution of trifluoroacetic anhydride (170 mg, 0.809 mmol) in dichloromethane (1.5 mL). The reaction mixture was stirred at 20° C. for 20 hours; pyridine (40.0 mg, 0.506 mmol) was then added, and stirring was continued for a further 12 hours at 25° C. After dilution with dichloromethane (15 mL), the reaction mixture was washed sequentially with hydrochloric acid (1 M; 10 mL), saturated aqueous sodium bicarbonate solution (3×10 mL), and saturated aqueous sodium chloride solution (10 mL), dried, filtered, and concentrated in vacuo. Silica gel chromatography (Gradient: 0% to 20% methanol in dichloromethane) was followed by supercritical fluid chromatography [Column: Chiral Technologies Chiralpak IC, 30×250 mm, 10 μm; Mobile phase: 3:1 carbon dioxide/(methanol containing 0.1% ammonium hydroxide); Flow rate: 70 mL/minute], affording the separated diastereomers (1R,2S,5S)—N-{(1S)-1-cyano-2-[(3S)-2-oxopyrrolidin-3-yl]ethyl}-3-[3-cyclobutyl-N-(trifluoroacetyl)-L-alanyl]-6,6-dimethyl-3-azabicyclo[3.1.0]hexane-2-carboxamide and (1R,2S,5S)—N-{(1S)-1-cyano-2-[(3S)-2-oxopyrrolidin-3-yl]ethyl}-3-[3-cyclobutyl-N-(trifluoroacetyl)-D-alanyl]-6,6-dimethyl-3-azabicyclo[3.1.0]hexane-2-carboxamide. Which material contained the D-alanyl configuration and which contained the L-alanyl configuration was not determined; the first-eluting diastereomer was designated as 88, and the second-eluting diastereomer was designated as 89. Both were obtained as white solids.

88—Yield: 9.3 mg, 18.2 μmol, 9% over 2 steps. LCMS m/z 512.1 [M+H]$^+$. $^1$H NMR (400 MHz, DMSO-d$_6$) δ 9.75 (br d, J=7.0 Hz, 1H), 8.96 (d, J=8.1 Hz, 1H), 7.71 (s, 1H), 5.00-4.90 (m, 1H), 4.32-4.23 (m, 1H), 4.13 (s, 1H), 3.82 (dd, component of ABX system, J=10.2, 5.4 Hz, 1H), 3.69 (d, half of AB quartet, J=10.2 Hz, 1H), 3.20-3.02 (m, 2H), 2.44-2.28 (m, 2H), 2.16-2.04 (m, 2H), 2.04-1.91 (m, 2H), 1.87-1.54 (m, 9H), 1.32 (d, half of AB quartet, J=7.6 Hz, 1H), 1.03 (s, 3H), 0.88 (s, 3H). Retention time: 2.78 minutes (Analytical conditions. Column: Chiral Technologies Chiralpak IC-3, 4.6×150 mm, 3 μm; Mobile phase A: carbon dioxide; Mobile phase B: methanol containing 0.05% diethylamine (v/v); Gradient: 5% to 40% B over 5 minutes, then 40% B for 2.5 minutes; Back pressure: 1500 psi; Flow rate: 2.5 mL/minute).

89—Yield: 23 mg, 45.0 mmol, 23% over 2 steps. $^1$H NMR analysis indicated that this material exists as a mixture of rotamers. LCMS m/z 512.1 [M+H]$^+$. $^1$H NMR (400 MHz, DMSO-d$_6$) δ [9.92 br (s) and 9.65 (br s), total 1H], [9.22 (d, J=7.7 Hz) and 8.85 (d, J=8.4 Hz), total 1H], [7.76 (s) and 7.67 (s), total 1H], [5.11-5.00 (m) and 4.98-4.87 (m), total 1H], [4.51 (s) and 4.07 (s), total 1H], [4.47-4.36 (m) and 4.09-4.00 (m), total 1H], [3.90 (dd, J=10.2, 5.3 Hz) and 3.60-3.45 (m), total 2H], 3.21-3.00 (m, 2H), 2.44-2.33 (m, 1H), 2.28-1.98 (m, 3H), 1.98-1.52 (m, 1 OH), [1.49-1.38 (m) and 1.32 (d, half of AB quartet, J=7.6 Hz), total 2H], [1.04 (s) and 1.02 (s), total 3H], [0.93 (s) and 0.82 (s), total 3H]. Retention time: 4.14 minutes (Analytical conditions identical to those used for 88).

Example 90

(1R,2S,5S)—N-{(1S)-1-Cyano-2-[(3S)-2-oxopyrrolidin-3-yl]ethyl}-6,6-dimethyl-3-[3-(pyridin-2-yl)-N-(trifluoroacetyl)-L-alanyl]-3-azabicyclo[3.1.0]hexane-2-carboxamide (90)

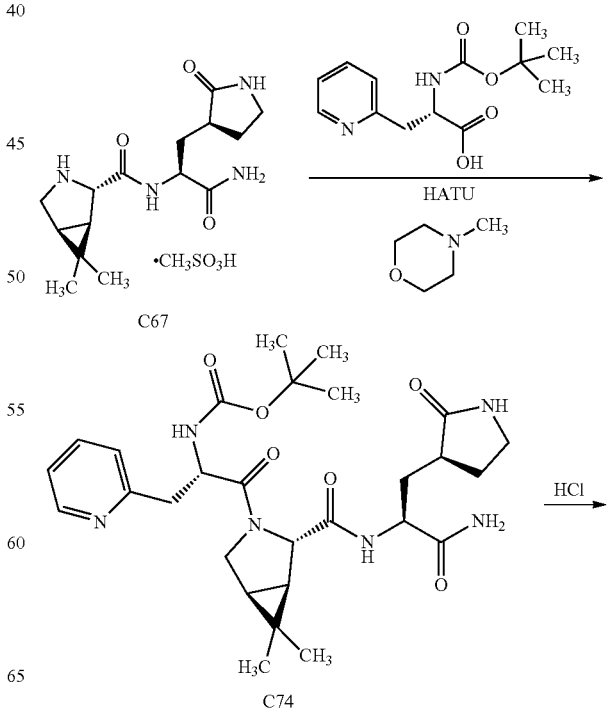

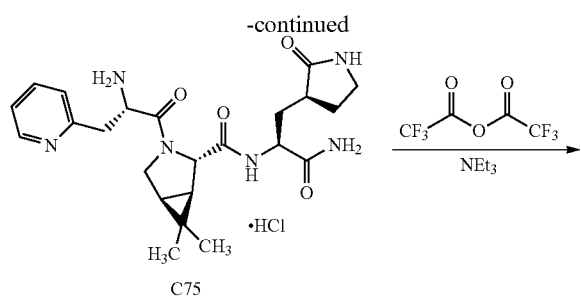

C75

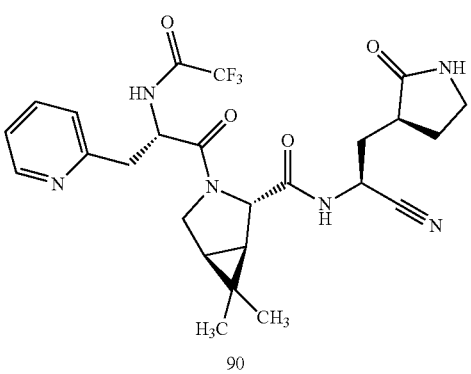

90

Step 1. Synthesis of tert-butyl [(2S)-1-[(1R,2S,5S)-2-({(2S)-1-amino-1-oxo-3-[(3S)-2-oxopyrrolidin-3-yl]propan-2-yl}carbamoyl)-6,6-dimethyl-3-azabicyclo[3.1.0]hexan-3-yl]-1-oxo-3-(pyridin-2-yl)propan-2-yl]carbamate (C74)

To a 0° C. solution of C67 (250 mg, 0.618 mmol) and N-(tert-butoxycarbonyl)-3-pyridin-2-yl-L-alanine (198 mg, 0.744 mmol) in N,N-dimethylformamide (2 mL) was added O-(7-azabenzotriazol-1-yl)-N,N,N',N'-tetramethyluronium hexafluorophosphate (HATU; 282 mg, 0.742 mmol), followed by drop-wise addition of a solution of 4-methylmorpholine (188 mg, 1.86 mmol) in N,N-dimethylformamide (1 mL). The reaction mixture was then warmed to 20° C. and stirred for 2 hours, whereupon it was diluted with water (10 mL) and extracted with ethyl acetate (10 mL). Solid sodium sulfate was added to the aqueous layer until saturation was achieved, whereupon the aqueous layer was extracted with a mixture of dichloromethane and methanol (10:1, 3×20 mL). The combined organic layers were concentrated in vacuo and purified via silica gel chromatography (Gradient: 0% to 10% methanol in dichloromethane), affording C74 as a yellow gum. Yield: 250 mg, 0.449 mmol, 73%. LCMS m/z 557.0 [M+H]$^+$. $^1$H NMR (400 MHz, methanol-d$_4$), characteristic peaks: δ 8.49 (d, J=5.2 Hz, 1H), 7.78-7.71 (m, 1H), 7.35 (d, J=7.8 Hz, 1H), 7.30-7.25 (m, 1H), 4.73 (dd, J=8.5, 5.2 Hz, 1H), 4.40 (dd, J=11.8, 4.2 Hz, 1H), 4.30 (s, 1H), 4.01-3.90 (m, 1H), 3.26 (dd, J=14.2, 5.6 Hz, 1H), 2.94 (dd, J=14.1, 8.9 Hz, 1H), 2.65-2.53 (m, 1H), 2.37-2.25 (m, 1H), 2.14-2.04 (m, 1H), 1.91-1.78 (m, 2H), 1.61-1.55 (m, 1H), 1.53 (d, half of AB quartet, J=7.7 Hz, 1H), 1.34 (s, 9H), 1.08 (s, 3H), 1.00 (s, 3H).

Step 2. Synthesis of (1R,2S,5S)—N-{(2S)-1-amino-1-oxo-3-[(3S)-2-oxopyrrolidin-3-yl]propan-2-yl}-6,6-dimethyl-3-[3-(pyridin-2-yl)-L-alanyl]-3-azabicyclo[3.1.0]hexane-2-carboxamide, hydrochloride salt (C75)

A solution of hydrogen chloride in 1,4-dioxane (4 M; 6 mL) was added to a 0° C. solution of C74 (250 mg, 0.449 mmol) in dichloromethane (2 mL), and the reaction mixture was stirred for 5 hours at 20° C. LCMS analysis indicated conversion to C75: LCMS m/z 457.1 [M+H]$^+$. Removal of solvents in vacuo afforded C75 as a yellow solid (250 mg); a portion of this material was used directly in the following step. $^1$H NMR (400 MHz, DMSO-d$_6$), characteristic peaks: δ 8.81 (br d, J=5.4 Hz, 1H), 8.43 (d, J=8.3 Hz, 1H), 8.39-8.31 (m, 1H), 7.90 (d, J=8.0 Hz, 1H), 7.87-7.81 (m, 1H), 7.65 (s, 1H), 7.43 (br s, 1H), 7.06 (br s, 1H), 4.77-4.67 (m, 1H), 4.35 (s, 1H), 4.32-4.23 (m, 1H), 3.94-3.86 (m, 1H), 3.80 (d, half of AB quartet, J=10.6 Hz, 1H), 3.36-3.25 (m, 1H), 3.20-3.08 (m, 2H), 2.35-2.23 (m, 1H), 2.17-2.06 (m, 1H), 2.01-1.90 (m, 1H), 1.55-1.48 (m, 1H), 1.43 (d, half of AB quartet, J=7.6 Hz, 1H), 1.04 (s, 3H), 0.96 (s, 3H).

Step 3. Synthesis of (1R,2S,5S)—N-{(1S)-1-cyano-2-[(3S)-2-oxopyrrolidin-3-yl]ethyl}-6,6-dimethyl-3-[3-(pyridin-2-yl)-N-(trifluoroacetyl)-L-alanyl]-3-azabicyclo[3.1.0]hexane-2-carboxamide (90)

To a 0° C. solution of C75 (from the previous step; 175 mg, 50.314 mmol) in dichloromethane (6 mL) was added pyridine (197 mg, 2.49 mmol), followed by a solution of trifluoroacetic anhydride (186 mg, 0.886 mmol) in dichloromethane (2 mL). After the reaction mixture had been stirred at 20° C. for 2 hours, it was diluted with water and extracted with a mixture of dichloromethane and methanol (10:1, 3×15 mL). The combined organic layers were concentrated in vacuo and subjected to silica gel chromatography (Gradient: 0% to 10% methanol in dichloromethane), followed by supercritical fluid chromatography [Column: Chiral Technologies Chiralpak AS, 30×250 mm, 10 μm; Mobile phase: 3:1 carbon dioxide/(ethanol containing 0.1% ammonium hydroxide); Flow rate: 70 mL/minute], to afford (1R,2S,5S)—N-{(1S)-1-cyano-2-[(3S)-2-oxopyrrolidin-3-yl]ethyl}-6,6-dimethyl-3-[3-(pyridin-2-yl)-N-(trifluoroacetyl)-L-alanyl]-3-azabicyclo[3.1.0]hexane-2-carboxamide (90) as a white solid. Yield: 25 mg, 46.8 μmol, 15% over 2 steps. LCMS m/z 535.1 [M+H]$^+$. $^1$H NMR (400 MHz, DMSO-d$_6$) δ 9.92 (d, J=7.5 Hz, 1H), 8.91 (d, J=8.0 Hz, 1H), 8.51 (br d, J=5 Hz, 1H), 7.75-7.68 (m, 2H), 7.28 (d, J=7.8 Hz, 1H), 7.25 (dd, J=7.3, 5.1 Hz, 1H), 5.00-4.88 (m, 2H), 4.15 (s, 1H), 3.86 (dd, component of ABX system, J=10.3, 5.4 Hz, 1H), 3.70 (d, half of AB quartet, J=10.3 Hz, 1H), 3.21-3.04 (m, 4H), 2.42-2.31 (m, 1H), 2.18-2.04 (m, 2H), 1.76 (ddd, J=13.5, 9.6, 6.6 Hz, 1H), 1.74-1.62 (m, 1H), 1.62-1.53 (m, 1H), 1.33 (d, half of AB quartet, J=7.6 Hz, 1H), 1.03 (s, 3H), 0.89 (s, 3H).

Example 91

(1R,2S,5S)—N-{(1S)-1-Cyano-2-[(3S)-2-oxopyrrolidin-3-yl]ethyl}-3-{N-[(4-fluorophenoxy)acetyl]-3-methyl-L-valyl}-6,6-dimethyl-3-azabicyclo[3.1.0]hexane-2-carboxamide (91)

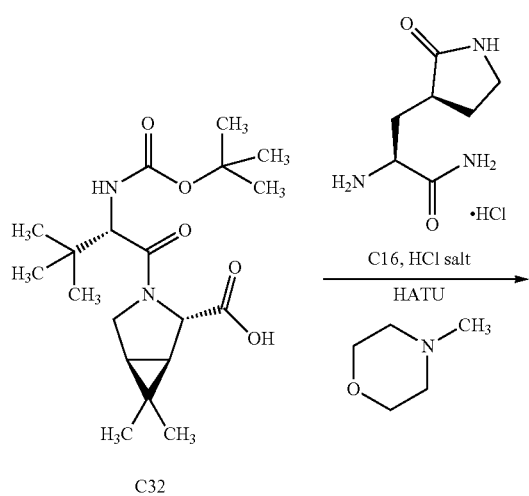

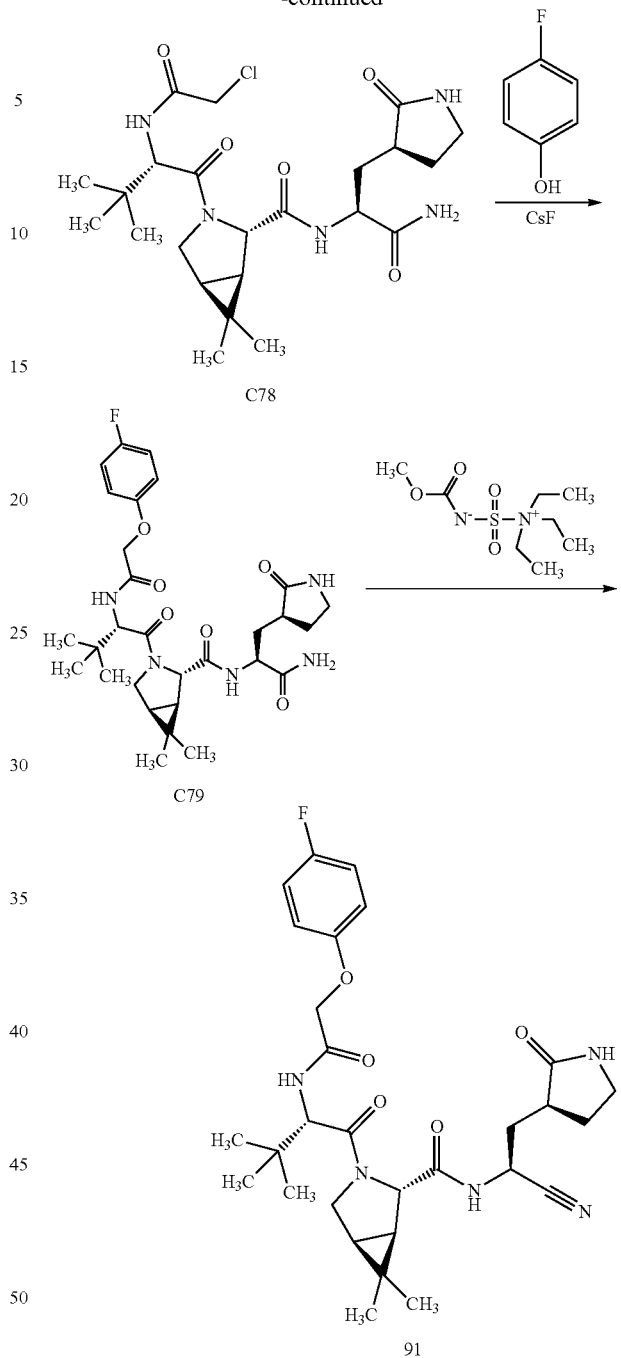

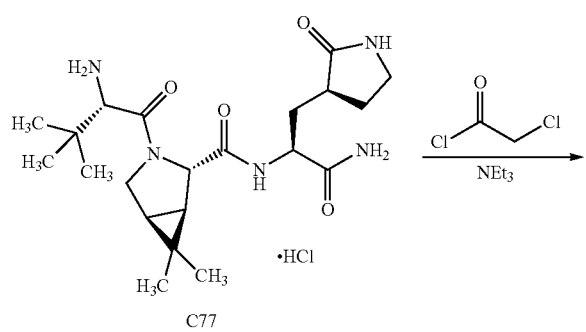

Step 1. Synthesis of tert-butyl {(2S)-1-[(1R,2S,5S)-2-({(2S)-1-amino-1-oxo-3-[(3S)-2-oxopyrrolidin-3-yl]propan-2-yl}carbamoyl)-6,6-dimethyl-3-azabicyclo[3.1.0]hexan-3-yl]-3,3-dimethyl-1-oxobutan-2-yl}carbamate (C76)

A solution of C32 (15.4 g, 41.8 mmol) and C16, HCl salt (75%, 11.6 g, 41.9 mmol) in N,N-dimethylformamide (380 mL) was cooled to −5° C. to 0° C. To this was added O-(7-azabenzotriazol-1-yl)-N,N,N',N'-tetramethyluronium hexafluorophosphate (HATU; 18.3 g, 48.1 mmol) and 4-methylmorpholine (12.7 g, 126 mmol) at −5° C. to 0° C. After the reaction mixture had been stirred at 0° C. for 1.5 hours, it was poured into ice water (400 mL), and the resulting mixture was extracted with ethyl acetate (3×200 mL). The combined organic layers were sequentially washed with aqueous citric acid solution (1 M; 120 mL), saturated aqueous sodium bicarbonate solution (120 mL), and saturated aqueous sodium chloride solution (3×60 mL), dried over sodium sulfate, filtered, concentrated in vacuo, and combined with the crude product from a similar reaction carried out using C32 (1.08 g, 2.93 mmol). Silica gel chromatography (Gradient: 0% to 10% methanol in dichloromethane) provided C76 as a white solid (9.80 g). The combined aqueous layers were extracted with a mixture of chloroform and 2-propanol (4:1, 3×100 mL); concentration of these combined extracts was followed by silica gel chromatography (Gradient: 0% to 10% methanol in dichloromethane) to afford additional C76 as a white solid (2.3 g). Combined yield: 12.1 gm, 23.2 mmol, 52%. LCMS m/z 522.5 [M+H]$^+$. $^1$H NMR (400 MHz, chloroform-d) δ 8.28 (br d, J=5.9 Hz, 1H), 7.20 (br s, 1H), 5.71 (br s, 1H), 5.38 (br s, 1H), 5.10 (br d, J=10.3 Hz, 1H), 4.47-4.38 (m, 1H), 4.28-4.20 (m, 2H), 4.12 (dd, component of ABX system, J=10.2, 4.0 Hz, 1H), 3.99 (d, half of AB quartet, J=10.2 Hz, 1H), 3.40-3.33 (m, 2H), 2.53-2.35 (m, 2H), 2.17-2.07 (m, 1H), 2.00-1.81 (m, 2H), 1.52-1.4 (m, 2H, assumed; largely obscured by water peak and tert-butyl signal), 1.39 (s, 9H), 1.02 (s, 3H), 1.01 (s, 9H), 0.88 (s, 3H).

Step 2. Synthesis of (1R,2S,5S)—N-{(2S)-1-amino-1-oxo-3-[(3S)-2-oxopyrrolidin-3-yl]propan-2-yl}-6,6-dimethyl-3-(3-methyl-L-valyl)-3-azabicyclo[3.1.0]hexane-2-carboxamide, hydrochloride salt (C77)

To a 0° C. solution of C76 (12.1 g, 23.2 mmol) in dichloromethane (50 mL) was added a solution of hydrogen chloride in 1,4-dioxane (4 M; 250 mL). After the reaction mixture had been stirred at 20° C. for 2 hours, it was filtered. The filter cake was stirred with methyl tert-butyl ether (250 mL) for 18 hours; filtration afforded C77 as a light-yellow/white solid (10.89 g). LCMS m/z 422.2 [M+H]$^+$. $^1$H NMR (400 MHz, DMSO-d$_6$) δ 8.38 (d, J=9.0 Hz, 1H), 8.19 (br s, 3H), 7.57 (br s, 1H), 7.41 (br s, 1H), 7.04 (br s, 1H), 4.35-4.27 (m, 1H), 4.34 (s, 1H), 3.85-3.72 (m, 2H), 3.65 (d, half of AB quartet, J=10.8 Hz, 1H), 3.16-3.09 (m, 1H), 3.05-2.95 (m, 1H), 2.43-2.31 (m, 1H), 2.17-2.04 (m, 1H), 2.00-1.89 (m, 1H), 1.71-1.42 (m, 3H), 1.38 (d, half of AB quartet, J=7.7 Hz, 1H), 1.02 (s, 3H), 1.02 (s, 9H), 0.97 (s, 3H).

Step 3. Synthesis of (1R,2S,5S)—N-{(2S)-1-amino-1-oxo-3-[(3S)-2-oxopyrrolidin-3-yl]propan-2-yl}-3-[N-(chloroacetyl)-3-methyl-L-valyl]-6,6-dimethyl-3-azabicyclo[3.1.0]hexane-2-carboxamide (C78)

Triethylamine (2.21 g, 21.8 mmol) was added to a 0° C. solution of C77 (from the previous step; 2.50 g, 55.33 mmol) in dichloromethane (100 mL). A solution of chloroacetyl chloride (1.23 g, 10.9 mmol) in dichloromethane (9 mL) was added to the reaction mixture in a drop-wise manner, and stirring was continued at 0° C. for 1 hour. Water (50 mL) was then added, and the resulting mixture was extracted with a mixture of chloroform and 2-propanol (4:1, 3×50 mL); the combined organic layers were washed with saturated aqueous sodium chloride solution (50 mL), dried over sodium sulfate, filtered, and concentrated in vacuo. Purification via silica gel chromatography (Gradient: 0% to 10% methanol in dichloromethane) afforded C78 as a white solid. Yield: 1.21 g, 2.43 mmol, 46% over 2 steps. LCMS m/z 498.1 (chlorine isotope pattern observed) [M+H]$^+$. $^1$H NMR (400 MHz, DMSO-d$_6$) δ 8.30-8.22 (m, 2H), 7.54 (br s, 1H), 7.30 (br s, 1H), 7.03 (br s, 1H), 4.35 (d, J=8.9 Hz, 1H), 4.29 (ddd, J=12.1, 8.7, 3.4 Hz, 1H), 4.24 (s, 1H), 4.11 (AB quartet, J$_{AB}$=12.4 Hz, Δν$_{AB}$=14.3 Hz, 2H), 3.86 (dd, component of ABX system, J=10.2, 5.4 Hz, 1H), 3.72 (d, half of AB quartet, J=10.3 Hz, 1H), 3.18-3.08 (m, 1H), 3.07-2.97 (m, 1H), 2.48-2.36 (m, 1H), 2.19-2.08 (m, 1H), 1.99-1.88 (m, 1H), 1.69-1.43 (m, 3H), 1.37 (d, half of AB quartet, J=7.7 Hz, 1H), 1.01 (s, 3H), 0.94 (s, 9H), 0.84 (s, 3H).

Step 4. Synthesis of (1R,2S,5S)—N-{(2S)-1-amino-1-oxo-3-[(3S)-2-oxopyrrolidin-3-yl]propan-2-yl}-3-{N-[(4-fluorophenoxy)acetyl]-3-methyl-L-valyl}-6,6-dimethyl-3-azabicyclo[3.1.0]hexane-2-carboxamide (C79)

4-Fluorophenol (49.5 mg, 0.442 mmol) was added to a mixture of cesium fluoride (67.1 mg, 0.442 mmol) in N,N-dimethylformamide (3 mL), and the mixture was stirred at 65° C. for 1 hour, whereupon C78 (110.0 mg, 0.221 mmol) was added, and the reaction mixture was stirred at 65° C. for 8 hours. It was then combined with a similar reaction carried out using C78 (30 mg, 60 μmol), poured into water (10 mL), and extracted with ethyl acetate (3×10 mL). The combined organic layers were washed sequentially with water (20 mL), hydrochloric acid (1 M; 10 mL), saturated aqueous sodium carbonate solution (10 mL), and saturated aqueous sodium chloride solution, dried over sodium sulfate, filtered, and concentrated in vacuo. Silica gel chromatography (Gradient: 0% to 10% methanol in dichloromethane) afforded C79 as a white glass. Combined yield: 100 mg, 0.174 mmol, 62%. LCMS m/z 574.2 [M+H]$^+$. $^1$H NMR (400 MHz, chloroform-d) δ 8.23 (br d, J=6 Hz, 1H), 7.19 (br s, 1H), 7.04 (br d, J=10.2 Hz, 1H), 6.99 (dd, J=9.2, 8.0 Hz, 2H), 6.85 (dd, component of ABX system, J=9.1, 4.2 Hz, 2H), 5.78 (br s, 1H), 5.46 (br s, 1H), 4.65 (d, J=9.8 Hz, 1H), 4.52-4.38 (m, 3H), 4.22 (s, 1H), 4.14 (dd, component of ABX system, J=10.3, 5.3 Hz, 1H), 3.93 (d, half of AB quartet, J=10.3 Hz, 1H), 3.41-3.32 (m, 2H), 2.55-2.34 (m, 2H), 2.14-2.05 (m, 1H), 2.03-1.80 (m, 3H), 1.03 (s, 3H), 1.00 (s, 9H), 0.86 (s, 3H).

Step 5. Synthesis of (1R,2S,5S)—N-{(1S)-1-cyano-2-[(3S)-2-oxopyrrolidin-3-yl]ethyl}-3-{N-[(4-fluorophenoxy)acetyl]-3-methyl-L-valyl}-6,6-dimethyl-3-azabicyclo[3.1.0]hexane-2-carboxamide (91)

A solution of methyl N-(triethylammoniosulfonyl)carbamate, inner salt (Burgess reagent; 125 mg, 0.524 mmol) in dichloromethane (2 mL) was added in a drop-wise manner to a 10° C. (room temperature) solution of C79 (100 mg, 0.174 mmol) in dichloromethane (4 mL). After the reaction mixture had been stirred at 10° C. for 16 hours, it was diluted with water (10 mL) and extracted with dichloromethane (3×10 mL). The combined organic layers were washed with saturated aqueous sodium chloride solution (2×10 mL) and concentrated in vacuo; silica gel chromatography (Gradient: 0% to 10% methanol in dichloromethane), followed by supercritical fluid chromatography [Column: Chiral Technologies Chiralcel OD, 30×250 mm, 10 μm; Mobile phase: 4:1 carbon dioxide/(ethanol containing 0.1% ammonium hydroxide); Flow rate: 60 mL/minute], afforded (1R,2S,5S)—N-{(1S)-1-cyano-2-[(3S)-2-oxopyrrolidin-3-yl]ethyl}-3-{N-[(4-fluorophenoxy)acetyl]-3-methyl-L-valyl}-6,6-dimethyl-3-azabicyclo[3.1.0]hexane-2-carboxamide (91) as a white solid. Yield: 55 mg, 99.0 μmol, 57%. LCMS m/z 556.3 [M+H]⁺. ¹H NMR (400 MHz, DMSO-d₆) δ 9.01 (d, J=8.5 Hz, 1H), 7.96 (d, J=9.1 Hz, 1H), 7.68 (s, 1H), 7.13-7.04 (m, 2H), 6.90-6.84 (m, 2H), 4.97 (ddd, J=10.9, 8.5, 5.1 Hz, 1H), 4.61-4.50 (m, 2H), 4.39 (d, J=8.9 Hz, 1H), 4.12 (s, 1H), 3.87 (dd, component of ABX system, J=10.4, 5.5 Hz, 1H), 3.73 (d, half of AB quartet, J=10.4 Hz, 1H), 3.19-3.09 (m, 1H), 3.09-2.99 (m, 1H), 2.47-2.36 (m, 1H, assumed; partially obscured by solvent peak), 2.21-2.02 (m, 2H), 1.79-1.65 (m, 2H), 1.53 (dd, J=7.6, 5.4 Hz, 1H), 1.29 (d, half of AB quartet, J=7.6 Hz, 1H), 1.00 (s, 3H), 0.93 (s, 9H), 0.75 (s, 3H).

Example 92

3-Methyl-N-[(4-methylphenyl)acetyl]-L-valyl-(4R)—N-{(1S)-1-cyano-2-[(3S)-2-oxopyrrolidin-3-yl]ethyl}-4-(trifluoromethyl)-L-prolinamide (92)

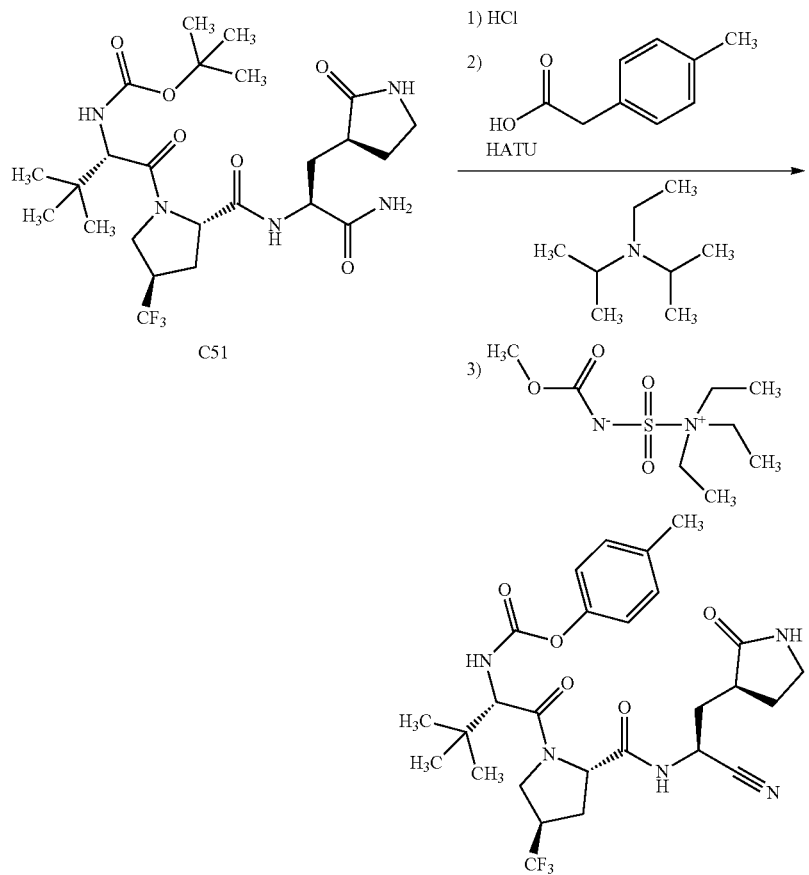

A mixture of C51 (68.0 mg, 0.12 mmol) and a solution of hydrogen chloride in 1,4-dioxane (4 M; 1 mL, 4 mmol) was stirred at room temperature for 5 minutes, whereupon the reaction mixture was concentrated in vacuo to remove the solvent, then further evacuated using high vacuum to eliminate residual hydrogen chloride. (4-Methylphenyl)acetic acid (18.6 mg, 0.124 mmol) was added to the residue; the resulting mixture was dissolved in N,N-dimethylformamide (1.0 mL) and cooled to −30° C. After addition of N,N-diisopropylethylamine (64.7 μL, 0.371 mmol), followed by 0-(7-azabenzotriazol-1-yl)-N,N,N',N'-tetramethyluronium hexafluorophosphate (HATU; 61.2 mg, 0.161 mmol), the reaction mixture was warmed to room temperature over 1 hour and subsequently treated with aqueous sodium bicarbonate solution. The mixture was extracted 5 times with ethyl acetate, and the combined organic layers were concentrated under reduced pressure. The residue was then dissolved in dichloromethane (1 mL), treated with methyl N-(triethylammoniosulfonyl)carbamate, inner salt (Burgess reagent; 88.5 mg, 0.371 mmol), and stirred at room temperature for 1 hour, whereupon the reaction mixture was treated with dilute aqueous sodium carbonate solution and extracted twice with ethyl acetate. The combined organic layers were dried over magnesium sulfate, filtered, concentrated in vacuo, and purified via reversed-phase HPLC (Column: Waters XBridge C18, 19×100 mm, 5 μm; Mobile phase A: water; Mobile phase B: acetonitrile; Gradient: 20% to 60% B over 8.5 minutes, then 60% to 95% B over 0.5 minutes, then 95% B for 1.0 minute; Flow rate: 25 mL/minute) to afford 3-methyl-N-[(4-methylphenyl)acetyl]-L-valyl-(4R)—N-{(1S)-1-cyano-2-[(3S)-2-oxopyrrolidin-3-yl]ethyl}-4-(trifluoromethyl)-L-prolinamide (92). Yield: 20.7 mg, 36.7 μmol, 31%. LCMS m/z 564.8 [M+H]⁺. Retention time: 2.71 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 93

(1R,2S,5S)—N-{(1S)-1-Cyano-2-[(3S)-2-oxopyrrolidin-3-yl]ethyl}-6,6-dimethyl-3-[3-(1H-pyrazol-1-yl)-N-(trifluoroacetyl)-L-alanyl]-3-azabicyclo[3.1.0]hexane-2-carboxamide (93)

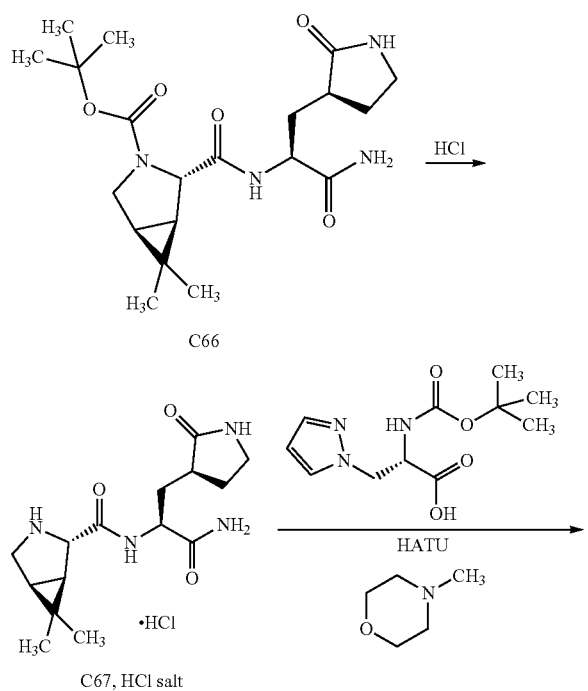

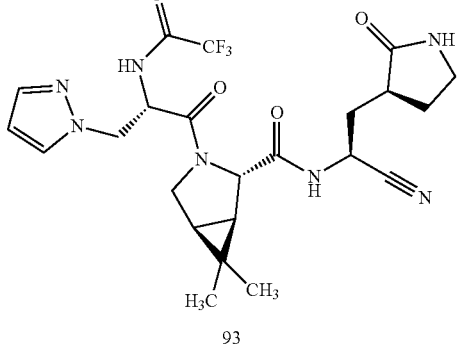

Step 1. Synthesis of (1R,2S,5S)—N-{(2S)-1-amino-1-oxo-3-[(3S)-2-oxopyrrolidin-3-yl]propan-2-yl}-6,6-dimethyl-3-azabicyclo[3.1.0]hexane-2-carboxamide, hydrochloride salt (C67, HCl salt)

To a solution of C66 (9.97 g, 24.4 mmol) in dichloromethane (50 mL) was added a solution of hydrogen chloride in 1,4-dioxane (4 M; 90 mL). The reaction mixture was stirred at room temperature (25° C.) for 2 hours, whereupon LCMS analysis indicated conversion to C67: LCMS m/z 309.0 [M+H]$^+$. Concentration in vacuo afforded C67, HCl salt as a white solid. Yield: 8.10 g, 23.5 mmol, 96%. $^1$H NMR (400 MHz, DMSO-d$_6$) δ 10.20-10.08 (m, 1H), 8.93 (d, J=8.0 Hz, 1H), 8.86-8.71 (m, 1H), 7.68 (br s, 1H), 7.63 (br s, 1H), 7.12 (br s, 1H), 4.30 (ddd, J=10.9, 8.1, 4.1 Hz, 1H), 4.09-4.02 (m, 1H), 3.63-3.53 (m, 1H, assumed; partially obscured by water peak), 3.22-2.99 (m, 3H), 2.34-2.22 (m, 1H), 2.21-2.11 (m, 1H), 2.01 (ddd, J=13.6, 11.1, 3.6 Hz, 1H), 1.80-1.66 (m, 3H), 1.55 (ddd, J=13.6, 11.4, 4.1 Hz, 1H), 1.08 (s, 3H), 1.05 (s, 3H).

Step 2. Synthesis of tert-butyl [(2S)-1-[(1R,2S,5S)-2-({(2S)-1-amino-1-oxo-3-[(3S)-2-oxopyrrolidin-3-yl]propan-2-yl}carbamoyl)-6,6-dimethyl-3-azabicyclo[3.1.0]hexan-3-yl]-1-oxo-3-(1H-pyrazol-1-yl)propan-2-yl]carbamate (C80)

A 0° C. solution of C67, HCl salt (300 mg, 0.870 mmol) and N-(tert-butoxycarbonyl)-3-(1H-pyrazol-1-yl)-L-alanine (222 mg, 0.870 mmol) in N,N-dimethylformamide (10 mL) was treated with O-(7-azabenzotriazol-1-yl)-N,N,N',N'-tetramethyluronium hexafluorophosphate (HATU; 430 mg, 1.13 mmol) and 4-methylmorpholine (264 mg, 2.61 mmol). After the reaction mixture had been stirred at 0° C. for 2 hours, it was diluted with water (50 mL) and extracted with ethyl acetate (20 mL). The aqueous layer was then saturated by the addition of solid sodium sulfate and extracted with a mixture of dichloromethane and methanol (10:1, 4×30 mL). The combined organic layers were concentrated in vacuo and subjected to silica gel chromatography twice (Gradient #1: 0% to 10% methanol in dichloromethane; Gradient #2: 0% to 25% methanol in dichloromethane), affording C80 as a canary-yellow solid. Yield: 340 mg, 0.623 mmol, 72%. LCMS m/z 546.1 [M+H]$^+$. $^1$H NMR (400 MHz, DMSO-d$_6$) δ 8.29 (br d, J=8.6 Hz, 1H), 7.70-7.66 (m, 1H), 7.64 (s, 1H), 7.51 (br s, 1H), 7.38 (br d, J=8.2 Hz, 1H), 7.15-7.06 (m, 2H), 6.23-6.19 (m, 1H), 4.53-4.43 (m, 1H), 4.34-4.18 (m, 3H), 4.17 (s, 1H), 3.76 (d, half of AB quartet, J=10.5 Hz, 1H), 3.65 (dd, component of ABX system, J=10.4, 5.4 Hz, 1H), 3.20-3.06 (m, 2H), 2.36-2.24 (m, 1H), 2.19-2.08 (m, 1H), 2.02-1.90 (m, 1H), 1.71-1.55 (m, 2H), 1.53-1.46 (m, 1H), 1.39 (d, half of AB quartet, J=7.6 Hz, 1H), 1.30 (s, 9H), 1.01 (s, 3H), 0.89 (s, 3H).

Step 3. Synthesis of (1R,2S,5S)—N-{(2S)-1-amino-1-oxo-3-[(3S)-2-oxopyrrolidin-3-yl]propan-2-yl}-6,6-dimethyl-3-[3-(1H-pyrazol-1-yl)-L-alanyl]-3-azabicyclo[3.1.0]hexane-2-carboxamide, hydrochloride salt (C81)

A solution of hydrogen chloride in 1,4-dioxane (4 M; 15 mL) was added to a 0° C. solution of C80 (340 mg, 0.623 mmol) in dichloromethane (4 mL). After the reaction mixture had been stirred at 20° C. for 1 hour, it was filtered, and the filter cake was washed with dichloromethane (3×10 mL). The combined filtrates were concentrated in vacuo to provide C81 as a white solid. Yield: 244 mg, 0.506 mmol, 81%. LCMS m/z 446.0 [M+H]$^+$. $^1$H NMR (400 MHz, DMSO-$d_6$), characteristic peaks: δ 8.57-8.48 (m, 3H), 8.42 (br d, J=8.6 Hz, 1H), 7.81 (d, J=2.3 Hz, 1H), 7.65 (br s, 1H), 7.58 (d, J=1.9 Hz, 1H), 7.35 (br s, 1H), 7.09 (br s, 1H), 6.27 (dd, J=2, 2 Hz, 1H), 4.59 (dd, component of ABX system, J=14.4, 4.7 Hz, 1H), 4.54-4.41 (m, 2H), 4.36-4.25 (m, 1H), 4.30 (s, 1H), 3.66-3.60 (m, 1H), 3.42-3.33 (m, 1H), 3.21-3.03 (m, 2H), 2.31-2.20 (m, 1H), 2.18-2.06 (m, 1H), 1.97 (ddd, J=13.5, 11.5, 3.7 Hz, 1H), 1.46 (dd, component of ABX system, J=7.7, 5.3 Hz, 1H), 1.41 (d, half of AB quartet, J=7.7 Hz, 1H), 1.01 (s, 3H), 0.92 (s, 3H).

Step 4. Synthesis of (1R,2S,5S)—N-{(1S)-1-cyano-2-[(3S)-2-oxopyrrolidin-3-yl]ethyl}-6,6-dimethyl-3-[3-(1H-pyrazol-1-yl)-N-(trifluoroacetyl)-L-alanyl]-3-azabicyclo[3.1.0]hexane-2-carboxamide (93)

A 0° C. solution of C81 (120 mg, 0.249 mmol) in dichloromethane (6.0 mL) was treated with pyridine (170 mg, 2.15 mmol), followed by addition of a solution of trifluoroacetic anhydride (158 mg, 0.752 mmol) in dichloromethane (2.0 mL). The reaction mixture was then warmed to 20° C. and allowed to stir for 3 hours, whereupon it was diluted with water (20 mL) and extracted with dichloromethane (3×20 mL). The combined organic layers were washed with hydrochloric acid (1 M; 20 mL) and with saturated aqueous sodium chloride solution (2×20 mL), dried, filtered, and concentrated in vacuo. Silica gel chromatography (Gradient: 0% to 10% methanol in dichloromethane), followed by supercritical fluid chromatography [Column: Chiral Technologies Chiralpak AD, 30×250 mm, 10 μm; Mobile phase: 4:1 carbon dioxide/(ethanol containing 0.1% ammonium hydroxide); Flow rate: 60 mL/minute], provided (1R,2S,5S)—N-{(1S)-1-cyano-2-[(3S)-2-oxopyrrolidin-3-yl]ethyl}-6,6-dimethyl-3-[3-(1H-pyrazol-1-yl)-N-(trifluoroacetyl)-L-alanyl]-3-azabicyclo[3.1.0]hexane-2-carboxamide (93) as a white solid. Yield: 15.0 mg, 28.6 μmol, 11%. LCMS m/z 524.0 [M+H]$^+$. $^1$H NMR (500 MHz, DMSO-$d_6$) δ 10.03 (br s, 1H), 8.92 (d, J=8.0 Hz, 1H), 7.74 (br s, 1H), 7.69 (d, J=2.3 Hz, 1H), 7.51 (d, J=1.9 Hz, 1H), 6.23 (dd, J=2, 2 Hz, 1H), 5.01-4.93 (m, 1H), 4.91-4.83 (m, 1H), 4.49-4.39 (m, 2H), 4.13 (s, 1H), 3.73 (dd, component of ABX system, J=10.4, 5.4 Hz, 1H), 3.60 (d, half of AB quartet, J=10.4 Hz, 1H), 3.21-3.09 (m, 2H), 2.40-2.31 (m, 1H), 2.20-2.10 (m, 2H), 1.79 (ddd, J=13.7, 9.5, 6.8 Hz, 1H), 1.76-1.66 (m, 1H), 1.56 (dd, J=7.5, 5.4 Hz, 1H), 1.36 (d, half of AB quartet, J=7.6 Hz, 1H), 1.02 (s, 3H), 0.85 (s, 3H).

Example 94

(1R,2S,5S)—N-{(1S)-1-Cyano-2-[(3S)-2-oxopyrrolidin-3-yl]ethyl}-3-[(2S)-4,4-difluoro-2-(2,2,2-trifluoroacetamido)butanoyl]-6,6-dimethyl-3-azabicyclo[3.1.0]hexane-2-carboxamide (94)

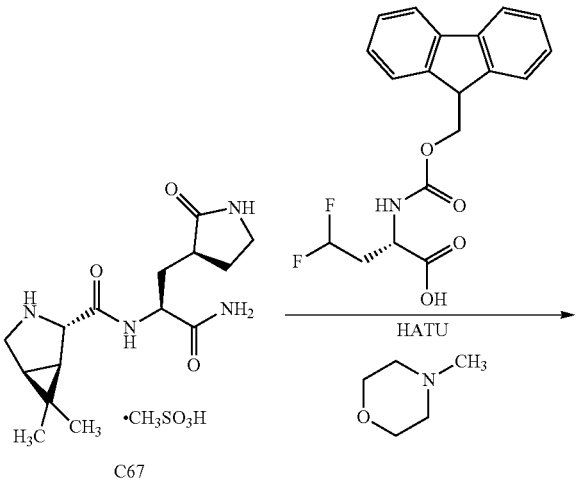

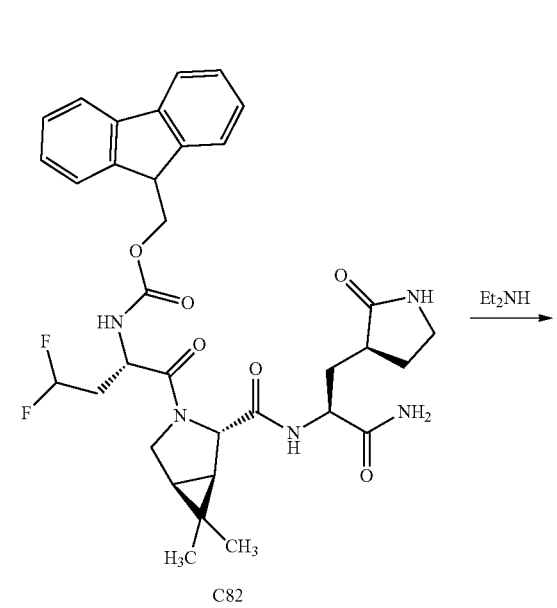

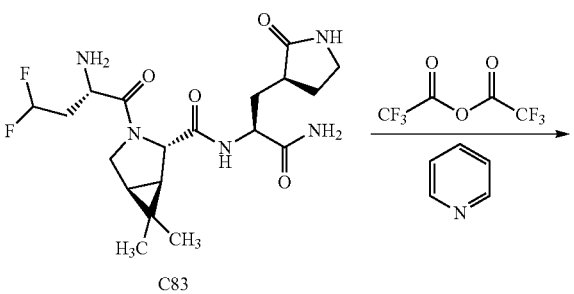

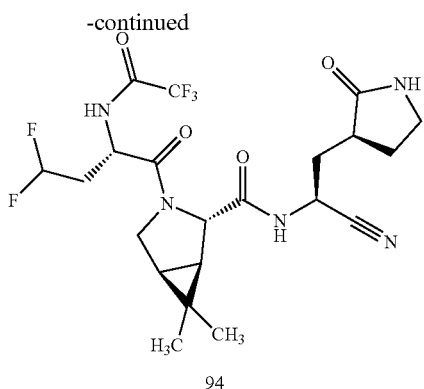

94

Step 1. Synthesis of 9H-fluoren-9-ylmethyl {(2S)-1-[(1R,2S,5S)-2-({(2S)-1-amino-1-oxo-3-[(3S)-2-oxopyrrolidin-3-yl]propan-2-yl}carbamoyl)-6,6-dimethyl-3-azabicyclo[3.1.0]hexan-3-yl]-4,4-difluoro-1-oxobutan-2-yl}carbamate (C82)

To a 0° C. solution of C67 (230 mg, 0.569 mmol) and (2S)-2-{[(9H-fluoren-9-ylmethoxy)carbonyl]amino}-4,4-difluorobutanoic acid (247 mg, 0.684 mmol) in N,N-dimethylformamide (5 mL) was added O-(7-azabenzotriazol-1-yl)-N,N,N',N'-tetramethyluronium hexafluorophosphate (HATU; 281 mg, 0.739 mmol) in one portion; 4-methylmorpholine (173 mg, 1.71 mmol) was then added drop-wise. After the reaction mixture had been stirred at 0° C. for 10 minutes, it was warmed to room temperature (20° C.) and stirring was continued for 2 hours, whereupon the reaction mixture was poured into ice water (15 mL) and extracted with ethyl acetate (2×15 mL). The combined organic layers were sequentially washed with 1 M hydrochloric acid, saturated aqueous sodium bicarbonate solution, and saturated aqueous sodium chloride solution, dried over sodium sulfate, filtered, concentrated in vacuo, and purified via silica gel chromatography (Gradient: 0% to 10% methanol in dichloromethane) to afford C82 as a white solid. Yield: 245 mg, 0.376 mmol, 66%. LCMS m/z 652.5 [M+H]$^+$. $^1$H NMR (400 MHz, chloroform-d) δ 8.86 (br s, 1H), 7.74 (d, J=7.6 Hz, 2H), 7.58-7.51 (m, 2H), 7.38 (dd, J=7.4, 7.4 Hz, 2H), 7.33-7.25 (m, 2H, assumed; partially obscured by solvent peak), 7.08 (br s, 1H), 6.49-6.32 (m, 1H), 6.17-5.79 (m, 3H), 4.78-4.67 (m, 1H), 4.41-4.24 (m, 4H), 4.22-4.07 (m, 2H), 3.83 (d, J=10.5 Hz, 1H), 3.45-3.32 (m, 2H), 2.62-2.36 (m, 3H), 2.26-2.10 (m, 2H), 1.99-1.83 (m, 2H), 1.53 (d, half of AB quartet, J=7.6 Hz, 1H), 1.51-1.44 (m, 1H), 1.03 (s, 3H), 0.89 (s, 3H).

Step 2. Synthesis of (1R,2S,5S)-3-[(2S)-2-amino-4,4-difluorobutanoyl]-N-{(2S)-1-amino-1-oxo-3-[(3S)-2-oxopyrrolidin-3-yl]propan-2-yl}-6,6-dimethyl-3-azabicyclo[3.1.0]hexane-2-carboxamide (C83)

To a 0° C. suspension of C82 (195 mg, 0.299 mmol) in dichloromethane (3 mL) was added a solution of diethylamine (32.8 mg, 0.448 mmol) in dichloromethane (0.5 mL). The reaction mixture was stirred at 30° C. for 16 hours, whereupon it was combined with a similar reaction carried out using C82 (50 mg, 77 μmol) and concentrated in vacuo. Purification via silica gel chromatography [Gradient: 0% to 10% (10:1 mixture of methanol and ammonium hydroxide) in dichloromethane] afforded C83 as a colorless gum. Combined yield: 149 mg, 0.347 mmol, 92%. LCMS m/z 452.3 [M+Na]$^+$. $^1$H NMR (400 MHz, chloroform-d) δ 8.73 (br d, J=5.3 Hz, 1H), 7.11 (br s, 1H), 6.03 (tdd, J=56.8, 6.2, 3.0 Hz, 1H), 5.64 (br s, 1H), 5.28 (br s, 1H), 4.35-4.27 (m, 1H), 4.27 (s, 1H), 4.11 (dd, J=10.3, 5.5 Hz, 1H), 3.72 (dd, J=9.3, 4.1 Hz, 1H), 3.61 (d, J=10.3 Hz, 1H), 3.41-3.35 (m, 2H), 2.53-2.36 (m, 3H), 2.20-2.11 (m, 1H), 2.00-1.84 (m, 3H), 1.6-1.45 (m, 2H, assumed; partially obscured by water peak), 1.06 (s, 3H), 0.94 (s, 3H).

Step 3. Synthesis of (1R,2S,5S)—N-{(1S)-1-cyano-2-[(3S)-2-oxopyrrolidin-3-yl]ethyl}-3-[(2S)-4,4-difluoro-2-(2,2,2-trifluoroacetamido)butanoyl]-6,6-dimethyl-3-azabicyclo[3.1.0]hexane-2-carboxamide (94)

To a 0° C. solution of C83 (99 mg, 0.23 mmol) in dichloromethane (4 mL) were added pyridine (146 mg, 1.85 mmol) and a solution of trifluoroacetic anhydride (194 mg, 0.924 mmol) in dichloromethane (2 mL). The reaction mixture was stirred at room temperature (15° C.) for 20 hours, treated with additional pyridine (30 mg, 0.38 mmol), and stirred at room temperature (15° C.) for a further 16 hours. It was then partitioned between dichloromethane (15 mL) and hydrochloric acid (1 M; 15 mL), and the organic layer was washed with saturated aqueous sodium bicarbonate solution (15 mL) and with saturated aqueous sodium chloride solution (10 mL), dried, filtered, and concentrated in vacuo. The residue was combined with the product from a similar reaction carried out using C83 (50 mg, 0.12 mmol) and purified using reversed-phase HPLC (Column: Waters XBridge BEH C18, 25×150 mm, 5 μm; Mobile phase A: water containing 0.05% ammonium hydroxide (v/v); Mobile phase B: acetonitrile; Gradient: 23% to 63% B). (1R,2S,5S)—N-{(1S)-1-Cyano-2-[(3S)-2-oxopyrrolidin-3-yl]ethyl}-3-[(2S)-4,4-difluoro-2-(2,2,2-trifluoroacetamido)butanoyl]-6,6-dimethyl-3-azabicyclo[3.1.0]hexane-2-carboxamide (94) was isolated as a white solid. Combined yield: 28.8 mg, 56.8 μmol, 16%. LCMS m/z 508.0 [M+H]$^+$. $^1$H NMR (400 MHz, DMSO-d$_6$) δ 10.01 (br s, 1H), 8.96 (d, J=8.0 Hz, 1H), 7.72 (s, 1H), 6.16 (tt, J=55.9, 4.6 Hz, 1H), 4.99-4.90 (m, 1H), 4.65-4.57 (m, 1H), 4.14 (s, 1H), 3.85 (dd, component of ABX system, J=10.2, 5.4 Hz, 1H), 3.67 (d, half of AB quartet, J=10.3 Hz, 1H), 3.21-3.04 (m, 2H), 2.42-2.19 (m, 3H), 2.17-2.04 (m, 2H), 1.83-1.64 (m, 2H), 1.60 (dd, J=7.6, 5.3 Hz, 1H), 1.35 (d, half of AB quartet, J=7.6 Hz, 1H), 1.03 (s, 3H), 0.89 (s, 3H).

Example 95
N-(Methoxycarbonyl)-3-methyl-L-valyl-(4R)—N-
{(1S)-1-cyano-2-[(3S)-2-oxopyrrolidin-3-yl]ethyl}-
4-(trifluoromethyl)-L-prolinamide (95)
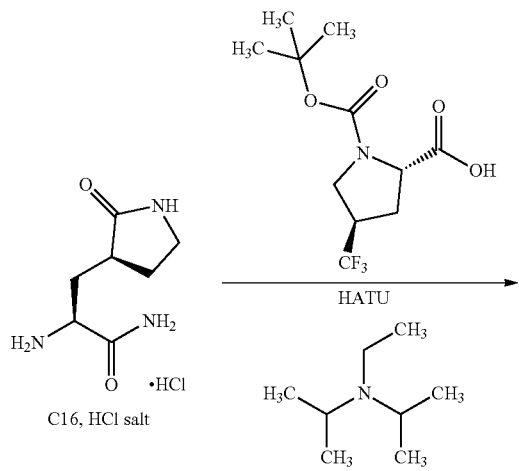
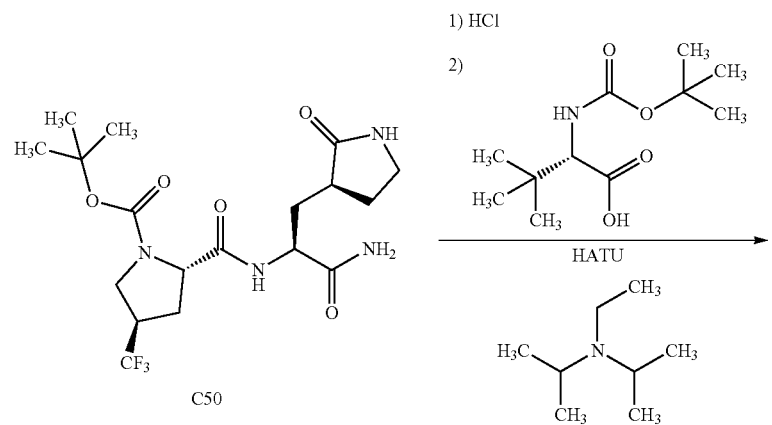
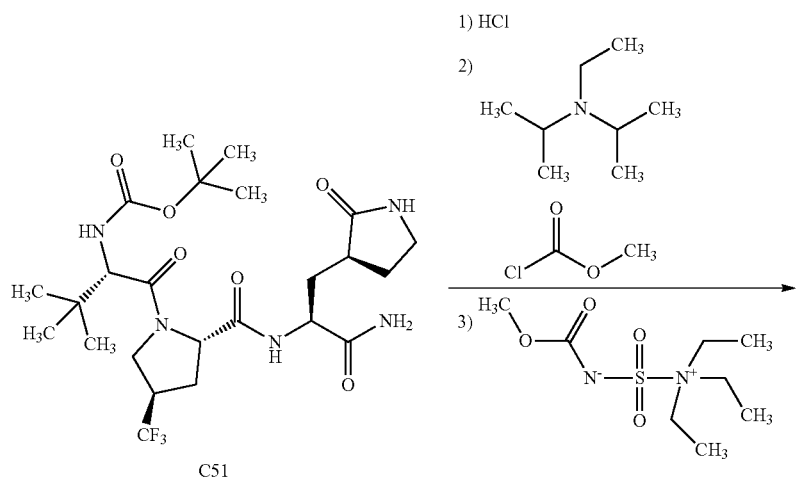

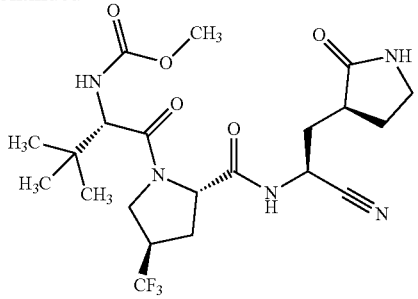

95

Step 1. Synthesis of (4R)-1-(tert-butoxycarbonyl)-4-(trifluoromethyl)-L-prolyl-3-[(3S)-2-oxopyrrolidin-3-yl]-L-alaninamide (C50)

N,N-Diisopropylethylamine (14.8 mL, 85.0 mmol) was added to a −30° C. mixture of (4R)-1-(tert-butoxycarbonyl)-4-(trifluoromethyl)-L-proline (8.00 g, 28.2 mmol), C16, HCl salt (6.45 g, 31.1 mmol), and O-(7-azabenzotriazol-1-yl)-N,N,N',N'-tetramethyluronium hexafluorophosphate (HATU; 11.8 g, 31.0 mmol) in N,N-dimethylformamide (100 mL). The reaction mixture was allowed to warm to 0° C. over 1 hour, whereupon LCMS analysis indicated the presence of C50: LCMS m/z 437.3 [M+H]$^+$. Aqueous sodium bicarbonate solution (300 mL) was added, and the resulting mixture was extracted with a mixture of 2-propanol and dichloromethane (1:4, 5×100 mL); the combined organic layers were concentrated in vacuo and purified via silica gel chromatography (Gradient: 0% to 100% methanol in dichloromethane), affording C50 as an oil. $^1$H NMR analysis indicated that this material exists as a mixture of rotamers. Yield: 10.9 g, 25.0 mmol, 89%. $^1$H NMR (400 MHz, DMSO-$d_6$), characteristic peaks: δ [8.28 (d, J=8.5 Hz) and 8.22 (d, J=8.2 Hz), total 1H], [7.64 (s) and 7.59 (s), total 1H], [7.38 (br s) and 7.27 (br s), total 1H], 7.05 (br s, 1H), 4.38-4.28 (m, 1H), 4.28-4.17 (m, 1H), 3.45-3.36 (m, 1H), 3.12-3.00 (m, 1H), 2.42-2.03 (m, 4H), 2.02-1.89 (m, 1H), 1.80-1.45 (m, 2H), [1.39 (s) and 1.32 (s), total 9H].

Step 2. Synthesis of N-(tert-butoxycarbonyl)-3-methyl-L-valyl-(4R)-4-(trifluoromethyl)-L-prolyl-3-[(3S)-2-oxopyrrolidin-3-yl]-L-alaninamide (C51)

A solution of hydrogen chloride in 1,4-dioxane (4 M; 80 mL) was added to a solution of C50 (7.00 g, 16.0 mmol) in dichloromethane (15 mL). After the reaction mixture had been stirred at room temperature for 5 minutes, it was concentrated in vacuo to remove solvent, and further evacuated via high vacuum to eliminate residual hydrogen chloride. The residue was mixed with N-(tert-butoxycarbonyl)-3-methyl-L-valine (4.08 g, 17.6 mmol) and O-(7-azabenzotriazol-1-yl)-N,N,N',N'-tetramethyluronium hexafluorophosphate (HATU; 6.71 g, 17.6 mmol) in N,N-dimethylformamide (25 mL), cooled to −30° C., and treated with N,N-diisopropylethylamine (8.38 mL, 48.1 mmol). The reaction mixture was allowed to warm to 0° C. over 1 hour, whereupon LCMS analysis indicated the presence of C51: LCMS m/z 550.4 [M+H]$^+$. The reaction mixture was then diluted with aqueous sodium bicarbonate solution and extracted three times with a 4:1 mixture of dichloromethane and 2-propanol. After the combined organic layers had been concentrated in vacuo, the residue was purified via silica gel chromatography (Gradient: 0% to 30% methanol in dichloromethane), providing C51 as a solid. Yield: 3.95 g, 7.19 mmol, 45%. $^1$H NMR (400 MHz, DMSO-$d_6$), characteristic peaks: δ 8.28 (d, J=8.8 Hz, 1H), 7.55 (s, 1H), 7.29 (br s, 1H), 7.03 (br s, 1H), 6.77 (br d, J=9.1 Hz, 1H), 4.52-4.43 (m, 1H), 4.24 (ddd, J=12.2, 8.7, 3.5 Hz, 1H), 4.12 (d, J=9.2 Hz, 1H), 4.02-3.84 (m, 2H), 3.16-3.08 (m, 1H), 3.08-2.98 (m, 1H), 2.50-2.37 (m, 1H), 2.31-2.20 (m, 1H), 2.19-2.05 (m, 2H), 2.00-1.87 (m, 1H), 1.69-1.55 (m, 1H), 1.55-1.44 (m, 1H), 1.36 (s, 9H), 0.93 (s, 9H).

Step 3. Synthesis of N-(methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide (95)

A mixture of C51 (230 mg, 0.418 mmol) and a solution of hydrogen chloride in 1,4-dioxane (4 M; 2 mL, 8 mmol) was stirred at room temperature for 5 minutes, whereupon the reaction mixture was concentrated in vacuo to remove solvent, then further evacuated using high vacuum to eliminate residual hydrogen chloride. The residue was dissolved in dichloromethane (2 mL), cooled to 0° C., and treated with N,N-diisopropylethylamine (0.219 mL, 1.26 mmol) followed by methyl chloroformate (59.3 mg, 0.628 mmol). After the reaction mixture had been stirred at 0° C. for 10 minutes, it was diluted with aqueous sodium bicarbonate solution and extracted three times with a 4:1 mixture of dichloromethane and 2-propanol; the combined organic layers were dried over magnesium sulfate, filtered, and concentrated in vacuo. The residue was dissolved in dichloromethane (3 mL); after addition of methyl N-(triethylammoniosulfonyl)carbamate, inner salt (Burgess reagent; 299 mg, 1.25 mmol), the reaction mixture was stirred at room temperature for 1 hour. It was then treated with dilute aqueous sodium carbonate solution and extracted 3 times with ethyl acetate. The combined organic layers were dried over magnesium sulfate, filtered, and purified via chromatography on silica gel (Gradient: 50% to 100% ethyl acetate in heptane). The resulting material was slurried in heptane (4 mL) at 50° C. for 2 hours, cooled to room temperature, and stirred at room temperature overnight; collection of the solid provided N-(methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide (95) as a solid. Yield: 123 mg, 0.251 mmol, 60%. LCMS m/z 490.4 [M+H]$^+$. $^1$H NMR (400 MHz, DMSO-$d_6$) δ 9.02 (d, J=8.6 Hz, 1H), 7.65 (s, 1H), 7.27 (br d, J=8.7 Hz, 1H), 4.94 (ddd, J=11.1, 8.5, 5.0 Hz, 1H), 4.36 (dd, J=7.3, 7.2 Hz, 1H), 4.14 (d, J=8.7 Hz, 1H), 4.00-3.91 (m, 2H), 3.52 (s, 3H), 3.46-3.34 (m, 1H, assumed; partially obscured by water peak), 3.18-2.98 (m, 2H), 2.5-2.39 (m, 1H, assumed; partially obscured by solvent peak), 2.35-2.23 (m, 1H), 2.22-2.01 (m, 3H), 1.77-1.63 (m, 2H), 0.94 (s, 9H).

Example 96

(1R,2S,5S)—N-{(1R)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (96) and (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13), Solid Form 5

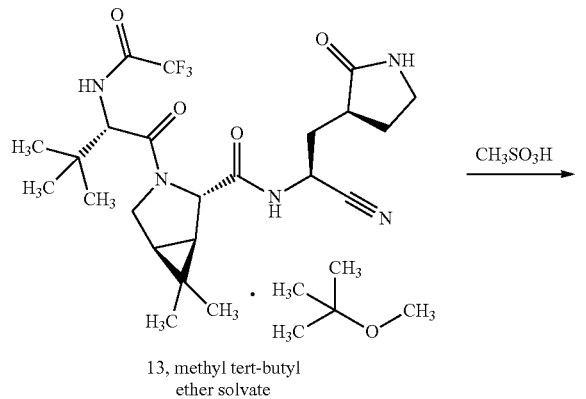

13, methyl tert-butyl ether solvate

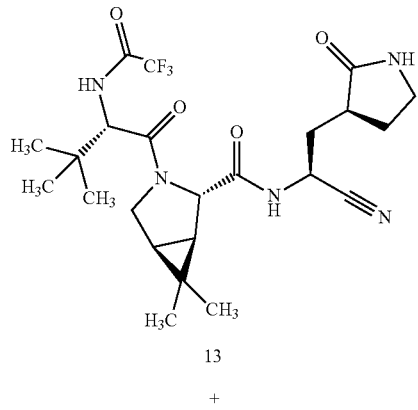

13

+

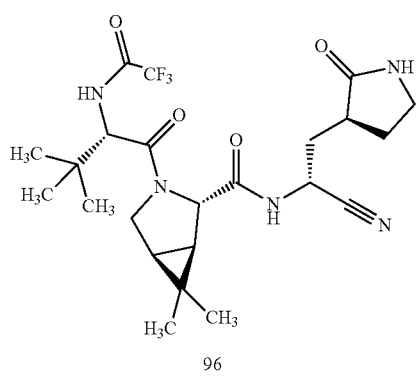

96

To a solution of 13, methyl tert-butyl ether solvate (from Alternate Synthesis of Example 13, methyl tert-butyl ether solvate; 15.0 g, 25.5 mmol) in acetonitrile (80 mL) was added methanesulfonic acid (6.4 mL, 99 mmol). The reaction mixture was stirred at room temperature for 4 hours, whereupon it was basified by addition of a mixture of saturated aqueous sodium bicarbonate solution (80 mL) and saturated aqueous sodium chloride solution (10 mL). The resulting mixture was extracted with dichloromethane (2×100 mL), and the combined organic layers were dried over sodium sulfate, filtered, and concentrated in vacuo. Separation of the two epimers was carried out via supercritical fluid chromatography (Column: Chiral Technologies Chiralcel OX-H, 30×250 mm, 5 μm; Mobile phase: 9:1 carbon dioxide/2-propanol; Back pressure: 100 bar; Flow rate: 80 mL/minute). The first-eluting material was recovered (1R,2S,5S)—N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (13). By powder X-ray diffraction analysis, this material was amorphous; this was designated as Solid Form 5. The second-eluting material was obtained as a glass, which was dissolved in dichloromethane, treated with heptane, and concentrated in vacuo to afford (1R,2S,5S)—N—{(1R)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (96) as a solid.

Figure 9:
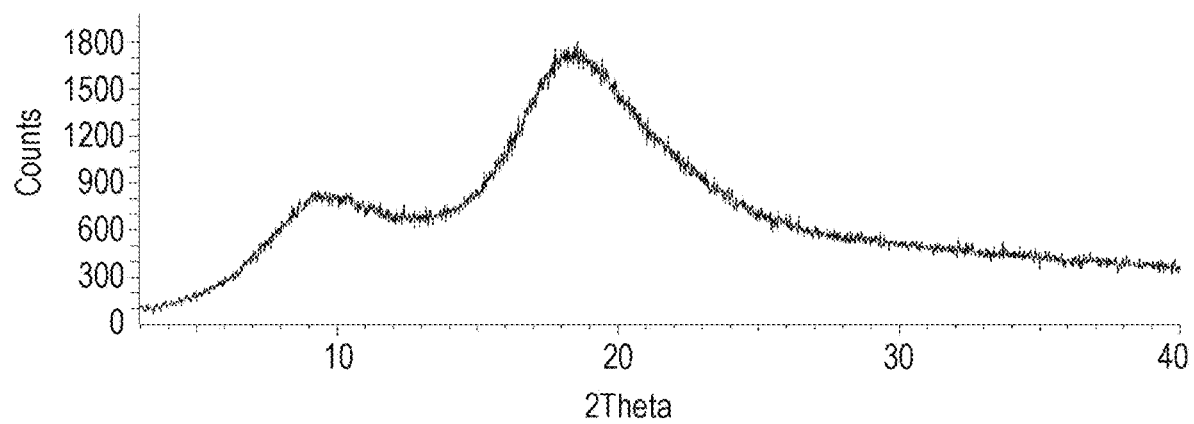
FIG. 9: Powder X-ray Diffraction Pattern of Example 13, Solid Form 5, from Example 96.

Recovered 13—Yield: 6.00 g, 12.0 mmol, 47%. LCMS m/z 500.3 [M+H]$^+$. $^1$H NMR (400 MHz, DMSO-d$_6$) δ 9.46-9.33 (m, 1H), 9.01 (d, J=8.5 Hz, 1H), 7.66 (s, 1H), 5.03-4.91 (m, 1H), 4.46-4.37 (m, 1H), 4.16 (s, 1H), 3.97-3.86 (m, 1H), 3.69 (d, half of AB quartet, J=10.4 Hz, 1H), 3.19-3.09 (m, 1H), 3.09-2.98 (m, 1H), 2.46-2.33 (m, 1H), 2.21-2.03 (m, 2H), 1.79-1.65 (m, 2H), 1.61-1.53 (m, 1H), 1.32 (d, half of AB quartet, J=7.7 Hz, 1H), 1.03 (s, 3H), 0.98 (s, 9H), 0.85 (s, 3H). Retention time: 3.93 minutes (Analytical conditions. Column: Chiral Technologies Chiralcel OX-H, 4.6×250 mm, 5 μm; Mobile phase A: carbon dioxide; Mobile phase B: 2-propanol; Gradient: 5% B for 1.00 minute, followed by 5% to 60% B over 8.00 minutes; Back pressure: 120 bar; Flow rate: 3.0 mL/minute). The powder X-ray diffraction pattern for this amorphous material is given in FIG. 9. The method of collection of the powder X-ray diffraction data is described in Alternate Synthesis of Example 13, methyl tert-butyl ether solvate, Step 8.

96—Yield: 2.58 g, 5.16 mmol, 20%. LCMS m/z 500.3 [M+H]$^+$. $^1$H NMR (400 MHz, DMSO-d$_6$) δ 9.42 (d, J=8.4 Hz, 1H), 9.06 (d, J=7.6 Hz, 1H), 7.79 (s, 1H), 4.96-4.86 (m, 1H), 4.41 (d, J=8.7 Hz, 1H), 4.20 (s, 1H), 3.92 (br dd, J=10.7, 5.4 Hz, 1H), 3.66 (d, half of AB quartet, J=10.5 Hz, 1H), 3.22-3.12 (m, 2H), 2.43-2.31 (m, 1H), 2.31-2.20 (m, 1H), 2.16-2.04 (m, 1H), 1.84-1.63 (m, 2H), 1.57-1.49 (m, 1H), 1.32 (d, half of AB quartet, J=7.7 Hz, 1H), 1.00 (br s, 12H), 0.84 (s, 3H). Retention time: 4.20 minutes (Analytical conditions identical to those used for recovered 13 above).

Example 97
(1R,2S,5S)—N-{(1S)-1-Cyano-2-[(3S)-2-oxopyrrolidin-3-yl]ethyl}-6,6-dimethyl-3-[2-(2,2,2-trifluoroacetamido)-3-(trifluoromethyl)pentanoyl]-3-azabicyclo[3.1.0]hexane-2-carboxamide, from C86 (DIAST-2) (97)
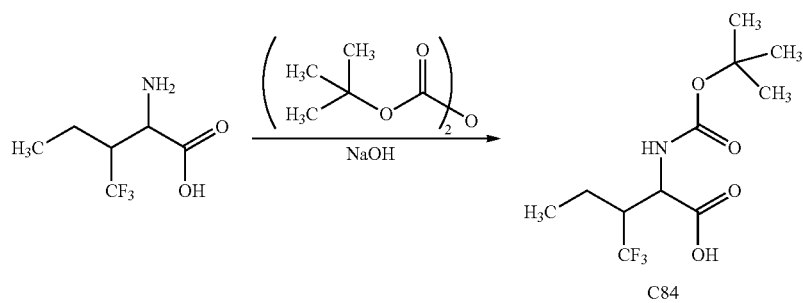
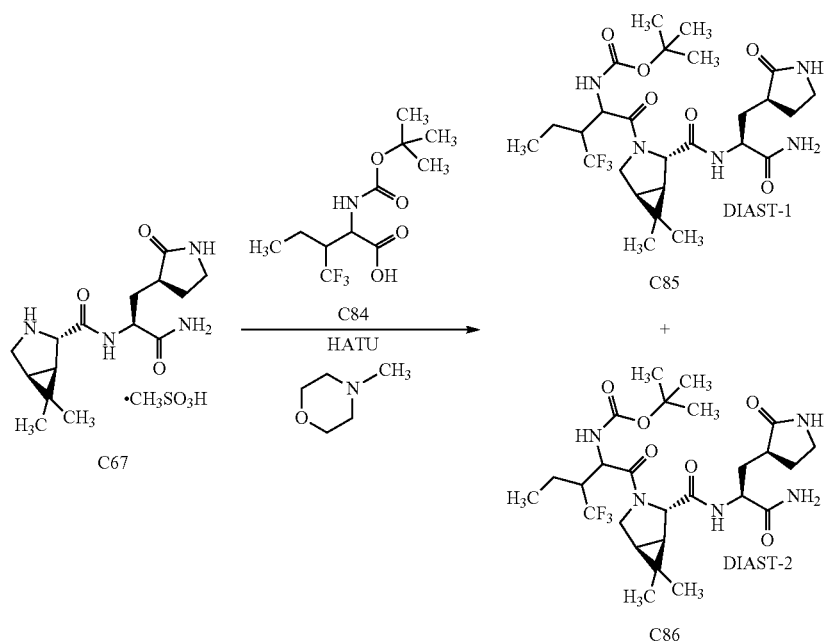
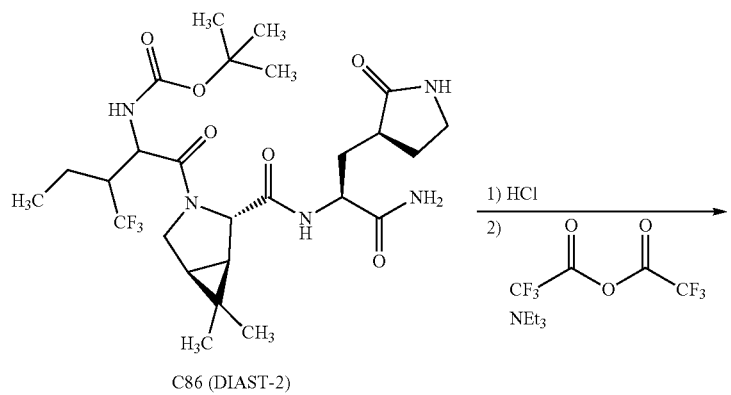

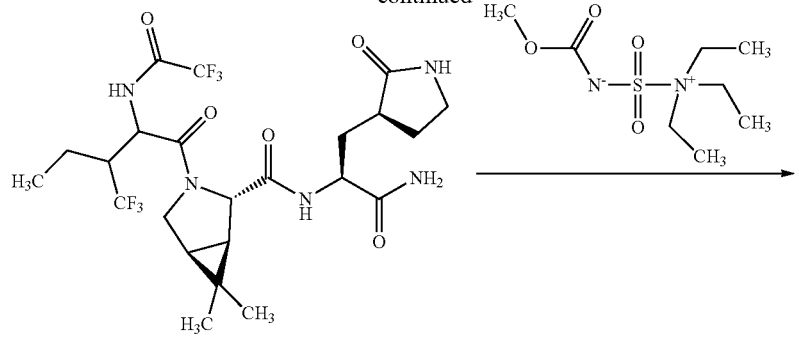

C87 [from C86 (DIAST-2)]

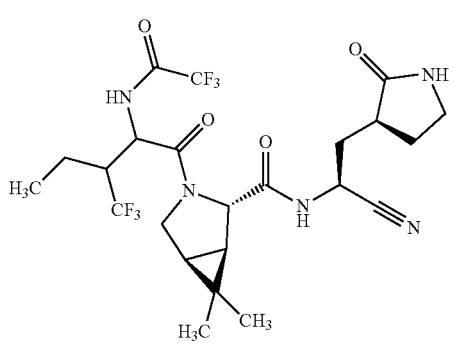

97 [from C86 (DIAST-2)]

Step 1. Synthesis of 2-[(tert-butoxycarbonyl)amino]-3-(trifluoromethyl)pentanoic acid (C84)

Aqueous sodium hydroxide solution (1 M; 1.48 mL, 1.48 mmol) was added to a suspension of 2-amino-3-(trifluoromethyl)pentanoic acid (Wang et al., J. Amer. Chem. Soc. 2003, 125, 6900-6906; 137 mg, 0.740 mmol) in 1,4-dioxane (3 mL) and the resulting mixture was cooled to 0° C. Di-tert-butyl dicarbonate (0.204 mL, 0.888 mmol) was slowly added, whereupon the reaction mixture was stirred at room temperature overnight. After dilution with ethyl acetate, the reaction mixture was cooled in an ice bath and then acidified to pH 2 by addition of a 1 M aqueous solution of potassium hydrogen sulfate. The aqueous layer was extracted twice with ethyl acetate, and the combined organic layers were dried over magnesium sulfate, filtered, and concentrated in vacuo, affording C84 as a solid. This material was presumed to consist of a mixture of 4 diastereomers, potentially exhibiting rotamers as well. Yield: 197 mg, 0.690 mmol, 93%. LCMS m/z 284.3 [M–H]⁻. $^1$H NMR (400 MHz, DMSO-$d_6$) δ 13.16 (br s, 1H), [7.29 (d, major, J=9.8 Hz) and 6.95-6.85 (m, minor), total 1H], [4.55 (dd, major, J=9.8, 3.3 Hz), 4.46 (br d, minor, J=9.1 Hz), and 4.40 (dd, minor, J=9.4, 4.5 Hz), total 1H], 2.86-2.67 (m, 1H), 1.71-1.47 (m, 2H), 1.39 (br s, 9H), [0.98 (t, minor, J=7.4 Hz) and 0.91 (t, major, J=7.5 Hz), total 3H].

Step 2. Synthesis of tert-butyl {1-[(1R,2S,5S)-2-({(2S)-1-amino-1-oxo-3-[(3S)-2-oxopyrrolidin-3-yl]propan-2-yl}carbamoyl)-6,6-dimethyl-3-azabicyclo[3.1.0]hexan-3-yl]-1-oxo-3-(trifluoromethyl)pentan-2-yl}carbamate, DIAST-1 (C85) and tert-butyl {1-[(1R,2S,5S)-2-({(2S)-1-amino-1-oxo-3-[(3S)-2-oxopyrrolidin-3-yl]propan-2-yl}carbamoyl)-6,6-dimethyl-3-azabicyclo[3.1.0]hexan-3-yl]-1-oxo-3-(trifluoromethyl)pentan-2-yl}carbamate, DIAST-2 (C86)

A 0° C. solution of C84 (128 mg, 0.449 mmol) in a mixture of acetonitrile (2.7 mL) and N,N-dimethylformamide (1.5 mL) was treated with 0-(7-azabenzotriazol-1-yl)-N,N,N',N'-tetramethyluronium hexafluorophosphate (HATU; 176 mg, 0.463 mmol) and 4-methylmorpholine (0.116 mL, 1.06 mmol). After the reaction mixture had been stirred at 0° C. for 30 minutes, C67 (170 mg, 0.420 mmol) was added as a solid, and stirring was continued for 2 hours. The reaction mixture was then diluted with ethyl acetate and water, and washed with saturated aqueous sodium bicarbonate solution. The aqueous layer was extracted twice with ethyl acetate, and the combined organic layers were washed with saturated aqueous sodium chloride solution, dried over magnesium sulfate, filtered, and concentrated in vacuo. The resulting oil was azeotroped twice with heptane and twice with methyl tert-butyl ether, then subjected to silica gel chromatography (Gradient: 0% to 20% methanol in dichloromethane). The first-eluting diastereomer was designated as C85, and the second-eluting diastereomer was designated as C86.

C85 (DIAST-1)—Yield: 77.3 mg, 0.134 mmol, 32%. This material comprised a mixture of isomers or rotamers by $^1$H NMR analysis. LCMS m/z 576.2 [M+H]$^+$. $^1$H NMR (400 MHz, DMSO-d$_6$), characteristic peaks, integrations are approximate: δ [8.35 (d, J=7.9 Hz) and 8.16 (d, J=8.5 Hz), total 1H], 7.62-7.54 (m, 1H), 7.41-7.18 (m, 2H), [7.02 (br s) and 6.98 (br s), total 1H], 4.59-4.50 (m, 1H), 4.29-4.13 (m, 2H), 3.89 (dd, J=10.4, 5.4 Hz, 1H), 3.44 (d, J=10.4 Hz, 1H), 3.20-3.04 (m, 2H), 2.70-2.59 (m, 1H), 2.43-2.31 (m, 1H), 2.21-2.08 (m, 1H), 1.99-1.88 (m, 1H), [1.38 (s) and 1.36 (s), total 9H], 1.01 (br s, 3H), 0.94-0.82 (m, 6H).

C86 (DIAST-2)—Yield: 87.8 mg, 0.153 mmol, 36%. This material was largely a single isomer by $^1$H NMR analysis. LCMS m/z 576.2 [M+H]$^+$. $^1$H NMR (400 MHz, DMSO-d$_6$), characteristic peaks: δ 8.27 (d, J=8.6 Hz, 1H), 7.59 (s, 1H), 7.31 (d, J=9.5 Hz, 1H), 7.22 (br s, 1H), 7.04 (br s, 1H), 4.55 (dd, J=9.5, 5.9 Hz, 1H), 4.30-4.17 (m, 1H), 4.23 (s, 1H), 3.79 (dd, component of ABX system, J=10.1, 5.2 Hz, 1H), 3.71 (d, half of AB quartet, J=10.1 Hz, 1H), 3.09-2.99 (m, 1H), 2.68-2.55 (m, 1H), 2.42-2.30 (m, 1H), 2.17-2.04 (m, 1H), 1.97-1.86 (m, 1H), 1.36 (s, 9H), 1.02 (s, 3H), 0.94-0.83 (m, 6H).

Step 3. Synthesis of (1R,2S,5S)—N-{(2S)-1-amino-1-oxo-3-[(3S)-2-oxopyrrolidin-3-yl]propan-2-yl}-6,6-dimethyl-3-[2-(2,2,2-trifluoroacetamido)-3-(trifluoromethyl)pentanoyl]-3-azabicyclo[3.1.0]hexane-2-carboxamide, from C86 (DIAST-2) (C87)

A solution of C86 (DIAST-2) (87.8 mg, 0.153 mmol) in dichloromethane (1 mL) was treated with a solution of hydrogen chloride in 1,4-dioxane (4 M; 0.381 mL, 1.52 mmol). After the reaction mixture had been stirred at room temperature for 40 minutes, methanol (0.5 mL) was added to improve solubility. After another 40 minutes, a solution of hydrogen chloride in 1,4-dioxane (4 M; 0.10 mL, 0.4 mmol) was added; 30 minutes later, LCMS analysis indicated complete removal of the protecting group: LCMS m/z 476.2 [M+H]$^+$. The reaction mixture was concentrated in vacuo and azeotroped twice with heptane; the residue was triturated twice with diethyl ether, suspended in dichloromethane (1.2 mL) and cooled to 0° C. After addition of triethylamine (42.4 μL, 0.304 mmol), followed by trifluoroacetic anhydride (47.9 μL, 0.339 mmol), the reaction mixture was stirred at 0° C. for 30 minutes, whereupon it was removed from the ice bath and partitioned between water and ethyl acetate. The aqueous layer was extracted with ethyl acetate, and the combined organic layers were washed with saturated aqueous sodium bicarbonate solution and with saturated aqueous sodium chloride solution, dried over magnesium sulfate, filtered, concentrated in vacuo, and azeotroped twice with methyl tert-butyl ether. By $^1$H NMR and LCMS analysis, this material contained a mixture of C87 and the corresponding methyl ester (LCMS m/z 587.4 [M+H]$^+$). $^1$H NMR (400 MHz, DMSO-d$_6$), characteristic peaks for C87: δ 8.31 (d, J=8.7 Hz, 1H), 7.59 (s, 1H), 7.26 (s, 1H), 7.05 (s, 1H), 3.59 (d, half of AB quartet, J=10.0 Hz, 1H), 1.97-1.87 (m, 1H), 1.40 (d, half of AB quartet, J=7.6 Hz, 1H), 1.03 (s, 3H), 0.84 (s, 3H). Purification via chromatography on silica gel (Gradient: 0% to 20% methanol in dichloromethane), followed by azeotroping of the resulting oil with heptane, followed by azeotroping with a mixture of diethyl ether and heptane, afforded C87 as a white solid. Yield: 17.9 mg, 31.3 μmol, 20%. LCMS m/z 572.0 [M+H]$^+$.

Step 4. Synthesis of (1R,2S,5S)—N-{(1S)-1-cyano-2-[(3S)-2-oxopyrrolidin-3-yl]ethyl}-6,6-dimethyl-3-[2-(2,2,2-trifluoroacetamido)-3-(trifluoromethyl)pentanoyl]-3-azabicyclo[3.1.0]hexane-2-carboxamide, from C86 (DIAST-2) (97)

Methyl N-(triethylammoniosulfonyl)carbamate, inner salt (Burgess reagent; 18.8 mg, 78.9 μmol) was added to a solution of C87 (18 mg, 31 μmol) in ethyl acetate (0.8 mL). After the reaction mixture had been stirred at room temperature for 1 hour, a spatula scoop of methyl N-(triethylammoniosulfonyl)carbamate, inner salt (Burgess reagent) was again added. Stirring was continued for 2 hours, whereupon the reaction mixture was filtered, and the filter cake was rinsed with ethyl acetate. The combined filtrates were washed with saturated aqueous sodium bicarbonate solution, and the aqueous layer was extracted once with ethyl acetate; the combined organic layers were washed with saturated aqueous sodium chloride solution, dried over magnesium sulfate, filtered, and concentrated in vacuo to provide the crude product. $^1$H NMR (600 MHz, DMSO-d$_6$), major component: δ 9.90 (d, J=8.8 Hz, 1H), 8.85 (d, J=8.1 Hz, 1H), 7.56 (br s, 1H), 4.97-4.89 (m, 2H), 4.17 (s, 1H), 3.89 (dd, J=10.1, 5.4 Hz, 1H), 3.62 (d, J=10.1 Hz, 1H), 3.21-3.14 (m, 1H), 3.12-3.06 (m, 1H), 2.92-2.82 (m, 1H), 2.43-2.35 (m, 1H), 2.18-2.10 (m, 2H), 1.78 (ddd, J=13.6, 9.6, 6.0 Hz, 1H), 1.75-1.66 (m, 2H), 1.62-1.55 (m, 2H), 1.35 (d, half of AB quartet, J=7.7 Hz, 1H), 1.04 (s, 3H), 0.97-0.92 (t, J=7.6 Hz, 3H), 0.85 (s, 3H). This material was purified via reversed-phase HPLC (Column: Waters Sunfire C18, 19×100 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 8.54 minutes, followed by 95% B for 1.46 minutes; Flow rate: 25 mL/minute) to afford (1R,2S,5S)—N-{(1S)-1-cyano-2-[(3S)-2-oxopyrrolidin-3-yl]ethyl}-6,6-dimethyl-3-[2-(2,2,2-trifluoroacetamido)-3-(trifluoromethyl)pentanoyl]-3-azabicyclo[3.1.0]hexane-2-carboxamide, from C86 (DIAST-2) (97). Yield: 8.3 mg, 15 μmol, 48%. LCMS m/z 554.6 [M+H]$^+$. Retention time: 2.72 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 98
(1R,2S,5S)—N-{(1S)-1-Cyano-2-[(3S)-2-oxopyrrolidin-3-yl]ethyl}-6,6-dimethyl-3-[2-(2,2,2-trifluoroacetamido)-3-(trifluoromethyl)pentanoyl]-3-azabicyclo[3.1.0]hexane-2-carboxamide, from C85 (DIAST-1) (98)
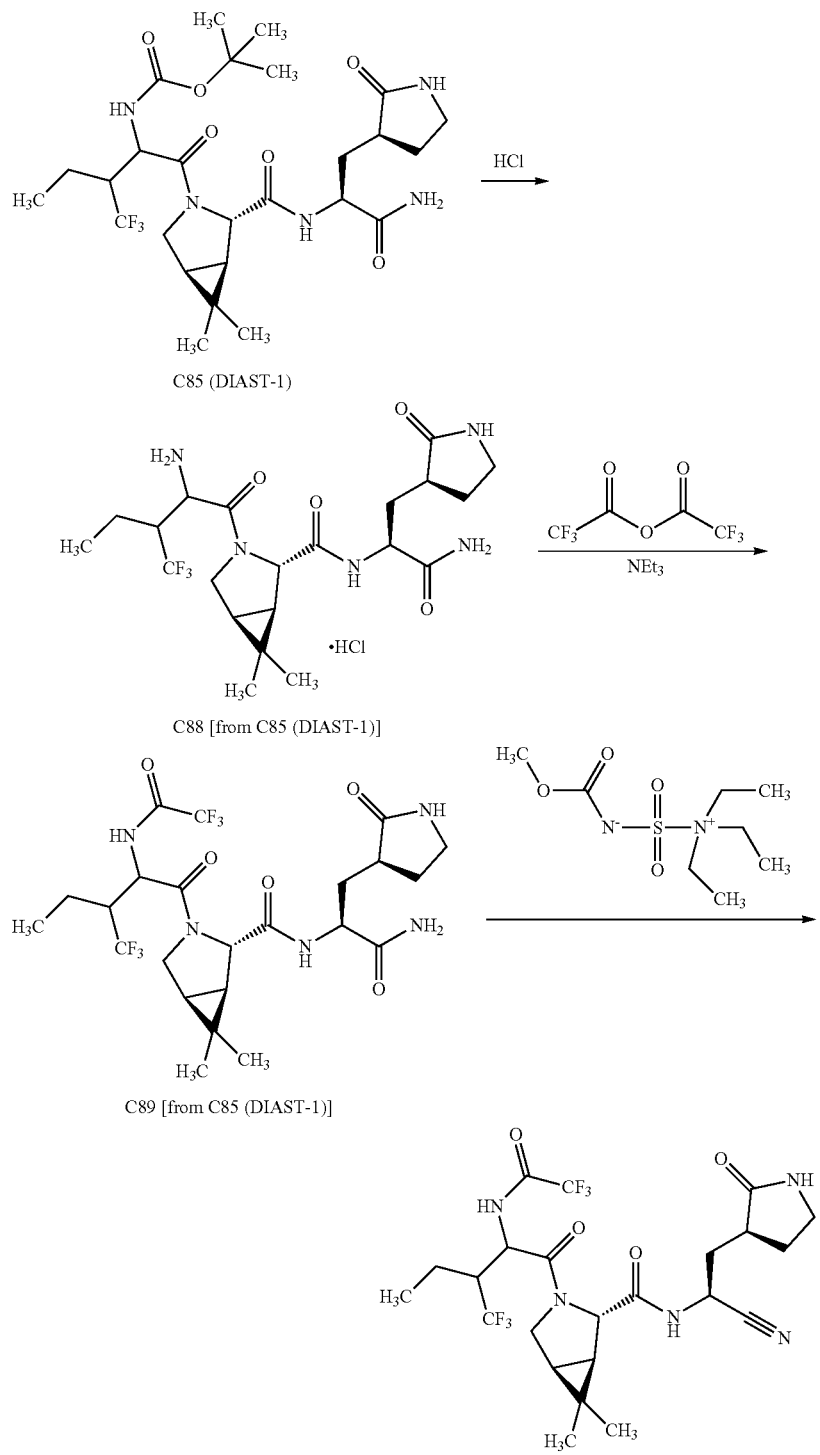

Step 1. Synthesis of (1R,2S,5S)—N-{(2S)-1-amino-1-oxo-3-[(3S)-2-oxopyrrolidin-3-yl]propan-2-yl}-3-[2-amino-3-(trifluoromethyl)pentanoyl]-6,6-dimethyl-3-azabicyclo[3.1.0]hexane-2-carboxamide, hydrochloride salt, from C85 (DIAST-1) (C88)

A solution of hydrogen chloride in 1,4-dioxane (4 M; 0.336 mL, 1.34 mmol) was added to a solution of C85 (DIAST-1) (77.3 mg, 0.134 mmol) in dichloromethane (1 mL). After the reaction mixture had been stirred at room temperature for 40 minutes, methanol (0.5 mL) was added to improve solubility. Stirring was continued for 2 hours, whereupon LCMS analysis indicated that the deprotection was complete: LCMS m/z 476.2 [M+H]$^+$. The reaction mixture was concentrated in vacuo; the residue was azeotroped twice with heptane, then triturated twice with diethyl ether to provide C88 as a white solid. Yield: 54.5 mg, 0.106 mmol, 79%. $^1$H NMR (400 MHz, DMSO-$d_6$), characteristic major peaks: δ 8.53 (br s, 3H), 8.36 (d, J=8.5 Hz, 1H), 7.61 (s, 1H), 7.28 (br s, 1H), 7.06 (br s, 1H), 4.25 (ddd, J=10.9, 8.4, 4.5 Hz, 1H), 4.17 (s, 1H), 4.08 (dd, J=10.5, 5.6 Hz, 1H), 2.80-2.68 (m, 1H), 2.37-2.26 (m, 1H), 2.23-2.13 (m, 1H), 2.05-1.96 (m, 1H), 1.73-1.51 (m, 5H), 1.44 (d, half of AB quartet, J=7.7 Hz, 1H), 1.04 (s, 3H), 0.90 (s, 3H).

Step 2. Synthesis of (1R,2S,5S)—N-{(2S)-1-amino-1-oxo-3-[(3S)-2-oxopyrrolidin-3-yl]propan-2-yl}-6,6-dimethyl-3-[2-(2,2,2-trifluoroacetamido)-3-(trifluoromethyl)pentanoyl]-3-azabicyclo[3.1.0]hexane-2-carboxamide, from C85 (DIAST-1) (C89)

A 0° C. suspension of C88 (54.5 mg, 0.106 mmol) in dichloromethane (1 mL) was treated with triethylamine (26 μL, 0.19 mmol), followed by trifluoroacetic anhydride (19.5 μL, 29.1 mg, 0.138 mmol). After the reaction mixture had been stirred at 0° C. for 1 hour and 10 minutes, trifluoroacetic anhydride (1 equivalent) was added; 30 minutes later, trifluoroacetic anhydride (9.4 μL, 67 μmol) was again added. Stirring was continued for 45 minutes, whereupon LCMS analysis indicated complete conversion to C89: LCMS m/z 572.4 [M+H]$^+$. The reaction mixture was partitioned between water and ethyl acetate, and the aqueous layer was extracted with ethyl acetate. The combined organic layers were washed sequentially with saturated aqueous sodium bicarbonate solution and saturated aqueous sodium chloride solution, dried over magnesium sulfate, filtered, and concentrated in vacuo to provide C89. Yield: 41.2 mg, 72.1 μmol, 68%. $^1$H NMR (400 MHz, DMSO-$d_6$), major component, characteristic peaks: δ 10.04 (d, J=9.3 Hz, 1H), 8.23 (d, J=8.5 Hz, 1H), 7.58 (s, 1H), 7.31 (br s, 1H), 7.01 (br s, 1H), 4.92-4.83 (m, 1H), 4.23 (s, 1H), 3.95 (dd, J=10.2, 5.5 Hz, 1H), 2.98-2.86 (m, 1H), 2.38-2.27 (m, 1H), 1.90 (ddd, J=13.5, 11.2, 4.0 Hz, 1H), 1.39 (d, half of AB quartet, J=7.7 Hz, 1H), 1.02 (s, 3H), 0.90 (s, 3H).

Step 3. Synthesis of (1R,2S,5S)—N-{(1S)-1-cyano-2-[(3S)-2-oxopyrrolidin-3-yl]ethyl}-6,6-dimethyl-3-[2-(2,2,2-trifluoroacetamido)-3-(trifluoromethyl)pentanoyl]-3-azabicyclo[3.1.0]hexane-2-carboxamide, from C85 (DIAST-1) (98)

Methyl N-(triethylammoniosulfonyl)carbamate, inner salt (Burgess reagent; 42.7 mg, 0.179 mmol) was added to a solution of C89 (41.0 mg, 71.7 μmol) in ethyl acetate (0.8 mL). After the reaction mixture had been stirred at room temperature for 1 hour, a spatula scoop of methyl N-(triethylammoniosulfonyl)carbamate, inner salt (Burgess reagent) was added. Stirring was continued for 2 hours, whereupon the reaction mixture was filtered, and the filter cake was rinsed with ethyl acetate. The combined filtrates were washed with saturated aqueous sodium bicarbonate solution, and the aqueous layer was extracted with ethyl acetate; the combined organic layers were washed with saturated aqueous sodium chloride solution, dried over magnesium sulfate, filtered, and concentrated in vacuo to provide the crude product. $^1$H NMR (600 MHz, DMSO-$d_6$), major component, characteristic peaks: δ 10.12 (d, J=9.1 Hz, 1H), 8.99 (d, J=8.1 Hz, 1H), 7.70 (s, 1H), 4.94 (ddd, J=9.4, 8.1, 6.5 Hz, 1H), 4.87 (dd, J=9.0, 9.0 Hz, 1H), 4.11 (s, 1H), 3.96 (dd, J=10.2, 5.6 Hz, 1H), 3.52 (d, J=10.0 Hz, 1H), 3.18-3.07 (m, 2H), 2.98-2.88 (m, 1H), 2.40-2.33 (m, 1H), 1.79-1.52 (m, 4H), 1.61 (dd, J=7.6, 5.5 Hz, 1H), 1.33 (d, half of AB quartet, J=7.7 Hz, 1H), 1.04 (s, 3H), 0.91-0.86 (m, 6H).

Purification of this material via reversed-phase HPLC (Column: Waters Sunfire C18, 19×100 mm, 5 μm; Mobile phase A: 0.05% trifluoroacetic acid in water; Mobile phase B: 0.05% trifluoroacetic acid in acetonitrile; Gradient: 5% to 95% B over 8.54 minutes, followed by 95% B for 1.46 minutes; Flow rate: 25 mL/minute) afforded (1R,2S,5S)—N-{(1S)-1-cyano-2-[(3S)-2-oxopyrrolidin-3-yl]ethyl}-6,6-dimethyl-3-[2-(2,2,2-trifluoroacetamido)-3-(trifluoromethyl)pentanoyl]-3-azabicyclo[3.1.0]hexane-2-carboxamide, from C85 (DIAST-1) (98). Yield: 4.3 mg, 7.8 μmol, 11%. LCMS m/z 554.6 [M+H]$^+$. Retention time: 2.80 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Preparation of 3-tert-butyl 2-methyl (1R,2S,5S)-6,6-dimethyl-3-azabicyclo[3.1.0]hexane-2,3-dicarboxylate (C90)

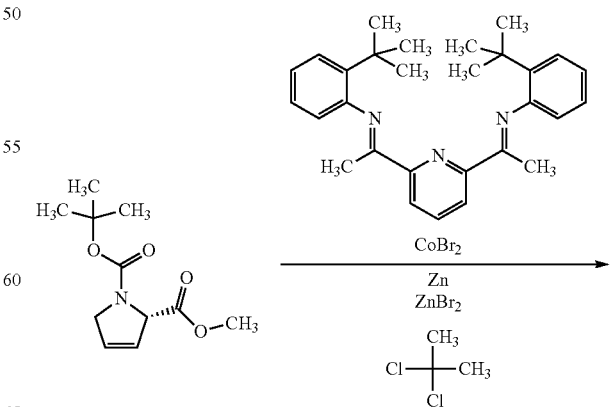

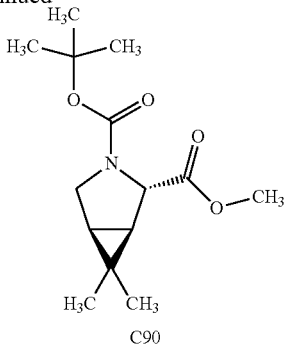

C90

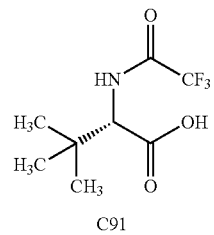

C91

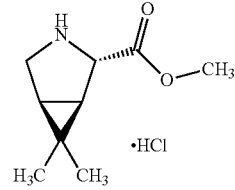

C92

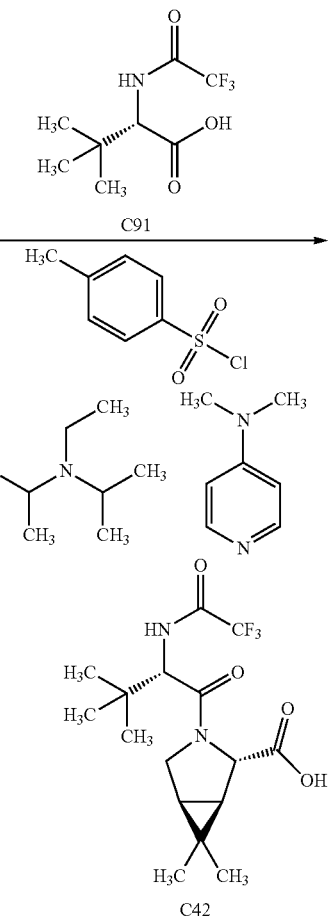

C42

This preparation was carried out using the general procedure reported by C. Uyeda and J. Werth, Angew. Chem. Int. Ed. 2018, 57, 13902-13906. A 3-neck flask equipped with magnetic stirring bar, reflux condenser, thermometer, and nitrogen inlet was charged with cobalt(II) bromide (0.15 equivalents; 0.146 g, 0.667 mmol), (1E,1'E)-1,1'-pyridine-2,6-diylbis[N-(2-tert-butylphenyl)ethanimine] ($^{2\text{-}t\text{-}Bu}$PDI; 0.15 equivalents; 0.284 g, 0.667 mmol) and tetrahydrofuran (11 mL). The thick, green suspension was stirred overnight at room temperature, and zinc (2.4 equivalents; 0.70 g, 11 mmol) and zinc bromide (1.1 equivalents; 1.1 g, 4.9 mmol) were added. After stirring for 15 minutes, the reaction mixture turned purple and a solution of 1-tert-butyl 2-methyl (2S)-2,5-dihydro-1H-pyrrole-1,2-dicarboxylate (1.0 equivalent; 1.0 g, 4.4 mmol) in tetrahydrofuran (7.5 mL) and 2,2-dichloropropane (2.0 equivalents; 1.0 g, 8.8 mmol) were added. The reaction mixture was stirred at room temperature for 5 days, whereupon it was filtered through a pad of diatomaceous earth and rinsed with tetrahydrofuran (10.8 mL). The filtrate was combined with saturated aqueous ammonium chloride solution (3.5 mL) and ethyl acetate (9.5 mL); the layers were then separated and the aqueous phase was extracted with ethyl acetate (8.4 mL). The combined organic extracts were washed with saturated aqueous sodium bicarbonate solution (10.5 mL), dried over magnesium sulfate, filtered, and concentrated to dryness, providing 3-tert-butyl 2-methyl (1R,2S,5S)-6,6-dimethyl-3-azabicyclo[3.1.0]hexane-2,3-dicarboxylate (C90) as a yellow oil. Yield: 0.90 g, 3.3 mmol, 75%. By $^1$H NMR analysis, this material existed as two carbamate rotamers (~3:2 ratio). $^1$H NMR (400 MHz, chloroform-d) δ 4.20 & 4.09 (2 s, 1H), 3.74 & 3.75 (2 s, 3H), 3.68-3.60 (m, 1H), 3.44 & 3.38 (2 d, J=10.9 Hz, 1H), 1.43 & 1.38 (2 s, 9H), 1.38-1.34 (m, 2H), 1.03 & 0.98 & 0.96 (3 s, 6H). ESI-MS (pos.) m/z (%)=255.1 (12.5) [M−Me+H]$^+$, 214.1 (100) [M−t−Bu+H]$^+$, 170.2 (50) [M−Boc+H]$^+$.

Alternate Preparation of C42

(1R,2S,5S)-6,6-Dimethyl-3-[3-methyl-N-(trifluoroacetyl)-L-valyl]-3-azabicyclo[3.1.0]hexane-2-carboxylic acid (C42)

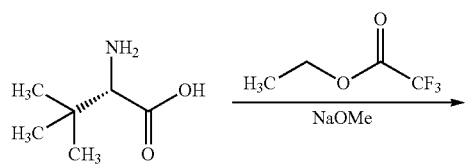

Step 1. Synthesis of 3-methyl-N-(trifluoroacetyl)-L-valine (C91)

A solution of sodium methoxide in methanol (25 weight %; 28.5 mL, 124 mmol) was added to a solution of 3-methyl-L-valine (99%, 15 g, 113 mmol) in methanol (30 mL). Ethyl trifluoroacetate (130 mmol) was then added and the reaction mixture was stirred at 40° C. until the reaction was complete (approximately 2.5 hours), whereupon it was cooled to 20° C. After addition of hydrochloric acid (1 M; 136 ml, 136 mmol), the mixture was diluted with ethyl acetate (150 mL) and the layers were separated. The organic layer was washed twice with saturated aqueous sodium chloride solution, dried over magnesium sulfate, and filtered. Heptane was added to the filtrate, whereupon the solution was concentrated at 50° C. to a volume of 5 mL/g. This procedure was carried out twice; after the second distillation, seed crystals of C91 (50 mg; see below) were added. The resulting solid was collected via filtration, washed with heptane, and dried at 40° C. to provide C91 as an off-white solid. Yield: 22.2 g, 97.7 mmol, 86%.

The seed crystals used above were obtained from a similar reaction carried out using 3-methyl-L-valine; after the organic layer containing C91 had been dried over magnesium sulfate and filtered, concentration in vacuo provided a solid. A portion of this solid was used as the seed material.

Figure 11:
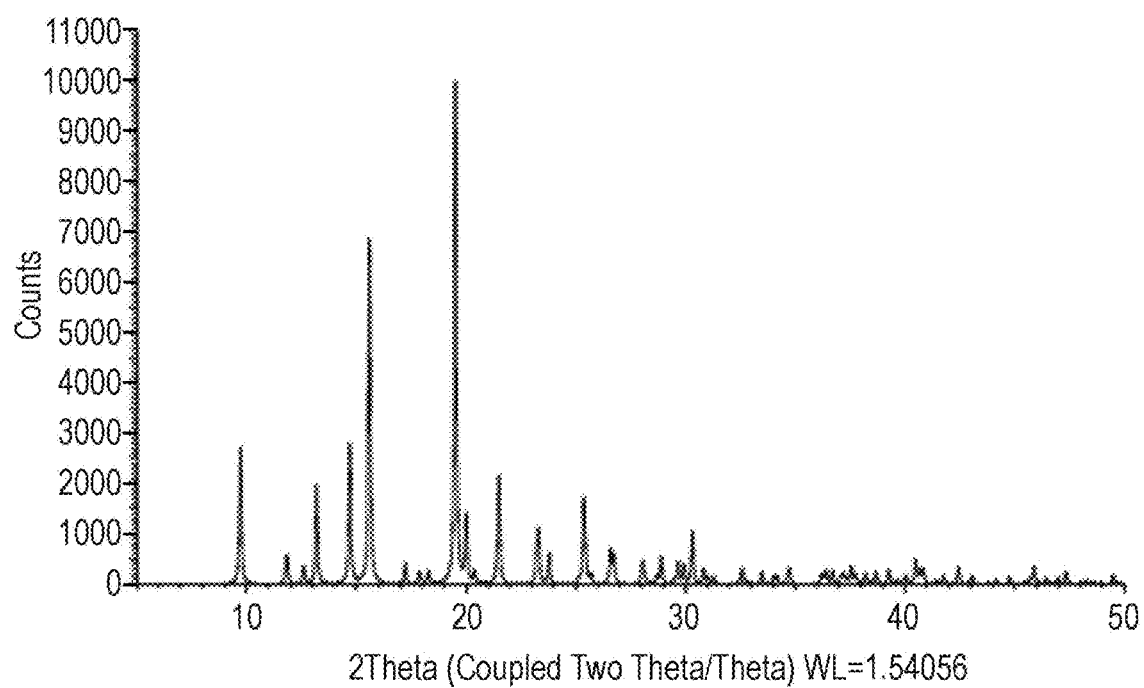
FIG. 11: Powder X-ray Diffraction Pattern of Intermediate C91.

Physicochemical data was obtained on samples of C91 obtained from reactions carried out in the same manner. HRMS-ESI+(m/z): [M+H]$^+$ Calculated for $C_8H_{13}F_3NO_3$, 228.0842; Found, 228.0842. Primary ion observed as $C_8H_{11}F_3NNa_2O_3$[M+Na$^+$]: Calculated, 272.0481; Found, 272.0482. $^1$H NMR (600 MHz, DMSO-d$_6$) δ 13.05 (s, 1H), 9.48 (d, J=8.9 Hz, 1H), 4.21 (d, J=8.9 Hz, 1H), 1.00 (6, 9H). $^{13}$C NMR (150.8 MHz, DMSO-d$_6$) 170.9, 156.6 (q, $^2J_{CF}$=36.9 Hz), 115.8 (q, $^1J_{CF}$=287.7 Hz), 61.0, 33.6, 26.5. The powder X-ray diffraction pattern for C91 is given in FIG. 11; characteristic peaks are listed in Table R.

TABLE R

Selected powder X-ray diffraction peaks for C91

| Angle (°2-theta) | Rel. Intensity |
| --- | --- |
| 9.7 | 27 |
| 11.8 | 6 |
| 12.6 | 3 |
| 13.2 | 20 |
| 14.7 | 28 |
| 15.6 | 69 |
| 17.2 | 4 |
| 17.9 | 2 |
| 18.3 | 2 |
| 19.5 | 100 |
| 20.0 | 14 |
| 20.4 | 2 |
| 21.5 | 22 |
| 23.2 | 8 |
| 23.3 | 11 |
| 23.8 | 6 |
| 25.2 | 1 |
| 25.4 | 17 |
| 25.7 | 2 |
| 26.6 | 7 |
| 26.7 | 6 |
| 28.1 | 4 |
| 28.7 | 2 |
| 28.9 | 5 |
| 29.7 | 4 |
| 29.9 | 4 |
| 30.3 | 10 |
| 30.8 | 3 |
| 31.0 | 1 |
| 31.3 | 1 |
| 32.6 | 3 |
| 33.5 | 2 |
| 34.0 | 1 |
| 34.2 | 2 |
| 34.7 | 3 |
| 36.2 | 2 |
| 36.4 | 3 |
| 36.7 | 2 |
| 37.1 | 1 |
| 37.2 | 2 |
| 37.4 | 1 |
| 37.6 | 3 |
| 37.7 | 1 |
| 38.2 | 2 |
| 38.7 | 2 |

TABLE R-continued

Selected powder X-ray diffraction peaks for C91

| Angle (°2-theta) | Rel. Intensity |
| --- | --- |
| 39.3 | 3 |
| 39.6 | 1 |
| 40.0 | 1 |
| 40.5 | 5 |
| 40.7 | 3 |
| 40.9 | 3 |
| 41.5 | 1 |
| 41.8 | 1 |
| 42.4 | 3 |
| 43.1 | 1 |
| 44.2 | 1 |
| 44.8 | 1 |
| 45.7 | 1 |
| 45.9 | 3 |
| 46.4 | 1 |
| 47.0 | 1 |
| 47.3 | 2 |
| 49.5 | 2 |

Figure 12:
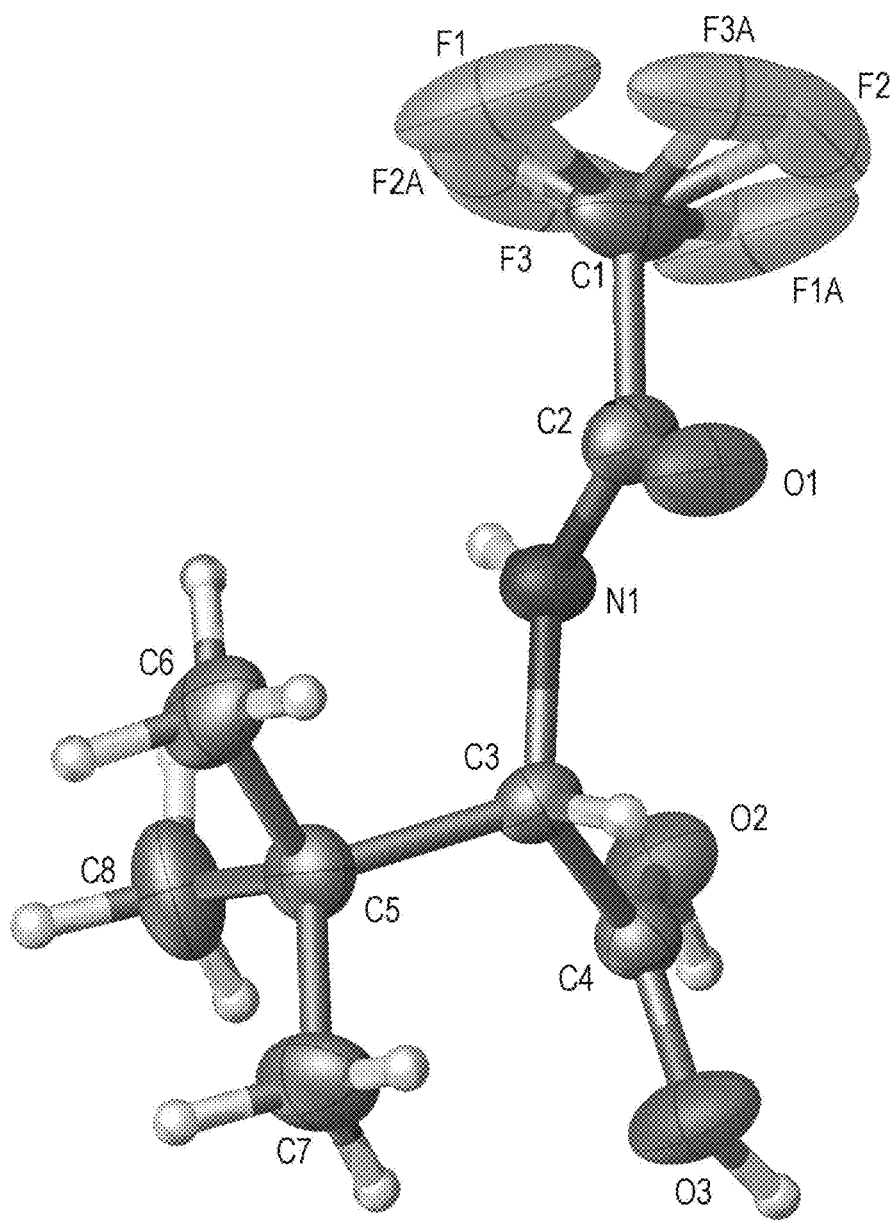
FIG. 12: Single-crystal X-ray Structural Determination of Intermediate C91. ORTEP diagram drawn with displacement parameters at 50% probability.

The crystal for X-ray crystallography was obtained via recrystallization from ethyl acetate and hexane, using seed crystals from the same batch as above. An ORTEP diagram of the single-crystal data for C91 is shown in FIG. 12.

Single-Crystal X-Ray Structural Determination of C91

Single Crystal X-Ray Analysis

Data collection was performed on a Bruker D8 Quest diffractometer at −100° C. Data collection consisted of omega and phi scans.

The structure was solved by intrinsic phasing using SHELX software suite in the tetragonal class chiral space group P4$_1$2$_1$2. The structure was subsequently refined by the full-matrix least squares method. All non-hydrogen atoms were found and refined using anisotropic displacement parameters.

The hydrogen atoms located on nitrogen and oxygen were found from the Fourier difference map and refined with distances restrained. Hydrogen on O2(H2Z) and O3(H3Z) was shared as a charge and refined as 10.5 occupancy each. The remaining hydrogen atoms were placed in calculated positions and were allowed to ride on their carrier atoms. The final refinement included isotropic displacement parameters for all hydrogen atoms.

Population occupancy disorder as a ratio of ~67/33 at the —CF3 segment was identified and modeled accordingly.

Analysis of the absolute structure using likelihood methods (Hooft, 2008) was performed using PLATON (Spek). The results indicate that the absolute structure has been correctly assigned. The method calculates that the probability that the structure is correctly assigned is 100%. The Hooft parameter is reported as 0.02 with an esd (estimated standard deviation) of (4) and the Parson's parameter is reported as 0.02 with an esd of (4).

The final R-index was 4.1%. A final difference Fourier revealed no missing or misplaced electron density.

Pertinent crystal, data collection, and refinement information is summarized in Table S. Atomic coordinates, bond lengths, bond angles, and displacement parameters are listed in Tables T-V.

The list of Software and References employed may be found in Single-crystal X-ray Structural Determination of Example 13, Solid Form 1.

TABLE S

Crystal data and structure refinement for C91.

| | |
|---|---|
| Empirical formula | $C_8H_{12}F_3NO_3$ |
| Formula weight | 227.19 |
| Temperature | 173(2) K |
| Wavelength | 1.54178 Å |
| Crystal system | Tetragonal |
| Space group | $P4_12_12$ |
| Unit cell dimensions | a = 9.9168(6) Å    α = 90° |
| | b = 9.9168(6) Å    β = 90° |
| | c = 22.721(2) Å    γ = 90° |
| Volume | 2234.5(4) Å$^3$ |
| Z | 8 |
| Density (calculated) | 1.351 Mg/m$^3$ |
| Absorption coefficient | 1.184 mm$^{-1}$ |
| F(000) | 944 |
| Crystal size | 0.200 × 0.170 × 0.080 mm$^3$ |
| Theta range for data collection | 4.866 to 70.114° |
| Index ranges | −11 <= h <= 10, −12 <= k <= 12, −27 <= l <= 27 |
| Reflections collected | 48160 |
| Independent reflections | 2122 [$R_{int}$ = 0.0392] |
| Completeness to theta = 67.679° | 99.8% |
| Absorption correction | Empirical |
| Refinement method | Full-matrix least-squares on F$^2$ |
| Data/restraints/parameters | 2122/9/158 |
| Goodness-of-fit on F$^2$ | 1.010 |
| Final R indices [I > 2σ(I)] | R1 = 0.0408, wR2 = 0.1012 |
| R indices (all data) | R1 = 0.0429, wR2 = 0.01039 |
| Absolute structure parameter | 0.03(4) |
| Extinction coefficient | n/a |
| Largest diff. peak and hole | 0.280 and −0.215 e · Å$^{-3}$ |

TABLE T

Atomic coordinates (×10$^4$) and equivalent isotropic displacement parameters (Å$^2$ × 10$^3$) for C91. U(eq) is defined as one-third of the trace of the orthogonalized U$^{ij}$ tensor.

| | x | y | z | U(eq) |
|---|---|---|---|---|
| F(1) | 9781(4) | 8042(4) | 5734(2) | 107(1) |
| F(2) | 10080(4) | 7982(5) | 6660(2) | 100(2) |
| F(3) | 9278(3) | 6313(2) | 6193(2) | 87(1) |
| F(1A) | 9349(11) | 6675(12) | 6782(5) | 107(1) |
| F(2A) | 9431(11) | 6825(16) | 5889(6) | 100(2) |
| F(3A) | 10149(10) | 8346(8) | 6346(8) | 87(1) |
| N(1) | 6809(2) | 7369(2) | 6335(1) | 32(1) |
| O(1) | 7784(2) | 9443(2) | 6392(1) | 48(1) |
| O(2) | 5226(2) | 6038(2) | 7066(1) | 45(1) |
| O(3) | 3695(2) | 7680(2) | 7101(1) | 55(1) |
| C(1) | 9239(3) | 7599(3) | 6263(2) | 51(1) |
| C(2) | 7850(3) | 8227(2) | 6339(1) | 38(1) |
| C(3) | 5426(2) | 7871(2) | 6390(1) | 31(1) |
| C(4) | 4731(2) | 7135(2) | 6890(1) | 32(1) |
| C(5) | 4628(3) | 7777(3) | 5796(1) | 39(1) |
| C(6) | 5489(3) | 8387(4) | 5311(1) | 55(1) |
| C(7) | 3336(3) | 8612(4) | 5846(1) | 58(1) |
| C(8) | 4303(4) | 6312(3) | 5650(1) | 61(1) |

TABLE U

Bond lengths [Å] and angles [°] for C91.

| | |
|---|---|
| F(1)—C(1) | 1.389(5) |
| F(2)—C(1) | 1.286(4) |
| F(3)—C(1) | 1.286(4) |
| F(1A)—C(1) | 1.498(10) |
| F(2A)—C(1) | 1.162(10) |
| F(3A)—C(1) | 1.183(9) |
| N(1)—C(2) | 1.338(3) |
| N(1)—C(3) | 1.464(3) |
| N(1)—H(1X) | 0.97(2) |
| O(1)—C(2) | 1.214(3) |
| O(2)—C(4) | 1.259(3) |
| O(2)—H(2Z) | 0.98(3) |
| O(3)—C(4) | 1.256(3) |
| O(3)—H(3Z) | 0.97(3) |
| C(1)—C(2) | 1.522(4) |
| C(3)—C(4) | 1.516(3) |
| C(3)—C(5) | 1.566(3) |
| C(3)—H(3) | 1.0000 |
| C(5)—C(6) | 1.520(4) |
| C(5)—C(8) | 1.525(4) |
| C(5)—C(7) | 1.530(4) |
| C(6)—H(6A) | 0.9800 |
| C(6)—H(6B) | 0.9800 |
| C(6)—H(6C) | 0.9800 |
| C(7)—H(7A) | 0.9800 |
| C(7)—H(7B) | 0.9800 |
| C(7)—H(7C) | 0.9800 |
| C(8)—H(8A) | 0.9800 |
| C(8)—H(8B) | 0.9800 |
| C(8)—H(8C) | 0.9800 |
| C(2)—N(1)—C(3) | 120.4(2) |
| C(2)—N(1)—H(1X) | 121.0(17) |
| C(3)—N(1)—H(1X) | 118.6(17) |
| C(4)—O(2)—H(2Z) | 113(4) |
| C(4)—O(3)—H(3Z) | 116(4) |
| F(2A)—C(1)—F(3A) | 114.0(9) |
| F(3)—C(1)—F(2) | 111.1(4) |
| F(3)—C(1)—F(1) | 101.2(3) |
| F(2)—C(1)—F(1) | 105.3(3) |
| F(2A)—C(1)—F(1A) | 99.3(10) |
| F(3A)—C(1)—F(1A) | 101.7(9) |
| F(2A)—C(1)—C(2) | 120.1(5) |
| F(3A)—C(1)—C(2) | 114.6(5) |
| F(3)—C(1)—C(2) | 116.6(2) |
| F(2)—C(1)—C(2) | 112.7(3) |
| F(1)—C(1)—C(2) | 108.6(3) |
| F(1A)—C(1)—C(2) | 103.1(4) |
| O(1)—C(2)—N(1) | 126.2(2) |
| O(1)—C(2)—C(1) | 117.8(2) |
| N(1)—C(2)—C(1) | 116.0(2) |
| N(1)—C(3)—C(4) | 109.07(19) |
| N(1)—C(3)—C(5) | 112.25(19) |
| C(4)—C(3)—C(5) | 112.80(19) |
| N(1)—C(3)—H(3) | 107.5 |
| C(4)—C(3)—H(3) | 107.5 |
| C(5)—C(3)—H(3) | 107.5 |
| O(3)—C(4)—O(2) | 124.7(2) |
| O(3)—C(4)—C(3) | 116.8(2) |
| O(2)—C(4)—C(3) | 118.4(2) |
| C(6)—C(5)—C(8) | 109.9(2) |
| C(6)—C(5)—C(7) | 108.0(2) |
| C(8)—C(5)—C(7) | 110.8(3) |
| C(6)—C(5)—C(3) | 108.5(2) |
| C(8)—C(5)—C(3) | 110.6(2) |
| C(7)—C(5)—C(3) | 109.1(2) |
| C(5)—C(6)—H(6A) | 109.5 |
| C(5)—C(6)—H(6B) | 109.5 |
| H(6A)—C(6)—H(6B) | 109.5 |
| C(5)—C(6)—H(6C) | 109.5 |
| H(6A)—C(6)—H(6C) | 109.5 |
| H(6B)—C(6)—H(6C) | 109.5 |
| C(5)—C(7)—H(7A) | 109.5 |
| C(5)—C(7)—H(7B) | 109.5 |
| H(7A)—C(7)—H(7B) | 109.5 |
| C(5)—C(7)—H(7C) | 109.5 |
| H(7A)—C(7)—H(7C) | 109.5 |
| H(7B)—C(7)—H(7C) | 109.5 |
| C(5)—C(8)—H(8A) | 109.5 |
| C(5)—C(8)—H(8B) | 109.5 |
| H(8A)—C(8)—H(8B) | 109.5 |
| C(5)—C(8)—H(8C) | 109.5 |
| H(8A)—C(8)—H(8C) | 109.5 |
| H(8B)—C(8)—H(8C) | 109.5 |

Symmetry transformations used to generate equivalent atoms.

TABLE V

Anisotropic displacement parameters ($Å^2 \times 10^3$) for C91. The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| F(1) | 84(2) | 107(3) | 129(3) | 42(2) | 67(2) | 41(2) |
| F(2) | 54(2) | 128(4) | 120(3) | −64(3) | −31(2) | 22(2) |
| F(3) | 36(1) | 29(1) | 195(4) | −15(2) | 21(2) | 0(1) |
| F(1A) | 84(2) | 107(3) | 129(3) | 42(2) | 67(2) | 41(2) |
| F(2A) | 54(2) | 128(4) | 120(3) | −64(3) | −31(2) | 22(2) |
| F(3A) | 36(1) | 29(1) | 195(4) | −15(2) | 21(2) | 0(1) |
| N(1) | 29(1) | 27(1) | 40(1) | 2(1) | 4(1) | −1(1) |
| O(1) | 43(1) | 30(1) | 72(1) | −5(1) | 14(1) | −3(1) |
| O(2) | 52(1) | 39(1) | 44(1) | 13(1) | 11(1) | 3(1) |
| O(3) | 50(1) | 60(1) | 54(1) | 17(1) | 23(1) | 12(1) |
| C(1) | 36(1) | 33(1) | 83(2) | −14(1) | 4(1) | −5(1) |
| C(2) | 38(1) | 30(1) | 44(1) | −5(1) | 7(1) | −3(1) |
| C(3) | 32(1) | 28(1) | 32(1) | 2(1) | 6(1) | 2(1) |
| C(4) | 31(1) | 33(1) | 32(1) | 2(1) | 2(1) | −2(1) |
| C(5) | 42(1) | 42(1) | 33(1) | 6(1) | −2(1) | 2(1) |
| C(6) | 63(2) | 67(2) | 35(1) | 10(1) | 8(1) | 9(2) |
| C(7) | 43(2) | 77(2) | 55(2) | 15(2) | −2(1) | 14(2) |
| C(8) | 77(2) | 54(2) | 50(2) | −4(1) | −22(2) | −11(2) |

Step 2. Synthesis of lithium (1R,2S,5S)-6,6-dimethyl-3-azabicyclo[3.1.0]hexane-2-carboxylate (C92)

Lithium hydroxide monohydrate (29.0 g, 678 mmol) was added to a mixture of methyl (1R,2S,5S)-6,6-dimethyl-3-azabicyclo[3.1.0]hexane-2-carboxylate, hydrochloride salt (68.5 g, 333 mmol) in tetrahydrofuran (950 mL) and water (48 mL). The reaction mixture was stirred at 25° C. until the hydrolysis was complete, whereupon the solid was collected via filtration, washed with a 5% solution of water in tetrahydrofuran (400 mL), and dried under vacuum at 70° C. to afford C92 as a white to off-white solid. Yield: 47.6 g, 295 mmol, 89%. Physicochemical data was obtained on samples of C92 obtained from reactions carried out in the same manner.

Figure 13:
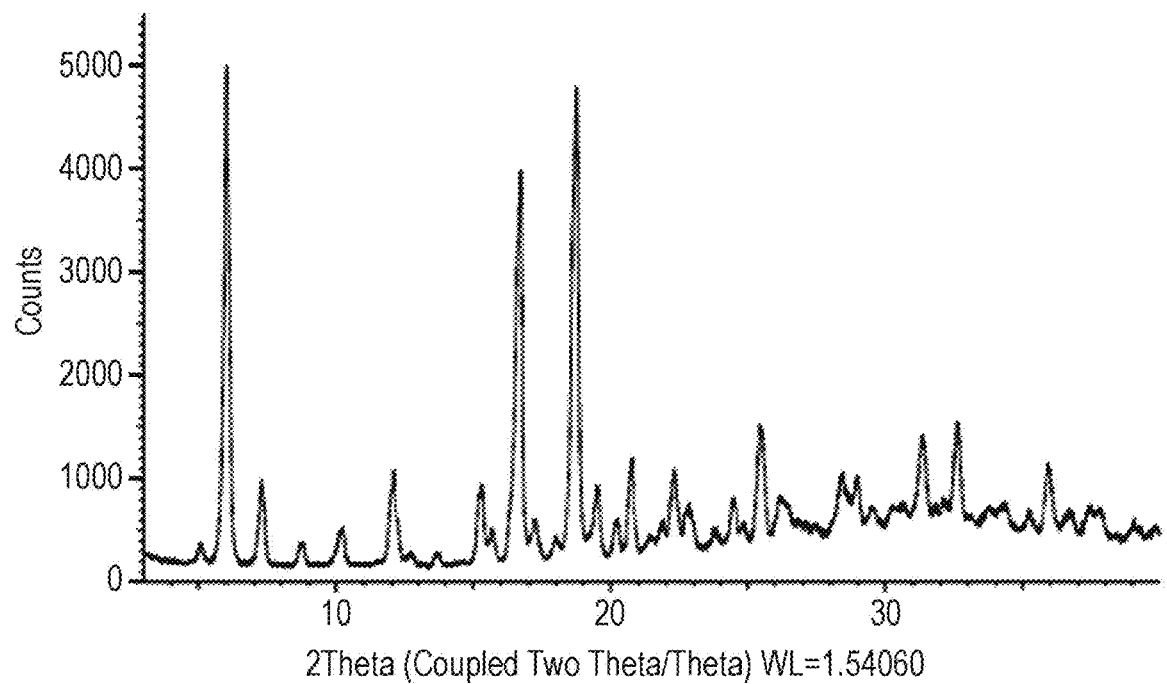
FIG. 13: Powder X-ray Diffraction Pattern of Intermediate C92.

HRMS-ESI⁺ (m/z): [M+H]⁺ Calculated for $C_8H_{14}NO_2$, 156.1019; Found, 156.1019. ¹H NMR (600 MHz, D₂O) δ 3.23 (d, J=1.1 Hz, 1H), 3.09 (dd, J=11.1, 5.2 Hz, 1H), 2.63 (d, J=11.1 Hz, 1H), 1.33-1.24 (m, 2H), 0.86 (s, 2H), 0.83 (s, 3H). ¹³C NMR (150.8 MHz, D₂O) δ 182.7, 62.3, 45.6, 35.5, 30.0, 25.8, 19.3, 12.7. The powder X-ray diffraction pattern for C92 is given in FIG. 13; characteristic peaks are listed in Table W.

TABLE W

Selected powder X-ray diffraction peaks for C92

| Angle (°2-theta) | Rel. Intensity |
|---|---|
| 5.1 | 4 |
| 6.0 | 100 |
| 7.3 | 17 |
| 8.7 | 3 |
| 10.2 | 6 |
| 12.1 | 20 |
| 12.7 | 2 |
| 13.7 | 2 |
| 15.3 | 15 |
| 15.7 | 6 |
| 16.7 | 78 |
| 17.2 | 8 |
| 18.0 | 3 |
| 18.8 | 95 |
| 19.5 | 14 |
| 20.2 | 6 |
| 20.8 | 19 |
| 21.4 | 2 |
| 21.9 | 4 |
| 22.3 | 16 |
| 22.8 | 7 |
| 23.8 | 3 |
| 24.5 | 9 |
| 24.8 | 3 |
| 25.5 | 21 |
| 26.2 | 5 |
| 26.5 | 4 |
| 28.4 | 10 |
| 29.0 | 10 |
| 29.5 | 4 |
| 30.2 | 4 |
| 30.5 | 2 |
| 31.4 | 18 |
| 32.2 | 5 |
| 32.6 | 22 |
| 33.8 | 3 |
| 34.3 | 3 |
| 35.2 | 3 |
| 35.9 | 10 |
| 36.7 | 4 |
| 37.4 | 4 |
| 37.8 | 4 |
| 39.0 | 2 |
| 39.2 | 1 |
| 39.8 | 1 |

Step 3. Synthesis of (1R,2S,5S)-6,6-dimethyl-3-[3-methyl-N-(trifluoroacetyl)-L-valyl]-3-azabicyclo[3.1.0]hexane-2-carboxylic acid (C42)

A mixture of C91 (1.29 g, 5.68 mmol), 4-(dimethylamino)pyridine (0.60 g, 4.8 mmol), and N,N-diisopropylethylamine (1.70 mL, 9.75 mmol) in tetrahydrofuran (10 mL), was treated with p-toluenesulfonyl chloride (0.99 g, 5.2 mmol). After the reaction mixture had been stirred for 2 hours at 20° C., C92 (75.7 mass %, 1.00 g, 4.70 mmol) was charged and stirring was continued overnight at 20° C. The resulting slurry was mixed with propan-2-yl acetate (10 mL) and washed sequentially with aqueous citric acid solution (10%, 10 mL) and with water (10 mL). The organic layer was then concentrated, whereupon propan-2-yl acetate (5 mL) was added, followed by drop-wise addition of heptane (15 mL) from an addition funnel. Solids were isolated via filtration and dried under vacuum to afford (1R,2S,5S)-6,6-dimethyl-3-[3-methyl-N-(trifluoroacetyl)-L-valyl]-3-azabicyclo[3.1.0]hexane-2-carboxylic acid (C42) as a white solid. Yield: 1.2 g. This compound displays two sets of NMR signals. The major and minor sets correspond to the Z and E isomers of the tertiary amide, respectively, with a molar ratio of 20:1. The sample also contains isopropyl acetate of 37% molar ratio relative to C42, showing ¹H resonances at 4.86, 1.96, and 1.17 ppm, and ¹³C resonances at 169.7, 66.9, 21.5, and 21.0 ppm. ¹H and ¹³C signals were referenced using the TMS signal, set to 0 ppm in both.

HRMS-ESI⁺ (m/z): [M+H]⁺ Calculated for $C_{16}H_{24}F_3N_2O_4$, 365.1683; Found: 365.1684. ¹H NMR (600 MHz, DMSO-d₆) δ major: 9.44 (d, J=8.5 Hz, 1H), 4.44 (d, J=8.5 Hz, 1H), 4.15 (s, 1H), 3.85 (dd, J=10.5, 5.4 Hz, 1H), 3.73 (d, J=10.5 Hz, 1H), 1.53 (dd, J=7.6, 5.3 Hz, 1H), 1.43 (d, J=7.6 Hz, 1H), 1.01 (s, 3H), 1.01 (s, 9H), 0.83 (s, 3H); minor: 9.11 (d, J=9.4 Hz, 1H), 4.53 (s, 1H), 4.33 (d, J=9.4

Figure 14:
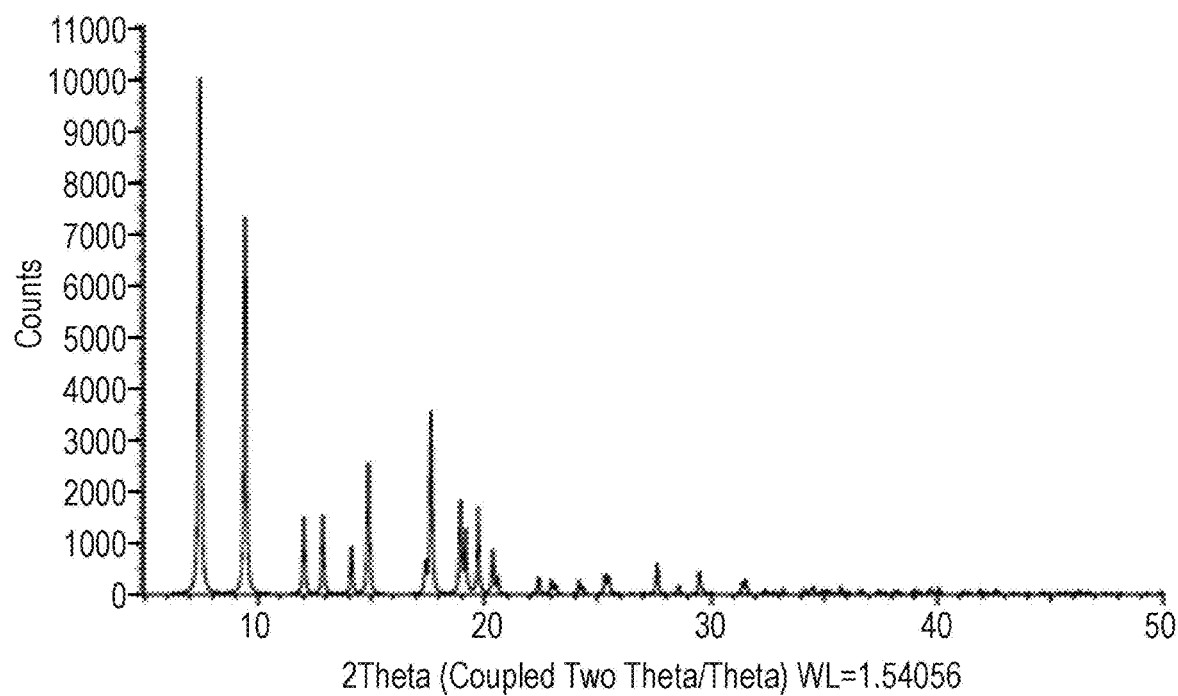
FIG. 14: Powder X-ray Diffraction Pattern of Intermediate C42.

Hz, 1H), 3.53 (dd, J=12.5, 5.3 Hz, 1H), 3.41 (d, J=12.5 Hz, 1H), 1.55 (d, J=7.5 Hz, 1H), 1.41 (dd, J=7.5, 5.3 Hz, 1H), 1.02 (s, 3H), 0.97 (s, 3H), 0.91 (s, 9H). $^{13}$C NMR (150.8 MHz, DMSO-d$_6$) δ major: 172.3, 167.5, 156.8 ($^2$J$_{CF}$=37.0 Hz), 115.7 (J$_{CF}$=287.7 Hz), 59.1, 58.0, 47.1, 34.6, 29.6, 26.7, 26.1, 25.6, 18.7, 12.0; minor: 172.3, 168.1, 155.9 ($^2$J$_{CF}$=36.8 Hz), 115.8 (0J$_{CF}$=288.1 Hz), 59.9, 57.3, 46.4, 36.2, 32.1, 26.2, 26.0, 24.4, 19.0, 12.7. The powder X-ray diffraction pattern for C42 is given in FIG. 14; characteristic peaks are listed in Table X.

Crystallization for both the powder X-ray diffraction work and the single-crystal X-ray structural determination was carried out as follows. A solution of C42 (2.96 g) in ethanol (9 mL) was heated to 40° C. with stirring (3500 rpm), whereupon water (10.5 m) was added over 10 minutes. Additional water (16.5 m) was then added over 4 hours, and the mixture was cooled to 10° C. and allowed to stir overnight. After filtration, the filter cake was washed with water (6 mL) and dried at 50° C. to afford crystalline C42 (2.6 g).

TABLE X

Selected powder X-ray diffraction peaks for C42

| Angle (°2-theta) | Rel. Intensity |
|---|---|
| 7.4 | 100 |
| 9.4 | 73 |
| 12.0 | 15 |
| 12.9 | 16 |
| 14.1 | 9 |
| 14.9 | 26 |
| 17.4 | 7 |
| 17.7 | 35 |
| 19.0 | 18 |
| 19.2 | 12 |
| 19.7 | 17 |
| 20.4 | 9 |
| 20.6 | 4 |
| 22.4 | 3 |
| 23.0 | 3 |
| 23.2 | 2 |
| 24.2 | 3 |
| 24.4 | 2 |
| 25.3 | 4 |
| 25.5 | 4 |
| 27.6 | 6 |
| 28.6 | 1 |
| 29.5 | 4 |
| 31.4 | 2 |
| 31.5 | 3 |
| 32.4 | 1 |
| 33.2 | 1 |
| 34.1 | 1 |
| 34.5 | 2 |
| 35.7 | 1 |
| 36.1 | 0 |
| 36.6 | 1 |
| 37.4 | 1 |
| 38.3 | 1 |
| 39.0 | 1 |
| 39.7 | 1 |
| 40.1 | 1 |
| 41.2 | 1 |
| 41.9 | 1 |
| 42.6 | 1 |
| 46.3 | 1 |

Figure 15:
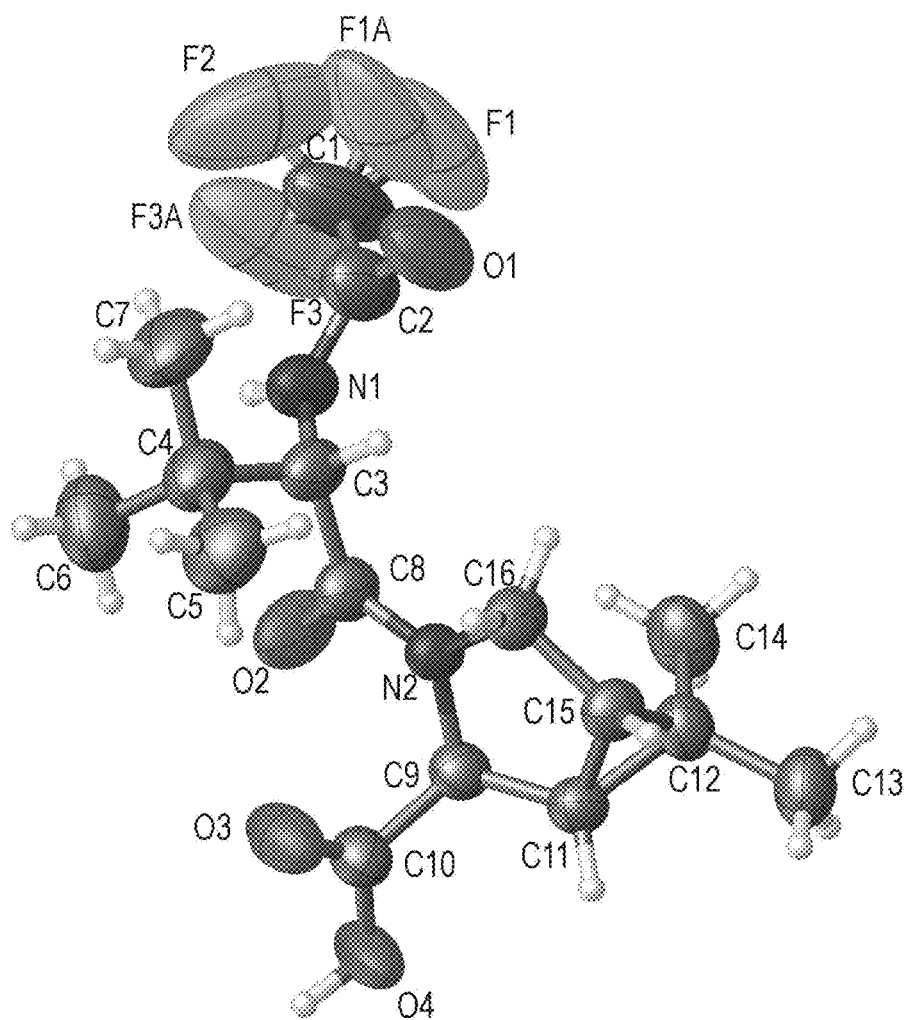
FIG. 15: Single-crystal X-ray Structural Determination of Intermediate C42. ORTEP diagram drawn with displacement parameters at 50% probability.

An ORTEP diagram of the single-crystal data for C42 is shown in FIG. 15.

Single-Crystal X-Ray Structural Determination of C42

Single Crystal X-Ray Analysis

Data collection was performed on a Bruker D8 Venture diffractometer at room temperature. Data collection consisted of omega and phi scans. A special data strategy of 0.3 degree Width per frames was applied in order to separate the domains, thereby eliminating any TWIN and pseudosymmetry issues.

The structure was solved by intrinsic phasing using SHELX software suite in the rhombohedral class group R3. The structure was subsequently refined by the full-matrix least squares method. All non-hydrogen atoms were found and refined using anisotropic displacement parameters.

The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned. The method calculates that the probability that the structure is correctly assigned is 100%. The Hooft parameter is reported as −0.08 with an esd (estimated standard deviation) of (7) and the Parson's parameter is reported as −0.09 with an esd of (6).

Population site disorder at the C1_F1_F2 segment as a ratio of 78:22 was identified and treated accordingly.

The final R-index was 5.8%. A final difference Fourier revealed no missing or misplaced electron density.

Pertinent crystal, data collection, and refinement information is summarized in Table Y. Atomic coordinates, bond lengths, bond angles, and displacement parameters are listed in Tables Z-BB.

The list of Software and References employed may be found in Single-crystal X-ray Structural Determination of Example 13, Solid Form 1.

TABLE Y

Crystal data and structure refinement for C42.

| | |
|---|---|
| Empirical formula | C$_{16}$H$_{23}$F$_3$N$_2$O$_4$ |
| Formula weight | 364.36 |
| Temperature | 296(2) K |
| Wavelength | 1.54178 Å |
| Crystal system | Trigonal |
| Space group | R3 |
| Unit cell dimensions | a = 14.1740(6) Å  α = 114.11° |
| | b = 14.1740(6) Å  β = 114.11° |
| | c = 14.1740(6) Å  γ = 114.11° |
| Volume | 1715.9(4) Å$^3$ |
| Z | 3 |
| Density (calculated) | 1.058 Mg/m$^3$ |
| Absorption coefficient | 0.788 mm$^{-1}$ |
| F(000) | 576 |
| Crystal size | 0.220 × 0.100 × 0.100 mm$^3$ |
| Theta range for data collection | 6.445 to 80.034° |
| Index ranges | −17 <= h <= 16, −14 <= k <= 16, −14 <= l <= 17 |
| Reflections collected | 13310 |
| Independent reflections | 4011 [R$_{int}$ = 0.0369] |
| Completeness to theta = 67.679° | 98.9% |
| Absorption correction | Empirical |
| Refinement method | Full-matrix least-squares on F$^2$ |
| Data/restraints/parameters | 4011/6/244 |
| Goodness-of-fit on F$^2$ | 1.056 |
| Final R indices [I > 2σ(I)] | R1 = 0.0582, wR2 = 0.1675 |
| R indices (all data) | R1 = 0.0611, wR2 = 0.1710 |

TABLE Y-continued

Crystal data and structure refinement for C42.

| | |
|---|---|
| Absolute structure parameter | −0.09(6) |
| Extinction coefficient | n/a |
| Largest diff. peak and hole | 0.292 and −0.174 e · Å$^{-3}$ |

TABLE Z

Atomic coordinates (×10$^4$) and equivalent isotropic displacement parameters (Å$^2$ × 10$^3$) for C42. U(eq) is defined as one-third of the trace of the orthogonalized U$^{ij}$ tensor.

| | x | y | z | U(eq) |
|---|---|---|---|---|
| C(1) | 9738(11) | 9749(11) | 7504(7) | 172(4) |
| F(1) | 9100(20) | 9860(20) | 7899(14) | 233(6) |
| F(3) | 9757(18) | 8823(16) | 7411(12) | 171(4) |
| F(1A) | 9950(80) | 10650(90) | 8270(60) | 233(6) |
| F(3A) | 10320(70) | 9400(60) | 7630(50) | 171(4) |
| F(2) | 11182(13) | 11032(10) | 8680(7) | 296(6) |
| N(1) | 9252(4) | 8810(4) | 5336(3) | 75(1) |
| N(2) | 6546(2) | 6624(2) | 1650(2) | 49(1) |
| O(1) | 9065(6) | 10407(6) | 6229(5) | 130(2) |
| O(2) | 7738(3) | 6229(3) | 2739(3) | 88(1) |
| O(3) | 7054(3) | 5611(3) | −16(3) | 79(1) |
| O(4) | 5159(3) | 3362(3) | −1315(3) | 80(1) |
| C(2) | 9318(6) | 9683(6) | 6263(5) | 97(2) |
| C(3) | 8891(4) | 8676(4) | 4135(3) | 66(1) |
| C(4) | 10197(4) | 9437(4) | 4311(4) | 80(1) |
| C(5) | 9748(5) | 9404(6) | 3121(6) | 98(1) |
| C(6) | 10798(6) | 8766(7) | 4324(7) | 109(2) |
| C(7) | 11359(5) | 10996(5) | 5744(6) | 110(2) |
| C(8) | 7683(3) | 7092(3) | 2793(3) | 60(1) |
| C(9) | 5449(3) | 5104(3) | 340(3) | 50(1) |
| C(10) | 5997(3) | 4749(3) | −338(3) | 56(1) |
| C(11) | 4191(3) | 4863(3) | −607(3) | 53(1) |
| C(12) | 3540(3) | 5182(4) | −65(3) | 60(1) |
| C(13) | 1999(4) | 4426(5) | −1228(5) | 78(1) |
| O(14) | 3859(5) | 5374(5) | 1178(5) | 80(1) |
| O(15) | 4643(3) | 6293(3) | 127(3) | 54(1) |
| O(16) | 6198(3) | 7435(3) | 1506(3) | 59(1) |

TABLE AA

Bond lengths [Å] and angles [°] for C42.

| | |
|---|---|
| C(1)—F(1A) | 1.09(5) |
| C(1)—F(3A) | 1.12(5) |
| C(1)—F(1) | 1.271(14) |
| C(1)—F(3) | 1.277(13) |
| C(1)—F(2) | 1.404(14) |
| C(1)—C(2) | 1.556(9) |
| N(1)—C(2) | 1.321(6) |
| N(1)—C(3) | 1.463(5) |
| N(1)—H(1X) | 0.94(2) |
| N(2)—C(8) | 1.333(4) |
| N(2)—C(9) | 1.464(4) |
| N(2)—C(16) | 1.477(3) |
| O(1)—C(2) | 1.230(6) |
| O(2)—C(8) | 1.231(4) |
| O(3)—C(10) | 1.199(4) |
| O(4)—C(10) | 1.311(4) |
| O(4)—H(4Y) | 0.98(2) |
| C(3)—C(8) | 1.517(5) |
| C(3)—C(4) | 1.556(6) |
| C(3)—H(3) | 0.9800 |
| C(4)—C(5) | 1.512(8) |
| C(4)—C(6) | 1.515(6) |
| C(4)—C(7) | 1.533(6) |
| C(5)—H(5A) | 0.9600 |
| C(5)—H(5B) | 0.9600 |
| C(5)—H(5C) | 0.9600 |
| C(6)—H(6A) | 0.9600 |
| C(6)—H(6B) | 0.9600 |
| C(6)—H(6C) | 0.9600 |
| C(7)—H(7A) | 0.9600 |
| C(7)—H(7B) | 0.9600 |
| C(7)—H(7C) | 0.9600 |
| C(9)—C(11) | 1.508(4) |
| C(9)—C(10) | 1.521(4) |
| C(9)—H(9) | 0.9800 |
| C(11)—C(15) | 1.507(4) |
| C(11)—C(12) | 1.510(4) |
| C(11)—H(11) | 0.9800 |
| C(12)—C(14) | 1.496(5) |
| C(12)—C(15) | 1.512(5) |
| C(12)—C(13) | 1.530(5) |
| C(13)—H(13A) | 0.9600 |
| C(13)—H(13B) | 0.9600 |
| C(13)—H(13C) | 0.9600 |
| C(14)—H(14A) | 0.9600 |
| C(14)—H(14B) | 0.9600 |
| C(14)—H(14C) | 0.9600 |
| C(15)—C(16) | 1.510(4) |
| C(15)—H(15) | 0.9800 |
| C(16)—H(16A) | 0.9700 |
| C(16)—H(16B) | 0.9700 |
| F(1A)—C(1)—F(3A) | 133(4) |
| F(1)—C(1)—F(3) | 109.3(14) |
| F(1A)—C(1)—C(2) | 105(2) |
| F(3A)—C(1)—C(2) | 109.0(19) |
| F(1)—C(1)—C(2) | 115.0(7) |
| F(3)—C(1)—C(2) | 118.2(6) |
| F(2)—C(1)—C(2) | 104.7(9) |
| C(2)—N(1)—C(3) | 119.5(3) |
| C(2)—N(1)—H(1X) | 112(3) |
| C(3)—N(1)—H(1X) | 128(3) |
| C(8)—N(2)—C(9) | 118.3(2) |
| C(8)—N(2)—C(16) | 128.7(2) |
| C(9)—N(2)—C(16) | 113.0(2) |
| C(10)—O(4)—H(4Y) | 103(3) |
| O(1)—C(2)—N(1) | 127.2(5) |
| O(1)—C(2)—C(1) | 118.2(4) |
| N(1)—C(2)—C(1) | 114.5(4) |
| N(1)—C(3)—C(8) | 106.8(3) |
| N(1)—C(3)—C(4) | 113.3(3) |
| C(8)—C(3)—C(4) | 113.4(3) |
| N(1)—C(3)—H(3) | 107.7 |
| C(8)—C(3)—H(3) | 107.7 |
| C(4)—C(3)—H(3) | 107.7 |
| C(5)—C(4)—C(6) | 111.0(5) |
| C(5)—C(4)—C(7) | 108.8(4) |
| C(6)—C(4)—C(7) | 108.5(4) |
| C(5)—C(4)—C(3) | 108.7(3) |
| C(6)—C(4)—C(3) | 112.1(4) |
| C(7)—C(4)—C(3) | 107.5(4) |
| C(4)—C(5)—H(5A) | 109.5 |
| C(4)—C(5)—H(5B) | 109.5 |
| H(5A)—C(5)—H(5B) | 109.5 |
| C(4)—C(5)—H(5C) | 109.5 |
| H(5A)—C(5)—H(5C) | 109.5 |
| H(5B)—C(5)—H(5C) | 109.5 |
| C(4)—C(6)—H(6A) | 109.5 |
| C(4)—C(6)—H(6B) | 109.5 |
| H(6A)—C(6)—H(6B) | 109.5 |
| C(4)—C(6)—H(6C) | 109.5 |
| H(6A)—C(6)—H(6C) | 109.5 |
| H(6B)—C(6)—H(6C) | 109.5 |
| C(4)—C(7)—H(7A) | 109.5 |
| C(4)—C(7)—H(7B) | 109.5 |
| H(7A)—C(7)—H(7B) | 109.5 |
| C(4)—C(7)—H(7C) | 109.5 |
| H(7A)—C(7)—H(7C) | 109.5 |
| H(7B)—C(7)—H(7C) | 109.5 |
| O(2)—C(8)—N(2) | 119.3(3) |
| O(2)—C(8)—C(3) | 121.0(3) |
| N(2)—C(8)—C(3) | 119.8(2) |
| N(2)—C(9)—C(11) | 105.0(2) |
| N(2)—C(9)—C(10) | 110.4(2) |
| C(11)—C(9)—C(10) | 112.2(2) |
| N(2)—C(9)—H(9) | 109.7 |
| C(11)—C(9)—H(9) | 109.7 |
| C(10)—C(9)—H(9) | 109.7 |

TABLE AA-continued

Bond lengths [Å] and angles [°] for C42.

| | |
|---|---|
| O(3)—C(10)—O(4) | 124.6(3) |
| O(3)—C(10)—C(9) | 125.1(3) |
| O(4)—C(10)—C(9) | 110.4(3) |
| C(15)—C(11)—C(9) | 107.9(2) |
| C(15)—C(11)—C(12) | 60.1(2) |
| C(9)—C(11)—C(12) | 118.0(2) |
| C(15)—C(11)—H(11) | 118.7 |
| C(9)—C(11)—H(11) | 118.7 |
| C(12)—C(11)—H(11) | 118.7 |
| C(14)—C(12)—C(11) | 121.8(3) |
| C(14)—C(12)—C(15) | 121.6(3) |
| C(11)—C(12)—C(15) | 59.8(2) |
| C(14)—C(12)—C(13) | 113.5(3) |
| C(11)—C(12)—C(13) | 114.8(3) |
| C(15)—C(12)—C(13) | 115.3(3) |
| C(12)—C(13)—H(13A) | 109.5 |
| C(12)—C(13)—H(13B) | 109.5 |
| H(13A)—C(13)—H(13B) | 109.5 |
| C(12)—C(13)—H(13C) | 109.5 |
| H(13A)—C(13)—H(13C) | 109.5 |
| H(13B)—C(13)—H(13C) | 109.5 |
| C(12)—C(14)—H(14A) | 109.5 |
| C(12)—C(14)—H(14B) | 109.5 |
| H(14A)—C(14)—H(14B) | 109.5 |
| C(12)—C(14)—H(14C) | 109.5 |
| H(14A)—C(14)—H(14C) | 109.5 |
| H(14B)—C(14)—H(14C) | 109.5 |
| C(11)—C(15)—C(16) | 108.6(2) |
| C(11)—C(15)—C(12) | 60.04(19) |
| C(16)—C(15)—C(12) | 120.2(3) |
| C(11)—C(15)—H(15) | 117.9 |
| C(16)—C(15)—H(15) | 117.9 |
| C(12)—C(15)—H(15) | 117.9 |
| N(2)—C(16)—C(15) | 104.0(2) |
| N(2)—C(16)—H(16A) | 111.0 |
| C(15)—C(16)—H(16A) | 111.0 |
| N(2)—C(16)—H(16B) | 111.0 |
| C(15)—C(16)—H(16B) | 111.0 |
| H(16A)—C(16)—H(16B) | 109.0 |

TABLE BB

Anisotropic displacement parameters (Å² × 10³) for C42.
The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(1) | 249(10) | 244(10) | 92(4) | 107(6) | 116(6) | 219(9) |
| F(1) | 349(14) | 444(17) | 236(8) | 274(10) | 264(10) | 348(15) |
| F(3) | 299(12) | 246(10) | 152(5) | 168(7) | 178(7) | 234(10) |
| F(1A) | 349(14) | 444(17) | 236(8) | 274(10) | 264(10) | 348(15) |
| F(3A) | 299(12) | 246(10) | 152(5) | 168(7) | 178(7) | 234(10) |
| F(2) | 294(11) | 235(8) | 94(3) | 84(4) | 57(5) | 147(2) |
| N(1) | 80(2) | 83(2) | 52(1) | 41(1) | 37(1) | 65(2) |
| N(2) | 52(1) | 49(1) | 44(1) | 31(1) | 30(1) | 39(1) |
| O(1) | 170(4) | 160(4) | 107(3) | 88(3) | 95(3) | 145(4) |
| O(2) | 83(2) | 74(2) | 73(2) | 50(1) | 32(1) | 59(1) |
| O(3) | 82(2) | 56(1) | 91(2) | 43(1) | 69(2) | 42(1) |
| O(4) | 71(1) | 50(1) | 93(2) | 32(1) | 61(1) | 39(1) |
| C(2) | 109(3) | 117(4) | 73(2) | 59(3) | 57(2) | 93(3) |
| C(3) | 62(2) | 62(2) | 51(2) | 33(1) | 28(1) | 47(2) |
| C(4) | 62(2) | 64(2) | 71(2) | 36(2) | 35(2) | 42(2) |
| C(5) | 76(2) | 85(3) | 94(3) | 58(2) | 54(2) | 44(2) |
| C(6) | 97(3) | 111(4) | 134(4) | 83(4) | 80(3) | 82(3) |
| C(7) | 69(2) | 70(2) | 84(3) | 30(2) | 32(2) | 34(2) |
| C(8) | 62(2) | 59(2) | 56(2) | 40(1) | 36(1) | 46(1) |
| C(9) | 55(1) | 48(1) | 49(1) | 33(1) | 35(1) | 37(1) |
| C(10) | 56(2) | 50(1) | 57(2) | 34(1) | 39(1) | 38(1) |
| C(11) | 53(1) | 54(1) | 45(1) | 31(1) | 32(1) | 38(1) |
| C(12) | 61(2) | 69(2) | 63(2) | 46(2) | 44(1) | 50(2) |

TABLE BB-continued

Anisotropic displacement parameters (Å² × 10³) for C42.
The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(13) | 62(2) | 85(2) | 86(2) | 57(2) | 50(2) | 54(2) |
| C(14) | 91(3) | 109(3) | 89(2) | 77(2) | 72(2) | 77(2) |
| C(15) | 57(2) | 57(2) | 50(1) | 38(1) | 33(1) | 43(1) |
| C(16) | 60(2) | 51(1) | 57(2) | 35(1) | 33(1) | 42(1) |

In addition to the preparation of (1R,2S,5S)-6,6-dimethyl-3-[3-methyl-N-(trifluoroacetyl)-L-valyl]-3-azabicyclo[3.1.0]hexane-2-carboxylic acid (C42) according to the methods described above the compound can also be prepared as depicted in the reaction schemes shown directly below. In step 1, methyl (1R,2S,5S)-6,6-dimethyl-3-azabicyclo[3.1.0]hexane-2-carboxylate hydrochloride is first treated with triethylamine in a mixture of tetrahydrofuran and water to neutralize the hydrochloride salt followed by hydrolysis of the methyl ester using sodium hydroxide in a mixture of tetrahydrofuran and water to provide sodium (1R,2S,5S)-6,6-dimethyl-3-azabicyclo[3.1.0]hexane-2-carboxylate.

Preparation of sodium (1R,2S,5S)-6,6-dimethyl-3-azabicyclo[3.1.0]hexane-2-carboxylate

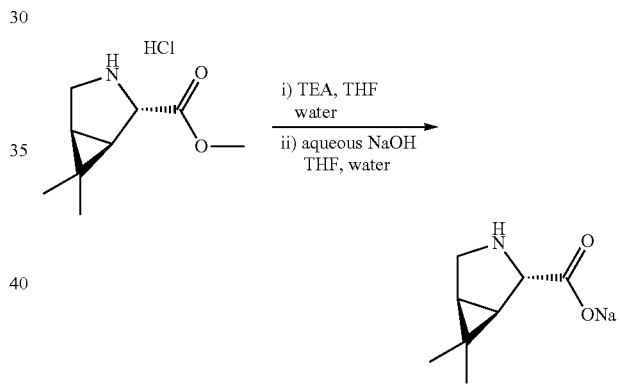

To a suitable vessel was added tetrahydrofuran (30 mL0), water (7.5 mL), triethylamine (7.62 mL, 54.7 mmol) and methyl (1R,2S,5S)-6,6-dimethyl-3-azabicyclo[3.1.0]hexane-2-carboxylate hydrochloride (7.59 g, 36.9 mmol). The mixture is stirred at 25° C. for at least 30 minutes. The stirring was halted and the layers separated. In a separate vessel 28 w/w % aqueous sodium hydroxide (4.19 mL, 38.3 mmol) and tetrahydrofuran (71 mL) were added with stirring at 40° C. 25% of the organic layer containing a solution of methyl (1R,2S,5S)-6,6-dimethyl-3-azabicyclo[3.1.0]hexane-2-carboxylate in tetrahydrofuran from the separation is added and the solution is seeded with sodium (1R,2S,5S)-6,6-dimethyl-3-azabicyclo[3.1.0]hexane-2-carboxylate (0.1182 g, 0.7336 mmol—previously prepared from analogous procedure). The mixture was held at 40° C. for at least 15 minutes and the remaining 75% of the organic layer was added slowly. The mixture was held with stirring at 40° C. for 16 hours, then cooled slowly to 20° C. and held for at least 4 h. The resulting solid sodium (1R,2S,5S)-6,6-dimethyl-3-azabicyclo[3.1.0]hexane-2-carboxylate was isolated by filtration, washed with a solution consisting of tetrahydrofuran (43 mL) and water (2.25 mL). The solid material was dried at 70° C. under vacuum to give 6.13 g (93.8%) of sodium (1R,2S,5S)-6,6-dimethyl-3-azabicyclo[3.1.0]hexane-2-carboxylate as a crystalline solid. The PXRD was determined according to methods as described above.

Selected PXRD Peaks of crystalline sodium (1R,2S,5S)-6,6-dimethyl-3-azabicyclo[3.1.0]hexane-2-carboxylate

| Angle degrees 2-Θ ± 0.2 °2-Θ | Relative Intensity |
|---|---|
| 5.5 | 19 |
| 5.9 | 9 |
| 6.6 | 59 |
| 10.7 | 2 |
| 16.0 | 9 |
| 16.3 | 6 |
| 16.7 | 10 |
| 17.0 | 52 |
| 17.3 | 42 |
| 17.7 | 15 |
| 18.5 | 7 |
| 19.0 | 15 |
| 19.3 | 100 |
| 21.3 | 45 |
| 23.2 | 12 |
| 23.5 | 17 |
| 24.2 | 20 |
| 25.8 | 11 |
| 26.0 | 8 |
| 26.7 | 4 |
| 28.1 | 3 |
| 28.9 | 6 |
| 29.8 | 4 |
| 30.3 | 8 |
| 30.8 | 8 |
| 32.0 | 3 |
| 32.5 | 5 |
| 33.8 | 7 |
| 34.6 | 4 |
| 35.8 | 6 |
| 36.6 | 8 |
| 36.9 | 7 |
| 37.6 | 3 |

Selected PXRD Peaks of (S)-3,3-dimethyl-2-(2,2,2-trifluoroacetamido)butanoic acid (C91)

| Angle degrees 2-Θ ± 0.2 °2-Θ | Relative Intensity |
|---|---|
| 9.7 | 27 |
| 11.8 | 6 |
| 12.6 | 3 |
| 13.2 | 20 |
| 14.7 | 28 |
| 15.6 | 69 |
| 17.2 | 4 |
| 17.9 | 2 |
| 18.3 | 2 |
| 19.5 | 100 |
| 20.0 | 14 |
| 20.4 | 2 |
| 21.5 | 22 |
| 23.2 | 8 |
| 23.3 | 11 |
| 23.8 | 6 |
| 25.2 | 1 |
| 25.4 | 17 |
| 25.7 | 2 |
| 26.6 | 7 |
| 26.7 | 6 |
| 28.1 | 4 |
| 28.7 | 2 |
| 28.9 | 5 |
| 29.7 | 4 |
| 29.9 | 4 |
| 30.3 | 10 |
| 30.8 | 3 |
| 31.0 | 1 |
| 31.3 | 1 |
| 32.6 | 3 |
| 33.5 | 2 |
| 34.0 | 1 |
| 34.2 | 2 |
| 34.7 | 3 |
| 36.2 | 2 |
| 36.4 | 3 |
| 36.7 | 2 |
| 37.1 | 1 |
| 37.2 | 2 |
| 37.4 | 1 |
| 37.6 | 3 |
| 37.7 | 1 |
| 38.2 | 2 |
| 38.7 | 2 |
| 39.3 | 3 |
| 39.6 | 1 |
| 40.0 | 1 |
| 40.5 | 5 |
| 40.7 | 3 |
| 40.9 | 3 |
| 41.5 | 1 |
| 41.8 | 1 |
| 42.4 | 3 |
| 43.1 | 1 |
| 44.2 | 1 |
| 44.8 | 1 |
| 45.7 | 1 |
| 45.9 | 3 |
| 46.4 | 1 |
| 47.0 | 1 |
| 47.3 | 2 |
| 49.5 | 2 |

Crystal Data and Structure Refinement for (S)-3,3-dimethyl-2-(2,2,2-trifluoroacetamido) butanoic acid (C91)

| | |
|---|---|
| Identification code | E178 |
| Empirical formula | C8 H12 F3 N O3 |
| Formula weight | 227.19 |
| Temperature | 173(2) K |
| Wavelength | 1.54178 Å |
| Crystal system | Tetragonal |
| Space group | P4$_1$2$_1$2 |
| Unit cell dimensions | a = 9.9168(6) Å       a = 90°. |
| | b = 9.9168(6) Å       b = 90°. |
| | c = 22.721(2) Å       g = 90°. |
| Volume | 2234.5(4) Å$^3$ |
| Z | 8 |
| Density (calculated) | 1.351 Mg/m$^3$ |
| Absorption coefficient | 1.184 mm$^{-1}$ |
| F(000) | 944 |
| Crystal size | 0.200 × 0.170 × 0.080 mm$^3$ |
| Theta range for data collection | 4.866 to 70.114°. |
| Index ranges | −11 <= h <= 10, −12 <= k <= 12, −27 <= l <= 27 |
| Reflections collected | 48160 |
| Independent reflections | 2122 [R(int) = 0.0392] |
| Completeness to theta = 67.679° | 99.8% |
| Absorption correction | Empirical |
| Refinement method | Full-matrix least-squares on F$^2$ |
| Data/restraints/parameters | 2122/9/158 |
| Goodness-of-fit on F$^2$ | 1.010 |
| Final R indices [I > 2sigma(I)] | R1 = 0.0408, wR2 = 0.1012 |

| | |
|---|---|
| R indices (all data) | R1 = 0.0429, wR2 = 0.1039 |
| Absolute structure parameter | 0.03(4) |
| Extinction coefficient | n/a |
| Largest diff. peak and hole | 0.280 and −0.215 e · Å$^{-3}$ |

In step 2 the resulting sodium (1R,2S,5S)-6,6-dimethyl-3-azabicyclo[3.1.0]hexane-2-carboxylate is then coupled with (S)-3,3-dimethyl-2-(2,2,2-trifluoroacetamido)butanoic acid in the presence of tosyl chloride and dimethylamino pyridine in tetrahydrofuran. The tetrahydrofuran is removed and replaced with isopropyl acetate followed by treatment with HCl in brine followed by workup with water and heptane to provide C42.

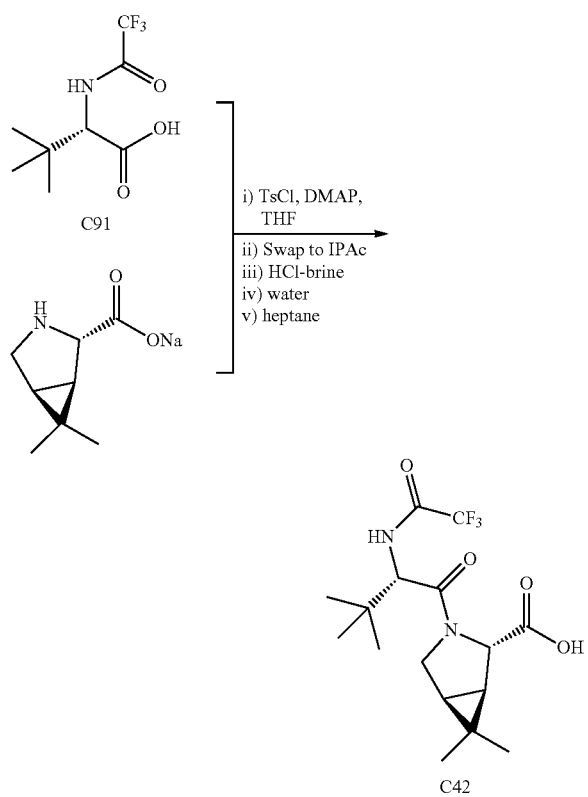

Crystalline C42 was characterized by PXRD and an additional form obtained from extended drying or higher temperature was identified.

Selected PXRD peaks for C42—Crystalline Form obtained from extended drying time or higher temperature

| Angle degrees 2-Θ ± 0.2 °2-Θ | Relative Intensity |
|---|---|
| 10.2 | 3 |
| 10.8 | 100 |
| 12.6 | 22 |
| 13.3 | 21 |
| 13.8 | 88 |
| 16.3 | 59 |
| 17.1 | 39 |
| 18.7 | 5 |
| 18.9 | 2 |
| 19.5 | 20 |
| 19.9 | 18 |
| 20.3 | 2 |
| 20.6 | 26 |
| 20.8 | 63 |
| 21.7 | 6 |
| 22.2 | 20 |
| 23.4 | 8 |
| 23.7 | 18 |
| 24.5 | 7 |
| 25.4 | 9 |
| 25.7 | 11 |
| 26.1 | 3 |
| 26.8 | 2 |
| 27.1 | 2 |
| 27.4 | 7 |
| 27.8 | 7 |
| 28.0 | 3 |
| 28.2 | 3 |
| 29.0 | 2 |
| 29.5 | 4 |
| 29.8 | 2 |
| 30.1 | 2 |
| 30.6 | 7 |
| 30.9 | 3 |
| 31.2 | 3 |
| 32.0 | 8 |
| 32.7 | 4 |
| 32.9 | 4 |
| 33.1 | 5 |
| 33.5 | 1 |
| 33.7 | 1 |
| 34.1 | 1 |
| 34.6 | 4 |
| 35.1 | 3 |
| 35.5 | 1 |
| 36.3 | 4 |
| 36.9 | 6 |
| 38.2 | 6 |
| 38.8 | 2 |
| 39.3 | 1 |
| 39.6 | 2 |
| 39.8 | 2 |
| 40.2 | 2 |
| 42.2 | 3 |
| 44.2 | 2 |
| 44.7 | 3 |
| 47.0 | 2 |
| 47.3 | 2 |

Antiviral Activity from SARS-CoV-2 Infection

The ability of compounds to prevent SARS-CoV-2 coronavirus-induced cell death or cytopathic effect can be assessed via cell viability, using an assay format that utilizes luciferase to measure intracellular ATP as an endpoint. In brief, VeroE6 cells that are enriched for hACE2 expression were batched inoculated with SARS-CoV-2 (USA_WA1/2020) at a multiplicity of infection of 0.002 in a BSL-3 lab. Virus-inoculated cells were then added to assay-ready compound plates at a density of 4,000 cells/well. Following a 3-day incubation, a time at which virus-induced cytopathic effect is 95% in the untreated, infected control conditions, cell viability was evaluated using Cell Titer-Glo (Promega), according to the manufacturer's protocol, which quantitates ATP levels. Cytotoxicity of the compounds was assessed in parallel non-infected cells. Test compounds are tested either alone or in the presence of the P-glycoprotein (P-gp) inhibitor CP-100356 at a concentration of 2 μM. The inclusion of CP-100356 is to assess if the test compounds are being effluxed out of the VeroE6 cells, which have high levels of expression of P-glycoprotein. Percent effect at each concentration of test compound was calculated based on the values for the no virus control wells and virus-containing control wells on each assay plate. The concentration required for a 50% response (EC$_{50}$) value was determined from these data using a 4-parameter logistic model. $EC_{50}$ curves were fit to a Hill slope of 3 when >3 and the top dose achieved 50% effect. If cytotoxicity was detected at greater than 30% effect, the corresponding concentration data was eliminated from the $EC_{50}$ determination.

For cytotoxicity plates, a percent effect at each concentration of test compound was calculated based on the values for the cell-only control wells and hyamine-containing control wells on each assay plate. The $CC_{50}$ value was calculated using a 4-parameter logistic model. A TI was then calculated by dividing the $CC_{50}$ value by the $EC_{50}$ value.

SARS-CoV-2 Coronavirus 3C Protease FRET Assay and Analysis

The proteolytic activity of the main protease, 3CLpro, of SARS-CoV-2 was monitored using a continuous fluorescence resonance energy transfer (FRET) assay. The SARS-CoV-2 3CLpro assay measures the activity of full-length SARS-CoV-2 3CL protease to cleave a synthetic fluorogenic substrate peptide with the following sequence: Dabcyl-KTSAVLQ-SGFRKME-Edans modelled on a consensus peptide (V. Grum-Tokars et al. Evaluating the 3C-like protease activity of SARS-coronavirus: recommendations for standardized assays for drug discovery. Virus Research 133 (2008) 63-73). The fluorescence of the cleaved Edans peptide (excitation 340 nm/emission 490 nm) is measured using a fluorescence intensity protocol on a Flexstation reader (Molecular Devices). The fluorescent signal is reduced in the present of PF-835231, a potent inhibitor of SARS-CoV-2 3CLpro. The assay reaction buffer contained 20 mM Tris-HCl (pH 7.3), 100 nM NaCl, 1 mM EDTA and 25 µM peptide substrate. Enzyme reactions were initiated with the addition of 15 nM SARS-CoV-2 3CL protease and allowed to proceed for 60 minutes at 23° C. Percent inhibition or activity was calculated based on control wells containing no compound (0% inhibition/100% activity) and a control compound (100% inhibition/0% activity). IC50 values were generated using a four-parameter fit model using ABASE software (IDBS). Ki values were fit to the Morrison equation with the enzyme concentration parameter fixed to 15 nM, the Km parameter fixed to 14 µM and the substrate concentration parameter fixed to 25 µM using ABASE software (IDBS).

Proteolytic activity of SARS-CoV-2 Coronavirus 3CL protease is measured using a continuous fluorescence resonance energy transfer assay. The SARS-CoV-2 3CL$^{pro}$ FRET assay measures the protease catalyzed cleavage of TAMRA-SITSAVLQSGFRKMK-(DABCYL)-OH to TAMRA-SITSAVLQ and SGFRKMK(DABCYL)-OH. The fluorescence of the cleaved TAMRA (ex. 558 nm/em. 581 nm) peptide was measured using a TECAN SAFIRE fluorescence plate reader over the course of 10 min. Typical reaction solutions contained 20 mM HEPES (pH 7.0), 1 mM EDTA, 4.0 µM FRET substrate, 4% DMSO and 0.005% Tween-20. Assays were initiated with the addition of 25 nM SARS 3CL$^{pro}$ (nucleotide sequence 9985-10902 of the Urbani strain of SARS coronavirus complete genome sequence (NCBI accession number AY278741)). Percent inhibition was determined in duplicate at 0.001 mM level of inhibitor. Data was analyzed with the non-linear regression analysis program Kalidagraph using the equation:

$$FU = \text{offset} + (\text{limit})(1 - e^{(kobs)t})$$

where offset equals the fluorescence signal of the un-cleaved peptide substrate, and limit equals the fluorescence of fully cleaved peptide substrate. The kobs is the first order rate constant for this reaction, and in the absence of any inhibitor represents the utilization of substrate. In an enzyme start reaction which contains an irreversible inhibitor, and where the calculated limit is less than 20% of the theoretical maximum limit, the calculated kobs represents the rate of inactivation of coronavirus 3C protease. The slope (kobs/l) of a plot of kobs vs. [I] is a measure of the avidity of the inhibitor for an enzyme. For very fast irreversible inhibitors, kobs/l is calculated from observations at only one or two [I] rather than as a slope.

TABLE 2

Biological activity and IUPAC name for Examples 1-84.

| Example Number | Geometric Mean $K_i$ (µM) | Count Used $K_i$ (µM) | Geometric Mean $EC_{50}$ (µM) | Count Used $EC_{50}$ (µM) | IUPAC Name |
|---|---|---|---|---|---|
| 1 | 0.013 | 4 | 0.246 | 7 | (1R,2S,5S)-N-{(1S)-1-cyano-2-[(3S)-2-oxopyrrolidin-3-yl]ethyl}-6,6-dimethyl-3-[N-(trifluoroacetyl)-L-valyl]-3-azabicyclo[3.1.0]hexane-2-carboxamide |
| 2 | 1.08 | 3 | 7.52 | 2 | N-{(1S)-1-cyano-2-[(3S)-2-oxopyrrolidin-S-yl]ethyl}-4-methyl-N$^2$-(pyrrolidin-1-ylacetyl)-L-leucinamide, trifluoroacetate salt |
| 3 | 0.439 | 2 | 6.74 | 6 | N-{(1S)-1-cyano-2-[(3S)-2-oxopyrrolidin-3-yl]ethyl}-N$^2$-(2,6-dichlorobenzoyl)-4-methyl-L-leucinamide |
| 4 | 0.026 | 3 | 1.36 | 15 | N-[(2S)-1-({(1S)-1-cyano-2-[(3S)-2-oxopyrrolidin-3-yl]ethyl}amino)-4-methyl-1-oxopentan-2-yl]-4-methoxy-1H-indole-2-carboxamide |
| 5 | >0.351 | 2 | >3.33 | 1 | N-[(2S)-1-({(1S)-1-cyano-2-[(3S)-2-oxopyrrolidin-3-yl]ethyl}amino)-4-methyl-1-oxopentan-2-yl]-4-methoxy-3-(trifluoromethyl)-1H-indole-2-carboxamide |
| 6 | 0.023 | 2 | 0.279 | 4 | N-[(2S)-1-({(1S)-1-cyano-2-[(3S)-2-oxopyrrolidin-3-yl]ethyl}amino)-4-methyl-1-oxopentan-2-yl]-4-methoxy-7- |

TABLE 2-continued

Biological activity and IUPAC name for Examples 1-84.

| Example Number | Geometric Mean K$_i$ (μM) | Count Used K$_i$ (μM) | Geometric Mean EC$_{50}$ (μM) | Count Used EC$_{50}$ (μM) | IUPAC Name |
|---|---|---|---|---|---|
| 7 | 0.798 | 1 | 43.1 | 2 | (trifluoromethyl)-1H-indole-2-carboxamide<br>N-[(2S)-1-({(1S)-1-cyano-2-[(3S)-2-oxopyrrolidin-3-yl]ethyl}amino)-4,4-dimethyl-1-oxopentan-2-yl]-3-methylimidazo[2,1-b][1,3]thiazole-2-carboxamide |
| 8 | 0.917 | 3 | 5.75 | 2 | N-{1-cyano-2-[(3S)-2-oxopyrrolidin-3-yl]ethyl}-N$^2$-[cyclohexyl(methoxy)acetyl]-4-methyl-L-leucinamide, DIAST-1 |
| 9 | 0.254 | 4 | 0.970 | 4 | N-{1-cyano-2-[(3S)-2-oxopyrrolidin-3-yl]ethyl}-N$^2$-[cyclohexyl(methoxy)acetyl]-4-methyl-L-leucinamide, DIAST-2 |
| 10 | 0.056 | 4 | 2.09 | 4 | N-[(2S)-1-({(1S)-1-cyano-2-[(3S)-2-oxopyrrolidin-3-yl]ethyl}amino)-4,4-dimethyl-1-oxopentan-2-yl]-4-methoxy-1H-indole-2-carboxamide |
| 11 | 0.297 | 3 | 4.78 | 4 | N$^2$-[(4-bromo-1-ethyl-3-methyl-1H-pyrazol-5-yl)carbonyl]-N-{(1S)-1-cyano-2-[(3S)-2-oxopyrrolidin-3-yl]ethyl}-4-methyl-L-leucinamide |
| 12 | 0.539 | 3 | 6.33 | 2 | N-{(1S)-1-cyano-2-[(3S)-2-oxopyrrolidin-3-yl]ethyl}-N$^2$-[(3,3-difluorocyclobutyl)acetyl]-4-methyl-L-leucinamide |
| 13 | 0.003 | 6 | 0.075 | 18 | (1R,2S,5S)-N-{(1S)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide |
| 14 | 0.302 | 2 | N.D.[1] | | N-[(2S)-1-({(1S)-1-cyano-2-[(3S)-2-oxopyrrolidin-3-yl]ethyl}amino)-5,5,5-trifluoro-1-oxopentan-2-yl]-4-methoxy-1H-indole-2-carboxamide |
| 15 | 0.002 | 1 | 0.360 | 2 | N-[(2S)-1-({(1S)-1-cyano-2-[(3S)-2-oxopyrrolidin-3-yl]ethyl}amino)-4-methyl-1-oxopentan-2-yl]-7-fluoro-4-methoxy-1H-indole-2-carboxamide |
| 16 | 0.018 | 2 | >2.53 | 2 | N-[(2S)-1-({(1S)-1-cyano-2-[(3S)-2-oxopyrrolidin-3-yl]ethyl}amino)-4-methyl-1-oxopentan-2-yl]-5-fluoro-4-methoxy-1H-indole-2-carboxamide |
| 17 | 0.053 | 1 | >0.333 | 1 | N-[(2S)-1-({(1S)-1-cyano-2-[(3S)-2-oxopyrrolidin-3-yl]ethyl}amino)-4-methyl-1-oxopentan-2-yl]-3-fluoro-4-methoxy-1H-indole-2-carboxamide |
| 18 | 0.019 | 2 | >0.333 | 1 | N-[(2S)-1-({(1S)-1-cyano-2-[(3S)-2-oxopyrrolidin-3-yl]ethyl}amino)-4-methyl-1-oxopentan-2-yl]-5,7-difluoro-4-methoxy-1H-indole-2-carboxamide |
| 19 | 0.208 | 2 | >0.333 | 1 | N-[(2S)-1-({(1S)-1-cyano-2-[(3S)-2-oxopyrrolidin-3-yl]ethyl}amino)-4-methyl-1-oxopentan-2-yl]-3,5-difluoro-4-methoxy-1H-indole-2-carboxamide |
| 20 | 0.005 | 1 | >0.333 | 1 | N-[(2S)-1-({(1S)-1-cyano-2-[(3S)-2-oxopyrrolidin-3-yl]ethyl}amino)-4,4-dimethyl-1-oxopentan-2-yl]-7-fluoro-4-methoxy-1H-indole-2-carboxamide |
| 21 | N.D. | N.D. | >3.17 | 2 | N-[(2S)-1-({(1S)-1-cyano-2-[(3S)-2-oxopyrrolidin-3-yl]ethyl}amino)-4,4-dimethyl-1-oxopentan-2-yl]-5-fluoro-4-methoxy-1H-indole-2-carboxamide |
| 22 | 0.066 | 1 | >0.333 | 1 | N-[(2S)-1-({(1S)-1-cyano-2-[(3S)-2-oxopyrrolidin-3-yl]ethyl}amino)-4,4-dimethyl-1-oxopentan-2-yl]-3-fluoro-4-methoxy-1H-indole-2-carboxamide |
| 23 | 0.021 | 1 | >0.333 | 1 | N-[(2S)-1-({(1S)-1-cyano-2-[(3S)-2-oxopyrrolidin-3-yl]ethyl}amino)-4,4-dimethyl-1-oxopentan-2-yl]-5,7-difluoro-4-methoxy-1H-indole-2-carboxamide |

TABLE 2-continued

Biological activity and IUPAC name for Examples 1-84.

| Example Number | Geometric Mean $K_i$ (µM) | Count Used $K_i$ (µM) | Geometric Mean $EC_{50}$ (µM) | Count Used $EC_{50}$ (µM) | IUPAC Name |
|---|---|---|---|---|---|
| 24 | 1.93 | 2 | 6.30 | 6 | N-{(1S)-1-cyano-2-[(3S)-2-oxopyrrolidin-3-yl]ethyl}-4-methyl-$N^2$-{[2-(trifluoromethyl)-1,3-thiazol-4-yl]carbonyl}-L-leucinamide |
| 25 | N.D. | | 37 | 2 | N-{1-cyano-2-[(3S)-2-oxopyrrolidin-3-yl]ethyl}-$N^2$-(cyclohexylcarbonyl)-4-methyl-L-leucinamide, DIAST-1 |
| 26 | N.D. | | >100 | 1 | N-{1-cyano-2-[(3S)-2-oxopyrrolidin-3-yl]ethyl}-$N^2$-(cyclohexylcarbonyl)-4-methyl-L-leucinamide, DIAST-2 |
| 27 | 4.50 | 2 | 44.9 | 2 | N-{(1S)-1-cyano-2-[(3S)-2-oxopyrrolidin-3-yl]ethyl}-4-methyl-$N^2$-[(propan-2-yloxy)acetyl]-L-leucinamide |
| 28 | 1.79 | 2 | 7.26 | 4 | N-{(1S)-1-cyano-2-[(3S)-2-oxopyrrolidin-3-yl]ethyl}-$N^2$-[(cyclohexyloxy)acetyl]-4-methyl-L-leucinamide |
| 29 | 2.23 | 2 | 28.1 | 2 | N-{(1S)-1-cyano-2-[(3S)-2-oxopyrrolidin-3-yl]ethyl}-4-methyl-$N^2$-(4,4,4-trifluoro-3-methylbutanoyl)-L-leucinamide |
| 30 | >10.8 | 1 | 9.37 | 2 | N-{(1S)-1-cyano-2-[(3S)-2-oxopyrrolidin-3-yl]ethyl}-$N^2$-[(2S)-2-(dimethylamino)-2-phenylacetyl]-4-methyl-L-leucinami |
| 31 | 0.606 | 3 | 40.7 | 2 | $N^2$-[(trans-4-cyanocyclohexyl)carbonyl]-N-{(1S)-1-cyano-2-[(3S)-2-oxopyrrolidin-3-yl]ethyl}-4-methyl-L-leucinamide or $N^2$-[(trans-4-cyanocyclohexyl)carbonyl]-N-{(1R)-1-cyano-2-[(3S)-2-oxopyrrolidin-3-yl]ethyl}-4-methyl-L-leucinamide |
| 32 | 0.690 | 3 | 4.90 | 2 | N-{(1S)-1-cyano-2-[(3S)-2-oxopyrrolidin-3-yl]ethyl}-$N^2$-[2-(cyclohexyloxy)propanoyl]-4-methyl-L-leucinamide or N-{(1R)-1-cyano-2-[(3S)-2-oxopyrrolidin-3-yl]ethyl}-$N^2$-[2-(cyclohexyloxy)propanoyl]-4-methyl-L-leucinamide |
| 33 | 0.068 | 2 | >0.333 | 1 | N-[(2S)-1-({(1S)-1-cyano-2-[(3S)-2-oxopyrrolidin-3-yl]ethyl}amino)-4-methyl-1-oxopentan-2-yl]-4-hydroxy-1H-indole-2-carboxamide |
| 34 | 0.074 | 2 | >0.333 | 1 | N-[(2S)-1-({(1S)-1-cyano-2-[(3S)-2-oxopyrrolidin-3-yl]ethyl}amino)-4-methyl-1-oxopentan-2-yl]-5-hydroxy-4-methoxy-1H-indole-2-carboxamide |
| 35 | 0.176 | 3 | 3.56 | 4 | $N^2$-[(4-chloro-1,3-dimethyl-1H-pyrazol-5-yl)carbonyl]-N-{(1S)-1-cyano-2-[(3S)-2-oxopyrrolidin-3-yl]ethyl}-4-methyl-L-leucinamide |
| 36 | 0.241 | 4 | 1.03 | 2 | N-{(1S)-1-cyano-2-[(3S)-2-oxopyrrolidin-3-yl]ethyl}-$N^2$-[(2R)-2-(dimethylamino)-2-phenylacetyl]-4-methyl-L-leucinamide |
| 37 | 0.168 | 1 | >3.33 | 1 | N-[(2S)-1-({(1S)-1-cyano-2-[(3S)-2-oxopyrrolidin-3-yl]ethyl}amino)-4,4-dimethyl-1-oxopentan-2-yl]-4-methoxy-3-(trifluoromethyl)-1H-indole-2-carboxamide |
| 38 | 0.023 | 1 | >0.333 | 1 | N-[(2S)-1-({(1S)-1-cyano-2-[(3S)-2-oxopyrrolidin-3-yl]ethyl}amino)-4,4-dimethyl-1-oxopentan-2-yl]-4-methoxy-7-(trifluoromethyl)-1H-indole-2-carboxamide |

TABLE 2-continued

Biological activity and IUPAC name for Examples 1-84.

| Example Number | Geometric Mean $K_i$ (μM) | Count Used $K_i$ (μM) | Geometric Mean $EC_{50}$ (μM) | Count Used $EC_{50}$ (μM) | IUPAC Name |
|---|---|---|---|---|---|
| 39 | 0.111 | 1 | >3.33 | 1 | N-[(2S)-1-({(1S)-1-cyano-2-[(3S)-2-oxopyrrolidin-3-yl]ethyl}amino)-4,4-dimethyl-1-oxopentan-2-yl]-4-methoxy-3,7-bis(trifluoromethyl)-1H-indole-2-carboxamide |
| 40 | 0.131 | 1 | >0.333 | 1 | N-[(2S)-1-({(1S)-1-cyano-2-[(3S)-2-oxopyrrolidin-3-yl]ethyl}amino)-4,4-dimethyl-1-oxopentan-2-yl]-4-methoxy-3,5-bis(trifluoromethyl)-1H-indole-2-carboxamide |
| 41 | 0.104 | 1 | >0.333 | 1 | N-[(2S)-1-({(1S)-1-cyano-2-[(3S)-2-oxopyrrolidin-3-yl]ethyl}amino)-4,4-dimethyl-1-oxopentan-2-yl]-4-methoxy-3,6-bis(trifluoromethyl)-1H-indole-2-carboxamide[2] |
| 42 | >0.356 | 1 | >0.333 | 1 | N-{(1S)-1-cyano-2-[(3S)-2-oxopyrrolidin-3-yl]ethyl}-$N^2$-{(2R)-2-(dimethylamino)-2-[3-(trifluoromethyl)phenyl]acetyl}-4-methyl-L-leucinamide |
| 43 | >0.356 | 1 | >0.333 | 1 | N-{(1S)-1-cyano-2-[(3S)-2-oxopyrrolidin-3-yl]ethyl}-$N^2$-{(2R)-2-(dimethylamino)-2-[4-(trifluoromethyl)phenyl]acetyl}-4-methyl-L-leucinamide |
| 44 | 0.302 | 2 | 5.88 | 2 | N-[(2S)-1-({(1S)-1-cyano-2-[(3S)-2-oxopyrrolidin-3-yl]ethyl}amino)-4-methyl-1-oxopentan-2-yl]-6-(trifluoromethyl)-1H-indole-2-carboxamide |
| 45 | 0.227 | 2 | 6.42 | 2 | N-[(2S)-1-({(1S)-1-cyano-2-[(3S)-2-oxopyrrolidin-3-yl]ethyl}amino)-4,4-dimethyl-1-oxopentan-2-yl]-6-(trifluoromethyl)-1H-indole-2-carboxamide |
| 46 | 0.283 | 1 | >3.33 | 1 | N-[(2S)-1-({(1S)-1-cyano-2-[(3S)-2-oxopyrrolidin-3-yl]ethyl}amino)-4-methyl-1-oxopentan-2-yl]-4-methoxy-3,7-bis(trifluoromethyl)-1H-indole-2-carboxamide |
| 47 | >0.359 | 1 | >3.33 | 1 | N-[(2S)-1-({(1S)-1-cyano-2-[(3S)-2-oxopyrrolidin-3-yl]ethyl}amino)-4-methyl-1-oxopentan-2-yl]-4-methoxy-3,6,7-tris(trifluoromethyl)-1H-indole-2-carboxamide |
| 48 | >0.359 | 1 | >3.33 | 1 | N-[(2S)-1-({(1S)-1-cyano-2-[(3S)-2-oxopyrrolidin-3-yl]ethyl}amino)-4-methyl-1-oxopentan-2-yl]-4-methoxy-3,5,7-tris(trifluoromethyl)-1H-indole-2-carboxamide |
| 49 | 0.083 | 3 | 2.68 | 2 | N-[(2S)-1-({(1S)-1-cyano-2-[(3S)-2-oxopyrrolidin-3-yl]ethyl}amino)-4-methyl-1-oxopentan-2-yl]-4-(trifluoromethoxy)-1H-indole-2-carboxamide |
| 50 | 0.147 | 3 | 3.95 | 1 | N-[(2S)-1-({(1S)-1-cyano-2-[(3S)-2-oxopyrrolidin-3-yl]ethyl}amino)-4,4-dimethyl-1-oxopentan-2-yl]-4-(trifluoromethoxy)-1H-indole-2-carboxamide |
| 51 | 0.192 | 3 | N.D. | | N-[(2S)-1-({(1S)-1-cyano-2-[(3S)-2-oxopyrrolidin-3-yl]ethyl}amino)-4,4-dimethyl-1-oxopentan-2-yl]-5-(trifluoromethyl)-1H-indole-2-carboxamide |
| 52 | 0.032 | 3 | N.D. | | 7-chloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide |
| 53 | 0.025 | 3 | N.D. | | N-[(2S)-1-({(1S)-1-cyano-2-[(3S)-2-oxopyrrolidin-3-yl]ethyl}amino)-4,4-dimethyl-1-oxopentan-2-yl]-4-methoxy-7-methyl-1H-indole-2-carboxamide |

TABLE 2-continued

Biological activity and IUPAC name for Examples 1-84.

| Example Number | Geometric Mean $K_i$ (μM) | Count Used $K_i$ (μM) | Geometric Mean $EC_{50}$ (μM) | Count Used $EC_{50}$ (μM) | IUPAC Name |
|---|---|---|---|---|---|
| 54 | 0.049 | 3 | N.D. | | 6-chloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide |
| 55 | 0.104 | 3 | N.D. | | 4-chloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide |
| 56 | 0.151 | 3 | N.D. | | 5-chloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide |
| 57 | 0.052 | 3 | N.D. | | N-[(2S)-1-({(1S)-1-cyano-2-[(3S)-2-oxopyrrolidin-3-yl]ethyl}amino)-4,4-dimethyl-1-oxopentan-2-yl]-7-(trifluoromethyl)-1H-indole-2-carboxamide |
| 58 | 0.091 | 3 | N.D. | | 4,6-dichloro-N-[(2S)-1-({(1S)-1-cyano-2-[(3S)-2-oxopyrrolidin-3-yl]ethyl}amino)-4,4-dimethyl-1-oxopentan-2-yl]-1H-indole-2-carboxamide |
| 59 | 0.152 | 3 | N.D. | | N-[(2S)-1-({(1S)-1-cyano-2-[(3S)-2-oxopyrrolidin-3-yl]ethyl}amino)-4,4-dimethyl-1-oxopentan-2-yl]-4-(trifluoromethyl)-1H-indole-2-carboxamide |
| 60 | 0.261 | 3 | N.D. | | N-[(2S)-1-({(1S)-1-cyano-2-[(3S)-2-oxopyrrolidin-3-yl]ethyl}amino)-4-methyl-1-oxopentan-2-yl]-5-(trifluoromethyl)-1H-indole-2-carboxamide |
| 61 | 0.034 | 3 | N.D. | | 7-chloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide |
| 62 | 0.029 | 3 | N.D. | | N-[(2S)-1-({(1S)-1-cyano-2-[(3S)-2-oxopyrrolidin-3-yl]ethyl}amino)-4-methyl-1-oxopentan-2-yl]-4-methoxy-7-methyl-1H-indole-2-carboxamide |
| 63 | 0.122 | 3 | N.D. | | 6-chloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide |
| 64 | 0.038 | 3 | N.D. | | 4-chloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide |
| 65 | 0.117 | 3 | N.D. | | 5-chloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide |
| 66 | 0.073 | 3 | N.D. | | N-[(2S)-1-({(1S)-1-cyano-2-[(3S)-2-oxopyrrolidin-3-yl]ethyl}amino)-4-methyl-1-oxopentan-2-yl]-7-(trifluoromethyl)-1H-indole-2-carboxamide |
| 67 | 0.041 | 3 | N.D. | | 4,6-dichloro-N-[(2S)-1-({(1S)-1-cyano-2-[(3S)-2-oxopyrrolidin-3-yl]ethyl}amino)-4-methyl-1-oxopentan-2-yl]-1H-indole-2-carboxamide |
| 68 | 0.092 | 3 | N.D. | | N-[(2S)-1-({(1S)-1-cyano-2-[(3S)-2-oxopyrrolidin-3-yl]ethyl}amino)-4-methyl-1-oxopentan-2-yl]-4-(trifluoromethyl)-1H-indole-2-carboxamide |
| 69 | 0.083 | 1 | >2.67 | 2 | N-[(2S)-1-({(1S)-1-cyano-2-[(3S)-2-oxopyrrolidin-3-yl]ethyl}amino)-4,4-dimethyl-1-oxopentan-2-yl]-3-methyl-5-(trifluoromethyl)imidazo[2,1-b][1,3]thiazole-2-carboxamide |
| 70 | 6.95 | 2 | 4.09 | 2 | N-{(1S)-1-cyano-2-[(3S)-2-oxopyrrolidin-3-yl]ethyl}-4-methyl-N$^2$- |

TABLE 2-continued

Biological activity and IUPAC name for Examples 1-84.

| Example Number | Geometric Mean $K_i$ (μM) | Count Used $K_i$ (μM) | Geometric Mean $EC_{50}$ (μM) | Count Used $EC_{50}$ (μM) | IUPAC Name |
| --- | --- | --- | --- | --- | --- |
| 71 | 0.254 | 3 | 4.99 | 2 | {[5-methyl-2-(trifluoromethyl)-1,3-thiazol-4-yl]carbonyl}-L-leucinamide N-{(1S)-1-cyano-2-[(3S)-2-oxopyrrolidin-3-yl]ethyl}-4-methyl-$N^2$-{[4-methyl-2-(trifluoromethyl)-1,3-thiazol-5-yl]carbonyl}-L-leucinamide |
| 72 | 0.173 | 3 | 1.35 | 2 | $N^2$-[(4-bromo-1-ethyl-3-methyl-1H-pyrazol-5-yl)carbonyl]-N-{(1S)-1-cyano-2-[(3S)-2-oxopyrrolidin-3-yl]ethyl}-L-leucinamide |
| 73 | 0.226 | 3 | 2.03 | 2 | $N^2$-[(4-chloro-1,3-dimethyl-1H-pyrazol-5-yl)carbonyl]-N-{(1S)-1-cyano-2-[(3S)-2-oxopyrrolidin-3-yl]ethyl}-L-leucinamide |
| 74 | >0.356 | 1 | >3.33 | 1 | 3-acetyl-N-[(2S)-1-({(1S)-1-cyano-2-[(3S)-2-oxopyrrolidin-3-yl]ethyl}amino)-4-methyl-1-oxopentan-2-yl]-4-methoxy-1H-indole-2-carboxamide |
| 75 | 0.017 | 2 | 0.551 | 4 | Diastereomer 1: (2S,4R)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide or (2R,4S)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide |
| 76 | >8.16 | 2 | >100 | 1 | Diastereomer 2: (2S,4R)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide or (2R,4S)-4-tert-butyl-N-{(1S)-1-cyano-2-[(3S)-2-oxopyrrolidin-3-yl]ethyl}-1-{N-[(trifluoromethyl)sulfonyl]-L-valyl}piperidine-2-carboxamide |
| 77 | 0.004 | 2 | 0.085 | 4 | 3-methyl-N-(trifluoroacetyl)-L-valyl-(4R)-N-{(1S)-1-cyano-2-[(3S)-2-oxopyrrolidin-3-yl]ethyl}-4-(trifluoromethyl)-L-prolinamide |
| 78 | 0.005 | 3 | 2.74 | 2 | (1R,2S,5S)-N-{(1S)-1-cyano-2-[(3S)-2-oxopyrrolidin-3-yl]ethyl}-6,6-dimethyl-3-[3-methyl-N-(methylcarbamoyl)-L-valyl]-3-azabicyclo[3.1.0]hexane-2-carboxamide |
| 79 | 0.001 | 4 | 0.080 | 4 | methyl {(2S)-1-[(1R,2S,5S)-2-({(1S)-1-cyano-2-[(3S)-2-oxopyrrolidin-3-yl]ethyl}carbamoyl)-6,6-dimethyl-3-azabicyclo[3.1.0]hexan-3-yl]-3,3-dimethyl-1-oxobutan-2-yl}carbamate |
| 80 | 0.037 | 2 | 0.158 | 3 | N-(trifluoroacetyl)-L-valyl-(4R)-N-{(1S)-1-cyano-2-[(3S)-2-oxopyrrolidin-3-yl]ethyl}-4-(trifluoromethyl)-L-prolinamide |
| 81 | 0.003 | 2 | 0.690 | 3 | (1R,2S,5S)-N-{(1S)-1-cyano-2-[(3R)-5-hydroxy-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide |
| 82 | 0.139 | 1 | N.D. | N.D. | (1R,2S,5S,6R)-N-{(1S)-1-cyano-2-[(3S)-2-oxopyrrolidin-3-yl]ethyl}-6-(hydroxymethyl)-6-methyl-3-[3-methyl-N-(trifluoroacetyl)-L-valyl]-3-azabicyclo[3.1.0]hexane-2-carboxamide |
| 83 | 0.092 | 1 | N.D. | N.D. | (1R,2S,5S,6S)-N-{(1S)-1-cyano-2-[(3S)-2-oxopyrrolidin-3-yl]ethyl}-6-(hydroxymethyl)-6-methyl-3-[3-methyl-N-(trifluoroacetyl)-L-valyl]-3-azabicyclo[3.1.0]hexane-2-carboxamide |

TABLE 2-continued

Biological activity and IUPAC name for Examples 1-84.

| Example Number | Geometric Mean $K_i$ (µM) | Count Used $K_i$ (µM) | Geometric Mean $EC_{50}$ (µM) | Count Used $EC_{50}$ (µM) | IUPAC Name |
| --- | --- | --- | --- | --- | --- |
| 84 | 0.003 | 1 | N.D. | N.D. | (1R,2S,5S)-N-{(1S)-1-cyano-2-[(3S)-2-oxopyrrolidin-3-yl]ethyl}-3-[3-(hydroxymethyl)-N-(trifluoroacetyl)-L-valyl]-6,6-dimethyl-3-azabicyclo[3.1.0]hexane-2-carboxamide |
| 85 | 0.004 | 1 | 0.334 | 2 | (1R,2S,5S)-N-{(1S)-1-cyano-2-[(3R)-2,5-dioxopyrrolidin-3-yl]ethyl}-6,6-dimethyl-3-[3-methyl-N-(trifluoroacetyl)-L-valyl]-3-azabicyclo[3.1.0]hexane-2-carboxamide |
| 86 | 0.018 | 2 | 0.237 | 2 | (1R,2S,5S)-N-{(1S)-1-cyano-2-[(3S)-2-oxopyrrolidin-3-yl]ethyl}-6,6-dimethyl-3-[5,5,5-trifluoro-2-(2,2,2-trifluoroacetamido)pentanoyl]-3-azabicyclo[3.1.0]hexane-2-carboxamide |
| 87 | 0.021 | 2 | 0.230 | 2 | (1R,2S,5S)-N-{(1S)-1-cyano-2-[(3S)-2-oxopyrrolidin-3-yl]ethyl}-3-[(2S)-2-cyclohexyl-2-{[(trifluoromethyl)sulfonyl]amino}acetyl]-6,6-dimethyl-3-azabicyclo[3.1.0]hexane-2-carboxamide |
| 88 | 0.006 | 2 | 0.050 | 4 | First-eluting diastereomer: (1R,2S,5S)-N-{(1S)-1-cyano-2-[(3S)-2-oxopyrrolidin-3-yl]ethyl}-3-[3-cyclobutyl-N-(trifluoroacetyl)-L-alanyl]-6,6-dimethyl-3-azabicyclo[3.1.0]hexane-2-carboxamide or (1R,2S,5S)-N-{(1S)-1-cyano-2-[(3S)-2-oxopyrrolidin-3-yl]ethyl}-3-[3-cyclobutyl-N-(trifluoroacetyl)-D-alanyl]-6,6-dimethyl-3-azabicyclo[3.1.0]hexane-2-carboxamide |
| 89 | 0.007 | 3 | 0.040 | 4 | Second-eluting diastereomer: (1R,2S,5S)-N-{(1S)-1-cyano-2-[(3S)-2-oxopyrrolidin-3-yl]ethyl}-3-[3-cyclobutyl-N-(trifluoroacetyl)-L-alanyl]-6,6-dimethyl-3-azabicyclo[3.1.0]hexane-2-carboxamide or (1R,2S,5S)-N-{(1S)-1-cyano-2-[(3S)-2-oxopyrrolidin-3-yl]ethyl}-3-[3-cyclobutyl-N-(trifluoroacetyl)-D-alanyl]-6,6-dimethyl-3-azabicyclo[3.1.0]hexane-2-carboxamide |
| 90 | 0.015 | 2 | 0.571 | 2 | (1R,2S,5S)-N-{(1S)-1-cyano-2-[(3S)-2-oxopyrrolidin-3-yl]ethyl}-6,6-dimethyl-3-[3-(pyridin-2-yl)-N-(trifluoroacetyl)-L-alanyl]-3-azabicyclo[3.1.0]hexane-2-carboxamide |
| 91 | 0.007 | 2 | 0.011 | 2 | (1R,2S,5S)-N-{(1S)-1-cyano-2-[(3S)-2-oxopyrrolidin-3-yl]ethyl}-3-{N-[(4-fluorophenoxy)acetyl]-3-methyl-L-valyl}-6,6-dimethyl-3-azabicyclo[3.1.0]hexane-2-carboxamide |
| 92 | 0.004 | 2 | 0.019 | 4 | 3-methyl-N-[(4-methylphenyl)acetyl]-L-valyl-(4R)-N-{(1S)-1-cyano-2-[(3S)-2-oxopyrrolidin-3-yl]ethyl}-4-(trifluoromethyl)-L-prolinamide |
| 93 | 0.014 | 2 | 0.882 | 2 | (1R,2S,5S)-N-{(1S)-1-cyano-2-[(3S)-2-oxopyrrolidin-3-yl]ethyl}-6,6-dimethyl-3-[3-(1H-pyrazol-1-yl)-N-(trifluoroacetyl)-L-alanyl]-3-azabicyclo[3.1.0]hexane-2-carboxamide |

TABLE 2-continued

Biological activity and IUPAC name for Examples 1-84.

| Example Number | Geometric Mean $K_i$ (μM) | Count Used $K_i$ (μM) | Geometric Mean $EC_{50}$ (μM) | Count Used $EC_{50}$ (μM) | IUPAC Name |
| --- | --- | --- | --- | --- | --- |
| 94 | 0.011 | 2 | 0.379 | 2 | (1R,2S,5S)-N-{(1S)-1-cyano-2-[(3S)-2-oxopyrrolidin-3-yl]ethyl}-3-[(2S)-4,4-difluoro-2-(2,2,2-trifluoroacetamido)butanoyl]-6,6-dimethyl-3-azabicyclo[3.1.0]hexane-2-carboxamide |
| 95 | 0.003 | 2 | 0.098 | 4 | N-(methoxycarbonyl)-3-methyl-L-valyl-(4R)-N-{(1S)-1-cyano-2-[(3S)-2-oxopyrrolidin-3-yl]ethyl}-4-(trifluoromethyl)-L-prolinamide |
| 96 | 0.844 | 1 | 9.190 | 2 | (1R,2S,5S)-N-{(1R)-1-cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide |
| 97 | 0.011 | 5 | 0.082 | 16 | (1R,2S,5S)-N-{(1S)-1-cyano-2-[(3S)-2-oxopyrrolidin-3-yl]ethyl}-6,6-dimethyl-3-[2-(2,2,2-trifluoroacetamido)-3-(trifluoromethyl)pentanoyl]-3-azabicyclo[3.1.0]hexane-2-carboxamide, from C86 (DIAST-2) |
| 98 | 0.188 | 1 | 1.738 | 2 | (1R,2S,5S)-N-{(1S)-1-cyano-2-[(3S)-2-oxopyrrolidin-3-yl]ethyl}-6,6-dimethyl-3-[2-(2,2,2-trifluoroacetamido)-3-(trifluoromethyl)pentanoyl]-3-azabicyclo[3.1.0]hexane-2-carboxamide, from C85 (DIAST-1) |

1. Not determined.
2. The regiochemistry of Example 41 was not rigorously determined, other possible structures for this example are N-[(2S)-1-({(1S)-1-cyano-2-[(3S)-2-oxopyrrolidin-3-yl]ethyl}amino)-4,4-dimethyl-1-oxopentan-2-yl]-4-methoxy-5,6-bis(trifluoromethyl)-1H-indole-2-carboxamide and N-[(2S)-1-({(1S)-1-cyano-2-[(3S)-2-oxopyrrolidin-3-yl]ethyl}amino)-4,4-dimethyl-1-oxopentan-2-yl]-4-methoxy-6,7-bis(trifluoromethyl)-1H-indole-2-carboxamide.

Predicted Pharmacokinetic Parameters of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide (the compound of Example 13) in Humans Based on physiologically based pharmacokinetic (PBPK) modeling of in-vitro data incorporating $CL_{int}$ from human liver microsomes and $CL_{bile}$ from human hepatocytes under sandwich-cultured conditions, the predicted human plasma CL and $V_{ss}$ of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide are 5.9 mL/min/kg and 0.97 L/kg, respectively, providing an effective half-life, $t_{1/2}$, of 1.9 hours. A target $C_{eff}$ of 0.16 μM (unbound plasma concentration) was defined based on antiviral inhibition data obtained from in vitro studies of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide with either VeroE6 cells in the presence of a P-gp inhibitor ($EC_{90}$ value of 0.156 μM) or in a differentiated normal human bronchial epithelial (dNHBE) cell assay ($EC_{90}$ value of 0.149 μM). A dose of 380 mg of (1R,2S,5S)—N-{(1S)-1-Cyano-2-[(3S)-2-oxopyrrolidin-3-yl]ethyl}-6,6-dimethyl-3-[3-methyl-N-(trifluoroacetyl)-L-valyl]-3-azabicyclo[3.1.0]hexane-2-carboxamide administered orally three times a day (TID) is projected to cover the efficacious unbound concentration of 0.16 μM at $C_{min}$.

All patents and publications described hereinabove are hereby incorporated by reference in their entirety. While the invention has been described in terms of various preferred embodiments and specific examples, the invention should be understood as not being limited by the foregoing detailed description, but as being defined by the appended claims and their equivalents.

What is claimed is:

1. The compound N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide having the structure

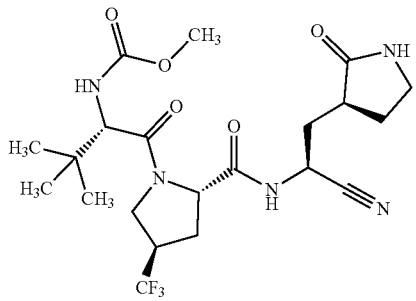

or a solvate or hydrate thereof.

2. The compound N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide having the structure

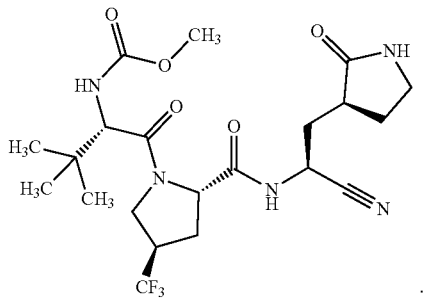 [SMILES: COC(=O)N[C@H](C(=O)N1C[C@H](C(F)(F)F)C[C@H]1C(=O)N[C@H](C#N)C[C@@H]1CCNC1=O)C(C)(C)C]

3. A pharmaceutical composition comprising the compound N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide having the structure

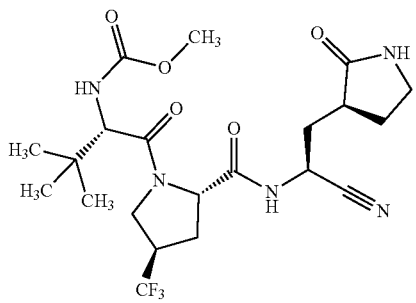

or a solvate or hydrate thereof together with a pharmaceutically acceptable carrier.

4. The pharmaceutical composition of claim 3 wherein the compound is N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide having the structure

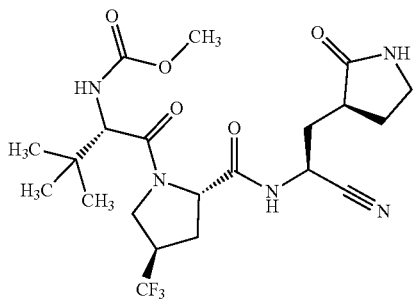

5. A method of treating a coronavirus infection in a patient, the method comprising administering a therapeutically effective amount of the compound N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide having the structure

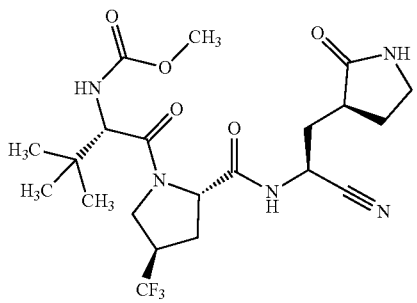

or a solvate or hydrate thereof to a patient in need thereof.

6. The method of claim 5 wherein the coronavirus infection is COVID-19.

7. The method of claim 5 wherein the compound is N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide having the structure

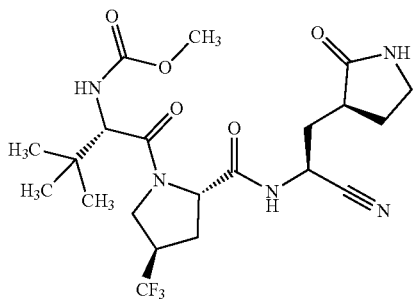

8. The method of claim 6 wherein the compound is N-(Methoxycarbonyl)-3-methyl-L-valyl-(4R)—N-{(1S)-1-cyano-2-[(3S)-2-oxopyrrolidin-3-yl]ethyl}-4-(trifluoromethyl)-L-prolinamide having the structure

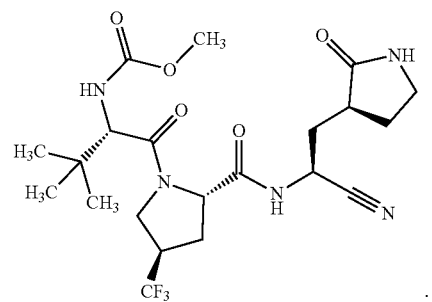 [SMILES: COC(=O)N[C@H](C(=O)N1C[C@H](C(F)(F)F)C[C@H]1C(=O)N[C@H](C#N)C[C@@H]1CCNC1=O)C(C)(C)C]
* * * * *